US006503737B1

(12) United States Patent
Reeves et al.

(10) Patent No.: US 6,503,737 B1
(45) Date of Patent: Jan. 7, 2003

(54) ISOLATED NUCLEIC ACIDS RELATING TO THE FKBA GENE WITHIN THE FK-520 POLYKETIDE SYNTHASE GENE CLUSTER

(75) Inventors: Christopher Reeves, Orinda, CA (US); Daniel Chu, Santa Clara, CA (US); Chaitan Khosla, Palo Alto, CA (US); Daniel Santi, San Francisco, CA (US); Kai Wu, Foster City, CA (US)

(73) Assignee: Kosan Biosciences, Inc., Hayward, CA (US)

( * ) Notice: Subject to any disclaimer, the term of this patent is extended or adjusted under 35 U.S.C. 154(b) by 0 days.

(21) Appl. No.: 09/410,551

(22) Filed: Oct. 1, 1999

Related U.S. Application Data

(60) Provisional application No. 60/102,748, filed on Oct. 2, 1998, provisional application No. 60/139,650, filed on Jun. 17, 1999, and provisional application No. 60/123,810, filed on Mar. 11, 1999.

(51) Int. Cl.[7] .................................................. C12P 19/62

(52) U.S. Cl. ................... 435/76; 435/320.1; 435/252.3; 435/252.35; 536/23.1; 536/23.2

(58) Field of Search .............................. 536/23.1, 23.2; 435/320.1, 76, 252.3, 252.35

(56) References Cited

U.S. PATENT DOCUMENTS

| | | | |
|---|---|---|---|
| 4,874,748 A | 10/1989 | Katz et al. | 514/29 |
| 5,063,155 A | 11/1991 | Cox et al. | 435/76 |
| 5,098,837 A | 3/1992 | Beckmann et al. | 435/172.3 |
| 5,149,639 A | 9/1992 | Katz et al. | 435/76 |
| 5,824,513 A | 10/1998 | Katz et al. | 435/76 |
| 5,830,750 A | 11/1998 | Khosla et al. | |
| 5,843,718 A | 12/1998 | Khosla et al. | |
| 5,962,290 A | 10/1999 | Khosla et al. | |
| 6,022,731 A | 2/2000 | Khosla et al. | |
| 6,077,696 A | 6/2000 | Khosla et al. | |
| 6,150,513 A | 11/2000 | Wu | 536/23.2 |

FOREIGN PATENT DOCUMENTS

| | | |
|---|---|---|
| EP | 0323042 A | 7/1989 |
| EP | 0356399 A | 2/1990 |
| EP | 0463690 A | 1/1992 |
| WO | WO 93/13663 | 7/1993 |
| WO | WO 95/08548 | 3/1995 |
| WO | WO 96/40968 | 12/1996 |
| WO | WO 97/02358 | 1/1997 |
| WO | WO 98/27203 | 6/1998 |
| WO | WO 98/49315 | 11/1998 |
| WO | WO 00/20601 | 4/2000 |

OTHER PUBLICATIONS

Wu et al. The FK520 gene cluster of *Streptomyces hygroscopicus* var. *ascomyceticus* (ATCC 14891) contains genes for biosynthesis of unusual polyketide extender units. Gene (2000) 251:81–90.*

Chen T.S. et al. (1992). "Microbial Transformation of Immunosupressive Compounds. II. Specific desmethylation of 13–methoxy group of FK 506 and FR 9500520 by Actinomycete sp. ATCC 53828," *J. Antibiot* 45(4):577–580.

Dumont F.J. et al. (1992). "The Immunosupressive and Toxic Effects of FK–506 Are Mechanically Related: Pharmacology of a Novel Antagonist of FK–506 and Rapamycin," *J of Exp Medicine* 176(3):751–760.

(List continued on next page.)

*Primary Examiner*—Ponnathapura Achutamurthy
*Assistant Examiner*—Kathleen M Kerr
(74) *Attorney, Agent, or Firm*—Brenda J. Wllach; Christine Ring; Kevin Kaster

(57) ABSTRACT

Host cells comprising recombinant vectors encoding the FK-520 polyketide synthase and FK-520 modification enzymes can be used to produce the FK-520 polyketide. Recombinant DNA constructs comprising one or more FK-520 polyketide synthase domains, modules, open reading frames, and variants thereof can be used to produce recombinant polyketide synthases and a variety of different polyketides with application as pharmaceutical and veterinary products.

34 Claims, 9 Drawing Sheets

OTHER PUBLICATIONS

Khosla C. (1997). "Harnessing the Biosynthetic Potential of Modular Polyketide Synthases," *Chemical Reviews* 97(7):2577–2590.

Reynolds K.A. et al. (1997). "Rapamycin, FK506, and Ascomycin–related Compounds," *Drugs Pharm Sci* 82:497–520.

Shafiee A. et al. (1993). "Enzymatic synthesis and Immunosupressive Activity of Novel Desmethylated Immunomycins (Ascomycins)," *J Antibiot* 46(9):1397–1405.

Stassi D.L. et al. (1998). "Ethyl–substituted Erythromycin Derivatives Produced by Directed Metabolic Engineering," *Proc Nalt Acad Sci USA* 95 (13):7305–7309.

Caffrey et al., FEBS Letters (1992) 304:205.

Fu et al., Biochemistry (1994) 33:9321–9326.

McDaniel et al., Science (1993) 262:1546–1550.

Rohr, Angew. Chem. Int. Ed. Engl. (1995) 34(8):881–888.

* cited by examiner

FIG. 7A
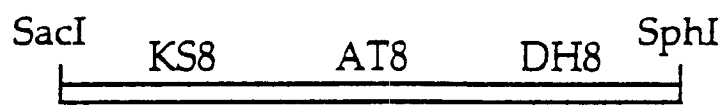
linker insertion
FIG. 7B
BglII
NsiI
PCR amplification
FIG. 7C
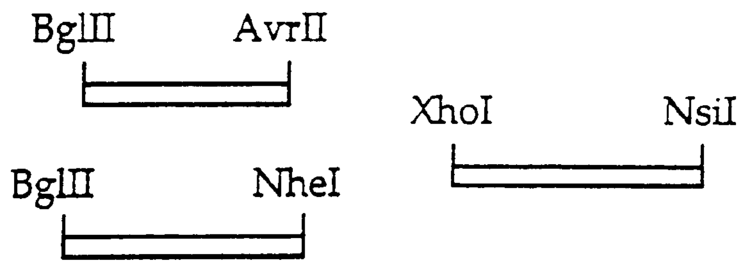
FIG. 7D
AvrII
XhoI
NheI
XhoI
ligation
FIG. 7E
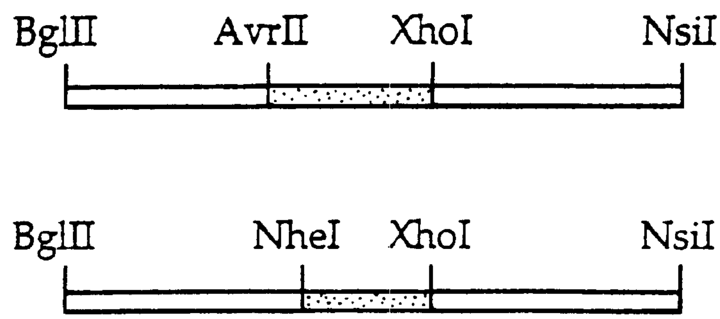

ISOLATED NUCLEIC ACIDS RELATING TO THE FKBA GENE WITHIN THE FK-520 POLYKETIDE SYNTHASE GENE CLUSTER

CROSS-REFERENCE TO RELATED APPLICATIONS

The present application claims priority to related U.S. Provisional application Ser. Nos. 60/102,748, filed Oct. 2, 1998; 60/139,650, filed Jun. 17, 1999; and 60/123,810, filed Mar. 11, 1999, each of which is incorporated herein by reference.

SUBMISSION ON COMPACT DISC

The contents of the following submission on compact discs are incorporated herein by reference in its entirety: A compact disc copy of the Sequence Listing (COPY 1) (file name: 3006220026.txt, date recorded: Jul. 11, 2001, size: 520 KB); a duplicate compact disc copy of Sequence Listing (COPY 2) (file name: 3006220026. txt, date recorded: Jul. 11, 2001, size: 520 KB); a computer readable form copy of the Sequence Listing (CRF COPY) (file name: 3006220026.txt, date recorded: Jul. 11, 2001, size: 520 KB).

FIELD OF THE INVENTION

The present invention relates to polyketides and the polyketide synthase (PKS) enzymes that produce them. The invention also relates generally to genes encoding PKS enzymes and to recombinant host cells containing such genes and in which expression of such genes leads to the production of polyketides. The present invention also relates to compounds useful as medicaments having immunosuppressive and/or neurotrophic activity. Thus, the invention relates to the fields of chemistry, molecular biology, and agricultural, medical, and veterinary technology.

BACKGROUND OF THE INVENTION

Polyketides are a class of compounds synthesized from 2-carbon units through a series of condensations and subsequent modifications. Polyketides occur in many types of organisms, including fungi and mycelial bacteria, in particular, the actinomycetes. Polyketides are biologically active molecules with a wide variety of structures, and the class encompasses numerous compounds with diverse activities. Tetracycline, erythromycin, epothilone, FK-506, FK-520, narbomycin, picromycin, rapamycin, spinocyn, and tylosin are examples of polyketides. Given the difficulty in producing polyketide compounds by traditional chemical methodology, and the typically low production of polyketides in wild-type cells, there has been considerable interest in finding improved or alternate means to produce polyketide compounds.

This interest has resulted in the cloning, analysis, and manipulation by recombinant DNA technology of genes that encode PKS enzymes. The resulting technology allows one to manipulate a known PKS gene cluster either to produce the polyketide synthesized by that PKS at higher levels than occur in nature or in hosts that otherwise do not produce the polyketide. The technology also allows one to produce molecules that are structurally related to, but distinct from, the polyketides produced from known PKS gene clusters. See, e.g., PCT publication Nos. WO 93/13663; 95/08548; 96/40968; 97/02358; 98/27203; and 98/49315; U.S. Pat. Nos. 4,874,748; 5,063,155; 5,098,837; 5,149,639; 5,672,491; 5,712,146; 5,830,750; and 5,843,718; and Fu et al., 1994, *Biochemistry* 33: 9321–9326; McDaniel et al., 1993, *Science* 262: 1546–1550; and Rohr, 1995, *Angew. Chem. Int. Ed. Engl.* 34(8): 881–888, each of which is incorporated herein by reference.

Polyketides are synthesized in nature by PKS enzymes. These enzymes, which are complexes of multiple large proteins, are similar to the synthases that catalyze condensation of 2-carbon units in the biosynthesis of fatty acids. PKSs catalyze the biosynthesis of polyketides through repeated, decarboxylative Claisen condensations between acylthioester building blocks. The building blocks used to form complex polyketides are typically acylthioesters, such as acetyl, butyryl, propionyl, malonyl, hydroxymalonyl, methylmalonyl, and ethylmalonyl CoA. Other building blocks include amino acid like acylthioesters. PKS enzymes that incorporate such building blocks include an activity that finctions as an amino acid ligase (an AMP ligase) or as a non-ribosomal peptide synthetase (NRPS). Two major types of PKS enzymes are known; these differ in their composition and mode of synthesis of the polyketide synthesized. These two major types of PKS enzymes are commonly referred to as Type I or "modular" and Type II "iterative" PKS enzymes.

In the Type I or modular PKS enzyme group, a set of separate catalytic active sites (each active site is termed a "domain", and a set thereof is terned a "module") exists for each cycle of carbon chain elongation and modification in the polyketide synthesis pathway. The typical modular PKS is composed of several large polypeptides, which can be segregated from amino to carboxy termini into a loading module, multiple extender modules, and a releasing (or thioesterase) domain. The PKS enzyme known as 6-deoxyerythronolide B synthase (DEBS) is a Type I PKS. In DEBS, there is a loading module, six extender modules, and a thioesterase (TE) domain. The loading module, six extender modules, and TE of DEBS are present on three separate proteins (designated DEBS-1, DEBS-2, and DEBS-3, with two extender modules per protein). Each of the DEBS polypeptides is encoded by a separate open reading frame (ORF) or gene; these genes are known as eryAI, eryAII, and eryAIII. See Caffrey et al., 1992, *FEBS Letters* 304: 205, and U.S. Pat. No. 5,824,513, each of which is incorporated herein by reference.

Generally, the loading module is responsible for binding the first building block used to synthesize the polyketide and transferring it to the first extender module. The loading module of DEBS consists of an acyltransferase (AT) domain and an acyl carrier protein (ACP) domain. Another type of loading module utilizes an inactivated ketosynthase (KS) domain and AT and ACP domains. This inactivated KS is in some instances called $KS^Q$, where the superscript letter is the abbreviation for the amino acid, glutamine, that is present instead of the active site cysteine required for ketosynthase activity. In other PKS enzymes, including the FK-506 PKS, the loading module incorporates an unusual starter unit and is composed of a CoA ligase like activity domain. In any event, the loading module recognizes a particular acyl-CoA (usually acetyl or propionyl but sometimes butyryl or other acyl-CoA) and transfers it as a thiol ester to the ACP of the loading module.

The AT on each of the extender modules recognizes a particular extender-CoA (malonyl or alpha-substituted malonyl, i.e., methylmalonyl, ethylmalonyl, and 2-hydroxymalonyl) and transfers it to the ACP of that extender module to form a thioester. Each extender module is responsible for accepting a compound from a prior module, binding a building block, attaching the building block to the compound from the prior module, optionally performing one or more additional functions, and transferring the resulting compound to the next module.

Each extender module of a modular PKS contains a KS, AT, ACP, and zero, one, two, or three domains that modify the beta-carbon of the growing polyketide chain. A typical (non-loading) minimal Type I PKS extender module is exemplified by extender module three of DEBS, which contains a KS domain, an AT domain, and an ACP domain. These three domains are sufficient to activate a 2-carbon extender unit and attach it to the growing polyketide molecule. The next extender module, in turn, is responsible for attaching the next building block and transferring the growing compound to the next extender module until synthesis is complete.

Once the PKS is primed with acyl- and malonyl-ACPs, the acyl group of the loading module is transferred to form a thiol ester (trans-esterification) at the KS of the first extender module; at this stage, extender module one possesses an acyl-KS and a malonyl (or substituted malonyl) ACP. The acyl group derived from the loading module is then covalently attached to the alpha-carbon of the malonyl group to form a carbon-carbon bond, driven by concomitant decarboxylation, and generating a new acyl-ACP that has a backbone two carbons longer than the loading building block (elongation or extension).

The polyketide chain, growing by two carbons each extender module, is sequentially passed as covalently bound thiol esters from extender module to extender module, in an assembly line-like process. The carbon chain produced by this process alone would possess a ketone at every other carbon atom, producing a polyketone, from which the name polyketide arises. Most commonly, however, additional enzymatic activities modify the beta keto group of each two carbon unit just after it has been added to the growing polyketide chain but before it is transferred to the next module.

Thus, in addition to the minimal module containing KS, AT, and ACP domains necessary to form the carbon-carbon bond, and as noted above, other domains that modify the beta-carbonyl moiety can be present. Thus, modules may contain a ketoreductase (KR) domain that reduces the keto group to an alcohol. Modules may also contain a KR domain plus a dehydratase (DH) domain that dehydrates the alcohol to a double bond. Modules may also contain a KR domain, a DH domain, and an enoylreductase (ER) domain that converts the double bond product to a saturated single bond using the beta carbon as a methylene function. An extender module can also contain other enzymatic activities, such as, for example, a methylase or dimethylase activity.

After traversing the final extender module, the polyketide encounters a releasing domain that cleaves the polyketide from the PKS and typically cyclizes the polyketide. For example, final synthesis of 6-dEB is regulated by a TE domain located at the end of extender module six. In the synthesis of 6-dEB, the TE domain catalyzes cyclization of the macrolide ring by formation of an ester linkage. In FK-506, FK-520, rapamycin, and similar polyketides, the TE activity is replaced by a RapP (for rapamycin) or RapP like activity that makes a linkage incorporating a pipecolate acid residue. The enzymatic activity that catalyzes this incorporation for the rapamycin enzyme is known as RapP, encoded by the rapP gene. The polyketide can be modified further by tailoring enzymes; these enzymes add carbohydrate groups or methyl groups, or make other modifications, i.e., oxidation or reduction, on the polyketide core molecule. For example, 6-dEB is hydroxylated at C-6 and C-12 and glycosylated at C-3 and C-5 in the synthesis of erythromycin A.

In Type I PKS polypeptides, the order of catalytic domains is conserved. When all beta-keto processing domains are present in a module, the order of domains in that module from N-to-C-terminus is always KS, AT, DH, ER, KR, and ACP. Some or all of the beta-keto processing domains may be missing in particular modules, but the order of the domains present in a module remains the same. The order of domains within modules is believed to be important for proper folding of the PKS polypetides into an active complex. Importantly, there is considerable flexibility in PKS enzymes, which allows for the genetic engineering of novel catalytic complexes. The engineering of these enzymes is achieved by modifying, adding, or deleting domains, or replacing them with those taken from other Type I PKS enzymes. It is also achieved by deleting, replacing, or adding entire modules with those taken from other sources. A genetically engineered PKS complex should of course have the ability to catalyze the synthesis of the product predicted from the genetic alterations made.

Alignments of the many available amino acid sequences for Type I PKS enzymes has approximately defined the boundaries of the various catalytic domains. Sequence alignments also have revealed linker regions between the catalytic domains and at the N- and C-termini of individual polypeptides. The sequences of these linker regions are less well conserved than are those for the catalytic domains, which is in part how linker regions are identified. Linker regions can be important for proper association between domains and between the individual polypeptides that comprise the PKS complex. One can thus view the linkers and domains together as creating a scaffold on which the domains and modules are positioned in the correct orientation to be active. This. organization and positioning, if retained, permits PKS domains of different or identical substrate specificities to be substituted (usually at the DNA level) between PKS enzymes by various available methodologies. In selecting the boundaries of, for example, an AT replacement, one can thus make the replacement so as to retain the linkers of the recipient PKS or to replace them with the linkers of the donor PKS AT domain, or, preferably, make both constructs to ensure that the correct linker regions between the KS and AT domains have been included in at least one of the engineered enzymes. Thus, there is considerable flexibility in the design of new PKS enzymes with the result that known polyketides can be produced more effectively, and novel polyketides useful as pharmaceuticals or for other purposes can be made.

By appropriate application of recombinant DNA technology, a wide variety of polyketides can be prepared in a variety of different host cells provided one has access to nucleic acid compounds that encode PKS proteins and polyketide modification enzymes. The present invention helps meet the need for such nucleic acid compounds by providing recombinant vectors that encode the FK-520 PKS enzyme and various FK-520 modification enzymes. Moreover, while the FK-506 and FK-520 polyketides have many useful activities, there remains a need for compounds with similar useful activities but with better pharmacokinetic profile and metabolism and fewer side-effects. The present invention helps meet the need for such compounds as well.

SUMMARY OF THE INVENTION

In one embodiment, the present invention provides recombinant DNA vectors that encode all or part of the FK-520 PKS enzyme. Illustrative vectors of the invention include cosmid pKOS034-120, pKOS034-124, pKOS065-C31, pKOS065-C3, pKOS065-M27, and pKOS065-M21.

The invention also provides nucleic acid compounds that encode the various domains of the FK-520 PKS, i.e., the KS, AT, ACP, KR, DH, and ER domains. These compounds can be readily used, alone or in combination with nucleic acids encoding other FK-520 or non-FK-520 PKS domains, as intermediates in the construction of recombinant vectors that encode all or part of PKS enzymes that make novel polyketides.

The invention also provides isolated nucleic acids that encode all or part of one or more modules of the FK-520 PKS, each module comprising a ketosynthase activity, an acyl transferase activity, and an acyl carrier protein activity. The invention provides an isolated nucleic acid that encodes one or more open reading frames of FK-520 PKS genes, said open reading frames comprising coding sequences for a CoA ligase activity, an NRPS activity, or two or more extender modules. The invention also provides recombinant expression vectors containing these nucleic acids.

In another embodiment, the invention provides isolated nucleic acids that encode all or a part of a PKS that contains at least one module in which at least one of the domains in the module is a domain from a non-FK-520 PKS and at least one domain is from the FK-520 PKS. The non-FK-520 PKS domain or module originates from the rapamycin PKS, the FK-506 PKS, DEBS, or another PKS. The invention also provides recombinant expression vectors containing these nucleic acids.

In another embodiment, the invention provides a method of preparing a polyketide, said method comprising transforming a host cell with a recombinant DNA vector that encodes at least one module of a PKS, said module comprising at least one FK-520 PKS domain, and culturing said host cell under conditions such that said PKS is produced and catalyzes synthesis of said polyketide. In one aspect, the method is practiced with a Streptomyces host cell. In another aspect, the polyketide produced is FK-520. In another aspect, the polyketide produced is a polyketide related in structure to FK-520. In another aspect, the polyketide produced is a polyketide related in structure to FK-506 or rapamycin.

In another embodiment, the invention provides a set of genes in recombinant form sufficient for the synthesis of ethylmalonyl CoA in a heterologous host cell. These genes and the methods of the invention enable one to create recombinant host cells with the ability to produce polyketides or other compounds that require ethylmalonyl CoA for biosynthesis. The invention also provides recombinant nucleic acids that encode AT domains specific for ethylmalonyl CoA. Thus, the compounds of the invention can be used to produce polyketides requiring ethylmalonyl CoA in host cells that otherwise are unable to produce such polyketides.

In another embodiment, the invention provides a set of genes in recombinant form sufficient for the synthesis of 2-hydroxymalonyl CoA and 2-methoxymalonyl CoA in a heterologous host cell. These genes and the methods of the invention enable one to create recombinant host cells with the ability to produce polyketides or other compounds that require 2-hydroxymalonyl CoA for biosynthesis. The invention also provides recombinant nucleic acids that encode AT domains specific for 2-hydroxymalonyl CoA and 2-methoxymalonyl CoA. Thus, the compounds of the invention can be used to produce polyketides requiring 2-hydroxymalonyl CoA or 2-methoxymalonyl CoA in host cells that are otherwise unable to produce such polyketides.

In another embodiment, the invention provides a compound related in structure to FK-520 or FK-506 that is useful in the treatment of a medical condition. These compounds include compounds in which the C-13 methoxy group is replaced by a moiety selected from the group consisting of hydrogen, methyl, and ethyl moieties. Such compounds are less susceptible to the main in vivo pathway of degradation for FK-520 and FK-506 and related compounds and thus exhibit an improved pharmacokinetic profile. The compounds of the invention also include compounds in which the C-15 methoxy group is replaced by a moiety selected from the group consisting of hydrogen, methyl, and ethyl moieties. The compounds of the invention also include the above compounds further modified by chemical methodology to produce derivatives such as, but not limited to, the C-18 hydroxyl derivatives, which have potent neurotrophin but not immunosuppresion activities.

Thus, the invention provides polyketides having the structure:

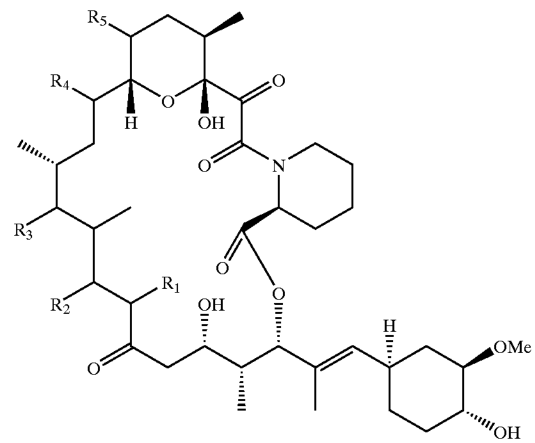

wherein, $R_1$ is hydrogen, methyl, ethyl, or allyl; $R_2$ is hydrogen or hydroxyl, provided that when $R_2$ is hydrogen, there is a double bond between C-20 and C-19; $R_3$ is hydrogen or hydroxyl; $R_4$ is methoxyl, hydrogen, methyl, or ethyl; and $R_5$ is methoxyl, hydrogen, methyl, or ethyl; but not including FK-506, FK-520, 18-hydroxy-FK-520, and 18-hydroxy-FK-506. The invention provides these compounds in purified form and in pharmaceutical compositions.

In another embodiment, the invention provides a method for treating a medical condition by administering a pharmaceutically efficacious dose of a compound of the invention. The compounds of the invention may be administered to achieve immunosuppresion or to stimulate nerve growth and regeneration.

These and other embodiments and aspects of the invention will be more fully understood after consideration of the attached Drawings and their brief description below, together with the detailed description, examples, and claims that follow.

Immediately under the third line are numbered segments showing where the loading module (L) and ten different extender modules (numbered 1–10) are encoded on the various genes shown. At the bottom of the 17 Figure, the DNA inserts of various cosmids of the invention (i.e., 34–124 is cosmid pKOS034-124) are shown in alignment with the FK-520 biosynthetic gene cluster.

Figure 2:
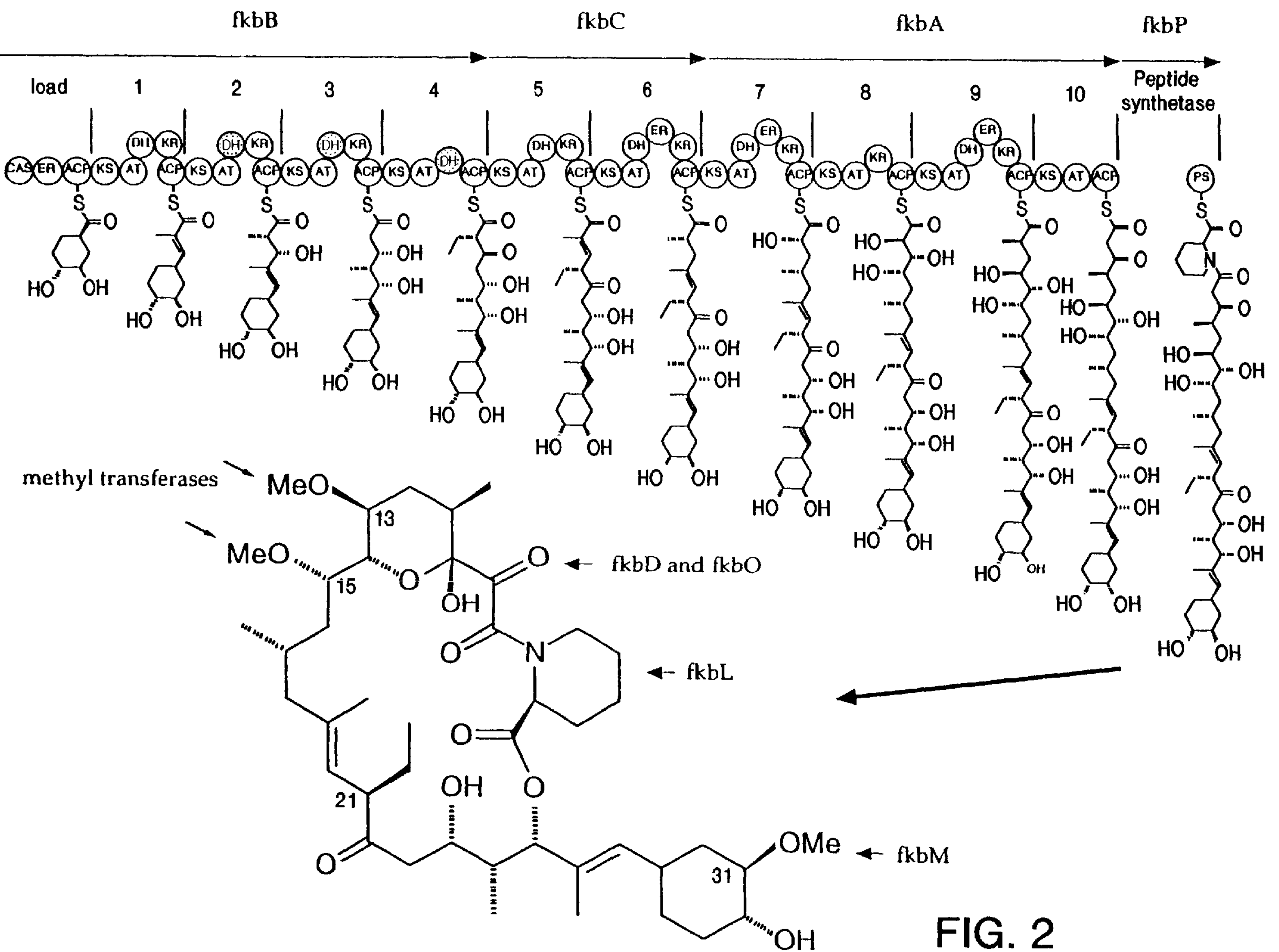

FIG. 2 shows the loading module (load), the ten extender modules, and the peptide synthetase domain of the FK-520 PKS, together with, on the top line, the genes that encode the various domains and modules. Also shown are the various intermediates in FK-520 biosynthesis, as well as the structure of FK-520, with carbons 13, 15, 21, and 31 numbered. The various domains of each module and subdomains of the loading module are also shown. The darkened circles showing the DH domains in modules 2,3, and 4 indicate that the dehydratase domain is not functional as a dehydratase; this domain may affect the stereochemistry at the corresponding position in the polyketide. The substituents on the FK-520 structure that result from the action of non-PKS enzymes are also indicated by arrows, together with the types of enzymes or the genes that code for the enzymes that mediate the action. Although the methyltransferase is shown acting at the C-13 and C-15 hydroxyl groups after release of the polyketide from the PKS, the methyltransferase may act on the 2-hydroxymalonyl substrate prior to or contemporaneously with its incorporation during polyketide synthesis. The inactive DH domain in module 8 is not shown.

Figure 3:
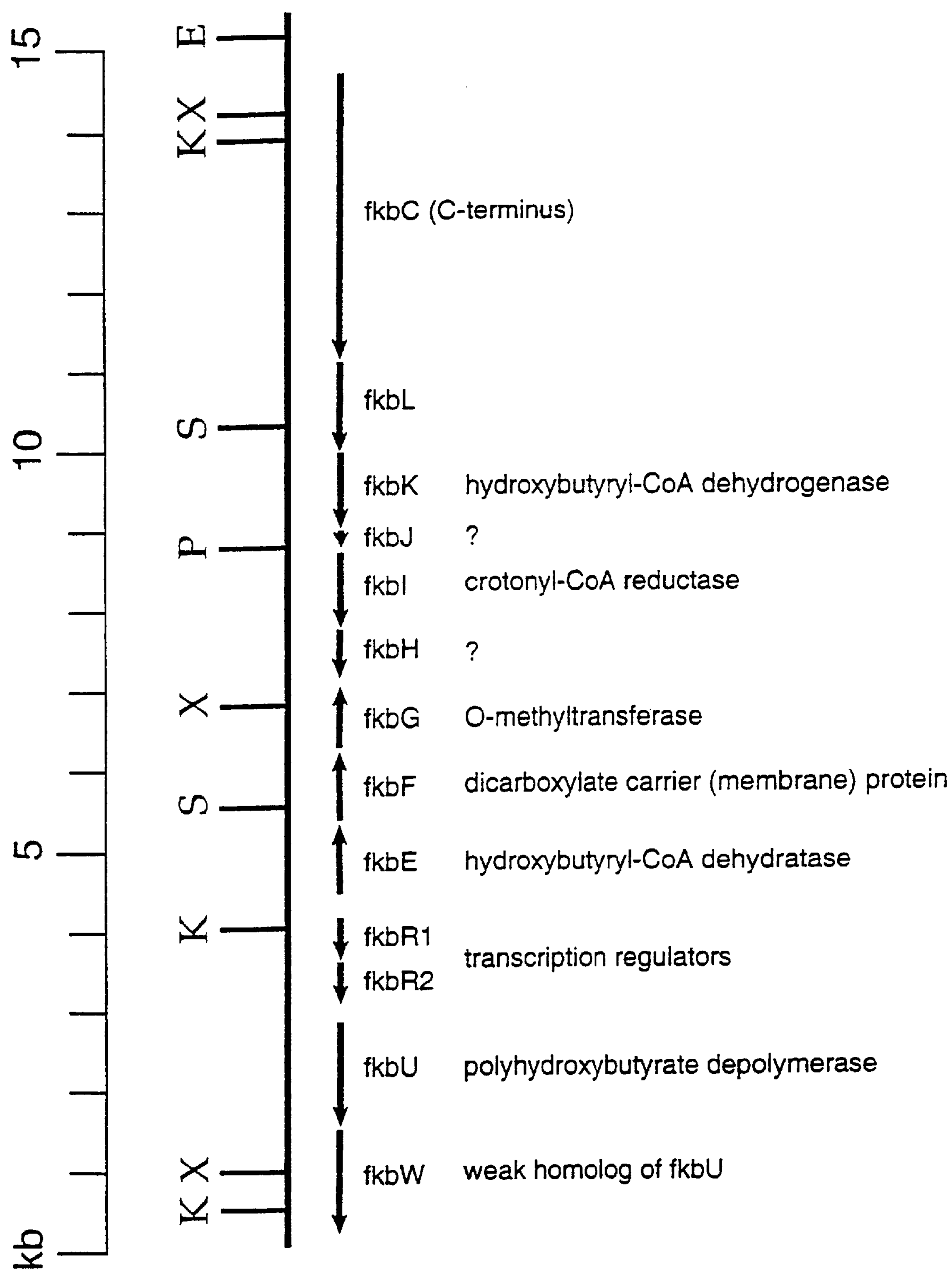

FIG. 3 shows a close-up view of the left end of the FK-520 gene cluster, which contains at least ten additional genes. The ethyl side chain on carbon 21 of FK-520 (FIG. 2) is derived from an ethylmalonyl CoA extender unit that is incorporated by an ethylmalonyl specific AT domain in extender module 4 of the PKS. At least four of the genes in this region code for enzymes involved in ethylmalonyl biosynthesis. The polyhydroxybutyrate depolymerase is involved in maintaining hydroxybutyryl-CoA pools during FK-520 production. Polyhydroxybutyrate accumulates during vegetative growth and disappears during stationary phase in other Streptomyces (Ranade and Vining, 1993*, Can. J. Microbiol.* 39:377). Open reading frames with unknown function are indicated with a question mark.

Figure 4:
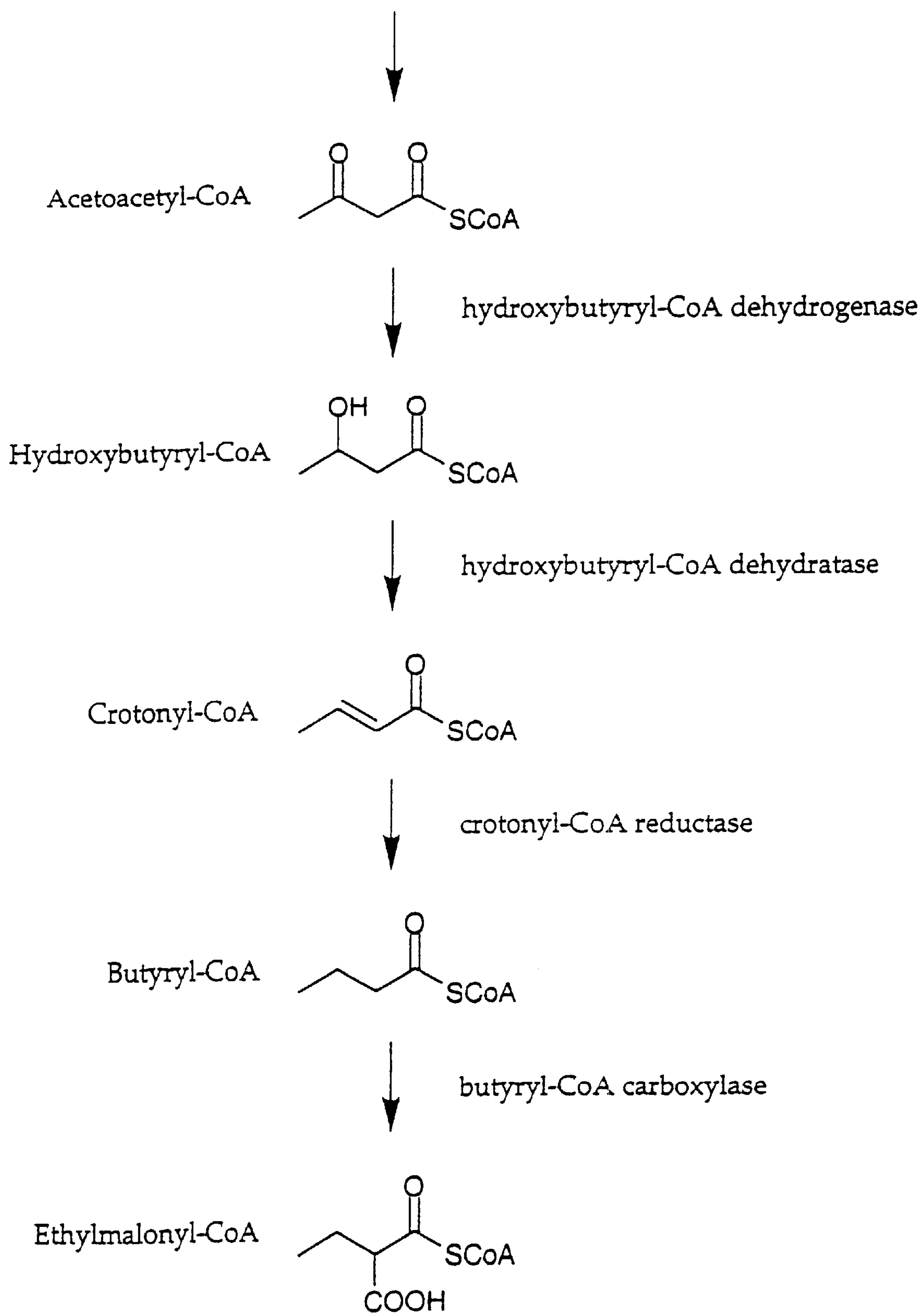

FIG. 4 shows a biosynthetic pathway for the biosynthesis of ethylmalonyl CoA from acetoacetyl CoA consistent with the function assigned to four of the genes in the FK-520 gene cluster shown in FIG. 3.

Figure 5:
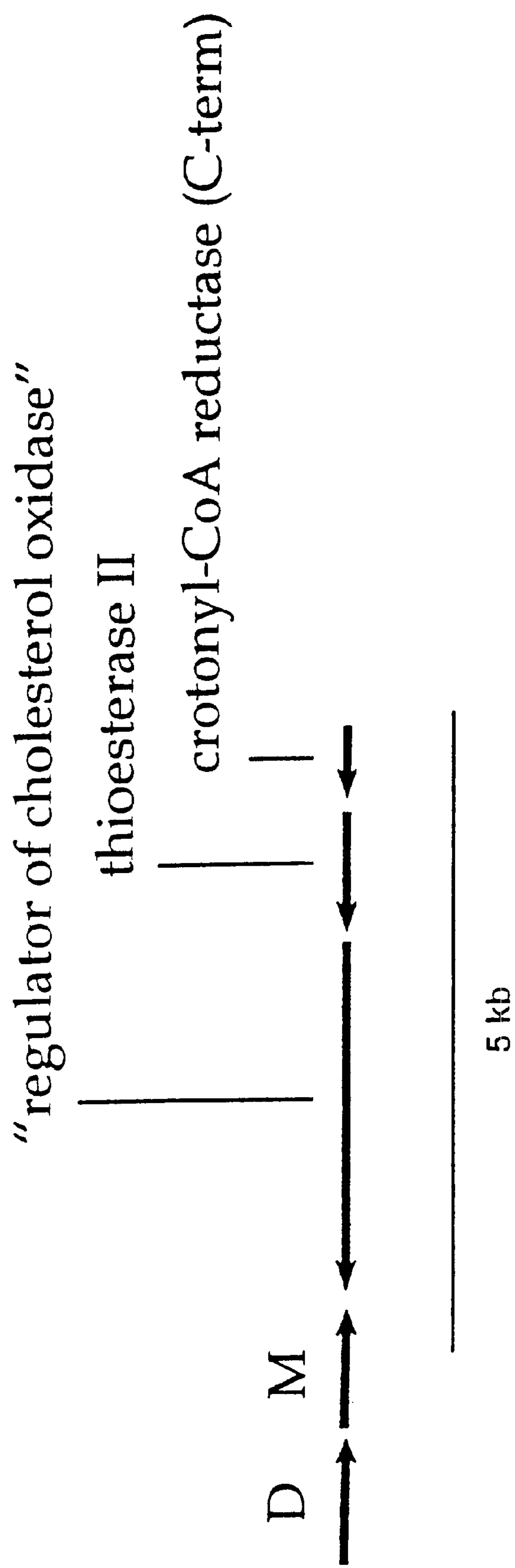

FIG. 5 shows a close-up view of the right-end of the FK-520 PKS gene cluster (and of the sequences on cosmid pKOS065-C31). The genes shown include fkbD,fkbM (a methyl transferase that methylates the hydroxyl group on C-31 of FK-520), fkbN (a homolog of a gene described as a regulator of cholesterol oxidase and that is believed to be a transcriptional activator),fkbQ (a type II thioesterase, which can increase polyketide production levels), and fkbS (a crotonyl-CoA reductase involved in the biosynthesis of ethylmalonyl CoA).

Figure 6:
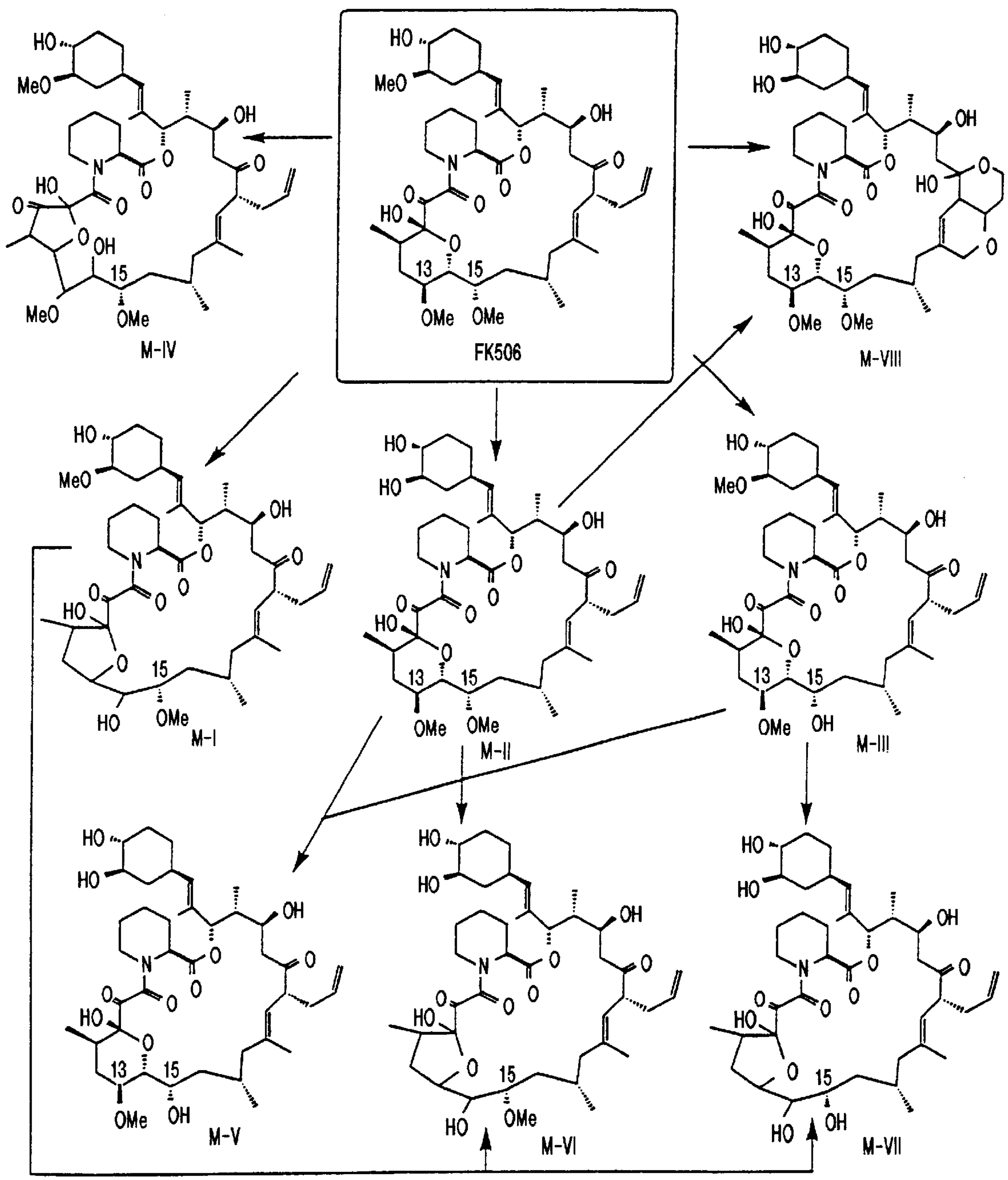

FIG. 6 shows the proposed degradative pathway for tacrolimus (FK-506) metabolism.

FIG. 7A through 7E show a schematic process for the construction of recombinant PKS genes of the invention that encode PKS enzymes that produce 13-desmethoxy FK-506 and FK-520 polyketides of the invention, as described in Example 4, below.

Figure 8A:
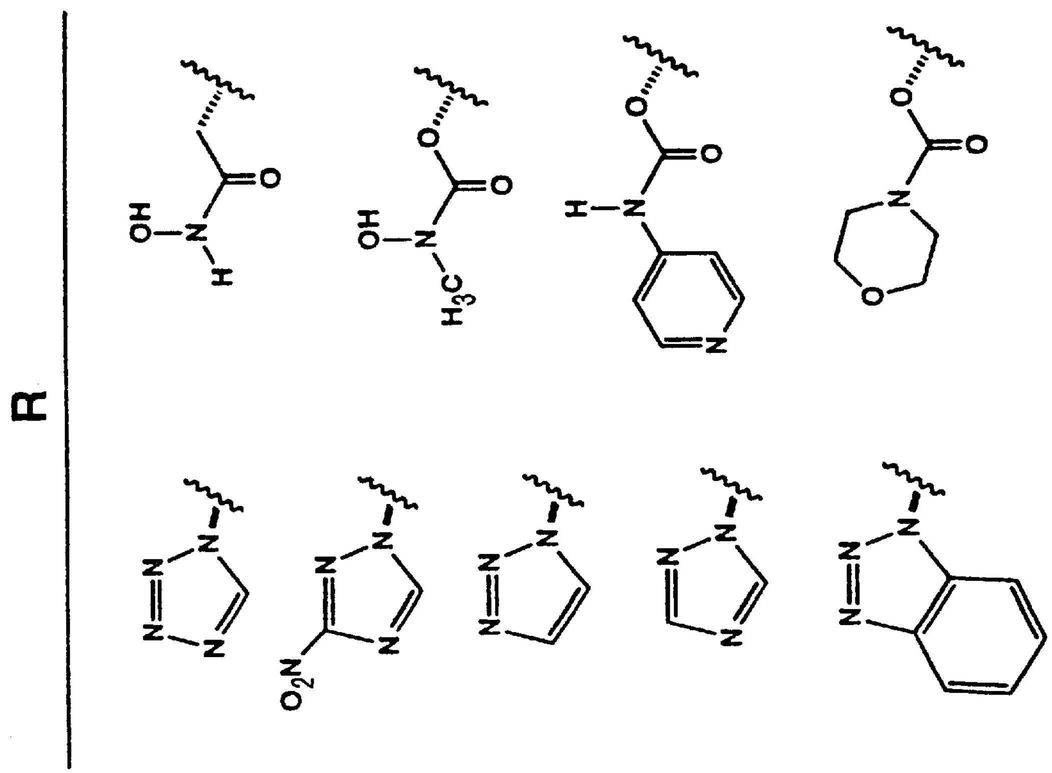

FIG. 8A shows certain compounds of the invention preferred for dermal application. FIG. 8B shows a synthetic route for making those compounds.

DETAILED DESCRIPTION OF THE INVENTION

Given the valuable pharmaceutical properties of polyketides, there is a need for methods and reagents for producing large quantities of polyketides, as well as for producing related compounds not found in nature. The present invention provides such methods and reagents, with particular application to methods and reagents for producing the polyketides known as FK-520, also known as ascomycin or L-683,590 (see Holt et al., 1993*, JACS* 115:9925), and FK-506, also known as tacrolimus. Tacrolimus is a macrolide immunosuppressant used to prevent or treat rejection of transplanted heart, kidney, liver, lung, pancreas, and small bowel allografts. The drug is also useful for the prevention and treatment of graft-versus-host disease in patients receiving bone marrow transplants, and for the treatment of severe, refractory uveitis. There have been additional reports of the unapproved use of tacrolimus for other conditions, including alopecia universalis. autoimmune chronic active hepatitis, inflammatory bowel disease. multiple sclerosis. primary biliary cirrhosis, and scleroderma. The invention provides methods and reagents for making novel polyketides related in structure to FK-520 and FK-506, and structurally related polyketides such as rapamycin.

The FK-506 and rapamycin polyketides are potent immunosuppressants, with chemical structures shown below.

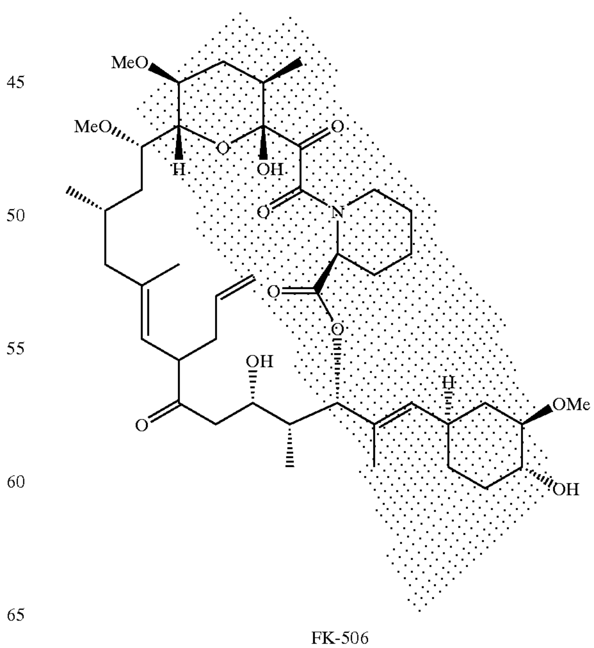

FK-506

-continued

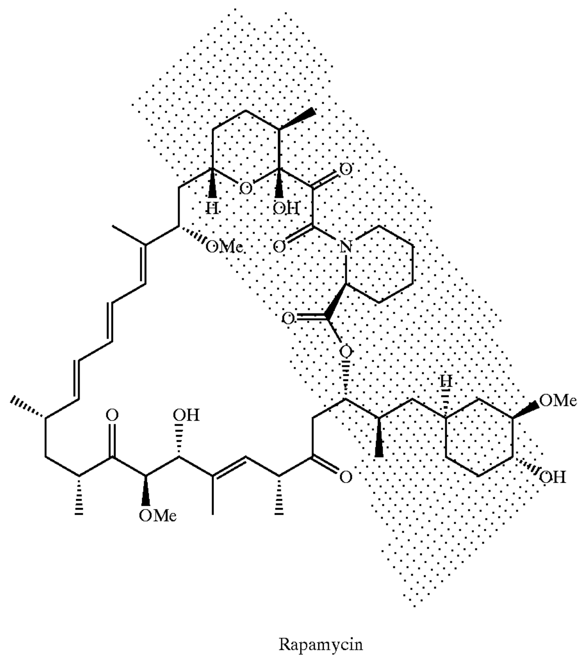

Rapamycin

FK-520 differs from FK-506 in that it lacks the allyl group at C-21 of FK-506, having instead an ethyl group at that position, and has similar activity to FK-506, albeit reduced immunosuppressive activity.

These compounds act through initial formation of an intermediate complex with protein "immunophilins" known as FKBPs (FK-506 binding proteins), including FKBP-12. Immunophilins are a class of cytosolic proteins that form complexes with molecules such as FK-506, FK-520, and rapamycin that in turn serve as ligands for other cellular targets involved in signal transduction. Binding of FK-506, FK-520, and rapamycin to FKBP occurs through the structurally similar segments of the polyketide molecules, known as the "FKBP-binding domain" (as generally but not precisely indicated by the stippled regions in the structures above). The FK-506-FKBP complex then binds calcineurin, while the rapamycin-FKBP complex binds to a protein known as RAFT-1. Binding of the FKBP-polyketide complex to these second proteins occurs through the dissimilar regions of the drugs known as the "effector" domains.

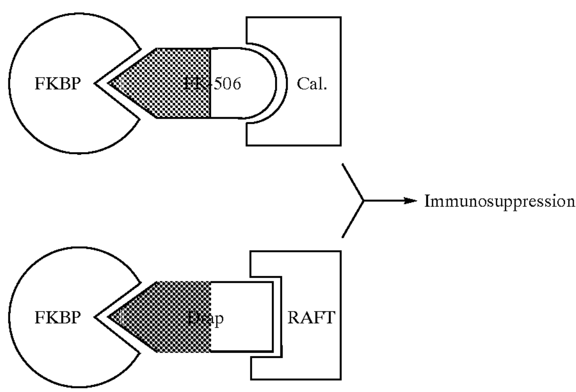

The three component FKBP-polyketide-effector complex is required for signal transduction and subsequent immunosuppressive activity of FK-506, FK-520, and rapamycin. Modifications in the effector domains of FK-506, FK-520, and rapamycin that destroy binding to the effector proteins (calcineurin or RAFT) lead to loss of immunosuppressive activity, even though FKBP binding is unaffected. Further, such analogs antagonize the immunosuppressive effects of the parent polyketides, because they compete for FKBP. Such non-immunosuppressive analogs also show reduced toxicity (see Dumont et al., 1992*, Journal of Experimental Medicine* 176, 751–760), indicating that much of the toxicity of these drugs is not linked to FKBP binding.

In addition to immunosuppressive activity, FK-520, FK-506, and rapamycin have neurotrophic activity. In the. central nervous system and in peripheral nerves, immunophilins are referred to as "neuroimmunophilins". The neuroimmunophilin FKBP is markedly enriched in the central nervous system and in peripheral nerves. Molecules that bind to the neuroimmunophilin FKBP, such as FK-506 and FK-520, have the remarkable effect of stimulating nerve growth. In vitro, they act as neurotrophins, i.e., they promote neurite outgrowth in NGF-treated PC12 cells and in sensory neuronal cultures, and in intact animals, they promote regrowth of damaged facial and sciatic nerves, and repair lesioned serotonin and dopamine neurons in the brain. See Gold et al., Jun. 1999*, J. Pharm. Exp. Ther*. 289(3): 1202–1210; Lyons et al., 1994*, Proc. National Academy of Science* 91: 3191–3195; Gold et al., 1995*, Journal of Neuroscience* 15: 7509–7516; and Steiner et al., 1997*, Proc. National Academy ofScience* 94: 2019–2024. Further, the restored central and peripheral neurons appear to be functional.

Compared to protein neurotrophic molecules (BNDF, NGF, etc.), the small-molecule neurotrophins such as FK-506, FK-520, and rapamycin have different, and often advantageous, properties. First, whereas protein neurotrophins are difficult to deliver to their intended site of action and may require intra-cranial injection, the small-molecule neurotrophins display excellent bioavailability; they are active when administered subcutaneously and orally. Second, whereas protein neurotrophins show quite specific effects, the small-molecule neurotrophins show rather broad effects. Finally, whereas protein neurotrophins often show effects on normal sensory nerves, the small-molecule neurotrophins do not induce aberrant sprouting of normal neuronal processes and seem to affect damaged nerves specifically. Neuroimmunophilin ligands have potential therapeutic utility in a variety of disorders involving nerve degeneration (e.g. multiple sclerosis, Parkinson's disease, Alzheimer's disease, stroke, traumatic spinal cord and brain injury, peripheral neuropathies).

Recent studies have shown that the immunosuppressive and neurite outgrowth activity of FK-506, FK-520, and rapamycin can be separated; the neuroregenerative activity in the absence of immunosuppressive activity is retained by agents which bind to FKBP but not to the effector proteins calcineurin or RAFT. See Steiner et al., 1997*, Nature Medicine* 3: 421–428.

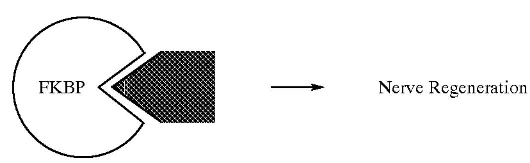

Available structure-activity data show that the important features for neurotrophic activity of rapamycin, FK-520, and FK-506 lie within the common, contiguous segments of the macrolide ring that bind to FKBP. This portion of the molecule is termed the "FKBP binding domain" (see VanDuyne et al., 1993*, Journal of Molecular Biology* 229: 105–124.). Nevertheless, the effector domains of the parent macrolides contribute to conformational rigidity of the binding domain and thus indirectly contribute to FKBP binding.

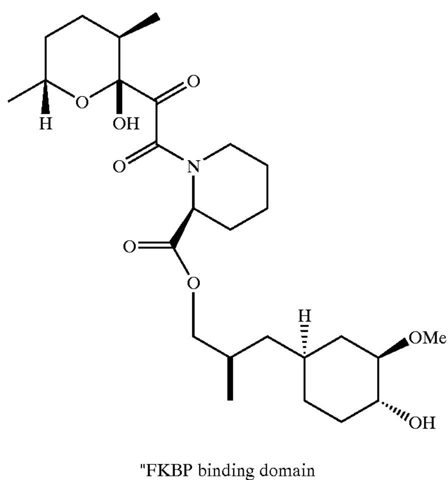

"FKBP binding domain

There are a number of other reported analogs of FK-506, FK-520, and rapamycin that bind to FKBP but not the effector protein calcineurin or RAFT. These analogs show effects on nerve regeneration without immunosuppressive effects.

Naturally occurring FK-520 and FK-506 analogs include the antascomycins, which are FK-506-like macrolides that lack the functional groups of FK-506 that bind to calcineurin (see Fehr et al., 1996*, The Journal of Antibiotics* 49: 230–233). These molecules bind FKBP as effectively as does FK-506; they antagonize the effects of both FK-506 and rapamycin, yet lack immunosuppressive activity.

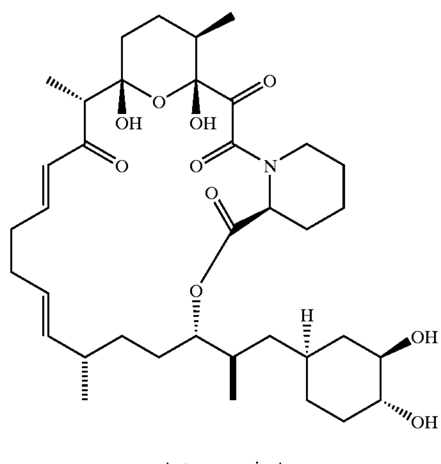

Antascomycin A

Other analogs can be produced by chemically modifying FK-506, FK-520, or rapamycin. One approach to obtaining neuroimmunophilin ligands is to destroy the effector binding region of FK-506, FK-520, or rapamycin by chemical modification. While the chemical modifications permitted on the parent compounds are quite limited, some useful chemically modified analogs exist. The FK-520 analog L-685,818 ($ED_{50}$=0.7 nM for FKBP binding; see Dumont et al., 1992), and the rapamycin analog WAY-124,466 ($IC_{50}$=12.5 nM; see Ocain et al., 1993*, Biochemistry Biophysical Research Communications* 192: 1340–134693) are about as effective as FK-506, FK-520, and rapamycin at promoting neurite outgrowth in sensory neurons (see Steiner et al., 1997).

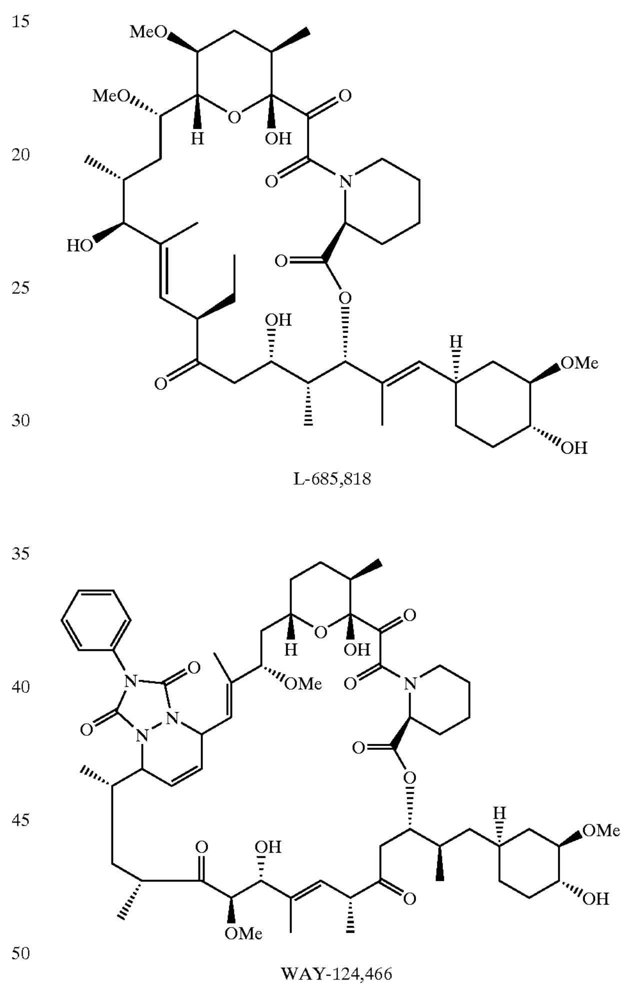

One of the few positions of rapamycin that is readily amenable to chemical modification is the allylic 16-methoxy group; this reactive group is readily exchanged by acid-catalyzed nucleophilic substitution. Replacement of the 16-methoxy group of rapamycin with a variety of bulky groups has produced analogs showing selective loss of immunosuppressive activity while retaining FKBP-binding (see Luengo et al., 1995*, Chemistry & Biology* 2: 471–481). One of the best compounds, 1, below, shows complete loss of activity in the splenocyte proliferation assay with only a 10-fold reduction in binding to FKBP.

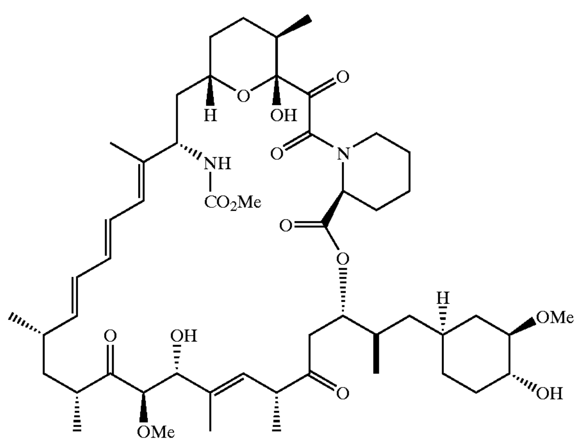

There are also synthetic analogs of FKBP binding domains. These compounds reflect an approach to obtaining neuroimmunophilin ligands based on "rationally designed" molecules that retain the FKBP-binding region in an appropriate conformation for binding to FKBP, but do not possess the effector binding regions. In one example, the ends of the FKBP binding domain were tethered by hydrocarbon chains (see Holt et al., 1993, *Journal of the American Chemical Society* 115: 9925–9938); the best analog, 2, below, binds to FKBP about as well as FK-506. In a similar approach, the ends of the FKBP binding domain were tethered by a tripeptide to give analog 3, below, which binds to FKBP about 20-fold poorer than FK-506. These compounds are anticipated to have neuroimmunophilin binding activity.

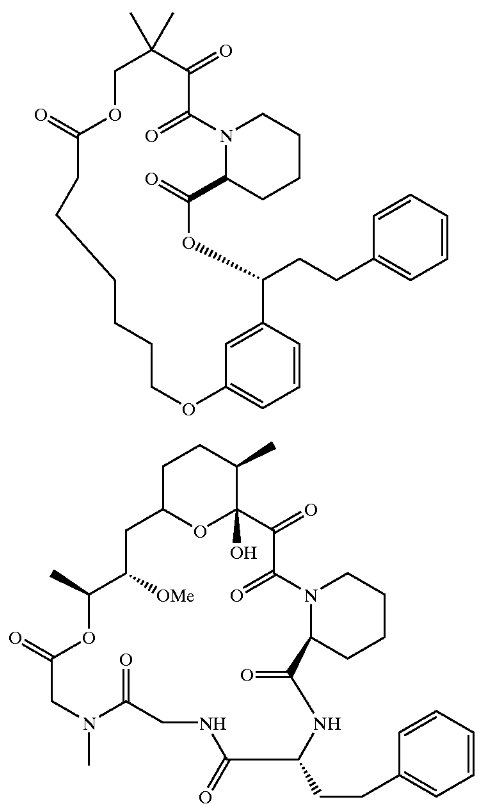

In a primate MPTP model of Parkinson's disease, administration of FKBP ligand GPI-1046 caused brain cells to regenerate and behavioral measures to improve. MPTP is a neurotoxin, which, when administered to animals, selectively damages nigral-striatal dopamine neurons in the brain, mimicking the damage caused by Parkinson's disease. Whereas, before treatment, animals were unable to use affected limbs, the FKBP ligand restored the ability of animals to feed themselves and gave improvements in measures of locomotor activity, neurological outcome, and fine motor control. There were also corresponding increases in regrowth of damaged nerve terminals. These results demonstrate the utility of FKBP ligands for treatment of diseases of the CNS.

From the above description, two general approaches towards the design of non-immunosuppressant, neuroimmunophilin ligands can be seen. The first involves the construction of constrained cyclic analogs of FK-506 in which the FKBP binding domain is fixed in a conformation optimal for binding to FKBP. The advantages of this approach are that the conformation of the analogs can be accurately modeled and predicted by computational methods, and the analogs closely resemble parent molecules that have proven pharmacological properties. A disadvantage is that the difficult chemistry limits the numbers and types of compounds that can be prepared. The second approach involves the trial and error construction of acyclic analogs of the FKBP binding domain by conventional medicinal chemistry. The advantages to this approach are that the chemistry is suitable for production of the numerous compounds needed for such interactive chemistry-bioassay approaches. The disadvantages are that the molecular types of compounds that have emerged have no known history of appropriate pharmacological properties, have rather labile ester functional groups, and are too conformationally mobile to allow accurate prediction of conformational properties.

The present invention provides useful methods and reagents related to the first approach, but with significant advantages. The invention provides recombinant PKS genes that produce a wide variety of polyketides that cannot otherwise be readily synthesized by chemical methodology alone. Moreover, the present invention provides polyketides that have either or both of the desired immunosuppressive and neurotrophic activities, some of which are produced only by fermentation and others of which are produced by fermentation and chemical modification. Thus, in one aspect, the invention provides compounds that optimally bind to FKBP but do not bind to the effector proteins. The methods and reagents of the invention can be used to prepare numerous constrained cyclic analogs of FK-520 in which the FKBP binding domain is fixed in a conformation optimal for binding to FKBP. Such compounds will show neuroimmunophilin binding (neurotrophic) but not immunosuppressive effects. The invention also allows direct manipulation of FK-520 and related chemical structures via genetic engineering of the enzymes involved in the biosynthesis of FK-520 (as well as related compounds, such as FK-506 and rapamycin); similar chemical modifications are simply not possible because of the complexity of the structures. The invention can also be used to introduce "chemical handles" into normally inert positions that permit subsequent chemical modifications.

Several general approaches to achieve the development of novel neuroimmunophilin ligands are facilitated by the methods and reagents of the present invention. One approach is to make "point mutations" of the functional groups of the parent FK-520 structure that bind to the effector molecules to eliminate their binding potential. These types of structural modifications are difficult to perform by chemical modification, but can be readily accomplished with the methods and reagents of the invention.

A second, more extensive approach facilitated by the present invention is to utilize molecular modeling to predict optimal structures ab initio that bind to FKBP but not effector molecules. Using the available X-ray crystal structure of FK-520 (or FK-506) bound to FKBP, molecular modeling can be used to predict polyketides that should optimally bind to FKBP but not calcineurin. Various macrolide structures can be generated by linking the ends of the FKBP-binding domain with "all possible" polyketide chains of variable length and substitution patterns that can be prepared by genetic manipulation of the FK-520 or FK-506 PKS gene cluster in accordance with the methods of the invention. The ground state conformations of the virtual library can be determined, and compounds that possess binding domains most likely to bind well to FKBP can be prepared and tested.

Once a compound is identified in accordance with the above approaches, the invention can be used to generate a focused library of analogs around the lead candidate, to "fine tune" the compound for optimal properties. Finally, the genetic engineering methods of the invention can be directed towards producing "chemical handles" that enable medicinal chemists to modify positions of the molecule previously inert to chemical modification. This opens the path to previously prohibited chemical optimization of lead compounds by time-proven approaches.

Moreover, the present invention provides polyketide compounds and the recombinant genes for the PKS enzymes that produce the compounds that have significant advantages over FK-506 and FK-520 and their analogs. The metabolism and pharmacokinetics of tacrolimus has been exstensively studied, and FK-520 is believed to be similar in these respects. Absorption of tacrolimus is rapid, variable, and incomplete from the gastrointestinal tract (Harrison's Principles of Internal Medicine, 14th edition, 1998, McGraw Hill, 14, 20, 21, 64–67). The mean bioavailability of the oral dosage form is 27%, (range 5 to 65%). The volume of distribution (VolD) based on plasma is 5 to 65 L per kg of body weight (L/kg), and is much higher than the VolD based on whole blood concentrations, the difference reflecting the binding of tacrolimus to red blood cells.

Whole blood concentrations may be 12 to 67 times the plasma concentrations. Protein binding is high (75 to 99%), primarily to albumin and alphal-acid glycoprotein. The half-life for distribution is 0.9 hour; elimination is biphasic and variable: terminal-11.3 hr (range, 3.5 to 40.5 hours). The time to peak concentration is 0.5 to 4 hours after oral administration.

Tacrolimus is metabolized primarily by cytochrome P450 3A enzymes in the liver and small intestine. The drug is extensively metabolized with less than 1% excreted unchanged in urine. Because hepatic dysfunction decreases clearance of tacrolimus, doses have to be reduced substantially in primary graft non-function, especially in children. In addition, drugs that induce the cytochrome P450 3A enzymes reduce tacrolimus levels, while drugs that inhibit these P450s increase tacrolimus levels. Tacrolimus bioavailability doubles with co-administration of ketoconazole, a drug that inhibits P450 3A. See, Vincent et al., 1992, In vitro metabolism of FK-506 in rat, rabbit, and human liver microsomes: Identification of a major metabolite and of cytochrome P450 3A as the major enzymes res ponsible for its metabolism, Arch. Biochem. Biophys. 294: 454–460; Iwasaki et al., 1993, Isolation, identification, and biological activities of oxidative metabolites of FK-506, a potent immunosuppressive macrolide lactone, *Drug Metabolism & Disposition* 21: 971–977; Shiraga et al., 1994, Metabolism of FK-506, a potent immunosuppressive agent, by cytochrome P450 3A enzymes in rat, dog, and human liver microsomes, Biochem. Pharmacol. 47: 727–73 5; and Iwasaki et al., 1995, Further metabolism of FK-506 (Tacrolimus); Identification and biological activities of the metabolites oxidized at multiple sites of FK-506*, Drug Metabolism & Disposition* 23: 28–34. The cytochrome P450 3A subfamily of isozymes has been implicated as important in this degradative process.

Structures of the eight isolated metabolites formed by liver microsomes are shown in FIG. 6. Four metabolites of FK-506 involve demethylation of the oxygens on carbons 13, 15, and 31, and hydroxylation of carbon 12. The 13-demethylated (hydroxy) compounds undergo cyclizations of the 13-hydroxy at C-10 to give MI, MVI and MVII, and the 12-hydroxy metabolite at C-10 to give I. Another four metabolites formed by oxidation of the four metabolites mentioned above were isolated by liver microsomes from dexamethasone treated rats. Three of these are metabolites doubly demethylated at the methoxy groups on carbons 15 and 31 (M-V), 13 and 31 (M-VI), and 13 and 15 (M-VII). The fourth, M-VIII, was the metabolite produced after demethylation of the 31-methoxy group, followed by formation of a fused ring system by further oxidation. Among the eight metabolites, M-II has immunosuppressive activity comparable to that of FK-506, whereas the other metabolites exhibit weak or negligible activities. Importantly, the major metabolite of human, dog, and rat liver microsomes is the 13-demethylated and cyclized FK-506 (M-I).

Thus, the major metabolism of FK-506 proceeds via 13-demethylation followed by cyclization to the inactive M-I, this representing about 90% of the metabolic products after a 10 minute incubation with liver microsomes. Analogs of tacrolimus that do not possess a C-13 methoxy group would not be susceptible to the first and most important biotransformation in the destructive metabolism of tacrolimus (i.e. cyclization of 13-hydroxy to C-10). Thus, a 13-desmethoxy analog of FK-506 should have a longer half-life in the body than does FK-506. The C-13 methoxy group is believed not to be required for binding to FKBP or calcineurin. The C-13 methoxy is not present on the identical position of rapamycin, which binds to FKBP with equipotent affinity as tacrolimus. Also, analysis of the 3-dimensional structure of the FKBP-tacrolimus-calcineurin complex shows that the C-13 methoxy has no interaction with FKBP and only a minor interaction with calcineurin. The present invention provides C-13-desmethoxy analogs of FK-506 and FK-520, as well as the recombinant genes that encode the PKS enzymes that catalyze their synthesis and host cells that produce the compounds.

These compounds exhibit, relative to their naturally occurring counterparts, prolonged immunosuppressive action in vivo, thereby allowing a lower dosage and/or reduced frequency of administration. Dosing is more predictable, because the variability in FK-506 dosage is largely due to variation of metabolism rate. FK-506 levels in blood can vary widely depending on interactions with drugs that induce or inhibit cytochrome P450 3A (summarized in USP Drug Information for the Health Care Professional). Of particular importance are the numerous drugs that inhibit or compete for CYP 3A, because they increase FK-506 blood levels and lead to toxicity (Prograf package insert, Fujisawa□US, Rev 4/97, Rec 6/97). Also important are the drugs that induce P450 3A (e.g. Dexamethasone), because they decrease FK-506 blood levels and reduce efficacy. Because the major site of CYP 3A action on FK-506 is removed in the analogs provided by the present invention, those analogs are not as susceptible to drug interactions as the naturally occurring compounds.

Hyperglycemia, nephrotoxicity, and neurotoxicity are the most significant adverse effects resulting from the use of FK-506 and are believed to be similar for FK-520. Because these effects appear to occur primarily by the same mechanism as the immunosuppressive action (i.e. FKBP-calcineurin interaction), the intrinsic toxicity of the desmethoxy analogs may be similar to FK-506. However, toxicity of FK-506 is dose related and correlates with high blood levels of the drug (Prograf package insert, Fujisawa□US, Rev 4/97, Rec 6/97). Because the levels of the compounds provided by the present invention should be more controllable, the incidence of toxicity should be significantly decreased with the 13-desmethoxy analogs. Some reports show that certain FK-506 metabolites are more toxic than FK-506 itself, and this provides an additional reason to expect that a CYP 3A resistant analog can have lower toxicity and a higher therapeutic index.

Thus, the present invention provides novel compounds related in structure to FK-506 and FK-520 but with improved properties. The invention also provides methods for making these compounds by fermentation of recombinant host cells, as well as the recombinant host cells, the recombinant vectors in those host cells, and the recombinant proteins encoded by those vectors. The present invention also provides other valuable materials useful in the construction of these recombinant vectors that have many other important applications as well. In particular, the present invention provides the FK-520 PKS genes, as well as certain genes involved in the biosynthesis of FK-520 in recombinant form.

FK-520 is produced at relatively low levels in the naturally occurring cells, *Streptomyces hygroscopicus* var. *ascomyceticus*, in which it was first identified. Thus, another benefit provided by the recombinant FK-520 PKS and related genes of the present invention is the ability to produce FK-520 in greater quantities in the recombinant host cells provided by the invention. The invention also provides methods for making novel FK-520 analogs, in addition to the desmethoxy analogs described above, and derivatives in recombinant host cells of any origin.

The biosynthesis of FK-520 involves the action of several enzymes. The FK-520 PKS enzyme, which is composed of the fkbA, fkbB, fkbC, and fkbP gene products, synthesizes the core structure of the molecule. There is also a hydroxylation at C-9 mediated by the P450 hydroxylase that is thejkbD gene product and that is oxidized by the fkbO gene product to result in the formation of a keto group at C-9. There is also a methylation at C-31 that is mediated by an O-methyltransferase that is the jkbM gene product. There are also methylations at the C-13 and C-15 positions by a methyltransferase believed to be encoded by the fkbG gene; this methyltransferase may act on the hydroxymalonyl CoA substrates prior to binding of the substrate to the AT domains of the PKS during polyketide synthesis. The present invention provides the genes encoding these enzymes in recombinant form. The invention also provides the genes encoding the enzymes involved in ethylmalonyl CoA and 2-hydroxymalonyl CoA biosynthesis in recombinant form. Moreover, the invention provides *Streptomyces hygroscopicus* var. *ascomyceticus* recombinant host cells lacking one or more of these genes that are useful in the production of useful compounds.

The cells are useful in production in a variety of ways. First, certain cells make a useful FK-520-related compound merely as a result of inactivation of one or more of the FK-520 biosynthesis genes. Thus, by inactivating the C-31 O-methyltransferase gene in *Streptomyces hygroscopicus* var. *ascomyceticus*, one creates a host cell that makes a desmethyl (at C-31) derivative of FK-520. Second, other cells of the invention are unable to make FK-520 or FK-520 related compounds due to an inactivation of one or more of the PKS genes. These cells are useful in the production of other polyketides produced by PKS enzymes that are encoded on recombinant expression vectors and introduced into the host cell.

Moreover, if only one PKS gene is inactivated, the ability to produce FK-520 or an FK-520 derivative compound is restored by introduction of a recombinant expression vector that contains the functional gene in a modified or unmodified form. The introduced gene produces a gene product that, together with the other endogenous and functional gene products, produces the desired compound. This methodology enables one to produce FK-520 derivative compounds without requiring that all of the genes for the PKS enzyme be present on one or more expression vectors. Additional applications and benefits of such cells and methodology will be readily apparent to those of skill in the art after consideration of how the recombinant genes were isolated and employed in the construction of the compounds of the invention.

The FK-520 biosynthetic genes were isolated by the following procedure. Genomic DNA was isolated from *Streptomyces hygroscopicus* var. *ascomyceticus* (ATCC 14891) using the lysozyme/proteinase K protocol described in Genetic Manipulation of Streptomyces —A Laboratory Manual (Hopwood et al., 1986). The average size of the DNA was estimated to be between 80–120 kb by electrophoresis on 0.3% agarose gels. A library was constructed in the SuperCos™ vector according to the manufacturer's instructions and with the reagents provided in the commercially available kit (Stratagene). Briefly, 100 $\mu$g of genomic DNA was partially digested with 4 units of Sau3A I for 20 min. in a reaction volume of 1 mL, and the fragments were dephosphorylated and ligated to SuperCos vector arms. The ligated DNA was packaged and used to infect log-stage XLI -BlueMR cells. A library of about 10,000 independent cosmid clones was obtained.

Based on recently published sequence from the FK-506 cluster (Motanedi and Shafiee, 1998, *Eur. J. Biochem.* 256: 528), a probe for the fkbO gene was isolated from ATCC 14891 using PCR with degenerate primers. With this probe, a cosmid designated pKOS034-124 was isolated from the library. With probes made from the ends of cosmid pKOS034-124, an additional cosmid designated pKOS034-120 was isolated. These cosmids (pKOS034-124 and pKOS034-120) were shown to contain DNA inserts that overlap with one another. Initial sequence data from these two cosmids generated sequences similar to sequences from the FK-506 and rapamycin clusters, indicating that the inserts were from the FK-520 PKS gene cluster. Two EcoRI fragments were subcloned from cosmids pKOS034-124 and pKOS034-120. These subclones were used to prepare shotgun libraries by partial digestion with Sau3AI, gel purification of fragments between 1.5 kb and 3 kb in size, and ligation into the pLitmus28 vector (New England Biolabs). These libraries were sequenced using dye terminators on a Beckmann CEQ2000 capillary electrophoresis sequencer, according to the manufacturer's protocols.

To obtain cosmids containing sequence on the left and right sides of the sequenced region described above, a new cosmid library of ATCC 14891 DNA was prepared essentially as described above. This new library was screened with a new fkbM probe isolated using DNA from ATCC 14891. A probe representing the fkbP gene at the end of cosmid pKOS034-124 was also used. Several additional cosmids to the right of the previously sequenced region were identified. Cosmids pKOS065-C31 and pKOS065-C3 were identified and then mapped with restriction enzymes. Initial sequences from these cosmids were consistent with the expected organization of the cluster in this region. More extensive sequencing showed that both cosmids contained in addition to the desired sequences, other sequences not contiguous to the desired sequences on the host cell chromosomal DNA. Probing of additional cosmid libraries identified two additional cosmids, pKOS065-M27 and pKOS065-M21, that contained the desired sequences in a contiguous segment of chromosomal DNA. Cosmids pKOS034-124, pKOS034-120, pKOS065-M27, and pKOS065-M21 have been deposited with the American Type Culture Collection, Manassas, VA, USA. Cosmids pKOs065-M27, pKOs034-124, pKOs034-120 and pKOs065-m21 were deposited on Sep. 20, 1999, and have patent deposit designations pta-726, PTA-729, PTA-728 and PTA-727, respectively. The complete nucleotide sequence of the coding sequences of the genes that encode the proteins of the FK-520 PKS are shown below but can also be determined from the cosmids of the invention deposited with the ATCC using standard methodology.

Figure 1:
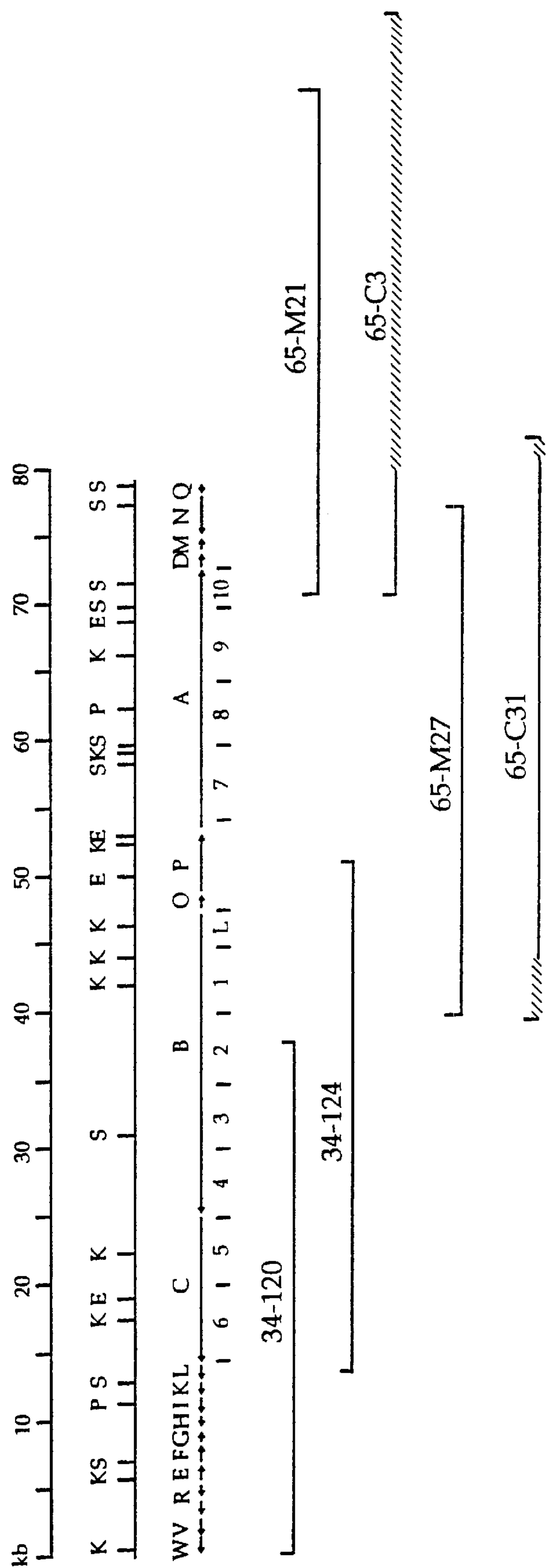
FIG. 1 shows a diagram of the FK-520 biosynthetic gene cluster. The top line provides a scale in kilobase pairs (kb). The second line shows a restriction map with selected restriction enzyme recognition sequences indicated. K is KpnI; X is XhoI, S is SacI; P is PstI; and E is EcoRI. The third line indicates the position of FK-520 PKS and related genes. Genes are abbreviated with a one letter designation, i.e., C is fkbC.

Referring to FIGS. 1 and 3, the FK-520 PKS gene cluster is composed of four open reading frames designated fkbB, fkbC, fkbA, and fkbP. The fkbB open reading frame encodes the loading module and the first four extender modules of the PKS. The fkbC open reading frame encodes extender modules five and six of the PKS. The kbA open reading frame encodes extender modules seven, eight, nine, and ten of the PKS. The fkbP open reading frame encodes the NRPS of the PKS. Each of these genes can be isolated from the cosmids of the invention described above. The DNA sequences of these genes arc provided below preceded by the following table identifying the start and stop codons of the open reading frames of each gene and the modules and domains contained therein.

| Nucleotides | Gene or Domain |
|---|---|
| complement (412–1836) | *fkbW* |
| complement (2020–3579) | *fkbV* |
| complement (3969–4496) | *fkbR2* |
| complement (4595–5488) | *fkbR1* |
| 5601–6818 | *fkbE* |
| 6808–8052 | *fkbF* |
| 8156–8824 | *fkbG* |
| complement (9122–9883) | *fkbH* |
| complement (9894–10994) | *fkbI* |
| complement (10987–11247) | *fkbJ* |
| complement (11244–12092) | *fkbK* |
| complement (12113–13150) | *fkbL* |
| complement (13212–23988) | *fkbC* |
| complement (23992–46573) | *fkbB* |
| 46754–47788 | *fkbO* |
| 47785–52272 | *fkbP* |
| 52275–71465 | *fkbA* (SEQ ID NO.72) |
| 71462–72628 | *fkbD* |
| 72625–73407 | *fkbM* |
| complement (73460–76202) | *fkbN* |
| complement (76336–77080) | *fkbQ* |
| complement (77076–77535) | *fkbS* |
| complement (44974–46573) | CoA ligase of loading domain |
| complement (43777–44629) | ER of loading domain |
| complement (43144–43660) | ACP of loading domain |
| complement (41842–43093) | KS of extender module 1 (KS1) |
| complement (40609–41842) | AT1 |
| complement (39442–40609) | DH1 |
| complement (38677–39307) | KR1 |
| complement (38371–38581) | ACP1 |
| complement (37145–38296) | KS2 |
| complement (35749–37144) | AT2 |
| complement (34606–35749) | DH2 (inactive) |
| complement (33823–34480) | KR2 |
| complement (33505–33715) | ACP2 |
| complement (32185–33439) | KS3 |
| complement (31018–32185) | AT3 |
| complement (29869–31018) | DH3 (inactive) |
| complement (29092–29740) | KR3 |
| complement (28750–28960) | ACP3 |
| complement (27430–28684) | KS4 |
| complement (26146–27430) | AT4 |
| complement (24997–26146) | DH4 (inactive) |
| complement (24163–24373) | ACP4 |
| complement (22653–23892) | KS5 |
| complement (21420–22653) | AT5 |
| complement (20241–21420) | DH5 |
| complement (19464–20097) | KR5 |
| complement (19116–19326) | ACP5 |
| complement (17820–19053) | KS6 |
| complement (16587–17820) | AT6 |
| complement (15438–16587) | DH6 |

-continued

```
complement (14517—15294)        ER6
complement (13761—14394)        KR6
complement (13452—13662)        ACP6
52362—53576                     KS7
53577—54716                     AT7
54717—55871                     DH7
56019—56819                     ER7
56943—57575                     KR7
57711—57920                     ACP7
57990—59243                     KS8
59244—60398                     AT8
60399—61412                     DH8 (inactive)
61548—62180                     KR8
62328—62537                     ACP8
62598—63854                     KS9
63855—65084                     AT9
65085—66254                     DH9
66399—67175                     ER9
67299—67931                     KR9
68094—68303                     ACP9
68397—69653                     KS10
69654—70985                     AT10
71064—71273                     ACP10
```

```
   1 GATCTCAGGC ATGAAGTCCT CCAGGCGAGG CGCCGAGGTG GTGAACACCT CGCCGCTGCT
  61 TGTACGGACC ACTTCAGTCA GCGGCGATTG CGGAACCAAG TCATCCGGAA TAAAGGGCGG
 121 TTACAAGATC CTCACATTGC GCGACCGCCA GCATACGCTG AGTTGCCTCA GAGGCAAACC
 181 GAAAGGGCGC GGGCGGTCCG CACCAGGGCG GAGTACGCGA CGAGAGTGGC GCACCCGCGC
 241 ACCGTCACCT CTCTCCCCCG CCGGCGGGAT GCCCGGCGTG ACACGGTTGG GCTCTCCTCG
 301 ACGCTGAACA CCCGCGCGGT GTGGCGTCGG GGACACCGCC TGGCATCGGC CGGGTGACGG
 361 TACGGGGAGG GCGTACGGCG GCCGTGGCTC GTGCTCACGG CCGCCGGGCG GTCATCCGTC
 421 GAGACGGCAC TCGGCGAGCA GGGACGCCTG GTCGGCACCT GCGGGCCGGA CGACCGTGTG
 481 GTTCGCGGGC GGGCGGTGGC CGGTGGTGAG CCAGCTCTCC AGGGCGGTGA AGGCTGAGCG
 541 GTGACACGGC AGCAAAGGCC GGAGTCGGTC GGGGAAGGTG TCGACGAGGG CGTCGGTGTG
 601 CGTGCCGTCC TCGATGCGGT AGTAGCGGTA CCGGCCGCCA GGCCGCTGCC GGACATACGC
 661 GCGTACACGT CGGAGCCCGG GCGGCAGGCA GCAGCACGTC GAGAGTGCCT GGATGGTGAT
 721 CAGCGGCTTG CCGATACGAC CGGTCAACGC GATGCGTTCC ACGGCCGCGT GGACGCCGGA
 781 GGAGCGGGTG GCGTAGTCGT AGTCGGCATC GCAGCCCGGG ACCGTCCCCG GGGCGCAATA
 841 CGGTGTGCCG GCTTCCTTCT CCCCATCGAA GCCGGGGTCG AACTCCTCGC GGTAGACGCG
 901 CTGCGTCAGA TCCCAGTAGA CCTCGTGGTG GTACGGCCAC AAGAACTCGG AGTCGGCCGG
 961 GAACCCGGCG CGGAGCAGCG CCTCGCGCGC CTGGCCGGCT GCGGGGCCGC CTGCCGCGTA
1021 GGTGGGGTAG TCGCGCAGGG CGGCCGGCAG GAAGGTGAAG AGGTTGGGAC CCTCCGCGCG
1081 CCACAGGGTG CCTTCCCAGT CGACTCCTCC GTCGTACAGC TCGGGATGGT TCTCCAGCTG
1141 CCAGCGCACG AGGTAGCCGC CGTTGGACAT CCCGGTGACC AGGGTGCGCT CGAGCGGCCG
1201 GTGGTAGCGC TGGGCGACCG ACGCGCGGGC GGCCCGGGTC AGCTGGGTGA GGCGGGTGTT
1261 CCACTCGGCG ACGGCGTCGC CCGGCCGGGA GCCATCACGG TAGAACGCGG GGCCGGTGTT
1321 GCCCTTGTCG GTGGCGGCGT AGGCGTAACC GCGGGCGAGC ACCCAGTCGG CGATGGCCCG
1381 GTCGTTGGCG TACTGCTCGC GGTTACCGGG GGTGCCGGCC ACGACCAGGC CACCGTTCCA
1441 GCGGTCGGGC AGCCGGATGA CGAACTGGGC GTCGTGGTTC CACCCGTGGT TGGTGTTGGT
1501 GGTGGAGGTG TCGGGGAAGT AGCCGTCGAT CTGGATCCCG GGCACTCCGG TGGGAGTGGC
1561 CAGGTTCTTG GGCGTCAGCC CTGCCCAGTC CGCCGGGTCG GTGTGGCCGG TGGCCGCCGT
1621 TCCCGCCGTG GTCAGCTCGT CCAGGCAGTC GGCCTGCTGA CGTGCCGCCG CCGGGACACG
1681 CAGCTGGGAC AGACGGGCGC AGTGACCGTC CGGGGCATCG GGAGCAGGCC GGGCCGTGGC
1741 CGGTGAGGGG AGCAGGACGG CGACTGCGGC CAGGGTGAGA GCGCCGAGGC CGGTGCGTCT
1801 TCTCGGGGCC CGTCCGACAC CGAGGGGCAG AACCATGGAG AGCCTCCAGA CGTGCGGATG
1861 GATGACGGAC TGGAGGCTAG GTCGCGCACG GTGGAGACGA ACATGGGTGC GCCCGCCATG
1921 ACTGAGGCCC CTCAGAGGTG GGCCGCCGCC ATGACGGGCG CGGGACCGCG GGCGCTCCGG
1981 GGCGGTGCCC GCGGCCGCCA CCGGTTCCGG GTCCCCGGGT CAGGGACAGG TGTCGTTCGC
2041 GACGGTGAAG TAGCCGGTCG GCGACTCTTT CAAGGTGGTC GTGACGAAGG TGTTGTACAG
2101 GCCCATGTTC TGGCCGGAGC CCTTGGCGTA GGTGTAACCG GCGCTCGTCG TGGCGCGGCC
2161 CGCCTGGACG TGAGCGTAGT TGCCGGCGGT CCAGCAGACG GCCGTGGCAC CGGTCGTCTG
2221 CGCGGTGACC GCGCCCGAGA GCGGTCCGGC CTTGCCGTCC GCGTCCCGGG CGGCGACCGC
2281 GTAGGTGTGC GATGTGCCCG CCCTCAGGCC GGTGTCCGTG TACGACGTCG TGGCGGACGT
2341 GGTGATCTGG GCACCGTCGC GGTGGACGGC GTAGTCGGTG GCGCCGTCGA CGGGTTTCCA
2401 GGTCAGGCTG ATGGTGGTGT CGGTGGCGCC GGTGGCGGCC AGGCCGGACG GAGCGGGCAG
2461 CGAACCGGGG TCGGAGGCGG ATCCGCTCAG GCCGAAGAAC TGCGTGATCC AGTAGCTGGA
2521 ACAGATCGAG TCCAGGAAGT AGGCGGCGCC GGTGCTGCCG CACTGCTGTG CTCCGGTGCC
2581 GGGATCGACC GGGGTGCCGT GCCCGATGCC CGGCACCCGG TTCACCTCCA CGGCCACCGA
2641 TCCGTCCGCG GCCAGGTACT CCTCGTGCCG GGTGGAGTTC GGGCCGATCA CCGAGGTACG
2701 GTCCGGCGTC TGGGACACGC CGTGCACAGC GGTCCACTGG TCGCGCAACT CGTCGGCGTT
2761 GCGCGGCGCG ACGGTGGTGT CCTTGTCGCC GTGCCAGATG GCCACGCGCG GCCACGGGCC
2821 CGACCACGAG GGGTAGCCGT CACGGACCCG CCGCGCCCAC TGGTCCGCGG TCAGGTCGGT
2881 CCCGGGGTTC ATGCACAGGT ACGCGCTGCT GACGTCGGTG GCACAGCCGA AGGGCAGGCC
2941 GGCGACGACC GCGCCGGCCT GGAAGACGTC CGGATAGGTG GCGAGCATCA CCGACGTCAT
3001 GGCACCGCCG GCGGACAGCC CGGTGATGTA GGTGCGCTGG GGGTCCGCGC CGTAGGCGGA
3061 GACGGTGTGA GCGGCCATCT GCCGGATCGA CGCGGCTTCG CCCTGGCCCC TGCGGTTGTC
3121 GCTGCTCTGG AACCAGTTGA AGCACCTGTT CGCGTTGTTC GACGACGTGG TCTCGGCGAA
3181 CACGAGCAGG AAGCCATAGC GGTCCGCGAA TGAGAGCAGG CCGGAGTTGT CGGCGTAGCC
3241 CTGGGCGTCC TGGGTGCAAC CGTGCAGGGC GAACACCACC GCCGGCTCCG CGGGCAGGGA
3301 CGCGGGCCGG TAGACGTACA TGTTCAGCCG GCCCGGGTTC GTGCCGAAGT CCGCGACCTC
```

-continued

```
3361 GGTCAGGTCC GCCTTGGTCA GACCGGGCTT GGCCAGGCCC GCCGCGGCGT GGGCCGTCGG
3421 CGCCGGGCCG AGCAGGGCCG CTCCGAGTAC GAGGGCCACG ACGGCCACGA GACGGGTGAG
3481 CACCCCCCGC CGTCCCGGAC GCGACAACGA CCCGACCGGC GGCGAGGAGG AGAGGGGGAA
3541 CAGCGGGGTG AGGATTCCCC GGAACGGCGG CGGCTGCATG GCGGCTCCCT CGATGTCGTG
3601 GGGGGGACAC GGAGGGCTCC CTGACGTCGA TCAGTGGGAG CGCCCCGGTG CCCGGCACCG
3661 TAGGGGTGGT TCAACCCGCA ACGGTATGGC CCGGAGCACC ACACCCCGCA CCGCGCGATG
3721 TGCGCCCGGA CGGATTGTGT CGCCTTGCGG AATCTGATAC CCGGACGCGA CGAACGCCCC
3781 ACCCGACACG GGTAGGGCGT CATGGTGTCC GACTCGGCCG GTCGGCCTTG CCTGCCCTGG
3841 ACGGACCGGG CGTCGGCGGA CCGGGCGTCG GCGGGCTGGG CGGTATGGCG GCCGAGGACG
3901 CCAGCCGCGT GGGGCGGCCG CGCCCAAGTG CAGTACGCCG ACCGTGGCCG GCGGGAGGGC
3961 CGGACCGGTC AGTGCAGTCC CGCGGCCCTG CGGGACCGCT CGTCCCAGAC GGGTTCCACC
4021 GCGGCGAACC GGGGTCCGTG TCCGCGGCGG TAGACCATCA GTGTCCGCTC GAAGGTGATG
4081 ACGATGACAC CGTCCTGGTT GTAGCCGATG GTGCGCACGC TGATGATGCC TACGTCAGGT
4141 CGGCTGGCGG ACTCCCGGGT GTTCAGGACC TCGGACTGCG AGTAGATGGT GTCGCCCTCG
4201 AAGACCGGGT TCGGCAGCCT GACCCGGTCC CAGCCGAGGT TGGCCATCAC ATGCTGGGAG
4261 ATGTCGGTGA CGCTCTGCCC GGTGACCAGG GCGAGGGTGA AGGTGGAGTC CACCAGCGGC
4321 TTGCCCCAGG TGGTGCCCGC CGAGTAGTGG CGGTCGAAGT GCAGCGGCGC GGTGTTCTGC
4381 GTCAGGAGCG TGAGCCAGGA GTTGTCGGTC TCCAGGACCG TGCGGCCCAG GGGGTGGCGG
4441 TACACGTCGC CGGTGGTGAA GTCCTCGAAG TAGCGGCCCT GCCAGCCCTC GACCACAGCG
4501 GTGCGGGTGG CGTCCTGGTC CGGGTTCTCA GTCGTCATGG CGCTCATTCT GGGAAGTCCC
4561 CGGTCCGCTG TGAAATGCCG AACCTTCACC GGGCTCATAC GTGCGGCGCA TGAGCCCTGG
4621 ACCGTACGTA GTCGTAGAAC CTCGCCACCA CTGGCGCGCG TGGTCCTCCG GCGAGTGTGA
4681 CCACGCCGAC CGTGCGCCGC GCCTGCGGGT CGTCGAGCGG CACGGCGACG GCGTGGTCAC
4741 CGGGCCCGGA CGGGCTGCCG GTGAGGGGGG CGACGGCCAC ACCGAGGCCG GCGGCGACCA
4801 GGGCCCGCAG CGTGCTCAGC TCGGTGCTCT CCAGGACGAC CCGCGGCACG AATCCGGCCG
4861 CGGCGCACAG CCGGTCGGTG ATCTGGCGCA GTCCGAAGAC CGGCTCCAGT GCCACGAACG
4921 CCTCATCGGC CAGCTCCGCG GTCCGCACCC GGCGGCGTCT GGCCAGCCGG TGTCCGGGTG
4981 GGACGAGCAG GCACAGTGCC TCGTCCCGCA GTGGTGTCCA CTCCACATCG TCCCCGGCGG
5041 GTCGTGGGCT GGTCAGCCCC AGGTCCAGCC TGCTGTTGCG GACGTCGTCG ACCACGGCGT
5101 CGGCGGCGTC GCCGCGCAGT TCGAAGGTGG TGCCGGGAGC CAGCCGGCGG TACCCGGCGA
5161 GGAGGTCGGG CACCAGCCAG GTGCCGTAGG AGTGCAGGAA ACCCAGTGCC ACGGTGCCGG
5221 TGTCGGGGTC GATCAGGGCG GTGATGCGCT GCTCGGCGCC GGAGACCTCA CTGATCGCGC
5281 GCAGGGCGTG GGCGCGGAAG ACCTCGCCGT ACTTGTTGAG CCGGAGCCGG TTCTGGTGCC
5341 GGTCGAACAG CGGCACGCCC ACTCGTCGCT CCAGCCGCCG GATGGCCCTG GACAGGGTCG
5401 GCTGGGAGAT GTTGAGCCGT TCCGCGGTGA TCGTCACGTG CTCGTGCTCG GCCAAGGCCG
5461 TGAACCACTG CAACTCCCGT ATCTCCATGC AGGGACTATA CGTACCGGGC ATGGTCCTGG
5521 CGAGGTTTCG TCATTTCACA GCGGCCGGGC GGCGGCCCAC AGTGAGTCCT CACCAACCAG
5581 GACCCCATGG GAGGGACCCC ATGTCCGAGC CGCATCCTCG CCCTGAACAG GAACGCCCCG
5641 CCGGGCCCCT GTCCGGTCTG CTCGTGGTTT CTTTGGAGCA GGCCGTCGCC GCTCCGTTCG
5701 CCACCCGCCA CCTGGCGGAC CTGGGCGCCC GTGTCATCAA GATCGAACGC CCCGGCAGCG
5761 GCGACCTCGC CCGCGGCTAC GACCGCACGG TGCGTGGCAT GTCCAGCCAC TTCGTCTGGC
5821 TGAACCGGGG GAAGGAGAGC GTCCAGCTCG ATGTGCGCTC GCCGGAGGGC AACCGGCACC
5881 TGCACGCCTT GGTGGACCGG GCCGATGTCC TGGTGCAGAA TCTGGCACCC GGCGCCGCGG
5941 GCCGCCTGGC ATCGGCCACC AGGTCCTCGC GCGGAGCCAC CGAGGCTGAT CACCTGCGGA
6001 CATATCCGGC TACGGCAGTA CCGGCTGCTA CCGCGGACCG CAAGGCGTAC GACCTCCTGG
6061 TCCAGTGCGA AGCGGGGCTG GTCTCCATCA CCGGCACCCC CGAGACCCCG TCCAAGGTGG
6121 GCCTGTCCAT CGCGGACATC TGTGCGGGGA TGTACGCGTA CTCCGGCATC CTCACGGCCC
6181 TGCTGAAGCG GGCCCGCACC GGCCGGGGCT CGCAGTTGGA GGTCTCGATG CTCGAAGCCC
6241 TCGGTGAATG GATGGGATAC GCCGAGTACT ACACGCGCTA CGGCGGCACC GCTCCGGCCC
6301 GCGCCGGCGC CAGCCACGCG ACGATCGCCC CCTACGGCCC GTTCACCACG CGCGACGGGC
6361 AGACGATCAA TCTCGGGCTC CAGAACGAGC GGGAGTGGGC TTCCTTCTGC GGTGTCGTGC
6421 TACAACGCCC CGGTCTCTGC GACGACCCGC GCTTTTCCGG CAACGCCGAC CGGGTGGCGC
6481 ACCGCACCGA GCTCGACGCC CTGGTGAGCG AGGTGACGGG CACGCTCACC GGCGAGGAAC
6541 TGGTGGCGCG GCTGGAGGAG GCGTCGATCG CCTACGCACG CCAGCGCACC GTGCGGGAGT
6601 TCAGCGAACA CCCCCAACTG CGTGACCGTG GACGCTGGGC TCCGTTCGAC AGCCCGGTCG
6661 GTGCGCTGGA GGGCCTGATC CCCCCGGTCA CCTTCCACGG CGAGCACCCG CGGCGGCTGG
6721 GCCGGGTCCC GGAGCTGGGC GAGCATACCG AGTCCGTCCT GGCGTGGCTG GCCGCGCCCC
6781 ACAGCGCCGA CCGCGAAGAG GCCGGCCATG CCGAATGAAC TCACCGGAGT CCTGATCCTG
6841 GCCGCCGTGT TCCTGCTCGC CGGCGTACGG GGCTGAACA TGGGCCTGCT CGCGCTGGTC
6901 GCCACCTTTC TGCTCGGGGT GGTCGCACTC GACCGAACGC CGGACGAGGT GCTGGCGGGT
6961 TTCCCCGCGA GCATGTTCCT GGTGCTGGTC GCCGTCACGT TCCTCTTCGG GATCGCCCGC
7021 GTCAACGGCA CGGTGGACTG GCTGGTACGT GTCGCGGTGC GGGCGGTGGG GGCCCGQGTG
7081 GGAGCCGTCC CCTGGGTGCT CTTCGGCCTG GCGGCACTGC TCTGCGCGAC AGGCGCGGCC
7141 TCGCCCGCGG CGGTGGCGAT CGTGGCGCCG ATCAGCGTCG CGTTCGCCGT CAGGCACCGC
7201 ATCGATCCGC TGTACGCCGG ACTGATGGCG GTGAACGGGG CCGCAGCCGG CAGTTTCGCC
7261 CCCTCCGGGA TCCTGGGCGG CATCGTCCAC TCGGCGCTGG AGAAGAACCA TCTGCCCGTC
7321 AGCGGCGGGC TGCTCTTCGC AGGCACCTTC GCCTTCAACC TGGCGGTCGC CGCGGTGTCA
7381 TGGCTCGTCC TCGGGCGCAG GCGCCTCGAA CCACATGACC TGGACGAGGA CACCGATCCC
7441 ACGGAAGGGG ACCCGGCTTC CCGCCCCGGC GCGGAACACG TGATGACGCT GACCGCGATG
7501 GCCGCGCTGG TGCTGGGAAC CACGGTCCTC TCCCTGGACA CCGGCTTCCT GGCCCTCACC
7561 TTGGCGGCGT TGCTGGCGCT GCTCTTCCCG CGCACCTCCC AGCAGGCCAC CAAGGAGATC
7621 GCCTGGCCCG TGGTGCTGCT GGTATGCGGG ATCGTGACCT ACGTCGCCCT GCTCCAGGAG
7681 CTGGGCATCG TGGACTCCCT GGGGAAGATG ATCGCGGCGA TCGGCACCCC GCTGCTGGCC
7741 GCCCTGGTGA TCTGCTACGT GGGCGGTGTC GTCTCGGCCT TCGCCTCGAC CACCGGGATC
7801 CTCGGTGCCC TGATGCCGCT GTCCGAGCCG TTCCTGAAGT CCGGTGCCAT CGGGACGACC
7861 GGCATGGTGA TGGCCCTGGC GGCCGCGGCG ACCGTGGTGG ACGCGAGTCC CTTCTCCACC
7921 AATGGTGCTC TGGTGGTGGC CAACGCTCCC GAGCGGCTGC GGCCCGGCGT GTACCAGGGG
7981 TTGCTGTGGT GGGGCGCCGG GGTGTGCGCA CTGGCTCCCG CGGCCGCCTG GGCGGCCTTC
8041 GTGGTGGCGT GAGCGCAGCG GAGCGGGAAT CCCCTGGAGC CCGTTTCCCG TGCTGTGTCG
8101 CTGACGTAGC GTCAAGTCCA CGTGCCGGGC GGGCAGTACG CCTAGCATGT CGGGCATGGC
```

-continued

8161 TAATCAGATA ACCCTGTCCG ACACGCTGCT CGCTTACGTA CGGAAGGTGT CCCTGCGCGA
8221 TGACGAGGTG CTGAGCCGGC TGCGCGCGCA GACGGCCGAG CTGCCGGGCG GTGGCGTACT
8281 GCCGGTGCAG GCCGAGGAGG GACAGTTCCT CGAGTTCCTG GTGCGGTTGA CCGGCGCGCG
8341 TCAGGTGCTG GAGATCGGGA CGTACACCGG CTACAGCACG CTCTGCCTGG CCCGCGGATT
8401 GGCGCCCGGG GGCCGTGTGG TGACGTGCGA TGTCATGCCG AAGTGGCCCG AGGTGGGCGA
8461 GCGGTACTGG GAGGAGGCCG GGGTTGCCGA CCGGATCGAC GTCCGGATCG GCGACGCCCG
8521 GACCGTCCTC ACCGGGCTGC TCGACGAGGC GGGCGCGGGG CCGGAGTCGT TCGACATGGT
8581 GTTCATCGAC GCCGACAAGG CCGGCTACCC CGCCTACTAC GAGGCGGCGC TGCCGCTGGT
8641 ACGCCGCGGC GGGCTGATCG TCGTCGACAA CACGCTGTTC TTCGGCCGGG TGGCCGACGA
8701 AGCGGTGCAG GACCCGGACA CGGTCGCGGT ACGCGAACTC AACGCGGCAC TGCGCGACGA
8761 CGACCGGGTG GACCTGGCGA TGCTGACGAC GGCCGACGGC GTCACCCTGC TGCGGAAACG
8821 GTGACCGGGG CGATGTCGGC GGCGGTCAGC GTCAGCGTCG TCGGCGCGGG CCTCGCGGAG
8881 GGCTCCAGAT GCAGGCGTTC GACGCCGGCG GCGGAAGCGC CCGCCACCTC GGACACGCAG
8941 GGGCAGTCGG AGTCCGCGAA GCCCGCGAAC CGGTAGGCGA TCTCCATCAT GCGGTTGCGG
9001 TCCGTACGCC GGAAGTCCGC CACCAGGTGC GCCCCCGCGC GGGCGCCCTG GTCCGTGAGC
9061 CAGTTCAGGA TCGTCGCACC GGCACCGAAC GACACGACCC GGCAGGACGT GGCGAGCAGT
9121 TTCAGGTGCC ACGTCGACGG CTTCTTCTCC AGCAGGATGA TGCCGACGGC GCCGTGCGGG
9181 CCGAAGCGGT CGCCCATGGT GACGACGAGG ACCTCATGGG CGGGATCGGT GAGCACGCGC
9241 GCAGGTCGGC GTCGGAGTAG TGCACGCCGG TCGCGTTCAT CTGGCTGGTC CGCAGCGTCA
9301 GTTCCTCGAC GCGGCTGAGT TCCTCCTCCC CCGCGGGTGC GATCGTCATG GAGAGGTCGA
9361 GCGAGCGCAG GAAGTCCTCG TCGGGACCGG AGTACGCCTC CCGGGCCTGG TCGCGCGCGA
9421 AACCCGCCTG GTACATCAGG CGGCGCCGAC GCGAGTCGAC CGTGGACACC GGCGGGCTGA
9481 ACTCCGGCAG CGACAGGAGC GTGGCCGCCT GCTCGGCCGG GTAGCACCGC ACCTCGGGCA
9541 GGTGGAACGC CACCTCGGCA CGCTCGGCGG GCTGGTCGTC GATGAACGCG ATCGTGGTCG
9601 GTGCGAAGTT CAGCTCCGTG GCGATCTCGC GGACGGACTG CGACTTCGGC CCCCATCCGA
9661 TGCGGGCCAG CACGAAGTAC TCCGCCACAC CGAGGCGTTC CAGACGCTCC CACGCGAGGT
9721 CGTGGTCGTT CTTGCTCGCC ACCGCCTGGA GGATGCCGCG GTCGTCGAGC GTGGTGATCA
9781 CCTCGCGGAT CTCGTCGGTG AGGACCACCT CGTCGTCCTC CAGCACGGTG CCCCGCCACA
9841 AGGTGTTGTC CAGGTCCCAG ACCAGACACT TGACAATGGT CATGGCTGTC CTCTCAAGCC
9901 GGGAGCGCCA GCGCGTGCTG GGCCAGCATC ACCCGGCACA TCTCGCTGCT GCCCTCGATG
9961 ATCTCCATGA GCTTGGCGTC GCGGTACGCC CGTTCGACGA CGTGTCCCTC TCTCGCGCCT
10021 GCCGACGCGA GCACCTGTGC GGCGGTCGCG GCCCCGGCGG CGGCTCGTTC GGCGGCGACG
10081 TGCTTGGCCA GGATCGTCGC GGGCACCATC TCGGGCGAGC CCTCGTCCCA GTGGTCGCTG
10141 GCGTACTCGC ACACGCGGGC CGCGATCTGC TCCGCGGTCC ACAGGTCGGC GATGTGCCCG
10201 GCGACGAGTT GGTGGTCGCC GAGCGGCCGG CCGAACTGCT CCCGGGTCCG GGCGTGGGCC
10261 ACCGCGGCGG TGCGGCAGGC CCGCAGGATC CCGACGCAGC CCCAGGCGAC CGACTTGCGC
10321 CCGTAGGCGA GTGACGCCGC GACCAGCATC GGCAGTGACG CGCCGGAGCC GGCCAGGACC
10381 GCGCCGGCCG GCACACGCAC CTGGTCCAGG TGCAGATCGG CGTGGCCGGC GGCGCGGCAG
10441 CCGGACGGCT TCGGGACGCG CTCGACGCGT ACGCCGGGGG TGTCGGCGGG CACGACCACC
10501 ACCGCACCGG AACCATCCTC CTGGAGACCG AAGACGACCA GGTGGTCCGC GTAGGCGGCG
10561 GCAGTCGTCC AGACCTTGTG GCCGTCGACG ACAGCGGTGT CCCCGTCGAG CCGAACCCGC
10621 GTCCGCATCG CCGACAGATC GCTGCCCGCC TGCCGCTCAC TGAACCCGAC GGCCGCGAGT
10681 TTCCCGCTGG TCAGCTCCTT CAGGAAGGTC GCCCGCTGAC CGGCGTCGCC GAGCCGCTGC
11741 ACGGTCCACG CGGCCATGCC CTGCGACGTC ATGACACTGC GCAGCGAACT GCAGAGGCTG
10801 CCGACGTGTG CGGTGAACTC GCCGTTCTCC CGGCTGCCGA GTCCCAGACC GCCGTGCTCG
10861 GCCGCCACTT CCGCGCAGAG CAGGCCGTCG GCGCCGAGCC GGACGAGCAG GTCGCGCGGC
10921 AGTTCGCCGG ACGTGTCCCA CTCGGCGGCC CGGTCACCGA CAAGCTCGGT CAGCAGCGCG
10981 TCACGCTCAG GCATCGACGG CCCGCAGCCG GTGGACGAGT GCGACCATGG ACTCGACGGT
11041 ACGGAAGTTC GCGAGCTGGA GGTCCGGGCC GGCGATCGTG ACGTCGAACG TCTTCTCCAG
11101 GTACACGACC AGTTCCATCG CGAACAGCGA CGTGAGGCCG CCCTCCGCGA ACAGGTCGCG
11161 GTCCACGGGC CAGTCCGACC TGGTCTTCGT CTTGAGGAAC GCGACCAACG CGTGCGCGAC
11221 GGGGTCGTCC TTGACGGGTG CGGTCATGAG AACACCTTCT CGTATTCGTA GAAGCCCCGG
11281 CCGGTCTTCC GGCCGTGGTG TCCCTCGCGG ACCTTGCCCA GCAGCAGGTC ACAGGGGCGG
11341 CTGCGCTCGT CGCCGGTGCG TTTGTGCAGC ACCCACAGCG CGTCGACGAG GTTGTCGATG
11401 CCGATCAGGT CCGCGGTGCG CAGCGGCCCG GTCGGATGGC CGAGGCACCC CGTCATGAGC
11461 GCGTCGACGT CCTCGACGGA CGCGGTGCCC TCCTGCACGA TCCGCGCCGC GTCGTTGATC
11521 ATCGGGTGGA GCAGCCGGCT CGTGACGAAG CCGGGCGCGT CCCGGACGAC GATCGGCTTG
11581 CGCCGCAGCG CCGCGAGCAG GTCCCCGGCG GCGGCCATGG CCTTCTCACC GGTCCGGGGT
11641 CCGCGGATCA CCTCGACCGT CGGGATCAGG TACGACGGGT TCATGAAGTG CGTGCCGAGC
11701 AGGTCCTCGG GCCGGGCCAC GGAGTCGGCC AGTTCGTCAA CCGGGATCGA CGACGTGTTC
11761 GTGATGACCG GGATACCGGG CGCCGCTGCC GAGACCGTGG CGAGTACCTC CGCCTTGACC
11821 TCGGCGTCCT CGACGACGGC CTCGATCACC GCGGTGGCCG TACCGATCGC GGGCAGCGCG
11881 GACGTGGCCG TCCGCAGCAC ACCGGGGTCG GCCTCGGCGG GCCCGGCCAC GAGTTGTGCC
11941 GTCCGCAGTT CGGTGGCGAT CCGCGCCCGC GCCGCCGTAA GGATCPCCTC GGACGTGTCG
12001 ACGAGTGTCA CCGGGACGCC GTGGCGCAGC GCGAGCGTGG TGATGCCGGT GCCCATCACT
12061 CCCGCGCCGA GCACGATCAG CTGGTGGTCC ACGCTGTTTC CTCCCTCCGG GGTCACCATG
12121 GCAGCGAGTA CGGGTCGAGG ACGTCTTCCG GGGTCGACCC GATCGCGTCC TTGCGGCCGA
12181 GGCCGAGTTC GTCGGCGAAG CCGAGCAGCA CGTCGAACGC GATGTGGTCG GCGAACGCGC
12241 TGCCCGTCGA GTCGAGGACG CTCAGGCTGT CCCGGTGGTC CGCCGCGGTG TCCGGTGCCG
12301 CGCACAGGGC CGCCAGCGAC GGGCCGAGCT CGCGGTCCGG CAGTTGCTGG TACTCGCCCT
12361 CGGCGCGGGC CTGCCCCGGA TGGTCGACGC AGATGAACGC GTCGTCGAGC AGGGTCTTCG
12421 GCAGTTCGGT CTTGCCCGGC TCGTCGGCGC CGATGGCGTT CACATGCAGG TGCGGCAGCC
12481 GCGGCTCGGC GGGCAGCACC GGCCCTTTGC CCGAGGGCAC CGAGGTGACG GTGGACAGGA
12541 CATCCGCGGC GGCGGCGGCC TCCGCCGGAT CGGTCACCTT GACCGGCAGT CCGAGGAACG
12601 CGATGCGGTC CGCGAACGAC GCCGCGTGGC CGGGGTCGGT GTCGQTGACC AGGATCCGCT
12661 CGATGGGCAG GACCCTGCTG AGCGCGTGCG CCTGGGTCAC CGCCCGTGCG CCCGCGCCGA
12721 TCAGCGTGAG CGTGGCGCTG TCGGACCGGG CCAGCAGCCG GCTCGCGACG GCGGCGACCG
12781 CGCCGGTCCG CATCGCGGTG ATCACGCCTG CGTCGGCGAG GGCGGTCAGA CTGCCGCTGT
12841 CGTCGTCGAG GCGCGACATC GTGCCGACGA TCGTCGGCAG CCGGAAGCGC GGATAGTTGT
12901 GCGGACTGTA CGAAACCGTC TTCATGGTCA CGCCGACACC GGGGACCCGG TACGGCATGA

-continued

```
12961 ACTCGATGAC GCCGGGAATG TCGCCGCCGC GGACGAATCC GGTACCCGGC GGCGCCTCGG
13021 CGAACTCGCC GCGGCCGAGC GCGGCGAACC CGTCGTGCAG CTCGCTGATC AGCCGGTCCA
13081 TCATCACGTC GCGGCCGATC ACGGAGAGAA TCCGCTTGAT GTCACGTTGG CGCAGGACCC
13141 TGGTCTGCAT GTGTCACCTC CCTTTCGTGG CCGGAGCTGT CTTGGTGGTG CCGCTCGGGG
13201 CGGCTTCCGT TCTCATCGCA GCTCCCTGTC GATGAGGTCG AAAATCTCGT CCGCGGTCGC
13261 GTCCGCGGAC AGCACGCCGG CCGGCGTGGT CGGGCGGGTC TCCCGCCGCC AGCGGTTGAG
13321 CAGGGCGTCC AGCCGGGTTC CGATCGCGTC CGCCTGGCGG GCGCCCGGGT CGACACCGGC
13381 AACGAGTGCT TCCAGCCGGT CGAGCTGCGC GAGCACCACG GTCACCGGGT CGTCCGGGGA
13441 CAGCAGTTCA CCGATGCGGT CGGCGAGTGC GCGCGGCGAC GGGTAGTCGA AGACGAGCGT
13501 GGCGGACAGT CGCAGACCGG TCGCCTCGTT GAGGCCGTTG CGCAGCTGCA CCGCGATGAG
13561 CGAGTCCACA CCGAGTTCCC GGAACGCCGC GTCCTCCGGG ATGTCCTCCG GGTCGGCGTG
13621 GCCCAGGACG GCCGCTGCCT TCTGCCGGAC GAGGGCGAGC AGGTCGGTGG GGCGTTCCTG
13681 CTCGTTGCGG GCGCTCCGGC GGGCCGACGG CTTGGGCCGG CCACGCAGCA GCGGGAGGTC
13741 CGGCGGCAGG TCGCCCGCCA CGGCGACGAC ACTGCCCGTT CCGGTGTGGA CGGCGGCGTC
13801 GTACATGCGC ATGCCCTGTT CGGCGGTGAG CGCGCTCGCC CCACCCTTGC GCATACGGCG
13861 CCGGTCGGCG TCGGTCAGGT CCGCGGTCAG GCCACTCGCC TGGTCCCACA GCCCCCACGC
13921 GATCGACAGC CCTGGCAGCC CTTGTGCACG CCGGTGTTCG GCGAGCGCGT CGAGGAACGC
13981 GTTCGCCGCC GCGTAGTTGC CCTGACCGGG GGTGCCCAGC ACACCGGCCG CCGACGAGTA
14041 GACGACGAAT GCGGCGAGGT CGGTGTCGCG GGTGAGCCGG TGCAGGTGCC AGGCGGCGTC
14101 GGCCTTGGGT TTGAGGACGG TGTCGATGCG GTCGGGGGTG AGGTTGTCGA GCAGGGCGTC
14161 GTCGAGGGTT CCGGCGGTGT GGAAGACGGC GGTGAGGGGT TGAGGGATGT GGGCGAGGGT
14221 GGTGGCGAGT TGGTGGGGGT CGCCGACGTC GCAGGGGAGG TGGGTGCCGG GGGTGGTGTC
14281 GGGGGGTGGG GTGCGGGAGA GGAGGTAGGT GTGGGGGTGG TTCAGGTGGC GGGCGAGGAT
14341 GCCGGCGAGG GTGCCGGAGC CGCCGGTGAT GACGACGGCC CCCTCGGGGT CCAGCGGCCG
14401 CGGGACCGTG AGGACGATCT TGCCGGTGTG CTCGCCGCGG CTCATGGTCG CCAGCGCCTC
14461 GCGGACCTGC CGCATGTCGT GCACCGTCAC CGGCAGCGGG TGCAGCACAC CGCGCGCGAA
14521 CAGGCCGAGC AGCTCCGCGA TGATCTCCTT GAGCCGGTCG GGCCCCGCGT CCATCAGGTC
14581 GAACGGTCGC TGGACGGCGT GCCGGATGTC CGTCTTCCCC ATCTCGATGA ACCGGCCACC
14641 CGGCGCGAGC AGGCCGACGG ACGCGTCGAG GAGTTCACCG GTGAGCGAGT TGAGCACGAC
14701 GTCGACCGGC GGGAACGCGT CGGCGAACGC GGTGCTGCGG GAATCGGCCA GATGCGCTCC
14761 GTCCAGGTCC ACCAGATGGC GCTTCGCGGC GCTGGTGGTC GCGTACACCT CCGCGCCCAG
14821 GTGCCGCGCG ATCTGCCGGG CGGCGGAACC GACACCGCCG GTGGCCGCGT GGATCAGGAC
14881 CTTCTCGCCG GGGCGCAGCC CGGCGAGGTC GACCAGGCCG TACCACGCGG TCGCGAACGC
14941 GGTCATCACG GACGCCGCCT GCGGGAACGT CCAGCCGTCC GGCATCCGGC CGAGCATCCG
15001 GTGGTCGGCG ATGACCGTGG GGCCGAAGCC GGTGCCGACG AGGCCGAAGA CGCGGTCGCC
15061 CGGTGCCAGA CCGGAGACGT CGGCGCCGGT CTCCAGGACG ATGCCCGCGG CCTCGCCGCC
15121 GAGCACGCCC TGACCGGGGT AGGTGCCGAG CGCGATCAGC ACATCCCGGA AGTTGAGGCC
15181 CGCCGCACGC ACACCGATCC GGACCTCGGC CGGGGCGAGG GGGCGCCGGG GCTCCGCCGA
15241 GTCGGCCGCG GTGAGGCCGT CGAGGGTGCC CGTCCGCGCC GGCCGCATCA GCCACGTGTC
15301 GCTGTCCGGC ACGGTGAGCG GCTCCGGCAC CCGGGTGAGG CGGGCCGCCT CGAACCGGCC
15361 GCCGCGCAGC CGCAGACGCG GCTCGCCGAG TGCGACGGCG ATGCGCTGCT GCTCGGGGGC
15421 GAGCGTGACG CCGGACTCGG TCTCGACGTG GACGAACCGG COGGGCTGCT CGGCCTGGGC
15481 GGCGCGCAGC AGTCCGGCCG CCGCGCCGGT GGCGAGGCCC GCGGTGGTGT GCACGAGCAG
15541 ATCCCCGCCG GAGCCGGTCA GGGCGGTCAG CAGCCGGGTG GTGAGCGCAC GCGTCTCGGC
15601 CACCGGGTCG TCGCCATCAG CGGCAGGCAA CGTGATGACG TCCACGTCGG TCGCGGGGAC
15661 ATCCGTGGGT GCGGCGACCT CGATCCAGGT GAGACGCATC AGGCCGGTGC CGACGGGTGG
15721 GGACAGCGGG CGGGTGCGGA CCGTCCGGAT CTCGGCGACG AGTTGGCCGG CGGAGTCGGC
15781 GACGCGCAGA CTCAGCTCGT CGCCGTCACG AGTGATCACG GCTCGGAGCA TGGCCGAGCC
15841 CGTGGCGACG AACCGGGCCC CCTTCCAGGC GAACGGCAGA CCCGCAGCGC TGTCGTCCGG
15901 CGTGGTGAGG GCGACGGCGT GCAGGGCCGC GTCGAGCAGC GCCGGATGCA CACCGAAACC
15961 GTCCGCCTCG GCGGCCTGCT CGTCGGGCAG CGCCACCTCG GCATACACGG TGTCACCATC
16021 ACGCCAGGCA GCCCGCAACC CCTGGAACGC CGACCCGTAC TCATAACCGG CATCCCGCAG
16081 TTCGTCATAG AACCCCGAGA CGTCGACGGC CACGGCCGTG ACCGGCGGCC ACTGCGAGAA
16141 CGGCTCCACA CCGACAACAC CGGGGGTGTC GGGGGTGTCG GGGGTCAGGG TGCCGCTGGC
16201 GTGCCGGGTC CAGCTGCCCG TGCCCTCGGT ACGCGCGTGG ACGGTCACCG GCCGCCGTCC
16261 GGCCTCATCA GCCCCTTCCA CGGTCACCGA CACATCCACC GCTGCGGTCA CCGGCACCAC
16321 AAGGGGGGAT TCGATGACCA GCTCGTCCAC TATCCCGCAA CCGGTCTCGT CACCGGCCCG
16381 GATGACCAGC TCCACAAACG CCGTACCCGG CAGCAGGACC GTGCCCCGCA CCGCGTGATC
16441 AGCCAGCCAG GGGTGAGTGC GCAATGAGAT CCGGCCAGTG AGAACAACAC CACCATCGTC
16501 GGCGGGCAGC GCTGTGACAG CGGCCAGCAT CGGATGCGCC GCACCCGTCA ACCCCGCCGC
16561 CGACAGATCG GTGGCACCGG CCGCCTCCAG CCAGTACCGC CTGTGCTCGA ACGCGTACGT
16621 GGGCAGATCC AGCAGCCGTC CCGGCACCGG TTCGACCACC GTGTCCCAGT CCACTGCCGT
16681 GCCCAGGGTC CACGCCTGCG CCAACGCCGT CAGCCACCGC TCCCAGCCGC CGTCACCGGT
16741 CCGCAACGAC GCCACCGTGT GAGCCTGCTC CATCGCCGGC AGCAGCACCG GATGGGCACT
16801 GCACTCCACG AACACCGACC CATCCAGCTC CGCCACCGCC GCGTCCAACG CCACCGGACG
16861 ACGCAGATTC CGGTACCAGT ACCCCTCATC CACCGGCTCC GTCACCCAGG CGCTGTCCAC
16921 GGTCGACCAC CACGCCACCG ACGCGGCCTT CCCTGCCACC CCCTCCAGTA CCTTGGCCAG
16981 TTCATCCTCG ATGGCTTCCA CGTGGGGCGT GTGGGAGGCG TAGTCGACCG CGATACGACG
17041 CACCCGCACG CCTTCGGCCT CATACCGCGC CACCACCTCC TCCACCGCCG ACGGGTCCCC
17101 CGCCACCACC GTCGAAGCCG GGCCGTTACG CGCCGCGATC CACACACCCT CGACCAGACC
17161 GACCTCACCG GCCGGCAACG CCACCGAAGC CATCGCTCCC CGCCCGGCCA GTCGCGCCGC
17221 GATGACCTGA CTGCGCAATG CCACCACGCG GGCGGCGTCC TCGAGGCTGA GGGCTCCGGC
17281 CACGCACGCC GCCGCGATCT CGCCCTGGGA GTGTCCGATC ACCGCGTCCG GCACGACCCC
17341 ATGCGCCTGC CACAGCGCGG CCAGGCTCAC CGCGACCGCC CAGCTGGCCG GCTGGACCAC
17401 CTCCACCCGC TCCGCCACAT CCGGCCGCGC CAACATCTCC CGCACATCCC AGCCCGTGTG
17461 CGGCAGCAAC GCCTGAGCGC ACTCCTCCAT ACGCGCGGCG AACACCGCGG AGTGGGCCAT
17521 GAGTTCCACG CCCATGCCGA GCCACTGGGC GCCCTGGCCG GGGAAGACGA ACACCGTACG
17581 CGGCTGGTCC ACCGCCACAC CCGTCACCCG GGCATCGCCC AGCAGCACCG CACGGTGACC
17641 GAAGACAGCA CGCTtCCGCA CCAACCCCTG CGCGACCGCG GCCACATCCA CACCACCCCC
17701 GCGCAGATAC CCCTCCAGCC GCTCCACCTG CCCCCGCAGA CTCACCTCAC CACGAGCCGA
```

-continued

```
17761 CACCGGCAAC GGCACCAACC CGTCAACAAC CGACTCCCCA CGCGACGGCC CAGGAACACC
17821 CTCAAGGATC ACGTGCGCGT TCGTACCGCT CACCCCGAAC GACGACACAC CCGCATGCGG
17881 TGCCCGATCC GACTCGGGCC ACGGCCTCGC CTCGGTGAGC AGCTCCACCG CACCGGCCGA
17941 CCAGTCCACA TGCGACGACG GCTCGTCCAC ATGCAGCGTC TTCGGCGCGA TCCCGTACCG
18001 CATCGCCATG ACCATCTTGA TCACACCGGC GACACCCGCC GCCGCCTGCG CATGACCGAT
18061 GTTCGACTTC AACGAACCCA GCAGCAGCGG AACCTCACGC TCCTGCCCGT ACGTCGCCAG
18121 AATGGCCTGC GCCTCGATGG GATCGCCCAG CGTCGTCCCC GTCCCGTGCG CCTCCACCAC
18181 GTCCACATCG GCGGCGCGCA GTCCGGCGTT CACCAACGCC TGCTGGATGA CACGCTGCTG
18241 GGACGGGCCG TTGGGGGCGG ACAGCCCGTT GGAGGCACCG TCCTGQTTCA CCGCCGACCC
18301 GCGGACGACC GCGAGAACGG TGTGTCCGTT GCGCTCGGCG TCGGAGAGCC GCTCCAGCAC
18361 AAGAACGCCG GQGCCCTCCG CCCAGCCGGT GCCGTTGGCG GCGTCCGCGA ACGCGCGGCA
18421 GCGGCCGTCG GGGGAGAGTC CGCCCTGCTG CTGGAATTCC ACGAACCCGG TCGGGGTCGC
18481 CATGACGGTG ACACCGCCGA CCAGCGCCAG CGAGCACTCC CCGTGGCGCA GTGCGTGCCC
18541 GGCCTGGTGC AGCGCGACCA GCGACGACGA GCACGCCGTG TCCACCGTGA ACGCCGGTCC
18601 CTGGAGCCCA TAGAAGTACG AGATCCGGCC GGTGAGCACG CTGGGCTGCA TGCCGATCGA
18661 GCCGAACCCG TCCAGGTCCG CGCCGACGCC GTACCCGTAC GAGAAGGCGC CCATGAACAC
18721 GCCGGTGTCG CTGCCGCGCA GTGTGCCCGG CACGATGCCC GCGCTCTCGA ACGCCTCCCA
18781 TGTCGTTTCC AGCAGGATCC GCTGCTGGGG GTCCATGGCC CGTGCCTCAC GGGGGCTGAT
18841 GCCGAAGAAC GCGGCATCGA AGCCGGCQGC GTCGGAGAGG AAGCCGCCGC GGTCCGTGTC
18901 CGATCCGCCG GTGAGGCCGG ACGGGTCCCA GCCACGGTCG GCCGGGAAGC CGGTGACCGC
18961 GTCGCCGCCA CTGTCCACCA TGCGCCACAG GTCGTCGGGC GAGGTGACGC CGCCCGGCAG
19021 TCGGCAGGCC ATGCCCACGA TGGCCAGCGG TTCGTCACGG GTCGCGGCGG CTGTGGGAAC
19081 AGCGACCGGT GCGGCACCAC CGACCAGAGC CTCGTCCAAC CGCGACGCGA TGGCCCGCGG
19141 CGTCGGGTAG TCGAAGACAA GCGTGGCGGG CAGTCGGACA CCGGTCGCCG CGGCGAGTCG
19201 GTTCCGCAGT TCGACGGCGG TCAGCGAGTC GATACCCAGT TCCTTGAAGG CCGCGTCCGC
19261 GGACACGTCC GCGGCGTCCG CGTGGCCGAG CACCGCCGCC GCGTTGTCGC GGACCAGTGC
19321 CAGCAGCGCG GTGTCCCGCT CAGCGCCGGA CATGGTGCCG AGCCGGTCGG CGAGCGGAAC
19381 GGCGGTGGCC GCCGCCGGGC GCGATACGGC GCGGCGCAGA TCGGCGAAAA GCGGCGATGT
19441 GTGCGCGGTG AGGTGCATCG TGGCCGCCAC GGCGAACGCG GTGCCGGTTC CGGCCGCGGC
19501 TTCCAGCAGG CGCATGCCCA CACCGGCCGA CATGGGGCGG AAACCGCCGC GGCGGACACG
19561 GGTGCGGTTG GTGCCGCTCA TGCTGCCGGT GAGTCCGCTG TCATCGGCCC AGAGGCCCCA
19621 GGCCAGCGAC AGCGCGGGCA GTCCTTCGGC ATGGCGCAGC GTCGCGAGTC CGTCGAGGAA
19681 CCCGTTCGCC GCCGAGTAGT TGCCCTGGCC GCGGCCGCCC ATGATGCCCG CGACGGACGA
19741 GTAGAGGACG AACGAGCGCA GGTCCGCGTC CCGGGTCAGC TCGTGCAGGT GCCAGGCGCC
19801 GTCGGCTTTG GGGCGCAGTG TGGTGGCGAG CCGCTCCGGG GTGAGTGCCG TGGTCACGCC
19861 GTCGTCGAGC ACGGCTGCCG TGTGGAAGAC CGCCGTGAGC GGCCTGCCGG CGGCGGCGAG
19921 CGCGGCGGCG AGCTGGTCCC GGTCGGCGAC GTCACAGCGG ATGTGGACAC CGGGAGTGTC
19981 CGCCGGCGGT TCGCTGCGCG ACAGCAACAG GAGGTGGCGG GCGCCATGCT CGGCGACGAG
20041 ATGCCGGGCG AGGAGACCTG CCAGCACACC CGAGCCGCCG GTGATGACCA CCGTGCCGTC
20101 CGGGTCGAGC AGCGGTTCGG GCGTTTCCGC GGCGGCCGTG CGGGTGAACC GCGGCGCTTC
20161 GTACCGGCCG TCGGTGACGC GGACGTACGG CTCGGCCAGT GTCGTGGCGG CGGCCAGCGC
20221 CTCGATGGGG GTGTCGGTGC CGGTCTCCAC CAGCACGAAC CGGCCCGGGT GCTCGGCCTG
20281 GGCGGACCGG ACGAGGCCGG CGACCGCTCC TCCGACCGGT CCCGCGTCGA TCCGGACGAC
20341 GAGGGTGGTC TCCGCAGGGC CGTCCTCGGC GATCACCCGG TGCAGCTCGC CGAGCACGAA
20401 CTCGGTGAGC CGGTACGTCT CGTCGAGGAC ATCCGCGCCC GGTTCCGGGA GCGCGGAGAC
20461 GATGTGGACC GCGTCCGCAG GACCGGGCCC GGGAGTGGGC AGCTCGGTCC AGGAGAGGCC
20521 GTACAAGGAG TTCCGTACGA CGGCGGCGTC GCCGTCGACG TTCACCGGTC GCGCGGTCAG
20581 CGCGGCGACG GTCACCACCG GTTGGCCGAC CGGGTCCGTC GCATGCACGG CAGCGCCGTC
20641 CGGGCCCTGA GTGATCGTGA CGCGCAGCGT GGTGGCCCCG GTCGTGTGGA ACCGCACGCC
20701 GCTCCACGAG AACGGCAGCC GCACCTCCGC TTCCTGTTCC GCGAGCAGCG GCAGGCAGGT
20761 GACGTGCAAG GCCGCGTCGA ACAGCGCCGG GTGGACGCCA TAGTGCGGCG TGTCGTCCGC
20821 CTGTTCCCCG GCGATCTCCA CCTCGGCGTA CAGGGTTTCG CCGTCGCGCC AGGCGGTGCG
20881 CAGTCCCTGG AACGCTGGGC CGTAGCTGTA GCCGGTCTCG GCCAGCCGCT CGTAGAACGC
20941 GCTCACGTCG ACGCGTCGCG CGCCCGGCGG CGGCCACGCG GGCGGCGGGA CCGCCGCGAC
21001 GCTTCCGGCC CGGCCGAGGG TGCCGCTGGC GTGCCGGGTC CAGCTGTCCG TGCCCTCGGT
21061 ACGCGCGTGG ACGGTCACTC GCCGCCGTCC GGCCTCATCG GCCCCTTCGA CGGTCACCGA
21121 CACATCCACC GCGCCGGTCA CCGGCACCAC GAGCGGGGTC TCGATGACCA GTTCATCCAC
21181 CACCCCGCAA CCGGTCTCGT CACCGGCCCG GATGACCAGC TCCACAAACG CCGTACCCGG
21241 CAGCAGAACC GTGCCCCGCA CCGCGTGATC AGCCAGCCAG GGATGCGTAC GCAACGAGAT
21301 CCGGCCAGTG AGAACAACAC CACCACCGTC GTCGGCGGGC AGTGCTGTGA CGGCGGCCAG
21361 CATCGGATGC GCCGCCCCGG TCAGCCCGGC CGCGGACAGA TCGGTGGCAC CGGCCGCCTC
21421 CAGCCAGTAC CGCCTGTGCT CGAACGCGTA GGTGGGCAGA TCGAGCAGCC GTCCCGGCAC
21481 CGGTTCGACC ACCGTGTCCC AGTCCACTGC CGTGCCCAGG GTCCACGCCT GCGCCAACGC
21541 CGTCAGCCAC CGCTCCCAGC CGCCGTCACC GGTCCGCAAC GACGCCACCG TGTGAGCCTG
21601 TTCCATCGCC GGCAGCAGCA CCGGATGGGC GCTGCACTCC ACGAACACGG ACCCGTCCAG
21661 CTCCGCCACC GCCGCGTCCA GCGCGACGGG GCGACGCAGG TTCCGGTACC AGTAGCCCTC
21721 ATCCACCGGC TCGGTCACCC AGGCGCTGTC CACCGTGGAC CACCAGGCCA CCGACCCGGT
21781 CCCGCCGGAA ATCCCCTCCA GTACCTCGGC CAACTCGTCC TCGATGGCTT CCACGTGGGG
21841 CGTGTGGGAG GCGTAGTCGA CCGCGATACG GCGCACTCGC ACGCCTTCGG CCTCGTACCG
21901 CGTCACCACT TCTTCCACCG CGGACGGGTC CCCCGCCACC ACAGTCGAAG ACGGGCCGTT
21961 ACGCGCCGCG ATCCACACGC CCTCGACCAG GTCCACCTCA CCGGCCGGCA ACGCCACCGA
22021 AGCCATCGCC CCCCGCCCGG CCAGCCGCCC GGCGATCACC TGGCTGCGCA AGGCCACCAC
22081 GCGGGCGGCG TCCTCAAGGC TGAGGGCTCC GGCCACACAC GCCGCCGCGA TCTCGCCCTG
22141 GGAGTGTCCG ACCACCGCGT CCGGCACGAC CCCATGCGCC TGCCACAGCG CGGCCAGGCT
22201 CACCGCGACC GCCCAGCTGG CCGGCTGGAC CACCTCCACC CGCTCCGCCA CATCCGGCCG
22261 CGCCAACATC TCCCGCACAT CCCAGCCCGT GTGCGGCAAC AACGCCCGCG CACACTCCTC
22321 CATACGAGCC GCGAACACCG CAGAACACGC CATCAACTCC ACACCCATGC CCACCCACTG
22381 AGCACCCTGC CCGGGAAAGA CGAACACCGT ACGCGGCTGA TCCACCGCCA CACCCATCAC
22441 CCGGGCATCG CCCAACAACA CCGCACGGTG ACCGAAGACA GCACGCTCAC GCACCAACCC
22501 CTGCGCGACC GCGGCCACAT CCACACCACC CCCGCGCAGA TACCCCTCCA GCCGCTCCAC
```

-continued

```
22561 CTGCCCCCGC AGACTCACCT CACTCCGAGC CGACACCGGC AACGGCACCA ACCCATCGAC
22621 AGCCGACTCC CCACGCGACG GCCCGGGAAC ACCCTCAAGG ATCACGTGCG CGTTCGTACC
22681 GCTCACCCCG AAAGCGGAGA CACCGGCCCG GCGCGGACGT CCCGCGTCGG GCCACGCCCG
22741 CGCCTCGGTG AGCAGTTCCA CCGCGCCCTC GGTCCAGTCC ACATGCGACG ACGGCTCGTC
22801 CACATGCAGC GTCTTCGGCG CGATGCCATA CCGCATCGCC ATGACCATCT TGATGACACC
22861 GGCGACACCC GCAGCCGCCT GCGCATGACC GATGTTCGAC TTCAACGAAC CCAGCAGCAG
22921 CGGAACCTCA CGCTCCTGCC CGTACGTCGC CAGAATCGCG TGCGCCTCGA TGGGATCGCC
22981 CAGCGTCGTC CCCGTCCCGT GCGCCTCCAC CACGTCCACG TCGGCGGGGG CGAGCCCCGC
23041 CTTGTGGAGG GCCTGGCGGA TGACGCGCTG CTGGGAGGGG CCGTTGGGTG CGGAGATGCC
23101 GTTGGAGGCG CCGTCCTGGT TGACGGCGGA GGAGCGGACG ACCGCGAGGA CGGTGTGTCC
23161 GTTGCGCTCG GCGTCGGAGA GCTTTTCGAC GACGAGGACG CCGGCCCCCT CGGCGAAACC
23221 GGTGCCGTCC GCCGCGTCAG CGAACGCCTT GCACCGTCCG TCCGGCGCGA CGCCGCCCTG
23281 CCGGGAGAAC TCCACGAAGG TCTGTGGTGA TGCCATCACT GTGACACCAC CGACCAGCGC
23341 CAGCGAGCAC TCCCCGGTCC GCAGCGCCTG CCCGGCCTGG TGCAGCGCGA CCAGCGACGA
23401 CGAACACGCC GTGTCGACCG TGACCGCCGG ACCCTCCATG CCGAAGAAGT ACGACAGCCG
23461 TCCGGCGAGC ACCGCGGGCT GTGTGCTGTA GGCGCCGAAT CCGCCCAGGT CCGCGCCCGT
23521 GCCGTAGCCG TAGTAGAAGC CGCCGACGAA GACGCCGGTG TCGCTGCCGC GCAGGGTGTC
23581 CGGCACGATG CCGGCGTGTT CGAGCGCCTC CCAGGCGATT TCGAGGAGGA TCCGCTGCTG
23641 CGGGTCGAGT GCGGTGGCCT CGCGCGGACT GATGCCGAAG AACGCGGCAT CGAAGTCGGC
23701 GGCGCCCGCG AGTGCGCCGG CCCGCCCGGT GGCGGACTCG GCGGCGGCGT GCAGCGCGGC
23761 CACGTCCCAG CCGCGGTCGG TGGGGAAGTC GCCGATCGCG TCGCGGCCGT CCGCGACGAG
23821 CTGCCACAGC TCTTCCGGTG AGGTGACGCC GCCCGGCAGT CGGCAGGCCA TGCCGACGAC
23881 GGCGAGCGGC TCGTTCGCCG CGGCGCGCAG CGCGGTGTTC TCCCGGCGGA GCTGCGCGTT
23941 GTCCTTGACC GACGTCCGCA GCGCCTCGAT CAGGTCGTTC TCGGCCATCG CCTCATCCCT
24001 TCAGCACGTG CGCGATGAGC GCGTCTGCGT CCATGTCGTC GAACA(TTCG TCGTCCGGCT
24061 CCGCGGTCGT GGTGCTCGCG GGTGCCTGTG CCGGTGGTTC ACCGCCGTCC GGGGTCCCGT
24121 TGTCGTCCGG GGTCCCGTTG ACGTCCGGGG CCAGGAGGGT CAGCAGATGA CGGGTGAGCG
24181 CGCCGGCGGC GGGATAGTCG AAGACGAGCG TGGCCGGCAG CGGAATGCCG AGGGCCTCGG
24241 AGAGCCGGTT GCGCAGGCCG AGCGCGGTGA GCGAGTCGAC CCCGAGGTCC TTGAACGCCG
24301 TGGTGGCCGT GACCGCCGCC GCGTCGGTGT GGCCCAGCAG GGTGGCGGCG GTGTCGCGGA
24361 CGACGCCGAG CAGCACCTGT TCCCGTTCCT TGTGGGGCAG GTCCGGCAGG CGTTCCAGCA
24421 GGGAGCCGCC GTCGGTCGCG GAGCGCCGGG TGGGGCGCTG GATCGGTCGC CACAGCGGTG
24481 ACGGGTCGCC GGGCCCGGGT GGGGCGGTCG CCACGACCAC GGCTTCCCCG GTGGCGCACG
24541 CGGCGTCGAG GAGGTCGGTC AGCCGGTCCG CCGCGGCGGT GAACGCCACG GCCGGCAGGC
24601 CTTGTGCCCG GCGCAGGTCG GCCAGGGCCT GGAGCGGTCC GGCCGCCTCG CCGGACGGAA
24661 CGGCGAGAAC GAACGCGGTC AGGTCGAGGT CGCGGGTCAG GCGGTGCAGT TCCCAGGCCG
24721 ACTCGGCGGT GCCGTCCGCG TGGACGACCG CGGTCACCGG GGTTTCCGGC ACTGTGCCCG
24781 GCTCGTACCG GATCACTTCG GCGCCGTGTC CGCCGAGGTG TCCGGCGAGT TCCTCCGAAC
24841 CGCCCGCGAG GAGGACGGTG TCGCCGTACG AGGCCGCGGC CGTGGTGGGC GCGGCGGGGA
24901 CGAGGCGGGG CGCTTCGAGG CGCCCGTCGG CCAGGCGCAG GTGCGGTTCG TCGAGGCGGG
24961 AGAGGGCGGC GGCGCGGCGG GGGGTGACCG TGTqGGTGGT CTCCAqGAGC ACGAGCCGGC
25021 CCGGTTCCGC GGTGTCGAGC AGTGCGGCGA CGGCACCGGC GACGGGCCCG GCCTCGGCGG
25081 ACACCACCAG CGTGGCGCCG GCGGTCCTCG GGTCGTCCAG TGCGGTACGG ACCTCGTCGG
25141 GACCGGATAC CGGGACGACG ATGACGTCGG GCGTGGCGTC GTCGCCGAGG TCGGTGTACC
25201 GGCGGGCCGT GGTGCCGGGT GCCGCCGGGG CCCGGACGCC GGTCCAGGTG CGCCGGAACA
25261 GCCGCACGTC CCCGTCCGGG CCCGTCGTGG CGGGGGGCCG GGTGATGAGC GAGCCGATCT
25321 GAGCCACCGG CCGTCCCAGT TCGTCGGCGA GGTGCACGCG GGCGCCGCCC TCGCCCTCGC
25381 CGTGGACGAA GGTGACGCGC AGTTTCGTGG CGCCGCTGGT GTGGACACGG ACGCCGGTGA
25441 ACGCGAACGG CAACCGTACC CCCGCGTTCT CGGCGGCCGC GCCGATGCTG CCCGCTTGCA
25501 GCGCGGTGAC GAGCAGCGCC GGGTGCAGTG TGTAGCGGGC GGCGTCCCTG GCGAGGGCGC
25561 CGTCGAGGGC GACTTCGGCG CAGACGGTGT CTCCGTGGCT CCACGCGGCG GACATGCCGC
25621 GGAACTCGGG GCCGAACTCG TATCCCGCGT CGTCGAGTCG CTGGTAGAAG GCCGCGACGT
25681 CGACCGGTTC CGCGTGCTCG GGCGGCCAGG GCCCCGGCGT GGTGGCCGGT TCGGTGGTGG
25741 CGATGCCGGC GAAGCCGGAG GCGTGGCGGG TCCATGTCCG GTCGCCGTCC GTCCGGGCGT
25801 GGACGCGCAC GGCACGGCGT CCGGTGTCGT CGGGCGCGGC GACGGTCACG CGCACCTGGA
25861 CGGCGCCGGT GGCGGGCAGG ACCAGCGGTG TCTCGACGAC CAGTTCGTCG AGCAGGTCGC
25921 AGCCTGCCTC GTCGGCGCCG CGTCCGGCCA ATTCCAGGAA GGCGGGTCCG GGCAGCAGTA
25981 CGGCGCCGTC GACGGAGTGA CCGGCCAGCC ATGGGTGGGT GGCCAGCGAG AACCGGCCGG
26041 TGAGCAGCAC CTCGTCGGAG TCGGGGAGCG CCACCGACGC GGCGAGCAGC GGGTGGTCGA
26101 CGGCGTCGAG TCCGAGGCCG GAAGCGTCCG TGCCGGCCGC GGTCTCGATC CAGTAGCGCT
26161 CATGGTGGAA GGCGTATGTG GGCAGGTCGT GTGCCGTCGC CGTCGCGGGG ACGACCGCCG
26221 CCCAGTCGAC GGGCACGCCG GTTGTGTGCG CCTCGGCCAG CGCGGTGAGC AGCCGGTGGA
26281 CTCCCCCGCC GCGGCGGAGC GTGGCGACGG TCGCGCCGTC GATCGCGGGC AGCAGCACGG
26341 GGTGCGCGCT GACCTCGACG AACACGGTGT CACCCGGCTC GCGGGCAGCG GTCACGGCCG
26401 TGGCGAAGCC TACGGGGTGG CGCATGTTGC GGAACCAGTA CTCGTCGTCG AGCGGCGCGT
26461 CGATCCAGCG TTCGTCGGCG GTGGAGAACC ACGGGATCTC GGGCGTGCGC GAGGTGGTGT
26521 CCGCGACGAT CCGCTGGAGT TCGTCGTACA GCGGGTCGAC GAACGGGGTG TGGGTCGGGC
26581 AGTCGACGGC GATGCGGCGC ACCCAGACGC CGCGGGCCTC GTAGTCGGCG ATCAGCGTTT
26641 CGACGGCGTC CGGGCGCCCG GCGACGGTCG TGGTGGTGGC GCCGTTGCGG CCCGCGACCC
26701 AGACGCCGTC GATCCGGGCG GCATCCGCCT CGACGTCGGC GGCCGGGAGC GCGACCGAGC
26761 CCATCGCGCC GCGTCCGGCG AGTTCGCGCA GGAGCAGGAG AACGCTGCGC AGCGCGACGA
26821 GGCGGGCACC GTCCTCCAGG GTGAGCGCTC CGGCGACACA GGCCGCGGCG ATCTCGCCCT
26881 GGGAGTGTCC GATGACGGCG TCCGGGCGTA CGCCCGCGGC CTCCCACACG GCGGCCAGCG
26941 ACACCATGAC GGCCCAGCAG ACGGGGTGCA CGACGTCGAC GCGGCGGGTC ACCTCCGGGT
27001 CGTCGAGCAT GGCGATGGGG TCCCAGCCCG TGTGCGGGAT CAGCGCGTCG GCGCATTGGC
27061 GCATCCTGGC GGCGAACACC GGGGAGGCCG CCATCAGTTC GACGCCCATG CCGCGCCACT
27121 GCGGTCCTTG TCCGGGGAAG ACGAAGACGG TGCGCGGCTC GGTGAGCGCC GTGCCGGTGA
27181 CGACGTCGTC GTCGAGCAGC ACGGCGCGGT GCGGGAACGT CGTACGCCTG GCGAGCAGGC
27241 CCGCGGCGAT GGCGCGCGGG TCGTGGCCGG GACGGGCGGC GAGGTCCTCG CGGAGTCGGC
27301 GGACCTGGCC GTCGAGGGCC GTGGCGGTCC GCGCCGAGAC GGGCACTGGT GTGAGCGGCG
```

-continued

27361 TGGCGATCAG CGGCTCACCG GGCTTCGAGG CCGACGGCTC CTCGGCCGGC GGCTCCCCGG
27421 CCGGGTGGGC TTCCAGCAGG ACGTGGGCGT TGGTGCCGCT GACGCCGAAG GAGGACACAC
27481 CGGCGCGCCG CGGGCGGTCG GTCTCGGGCC AGGGCCGGGC ATCGGTGAGG AGTTCGACGG
27541 CGCCGGCCGT CCAGTCGACG TGCGAGGACG GCGTGTCCAC GTGCAGGGTG CGCGGCAGGG
27601 TGCCGTGCCG CATGGCGAGG ACCATCTTGA TGACACCGGC GACACCCGCG GCGGCCTGAG
27661 TGTGGCCGAT GTTGGACTTC AGCGAGCCCA GCAGCACCGG GGTGTCGCGC CCCTGCCCGT
27721 AGGTGGCCAG CACCGCCTGT GCCTCGATGG GATCGCCCAG CCTGGTGCCG GTGCCGTGCG
27781 CCTCCACGGC GTCCACGTCC GCCGGGGTGA GCCCGGCGTT GGCCAGGGCC TGCCGGATCA
27841 CCCGCTCCTG CGAGGGCCCG TTCGGCGCCG ACAACCCGTT GGAAGCACCG TCCTGGTTGA
27901 CCGCCGAACC CCGGACAACC GGCAGCACAC GGTGGCCGTT GCGCTCGGCA TCGGAGAGCC
27961 TCTCGACGAT CAGCACACCG GACCCCTCGG CGAAACCGGT GCCGTCAGCC GCATCCGCGA
28021 ACGCCTTGCA GCGCGCGTCG GGCGCGAGAC CCCGCTGCTG GGAGAACTCG ACGAAGCCGG
28081 ACGGCGAGGC CATQACCGTG ACGCCGCCGA CCAGGGCGAG CGAGCATTCG CCGGAGCGCA
28141 GTGACTGCCC GGCCTGGTGC AGCGCCACCA GCGACGACGA ACACGCCGTG TCGACCGTGA
28201 CCGCCGGACC CTCCAGACCG TAGAAGTACG ACAGCCGACC GGACAGCACA CTGGTCTGGG
28261 TGCCGGTCGC GCCGAAACCG CCCAGGTCGG TGCCGAGTCC GTACCCGTCG GAGAAGGCGC
28321 CCATGAACAC GCCGGTGTCG CTTCCGCGCA GCGACTCCGG GAGGATCCCG GCGTGTTCCA
28381 GCGCCTCCCA CGAGGTCTCC AGGACCAGAC GCTGCTGCGG GTCCATCGCC AGCGCCTCAC
28441 GCGGACTGAT CCCGAAGAAC GCCGCGTCGA AGTCCGCCAC CCCGGCGAGG AAGCCACCAT
28501 GACGCACGGT CGACGTGCCC GGATGATCCG GATCGGGATC GTACAGCCCG TCCACGTCCC
28561 AACCACGGTC CGTCGGAAAC GCCGTGATCC CGTCACCACC CGACTCCAGC AGCCGCCACA
28621 AGTCCTCCGG CGACGCGACC CCACCCGGCA GCCGGCAGGC CATCCCCACG ATCGCCAACG
28681 GCTCGTCCTG CCGGACGGCC GCGGTCGTGG TGCGGGTCGG CGATGCCGTC CGGCCGGACA
28741 GCGCCGCGGT GAGCTTCGCC GCGACGGCGC GCGGCGTCGG GAAGTCGAAG ACCGCGGTGG
28801 CGGGCAGCCG TACGCCCGTC GCCTCGGTGA AGGCGTTGCG CAGCCGGATC GCCATGAGCG
28861 AGTCGACGCC GAGTTCCTTG AACGTGGCGG TCGCCTCGAC CCGTGCGGCA CCGTCGTGGC
28921 CGAGTACGGC CGCGGTGCAC TGCCGGACGA CGGCGAGCAC GTCCTTTTCG GCGTCCGCGG
28981 CGGAGAGCCG CGCGATCCGG TCGGCGAGGG TGGTGGCGCC GGCCGCCCGG CGCCGCGGCT
29041 CCCGGCGCGG TGCGCGCAGC AGGGGCGAGC TGCCGAGGCC GGCCGGGTCG GCGGCGACCA
29101 GCGCCGGGTC CGAGGACCGC AACGCCGCGT CGAACAGCGT CAGTCCGCCT TCGGCGGTCA
29161 GCGCCGTCAC GCCGTCGCGG CGCATGCGGG CGCCGGTGCC GACCGTCAGC CCGCTCTCCG
29221 GTTCCCACAG GCCCCAGGCC ACGGACAACG CGGGCAGTCC GGCTGCCCGG CGCTGTTCGG
29281 CCAGCGCGTC GAGGAACGCG TTCGCGGCCG CGTAGTTGCC CTGTCCGGGG CTGCCGAGCA
29341 CACCGGCGGC CGACGAGTAG AGGACGAACG CGGCCAGTTC CGTGTTCTGG GTGAGTTCGT
29401 GCAGGTGCCA CGCGGCGTCC ACCTTCGGGC GCAGCACCGT CTCGAGCCGG TCGGGGGTGA
29461 GCGCGGTGAG GACGCCGTCG TCGAGGACGG CCGCGGTGTG CACGACGGCC GTGAGCGGGT
29521 GCGCCGGGTC GATCCCCGCC AGTACGGAGG CGAGTTCGTC CCGGTCGGCG ACGTCGCAGG
29581 CGATCGCCGT GACCTCGGCG CCGGGCACGT CGCTCGCCGT GCCGCTGCGC GACAGCATCA
29641 GCAGCCGGCG CACGCCGTGG CGTTCGACGA GGTGGCGGCT GATGATGCCG GCCAGCGTCC
29701 CGGAGCCACC GGTGACGAGC ACGGTGCCGT CCGGGTCGAG CGCCGGAGCG TCACCCGCCG
29761 GGACCGCCGG GGCCAGACGG CGGGCGTACA CCTGGCCGTC ACGCAGCACC ACCTGGGGCT
29821 CATCGAGCGC GGTGGCCGCT GCGAGCAGCG GCTCGGCGGT GTCCGGGGCG GCGTCGACGA
29881 GGACGATCCG GCCGGGGTGT TCGGCCTGCG CGGTCCGCAC CAGTCCGGCG GCCGCGGCCG
29941 ACGCGAGACC GGGCCCGGTG TGGACGGCCA GGACCGCGTC GGCGTACCGG TCGTCGGTGA
30001 GGAAGCGCTG CACGGCGGTC AGGACGCCGG CGCCCAGTTC GCGGGTGTCG TCGAGCGGGG
30061 CACCGCCGCC GCCGTGCGCG GGGAGGATCA CCACGTCCGG GACCGTCGGG TCGTCGAGGC
30121 GGCCGGTCGT CGCGGTCGTG GGCGGCAGCT CCGGGAGCTC GGCCAGCACC GGGCGCAGCA
30181 GGCCCGGAAC GGCTCCCGTG ATCGTCAGGG GGCGCCTGCG CACGGCGCCG ATGGTGGCGA
30241 CGGGCCCGCC GGTCTCGTCC GCGAGGTGTA CGCCGTCAGC GGTGACGGCG ACGCGTACCG
30301 CCGTGGCGCC GGTGGCGTGG ACGCGGACGT CGTCGAACGC GTACGGAAGG TGGTCCCCTT
30361 CCGCGGCGAG GCGGAGTGCG GCGCCGAGCA GCGCCGGGTG CAGGCCGTAC CGTCCGGCGT
30421 CGGCGAGCTG TCCGTCGGCG AGGGCCACTT CCGCCCAGAC GGCGTCGTCG TCGGCCCAGA
30481 CGGCGCGCGG GCGGGGCAGC GCGGGCCCGT CCGTGTACCC GGCTCGGGCC AGACGGTCGG
30541 CGATGTCGTC GGGGTCCACC GGCCGGGCCG TGGCGGGCGG CCACGTCGAC GGCATCTCCC
30601 GCACGGCCGG GGCCGTCCGC GGGTCGGGGG CGAGGATTCC GTGCGCGTGC TCGGTCCACT
30661 CCCCCGCCGC GTGCCGCGTG TGCACGGTGA CCGCGCGGCG GCCGTCCGCC CCGGGCGCGC
30721 TCACCGTGAC GGAGAGCGCG AGCGCACCGG ACCGCGGCAG CGTGAGGGGG GTGTCCACGG
30781 TGAACGTGTC GAGGGCGCCG CAGCCGGCTT CGTCGCCCGC CCGGATCGCC AGATCCAGGA
30841 GGGCCGCGGC GGGCAGCACC GCGAGGCCGT GCAGGGAGTG CGCCAGCGGA TCGGCGGCGT
30901 CGACCCGGCC GGTGAGCACC AGGTCGCCGG TGCCGGGCAG GGTGACCGCC GCGGTCAGCG
30961 CCGGGTGCGC GACCGGCGTC TGTCCGGCCG GGGCCGCGTC GCCCGCGGTC TGGGTGCCGA
31021 GCCAGTAGCG GACCCGCTCG AACGGGTACG TCGGCGGGTG CGAGGCGCGT GCCGGCGCGG
31081 GGTCGATGAC CTTCGGCCAG TCGACCGTGA CGCCGTCGGT GTGCAGCCGG GCGAGCGCGG
31141 TCAGGGCGGA TCGCGGTTCG TCGTCGGCGT GCAGCATCGG GATGCCGTCG ACGAGTCGGG
31201 TCAGGCTCCG GTCCGGGCCG ATCTCCAGGA GCACCGCCCC GTCGTGCGCG GCGACCTGTT
31261 CCCCGAACCG GACGGTGTCG CGGACCTGTC GTACCCAGTA CTCCGGCGTG GTGCAGGCGG
31321 CGCCCGCGGC CATCGGGATC CTCGGCTCGT GGTACGTCAG GCTCTCCGCG ACCTTGCGGA
31381 ACTCCTCGAG CATCGGCTCC ATCCGCGCCG AGTGGAACGC GTGGCTGGTC CGCAGGCGGG
31441 TGAAGCGGCC GAGCCGGGCC GCGACGTCGA GCACCGCCTC CTCGTCACCG GAGAGCACGA
31501 TCGACGCGGG CCCGTTGACC GCGGCGATCT CCACGCCGTC CCGCAGCAGC GGCAGCGCGT
31561 CCCGTTCCGA CGCGATCACG GCGGCCATCG CCCCGCCGGA CGGCAGCGCC TGCATCAGGC
31621 GGGCCCGTGC GGACACCAGC CTGCACGCGT CCTCCAGGGA CCAGACGCCG GCGACGTACG
31681 CGGCGGCCAG CTCGCCGATC GAATGGCCCA CGAAGGCGTC CGGGCGTACG CCCCACGCCT
31741 CGAGCTGTGC GCCGAGTGCG ACCTGGAGCG CGAACACCGC GGGCTGGGCG TACCCGGTGT
31801 CGTGGAGGTC GAGCCCGGCG GGCACGTCGA GGGCGTCCAG CACCTCGCGG CGAGTGCGGG
31861 CGAAGACGTC GTAGGCGGCG GCCAGTCCGT CGCCCATGCC GGGACGTTGT GAGCCCTGTC
31921 CGGAGAAGAG CCACACGAGG CGGCGGTCCG GTTCTGCGGC GCCCGTGACC GTGTCGGTGC
31981 CGATCAGCGC GGCCCGGTGC GGGAAGGCCG TGCGGGCGAG CAGGGCCGCG GCCACCGCGC
32041 GCTCGTCCTC CTCGCCGGTG GCGAGGTGGG CGCGCAGGCG GTGTACCTGT GCGTCGAGTG
32101 CCTGCGGGGT GCGTGCCGAG AGCAGCAGGG GCAGCGGTCC GGTGTCGGGT GCCGGGGCGG

-continued

```
32161 GTTCGGGGGC CGGTCGGGGG TGGCTTTCGA GGATQATGTG AGCGTTGGTG CCGCTAACGC
32221 CGAAGGAGGA CACCCCGGCG CGCCGTGGGC GGTCGGTTTC GGGCCAGGGG CGGGCGTCGG
32281 TGAGGAGTTC GACGGCGCCG GCCGTCCAGT CGACGTGCGA GGACGGCGTG TCCACGTGCA
32341 GGGTGCGCGG CAGGGTGCCG TGCCGCATGG CGAGGACCAT CTTGATGACA CCGGCGACGC
32401 CCGCGGCGGC CTGAGTGTGG CCGATGTTGG ACTTCAGCGA GCCCAGCAGC ACCGGGGTGT
32461 CGCGATGCTG CCCGTAGGTQ GCCAGTACCG CCTGCGCCTC GATGGGGTCG CCCAGCCTGG
32521 TCCCGGTGCC ATGCGCCTCG ACAGCGTCCA CATCCGCCGG GGTGAGCCCG GCGTTGGCCA
32581 GCGCCTGCCG GATCACCCGC TCCTGCGACG GCCCGTTCGG CGCCGACAAC CCGTTGGAAG
32641 CACCGTCCTG GTTGACCGCC GAACCACGCA CGACCGCCAG GACATTGTGG CCGTGCQGCT
32701 CGGCGTCGGA GAGCCTCTCG ACGATCAGCA CACCGGATCC CTCGGCGAAA CCGGTGCCAT
32761 CAGCCGCATC CGCGAACGCC TTGCAGCGGC CGTCCGGGGA GAGGCCCCGC TGCTGGGAGA
32821 AGTCCACGAA GCCGGACGGC GAGGCCATCA CCGTGACGCC GCCGACCACG GCGAGCGAGC
32881 ACTCCCCCGA GCGCAGCGAC TGCCCGGCCT GGTGCAGCGC CACCAGCGAC GACGAACACG
32941 CCGTGTCCAC CGTGACCGCC GGACCCTCCA AACCGTAGAA GTACGACAGC CGACCGGACA
33001 GCACACTGGT CTGGGTGCTG GTGGCACCGA AACCGCCGCG GTCGGCTCCA GTGCCGTACC
33061 CGTAGAAGTA GCCGCCCATG AACACGCCGG TGTCGCTTCC GCGCAGCGAC TCCGGGAGGA
33121 TCCCGGCGTG TTCCAGCGCC TCCCACGAGG TCTCCAGGAC CAGACGCTGC TGCGGGTCCA
33181 TCGCCAGCGC CTCACGCGGA CTGATCCCGA AGAACGCCGC GTCGAAGTCC GCCACCCCGG
33241 CGAGGAAGCC ACCATGACGC ACGGTCGACG TGCCCGGATG ATCCGGATCG GGATCGTACA
33301 GCCCGTCCAC GTCCCAACCA CGGTCCGTCG GAAACGCCGT GATCCCGTCA CCACCCGACT
33361 CCAGCAGCCG CCACAAGTCC TCCGGCGACG CGACCCCACC CGGCAGCCGG CAGGCCATCC
33421 CCACGATCGC CAACGGCTCG TCCTGCCGGA CGGCCGCGGT CGGGGTACGC CGCCGGGTGG
33481 TGGCCCGCGC GCCGGCCAGT TCGTCCAGGT GGGCGGCGAG CGCCTGCGCC GTGGGGTGGT
33541 CGAAGACGAG CGTAGCGGGC AGCGTCAGGC CCGTCGCGTC GGCCAGCCGG TTGCGCAGTT
33601 CGACGCCGGT CAGCGAGTCG AAGCCCACTT CCCTGAACGC GCGCGCGGGT GCGATGGCGT
33661 GGGCGTCGCG GTGGCCGAGC ACCGCGGCAG CGCTGGTACG GACGAGGTCG AGCATGTCGC
33721 GCGCGGCCGG AGGTGCGGAC GTGCGCCGGA CGGCCGGCAC GAGGGTGCGT AGGACCGGCG
33781 GGACCCGGTC GGACGCGGCG ACGGCGGCGA GGTCGAGCCG GATCGGCACG AGCGCGGGCC
33841 GGTCGGTGTG CAGGGCCGCG TCGAACAGGG CGAGCCCCTG TGCGGCCGTC ATCGGGGTCA
33901 TGCCGTTGCG GGCGATGCGG GCCAGGTCGG TGGCGGTCAG CCGCCCGCCC ATCCCGTCCG
33961 CCGCGTCCCA CAGTCCCCAG GCGAGCGAGA CGGCGGGCAG CCCCTGGTGG TGCCGGTGGC
34021 GGGCGAGCGC GTCGAGGAAC GCGTTGCCGG TCGCGTAGTT GGCCTGACCC GCGCCGCCGA
34081 ACGTGGCGGA TATGGACGAG TACAGGACGA ACGCGGCCAG GTCGAGATCG CGCGTCAGCT
34141 CGTGCAGGTG CCAGGCGACG TCCGCCTTGA CCCGCAGCAC GGCGTCCCAC TGCTCCGGCC
34201 GCATGGTCGT CACGGCCGCG TCGTCGACGA TCCCGGCCAT GTGCACGACG GCGCGCAGCC
34261 GCTGGGCGAC GTCGGCGACG ACTGCGGCCA GCTCGTCGCG GTCPACGACG TCGGCGGCCA
34321 CGTACCGCAC GCGGTCGTCC TCCGGCGTGT CGCCGGGCCG GCCGTTGCGG GACACCACGA
34381 CGACCTCGGC GGCCTCGTGC ACGGTGAGCA GGTGGTCCAC GAGGAGGCGG CCGAGCCCGC
34441 CGGTGCCGCC GGTGACGAGG ACGGTCCCGC CGGTCAGCGG GGAGGTTCCG GTGGCCGCGG
34501 CGACACGGCG CAGACGGGCC GCACGCGCTG TGCCGTCGGC GACCCGGACG TGCCGCTCGT
34561 CGCCGGCGGC GAGCCCGGCC GCTATGGCGG CGGGCGTGAT CTCGTCCGCT TCGATCAGGG
34621 CGACGCGGCC GGGATGCTCC GTCTCCGCCG TCCGGACCAG GCCGCCGAGC GCTTCCTGCG
34681 CGGGATCGCC GGTACGGGTG GCCACGATGA GCCGGGATCG CGCCCAGCGC GGCTCGGCGA
34741 GCCAGGTCTG CACGGTGGTG AGCAGGTCGC GGCCCAGCTC CCGQGTCCGG GCGCCGGGCG
34801 AGGTGCCCGG GTCGCCGGGT TCCACGGCCA GGACCACGAC CGGGGGGTGC TCGCCGTCGG
34861 GCACGTCGGC GAGGTACGTC CAGTCGGGGA CGGGTGACGC GGGCACGGGC ACCCAGGCGA
34921 TCTCGAACAG CGCCTCGGCA TCGGGGTCGG CGGCCCGCAC GGTCAGGCTG TCGACGTCAA
34981 GGACCGGTGA GCCGTGCTCG TCCGTGGCGA CGATGCGGAC CATGTCGGGG CCGACGCGTT
35041 CCAGCAGCAC GCGCACCGCG GTCGCGGCGC GCGCGTGGAT CCTCACGCCG GACCAGGAGA
35101 ACGCCAGCCG GCGCCGCTCC GGGTCCGTGA AGACCGTCCC GAGGGCGTGC AGGGCCGCGT
35161 CGAGCAGCAC GGGGTGCAGC CCGTACCGGG CGTCGGTGAG CTGTTCGGCG AGGCGGACCG
35221 ACGCGTAGGC GCGGCCCTCC CCCGTCCACA TCGCGGTCAT GGCCCGGAAC GCGGGCCCGT
35281 ACGAGAGCGG CAGCGCGTCG TAGAAGCCGG TCAGGTCGGC CGGGTCGGCG TCGGCGGGCG
35341 GCCAGTCCAC GGGCTCCGCC GGACCGCCAG TGTCCACGCT CAGCGCTCCG GTCGCACTGA
35401 GCGCCCAGGG GCCCGTGCCG GTACGGCTGT GCAGACTCAC CGACCGCCGT CCGGACACCT
35461 CGGTTCCGAC GGTGGCCTGG ATCTCCGTGT CGCCGTCGCC GTCGACCACC ACCGGCGCGA
35521 CGATGGTCAG CTCCGCGATC TCCGGCGTGC CGAGCCGGGC TCCCGCTTCG GCGAGCAGTT
35581 CCACGAGCGC CGAGCCGGGC ACGATGACCC GGCCGTCCAC CTCGTGGTCG GCGAGCCAGG
35641 GCTGACGGCG TACCGAGACA CCGCGGTGGC CAGCGCGCCC TCGCCGTCGG GCGAGGTCGA
35701 CCCACGAGCC GAGCAGCGGG TGGCCGGACG TTCCCGCCGG TTCCGCGTCG ATCCAGTAGC
35761 GGTCACGGCG GAACGGGTAC GTGGGCAGCG GCACCACCCG ACCCGTCGCG AACGACCAGG
35821 TGACGGGCAC GCCCCGGACC CAGAGCGCGG CGAGCGACCG AGTGAAGCGG TCCAGGCCGC
35881 CCTCGCCTCG CCGCAGTGTG CCGGTGACGA CCGTATGCGC ATCCCCGGCG AGCGTCTCCT
35941 CCAGTGCGGT GGTGAGCACG GGATGCGCGC TGACCTCGAC GAACGCGCGG TATCCGCGGT
36001 CCGCCAGGTG GCCGGTCGCG GCGGCGAACC GAACGGTGCG GCGCAGGTTG TCGTACCAGT
36061 AGGCGGCGTC CGCGGGCCGG TCCAGCCACG CCTCGTCCAC GGTGGAGAAG AACGGGACGT
36121 CCGGCGTGCG CGGAGTGATG CCGGCGAGAG CGTCGAGCAG CGCGCCGCGG ATCGTTTCGA
36181 CATGCGCGGT GTGCGACGCG TAGTCGACGG CGATCCGGCG GGCGCGGGGG GTGGCGGCCA
36241 GCAGCTCCTC CACGGCGTCG GCCGCACCGG CGACAACGAT CGACGCGGGT CCGTTGACCG
36301 CGGCGACCTC CAGGCGCCCG GCCCACACGG CGGCGTCGAA GTCGGCGGGC GGCACCGAGA
36361 CCATGCCGCC CTGCCCGGCC AGTTCGGTGG CGACGAGTCG GCTGCGCACC GCGACGACCT
36421 TCGCGGCGTC GTCCAGGGTG AGCACCCCGG CGACGCAGGC CGCGGCGACT TCGCCCTGGG
36481 AGTGGCCGAC GACCGCGGCC GGGGCGACCC CGTGCGCACG CCACAGCTCC GCCAGCGCCA
36541 CCATCACCGC GAACGACGCG GGCTCCACGA CATCGACCCG GTCGAACGCG GGCGCTCCGG
36601 GCCGCTGGGC GATGACGTCC AGCAGGTCCC ATCCGGTGTG CGGGGCGAGC GCCGTGGCGC
36661 ACTCGCGGAG CCGCCGGGCG AACACGGGCT CGGTGGCGAG CAGTTCGGCA CCCATGCCGG
36721 CCCACTGGGA GCCCTGCCCG GGGAACGCGA ACACGACACG TGTGTCGGTG ACGTCGGCGG
36781 TTCCCGTCAC GGCCCCCGGC ACTTCGGCAC CACGGGCGAA CGCCTCCGCC TCTCGGGCCG
36841 GCACGACCGC CCGGTGGCGC ATGGCCGTCC GGGTGGTGGC GAGCGAGTGG CCGACCGCGG
36901 CCGCGGCGCC AGTGAGCGGG GCCAGCTGTC CCGCGACGTC CCGCAGTCCC TCCGGGGTCC
```

-continued

```
36961 GGGCCGACAT CGGCCAGACC ACGTCCTCGG GCACCGGCTC GGCTTCGGGT GCGGACACGG
37021 GTGCGGGCGC GGCGGGGGGC CCGGCCTCCA GGACGACATG GGCGTTGGTG CCGCTGATGC
37081 CGAACGACGA GACACCCGCA CGCCGGGCGC GCCCGGTGAC CGGCCACGGC TCACTGCGGT
37141 GCAGCAGCCG GATGTCGCCG TCCCAGTCGA CGTGCCGGGA CGGCTCGTCG ACGTGCAGCG
37201 TGCGCGGCAG GACGCCGTGC CGCATCGCCA TGACCATCTT GATGACGCCG GCGACGCCGG
37261 CCGCGGCCTG GGTGTGGCCG ATGTTCGACT TGAGCGAGCC GATCAGCAGC GGATGCACGC
37321 GTTCGCGCCC GTAGGCCACT TGCAGGGCCT GGGCCTCGAC GGGGTCGCCG AGACGGGTGC
37381 CGGTGCCGTG TGCCTCCACG GCGTCGACGT CACCCGGCGC CAGGCCGGCG TCGGCGAGCG
37441 CACGCTGGAT GACGCGCTGC TGCGCAGGCC CGTTCGGGGC GGACAGCCCG TTCGACGCGC
37501 CGTCGGAGTT GACCGCGGAG CCGCGCACCA GCGCCAGCAC GGGGTGGCCG TGGCGGGTGG
37561 CGTCGGAGAG CCGCTCCAGC ACCAGGACAC CGGCGCCCTC GGCGAAGCTC GTGCCGTCCG
37621 CGGTGTCCGC GAAGGCCTTG GCACGGCCGT CGGGGGCGAG CCCGCGCTGC CGGGAGAACT
37681 CGACGAACCC GGTCGTCGTC GCCATCACCG TGACACCGCC GACCAGGGCG AGCGAGCACT
37741 CCCCCGAGCG CAGCGACCGC GCGGCCTGGT GCAGCGCCAC CAGCGACGAC GAACACGCCG
37801 TGTCGACGGT GACCGACGGG CCCTCCAGAC CGAAGTAGTA CGAGAGCCGC CCGGAGAGAA
37861 CGCTGGTCGG CGTGCCGGTC GCCCCGAAAC CGCCCAGGTC CACGCCCGCG CCGTAGCCCT
37921 GGGTGAACGC GCCCATGAAT ACGCCGGTGT CGCTGCCGCG GACGCTTTCG GGCAGGATGC
37981 CCGCTCGTTC GAACGCCTCC CACGACGCTT CGAGGACCAG ACGCTGCTGC GGGTCCATCG
38041 CCAGCGCCTC ACGCGGGCTG ATCCCGAAGA ACGCGGCGTC GAAGTCGGCG GCGCCGGTGA
38101 GGAAGCCGCC GTGACGCACG GAAACCTTGC CGACCGCGTC GGGGTTCGGG TCGTAGAGCG
38161 CGGCGAGGTC CCAGCCGCGG TCGGCGGGGA ACTCGGTGAT CGCGTCCCCG CCGGAGTCGA
38221 CCAGCCGCCA CAGGTCCTCC GGTGACCGCA CGCCACCGGG CATCCGGCAC GCCATGGCCA
38281 CGATCGCCAG CGGCTCGTTC CCCGCCACCG TCGGTGCGGG CACTGTCGCC GCCGGAGCGG
38341 CAGGGGCCGG CTCACCCCGC CGTTCCTCAT CCAGGCGGGC GGCGAGCGCG GCCGGTGTCG
38401 GGTGGTCGAA GACGGCCGTC GCGGAGAGCC GTACCCCCGT CGTCTCGGCG AGGCTGTTGC
38461 GCAACCGGAC ACCGCTGAGC GAGTCGATGC CGAGGTCCTT GAACGCCGTC GTGGGCGTGA
38521 TCTCGGAGGC GTCGGCGTGG CCGAGCACGG CGGCCGTGGC CGCACACACG ATGGCCAGCA
38581 GGTCACGATC GCGGTCGCGG TCGCGGTCGC GGTTGTCCTC CGCACGGGCG GCGATGCGGC
38641 GCTCGGTCCG CTGCCGGACG GGCTCGGTGG GAATCGCCGC GACCATGAAC GGCACGTCCG
38701 CGGCGAGGCT CGCGTCGATG AAGTGGGTGC CCTCGGCCTC GGTGAGCGGC CGGAACCCGT
38761 CGCGCACCCG CTGCCGGTCG GCGTCGTCAA GTTGTCCGGT GAGGGTGCTG GTGGTGTGCC
38821 ACATGCCCCA GGCGATGGAG GTGGCGGGTT GGCCGAGGGT GTGGCGGTGG GTGGCGAGGG
38881 CGTCGAGGAA GGCGTTGGCG GCGGCGTAGT TTCCTTGTCC GGGGCTGCCG AGGACGGCGG
38941 CGGCGCTGGA GTAGAGGACG AAGTGGGTGA GGGGTTGGTT TTGGGTGAGG TGGTGCAGGT
39001 GCCAGGCGGC GTTGGCTTTG GGGTGGAGGA CGGTGGTGAG GCGGTCGGGG GTGAGGGCGT
39061 CGAGGATGCC GTCGTCGAGG GTGGCGGCGG TGTGGAAGAC GGCGGTGAGG GGTTGGGGGA
39121 TGTGGGCGAG GGTGGTGGCG AGTTGGTGGG GGTCGCCGAC GTCGCAGGGG AGGTGGGTGC
39181 CGGGGGTGGT GTCGGGGGGT GGGGTGCGGG AGAGGAGGTA GGTGTGGGGG TGGTTCAGGT
39241 GGCGGGCGAG GATGCCGGCG AGGGTGCCGG AGCCGCCGGT GATGATGATG GCGTGTTCGG
39301 GGTTGAGGGG GGTGGTGGTG GGTGGGGTGG TGGTGTGGAG GGGGCTGAGG TGGGGTCGGT
39361 GGAGGGTGTG GTGGGTGAGG CGGAGGTGGG GGTGGTCGAG GGTGGCGAGT TGGGCCAGGG
39421 GGAGGGGAGT GTGGGGGTGG TCGGTTTCGA TGAGGCGGAT GCGGTGGGGG TGTTCGTTCT
39481 GGGCGGTGCG GGTGAGGCCG GTGACGGTGG CGCCGGCGGG GTCGGTGGTG GTGTGGACGA
39541 TGAGGGTGTG GTCGGTGGTG GTGAGGTGGT GTTGCAGGGC GGTCAGGACG CGGGTGGCGC
39601 GGGTGTGGGC GCGGGTGGGT ATGTCCTCGG GGTCGTCGGG GTGGGCGGCG GTGATCAGGA
39661 CGTGTCCCTC GGGCAGGTCA CCGTCGTAGA CCGCCTCGGC GACCGCGAGC CACTCCAACC
39721 GGAGCGGGTT CGGCCCCGAC GGGGTGTCGG CCCGCTCCCT CAGCACCAGC GAGTCCACCG
39781 ACACGACAGG ACGGCCATCC GGGTCGGCCA CGCGCACGGC GACGCCGGCC TCCCCCCGGG
39841 TGAGGGCGAC GCGCACCGCG GCGGCCCCGG TGGCGTTCAG GCGCACGCCC GTCCAGGAGA
39901 ACGGCAGCTC GATCCCGCCG CCCGCGTCGA GGCGCCCGGC GTGCAGGGCC GCGTCGAGCA
39961 GTGCCGGATG CACACCGAAA CCGTCCGCCT CGGCGGCCTG CTCGTCGGGC AGCGCCACCT
40021 CGGCATACAC GGTGTCACCA TCACGCCAGG CAGCCCGCAA CCCCTGGAAC GCCGACCCGT
40081 ACTCATAACC GGCATCCCGC AGTTCGTCAT AGAACCCCGA GACGTCGACG GCCGCGGCCG
40141 TGGCCGGCGG CCACTGCGAG AACGGCTCAC CGGAAGCGTT GGAGGTATCC GGGGTGTCGG
40201 GGGTCAGGGT GCCGCTGGCG TGCCGGGTCC AGCTGCCCGT GCCCTCGGTA CGCGCGTGGA
40261 CGGTCACCGG CCGCCGTCCG GCCTCATCGG CCCCTTCCAC GGTCACCGAC ACATCCACCG
40321 CTGCGGTCAC CGGCACCACG AGCGGGGATT CGATGACCAG TTCATCCACC ACCCCGCAAC
40381 CGGTCTCGTC ACCGGCCCGG ATGACCAGCT CCACAAACGC CGTACCCGGC AGCAGAACCG
40441 TGCCCCGCAC CGCGTGATCA GCCAGCCAGG GATGCGTACG CAATGAGATC CGGCCGGTGA
40501 GAACAACACC ACCACCGTCG TCGGCGGGCA GTGCTGTGAC GGCGGCCAGC ATCGGATGCG
40561 CCGCCCCGGT CAGCCCGGCC GCGGACAGGT CGGTGGCACC GGCCGCCTCC AGCCAGTACC
40621 GCCTGTGCTC GAACGCGTAG GTGGGCAGAT CCAGCAGCCG CCCCGGCACC GGTTCGACCA
40681 CCGTGCCCCA GTCCACCCCC GCACCCAGAG TCCACGCCTG CGCCAACGCC CCCAGCCACC
40741 GCTCCCAGCC ACCGTCACCA GTCCGCAACG ACGCCACCGT GCGGGCCTGT TCCATCGCCG
40801 GCAGCAGCAC CGGATGGGCA CTGCACTCCA CGAACACCGA CCCGTCCAGC TCCGCCACCG
40861 CCGCATCCAG CGCGACAGGG CGACGCAGGT TCCGGTACCA GTACCCCTCA TCCACCGGCT
40921 CGGTCACCCA GGCGCTGTCC ACGGTCGACC ACCACGCCAC CGACCCGGTC CCGCCGGAAA
40981 TTCCCTTCAG TACCTCAGCG AGTTCGTCCT CGATGGCCTC CACGTGAGGC GTGTGGGAGG
41041 CGTAGTCGAC CGCGATACGA CGCACCCGCA CCCCATCAGC CTCATACCGC GCCACCACCT
41101 CCTCCACCGC CGACGGGTCC CCCGCCACCA CCGTCGAAGC CGGACCATTA CGCGCCGCGA
41161 TCCACACACC CTCGACCAGA CCCACCTCAC CGGCCGGCAA CGCCACCGAA GCCATCGCCC
41221 CCCGGCCGGC CAGCCGCGCC GCGATCACCC GACTGCGCAA CGCCACCACG CGGGCGGCGT
41281 CCTCCAGGCT GAGGGCTCCG GCCACACACG CCGCCGCGAT CTCCCCCTGC GAGTGTCCGA
41341 CCACAGCGTC CGGCACGACC CCATGCGCCT GCCACAGCGC GGCCAGGCTC ACCGCGACCG
41401 CCCAGCTGGC CGGCTGGACC ACCTCCACCC GCTCCGCCAC ATCCGACCGC GACAACATCT
41461 CCCGCACATC CCAGCCCGTG TGCGGCAACA ACGCCCGCGC ACACTCCTCC ATACGAGCCG
41521 CGAACACCGC GGAACGGTCC ATGAGTTCCA CGCCCATGCC CACCCACTGG GCACCCTGCC
41581 CGGGGAAGAC GAACACCGTA CGCGGCTGAT CCACCGCCAC ACCCATCACC CGGGCATCAC
41641 CCAGCAGCAC CGCACGGTGA CCGAAGACAG CACGCTCACG CACCAACCCC TGCGCGACCG
41701 CGGCCACATC CACCCCACCC CCGCGCAGAT ACCCCTCCAG CCGCTCCACC TGCCCCCGCA
```

-continued

```
41761 GACTCACCTC ACCACGAGCC GACACCGGCA ACGGCACCAA CCCATCACCA CCCGACTCCA
41821 CACGCGACGG CCCAGGAACA CCCTCCAGGA TCACGTGCGC GTTCGTACCG CTCACCCCGA
41881 ACGACGACAC ACCCGCATGC GGTGCCCGAT CCGACTCGGG CCACGGCCTC GCCTCGGTGA
41941 GCAGCTCCAC CGCACCGGCC GACCAGTCCA CATGCGACGA CGGCTCGTCC ACGTGCAGCG
42001 TCTTCGGCGC GATCCCATGC CGCATCGCCA TGACCATCTT GATGACACCG GCGACACCCG
42061 CAGCCGCCTG CGCATGACCG ATGTTCGACT TGACCGAACC GAGGTAGAGC GGCGTGTCGC
42121 GGTCCTGCCC GTAGGCCGCG AGGACGGCCT GCGCCTCGAT CGGGTCGCCC AGCCGCGTGC
42181 CGGTGCCGTG CGCCTCCACC ACGTCCACAT CGGCGGCGCG CAGTCCGGCG TTGACCAACG
42241 CCTGCCGGAT CACGCGCTGC TGGGCGACGC CGTTGGGGGC GGACAGTCCG TTGGAGGCAC
42301 CGTCCTGGTT CACCGCCGAG CCGCGGACGA CCGCGAGAAC GGTGTGCCCG TTGCGCTCGG
42361 CGTCGGAGAG CCGCTCCAGC ACGAGAACGC CGACGCCCTC GGCGAAGCCG GTCCCGTCCG
42421 CCGCGTCGGC GAACGCCTTG CACCGTCCGT CCGGGGAGAG TCCGCGCTGC CGGGAGAACT
42481 CCACGAGCTC TGCGGTGTTC GCCATGACGG TGACACCGCC GACCAGCGCC AGGGAGCACT
42541 CCCCGGCCCG CAGTGCCTGT GCCGCCTGGT GCAGGGCGAC CAGCGACGAC GAGCACGCCG
42601 TGTCGACCGT GACCGCCGGG CCCTGAAGTC CGTACACGTA CGAGAGGCGC CCGGACAGGA
42661 CGCTCGTCTG CGTCGCCGTG ACACCGAGCC CGCCCAGGTC CCGGCCGACG CCGTAGCCCT
42721 GGTTGAACGC GCCCATGAAC ACGCCGGTGT CGCTCTCCCG GAGCCTGTCC GGCACGATGC
42781 CGGCGTTCTC GAACGCCTCC CAGGAGGTCT CCAGGATCAG GCGCTGCTGG GGGTCCATCG
42841 CCAGCGCCTC GTTCGGACTG ATGCCGAAGA ACGCGGCGTC GAACCCGGCG CCGGCCAGGA
42901 ATCCGCCGTG GCGTGTCGTG GAGCGGCCGG CCGCGTCCGG GTCCGGGTCG TACAGCGCGT
42961 CGACGTCCCA GCCCCGGTCG GTGGGGAACT CGGTGATCGC CTCGGTACCG GCGGCGACGA
43021 GCCGCCACAG GTCCTCCGGC GAGGCGACCC CGCCGGGCAG TCGGCACGCC ATGCCGACGA
43081 TCGCGACGGG GTCGCCGGAG CCGAGGGTCT GGGCGGTCGC GGGTGCCGCT GTCGCGGAGC
43141 CGGCGAGGTG GGCGGCGAAC GCACGCGGAG TGGGGTGGTC GAACGCGGTT GACGCGGGCA
43201 CCCGCAGACC CGTCCGCGCG GCGACGGTGT TGGTGAACTC GACGGTGGTG AGCGAGTCGA
43261 GGCCGTTCTC GCGGAACGTG CGGTCCGGGG AGCAGTGTCC GGCGCCCGGC AGGCCCAGGA
43321 CGGTGGCGAC GCTGTCGCGG ACCAGGTCGA GCAGTACGTC CTCCCGGCCC GCACGGGCCG
43381 CGGCGAGGCG GTTCGCCCAC TCCTGTTCCG TGGCGTCGGG CTCGGCCGGT CCGGTCAGTG
43441 CGGTGAGGAT CGGCGGCGTG GCGCCCGCCA TCGTCGCGGC CCGCGCCCCG GCGGAACCGG
43501 TCCGGGCCAC GATGTACGAG CCGCCGCCCG CGATGGCCTT CTCGATCAGG TCGCCGGTGA
43561 GCGCCGGCCG TTCGATGCCG GGCAGCGCGC GGACGGTGAC GGTGGGGAGT CCCTCCGCGG
43621 CCCGTGGCCG GGTGTGGGCG TCGGCGCCGG CCGGGCCGTC GAGCAGGACG TGCACGAGCG
43681 CGCCGGGGTT CGCGGCTTCC TCGGCTGCGG TGGTCACGTG GGTGAGGCCG GTCTCGTCGC
43741 GGAGCAGGCC GGCGACGGTG TCGGCGTCCT CCCCGGTGAC CAGGACCGGC GCGTCCGGGC
43801 CGATCGGAGG CGGCACGGTG AGGACCATCT TGCCGGTGTG CCGGGCGTGG CTCATCCACG
43861 CGAACGCGTC CCGCGCACGG CGGATGTCCC ACGGCTGCAC CGGCAGCGGG CACAGCTCAC
43921 CGCGGTCGAA CAGGTCGAGG AGCAGTTCGA GGATCTCCCG CAGGCGCGCG GGATCCACGT
43981 CGGCCAGGTC GAACGGCTGC TGGGCGGCGT GGCGGATGTC GGTCTTGCCC ATCTCGACGA
44041 ACCGGCCGCC CGGTGCGAGC AGGCCGATGG ACGCGTCGAG GAGTTCACCG GTGAGCGAGT
44101 TGAGCACGAC GTCGACCGGC GGGAAGGTGT CGGQGAACGC GGCGCTGCGG GAGTTCGCCA
44161 CATGGTCGGT GTCGAAGCCG TCGGCGTGCA GCAGGTGTTG TTTGGCGGGA CTGGCGGTGG
44221 CGTACACCTC GGCGCCGAGG TGGCGGGCGA TCCGGGTCGC CGCCATGCCG ACACCGCCCG
44281 TCGCGGCGTG GACCAGGACC TTCTGGCCGG GTCGCAGCTC GCCCGCGTCG ACGAGGCCGT
44341 ACCAGGCGGT GGCGAACACG ATGGGCACGG ACGCGGCGAT GGGGAACGAC CATCCCCGTG
44401 GGATCCGTGC GACCAGCCGC CGGTCCGCGA CCACGCTGCG CCGGAACGCG TCCTGCACGA
44461 GACCGAACAC GCGGTCGCCG GGGGCCAGGT CGTCGACGCC GGGTCCGACT TCGGTCACGA
44521 TGCCCGCGGC CTCCCCGCCC ATCTCGCCCT CGCCCGGGTA GGTGCCGAGC GCGATCAGCA
44581 CGTCGCGGAA GTTCAGCCCC GCGGCGCGGA CGTCGATGCG GACCTCGCCG GCGGCCAGGG
44641 GCGCGGCGGG ACGTCGAGCG GGGCGACGAC GAGGTCGCGG AGCGTTCCGG AGGCGGGCGG
44701 GCGCAGCGCC CACTGGCGCG GTCGGCAGGG GGGTGGTGTC CGCGCGTACC AGCCGGGGCA
44761 CGTAGGCCAC GCCGGCCCGC AGCGCGATCT GGGGTTCGCC GAGCGAGGCC GCGGCGGGGA
44821 CGAGGTCGTC ATCGCCGTCC GTGTCCACCA GCACGAACGA TCCGGGTTCG GCGGCCTGGC
44881 GGCGCAGCGC CTCGTCCCAG AGCCGGGCCT GGTCCGCGTC CGGGATCTCG GCCGGGCCGA
44941 CGCCCACCGC GCGGCGGGTG ACGACCGTCC GGCGGGGTGA CGGGGTGCCG GGCAGGTCGC
45001 GCCGCTCCCA GACCAGTTCG CACAGCGTGG CCTCGCCACT GCCGGTGGCG ACCAGATGGG
45061 CCGGCAGCCC CGCGAGCCGC GCGCGCTGGA CCTTGCqCGA CGCGGTGCGG GGGATCGTGG
45121 TGACGTGCCA GATCTCGTCG GGCACCTTGA AGTAGGCGAG CCGGCGGCGG CACTCGGCGA
45181 GGATCGCCTC GGCGGGGACG CGGGGGCCGT CGGAAACGAC GTAGAqCACG GGTATGTCGC
45241 CGAGGACGGG GTGCGGGCGG CCCGCCGCGG CGGCGTCCCG GACACCGGCC ACCTCCTGGG
45301 CGACGGTCTC GATCTCCCGG GGGTGGATGT TCTCCCCGCC GCGGATGATC AGCTCCTTGA
45361 CCCGGCCGGT GATCGTCACG TGTCCGGTCT CGGCCTGACG TGCGAGGTCC CCGGTGCGGT
45421 ACCAGCCGTC CACGAGCACC TGGGCGGTCG CCTCCGGCTG GGCGTGGTAG CCGAGCATGA
45481 GGCTCGGCCC GCTCGCCCAC AGCTCGCCCT CCTCGCCGGG TGCCACGTCG GCGCCGGACA
45541 CCGGGTCGAC GAACCGCAGC GACAGGCCCG GCACGGGCAG CCCGCACGAG CCGGGAACCC
45601 GCGCATCCTC CAGGGTGTTG GCGGTGAGCG AGCCGGTCGT CTCGGTGCAG CCGTACGTGT
45661 CGAGCAGGGG CACGCCGAAC GTCGCCTCGA AATCCCTGGT GAGCGACGCC GGCGAGGTGG
45721 ATCCGGCGAC CAGCGCCACG CGCAGCGCGC GAGCCCGCGG CTCGCCGGAC ACGGCGCCGA
45781 GGAGGTAGCG GTACATCGTC GGCACGCCGA CGAGCACGGT GCTGGAGTGT TCGGCCAGGG
45841 CGTCGAGGAC GTCACGCGCG ACGAAGCCGC CCAGGATACG GGCGGACGCG CCGACCGTGA
45901 GGACGGCGAG CAGGCAGAGG TGGTGGCCGA GGCTGTGGAA CAGCGGGGCG GGCCAGAGCA
45961 GTTCGTCGTC CTCGGTCAGC CGCCAGGACG GCACGTCGCA GTGCATCGCG GACCACAGGC
46021 CGCTGCGCTG TGCGGAAACC ACGCCCTTGG GACGGCCGGT GGTGCCGGAG GTGTAGAGCA
46081 TCCAGGCGGG TTCGTCCAGG CCGAGGTCGT CGCGGGGCGG GCACGGCGGC TCGGTCCCGG
46141 CGAGGTCCTC GTAGGAGACG CAGTCCGGTG CCCGGCGCCC GACGAGCACG ACGGTGGCGT
46201 CGGTGCCGGT GCGGCGCACC TGGTCGAGGT GGGTTTCGTC GGTGACCAGC ACGGTCGCGC
46261 CGGAGTCCGT CAGGAAGTGG GCGAGTTCGG CGTCGGCGGC GTCCGGGTTG AGCGGGACGG
46321 CGACGGCGGC GGCGCGGGCG GCGGCGAGGT AGACCTCGAT GGTCTCGATC CGGTTGCCGA
46381 GCAGCATCGC GACCCGGTCG CCGCGGTCGA CGCCGGACGC GGCGAGGTGT CCGGCGAGCC
46441 GGCCGGCCCG GAGCCGGAGT TGCGTGTACG TCACGGCGCG TTGGGAATCC GTGTAGGCGA
46501 TCCGGTCGCC GCGTCGCTCG GCATGGATGC GGAGCAATTC GTGCAACGGC CGGATTGGTT
```

-continued

```
46561 CCACACGCGC CATGGAAACA CCTTTCTCTC GACCAACCGC ACAACAGCAC GGAACCGGCC
46621 ACGAGTAGAC GCCGGCGACG CTAGCAGCGT TTTCCGGACC GCCACCCCCT GAAGATCCCC
46681 CTACCGTGGC CGGCCTCCCC GGACGCTCAT CTAGGGGGTT GCACGCATAC CGCCGTGCGT
46741 AATTGCCTTC CTGATGACCG ATGCCGGACG CCAGGGAAGG GTGGAGGCGT TGTCCATATC
46801 TGTCACGGCG CCGTATTGCC GCTTCGAGAA GACCGGATCA CCGGACCTCG AGGGTGACGA
46861 GACGGTGCTC GGCCTGATCG AGCACGGCAC CGGCCACACC GACGTGTCGC TGGTGGACGG
46921 TGCTCCCCGG ACCGCCGTGC ACACCACGAC CCGTGACGAC GAGGCGTTCA CCGAGGTCTG
46981 GCACGCACAG CGCCCTGTCG AGTCCGGCAT GGACAACGGC ATCGCCTGGG CCCGCACCGA
47041 CGCGTACCTG TTCGGTGTCG TGCGCACCGG CGAGAGCGGC AGGTACGCCG ATGCCACCGC
47101 GGCCCTCTAC ACGAACGTCT TCCAGCTCAC CCGGTCGCTG GGGTATCCCC TGCTCGCCCG
47161 GACCTGGAAC TACGTCAGCG GTATCAACAC GACGAACGCG GACGGGCTGG AGGTGTACCG
47221 GGACTTCTGC GTGGGCCGCG CCCAGGCGCT CGACGAGGGC GGGATCGACC CGGCCACCAT
47281 GCCCGCGGCC ACCGGTATCG GCGCCCACGG GGGCGGCATC ACCTGCGTGT TCCTCGCCGC
47341 CCGGGGCGGA GTGCGGATCA ACATCGAGAA CCCCGCCGTC CTCACGGCCC ACCACTACCC
47401 GACGACGTAC GGTCCGCGGC CCCCGGTCTT CGCACGGGCC ACCTGGCTGG GCCCGCCGGA
47461 GGGGGGCCGG CTGTTCATCT CCGCGACGGC CGGCATCCTC GGACACCGAA CGGTGCACCA
47521 CGGTGATGTG ACCGGCCAGT GCGAGGTCGC CCTCGACAAC ATGGCCCGGG TCATCGGCGC
47581 GGAGAACCTG CGGCGCCACG GCGTCCAGCG GGGGCACGTC CTCGCCGACG TGGACCACCT
47641 CAAGGTCTAC GTCCGCCGCC GCGAGGATCT CGATACGGTC CGCCGGGTCT GCGCCGCACG
47701 CCTGTCGAGC ACCGCGGCCG TCGCCCTTTT GCACACCGAC ATAGCCCGCG AGGATCTGCT
47761 CGTCGAAATC GAAGGCATGG TGGCGTGACA ATACCCGGTA AAAGGCCCGC GACGCTGCGC
47821 CTCGGCGGAT CCGCGAAGAG AAAGAAGAGC GTCACCGCAC AGCGCCGCAG CCCGGTCCTT
47881 TCGTCCTTCG CACAGCGGCG GATCTGGTTT CTCCAGCAAT TGGACCCGGA GAGCAACGCC
47941 TATAATCTCC CGCTCGTGCA ACGCCTGCGC GGTCTATTGG ACGCGCCGGC CCTGGAGCGT
48001 GCGCTGGCGC TCGTCGTCGC GCGCCACGAG GCGTTGCGGA CGGTGTTCGA CACCGCCGAC
48061 GGCGAGCCCC TCCAGCGGGT GCTTCCCGCC CCGGAACACC TCCTGCGCCA CGCGCGGGCG
48121 GGCAGCGAGG AGGACGCCGC CCGGCTCGTC CGCGACGAGA TCGCCCCGCC GTTCGACCTC
48181 GCCACCGGGC CGTTGATCAG GGCCCTGCTG ATCCGCCTCG GTGACGACGA CCACGTTCTC
48241 GCGGTGACCG TGCACCATGT CGCCGGCGAC GGCTGGTCGT TCGGGCTCCT CCAACATGAA
48301 CTCGCAGCCC ACTACACGGC GCTGCGCGAC ACTGCCCGCC CTGCCGAACT GCCGCCGTTG
48361 CCGGTGCAGT ACGCCGACTT CGCCGCCTGG GAGCGGCGCG AACTCACCGG CGCCGGACTG
48421 GACAGGCGTC TGGCCTACTG GCGCGAGCAA CTCCGGGGCG CCCCGGCGCG GCTCGCCCTC
48481 CCCACCGACC GTCCCCGCCC GCCGGTCGCC GACGCGGACG CGGGCATGGC CGAGTGGCGG
48541 CCGCCGGCCG CGCTGGCCAC CGCGGTCCTC ACGCTCGCGC GCGACTCCGG TGCGTCCGTG
48601 TTCATGACCC TGCTGGCGGC CTTCCAAGCG GTCCTCGCCC GGCAGCCGGG CACGCGGGAC
48661 GTGCTGGTCG GCACGCCCGT GGCGAACCGT ACGCGGGCGG CGTACGAGGG CCTGATCGGC
48721 ATGTTCGTCA ACACGCTCGC GCTGCGCGGC GACCTCTCGG GCGATCCGTC GTTCCGGGAA
48781 CTCCTCGACC GCTGCCGGGC CACGACCACG GACGCGTTCG CCCACGCCGA CCTGCCGTTC
48841 GAGAACGTCA TCGAACTCGT CGCACCCGAA CGCGACCTGT CGGTCAACCC GGTCGTCCAG
48901 GTGCTGTTGC AGGTGCTGCG GCGCGACGCG GCGACGGCCG CGCTGCCCGG CATCGCGGCC
48961 GAACCGTTCC GCACCGGACG CTGGTTCACC CGCTTCGACC TCGAATTCCA TGTGTACGAG
49021 GAGCCGGGTG GCGCGCTGAC CGGCGAACTG CTCTACAGCC GTGCGCTGTT CGACGAGCCA
49081 CGGATCACGG GGTTGCTGGA GGAGTTCACG GCGGTGCTTC AGGCGGTCAC CGCCGACCCG
49141 GACGTACGGC TGTCGCGGCT GCCGGCCGGC GACGCGACGG CGGCAGCGCC CGTGGTGCCC
49201 TCGAACGACA CGGCGCGGGA CCTGCCCGTC GACACGCTGC CGGGCCTGCT GGCCCGGTAC
49261 GCCGCACGCA CCCCCGGCGC CGTGGCCGTC ACCGACCCGC ACATCTCCCT CACCTACGCG
49321 CAGCTGGACC GGCGGGCGAA CCGCCTCGCG CACCTGCTCC GCGCGCGCGG CACCGCCACC
49381 GGCGACCTGG TCGGGATCTG CGCCGATCGC GGCGCCGACC TGATCGTCGG CATCGTGGGG
49441 ATCCTCAAGG CGGGCGCCGC TTATGTGCCG CTGGACCCCG AACATCCTCC GGAGCGCACG
49501 GCGTTCGTGC TGGCCGACGC GCAGCTGACC ACGGTGGTGG CGCACCAGGT CTACCGTTCC
49561 CGGTTCCCCG ATGTGCCGCA CGTGGTGGCG TTGGACGACC CGGAGCTGGA CCGGCAGCCG
49621 GACGACACGG CGCCGGACGT CGAGCTGGAC CGGGACAGCC TCGCCTACGC GATCTACACG
49681 TCCGGGTCGA CCGGCAGGCC GAAGGCCGTG CTCATGCCGG GTGTCAGCGC CGTCAACCTG
49741 CTGCTCTGGC AGGAGCGCAC GATGGGCCGC GAGCCGGCCA GCCGCACCGT CCAGTTCGTG
49801 ACGCCCACGT TCGACTACTC GGTGCAGGAG ATCTTTTCCG CGCTGCTGGG CGGCACGCTC
49861 GTCATCCCGC CGGACGAGGT GCGGTTCGAC CCGCCGGGAC TCGCCCGGTG GATGGACGAA
49921 CAGGCGATTA CCCGGATCTA CGCGCCGACG GCCGTACTGC GCGCGCTGAT CGAGCACGTC
49981 GATCCGCACA GCGACCAGCT CGCCGCCCTG CGGCACCTGT GCCAGGGCGG CGAGGCGCTG
50041 ATCCTCGACG CGCGGTTGCG CGAGCTGTGC CGGCACCGGC CCCACCTGCG CGTGCACAAT
50101 CACTACGGTC CGGCCGAAAG CCAGCTCATC ACCGGGTACA CGCTGCCCGC CGACCCCGAC
50161 GCGTGGCCCG CCACCGCACC GATCGGCCCG CCGATCGACA ACACCCGCAT CCATCTGCTC
50221 GACGAGGCGA TGCGGCCGGT TCCGGACGGT ATGCCGGGGC AGCTCTGCGT CGCCGGCGTC
50281 GGCCTCGCCC GTGGGTACCT GGCCCGTCCC GAGCTGACCG CCGAGCGCTG GGTGCCGGGA
50341 GATGCGGTCG GCGAGGAGCG CATGTACCTC ACCGGCGACC TGGCCCGCCG CGCGCCCGAC
50401 GGCGACCTGG AATTCCTCGG CCGGATCGAC GACCAGGTCA AGATCCGCGG CATCCGCGTC
50461 GAACCGGGTG AGATCGAGAG CCTGCTCGCC GAGGACGCCC GCGTCACGCA GGCGGCGGTG
50521 TCCGTGCGCG AGGACCGGCG GGGCGAGAAG TTCCTGGCCG CGTACGTCGT ACCGGTGGCC
50581 GGCCGGCACG GCGACGACTT CGCCGCGTCG CTGCGCGCGG GACTGGCCGC CCGGCTGCCC
50641 GCCGCGCTCG TGCCCTCCGC CGTCGTCCTG GTGGAGCGAC TGCCGAGGAC CACGAGCGGC
507C1 AAGGTGGACC GGCGCGCGCT GCCCGACCCG GAGCCGGGCC CGGCGTCGAC CGGGGCGGTT
50761 ACGCCCCGCA CCGATGCCGA GCGGACGGTG TGCCGGATCT TCCAGGAGGT GCTCGACGTC
50821 CCGCGGGTCG GTGCCGACGA CGACTTCTTC ACGCTCGGCG GGCACTCCCT GCTCGCCACC
50881 CGGGTCGTCT CCCGCATCCG CGCCGAGCTG GGTGCCGATG TCCCGCTGCG TACGCTCTTC
50941 GACGGGCGGA CGCCCGCCGC GCTCGCCCGT GCGGCGGACG AGGCCGGCCC GGCCGCCCTG
51001 CCCCCGATCG CGCCCTCCGC GGAGAACGGG CCGGCCCCCC TCACCGCGGC ACAGGAACAG
51061 ATGCTGCACT CGCACGGCTC GCTGCTCGCC GCGCCCTCCT ACACGGTCGC CCCGTACGGG
51121 TTCCGGCTGC GCGGGCCACT CGACCGCGAA GCGCTCGACG CGGCACTGAC CCGGATCGCC
51181 GCGCGCCACG AGCCGCTGCG GACCGGGTTC CGCGATCGGG AACAGGTCGT CCGGCCGCCC
51241 GCTCCGGTGC GCGCCGAGGT GGTTCCGGTG CCGGTCGGCG ACGTCGACGC CGCGGTCCGG
51301 GTCGCCCACC GGGAGCTGAC CCGGCCGTTC GACCTCGTGA ACGGGTCGTT GCTGCGTGCC
```

-continued

```
51361 GTGCTGCTGC CGCTGGGCGC CGAGGATCAC GTGCTGCTGC TGATGCTGCA CCACCTCGCC
51421 GGTGACGGAT GGTCCTTCGA CCTCCTGGTC CGGGAGTTGT CGGGGACGCA ACCGGACCTT
51481 CCGGTGTCCT ACACGGACGT GGCCCGGTGG GAACGGAGTC CGGCCGTGAT CGCGGCCAGG
51541 GAGAACGACC GGGCCTACTG GCGCCGGCGG CTGGGGGGCG CCACCGCGCC GGAGCTGCCC
51601 GCGGTCCGGC CCGGCGGGGC ACCGACCGGG CGGGCGTTCC TGTGGACGCT CAAGGACACC
51661 GCCGTCCTGG CGGCACGCCG GGTCGCGGAC GCCCACGACG CGACGTTGCA CGAAACCGTG
51721 CTCGGCGCCT TCGCCCTGGT CGTGGCGGAG ACCGCCGACA CCGACGACGT GCTCGTCGCG
51781 ACGCCGTTCG CGGACCGGGG GTACGCCGGG ACCGACCACC TCATCGGCTT CTTCGCGAAG
51841 GTCCTCGCGC TGCGCCTCGA CCTCGGCGGC ACGCCGTCGT TCCCCGAGGT GCTGCGCCGG
51901 GTGCACACCG CGATGGTGGG CGCGCACGCC CACCAGGCGG TGCCCTACTC CGCGCTGCGC
51961 GCCGAGGACC CCGCGCTGCC GCCGGCCCCC GTGTCGTTCC AGCTCATCAG CGCGCTCAGC
52021 GCGGAACTGC GGCTGCCCGG CATGCACACC GAGCCGTTCC CCGTCGTCGC CGAGACCGTC
52081 GACGAGATGA CCGGCGAACT GTCGATCAAC CTCTTCGACG ACGGTCGCAC CGTCTCCGGC
52141 GCGGTGGTCC ACGATGCCGC GCTGCTCGAC CGTGCCACCG TCGACGATTT GCTCACCCGG
52201 GTGGAGGCGA CGCTGCGTGC CGCCGCGGGC GACCTCACCG TACGCGTCAC CGGTTACGTG
52261 GAAAGCGAGT AGCCATGCCC GAGCAGGACA AGACAGTCGA GTACCTTCGC TGGGCGACCG
52321 CGGAACTCCA GAAGACCCGT GCGGAACTCG CCGCGCACAG CGAGCCGTTG GCGATCGTGG
52381 GGATGGCCTG CCGGCTGCCC GGCGGGGTCG CGTCGCCGGA GGACCTGTGG CAGTTGCTGG
52441 AGTCCGGTGG CGACGGCATC ACCGCGTTCC CCACGGACCG GGGCTCGGAG ACCACCGCCG
52501 ACGGTCGCGG CGGCTTCCTC ACCGGGGCGG CCGGCTTCGA CGCGGTGTTC TTCGGCATCA
52561 GCCCGCGCGA GGCGCTGGCG ATGGACCCGC AGCAGCGCCT GGCCCTCGAG ACCTCGTGGG
52621 AGGCGTTCGA GCACGCGGGC ATCGATCCGC AGACGCTGCG GGGCAGTGAC ACGGGGGTGT
52681 TCCTCGGCGC GTTCTTCCAG GGGTACGGCA TCGGCGCCGA CTTCGACGGT TACQGCACCA
52741 CGAGCATTCA CACGAGCGTG CTCTCCGGCC GCCTCGCGTA CTTCTACGGT CTGGAGGGTC
52801 CGGCGGTCAC GGTCGACACG GCGTGTTCGT CGTCGCTGGT GGCGCTGCAC CAGGCCGGGC
52861 AGTCGCTGCG CTCCGGCGAA TGCTCGCTCG CCCTGGTCGG CGGCGTCACG GTGATGGCCT
52921 CGCCGGCGGG GTTCGCGGAC TTCTCCGAGC AGGGCGGCCT GGCCCCCGAC GCGCGCTGCA
52981 AGGCCTTCGC GGAAGCGGCT GACGGCACCG GTTTCGCCGA GGGGTCCGGC GTCCTGATCG
53041 TCGAGAAGCT CTCCGACGCC GAGCGCAACG GCCACCGCGT GCTGGCGGTC GTCCGGGGTT
53101 CCGCCGTCAA CCAGGACGGT GCCTCCAACG GGCTGTCCGC GCCGAACGGG CCGTCGCAGG
53161 AGCGGGTGAT CCGGCAGGCC CTGGCCAACG CCGGACTCAC CCCGGCGGAC GTGGACGCCG
53221 TCGAGGCCCA CGGCACCGGC ACCAGGCTGG GCGACCCCAT CGAGGCACAG GCCGTGCTGG
53281 CCACCTACGG GCAGGGGCGC GACACCCCTG TGCTGCTGGG.CTCGCTGAAG TCCAACATCG
53341 GCCACACCCA GGCCGCCGCG GGCGTCGCCG GTGTCATCAA GATGGTCCTC GCCATGCGGC
53401 ACGGCACCCT GCCCCGCACC CTGCACGTGG ACACGCCGTC CTCGCACGTC GACTGGACGG
53461 CCGGCGCCGT CGAACTCCTC ACCGACGCCC GGCCCTGGCC CGAAACCGAC CGCCCACGGC
53521 GCGCCGGTGT CTCCTCCTTC GGCGTCAGCG GCACCAACGC CCACATCATC CTCGAAAGCC
53581 ACCCCCGACC GGCCCCCGAA CCCGCCCCGG CACCCGACAC CGGACCGCTG CCGCTGCTGC
53641 TCTCGGCCCG CACCCCGCAG GCACTCGACG CACAGGTACA CCGCCTGCGC GCGTTCCTCG
53701 ACGACAACCC CGGCGCGGAC CGGGTCGCCG TCGCGCAGAC ACTCGCCCGG CGCACCCAGT
53761 TCGAGCACCG CGCCGTGCTG CTCGGCGACA CGCTCATCAC CGTGAGCCCG AACGCCGGCC
53821 GCGGACCGGT GGTCTTCGTC TACTCGGGGC AAAGCACGCT GCACCCGCAC ACCGGGCGGC
53881 AACTCGCGTC CACCTACCCC GTGTTCGCCG AAGCGTGGCG CGAGGCCCTC GACCACCTCG
53941 ACCCCACCCA GGGCCCGGCC ACGCACTTCG CCCACCAGAC CGCGCTCACC GCGCTCCTGC
54001 GGTCCTGGGG CATCACCCCG CACGCGGTCA TCGGCCACTC CCTCGGTGAG ATCACCGCCG
54061 CGCACGCCGC CGGTGTCCTG TCCCTGAGGG ACGCGGGCGC GCTCCTCACC ACCCGCACCC
54121 GCCTGATGGA CCAACTGCCG TCGGGCGGCG CGATGGTCAC CGTCCTGACC AGCGAGGAAA
54181 AGGCACGCCA GGTGCTGCGG CCGGGCGTGG AGATCGCCGC CGTCAACGGC CCCCACTCCC
54241 TCGTGCTGTC CGGGGACGAG GAAGCCGTAC TCGAAGCCGC CCGGCAGCTC GGCATCCACC
54301 ACCGCCTGCC GACCCGCCAC GCCGGCCACT CCGAGCGCAT GCAGCCACTC GTCGCCCCCC
54361 TCCTCGACGT CGCCCGGACC CTGACGTACC ACCAGCCCCA CACCGCCATC CCCGGCGACC
54421 CCACCACQGC CGAATACTGG GCGCACCAGG TCCGCGACCA AGTACGTTTC CAGGCGCACA
54481 CCGAGCAGTA CCCGGGCGCG ACGTTCCTCG AGATCGGCCC CAACCAGGAC CTCTCGCCGC
54541 TCGTCGACGG CGTTGCCCCC CAGACCGGTA CGCCCGACGA GGTGCGGGCG CTGCACACCG
54601 CGCTCGCGCA GCTCCACGTC CGCGGCGTCG CGATCGACTG GACGCTCGTC CTCGGCGGGG
54661 ACCGCGCGCC CGTCACGCTG CCCACGTATC CGTTCCAGCA CAAGGACTAC TGGCTGCGGC
54721 CCACCTCCCG GGCCGATGTG ACCGGCGCGG GGCAGGAGCA GGTGGCGCAC CCGCTGCTCG
54781 GCGCCGCGGT CGCGCTGCCC GGCACGGGCG GAGTCGTCCT GACCGGCCGC CTGTCGCTGG
54841 CCTCCCATCC GTGGCTCGGC GAGCACGCGG TCGACGGCAC CGTGCTCCTG CCCGGCGCGG
54901 CCTTCCTCGA ACTCGCGGCG CGCGCCGGCG ACGAGGTCGG CTGCGACCTG CTGCACGAAC
54961 TCGTCATCGA GACGCCGCTC GTGCTGCCCG CGACCGGCGG TGTGGCGGTC TCCGTCGAGA
55021 TCGCCGAACC CGACGACACG GGGCGGCGGG CGGTCACCGT CCACGCGCGG GCCGACGGCT
55081 CGGGCCTGTG GACCCGACAC GCCGGCGGAT TCCTCGGCAC GGCACCGGCA CCGGCCACGG
55141 CCACGGACCC GGCACCCTGG CCGCCCGCGG AAGCCGGACC GGTCGACGTC GCCGACGTCT
55201 ACGACCGGTT CGAGGACATC GGGTACTCCT ACGGACCGGG CTTCCGGGGG CTGCGGGCCG
55261 CCTGGCGCGC CGGCGACACC GTGTACGCCG AGGTCGCGCT CCCCGACGAG CAGAGCGCCG
55321 ACQCCGCCCG TTTCACGCTG CACCCCGCGC TGCTCGACGC CGCGTTCCAG GCCGGCGCGC
55381 TGGCCGCGCT CGACGCACCC GGCGGGGCGG CCCGACTGCC GTTCTCGTTC CAGGACGTCC
55441 GCATCCACGC GGCCGGGGCG ACGCGGCTGC GGGTCACGGT CGGCCGCGAC GGCGAGCGCA
55501 GCACCGTCCG CATGACCGGC CCGGACGGGC AGCTGGTGGC CGTGGTCGGT GCCGTGCTGT
55561 CGCGCCCGTA CGCGGAAGGC TCCGGTGACG GCCTGCTGCG CCCGGTCTGG ACCGAGCTGC
55621 CGATGCCCGT CCCGTCCGCG GACGATCCGC GCGTGGAGGT CCTCGGCGCC GACCCGGGCG
55681 ACGGCGACGT TCCGGCGGCC ACCCGGGAGC TGACCGCCCG CGTCCTCGGC GCGCTCCAGC
55741 GCCACCTGTC CGCCGCCGAG GACACCACCT TGGTGGTACG GACCGGCACC GGCCCGGCCG
55801 CTGCCGCCGC CGCGGGTCTG GTCCGCTCGG CGCAGGCGGA GAACCCCGGC CGCGTCGTGC
55861 TCGTCGAGGC GTCCCCGGAC ACCTCGGTGG AGCTGCTCGC CGCGTGCGCC GCGCTGGACG
55921 AACCGCAGCT GGCCGTCCGG GACGGCGTGC TCTTCGCGCC GCGGCTGGTC CGGATGTCCG
55981 ACCCCGCGCA CGGCCCGCTG TCCCTGCCGG ACGGCGACTG GCTGCTCACC CGGTCCGCCT
56041 CCGGCACGTT GCACGACGTC GCGCTCATAG CCGACGACAC GCCCCGGCGG GCGCTCGAAG
56101 CCGGCGAGGT CCGCATCGAC GTCCGCGCGG CCGGACTGAA CTTCCGCGAT GTGCTGATCG
```

-continued

```
56161 CGCTCGGGAC GTACACCGGG GCCACGGCCA TGGGCGGCGA GGCCGCGGGC GTCGTGGTGG
56221 AGACCGGGCC CGGCGTGGAC GACCTGTCCC CCGGCGACCG GGTGTTCGGC CTGACCCGGG
56281 GCGGCATCGG CCCGACGGCC GTCACCGACC GGCGCTGGCT GGCCCGGATC CCCGACGGCT
56341 GGAGCTTCAC CACGGCGGCG TCCGTCCCGA TCGTGTTCGC GACCGCGTGG TACGGCCTGG
56401 TCGACCTCGG CACACTGCGC GCCGGCGAGA AGGTCCTCGT CCACGCGGCC ACCGGCGGTG
56461 TCGGCATGGC CGCCGCACAG ATCGCCCGCC ACCTGGGCGC CGAGCTCTAC GCCACCGCCA
56521 GTACCGGCAA GCAGCACGTC CTGCGCGCCG CCGGGCTGCC CGACACGCAC ATCGCCGACT
56581 CTCGGACGAC CGCGTTCCGG ACCGCTTTCC CGCGCATGGA CGTCGTCCTG AACGCGCTGA
56641 CCGGCGAGTT CATCGACGCG TCGCTCGACC TGCTGGACGC CGACGGCCGG TTCGTCGAGA
56701 TGGGCCGCAC CGAGCTGCGC GACCCGGCCG CGATCGTCCC CGCCTACCTG CCGTTCGACC
56761 TGCTGGACGC GGGCGCCGAC CGCATCGGCG AGATCCTGGG CGAACTGCTC CGGCTGTTCG
56821 ACGCGGGCGC GCTGGAGCCG CTGCCGGTCC GTGCCTGGGA CGTCCGGCAG GCACGCGACG
56881 CGCTCGGCTG GATGAGCCGC GCCCGCCACA TCGGCAAGAA CGTCCTGACG CTGCCCCGGC
56941 CGCTCGACCC GGAGGGCGCC GTCGTCCTCA CCGGCGGCTC CGGCACGCTC GCCGGCATCC
57001 TCGCCCGCCA CCTGCGCGAA CGGCATGTCT ACCTGCTGTC CCGGACGGCA CCGCCCGAGG
57061 GGACGCCCGG CGTCCACCTG CCCTGCGACG TCGGTGACCG GGACCAGCTG GCGGCGGCCC
57121 TGGAGCGGGT GGACCGGCCG ATCACCGCCG TGGTGCACCT CGCCGGTGCG CTGGACGACG
57181 GCACCGTCGC GTCGCTCACC CCCGAGCGTT TCGACACGGT GCTGCGCCCG AAGGCCGACG
57241 GCGCCTGGTA CCTGCACGAG CTGACGAAGG AGCAGGACCT CGCCGCGTTC GTGCTCTACT
57301 CGTCGGCCGC CGGCGTGCTC GGCAACGCCG GCCAGGGCAA CTACGTCGCC GCGAACGCGT
57361 TCCTCGACGC GCTCGCCGAG CTGCGCCACG GTTCCGGGCT GCCGGCCCTC TCCATCGCCT
57421 GGGGGCTCTG GGAGGACGTG AGCGGGCTCA CCGCGGCGCT CGGCGAAGCC GACCGGGACC
57481 GGATGCGGCG CAGCGGTTTC CGGGCCATCA CCGCGCAACA GGGCATGCAC CTGTACGAGG
57541 CGGCCGGCCG CACCGGAAGT CCCGTGGTGG TCGCGGCGGC GCTCGACGAC GCGCCGGACG
57601 TGCCGCTGCT GCGCGGCCTG CGGCGGACGA CCGTCCGGCG GGCCGCCGTC CGGGAGTGTT
57661 CGTCCGCCGA CCGGCTCGCC GCGCTGACCG GCGACGAGCT CGCCGAAGCG CTGCTGACGC
57721 TCGTCCGGGA GAGCACCGCC GCCGTGCTCG GCCACGTGGG TGGCGAGGAC ATCCCCGCGA
57781 CGGCGGCGTT CAAGGACCTC GGCATCGACT CGCTCACCGC GGTCCAGCTG CGCAACGCCC
57841 TCACCGAGGC GACCGGTGTG CGGCTGAACG CCACGGCGGT CTTCGACTTC CCGACCCCGC
57901 ACGTGCTCGC CGGGAAGCTC GGCGACGAAC TGACCGGCAC CCGCGCGCCC GTCGTGCCCC
57961 GGACCGCGGC CACGGCCGGT GCGCACGACG AGCCGCTGGC GATCGTGGGA ATGGCCTGCC
58021 GGCTGCCCGG CGGGGTCGCG TCACCCGAGG AGCTGTGGCA CCTCGTGGCA TCCGGCACCG
58081 ACGCCATCAC GGAGTTCCCG ACGGACCGCG GCTGGGACGT CGACGCGATC TACGACCCGG
58141 ACCCCGACGC GATCGGCAAG ACCTTCGTCC GGCACGGTGG CTTCCTCACC GGCGCGACAG
58201 GCTTCGACGC GGCGTTCTTC GGCATCAGCC CGCGCGAGGC CCTCGCGATG GACCCGCAGC
58261 AGCGGGTGCT CCTGGAGACG TCGTGGGAGG CGTTCGAAAG CGCCGGCATC ACCCCGGACT
58321 CGACCCGCGG CAGCGACACC GGCGTGTTCG TCGGCGCCTT CTCCTACGGT TACGGCACCG
58381 GTGCGGACAC CGACGGCTTC GGCGCGACCG GCTCGCAGAC CAGTGTGCTC TCCGGCCGGC
58441 TGTCGTACTT CTACGGTCTG GAGGGTCCGG CGGTCACGGT CGACACGGCG TGTTCGTCGT
58501 CGCTGGTGGC GCTGCACCAG GCCGGGCAGT CGCTGCGCTC CGGCGAATGC TCGCTCGCCC
58561 TGGTCGGCGG CGTCACGGTG ATGGCGTCTC CCGGCGGCTT CGTGGAGTTC TCCCGGCAGC
58621 GCGGCCTCGC GCCGGACGGC CGGGCGAAGG CGTTCGGCGC GGGTGCGGAC GGCACGAGCT
58681 TCGCCGAGGG TGCCGGTGTG CfGATCGTCG AGAGGCTCTC CGACGCCGAA CGCAACGGTC
58741 ACACCGTCCT GGCGGTCGTC CGTGGTTCGG CGGTCAACCA GGATGGTGCC TCCAACGGGC
58801 TGTCGGCGCC GAACGGGCCG TCGCAGGAGC GGGTGATCCG GCAGGCCCTG GCCAACGCCG
58861 GGCTCACCCC GGCGGACGTG GACGCCGTCG AGGCCCACGG CACCGGCACC AGGCTGGGCG
58921 ACCCCATCGA GGCACAGGCG GTACTGGCCA CCTACGGACA GGAGCGCGCC ACCCCCCTGC
58981 TGCTGGGCTC GCTGAAGTCC AACATCGGCC ACGCCCAGGC CGCGTCCGGC GTCGCCGGCA
59041 TCATCAAGAT GGTGCAGGCC CTCCGGCACG GGGAGCTGCC GCCGACGCTG CACGCCGACG
59101 AGCCGTCGCC GCACGTCGAC TGGACGGCCG GCGCCGTCGA ACTGCTGACG TCGGCCCGGC
59161 CGTGGCCCGA GACCGACCGG CCACGGCGTG CCGCCGTCTC CTCGTTCGGG GTGAGCGGCA
59221 CCAACGCCCA CGTCATCCTG GAGGCGGACC CGGTAACGGA GACGCCCGCG GCATCGCCTT
59281 CCGGTGACCT TCCCCTGCTG GTGTCGGCAC GCTCACCGGA AGCGCTCGAC GAGCAGATCC
59341 GCCGACTGCG CGCCTACCTG GACACCACCC CGGACGTCGA CCGGGTGGCC GTGGCACAGA
59401 CGCTGGCCCG GCGCACACAC TTCGCCCACC GCGCCGTGCT GCTCGGTGAC ACCGTCATCA
59461 CCACACCCCC CGCGGACCGG CCCGACGAAC TCGTCTTCGT CTACTCCGGC CAGGGCACCC
59521 AGCATCCCGC GATGGGCGAG CAGCTCGCCG CCGCCCATCC CGTGTTCGCC GACGCCTGGC
59581 ATGAAGCGCT CCGCCGCCTT GACAACCCCG ACCCCCACGA CCCCACGCAC AGCCAGCATG
59641 TGCTCTTCGC CCACCAGGCG GCGTTCACCG CCCTCCTGCG GTCCTGGGGC ATCACCCCGC
59701 ACGCGGTCAT CGGCCACTCG CTGGGCGAGA TCACCGCGGC GCACGCCGCC GGCATCCTGT
59761 CGCTGGACGA CGCGTGCACC CTGATCACCA CGCGCGCCCG CCTCATGCAC ACGCTCCCGC
59821 CACCCGGTGC CATGGTCACC GTACTGACCA GCGAAGAGAA GGCACGCCAG GCGTTGCGGC
59881 CGGGCGTGGA GATCGCCGCC GTCAACGGGC CCCACTCCAT CGTGCTGTCC GGGGACGAGG
59941 ACGCCGTGCT CACCGTCGCC GGGCAGCTCG GCATCCACCA CCGCCTGCCC GCCCCGCACG
60001 CCGGGCACTC CGCGCACATG GAGCCCGTGG CCGCCGAGCT GCTCGCCACC ACCCGCGGGC
60061 TCCGCTACCA CCCTCCCCAC ACCTCCATTC CGAACGACCC CACCACCGCT GAGTACTGGG
60121 CCGAGCAGGT CCGCAAGCCC GTGCTGTTCC ACGCCCACGC GCAGCAGTAC CCGGACGCCG
60181 TGTTCGTGGA GATCGGCCCC GCCCAGGACC TCTCCCCGCT CGTCGACGGG ATCCCGCTGC
60241 AGAACGGCAC CGCGGACGAG GTGCACGCGC TGCACACCGC GCTCGCGCAC CTCTACGCGC
60301 GCGGTGCCAC GCTCGACTGG CCCCGCATCC TCGGGGCTGG GTCACGGCAC GACGCGGATG
60361 TGCCCGCGTA CGCGTTCCAA CGGCGGCACT ACTGGATCGA GTCGGCACGC CCGGCCGCAT
60421 CCGACGCGGG CCACCCCGTG CTGGGCTCCG GTATCGCCCT CGCCGGGTCG CCGGGCCGGG
60481 TGTTCACGGG TTCCGTGCCG ACCGGTGCGG ACCGCGCGGT GTTCGTCGCC GAGCTGGCGC
60541 TGGCCGCCGC GGACGCGGTC GACTGCGCCA CGGTCGAGCG GCTCGACATC GCCTCCGTGC
60601 CCGGCCGGCC GGGCCATGGC CGGACGACCG TACAGACCTG GGTCGACGAG CCGGCGGACG
60661 ACGGCCGGCG CCGGTTCACC GTCCACACCC GCACCGGCGA CGCCSCGTGG ACGCTGCACG
60721 CCGAGGGGGT GCTGCGCCCC CATGGCACGG CCCTGCCCGA TGCGGCCGAC GCCGAGTGGC
60781 CCCCACCGGG CGCGGTGCCC GCGGACGGGC TGCCGGGTGT GTGGCGCCGG GGGGACCAGG
60841 TCTTCGCCGA GGCCGAGGTG GACGGACCGG ACGGTTTCGT GGTGCACCCC GACCTGCTCG
60901 ACGCGGTCTT CTCCGCGGTC GGCGACGGAA GCCGCCAGCC GGCCGGATGG CGCGACCTGA
```

-continued

```
60961 CGGTGCACGC GTCGGACGCC ACCGTACTGC GCGCCTGCCT CACCCGGCGC ACCGACGGAG
61021 CCATGGGATT CGCCGCCTTC GACGGCGCCG GCCTGCCGGT ACTCACCGCG GAGGCGGTGA
61081 CGCTGCGGGA GGTGGCGTCA CCGTCCGGCT CCGAGGAGTC GGACGGCCTG CACCGGTTGG
61141 AGTGGCTCGC GGTCGCCGAG GCGGTCTACG ACGGTGACCT GCCCGAGGGA CATGTCCTGA
61201 TCACCGCCGC CCACCCCGAC GACCCCGAGG ACATACCCAC CCGCGCCCAC ACCCGCGCCA
61261 CCCGCGTCCT GACCGCCCTG CAACACCACC TCACCACCAC CGACCACACC CTCATCGTCC
61321 ACACCACCAC CGACCCCGCC GGCGCCACCG TCACCGGCCT CACCCGCACC GCCCAGAACG
61381 AACACCCCCA CCGCATCCGC CTCATCGAAA CCGACCACCC CCACACCCCC CTCCCCCTGG
61441 CCCAACTCGC CACCCTCGAC CACCCCCACC TCCGCCTCAC CCACCACACC CTCCACCACC
61501 CCCACCTCAC CCCCCTCCAC ACCACCACCC CACCCACCAC CACCCCCCTC AACCCCGAAC
61561 ACGCCATCAT CATCACCGGC GQCTCCGGCA CCCTCGCCGG CATCCTCGCC CGCCACCTGA
61621 ACCACCCCCA CACCTACCTC CTCTCCCGCA CCCCACCCCC CGACGCCACC CCCGGCACCC
61681 ACCTCCCCTG CGACGTCGGC GACCCCCACC AACTCGCCAC CACCCTCACC CACATCCCCC
61741 AACCCCTCAC CGCCATCTTC CACACCGCCG CCACCCTCGA CGACGGCATC CTCCACGCCC
61801 TCACCCCCGA CCGCCTCACC ACCGTCCTCC ACCCCAAAGC CAACGCCGCC TGGCACCTGC
61861 ACCACCTCAC CCAAAACCAA CCCCTCACCC ACTTCGTCCT CTACTCCAGC GCCGCCGCCG
61921 TCCTCGGCAG CCCCGGACAA GGAAACTACG CCGCCGCCAA CGCCTTCCTC GACGCCCTCG
61981 CCACCCACCG CCACACCCTC GGCCAACCCG CCACCTCCAT CGCCTGGGGC ATGTGGCACA
62041 CCACCAGCAC CCTCACCGGA CAACTCGACG ACGCCGACCG GGACCGCATC CGCCGCGGCG
62101 GTTTCCTCCC GATCACGGAC GACGAGGGCA TGCGCCTCTA CGAGGCGGCC GTCGGCTCCG
62161 GCGAGGACTT CGTCATGGCC GCCGCGATGG ACCCGGCACA GCCGATGACC GGCTCCGTAC
62221 CGCCCATCCT GAGCGGCCTG CGCAGGAGCG CGCGGCGCGT CGCCCGTGCC GGGCAGACGT
62281 TCGCCCAGCG GCTCGCCGAG CTGCCCGACG CCGACCGCGG CGCGGCGCTG ACCACCCTCG
62341 TCTCGGACGC CACGGCCGCC GTGCTCGGCC ACGCCGACGC CTCCGAGATC GCGCCGACCA
62401 CGACGTTCAA GGACCTCGGC ATCGACTCGC TCACCGCGAT CGAGCTGCGC AACCGGCTCG
62461 CGGAGGCGAC CGGGCTGCGG CTGAGTGCCA CGCTGGTGTT CGACCACCCG ACACCTCGGG
62521 TCCTCGCCGC CAAGCTCCGC ACCGATCTGT TCGGCACGGC CGTGCCCACG CCCGCGCGGA
62581 CGGCACGGAC CCACCACGAC GAGCCACTCG CGATCGTCGG CATGGCGTGC CGACTGCCCG
62641 GCGGGGTCGC CTCGCCGGAG GACCTGTGGC AGCTCGTGGC GTCCGGCACC GACGCGATCA
62701 CCGAGTTCCC CACCGACCGC GGCTGGGACA TCGACCGGCT GTTCGACCCG GACCCGGACG
62761 CCCCCGGCAA GACCTACGTC CGGCACGGCG GCTTCCTCGC CGAGGCCGCC GGCTTCGATG
62821 CCGCGTTCTT CGGCATCAGC CCGCGCGAGG CACGGGCCAT GGACCCGCAG CAGCGCGTCA
62881 TCCTCGAAAC CTCCTGGGAG GCGTTCGAGA ACGCGGGCAT CGTGCCGGAC ACGCTGCGCG
62941 GCAGCGACAC CGGCGTGTTC ATGGGCGCGT TCTCCCATGG GTACGGCGCC GGCGTCGACC
63001 TGGGCGGGTT CGGCGCCACC GCCACGCAGA ACAGCGTGCT CTCCGGCCGG TTGTCGTACT
63061 TCTTCGGCAT GGAGGGCCCG GCCGTCACCG TCGACACCGC CTGCTCGTCG TCGCTGGTCG
63121 CCCTGCACCA GGCGGCACAG GCGCTGCGGA CTGGAGAATG CTCGCTGGCG CTCGCCGGCG
63181 GTGTCACGGT GATGCCCACC CCGCTGGGCT ACGTCGAGTT CTGCCCCCAG CGGGGACTCG
63241 CCCCCGACGG CCGTTGCCAG GCCTTCGCGG AAGGCGCCGA CGGCACGAGC TTCTCGGAGG
63301 GCGCCGGCGT TCTTGTGCTG GAGCGGCTCT CCGACGCCGA GCGCAACGGA CACACCGTCC
63361 TCGCGGTCGT CCGCTCCTCC GCCGTCAACC AGGACGGCGC CTCCAACGGC ATCTCCGCAC
63421 CCAACGGCCC CTCCCAGCAG CGCGTCATCC GCCAGGCCCT CGACAAGGCC GGGCTCGCCC
63481 CCGCCGACGT GGACGTGGTG GAGGCCCACG GCACCGGAAC CCCGCTGGGC GACCCGATCG
63541 AGGCACAGGC CATCATCGCG ACCTACGGCC AGGACCGCGA CACACCGCTC TACCTCGGTT
63601 CGGTCAAGTC GAACATCGGA CACACCCAGA CCACCGCCGG TGTCGCCGGC GTCATCAAGA
63661 TGGTCATGGC GATGCGCCAC GGCATCGCGC CGAAGACACT GCACGTGGAC GAGCCGTCGT
63721 CGCATGTGGA CTGGACCGAG GGTGCGGtGG AACTGCTCAC CGAGGCGAGG CCGTGGCCCG
63781 ACGCGGGACG CCCGCGCCGC GCGGGCGTGT CGTCGCTCGG TATCAGCGGT ACGAACGCCC
63841 ACGTGATCCT TGAGGGTGTT CCCGGGCCGT CGCGTGTGGA GCCGTCTGTT GACGGGTTGG
63901 TGCCGTTGCC GGTGTCGGCT CGGAGTGAGG CGAGTCTGCG GGGGCAGGTG GAGCGGCTGG
63961 AGGGGTATCT GCGCGGGAGT GTGGATGTGG CCGCGGTCGC GCAGGGGTTG GTGCGTGAGC
64021 GTGCTGTCTT CGGTCACCGT GCGGTACTGC TGGGTGATGC CCGGGTGATG GGTGTGGCGG
64081 TGGATCAGCC GCGTACGGTG TTCGTCTTTC CCGGGCAGGG TGCTCAGTGG GTGGGCATGG
64141 GTGTGGAGTT GATGGACCGT TCTGCGGTGT TCGCGGCTCG TATGGAGGAG TGTGCGCGGG
64201 CGTTGTTGCC GCACACGGGC TGGGATGTGC GGGAGATGTT GGCGCGGCCG GATGTGGCGG
64261 AGCGGGTGGA GGTGGTCCAG CCGGCCAGCT GGGCGGTCGC GGTCAGCCTG GCCGCACTGT
64321 GGCAGGCCCA CGGGGTCGTA CCCGACGCGG TGATCGGACA CTCCCAGGGC GAGATCGCGG
64381 CGGCGTGCGT GGCCGGGGCC CTCAGCCTTG AGGACGCCGC CCGCGTGGTG GCCTTGCGCA
64441 GCCAGGTCAT CGCGGCGCGA CTGGCCGGGC GGGGAGCGAT GGCTTCGGTG GCATTGCCGG
64501 CCGGTGAGGT CGGTCTGGTC GAGGGCGTGT GGATCGCGGC GCGTAACGGC CCCGCCTCGA
64561 CAGTCGTGGC CGGCGAGCCG TCGGCGGTGG AGGACGTGGT GACGCGGTAT GAGACCGAAG
64621 GCGTGCGAGT GCGTCGTATC GCCGTCGACT ACGCCTCCCA CACGCCCCAC GTGGAAGCCA
64681 TCGAGGACGA ACTCGCTGAG GTACTGAAGG GAGTTGCAGG GAAGGCCGCG TCGGTGGCGT
64741 GGTGGTCGAC CGTGGACAGC GCCTGGGTGA CCGAGCCGGT GGATGAGAGT TACTGGTACC
64801 GGAACCTGCG TCGCCCCGTC GCGCTGGACG CGGCGGTGGC GGAGCTGGAC GGGTCCGTGT
64861 TCGTGGAGTG CAGCGCCCAT CCGGTGCTGC TGCCGGCGAT GGAACAGGCC CACACGGTGG
64921 CGTCGTTGCG CACCGGTGAC GGCGGCTGGG AGCGATGGCT GACGGCGTTG GCGCAGGCGT
64981 GGACCCTGGG CGCGGCAGTG GACTGGGACA CGGTGGTCGA ACCGGTGCCA GGGCGGCTGC
65041 TCGATCTGCC CACCTACGCG TTCGAGCGCC GGCGCTACTG GCTGGAAGCG GCCGGTGCCA
65101 CCGACCTGTC CGCGGCCGGG CTGACAGGGG CAGCACATCC CATGCTGGCC GCCATCACGG
65161 CACTACCCGC CGACGACGGT GGTGTTGTTC TCACCGGCCG GATCTCGTTG CGCACGCATC
65221 CCTGGCTGGC TGATCACGCG GTGCGGGGCA CGGTCCTGCT GCCGGGCACG GCCTTTGTGG
65281 AGCTGGTCAT CCGGGCCGGT GACGAGACCG GTTGCGGGAT AGTGGATGAA CTGGTCATCG
65341 AATCCCCCCT CGTGGTGCCG GCGACCGCAG CCGTGGATCT GTCGGTGACC GTGGAAGGAG
65401 CTGACGAGGC CGGACGGCGG CGAGTGACCG TCCACGCCCG CACCGAAGGC ACCGGCAGCT
65461 GGACCCGGCA CGCCAGCGGC ACCCTGACCC CCGACACCCC CGACACCCCC AACGCTTCCG
65521 GTGTTGTCGG TGCGGAGCCG TTCTCGCAGT GGCCACCTGC CACTGCCGCG GCCGTCGACA
65581 CCTCGGAGTT CTACTTGCGC CTGGACGCGC TGGGCTACCG GTTCGGACCC ATGTTCCGCG
65641 GAATGCGGGC TGCCTGGCGT GATGGTGACA CCGTGTACGC CGAGGTCGCG CTCCCCGAGG
65701 ACCGTGCCGC CGACGCGGAC GGTTTCGGCA TGCACCCGGC GCTGCTCGAC GCGGCCTTGC
```

-continued

65761 AGAGCGGCAG CCTGCTCATG CTGGAATCGG ACGGCGAGCA GAGCGTGCAA CTGCCGTTCT
65821 CCTGGCACGG CGTCCGGTTC CACGCGACGG GCGCGACCAT GCTGCGGGTG GCGGTCGTAC
65881 CGGGCCCGGA CGGCCTCCGG CTGCATGCCG CGGACAGCGG GAACCGTCCC GTCGCGACGA
65941 TCGACGCGCT CGTGACCCGG TCCCCGGAAG CGGACCTCGC GCCCGCCGAT CCGATGCTGC
66001 GGGTCGGGTG GGCCCCGGTG CCCGTACCTG CCGGGGCCGG TCCGTCCGAC GCGGACGTGC
66061 TGACGCTGCG CGGCGACGAC GCCGACCCGC TCGGGGAGAC CCGGGACCTG ACCACCCGTG
66121 TTCTCGACGC GCTGCTCCGG GCCGACCGGC CGGTGATCTT CCAGGTGACC GGTGGCCTCG
66181 CCGCCAAGGC GGCCGCAGGC CTGGTCCGCA CCGCTCAGAA CGAGCAGCCC GGCCGCTTCT
66241 TCCTCGTCGA AACGGACCCG GGAGAGGTCC TGGACGGCGC GAAGCGCGAC GCGATCGCGG
66301 CACTCGGCGA GCCCCATGTG CGGCTGCGCG ACGGCCTCTT CGAGGCAGCC CGGCTGATGC
66361 GGGCCACGCC GTCCCTGACG CTCCCGGACA CCGGGTCGTG GCAGCTGCGG CCGTCCGCCA
66421 CCGGTTCCCT CGACGACCTT GCCGTCGTCC CCACCGACGC CCCGGACCGG CCGCTCGCGG
66481 CCGGCGAGGT GCGGATCGCG GTACGCGCGG CGGGCCTGAA CTTCCGGGAT GTCACGGTCG
66541 CGCTCGGTGT GGTCGCCGAT GCGCGTCCGC TCGGCAGCGA GGCCGCGGGT GTCGTCCTGG
66601 AGACCGGCCC CGGTGTGCAC GACCTGGCGC CCGGCGACCG GGTCCTGGGG ATGCTCGCGG
66661 GCGCCTTCGG ACCGGTCGCG ATCACCGACC GGCGGCTGCT CGGCCGGATG CCGGACGGCT
66721 GGACGTTCCC GCAGGCGGCG TCCGTGATGA CCGCGTTCGC GACCGCGTGG TACGGCCTGG
66781 TCGACCTGGC CGGGCTGCGC CCCGGCGAGA AGGTCCTGAT CCACGCGGCG GCGACCGGTG
66841 TCGGCGCGGC GGCCGTCCAG ATCGCGCGGC ATCTGGGCGC GGAGGTGTAC GCGACCACCA
66901 GCGCCGCGAA GCGCCATCTG GTGGACCTGG ACGGAGCGCA TCTGGCCGAT TCCCGCAGCA
66961 CCGCGTTCGC CGACGCGTTC CCGCCGGTCG ATGTCGTGCT CAACTCGCTC ACCGGTGAAT
67021 TCCTCGACGC GTCCGTCGGC CTGCTCGCGG CGGGTGGCCG GTTCATCGAG ATGGGGAAGA
67081 CGGACATCCG GCACGCCGTC CAGCAGCCGT TCGACCTGAT GGACGCCGGC CCCGACCGGA
67141 TGCAGCGGAT CATCGTCGAG CTGCTCGGCC TGTTCGCGCG CGACGTGCTG CACCCGCTGC
67201 CGGTCCACGC CTGGGACGTG CGGCAGGCGC GGGAGGCGTT CGGCTGGATG AGCAGCGGGC
67261 GTCACACCGG CAAGCTGGTG CTGACGGTCC CGCGGCCGCT GGATCCCGAG GGGGCCGTCG
67321 TCATCACCGG CGGCTCCGGC ACCCTCGCCG GCATCCTCGC CCGCCACCTG GGCCACCCCC
67381 ACACCTACCT GCTCTCCCGC ACCCCACCCC CCGACACCAC CCCCGGCACC CACCTCCCCT
67441 GCGACGTCGG CGACCCCCAC CAACTCGCCA CCACCCTCGC CCGCATCCCC CAACCCCTCA
67501 CCGCCGTCTT CCACACCGCC GGAACCCTCG ACGACGCCCT GCTCGACAAC CTCACCCCCG
67561 ACCGCGTCGA CACCGTCCTC AAACCCAAGG CCGACGCCGC CTGGCACCTG CACCGGCTCA
67621 CCCGCGACAC CGACCTCGCC GCGTTCGTCG TCTACTCCGC GGTCGCCGGC CTCATGGGCA
67681 GCCCGGGGCA GGGCAACTAC GTCGCGGCGA ACGCGTTCCT CGACGCGCTC GCCGAACACC
67741 GCCGTGCGCA AGGGCTGCCC GCGCAGTCCC TCGCATGGGG CATGTGGGCG GACGTCAGCG
67801 CGCTCACCGC GAAACTCACC GACGCGGACC GCCAGCGCAT CCGGCGCAGC GGATTCCCGC
67861 CGTTGAGCGC CGCGGACGGC ATGCGGCTGT TCGACGCGGC GACGCGTACC CCGGAACCGG
67921 TCGTCGTCGC GACGACCGTC GACCTCACCC AGCTCGACGG CGCCGTCGCG CCGTTGCTCC
67981 GCGGTCTGGC CGCGCACCGG GCCGGGCCGG CGCGCACGGT CGCCCGCAAC GCCGGCGAAG
68041 AGCCCCTGGC CGTGCGTCTT GCCGGGCGTA CCGCCGCCGA GCAGCGGCGC ATCATGCAGG
68101 AGGTCGTGCT CCGCCACGCG GCCGCGGTCC TCGCGTACGG GCTGGGCGAC CGCGTGGCGG
68161 CGGACCGTCC GTTCCGCGAG CTCGGTTTCG ATTCGCTGAC CGCGGTCGAC CTGCGCAATC
68221 GGCTCGCGGC CGAGACGGGG CTGCGGCTGC CGACGACGCT GGTGTTCAGC CACCCGACGG
68281 CGGAGGCGCT CACCGCCCAC CTGCTCGACC TGATCGACGC TCCCACCGCC CGGATCGCCG
68341 GGGAGTCCCT GCCCGCGGTG ACGGCCGCTC CCGTGGCGGC CGCGCGGGAC CAGGACGAGC
68401 CGATCGCCAT CGTGGCGATG GCGTGCCGGC TGCCCGGTGG TGTGACGTCG CCCGAGGACC
68461 TGTGGCGGCT CGTCGAGTCC GGCACCGACG CGATCACCAC GCCTCCTGAC GACCGCGGCT
68521 GGGACGTCGA CGCGCTGTAC GACGCGGACC CGGACGCGGC CGGCAAGGCG TACAACCTGC
68581 GGGGCGGTTA CCTGGCCGGG GCGGCGGAGT TCGACGCGGC GTTCTTCGAC ATCAGTCCGC
68641 GCGAAGCGCT CGGCATGGAC CCGCAGCAAC GCCTGCTGCT CGAAACGGCG TGGGAGGCGA
68701 TCGAGCGCGG CCGGATCAGT CCGGCGTCGC TCCGCGGCCG GGAGGTCGGC GTCTATGTCG
68761 GTGCGGCCGC GCAGGGCTAC GGGCTGGGCG CCGAGGACAC CGAGGGCCAC GCGATCACCG
68821 GTGGTTCCAC GAGCCTGCTG TCCGGACGGC TGGCGTACGT GCTCGGGCTG GAGGGCCCGG
68881 CGGTCACCGT GGACACGGCG TGCTCGTCGT CTCTGGTCGC GCTGCATCTG GCGTGCCAGG
68941 GGCTGCGCCT GGGCGAGTGC GAACTCGCTC TGGCCGGAGG GGTCTCCGTA CTGAGTTCGC
69001 CGGCCGCGTT CGTGGAGTTC TCCCGCCAGC GCGGGCTCGC GGCCGACGGG CGCTGCAAGT
69061 CGTTCGGCGC GGGCGCGGAC GGCACGACGT GGTCCGAGGG CGTGGGCGTG CTCGTACTGG
69121 AACGGCTCTC CGACGCCGAG CGGCTCGGGC ACACCGTGCT CGCCGTCGTC CGCGGCAGCG
69181 CCGTCACGTC CGACGGCGCC TCCAACGGCC TCACCGCGCC GAACGGGCTC TCGCAGCAGC
69241 GGGTCATCCG GAAGGCGCTC GCCGCGGCCG GGCTGACCGG CGCCGACGTG GACGTCGTCG
69301 AGGGGCACGG CACCGGCACC CGGCTCGGCG ACCCGGTCGA GGCGGACGCG CTGCTCGCGA
69361 CGTACGGGCA GGACCGTCCG GCACCGGTCT GGCTGGGCTC GCTGAAGTCG AACATCGGAC
69421 ATGCCACGGC CGCGGCCGGT GTCGCGGGCG TCATCAAGAT GGTGCAGGCG ATCGGCGCGG
69481 GCACGATGCC GCGGACGCTG CATGTGGAGG AGCCCTCGCC CGCCGTCGAC TGGAGCACCG
69541 GACAGGTGTC CCTGCTCGGC TCCAACCGGC CCTGGCCGGA CGACGAGCGT CCGCGCCGGG
69601 CGGCCGTCTC CGCGTTCGGG CTCAGCGGGA CGAACGCGCA CGTCATCCTG GAACAGCACC
69661 GTCCGGCGCC CGTGGCGTCC CAGCCGCCCC GGCCGCCCCG TGAGGAGTCC CAGCCGCTGC
69721 CGTGGGTGCT CTCCGCGCGG ACTCCGGCCG CGCTGCGGGC CCAGGCGGCC CGGCTGCGCG
69781 ACCACCTCGC GGCGGCACCG GACGCGGATC CGTTGGACAT CGGGTACGCG CTGGCCACCA
69841 GCCGCGCCCA GTTCGCCCAC CGTGCCGCGG TCGTCGCCAC CACCCCGGAC GGATTCCGTG
69901 CCGCGCTCGA CGGCCTCGCG GACGGCGCGG AGGCGCCCGG AGTCGTCACC GGGACCGCTC
69961 AGGAGCGGCG CGTCGCCTTC CTCTTCGACG GCCAGGGCGC CCAGCGCGCC GGAATGGGGC
70021 GCGAGCtCCA CCGCCGGTTC CCCGTCTTCG CCGCCGCGTG GGACGAGGTC TCCGACGCGT
70081 TCGGCAAGCA CCTCAAGCAC TCCCCCACGG ACGTCTACCA CGGCGAACAC GGCGCTCTCG
70141 CCCATGACAC CCTGTACGCC CAGGCCGGCC TGTTCACGCT CGAAGTGGCG CTGCTGCGGC
70201 TGCTGGAGCA CTGGGGGGTG CGGCCGGACG TGCTCGTCGG GCACTCCGTC GGCGAGGTGA
70261 CCGCGGCGTA CGCGGCGGGG GTGCTCACCC TGGCGGACGC GACGGAGTTG ATCGTGGCCC
70321 GGGGGCGGGC GCTGCGGGCG CTGCCGCCCG GGGCGATGCT CGCCGTCGAC GGAAGCCCGG
70381 CGGAGGTCGG CGCCCGCACG GATCTGGACA TCGCCGCGGT CAACGGCCCG TCCGCCGTGG
70441 TGCTCGCCGG TTCGCCGGAC GATGTGGCGG CGTTCGAACG GGAGTGGTCG GCGGCCGGGC
70501 GGCGCACGAA ACGGCTCGAC GTCGGGCACG CGTTCCACTC CCGGCACGTC GACGGTGCGC

-continued

```
70561 TCGACGGCTT CCGTACGGTG CTGGAGTCGC TCGCGTTCGG CGCGGCGCGG CTGCCGGTGG
70621 TGTCCACGAC GACGGGCCGG GACGCCGCGG ACGACCTCAT AACGCCCGCG CACTGGCTGC
70681 GCCATGCGCG TCGGCCGGTG CTGTTCTCGG ATGCCGTCCG GGAGCTGGCC GACCGCGGCG
70741 TCACCACGTT CGTGGCCGTC GGCCCCTCCG GCTCCCTGGC GTCGGCCGCG GCGGAGAGCG
70801 CCGGGGAGGA CGCCGGGACC TACCACGCGG TGCTGCGCGC CCGGACCGGT GAGGAGACCG
70861 CGGCGCTGAC CGCCCTCGCC GAGCTGCACG CCCACGGCGT CCCGGTCGAC CTGGCCGCGG
70921 TACTGGCCGG TGGCCGGCCA GTGGACCTTC CCGTGTACGC GTTCCAGCAC CGTTCCTACT
70981 GGCTGGCCCC GGCCGTGGCG GGGGCGCCGG CCACCGTGGC GGACACCGGG GGTCCGGCGG
71041 AGTCCGAGCC GGAGGACCTC ACCGTCGCCG AGATCGTCCG TCGGCGCACC GCGGCGCTGC
71101 TCGGCGTCAC GGACCCCGCC GACGTCGATG CGGAAGCGAC GTTCTTCGCG CTCGGTTTCG
71161 ACTCACTGGC GGTGCAGCGG CTGCGCAACC AGCTCGCCTC GGCAACCGGG CTGGACCTGC
71221 CGGCGGCCGT CCTGTTCGAC CACGACACCC CGGCCGCGCT CACCGCGTTC CTCCAGGACC
71281 GGATCGAGGC CGGCCAGGAC CGGATCGAGG CCGGCGAGGA CGACGACGCG CCCACCGTGC
71341 TCTCGCTCCT GGAGGAGATG GAGTCGCTCG ACGCCGCGGA CATCGCGGCG ACGCCGGCCC
71401 CGGAGCGTGC GGCCATCGCC GATCTGCTCG ACAAGCTCGC CCATACCTGG AAGGACTACC
71461 GATGAGCACC GATACGCACG AGGGAACGCC GCCCGCCGGC CGCTGCCCAT TCGCGATCCA
71521 GGACGGTCAC CGCGCCATCC TGGAGAGCGG CACGGTGGGT TCGTTCGACC TGTTCGGCGT
71581 CAAGCACTGG CTGGTCGCCG CCGCCGAGGA CGTCAAGCTG GTCACCAACG ATCCGCGGTT
71641 CAGCTCGGCC GCGCCGTCCG AGATGCTGCC CGACCGGCGG CCCGGCTGGT TCTCCGGGAT
71701 GCACTCACCG GAGCACAACC GCTACCGGCA GAAGATCGCG GGGGACTTCA CACTGCGCGC
71761 GGCGCGCAAG CGGGAGGACT TCGTCGCCGA GGCCGCCGAC GCCTGCCTGG ACGACATCGA
71821 GGCCGCGGGA CCCGGCACCG ACCTCATCCC CGGGTACGCC AAGCGGCTGC CCTCCCTCGT
71881 CATCAACGCG CTGTACGGGC TCACCCCTGA GGAGGGGGCC GTGCTGGAGG CACGGATGCG
71941 CGACATCACC GGCTCGGCCG ATCTGGACAG CGTCAAGACG CTGACCGACG ACTTCTTCGG
72001 GCACGCGCTG CGGCTGGTCC GCGCGAAGCG TGACGAGCGG GGCGAGGACC TGCTGCACCG
72061 GCTGGCCTCG GCCGACGACG GCGAGATCTC GCTCAGCGAC GACGAGGCGA CGGGCGTGTT
72121 CGCGACGCTG CTGTTCGCCG GCCACGACTC GGTGCAGCAG ATGGTCGGCT ACTGCCTCTA
72181 CGCACTGCTC AGCCACCCCG AGCAGCAGGC GGCGCTGCGC GCGCGCCCGG AGCTGGTCGA
72241 CAACGCGGTC GAGGAGATGC TCCGTTTCCT GCCCGTCAAC CAGATGGGCG TACCGCGCGT
72301 CTGTGTCGAG GACGTCGATG TGCGGGGCGT GCGCATCCGT GCGGGCGACA ACGTGATCCC
72361 GCTCTACTCG ACGGCCAACC GCGACCCCGA GGTGTTCCCG CAGCCCGACA CCTTCGATGT
72421 GACGCGCCCG CTGGAGGGCA ACTTCGCGTT CGGCCACGGC ATTCACAAGT GTCCCGGCCA
72481 GCACATCGCC CGGGTGCTCA TCAAGGTCGC CTGCCTGCGG TTGTTCGAGC GTTTCCCGGA
72541 CGTCCGGCTG GCCGGCGACG TGCCGATGAA CGAGGGGCTC GGGCTCTTCA GCCCGGCCGA
72601 GCTGCGGGTC ACCTGGGGGG CGGCATGAGT CACCCGGTGG AGACG7TGCG GTTGCCGAAC
72661 GGGACGACGG TCGCGCACAT CAACGCGGGC GAGGCGCAGT TCCTCTACCG GGAGATCTTC
72721 ACCCAGCGCT GCTACCTGCG CCACGGTGTC GACCTGCGCC CGGGGGACGT GGTGTTCGAC
72781 GTCGGCGCGA ACATCGGCAT GTTCACGCTT TTCGCGCATC TGGAGTGTCC TGGTGTGACC
72841 GTGCACGCCT TCGAGCCCGC GCCCGTGCCG TTCGCGGCGC TGCGGGCGAA CGTGACGCGG
72901 CACGGCATCC CGGGCCAGGC GGACCAGTGC GCGGTCTCCG ACAGCTCCGG CACCCGGAAG
72961 ATGACCTTCT ATCCCGACGC CACGCTGATG TCCGGTTTCC ACGCGGATGC CGCGGCCCGG
73021 ACGGAGCTGT TGCGCACGCT CGGCCTCAAC GGCGGCTACA CCGCCGAGGA CGTCGACACC
73081 ATGCTCGCGC AACTGCCCGA CGTCAGCGAG GAGATCGAAA CCCCTGTGGT CCGGCTCTCC
73141 GACGTCATCG CGGAGCGCGG TATCGAGGCC ATCGGCCTGC TGAAGGTCGA CGTGGAGAAG
73201 AGCGAACGGC AGGTCTTCGC CGGCCTCGAG GACACCGACT GGCCCCGTAT CCGCCAGGTC
73261 GTCGCGGAGG TCCACGACAT CGACGGCGCG CTCGAGGAGG TCGTCACGCT GCTCCGCGGC
73321 CATGGCTTCA CCGTGGTCGC CGAGCAGGAA CCGCTGTTCG CCGGCACGGG CATCCACCAG
73381 GTCGCCGCGC GGCGGGTGGC CGGCTGAGCG CCGTCGGGGC CGCGGSCGTC CGCACCGGCG
73441 GCCGCGGTGC GGACGGCGGC TCAGCCGGCG TCGGACAGTT CCTTCGGCAG TTGCTGACGG
73501 CCCTTCACCC CCAGCTTGCG GAACACGTTG GTGAGGTGCT GTTCCACCGT GCTGGAGGTG
73561 ACGAACAGCT GGCTGGCGAT CTCCTTGTTG GTGCGCCCGA CCGCGGCGTG CGACGCCACC
73621 CGCCGCTCCG CCTCGGTCAG CGATGTGATC CGCTGCGCCG GCGTCACGTC CTGGGTGCCG
73681 TCCGCGTCCG AGGACTCCCC ACCGAGCCGC CGGAGGAGCG GCACGGCTCC GCACTGGGTC
73741 GCGAGGTGCC GTGCGCGGCG GAACAGTCCC CGCGCACGGC TGTGCCGCCG GAGCATGCCG
73801 CACGCTTCGC CCATGTCGGC GAGGACGCGG GCCAGCTCGT ACTGGTCGCG GCACATGATG
73861 AGCAGATCGG CGGCCTCGTC GAGCAGTTCG ATCCGCTTGG CCGGCGGACT GTAGGCCGCC
73921 TGCACCCGCA GCGTCATCAC CCGCGCCCGG GACCCCATCG GCCGGGACAG CTGCTCGGAG
73981 ATGAGCCTCA GCCCCTCGTC ACGGCCGCGG CCGAGCAGCA GAAGCGCTTC GGCGGCGTCG
74041 ACCCGCCACA GGGCCAGGCC CGGCACGTCG ACGGACCAGC GTCGCATCCG CTCCCCGCAG
74101 TCCCGGAACG CGTTGTAQGC CGCCCGGTAC CGCCCGGCCG CGAGATGGTG TTGCCCACGG
74161 GCCCAGACCA TGTGCAGTCC GAAGAGGCTG TCGGAGGTCT CCTCCGGCAA CGGCTCGGCG
74221 AGCCACCGCT CCGCCCGGTC CAGGTCGCCC AGTCGGATCG CGGCGGCCAC GGTGCTGCTC
74281 AGCGGCAATG CGGCGGCCAT CCCCCAGGAG GGCACGACCC GGGGCGCGAG CGCGGCCTCG
74341 CCGCATTCGA CGGCGGCGGT CAGGTCGCCG CGGCGCAGCG CGGCCTCGGC GCGGAACCCC
74401 GCGTGGACCG CCTCGTCGGC CGGGGTCCGC ATGTTGTCGT CACCGGCCAG CTTGTCGACC
74461 CAGGACTGGA CGGCATCGGT GTCCTCGGCG TAGAGCAGGG CCAGCAACGC CATCATGGTC
74521 GTGGTCCGGT CCGTCGTGAC CCGGGAGTGC TGGAGCACGT ACTCGGQTTT GGCCTCGGCC
74581 TGTTCGGACC AGCCGCGCAG CGCGTTGCTC AGGGCCTTGT CGGCGACGGC GCGGTGCCGG
74641 ACGGCTCCGG AAAACGAGGC GACCTCGTCC TCGGCCGGCG GATCGGCCGG ACGCGGCGGA
74701 TCGGCCGCGC CGGGATAGAT CAGCGCGAGG GACAGGTCCG CGACGCGCAG GTGCGCCCGG
74761 CCCTGCTCGC TCGGGGCGGC GGAGCGCTGG GCCGCCAGGA CCTCGGCGGC CTCGCCCGGC
74821 CGCCCGTCCA TCGCCAGCCA GCAGGCGAGC GACACGGCGT GCTCGCTGGA GAGGAGCCGT
74881 TCCCGCGACG CGGTGAGCAG CTCGGGCACA TGCCGGCCGG ATCTGGCGGG ATCGCAGAGC
74941 CGCTCGATGG CGGCGGTGTC GACGCGCAGT GCGGCGTGGA CGGCGGGGTC GTCGGAGGCC
75001 CGGTAGGCGA ACTCCAGGTA GGTGACGGCC TCGTCGAGCT CGCCGCGCAG GTGGTGCTCG
75061 CGCGCGGCGT CGGTGAACAG CCCGGCGACC TCGGCGCCGT GCACCCGGCC GGTACCCATC
75121 TGGTGGCGGG CGAGCACCTT GCTGGCCACG CCGCGGTCCC GCAGCAGTTC CAGCGCCAGC
75181 TCGTGCAGGC CACGCCGCTC GGCGGCGGAG AGGTCGTCGA GTACQACGGA GCGGGCCGCG
75241 GGGTGCGGGA ACCGCCCTTC CCGCAGCAGC CGCCCCTCGA CCAGCTGTTC GTGGGCCTGC
75301 TCGACCGCCT CGGTGTCGAG GCCGGTCATC CGCTGGACGA GGGTGAGTTC GACACTCTCG
```

-continued

```
75361 CCGAGCACGG CGGAAGCTCG GGCGACGCTC AGCGCGGCCG GGCCGCAACG ATAGAGCGAC
75421 CCGAGGTAGG CGAGCCGGTA CGCCCGCCCC GCGACCACTT CCAGGCACCC TGAGGTCCGT
75481 GTCCGTGCCT CCCGGATGTC GTCGATCAGG CCGTGGCCGA GGAGCAGGTT GCCGCCGGTC
75541 GCCCGGAACG CCTGGGCCAC CACGTCGTCG TGCGCGTCCT GGCCGAGGTG CCGGCGCACG
75601 AGTTCGGTGG TCTGCGCCTC GGTGAGCGGG CGCAGCGCGA TCTCCTGGTA GTGGCGCAGA
75661 CTCAGCAGTG CCGCCCGGAA TTGGGAGTGG GCGGGCGTCG GCCGGAGCAG CTCGGTCAGC
75721 ACGATGGCGA CACGGGCCCG GCTGATGCGG CGCGCGAGGT GGAGCAGGCA GCGCAGCGAC
75781 GGCGCGTCGG CGTGGTGCAC GTCGTCGATG CCGATCAGTA CGGGCCGCTC CGCGGCGAGC
75841 GTCAGCACCG TGCGGGTGAG TTCGGTCCCC AGGCGGTTGT CGACGTCGGC CGGCAGGTTT
75901 TCGCACGATG CCGTCAGCCG GACCAGCTCC GGTGTCCGGG CGGCCAGCTC GGGCTGGTCG
75961 AGGAGCTGGC CGAGCATGCC GTACGGCAGG GCCCGCTCCT CCATGGAGCA CACCGCGCGA
76021 AGGGTGACGA AGCCGGCCTT GGCCGCGGCG GCGTCGAGGA GTTCGGTCTT GCCGCAGGCG
76081 ATCGGCCCGG TGACGGCGGC GACGACGCCC CGCCCGCCCC CCGCTCGGGT GAGCGCCCGG
76141 TGGAGGGAAC CGAACTCGTC ATCGCGGGCG ATCAGGTCTG GGGGAGATAA GCGCGCTATC
76201 ACGAATGGAA CTACCTCGCG ACCGTCGTGG AAACCCATAG GCATCACATG GCTTGTTGAT
76261 CTGTACGGCT GTGATTCAGC CTGGCGGGAT GCTGTGCTAC AGATGGGAAG ATGTGATCTA
76321 GGGCCGTGCC GTTCCCTCAG GAGCCGACCG CCCCCGGCGC CACCCGCCGT ACCCCCTGGG
76381 CCACCAGCTC GGCGACCCGC TCCTGGTGGT CGACGAGGTA GAAGTGCCCG CCGGGGAAGA
76441 CCTCCACCGT GGTCGGCGCG GTCGTGTGCC CGGCCCAGGC GTGGG(CTGC TCCACCGTCG
76501 TCTTCGGATC GTCGTCACCG ATGCACACCG TGATCGGCGT CTCCAGCGGC GGCGCGGGCT
76561 CCCACCGGTA CGTCTCCGCC GCGTAGTAGT CCGCCCGCAA CGGCGCCAGG ATCAGCGCGC
76621 GCATTTCGTC GTCCGCCATC ACATCGGCGC TCGTCCCGCC GAGGCCGATG ACCGCCGCCA
76681 GCAGCTCGTC GTCGGACGCG AGGTGGTCCT GGTCGGCGCG CGGCTGCGAC GGCGCCCGCC
76741 GGCCCGAGAC GATCAGGTGC GCCACCGGGA GCCGCTGGGC CAGCTCGAAC GCGAGTGTCG
76801 CGCCCATGCT GTGGCCGAAC AGCACCAGCG GACGGTCCAG CCCCGGCTTC AACGCCTCGG
76861 CCACGAGGCC GGCGAGAACA CGCAGGTCGC GCACCGCCTC CTCGTCGCGG CGGTCCTGGC
76921 GGCCGGGGTA CTGCACGGCG TACACGTCCG CCACCGGGGC GAGCGCACGG GCCAGCGGAA
76981 GGTAGAACGT CGCCGATCCG CCGGCGTGGG GCAGCAGCAC CACCCGTACC GGGGCCTCGG
77041 GCGTGGGGAA GAACTGCCGC AGCCAGAGTT CCGAGCTCAC CGCACCCCCT CGGCCGCGAC
77101 CTGGGGAGCC CGGAACCGGG TGATCTCGGC CAAGTGCTTC TCCCGCATCT CCGGGTCGGT
77161 CACGCCCCAT CCCTCCTCCG GCGCCAGACA GAGGACGCCG ACTTTGCCGT TGTGCACATT
77221 GCGATGCACA TCGCGCACCG CCGACCCGAC GTCGTCGAGC GGGTAGGTCA CCGACAGCGT
77281 CGGGTGCACC ATCCCCTTGC AGATCAGGCG GTTCGCCTCC CACGCCTCAC GATAGTTCGC
77341 GAAGTGGGTA CCGATGATCC GCTTCACGGA CATCCACAGG TACCGATTGT CAAAGGCGTG
77401 CTCGTATCCC GAGGTTGACG CGCAGGTGAC GATCGTGCCA CCCCGACGTG TCACGTAGAC
77461 ACTCGCGCCG AACGTCGCGC GCCCCGGGTG CTCGAACACG ATGTCGGGAT CGTCACCGCC
77521 GGTCAGCTCC CGGATC (SEQ ID NO:1)
```

Those of skill in the art will recognize that, due to the degenerate nature of the genetic code, a variety of DNA compounds differing in their nucleotide sequences can be used to encode a given amino acid sequence of the invention. The native DNA sequence encoding the FK-520 PKS of *Streptomyces hygroscopicus* is shown herein merely to illustrate a preferred embodiment of the invention, and the present invention includes DNA compounds of any sequence that encode the amino acid sequences of the polypeptides and proteins of the invention. In similar fashion, a polypeptide can typically tolerate one or more amino acid substitutions, deletions, and insertions in its amino acid sequence without loss or significant loss of a desired activity. The present invention includes such polypeptides with alternate amino acid sequences, and the amino acid sequences shown merely illustrate preferred embodiments of the invention.

The recombinant nucleic acids, proteins, and peptides of the invention are many and diverse. To facilitate an understanding of the invention and the diverse compounds and methods provided thereby, the following general description of the FK-520 PKS genes and modules of the PKS proteins encoded thereby is provided. This general description is followed by a more detailed description of the various domains and modules of the FK-520 PKS contained in and encoded by the compounds of the invention. In this description, reference to a heterologous PKS refers to any PKS other than the FK-520 PKS. Unless otherwise indicated, reference to a PKS includes reference to a portion of a PKS. Moreover, reference to a domain, module, or PKS includes reference to the nucleic acids encoding the same and vice-versa, because the methods and reagents of the invention provide or enable one to prepare proteins and the nucleic acids that encode them.

The FK-520 PKS is composed of three proteins encoded by three genes designated fkbA,fkbB, and fkbC. The fkbA ORF encodes extender modules 7–10 of the PKS. The fkbB ORE encodes the loading module (the CoA ligase) and extender modules 1–4 of the PKS. The fkbC ORF encodes extender modules 5–6 of the PKS. The fkbP ORF encodes the NRPS that attaches the pipecolic acid and cyclizes the FK-520 polyketide.

The loading module of the FK-520 PKS includes a CoA ligase, an ER domain, and an ACP domain. The starter building block or unit for FK-520 is believed to be a dihydroxycyclohexene carboxylic acid, which is derived from shikimate. The recombinant DNA compounds of the invention that encode the loading module of the FK-520 PKS and the corresponding polypeptides encoded thereby are useful for a variety of methods and in a variety of compounds. In one embodiment, a DNA compound comprising a sequence that encodes the FK-520 loading module is inserted into a DNA compound that comprises the coding sequence for a heterologous PKS. The resulting construct, in which the coding sequence for the loading module of the heterologous PKS is replaced by the coding sequence for the FK-520 loading module, provides a novel PKS coding sequence. Examples of heterologous PKS coding sequences include the rapamycin, FK-506, rifamycin, and avermectin PKS coding sequences. In another embodiment, a DNA compound comprising a sequence that encodes the FK-520 loading module is inserted into a DNA compound that comprises the coding sequence for the FK-520 PKS or a recombinant FK-520 PKS that produces an FK-520 derivative.

In another embodiment, a portion of the loading module coding sequence is utilized in conjunction with a heterologous coding sequence. In this embodiment, the invention provides, for example, either replacing the CoA ligase with a different CoA ligase, deleting the ER, or replacing the ER with a different ER. In addition, or alternatively, the ACP can be replaced by another ACP. In similar fashion, the corresponding domains in another loading or extender module can be replaced by one or more domains of the FK-520 PKS. The resulting heterologous loading module coding sequence can be utilized in conjunction with a coding sequence for a PKS that synthesizes FK-520, an FK-520 derivative, or another polyketide.

The first extender module of the FK-520 PKS includes a KS domain, an AT domain specific for methylmalonyl CoA, a DH domain, a KR domain, and an ACP domain. The recombinant DNA compounds of the invention that encode the first extender module of the FK-520 PKS and the corresponding polypeptides encoded thereby are useful for a variety of applications. In one embodiment, a DNA compound comprising a sequence that encodes the FK-520 first extender module is inserted into a DNA compound that comprises the coding sequence for a heterologous PKS. The resulting construct, in which the coding sequence for a module of the heterologous PKS is either replaced by that for the first extender module of the FK-520 PKS or the latter is merely added to coding sequences for modules of the heterologous PKS, provides a novel PKS coding sequence. In another embodiment, a DNA compound comprising a sequence that encodes the first extender module of the FK-520 PKS is inserted into a DNA compound that comprises the remainder of the coding sequence for the FK-520 PKS or a recombinant FK-520 PKS that produces an FK-520 derivative.

In another embodiment, all or only a portion of the first extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting either the DH or KR or both; replacing the DH or KR or both with another DH or KR; and/or inserting an ER. In replacing or inserting KR, DH, and ER domains, it is often beneficial to replace the existing KR, DH, and ER domains with the complete set of domains desired from another module. Thus, if one desires to insert an ER domain, one may simply replace the existing KR and DH domains with a KR, DH, and ER set of domains from a module containing such domains. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a gene for a PKS that produces a polyketide other than FK-520, or from chemical synthesis. The resulting heterologous first extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the first extender module of the FK-520 PKS.

In an illustrative embodiment of this aspect of the invention, the invention provides recombinant PKSs and recombinant DNA compounds and vectors that encode such PKSs in which the KS domain of the first extender module has been inactivated. Such constructs are especially useful when placed in translational reading frame with the remaining modules and domains of an FK-520 or FK-520 derivative PKS. The utility of these constructs is that host cells expressing, or cell free extracts containing, the PKS encoded thereby can be fed or supplied with N-acylcysteamine thioesters of novel precursor molecules to prepare FK-520 derivatives. See U.S. patent application Ser. No. 60/117,384, filed Jan. 27, 1999, and PCT patent publication Nos. US97/02358 and US99/03986, each of which is incorporated herein by reference.

The second extender module of the FK-520 PKS includes a KS, an AT specific for methylmalonyl CoA, a KR, an inactive DH, and an ACP. The recombinant DNA compounds of the invention that encode the second extender module of the FK-520 PKS and the corresponding polypeptides encoded thereby are useful for a variety of applications. In one embodiment, a DNA compound comprising a sequence that encodes the FK-520 second extender module is inserted into a DNA compound that comprises the coding sequence for a heterologous PKS. The resulting construct, in which the coding sequence for a module of the heterologous PKS is either replaced by that for the second extender module of the FK-520 PKS or the latter is merely added to coding sequences for the modules of the heterologous PKS, provides a novel PKS coding sequence. In another embodiment, a DNA compound comprising a sequence that encodes the second extender module of the FK-520 PKS is inserted into a DNA compound that comprises the coding sequence for the remainder of the FK-520 PKS or a recombinant FK-520 PKS that produces an FK-520 derivative.

In another embodiment, all or a portion of the second extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting the KR and/or the inactive DH; replacing the KR with another KR; and/or inserting an active DH or an active DH and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous second extender module coding sequence can be utilized in conjunction with a coding sequence from a PKS that synthesizes FK-520, an FK-520 derivative, or another polyketide. In similar fashion, the corresponding domains in a module of a heterologous PKS can be replaced by one or more domains of the second extender module of the FK-520 PKS.

The third extender module of the FK-520 PKS includes a KS, an AT specific for malonyl CoA, a KR, an inactive DH, and an ACP. The recombinant DNA compounds of the invention that encode the third extender module of the FK-520 PKS and the corresponding polypeptides encoded thereby are useful for a variety of applications. In one embodiment, a DNA compound comprising a sequence that encodes the FK-520 third extender module is inserted into a DNA compound that comprises the coding sequence for a heterologous PKS. The resulting construct, in which the coding sequence for a module of the heterologous PKS is either replaced by that for the third extender module of the FK-520 PKS or the latter is merely added to coding sequences for the modules of the heterologous PKS, provides a novel PKS coding sequence. In another embodiment, a DNA compound comprising a sequence that encodes the third extender module of the FK-520 PKS is inserted into a DNA compound that comprises the coding sequence for the remainder of the FK-520 PKS or a recombinant FK-520 PKS that produces an FK-520 derivative.

In another embodiment, all or a portion of the third extender module coding sequence is utilized in conjunction with other PKS coding sequences to create a hybrid module. In this embodiment, the invention provides, for example, either replacing the malonyl CoA specific AT with a methylmalonyl CoA, ethylmalonyl CoA, or 2-hydroxymalonyl CoA specific AT; deleting the KR and/or the inactive DH; replacing the KR with another KR; and/or inserting an active DH or an active DH and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous third extender module coding sequence can be utilized in conjunction with a coding sequence from a PKS that synthesizes FK-520, an FK-520 derivative, or another polyketide. In similar fashion, the corresponding domains in a module of a heterologous PKS can be replaced by one or more domains of the third extender module of the FK-520 PKS.

The fourth extender module of the FK-520 PKS includes a KS, an AT that binds ethylmalonyl CoA, an inactive DH, and an ACP. The recombinant DNA compounds of the invention that encode the fourth extender module of the FK-520 PKS and the corresponding polypeptides encoded thereby are useful for a variety of applications. In one embodiment, a DNA compound comprising a sequence that encodes the FK-520 fourth extender module is inserted into a DNA compound that comprises the coding sequcnce for a heterologous PKS. The resulting construct, in which the coding sequence for a module of the heterologous PKS is either replaced by that for the fourth extender module of the FK-520 PKS or the latter is merely added to coding sequences for the modules of the heterologous PKS, provides a novel PKS coding sequence. In another embodiment, a DNA compound comprising a sequence that encodes the fourth extender module of the FK-520 PKS is inserted into a DNA compound that comprises the remainder of the coding sequence for the FK-520 PKS or a recombinant FK-520 PKS that produces an FK-520 derivative.

In another embodiment, a portion of the fourth extender module coding sequence is utilized in conjunction with other PKS coding sequences to create a hybrid module. In this embodiment, the invention provides, for example, either replacing the ethylmalonyl CoA specific AT with a malonyl CoA, methylmalonyl CoA, or 2-hydroxymalonyl CoA specific AT; and/or deleting the inactive DH, inserting a KR, a KR and an active DH, or a KR, an active DH, and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, a PKS for a polyketide other than FK-520, or from chemical synthesis. The resulting heterologous fourth extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the fourth extender module of the FK-520 PKS.

As illustrative examples, the present invention provides recombinant genes, vectors, and host cells that result from the conversion of the FK-506 PKS to an FK-520 PKS and vice-versa. In one embodiment, the invention provides a recombinant set of FK-506 PKS genes but in which the coding sequences for the fourth extender module or at least those for the AT domain in the fourth extender module have been replaced by those for the AT domain of the fourth extender module of the FK-520 PKS. This recombinant PKS can be used to produce FK-520 in recombinant host cells. In another embodiment, the invention provides a recombinant set of FK-520 PKS genes but in which the coding sequences for the fourth extender module or at least those for the AT domain in the fourth extender module have been replaced by those for the AT domain of the fourth extender module of the FK-506 PKS. This recombinant PKS can be used to produce FK-506 in recombinant host cells.

Other examples of hybrid PKS enzymes of the invention include those in which the AT domain of module 4 has been replaced with a malonyl specific AT domain to provide a PKS that produces 21-desethyl-FK520 or with a methylmalonyl specific AT domain to provide a PKS that produces 21-desethyl-21-methyl-FK520. Another hybrid PKS of the invention is prepared by replacing the AT and inactive KR domain of FK-520 extender module 4 with a methylmalonyl specific AT and an active KR domain, such as, for example, from module 2 of the DEBS or oleandolide PKS enzymes, to produce 21-desethyl-21-methyl-22-desoxo-22-hydroxy-FK520. The compounds produced by these hybrid PKS enzymes are neurotrophins.

The fifth extender module of the FK-520 PKS includes a KS, an AT that binds methylmalonyl CoA, a DH, a KR, and an ACP. The recombinant DNA compounds of the invention that encode the fifth extender module of the FK-520 PKS and the corresponding polypeptides encoded thereby are useful for a variety of applications. In one embodiment, a DNA compound comprising a sequence that encodes the FK-520 fifth extender module is inserted into a DNA compound that comprises the coding sequence for a heterologous PKS. The resulting construct, in which the coding sequence for a module of the heterologous PKS is either replaced by that for the fifth extender module of the FK-520 PKS or the latter is merely added to coding sequences for the modules of the heterologous PKS, provides a novel PKS. In another embodiment, a DNA compound comprising a sequence that encodes the fifth extender module of the FK-520 PKS is inserted into a DNA compound that comprises the coding sequence for the FK-520 PKS or a recombinant FK-520 PKS that produces an FK-520 derivative.

In another embodiment, a portion of the fifth extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting any one or both of the DH and KR; replacing any one or both of the DH and KR with either a KR and/or DH; and/or inserting an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous fifth extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the fifth extender module of the FK-520 PKS.

In an illustrative embodiment, the present invention provides a set of recombinant FK-520 PKS genes in which the coding sequences for the DH domain of the fifth extender module have been deleted or mutated to render the DH non-functional. In one such mutated gene, the KR and DH coding sequences are replaced with those encoding only a KR domain from another PKS gene. The resulting PKS genes code for the expression of an FK-520 PKS that produces an FK-520 analog that lacks the C-19 to C-20 double bond of FK-520 and has a C-20 hydroxyl group. Such analogs are preferred neurotrophins, because they have little or no immunosuppressant activity. This recombinant fifth extender module coding sequence can be combined with other coding sequences to make additional compounds of the invention. In an illustrative embodiment, the present invention provides a recombinant FK-520 PKS that contains both this fifth extender module and the recombinant fourth extender module described above that comprises the coding sequence for the fourth extender module AT domain of the FK-506 PKS. The invention also provides recombinant host cells derived from FK-506 producing host cells that have been mutated to prevent production of FK-506 but that express this recombinant PKS and so synthesize the corresponding (lacking the C-19 to C-20 double bond of FK-506 and having a C-20 hydroxyl group) FK-506 derivative. In another embodiment, the present invention provides a recombinant FK-506 PKS in which the DH domain of module 5 has been deleted or otherwise rendered inactive and thus produces this novel polyketide.

The sixth extender module of the FK-520 PKS includes a KS, an AT specific for methylmalonyl CoA, a KR, a DH, an ER, and an ACP. The recombinant DNA compounds of the invention that encode the sixth extender module of the FK-520 PKS and the corresponding polypeptides encoded thereby are useful for a variety of applications. In one embodiment, a DNA compound comprising a sequence that encodes the FK-520 sixth extender module is inserted into a DNA compound that comprises the coding sequence for a heterologous PKS. The resulting construct, in which the coding sequence for a module of the heterologous PKS is either replaced by that for the sixth extender module of the FK-520 PKS or the latter is merely added to coding sequences for the modules of the heterologous PKS, provides a novel PKS coding sequence. In another embodiment, a DNA compound comprising a sequence that encodes the sixth extender module of the FK-520 PKS is inserted into a DNA compound that comprises the coding sequence for the remainder of the FK-520 PKS or a recombinant FK-520 PKS that produces an FK-520 derivative.

In another embodiment, a portion of the sixth extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting any one, two, or all three of the KR, DH, and ER; and/or replacing any one, two, or all three of the KR, DH, and ER with another KR, DH, and ER. In addition, the KS and/or ACP can be replaced with another KS and/or ACP. In each of these replacements, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous sixth extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the sixth extender module of the FK-520 PKS.

In an illustrative embodiment, the present invention provides a set of recombinant FK-520 PKS genes in which the coding sequences for the DH and ER domains of the sixth extender module have been deleted or mutated to render them non-functional. In one such mutated gene, the KR, ER, and DH coding sequences are replaced with those encoding only a KR domain from another PKS gene. This can also be accomplished by simply replacing the coding sequences for extender module six with those for an extender module having a methylmalonyl specific AT and only a KR domain from a heterologous PKS gene, such as, for example, the coding sequences for extender module two encoded by the eryAI gene. The resulting PKS genes code for the expression of an FK-520 PKS that produces an FK-520 analog that has a C-18 hydroxyl group. Such analogs are preferred neurotrophins, because they have little or no immunosuppressant activity. This recombinant sixth extender module coding sequence can be combined with other coding sequences to make additional compounds of the invention. In an illustrative embodiment, the present invention provides a recombinant FK-520 PKS that contains both this sixth extender module and the recombinant fourth extender module described above that comprises the coding sequence for the fourth extender module AT domain of the FK-506 PKS. The invention also provides recombinant host cells derived from FK-506 producing host cells that have been mutated to prevent production of FK-506 but that express this recombinant PKS and so synthesize the corresponding (having a C-18 hydroxyl group) FK-506 derivative. In another embodiment, the present invention provides a recombinant FK-506 PKS in which the DH and ER domains of module 6 have been deleted or otherwise rendered inactive and thus produces this novel polyketide.

The seventh extender module of the FK-520 PKS includes a KS, an AT specific for 2-hydroxymalonyl CoA, a KR, a DH, an ER, and an ACP. The recombinant DNA compounds of the invention that encode the seventh extender module of the FK-520 PKS and the corresponding polypeptides encoded thereby are useful for a variety of applications. In one embodiment, a DNA compound comprising a sequence that encodes the FK-520 seventh extender module is inserted into a DNA compound that comprises the coding sequence for a heterologous PKS. The resulting construct, in which the coding sequence for a module of the heterologous PKS is either replaced by that for the seventh extender module of the FK-520 PKS or the latter is merely added to coding sequences for the modules of the heterologous PKS, provides a novel PKS coding sequence. In another embodiment, a DNA compound comprising a sequence that encodes the seventh extender module of the FK-520 PKS is inserted into a DNA compound that comprises the coding sequence for the remainder of the FK-520 PKS or a recombinant FK-520 PKS that produces an FK-520 derivative.

In another embodiment, a portion or all of the seventh extender module coding sequence is utilized in conjunction with other PKS coding sequences to create a hybrid module. In this embodiment, the invention provides, for example, either replacing the 2-hydroxymalonyl CoA specific AT with a methylmalonyl CoA, ethylmalonyl CoA, or malonyl CoA specific AT; deleting the KR, the DH, and/or the ER; and/or replacing the KR, DH, and/or ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous seventh extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the seventh extender module of the FK-520 PKS.

In an illustrative embodiment, the present invention provides a set of recombinant FK-520 PKS genes in which the coding sequences for the AT domain of the seventh extender module has been replaced with those encoding an AT domain for malonyl, methylmalonyl, or ethylmalonyl CoA from another PKS gene. The resulting PKS genes code for the expression of an FK-520 PKS that produces an FK-520 analog that lacks the C-15 methoxy group, having instead a hydrogen, methyl, or ethyl group at that position, respectively. Such analogs are preferred, because they are more slowly metabolized than FK-520. This recombinant seventh extender module coding sequence can be combined with other coding sequences to make additional compounds of the invention. In an illustrative embodiment, the present invention provides a recombinant FK-520 PKS that contains both this seventh extender module and the recombinant fourth extender module described above that comprises the coding sequence for the fourth extender module AT domain of the FK-506 PKS. The invention also provides recombinant host cells derived from FK-506 producing host cells that have been mutated to prevent production of FK-506 but that express this recombinant PKS and so synthesize the corresponding (C-15-desmethoxy) FK-506 derivative. In another embodiment, the present invention provides a recombinant FK-506 PKS in which the AT domain of module 7 has been replaced and thus produces this novel polyketide.

In another illustrative embodiment, the present invention provides a hybrid PKS in which the AT and KR domains of module 7 of the FK-520 PKS are replaced by a methylmalonyl specific AT domain-and an inactive KR domain, such as, for example, the AT and KR domains of extender module 6 of the rapamycin PKS. The resulting hybrid PKS produces 15-desmethoxy-15-methyl-16-oxo-FK-520, a neurotrophin compound.

The eighth extender module of the FK-520 PKS includes a KS, an AT specific for 2-hydroxymalonyl CoA, a KR, and an ACP. The recombinant DNA compounds of the invention that encode the eighth extender module of the FK-520 PKS and the corresponding polypeptides encoded thereby are useful for a variety of applications. In one embodiment, a DNA compound comprising a sequence that encodes the FK-520 eighth extender module is inserted into a DNA compound that comprises the coding sequence for a heterologous PKS. The resulting construct, in which the coding sequence for a module of the heterologous PKS is either replaced by that for the eighth extender module of the FK-520 PKS or the latter is merely added to coding sequences for the modules of the heterologous PKS, provides a novel PKS coding sequence. In another embodiment, a DNA compound comprising a sequence that encodes the eighth extender module of the FK-520 PKS is inserted into a DNA compound that comprises the coding sequence for the remainder of the FK-520 PKS or a recombinant FK-520 PKS that produces an FK-520 derivative.

In another embodiment, a portion of the eighth extender module coding sequence is utilized in conjunction with other PKS coding sequences to create a hybrid module. In this embodiment, the invention provides, for example, either replacing the 2-hydroxymalonyl CoA specific AT with a methylmalonyl CoA, ethylmalonyl CoA, or malonyl CoA specific AT; deleting or replacing the KR; and/or inserting a DH or a DH and an ER. In addition, the KS and/or ACP can be replaced with another KS and/or ACP. In each of these replacements, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous eighth extender module coding sequence can be utilized in conjunction with a PKS that synthesizes FK-520, an FK-520 derivative, or another polyketide. In similar fashion, the corresponding domains in a module of a heterologous PKS can be replaced by one or more domains of the eighth extender module of the FK-520 PKS.

In an illustrative embodiment, the present invention provides a set of recombinant FK-520 PKS genes in which the coding sequences for the AT domain of the eighth extender module has been replaced with those encoding an AT domain for malonyl, methylmalonyl, or ethylmalonyl CoA from another PKS gene. The resulting PKS genes code for the expression of an FK-520 PKS that produces an FK-520 analog that lacks the C-13 methoxy group, having instead a hydrogen, methyl, or ethyl group at that position, respectively. Such analogs are preferred, because they are more slowly metabolized than FK-520. This recombinant eighth extender module coding sequence can be combined with other coding sequences to make additional compounds of the invention. In an illustrative embodiment, the present invention provides a recombinant FK-520 PKS that contains both this eighth extender module and the recombinant fourth extender module described above that comprises the coding sequence for the fourth extender module AT domain of the FK-506 PKS. The invention also provides recombinant host cells derived from FK-506 producing host cells that have been mutated to prevent production of FK-506 but that express this recombinant PKS and so synthesize the corresponding (C-13-desmethoxy) FK-506 derivative. In another embodiment, the present invention provides a recombinant FK-506 PKS in which the AT domain of module 8 has been replaced and thus produces this novel polyketide.

The ninth extender module of the FK-520 PKS includes a KS, an AT specific for methylmalonyl CoA, a KR, a DH, an ER, and an ACP. The recombinant DNA compounds of the invention that encode the ninth extender module of the FK-520 PKS and the corresponding polypeptides encoded thereby are useful for a variety of applications. In one embodiment, a DNA compound comprising a sequence that encodes the FK-520 ninth extender module is inserted into a DNA compound that comprises the coding sequence for a heterologous PKS. The resulting construct, in which the coding sequence for a module of the heterologous PKS is either replaced by that for the ninth extender module of the FK-520 PKS or the latter is merely added to coding sequences for the modules of the heterologous PKS, provides a novel PKS coding sequence. In another embodiment, a DNA compound comprising a sequence that encodes the ninth extender module of the FK-520 PKS is inserted into a DNA compound that comprises the coding sequence for the remainder of the FK-520 PKS or a recombinant FK-520 PKS that produces an FK-520 derivative.

In another embodiment, a portion of the ninth extender module coding sequence is utilized in conjunction with other PKS coding sequences to create a hybrid module. In this embodiment, the invention provides, for example, either replacing the methylmalonyl CoA specific AT with a malonyl CoA, ethylmalonyl CoA, or 2-hydroxymalonyl CoA specific AT; deleting any one, two, or all three of the KR, DH, and ER; and/or replacing any one, two, or all three of the KR, DH, and ER with another KR, DH, and/or ER. In addition, the KS and/or ACP can be replaced with another KS and/or ACP. In each of these replacements, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous ninth extender module coding sequence can be utilized in conjunction with a PKS that synthesizes FK-520, an FK-520 derivative, or another polyketide. In similar fashion, the corresponding domains in a module of a heterologous PKS can be replaced by one or more domains of the ninth extender module of the FK-520 PKS.

The tenth extender module of the FK-520 PKS includes a KS, an AT specific for malonyl CoA, and an ACP. The recombinant DNA compounds of the invention that encode the tenth extender module of the FK-520 PKS and the corresponding polypeptides encoded thereby are useful for a variety of applications. In one embodiment, a DNA compound comprising a sequence that encodes the FK-520 tenth extender module is inserted into a DNA compound that comprises the coding sequence for a heterologous PKS. The resulting construct, in which the coding sequence for a module of the heterologous PKS is either replaced by that for the tenth extender module of the FK-520 PKS or the latter is merely added to coding sequences for the modules of the heterologous PKS, provides a novel PKS coding sequence. In another embodiment, a DNA compound comprising a sequence that encodes the tenth extender module of the FK-520 PKS is inserted into a DNA compound that comprises the coding sequence for the remainder of the FK-520 PKS or a recombinant FK-520 PKS that produces an FK-520 derivative.

In another embodiment, a portion or all of the tenth extender module coding sequence is utilized in conjunction with other PKS coding sequences to create a hybrid module. In this embodiment, the invention provides, for example, either replacing the malonyl CoA specific AT with a methylmalonyl CoA, ethylmalonyl CoA, or 2-hydroxymalonyl CoA specific AT; and/or inserting a KR, a KR and DH, or a KR, DH, and an ER. In addition, the KS and/or ACP can be replaced with another KS and/or ACP. In each of these replacements or insertions, the heterologous KS, AT, DH, KR, ER, or ACP coding sequence can originate from a coding sequence for another module of the FK-520 PKS, from a coding sequence for a PKS that produces a polyketide other than FK-520, or from chemical synthesis. The resulting heterologous tenth extender module coding sequence can be utilized in conjunction with a coding sequence for a PKS that synthesizes FK-520, an FK-520 derivative, or another polyketide. In similar fashion, the corresponding domains in a module of a heterologous PKS can be replaced by one or more domains of the tenth extender module of the FK-520 PKS.

The FK-520 polyketide precursor produced by the action of the tenth extender module of the PKS is then attached to pipecolic acid and cyclized to form FK-520. The enzyme FkbP is the NRPS like enzyme that catalyzes these reactions. FkbP also includes a thioesterase activity that cleaves the nascent FK-520 polyketide from the NRPS. The present invention provides recombinant DNA compounds that encode the fkbP gene and so provides recombinant methods for expressing the fkbP gene product in recombinant host cells. The recombinant fkbP genes of the invention include those in which the coding sequence for the adenylation domain has been mutated or replaced with coding sequences from other NRPS like enzymes so that the resulting recombinant FkbP incorporates a moiety other than pipecolic acid. For the construction of host cells that do not naturally produce pipecolic acid, the present invention provides recombinant DNA compounds that express the enzymes that catalyze at least some of the biosynthesis of pipecolic acid (see Nielsen et al., 1991, *Biochem.* 30: 5789–96). The fkbL gene encodes a homolog of RapL, a lysine cyclodeaminase responsible in part for producing the pipecolate unit added to the end of the polyketide chain. The fkbB and fkbL recombinant genes of the invention can be used in heterologous hosts to produce compounds such as FK-520 or, in conjunction with other PKS or NRPS genes, to produce known or novel polyketides and non-ribosmal peptides.

The present invention also provides recombinant DNA compounds that encode the P450 oxidase and methyltransferase genes involved in the biosynthesis of FK-520. FIG. 2 shows the various sites on the FK-520 polyketide core structure at which these enzymes act. By providing these genes in recombinant form, the present invention provides recombinant host cells that can produce FK-520. This is accomplished by introducing the recombinant PKS, P450 oxidase, and methyltransferase genes into a heterologous host cell. In a preferred embodiment, the heterologous host cell is *Streptomyces coelicolor* CH999 or *Streptomyces lividans* K4–114, as described in U.S. Pat. No. 5,830,750 and U.S. patent application Ser. Nos. 08/828,898, filed Mar. 31, 1997, and 09/181,833, filed Oct. 28, 1998, each of which is incorporated herein by reference. In addition, by providing recombinant host cells that express only a subset of these genes, the present invention provides methods for making FK-520 precursor compounds not readily obtainable by other means.

In a related aspect, the present invention provides recombinant DNA compounds and vectors that are useful in generating, by homologous recombination, recombinant host cells that produce FK-520 precursor compounds. In this aspect of the invention, a native host cell that produces FK-520 is transformed with a vector (such as an SCP2* derived vector for Streptomyces host cells) that encodes one or more disrupted genes (i.e., a hydroxylase, a methyltransferase, or both) or merely flanking regions from those genes. When the vector integrates by homologous recombination, the native, functional gene is deleted or replaced by the non-functional recombinant gene, and the resulting host cell thus produces an FK-520 precursor. Such host cells can also be complemented by introduction of a modified form of the deleted or mutated non-functional gene to produce a novel compound.

In one important embodiment, the present invention provides a hybrid PKS and the corresponding recombinant DNA compounds that encode those hybrid PKS enzymes. For purposes of the present invention a hybrid PKS is a recombinant PKS that comprises all or part of one or more modules and thioesterase/cyclase domain of a first PKS and all or part of one or more modules, loading module, and thioesterase/cyclase domain of a second PKS. In one preferred embodiment, the first PKS is all or part of the FK-520 PKS, and the second PKS is only a portion or all of a non-FK-520 PKS.

One example of the preferred embodiment is an FK-520 PKS in which the AT domain of module 8, which specifies a hydroxymalonyl CoA and from which the C-13 methoxy group of FK-520 is derived, is replaced by an AT domain that specifies a malonyl, methylmalonyl, or ethylmalonyl CoA. Exarnples of such replacement AT domains include the AT domains from modules 3, 12, and 13 of the rapaymycin PKS and from modules 1 and 2 of the erythromycin PKS. Such replacements, conducted at the level of the gene for the PKS, are illustrated in the examples below. Another illustrative example of such a hybrid PKS includes an FK-520 PKS in which the natural loading module has been replaced with a loading module of another PKS. Another example of such a hybrid PKS is an FK-520 PKS in which the AT domain of module three is replaced with an AT domain that binds methylmalonyl CoA.

In another preferred embodiment, the first PKS is most but not all of a non-FK-520 PKS, and the second PKS is only a portion or all of the FK-520 PKS. An illustrative example of such a hybrid PKS includes an erythromycin PKS in which an AT specific for methylmalonyl CoA is replaced with an AT from the FK-520 PKS specfic for malonyl CoA.

Those of skill in the art will recognize that all or part of either the first or second PKS in a hybrid PKS of the invention need not be isolated from a naturally occurring source. For example, only a small portion of an AT domain determines its specificity. See U.S. provisional patent application Serial No. 60/091,526, incorporated herein by reference. The state of the art in DNA synthesis allows the artisan to construct de novo DNA compounds of size sufficient to construct a useful portion of a PKS module or domain. For purposes of the present invention, such synthetic DNA compounds are deemed to be a portion of a PKS.

Thus, the hybrid modules of the invention are incorporated into a PKS to provide a hybrid PKS of the invention. A hybrid PKS of the invention can result not only:

(i) from fusions of heterologous domain (where heterologous means the domains in that module are from at least two different naturally occurring modules) coding sequences to produce a hybrid module coding sequence contained in a PKS gene whose product is incorporated into a PKS, but also:

(ii) from fusions of heterologous module (where heterologous module means two modules are adjacent to one another that are not adjacent to one another in naturally occurring PKS enzymes) coding sequences to produce a hybrid coding sequence contained in a PKS gene whose product is incorporated into a PKS, (iii) from expression of one or more FK-520 PKS genes with one or more non-FK-520 PKS genes, including both naturally occurring and recombinant non-FK-520 PKS genes, and (iv) from combinations of the foregoing. Various hybrid PKSs of the invention illustrating these various alternatives are described herein.

Examples of the production of a hybrid PKS by co-expression of PKS genes from the FK-520 PKS and another non-FK-520 PKS include hybrid PKS enzymes produced by coexpression of FK-520 and rapamycin PKS genes. Preferably, such hybrid PKS enzymes are produced in recombinant Streptomyces host cells that produce FK-520 or FK-506 but have been mutated to inactivate the gene whose function is to be replaced by the rapamycin PKS gene introduced to produce the hybrid PKS. Particular examples include (i) replacement of the fkbC gene with the rapB gene; and (ii) replacement of the fkbA gene with the rapC gene. The latter hybrid PKS produces 13,15-didesmethoxy-FK-520, if the host cell is an FK-520 producing host cell, and 13,15-didesmethoxy-FK-506, if the host cell is an FK-506 producing host cell. The compounds produced by these hybrid PKS enzymes are immunosuppressants and neurotrophins but can be readily modified to act only as neurotrophins, as described in Example 6, below.

Other illustrative hybrid PKS enzymes of the invention are prepared by replacing the fkbA gene of an FK-520 or FK-506 producing host cell with a hybrid fkbA gene in which: (a) the extender module 8 through 10, inclusive, coding sequences have been replaced by the coding sequnces for extender modules 12 to 14, inclusive, of the rapamycin PKS; and (b) the module 8 coding sequences have been replaced by the module 8 coding sequence of the rifamycin PKS. When expressed with the other, naturally occurring FK-520 or FK-506 PKS genes and the genes of the modification enzymes, the resulting hybrid PKS enzymes produce, respectively, (a) 13-desmethoxy-FK-520 or 13-desmethoxy-FK-506; and (b) 13-desmethoxy-13-methyl-FK-520 or 13-desmethoxy-13-methyl-FK-506. In a preferred embodiment, these recombinant PKS genes of the invention are introduced into the producing host cell by a vector such as pHU204, which is a plamsid pRM5 derivative that has the well-characterized SCP2* replicon, the colEI replicon, the tsr and bla resistance genes, and a cos site. This vector can be used to introduce the recombinant fkbA replacement gene in an FK-520 or FK-506 producing host cell (or a host cell derived therefrom in which the endogenous fkbA gene has either been rendered inactive by mutation, deletion or homologous recombination with the gene that replaces it) to produce the desired hybrid PKS.

In constructing hybrid PKSs of the invention, certain general methods may be helpful. For example, it is often beneficial to retain the framework of the module to be altered to make the hybrid PKS. Thus, if one desires to add DH and ER functionalities to a module, it is often preferred to replace the KR domain of the original module with a KR, DH, and ER domain-containing segment from another module, instead of merely inserting DH and ER domains. One can alter the stereochemical specificity of a module by replacement of the KS domain with a KS domain from a module that specifies a different stereochemistry. See Lau et al., 1999, "Dissecting the role of acyltransferase domains of modular polyketide synthases in the choice and stereochemical fate of extender units," *Biochemistry* 38(5):1643–1651, incorporated herein by reference. Stereochemistry can also be changed by changing the KR domain. Also, one can alter the specificity of an AT domain by changing only a small segment of the domain. See Lau et al., supra. One can also take advantage of known linker regions in PKS proteins to link modules from two different PKSs to create a hybrid PKS. See Gokhale et al., Apr. 16, 1999, "Dissecting and Exploiting Intermodular Communication in Polyketide Synthases," *Science* 284: 482–485, incorporated herein by reference.

The following Table lists references describing illustrative PKS genes and corresponding enzymes that can be utilized in the construction of the recombinant PKSs and the corresponding DNA compounds that encode them of the invention. Also presented are various references describing tailoring enzymes and corresponding genes that can be employed in accordance with the methods of the present invention.

Avermectin

U.S. Pat. No. 5,252,474 to Merck.

MacNeil et al., 1993, *Industrial Microorganisms: Basic and Applied Molecular Genetics*, Baltz, Hegeman, & Skatrud, eds. (ASM), pp. 245–256, A Comparison of the Genes Encoding the Polyketide Synthases for Avermectin, Erythromycin, and Nemadectin.

MacNeil et al., 1992, *Gene* 115: 119–125, Complex Organization of the *Streptomyces avermitilis* genes encoding the avermectin polyketide synthase.

Ikeda et al., Aug. 1999, Organization of the biosynthetic gene cluster for the polyketide anthelmintic macrolide avermectin in *Streptomyces avermitilis, Proc. Natl. Acad. Sci. USA* 96: 9509–9514.

Candicidin (FR008)

Hu et al., 1994, Mol. *Microbiol.* 14: 163–172.

Epothilone

U.S. Pat. App. Ser. No. 60/130,560, filed Apr. 22, 1999.

Erythromycin

PCT Pub. No. 93/13663 to Abbott.

U.S. Pat. No. 5,824,513 to Abbott.

Donadio et al., 1991, *Science* 252:675–9.

Cortes et al., 8 Nov. 1990, *Nature* 348:176–8, An unusually large multifunctional polypeptide in the erythromycin producing polyketide synthase of *Saccharopolyspora erythraea.*

Glycosylation Enzymes

PCT Pat. App. Pub. No. 97/23630 to Abbott.

FK-506

Motamedi et al., 1998, The biosynthetic gene cluster for the macrolactone ring of the immunosuppressant FK-506, *Eur. J. biochem.* 256: 528–534.

Motamedi et al., 1997, Structural organization of a multifunctional polyketide synthase involved in the biosynthesis of the macrolide immunosuppressant FK-506, *Eur. J. Biochem.* 244: 74–80.

Methyltransferase

U.S. Pat. No. 5,264,355, issued Nov. 23, 1993, Methylating enzyme from Streptomyces MA6858. 31-O-desmethyl-FK-506 methyltransferase.

Motamedi et al., 1996, Characterization of methyltransferase and hydroxylase genes involved in the biosynthesis of the immunosuppressants FK-506 and FK-520, *J. Bacteriol.* 178: 5243–5248.

*Streptomyces hygroscopicus*

U.S. patent application Ser. No. 09/154,083, filed Sep. 16, 1998.

Lovastatin

U.S. Pat. No. 5,744,350 to Merck.

Narbomycin

U.S. patent application Ser. No. 60/107,093, filed Nov. 5, 1998, and Ser. No. 60/120,254, filed Feb. 16, 1999.

Nemadectin

MacNeil et al., 1993, supra.

Niddamycin

Kakavas et al., 1997, Identification and characterization of the niddamycin polyketide synthase genes from *Streptomyces caelestis, J. Bacteriol.* 179: 7515–7522.

Oleandomycin

Swan et al., 1994, Characterisation of a *Streptomyces antibioticus* gene encoding a type I polyketide synthase which has an unusual coding sequence, *Mol. Gen. Genet.* 242: 358–362.

U.S. patent application Ser. No. 60/120,254, filed Feb. 16, 1999.

Olano et al., 1998, Analysis of a *Streptomyces antibioticus* chromosomal region involved in oleandomycin biosynthesis, which encodes two glycosyltransferases responsible for glycosylation of the macrolactone ring, *Mol. Gen. Genet.* 259(3): 299–308.

Picromycin

PCT patent application US99/15047, filed Jul. 2, 1999.

Xue et al., 1998, Hydroxylation of macrolactones YC-17 and narbomycin is mediated by the pikc-encoded cytochrome P450 in *Streptomyces venezuelae, Chemistry & Biology* 5(11): 661–667.

Xue et al., Oct. 1998, A gene cluster for macrolide antibiotic biosynthesis in *Streptomyces venezuelae*: Architecture of metabolic diversity, *Proc. Natl. Acad. Sci. USA* 95: 12111 12116.

Platenolide

EP Pat. App. Pub. No. 791,656 to Lilly.

Rapamycin

Schwecke et al., Aug. 1995, The biosynthetic gene cluster for the polyketide rapamycin, *Proc. Natl. Acad. Sci. USA* 92:7839–7843.

Aparicio et al., 1996, Organization of the biosynthetic gene cluster for rapamycin in *Streptomyces hygroscopicus*: analysis of the enzymatic domains in the modular polyketide synthase, *Gene* 169: 9–16.

Rifamycin

August et al., Feb. 13, 1998, Biosynthesis of the ansamycin antibiotic rifamycin: deductions from the molecular analysis of the rif biosynthetic gene cluster of *Amycolatopsis mediterranei* S669, *Chemistry & Biology*, 5(2): 69–79.

Sorangium PKS

U.S. patent application Ser. No. 09/144,085, filed Aug. 31, 1998.

Soraphen

U.S. Pat. No. 5,716,849 to Novartis.

Schupp et al., 1995, *J. Bacteriology* 177: 3673–3679. *A Sorangium cellulosum* (Myxobacterium) Gene Cluster for the Biosynthesis of the Macrolide Antibiotic Soraphen A: Cloning, Characterization, and Homology to Polyketide Synthase Genes from Actinomycetes.

Spiramycin

U.S. Pat. No. 5,098,837 to Lilly.

Activator Gene

U.S. Pat. No. 5,514,544 to Lilly.

Tylosin

EP Pub. No. 791,655 to Lilly.

U.S. Pat. No. 5,876,991 to Lilly.

Kuhstoss et al., 1996, *Gene* 183:231–6., Production of a novel polyketide through the construction of a hybrid polyketide synthase.

Tailoring enzymes

Merson-Davies and Cundliffe, 1994, *Mol. Microbiol.* 13: 349–355. Analysis of five tylosin biosynthetic genes from the tyIBA region of the *Streptomyces fradiae* genome.

As the above Table illustrates, there are a wide variety of polyketide synthase genes that serve as readily available sources of DNA and sequence information for use in constructing the hybrid PKS-encoding DNA compounds of the invention. Methods for constructing hybrid PKS-encoding DNA compounds are described without reference to the FK-520 PKS in PCT patent publication No. 98/51695; U.S. Pat. Nos. 5,672,491 and 5,712,146 and U.S. patent application Ser. Nos. 09/073,538, filed May 6, 1998, and 09/141,908, filed Aug. 28, 1998, each of which is incorporated herein by reference.

The hybrid PKS-encoding DNA compounds of the invention can be and often are hybrids of more than two PKS genes. Moreover, there are often two or more modules in the hybrid PKS in which all or part of the module is derived from a second (or third) PKS. Thus, as one illustrative example, the present invention provides a hybrid FK-520 PKS that contains the naturally occurring loading module and FkbP as well as modules one, two, four, six, seven, and eight, nine, and ten of the FK-520 PKS and further contains hybrid or heterologous modules three and five. Hybrid or heterologous module three contains an AT domain that is specific of methylmalonyl CoA and can be derived for example, from the erythromycin or rapamycin PKS genes. Hybrid or heterologous module five contains an AT domain that is specific for malonyl CoA and can be derived for example, from the picromycin or rapamycin PKS genes.

While an important embodiment of the present invention relates to hybrid PKS enzymes and corresponding genes, the present invention also provides recombinant FK-520 PKS genes in which there is no second PKS gene sequence present but which differ from the FK-520 PKS gene by one or more deletions. The deletions can encompass one or more modules and/or can be limited to a partial deletion within one or more modules.

When a deletion encompasses an entire module, the resulting FK-520 derivative is at least two carbons shorter than the gene from which it was derived. When a deletion is within a module, the deletion typically encompasses a KR, DH, or ER domain, or both DH and ER domains, or both KR and DH domains, or all three KR, DH, and ER domains.

To construct a hybrid PKS or FK-520 derivative PKS gene of the invention, one can employ a technique, described in PCT Pub. No. 98/27203 and U.S. patent application Ser. No. 08/989,332, filed Dec. 11, 1997, now U.S. Pat. No. 6,033,883 each of which is incorporated herein by reference, in which the large PKS gene is divided into two or more, typically three, segments, and each segment is placed on a separate expression vector. In this manner, each of the segments of the gene can be altered, and various altered segments can be combined in a single host cell to provide a recombinant PKS gene of the invention. This technique makes more efficient the construction of large libraries of recombinant PKS genes, vectors for expressing those genes, and host cells comprising those vectors.

Thus, in one important embodiment, the recombinant DNA compounds of the invention are expression vectors. As used herein, the term expression vector refers to any nucleic acid that can be introduced into a host cell or cell-free transcription and translation medium. An expression vector can be maintained stably or transiently in a cell, whether as part of the chromosomal or other DNA in the cell or in any cellular compartment, such as a replicating vector in the cytoplasm. An expression vector also comprises a gene that serves to produce RNA that is translated into a polypeptide in the cell or cell extract. Furthermore, expression vectors typically contain additional functional elements, such as resistance-conferring genes to act as selectable markers.

The various components of an expression vector can vary widely, depending on the intended use of the vector. In particular, the components depend on the host cell(s) in which the vector will be used or is intended to function. Vector components for expression and maintenance of vectors in *E. coli* are widely known and commercially available, as are vector components for other commonly used organisms, such as yeast cells and Streptomyces cells.

In a preferred embodiment, the expression vectors of the invention are used to construct recombinant Streptomyces host cells that express a recombinant PKS of the invention. Preferred Streptomyces host cell/vector combinations of the invention include *S. coelicolor* CH999 and *S. lividans* K4–114 host cells, which do not produce actinorhodin, and expression vectors derived from the pRM1 and pRM5 vectors, as described in U.S. Pat. No. 5,830,750 and U.S. patent application Ser. Nos. 08/828,898, filed Mar. 31, 1997, and 09/181,833, filed Oct. 28, 1998, each of which is incorporated herein by reference.

The present invention provides a wide variety of expression vectors for use in Streptomyces. For replicating vectors, the origin of replication can be, for example and without limitation, a low copy number vector, such as SCP2* (see Hopwood et al., *Genetic Manipulation of Streptomyces: A Laboratory manual* (The John Innes Foundation, Norwich, U.K., 1985); Lydiate et al., 1985, *Gene* 35: 223–235; and Kieser and Melton, 1988, *Gene* 65: 83–91, each of which is incorporated herein by reference), SLP 1.2 (Thompson et al., 1982, *Gene* 20: 51–62, incorporated herein by reference), and SG5(ts) (Muth et al., 1989, *Mol. Gen. Genet.* 219: 341–348, and Bierman et al., 1992, *Gene* 116: 43–49, each of which is incorporated herein by reference), or a high copy number vector, such as pIJ101 and pJV1 (see Katz et al., 1983, *J. Gen. Microbiol.* 129: 2703–2714; Vara et al., 1989, *J. Bacteriol.* 171: 5782–5781; and Servin-Gonzalez, 1993, *Plasmid* 30: 131–140, each of which is incorporated herein by reference). Generally, however, high copy number vectors are not preferred for expression of genes contained on large segments of DNA. For non-replicating and integrating vectors, it is useful to include at least an *E. coli* origin of replication, such as from pUC, p1P, p1I, and pBR. For phage based vectors, the phages phiC31 and KC515 can be employed (see Hopwood et al., supra).

Typically, the expression vector will comprise one or more marker genes by which host cells containing the vector can be identified and/or selected. Useful antibiotic resistance conferring genes for use in Streptomyces host cells include the ermE (confers resistance to erythromycin and other macrolides and lincomycin), tsr (confers resistance to thiostrepton), aadA (confers resistance to spectinomycin and streptomycin), aacC4 (confers resistance to apramycin, kanamycin, gentamicin, geneticin (G418), and neomycin), hyg (confers resistance to hygromycin), and vph (confers resistance to viomycin) resistance conferring genes.

The recombinant PKS gene on the vector will be under the control of a promoter, typically with an attendant ribosome binding site sequence. The present invention provides the endogenous promoters of the FK-520 PKS and related biosynthetic genes in recombinant form, and these promoters are preferred for use in the native hosts and in heterologous hosts in which the promoters function. A preferred promoter of the invention is the fkbO gene promoter, comprised in a sequence of about 270 bp between the start of the open reading frames of the fkbO and fkbB genes. The fkbO promoter is believed to be bi-directional in that it promotes transcription of the genes fkbO, fkbP, and fkbA in one direction and fkbB,fkbC, and fkbL in the other. Thus, in one aspect, the present invention provides a recombinant expression vector comprising the promoter of the fkbO gene of an FK-520 producing organism positioned to transcribe a gene other than fkbo. In a preferred embodiment the transcribed gene is an FK-520 PKS gene. In another preferred embodiment, the transcribed gene is a gene that encodes a protein comprised in a hybrid PKS.

Heterologous promoters can also be employed and are preferred for use in host cells in which the endogenous FK-520 PKS gene promoters do not function or function poorly. A preferred heterologous promoter is the actI promoter and its attendant activator gene actII-ORF4, which is provided in the pRM1 and pRM5 expression vectors, supra. This promoter is activated in the stationary phase of growth when secondary metabolites are normally synthesized. Other useful Streptomyces promoters include without limitation those from the ermE gene and the melCi gene, which act constitutively, and the tipA gene and the merA gene, which can be induced at any growth stage. In addition, the T7 RNA polymerase system has been transferred to Streptomyces and can be employed in the vectors and host cells of the invention. In this system, the coding sequence for the T7 RNA polymerase is inserted into a neutral site of the chromosome or in a vector under the control of the inducible merA promoter, and the gene of interest is placed under the control of the T7 promoter. As noted above, one or more activator genes can also be employed to enhance the activity of a promoter. Activator genes in addition to the actII-ORF4 gene discussed above include dnri, redD, and ptpA genes (see U.S. patent application Ser. No. 09/181,833, supra) to activate promoters under their control.

In addition to providing recombinant DNA compounds that encode the FK-520 PKS, the present invention also provides DNA compounds that encode the ethylmalonyl CoA and 2-hydroxymalonyl CoA utilized in the synthesis of FK-520. Thus, the present invention also provides recombinant host cells that express the genes required for the biosynthesis of ethylmalonyl CoA and 2-hydroxymalonyl CoA. FIGS. 3 and 4 show the location of these genes on the cosmids of the invention and the biosynthetic pathway that produces ethylmalonyl CoA.

For 2-hydroxymalonyl CoA biosynthesis, the fkbH,fkbI, fkbJ, and fkbK genes are sufficient to confer this ability on Streptomcyces host cells. For conversion of 2-hydroxymalonyl to 2-methoxymalonyl, the fkbG gene is also employed. While the complete coding sequence for fkbH is provided on the cosmids of the invention, the sequence for this gene provided herein may be missing a T residue, based on a comparison made with a similar gene cloned from the ansamitocin gene cluster by Dr. H. Floss. Where the sequence herein shows one T, there may be two, resulting in an extension of the fkbH reading frame to encode the amino acid sequence: (SEQ ID NO:2) MTIVKCLVWDLDNTLWRGTVLEDDEVVLTDEIREVITTLDDRGILQAVASKNDH DLAWERLERLGVAEYFVLARIGWGPKSQSVREIATELNFAPTTIAFIDDQPAE RA EVAFHLPEVRCYPAEQAATLLSLPEFSPPVSTVDSRRRRLMYQAGFARDQAREA YSGPDEDFLRSLDLSMTIAPAGEEELSRVEELTLRTSQMNATGVHYSDADLRALL TDPAHEVLVVTMGDRFGPHGAVGIILLEKKPSTWHLKLLATSCRVVSFGAGATIL NWLTDQGARAGAHLVADFRRTDRNRMMEIAYRFAGFADSDCPCVSEVAGASA AGVERLHLEPSAR PAPAPTTLTLTAADIAPVTVSAAG.

For ethylmalonyl CoA biosynthesis, one requires only a crotonyl CoA reductase, which can be supplied by the host cell but can also be supplied by recombinant expression of the fkbS gene of the present invention. To increase yield of ethylmalonyl CoA, one can also express the fkbE and fkbU genes as well. While such production can be achieved using only the recombinant genes above, one can also achieve such production by placing into the recombinant host cell a large segment of the DNA provided by the cosmids of the invention. Thus, for 2-hydroxymalonyl and 2-methoxymalonyl CoA biosynthesis, one can simply provide the cells with the segment of DNA located on the left side of the FK-520 PKS genes shown in FIG. 1. For ethylmalonyl CoA biosynthesis, one can simply provide the cells with the segment of DNA located on the right side of the FK-520 PKS genes shown in FIG. 1 or, alternatively, both the right and left segments of DNA.

The recombinant DNA expression vectors that encode these genes can be used to construct recombinant host cells that can make these important polyketide building blocks from cells that otherwise are unable to produce them. For example, *Streptomyces coelicolor* and *Streptomyces lividans* do not synthesisze ethylmalonyl CoA or 2-hydroxymalonyl CoA. The invention provides methods and vectors for constructing recombinant *Streptomyces coelicolor* and *Streptomyces lividans* that are able to synthesize either or both ethylmalonyl CoA and 2-hydroxymalonyl CoA. These host cells are thus able to make polyketides, those requiring these substrates, that cannot otherwise be made in such cells.

In a preferred embodiment, the present invention provides recombinant Streptomyces host cells, such as *S. coelicolor* and *S. lividans*, that have been transformed with a recombinant vector of the invention that codes for the expression of the ethylmalonyl CoA biosynthetic genes. The resulting host cells produce ethylmalonyl CoA and so are preferred host cells for the production of polyketides produced by PKS enzymes that comprise one or more AT domains specific for ethylmalonyl CoA. Illustrative PKS enzymes of this type include the FK-520 PKS and a recombinant PKS in which one or more AT domains is specific for ethylmalonyl CoA.

In a related embodiment, the present invention provides Streptomyces host cells in which one or more of the ethylmalonyl or 2-hydroxymalonyl biosynthetic genes have been deleted by homologous recombination or rendered inactive by mutation. For example, deletion or inactivation of the fkbG gene can prevent formation of the methoxyl groups at C-13 and C-15 of FK-520 (or, in the corresponding FK-506 producing cell, FK-506), leading to the production of 13,15-didesmethoxy-13,15-dihydroxy-FK-520 (or, in the corresponding FK-506 producing cell, 13,15-didesmethoxy-13,15-dihydroxy-FK-506). If the fkbG gene product acts on 2-hydroxymalonyl and the resulting 2-methoxymalonyl substrate is required for incorporation by the PKS, the AT domains of modules 7 and 8 may bind malonyl CoA and methylmalonyl CoA. Such incorporation results in the production of a mixture of polyketides in which the methoxy groups at C-13 and C-15 of FK-520 (or FK-506) are replaced by either hydrogen or methyl.

This possibility of non-specific binding results from the construction of a hybrid PKS of the invention in which the AT domain of module 8 of the FK-520 PKS replaced the AT domain of module 6 of DEBS. The resulting PKS produced, in *Streptomyces lividans*, 6-dEB and 2-desmethyl-6-dEB, indicating that the AT domain of module 8 of the FK-520 PKS could bind malonyl CoA and methylmalonyl CoA substrates. Thus, one could possibly also prepare the 13,15-didesmethoxy-FK-520 and corresponding FK-506 compounds of the invention by deleting or otherwise inactivating one or more or all of the genes required for 2-hydroxymalonyl CoA biosynthesis, i.e., the fkbH,fkbI, fkbJ, and fkbK genes. In any event, the deletion or inactivation of one or more biosynthetic genes required for ethylmalonyl and/or 2-hydroxymalonyl production prevents the formation of polyketides requiring ethylmalonyl and/or 2-hydroxymalonyl for biosynthesis, and the resulting host cells are thus preferred for production of polyketides that do not require the same.

The host cells of the invention can be grown and fermented under conditions known in the art for other purposes to produce the compounds of the invention. See, e.g., U.S. Pat. Nos. 5,194,378; 5,116,756; and 5,494,820, incorporated herein by reference, for suitable fermentation processes. The compounds of the invention can be isolated from the fermentation broths of these cultured cells and purified by standard procedures. Preferred compounds of the invention include the following compounds: 13-desmethoxy-FK-506; 13-desmethoxy-FK-520; 13,15-didesmethoxy-FK-506; 13,15-didesmethoxy-FK-520; 13-desmethoxy-18-hydroxy-FK-506; 13-desmethoxy-18-hydroxy-FK-520; 13,15- didesmethoxy-18-hydroxy-FK-506; and 13,15-didesmethoxy-18-hydroxy-FK-520. These compounds can be further modified as described for tacrolimus and FK-520 in U.S. Pat. Nos. 5,225,403; 5,189,042; 5,164,495; 5,068,323; 4,980,466; and 4,920,218, incorporated herein by reference.

Figure 8A:
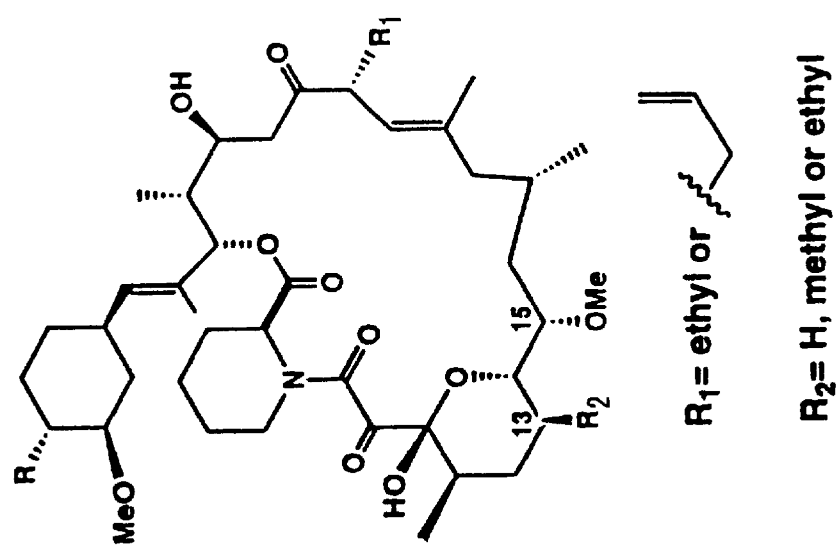
Figure 8B:
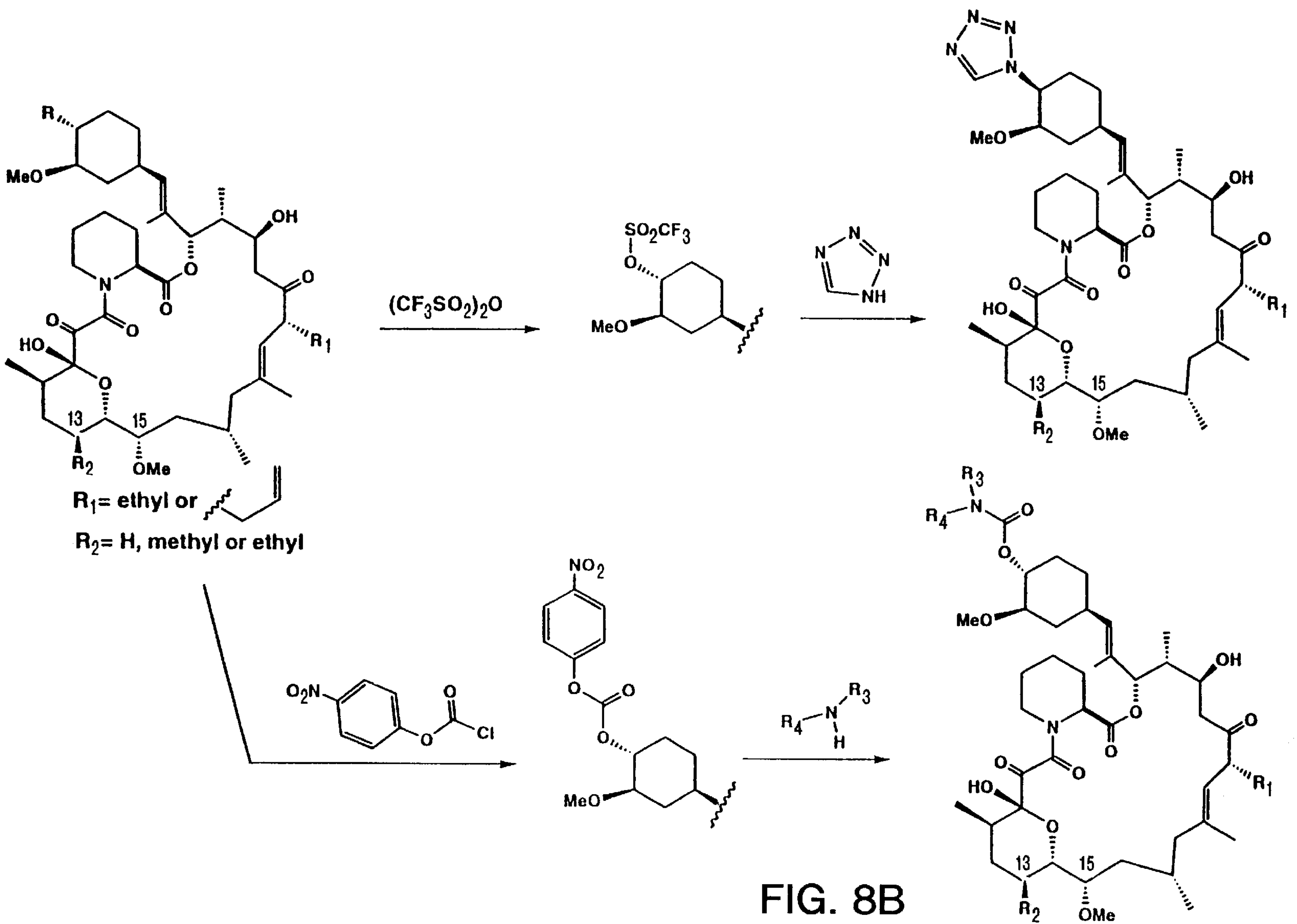

Other compounds of the invention are shown in FIG. 8, Parts A and B. In FIG. 8, Part A, illustrative C-32-substituted compounds of the invention are shown in two columns under the heading R. The substituted compounds are preferred for topical administration and are applied to the dermis for treatment of conditions such as psoriasis. In FIG. 8, Part B, illustrative reaction schemes for making the compounds shown in FIG. 8, Part A, are provided. In the upper scheme in FIG. 8, Part B, the C-32 substitution is a tetrazole moiety, illustrative of the groups shown in the left column under R in FIG. 8, Part A. In the lower scheme in FIG. 8, Part B, the C-32 substitution is a disubstituted amino group, where $R_3$ and $R_4$ can be any group similar to the illustrative groups shown attached to the amine in the right column under R in FIG. 8, Part A. While FIG. 8 shows the C-32-substituted compounds in which the C-15-methoxy is present, the invention includes these C-32-substituted compounds in which C-15 is ethyl, methyl, or hydrogen. Also, while C-21 is shown as substituted with ethyl or allyl, the compounds of the invention includes the C-32-substituted compounds in which C-21 is substituted with hydrogen or methyl.

To make these C-32-substituted compounds, FIG. 8, Part B, provides illustrative reaction schemes. Thus, a selective reaction of the starting compound (see FIG. 8, Part B, for an illustrative starting compound) with trifluoromethanesulfonic anhydride in the presence of a base yields the C-320-triflate derivative, as shown in the upper scheme of FIG. 8, Part B. Displacement of the triflate with 1H-tetrazole or triazole derivatives provides the C-32 tetrazole or teiazole derivative. As shown in the lower scheme of FIG. 8, Part B, reacting the starting compound with p-nitrophenylchloroformate yields the corresponding carbonate, which, upon displacement with an amino compound, provides the corresponding carbamate derivative.

The compounds can be readily formulated to provide the pharmaceutical compositions of the invention. The pharmaceutical compositions of the invention can be used in the form of a pharmaceutical preparation, for example, in solid, semisolid, or liquid form. This preparation contains one or more of the compounds of the invention as an active ingredient in admixture with an organic or inorganic carrier or excipient suitable for external, enteral, or parenteral application. The active ingredient may be compounded, for example, with the usual non-toxic, pharmaceutically acceptable carriers for tablets, pellets, capsules, suppositories, solutions, emulsions, suspensions, and any other form suitable for use. Suitable formulation processes and compositions for the compounds of the present invention are described with respect to tacrolimus in U.S. Pat. Nos. 5,939,427; 5,922,729; 5,385,907; 5,338,684; and 5,260,301, incorporated herein by reference. Many of the compounds of the invention contain one or more chiral centers, and all of the stereoisomers are included within the scope of the invention, as pure compounds as well as mixtures of stereoisomers. Thus the compounds of the invention may be supplied as a mixture of stereoisomers in any proportion.

The carriers which can be used include water, glucose, lactose, gum acacia, gelatin, mannitol, starch paste, magnesium trisilicate, talc, corn starch, keratin, colloidal silica, potato starch, urea, and other carriers suitable for use in manufacturing preparations, in solid, semi-solid, or liquified form. In addition, auxiliary stabilizing, thickening, and coloring agents and perfumes may be used. For example, the compounds of the invention may be utilized with hydroxypropyl methylcellulose essentially as described in U.S. Pat. No. 4,916,138, incorporated herein by reference, or with a surfactant essentially as described in EPO patent publication No. 428,169, incorporated herein by reference.

Oral dosage forms may be prepared essentially as described by Hondo et al., 1987*, Transplantation Proceedings* XIX, Supp. 6: 17–22, incorporated herein by reference. Dosage forms for external application may be prepared essentially as described in EPO patent publication No. 423,714, incorporated herein by reference. The active compound is included in the pharmaceutical composition in an amount sufficient to produce the desired effect upon the disease process or condition.

For the treatment of conditions and diseases relating to immunosuppresion or neuronal damage, a compound of the invention may be administered orally, topically, parenterally, by inhalation spray, or rectally in dosage unit formulations containing conventional non-toxic pharmaceutically acceptable carriers, adjuvant, and vehicles. The term parenteral, as used herein, includes subcutaneous injections, and intravenous, intramuscular, and intrasternal injection or infusion techniques.

Dosage levels of the compounds of the present invention are of the order from about 0.01 mg to about 50 mg per kilogram of body weight per day, preferably from about 0.1 mg to about 10 mg per kilogram of body weight per day. The dosage levels are useful in the treatment of the above-indicated conditions (from about 0.7 mg to about 3.5 mg per patient per day, assuming a 70 kg patient). In addition, the compounds of the present invention may be administered on an intermittent basis, i.e., at semi-weekly, weekly, semi-monthly, or monthly intervals.

The amount of active ingredient that may be combined with the carrier materials to produce a single dosage form will vary depending upon the host treated and the particular mode of administration. For example, a formulation intended for oral administration to humans may contain from 0.5 mg to 5 g of active agent compounded with an appropriate and convenient amount of carrier material, which may vary from about 5 percent to about 95 percent of the total composition. Dosage unit forms will generally contain from about 0.5 mg to about 500 mg of active ingredient. For external administration, the compounds of the invention can be formulated within the range of, for example, 0.00001% to 60% by weight, preferably from 0.001% to 10% by weight, and most preferably from about 0.005% to 0.8% by weight. The compounds and compositions of the invention are useful in treating disease conditions using doses and administration schedules as described for tacrolimus in U.S. Pat. Nos. 5,542,436; 5,365,948; 5,348,966; and 5,196,437, incorporated herein by reference. The compounds of the invention can be used as single therapeutic agents or in combination with other therapeutic agents. Drugs that can be usefully combined with compounds of the invention include one or more immunosuppressant agents such as rapamycin, cyclosporin A, FK-506, or one or more neurotrophic agents.

It will be understood, however, that the specific dosage level for any particular patient will depend on a variety of factors. These factors include the activity of the specific compound employed; the age, body weight, general health, sex, and diet of the subject; the time and route of administration and the rate of excretion of the drug; whether a drug combination is employed in the treatment; and the severity of the particular disease or condition for which therapy is sought.

A detailed description of the invention having been provided above, the following examples are given for the purpose of illustrating the present invention and shall not be construed as being a limitation on the scope of the invention or claims.

EXAMPLE 1

Replacement of Methoxyl with Hydrogen or Methyl at C-13 of FK-520

The C-13 methoxyl group is introduced into FK-520 via an AT domain in extender module 8 of the PKS that is specific for hydroxymalonyl and by methylation of the hydroxyl group by an S-adenosyl methionine (SAM) dependent methyltransferase. Metabolism of FK-506 and FK-520 primarily involves oxidation at the C-13 position into an inactive derivative that is further degraded by host P450 and other enzymes. The present invention provides compounds related in structure to FK-506 and FK-520 that do not contain the C-13 methoxy group and exhibit greater stability and a longer half-life in vivo. These compounds are useful medicaments due to their immunosuppressive and neurotrophic activities, and the invention provides the compounds in purified form and as pharmaceutical compositions.

The present invention also provides the novel PKS enzymes that produce these novel compounds as well as the expression vectors and host cells that produce the novel PKS enzymes. The novel PKS enzymes include, among others, those that contain an AT domain specific for either malonyl CoA or methylmalonyl CoA in module 8 of the FK-506 and FK-520 PKS. This example describes the construction of recombinant DNA compounds that encode the novel FK-520 PKS enzymes and the transformation of host cells with those recombinant DNA compounds to produce the novel PKS enzymes and the polyketides produced thereby.

To construct an expression cassette for performing module 8 AT domain replacements in the FK-520 PKS, a 4.6 kb SphI fragment from the FK-520 gene cluster was cloned into plasmid pLitmus 38 (a cloning vector available from New England Biolabs). The 4.6 kb SphI fragment, which encodes the ACP domain of module 7 followed by module 8 through the KR domain, was isolated from an agarose gel after digesting the cosmid pKOS65-C31 with SphI. The clone having the insert oriented so the single SacI site was nearest to the SpeI end of the polylinker was identified and designated as plasmid pKOS60-21-67. To generate appropriate cloning sites, two linkers were ligated sequentially as follows. First, a linker was ligated between the SpeI and SacI sites to introduce a BglII site at the 5' end of the cassette, to eliminate interfering polylinker sites, and to reduce the total insert size to 4.5 kb (the limit of the phage KC515). The ligation reactions contained 5 picomolar unphosphorylated linker DNA and 0.1 picomolar vector DNA, i.e., a 50-fold molar excess of linker to vector. The linker had the following sequence:

5'-CTAGTGGGCAGATCTGGCAGCT-3'

3'-ACCCGTCTAGACCG-5' (SEQ ID NOS 3–4)

The resulting plasmid was designated pKOS60-27-1.

Next, a linker of the following sequence was ligated between the unique SphI and AflII sites of plasmid pKOS60-27-1 to introduce an NsiI site at the 3' end of the module 8 cassette. The linker employed was:

5'-GGGATGCATGGC-3'

3'-GTACCCCTACGTACCGAATT-5' (SEQ ID NOS 5–6)

The resulting plasmid was designated pKOS60-29-55.

To allow in-frame insertions of alternative AT domains, sites were engineered at the 5' end (Avr II or Nhe I) and 3' end (Xho I) of the AT domain using the polymerase chain reaction (PCR) as follows. Plasmid pKOS60-29-55 was used as a template for the PCR and sequence 5' to the AT domain was amplified with the primers SpeBgl-fwd and either Avr-rev or Nhe-rev:

SpeBgl-fwd 5'-CGACTCACTAGTGGGCAGATCTGG-3'

Avr-rev 5'-CACGCCTAGGCCGGTCGGTCTCGGGCCAC-3'

Nhe-rev 5'-GCGGCTAGCTGCTCGCCCATCGC GGGATGC-3' (SEQ ID NOS 7–9)

The PCR included, in a 50 $\mu$l reaction, 5 $\mu$l of 10× Pfu polymerase buffer (Stratagene), 5 $\mu$l 10× z-dNTP mixture (2 mM dATP, 2 mM dCTP, 2 mM dTTP, 1 mM dGTP, 1 mM 7-deaza-GTP), 5 $\mu$l DMSO, 2 $\mu$l of each primer (10 $\mu$M), 1 $\mu$l of template DNA (0.1 $\mu$g/$\mu$l), and 1 $\mu$l of cloned Pfu polymerase (Stratagene). The PCR conditions were 95° C. for 2 min., 25 cycles at 95° C. for 30 sec., 60° C. for 30 sec., and 72° C. for 4 min., followed by 4 min. at 72° C. and a hold at 0° C. The amplified DNA products and the Litmus vectors were cut with the appropriate restriction enzymes (BglII and AvrII or SpeI and NheI), and cloned into either pLitmus 28 or pLitmus38 (New England Biolabs), respectively, to generate the constructs designated pKOS60–37–4 and pKOS60-37-2, respectively.

Plasmid pKOS60-29-55 was again used as a template for PCR to amplify sequence 3' to the AT domain using the primers BsrXho-fwd and NsiAfl-rev:

BsrXho-fwd 5'-GATGTACAGCTCGAGTCGGCACGCCCG-GCCGCATC-3'

NsiAfl-rev 5'-CGACTCACTTAAGCCAT GCATCC-3' (SEQ ID NOS 10–11)

PCR conditions were as described above. The PCR fragment was cut with BsrGI and AflII, gel isolated, and ligated into pKOS60-37-4 cut with Asp7 18 and AflII and inserted into pKOS60-37-2 cut with BsrGI and AflII, to give the plasmids pKOS60-39-1 and pKOS60-39-13, respectively. These two plasmids can be digested with AvrII and XhoI or NheI and XhoI, respectively, to insert heterologous AT domains specific for malonyl, methylmalonyl, ethylmalonyl, or other extender units.

Malonyl and methylmalonyl-specific AT domains were cloned from the rapamycin cluster using PCR amplification with a pair of primers that introduce an AvrII or NheI site at the 5' end and an XhoI site at the 3' end. The PCR conditions were as given above and the primer sequences were as follows:

RATN1 5'-ATCCTAGGCGGGCRGGYGTGTCGTCCTTCGG-3'

(3' end of Rap KS sequence and universal for malonyl and methylmalonyl CoA),

RATMN2 5'-ATGCTAGCCGCCGCGTTCCCCGTCTTCGCGCG-3'

(Rap AT shorter version 5'- sequence and specific for malonyl CoA),

RATMMN2 5'-ATGCTAGCGGATTCGTCGGTGGTGT-TCGCCGA-3'

(Rap AT shorter version 5'- sequence and specific for methylmalonyl CoA), and

RATC 5'-ATCTCGAGCCAGTASCGCTGGTGYTGGAAGG-3'

(Rap DH 5'-sequence and universal for malonyl and methylmalonyl CoA). (SEQ ID NOS 12–15)

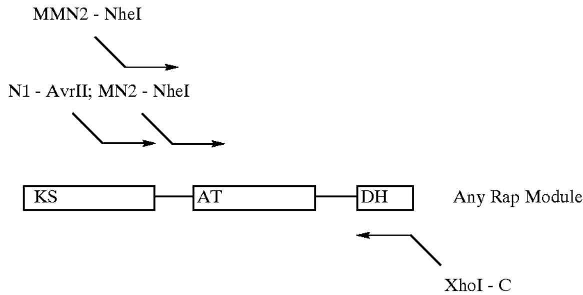

Because of the high sequence similarity in each module of the rapamycin cluster, each primer was expected to prime any of the AT domains. PCR products representing ATs specific for malonyl or methylmalonyl extenders were identified by sequencing individual cloned PCR products. Sequencing also confirmed that the chosen clones contained no cloning artifacts. Examples of hybrid modules with the rapamycin AT12 and AT 13 domains are shown in a separate figure.

The AvrII-XhoI restriction fragment that encodes module 8 of the FK-520 PKS with the endogenous AT domain replaced by the AT domain of module 12 of the rapamycin PKS has the DNA sequence and encodes the amino acid sequence shown below. The AT of rap module 12 is specific for incorporation of malonyl units.(SEQ ID NOS 16–17)

```
AGATCTGGCAGCTCGCCGAAGCGCTGCTGACGCTCGTCCGGGAGAGCACC      50
  I  W  Q  L  A  E  A  L  L  T  L  V  R  E  S  T
GCCGCCGTGCTCGGCCACGTGGGTGGCGAGGACATCCCCGCGACGGCGGC     100
 A  A  V  L  G  H  V  G  G  E  D  I  P  A  T  A  A
GTTCAAGGACCTCGGCATCGACTCGCTCACCGCGGTCCAGCTGCGCAACG     150
  F  K  D  L  G  I  D  S  L  T  A  V  Q  L  R  N
CCCTCACCGAGGCGACCGGTGTGCGGCTGAACGCCACGGCGGTCTTCGAC     200
A  L  T  E  A  T  G  V  R  L  N  A  T  A  V  F  D
TTCCCGACCCCGCACGTGCTCGCCGGGAAGCTCGGCGACGAACTGACCGG     250
 F  P  T  P  H  V  L  A  G  K  L  G  D  E  L  T  G
CACCCGCGCGCCCGTCGTGCCCCGGACCGCGGCCACGGCCGGTGCGCACG     300
  T  R  A  P  V  V  P  R  T  A  A  T  A  G  A  H
ACGAGCCGCTGGCGATCGTGGGAATGGCCTGCCGGCTGCCCGGCGGGGTC     350
D  E  P  L  A  I  V  G  M  A  C  R  L  P  G  G  V
GCGTCACCCGAGGAGCTGTGGCACCTCGTGGCATCCGGCACCGACGCCAT     400
 A  S  P  E  E  L  W  H  L  V  A  S  G  T  D  A  I
CACGGAGTTCCCGACGGACCGCGGCTGGGACGTCGACGCGATCTACGACC     450
  T  E  F  P  T  D  R  G  W  D  V  D  A  I  Y  D
CGGACCCCGACGCGATCGGCAAGACCTTCGTCCGGCACGGTGGCTTCCTC     500
P  D  P  D  A  I  G  K  T  F  V  R  H  G  G  F  L
ACCGGCGCGACAGGCTTCGACGCGGCGTTCTTCGGCATCAGCCCGCGCGA     550
 T  G  A  T  G  F  D  A  A  F  F  G  I  S  P  R  E
GGCCCTCGCGATGGACCCGCAGCAGCGGGTGCTCCTGGAGACGTCGTGGG     600
  A  L  A  M  D  P  Q  Q  R  V  L  L  E  T  S  W
AGGCGTTCGAAAGCGCCGGCATCACCCCGGACTCGACCCGCGGCAGCGAC     650
E  A  F  E  S  A  G  I  T  P  D  S  T  R  G  S  D
ACCGGCGTGTTCGTCGGCGCCTTCTCCTACGGTTACGGCACCGGTGCGGA     700
 T  G  V  F  V  G  A  F  S  Y  G  Y  G  T  G  A  D
CACCGACGGCTTCGGCGCGACCGGCTCGCAGACCAGTGTGCTCTCCGGCC     750
  T  D  G  F  G  A  T  G  S  Q  T  S  V  L  S  G
GGCTGTCGTACTTCTACGGTCTGGAGGGTCCGGCGGTCACGGTCGACACG     800
R  L  S  Y  F  Y  G  L  E  G  P  A  V  T  V  D  T
GCGTGTTCGTCGTCGCTGGTGGCGCTGCACCAGGCCGGGCAGTCGCTGCG     850
 A  C  S  S  S  L  V  A  L  H  Q  A  G  Q  S  L  R
CTCCGGCGAATGCTCGCTCGCCCTGGTCGGCGGCGTCACGGTGATGGCGT     900
  S  G  E  C  S  L  A  L  V  G  G  V  T  V  M  A
CTCCCGGCGGCTTCGTGGAGTTCTCCCGGCAGCGCGGCCTCGCGCCGGAC     950
S  P  G  G  E  V  E  F  S  R  Q  R  G  L  A  P  D
GGCCGGGCGAAGGCGTTCGGCGCGGGTGCGGACGGCACGAGCTTCGCCGA    1000
 G  R  A  K  A  F  G  A  G  A  D  G  T  S  F  A  E
GGGTGCCGGTGTGCTGATCGTCGAGAGGCTCTCCGACGCCGAACGCAACG    1050
  G  A  G  V  L  I  V  E  R  L  S  D  A  E  R  N
GTCACACCGTCCTGGCGGTCGTCCGTGGTTCGGCGGTCAACCAGGATGGT    1100
G  H  T  V  L  A  V  V  R  G  S  A  V  N  Q  D  G
GCCTCCAACGGGCTGTCGGCGCCGAACGGGCCGTCGCAGGAGCGGGTGAT    1150
 A  S  N  G  L  S  A  P  N  G  P  S  Q  E  R  V  I
CCGGCAGGCCCTGGCCAACGCCGGGCTCACCCCGGCGGACGTGGACGCCG    1200
  R  Q  A  L  A  N  A  G  L  T  P  A  D  V  D  A
TCGAGGCCCACGGCACCGGCACCAGGCTGGGCGACCCCATCGAGGCACAG    1250
V  E  A  H  G  T  G  T  R  L  G  D  P  I  E  A  Q
GCGGTACTGGCCACCTACGGACAGGAGCGCGCCACCCCCCTGCTGCTGGG    1300
 A  V  L  A  T  Y  G  Q  E  R  A  T  P  L  L  L  G
CTCGCTGAAGTCCAACATCGGCCACGCCCAGGCCGCGTCCGGCGTCGCCG    1350
  S  L  K  S  N  I  G  H  A  Q  A  A  S  G  V  A
```

-continued

```
GCATCATCAAGATGGTGCAGGCCCTCCGGCACGGGGAGCTGCCGCCGACG   1400
G  I  I  K  M  V  Q  A  L  R  H  G  E  L  P  P  T
CTGCACGCCGACGAGCCGTCGCCGCACGTCGACTGGACGGCCGGCGCCGT   1450
 L  H  A  D  E  P  S  P  H  V  D  W  T  A  G  A  V
CGAACTGCTGACGTCGGCCCGGCCGTGGCCCGAGACCGACCGGCCTAGGC   1500
  E  L  L  T  S  A  R  P  W  P  E  T  D  R  P  R
GGGCAGGCGTGTCGTCCTTCGGGATCAGTGGCACCAACGCCCACGTCATC   1550
R  A  G  V  S  S  F  G  I  S  G  T  N  A  H  V  I
CTGGAAAGCGCACCCCCCACTCAGCCTGCGGACAACGCGGTGATCGAGCG   1600
 L  E  S  A  P  P  T  Q  P  A  D  N  A  V  I  E  R
GGCACCGGAGTGGGTGCCGTTGGTGATTTCGGCCAGGACCCAGTCGGCTT   1650
  A  P  E  W  V  P  L  V  I  S  A  R  T  Q  S  A
TGACTGAGCACGAGGGCCGGTTGCGTGCGTATCTGGCGGCGTCGCCCGGG   1700
L  T  E  H  E  G  R  L  R  A  Y  L  A  A  S  P  G
GTGGATATGCGGGCTGTGGCATCGACGCTGGCGATGACACGGTCGGTGTT   1750
 V  D  M  R  A  V  A  S  T  L  A  M  T  R  S  V  E
CGAGCACCGTGCCGTGCTGCTGGGAGATGACACCGTCACCGGCACCGCTG   1800
  E  H  R  A  V  L  L  G  D  D  T  V  T  G  T  A
TGTCTGACCCTCGGGCGGTGTTCGTCTTCCCGGGACAGGGGTCGCAGCGT   1850
V  S  D  P  R  A  V  F  V  F  P  G  Q  G  S  Q  R
GCTGGCATGGGTGAGGAACTGGCCGCCGCGTTCCCCGTCTTCGCGCGGAT   1900
 A  G  M  G  E  E  L  A  A  A  F  P  V  F  A  R  I
CCATCAGCAGGTGTGGGACCTGCTCGATGTGCCCGATCTGGAGGTGAACG   1950
  H  Q  Q  V  W  D  L  L  D  V  P  D  L  E  V  N
AGACCGGTTACGCCCAGCCGGCCCTGTTCGCAATGCAGGTGGCTCTGTTC   2000
E  T  G  Y  A  Q  P  A  L  F  A  M  Q  V  A  L  F
GGGCTGCTGGAATCGTGGGGTGTACGACCGGACGCGGTGATCGGCCATTC   2050
 G  L  L  E  S  W  G  V  R  P  D  A  V  I  G  H  S
GGTGGGTGAGCTTGCGGCTGCGTATGTGTCCGGGGTGTGGTCGTTGGAGG   2100
  V  G  E  L  A  A  A  Y  V  S  G  V  W  S  L  E
ATGCCTGCACTTTGGTGTCGGCGCGGGCTCGTCTGATGCAGGCTCTGCCC   2150
D  A  C  T  L  V  S  A  R  A  R  L  M  Q  A  L  P
GCGGGTGGGGTGATGGTCGCTGTCCCGGTCTCGGAGGATGAGGCCCGGGC   2200
 A  G  G  V  M  V  A  V  P  V  S  E  D  E  A  R  A
CGTGCTGGGTGAGGGTGTGGAGATCGCCGCGGTCAACGGCCCGTCGTCGG   2250
  V  L  G  E  G  V  E  I  A  A  V  N  G  P  S  S
TGGTTCTCTCCGGTGATGAGGCCGCCGTGCTGCAGGCCGCGGAGGGGCTG   2300
V  V  L  S  G  D  E  A  A  V  L  Q  A  A  E  G  L
GGGAAGTGGACGCGGCTGGCGACCAGCCACGCGTTCCATTCCGCCCGTAT   2350
 G  K  W  T  R  L  A  T  S  H  A  F  H  S  A  R  M
GGAACCCATGCTGGAGGAGTTCCGGGCGGTCGCCGAAGGCCTGACCTACC   2400
  E  P  M  L  E  E  F  R  A  V  A  E  G  L  T  Y
GGACGCCGCAGGTCTCCATGGCCGTTGGTGATCAGGTGACCACCGCTGAG   2450
R  T  P  Q  V  S  M  A  V  G  D  Q  T  T  A  E
TACTGGGTGCGGCAGGTCCGGGACACGGTCCGGTTCGGCGAGCAGGTGGC   2500
 Y  W  V  R  Q  V  R  D  T  V  R  F  G  E  Q  V  A
CTCGTACGAGGACGCCGTGTTCGTCGAGCTGGGTGCCGACCGGTCACTGG   2550
  S  Y  E  D  A  V  F  V  E  L  G  A  D  R  S  L
CCCGCCTGGTCGACGGTGTCGCGATGCTGCACGGCGACCACGAAATCCAG   2600
A  R  L  V  D  G  V  A  M  L  H  G  D  H  E  I  Q
GCCGCGATCGGCGCCCTGGCCCACCTGTATGTCAACGGCGTCACGGTCGA   2650
 A  A  I  G  A  L  A  H  L  Y  V  N  G  V  T  V  D
CTGGCCCGCGCTCCTGGGCGATGCTCCGGCAACACGGGTGCTGGACCTTC   2700
  W  P  A  L  L  G  D  A  P  A  T  R  V  L  D  L
CGACATACGCCTTCCAGCACCAGCGCTACTGGCTCGAGTCGGCACGCCCG   2750
P  T  Y  A  F  Q  H  Q  R  Y  W  L  E  S  A  R  P
GCCGCATCCGACGCGGGCCACCCCGTGCTGGGCTCCGGTATCGCCCTCGC   2800
 A  A  S  D  A  G  H  P  V  L  G  S  G  I  A  L  A
CGGGTCGCCGGGCCGGGTGTTCACGGGTTCCGTGCCGACCGGTGCGGACC   2850
  G  S  P  G  R  V  F  T  G  S  V  P  T  G  A  D
GCGCGGTGTTCGTCGCCGAGCTGGCGCTGGCCGCCGCGGACGCGGTCGAC   2900
R  A  V  F  V  A  E  L  A  L  A  A  A  D  A  V  D
TGCGCCACGGTCGAGCGGCTCGACATCGCCTCCGTGCCCGGCCGGCCGGG   2950
 C  A  T  V  E  R  L  D  I  A  S  V  P  G  R  P  G
CCATGGCCGGACGACCGTACAGACCTGGGTCGACGAGCCGGCGGACGACG   3000
  H  G  R  T  T  V  Q  T  W  V  D  E  P  A  D  D
GCCGGCGCCGGTTCACCGTGCACACCCGCACCGGCGACGCCCCGTGGACG   3050
G  R  R  R  F  T  V  H  T  R  T  G  D  A  P  W  T
CTGCACGCCGAGGGGGTGCTGCGCCCCCATGGCACGGCCCTGCCCGATGC   3100
 L  H  A  E  G  V  L  R  P  H  G  T  A  L  P  D  A
GGCCGACGCCGAGTGGCCCCCACCGGGCGCGGTGCCCGCGGACGGGCTGC   3150
  A  D  A  E  W  P  P  P  G  A  V  P  A  D  G  L
CGGGTGTGTGGCGCCGGGGGGACCAGGTCTTCGCCGAGGCCGAGGTGGAC   3200
P  G  V  W  R  R  G  D  Q  V  F  A  E  A  E  V  D
GGACCGGACGGTTTCGTGGTGCACCCCGACCTGCTCGACGCGGTCTTCTC   3250
 G  P  D  G  F  V  V  H  P  D  L  L  D  A  V  F  S
CGCGGTCGGCGACGGAAGCCGCCAGCCGGCCGGATGGCGCGACCTGACGG   3300
  A  V  G  D  G  S  R  Q  P  A  G  W  R  D  L  T
TGCACGCGTCGGACGCCACCGTACTGCGCGCCTGCCTCACCCGGCGCACC   3350
V  H  A  S  D  A  T  V  L  R  A  C  L  T  R  R  T
```

-continued

```
GACGGAGCCATGGGATTCGCCGCCTTCGACGGCGCCGGCCTGCCGGTACT    3400
 D  G  A  M  G  F  A  A  F  D  G  A  G  L  P  V  L
CACCGCGGAGGCGGTGACGCTGCGGGAGGTGGCGTCACCGTCCGGCTCCG    3450
  T  A  E  A  V  T  L  R  E  V  A  S  P  S  G  S
AGGAGTCGGACGGCCTGCACCGGTTGGAGTGGCTCGCGGTCGCCGAGGCG    3500
E  E  S  D  G  L  H  R  L  E  W  L  A  V  A  E  A
GTCTACGACGGTGACCTGCCCGAGGGACATGTCCTGATCACCGCCGCCCA    3550
 V  Y  D  G  D  L  P  E  G  H  V  L  I  T  A  A  R
CCCCGACGACCCCGAGGACATACCCACCCGCGCCCACACCCGCGCCACCC    3600
  P  D  D  P  E  D  I  P  T  R  A  R  T  R  A  T
GCGTCCTGACCGCCCTGCAACACCACCTCACCACCACCGACCACACCCTC    3650
R  V  L  T  A  L  Q  H  H  L  T  T  T  D  H  T  L
ATCGTCCACACCACCACCGACCCCGCCGGCGCCACCGTCACCGGCCTCAC    3700
 I  V  H  T  T  T  D  P  A  G  A  T  V  T  G  L  T
CCGCACCGCCCAGAACGAACACCCCCACCGCATCCGCCTCATCGAAACCG    3750
  R  T  A  Q  N  E  H  P  H  R  I  R  L  I  E  T
ACCACCCCCACACCCCCCTCCCCCTGGCCCAACTCGCCACCCTCGACCAC    3800
D  H  P  H  T  P  L  P  L  A  Q  L  A  T  L  D  H
CCCCACCTCCGCCTCACCCACCACACCCTCCACCACCCCCACCTCACCCC    3850
 P  R  L  R  L  T  H  H  T  L  H  H  P  H  L  T  P
CCTCCACACCACCACCCCACCCACCACCACCCCCCTCAACCCCGAACACG    3900
  L  H  T  T  T  P  P  T  T  T  P  L  N  P  E  H
CCATCATCATCACCGGCGGCTCCGGCACCCTCGCCGGCATCCTCGCCCGC    3950
A  I  I  I  T  G  G  S  G  T  L  A  G  I  L  A  R
CACCTGAACCACCCCCACACCTACCTCCTCTCCCGCACCCCACCCCCCGA    4000
 H  L  N  H  P  R  T  Y  L  L  S  R  T  P  P  P  D
CGCCACCCCCGGCACCCACCTCCCCTGCGACGTCGGCGACCCCCACCAAC    4050
  A  T  P  G  T  H  L  P  C  D  V  G  D  P  H  Q
TCGCCACCACCCTCACCCACATCCCCCAACCCCTCACCGCCATCTTCCAC    4100
L  A  T  T  L  T  H  I  P  Q  P  L  T  A  I  F  H
ACCGCCGCCACCCTCGACGACGGCATCCTCCACGCCCTCACCCCCGACCG    4150
 T  A  A  T  L  D  D  G  I  L  H  A  L  T  P  D  R
CCTCACCACCGTCCTCCACCCCAAAGCCAACGCCGCCTGGCACCTGCACC    4200
  L  T  T  V  L  H  P  K  A  N  A  A  W  H  L  H
ACCTCACCCAAAACCAACCCCTCACCCACTTCGTCCTCTACTCCAGCGCC    4250
H  L  T  Q  N  Q  P  L  T  H  F  V  L  Y  S  S  A
GCCGCCGTCCTCGGCAGCCCCGGACAAGGAAACTACGCCGCCGCCAACGC    4300
 A  A  V  L  G  S  P  G  Q  G  N  Y  A  A  A  N  A
CTTCCTCGACGCCCTCGCCACCCACCGCCACACCCTCGGCCAACCCGCCA    4350
  F  L  D  A  L  A  T  H  R  H  T  L  G  Q  P  A
CCTCCATCGCCTGGGGCATGTGGCACACCACCAGCACCCTCACCGGACAA    4400
T  S  I  A  W  G  M  W  H  T  T  S  T  L  T  G  Q
CTCGACGACGCCGACCGGGACCGCATCCGCCGCGGCGGTTTCCTCCCGAT    4450
 L  D  D  A  D  R  D  R  I  R  R  G  G  F  L  P  I
CACGGACGACGAGGGCATGGGGATGCAT
T  D  D  E  G
```

The AvrII-XhoI restriction fragment that encodes module 8 of the FK-520 PKS with the endogenous AT domain replaced by the AT domain of module 13 (specific for methylmalonyl CoA) of the rapamycin PKS has the DNA sequence and encodes the amino acid sequence shown below. (SEQ ID NOS 18–19)

```
AGATCTGGCAGCTCGCCGAAGCGCTGCTGACGCTCGTCCGGGAGAGCACC      50
 Q  L  A  E  A  L  L  T  L  V  R  E  S  T
GCCGCCGTGCTCGGCCACGTGGGTGGCGAGGACATCCCCGCGACGGCGGC     100
 A  A  V  L  G  H  V  G  G  E  D  I  P  A  T  A  A
GTTCAAGGACCTCGGCATCGACTCGCTCACCGCGGTCCAGCTGCGCAACG     150
  F  K  D  L  G  I  D  S  L  T  A  V  Q  L  R  N
CCCTCACCGAGGCGACCGGTGTGCGGCTGAACGCCACGGCGGTCTTCGAC     200
A  L  T  E  A  T  G  V  R  L  N  A  T  A  V  F  D
TTCCCGACCCCGCACGTGCTCGCCGGGAAGCTCGGCGACGAACTGACCGG     250
 F  P  T  P  H  V  L  A  G  K  L  G  D  E  L  T  G
CACCCGCGCGCCCGTCGTGCCCCGGACCGCGGCCACGGCCGGTGCGCACG     300
  T  R  A  P  V  V  P  R  T  A  A  T  A  G  A  H
ACGAGCCGCTGGCGATCGTGGGAATGGCCTGCCGGCTGCCCGGCGGGGTC     350
D  E  P  L  A  I  V  G  M  A  C  R  L  P  G  G  V
GCGTCACCCGAGGAGCTGTGGCACCTCGTGGCATCCGGCACCGACGCCAT     400
 A  S  P  E  E  L  W  H  L  V  A  S  G  T  D  A  I
CACGGAGTTCCCGACGGACCGCGGCTGGGACGTCGACGCGATCTACGACC     450
  T  E  F  P  T  D  R  G  W  D  V  D  A  I  Y  D
CGGACCCCGACGCGATCGGCAAGACCTTCGTCCGGCACGGTGGCTTCCTC     500
P  D  P  D  A  I  G  K  T  F  V  R  H  G  G  F  L
ACCGGCGCGACAGGCTTCGACGCGGCGTTCTTCGGCATCAGCCCGCGCGA     550
 T  G  A  T  G  F  D  A  A  F  F  G  I  S  P  R  E
GGCCCTCGCGATGGACCCGCAGCAGCGGGTGCTCCTGGAGACGTCGTGGG     600
  A  L  A  M  D  P  Q  Q  R  V  L  L  E  T  S  W
AGGCGTTCGAAAGCGCCGGCATCACCCCGGACTCGACCCGCGGCAGCGAC     650
```

-continued

```
E  A  F  E  S  A  G  I  T  P  D  S  T  R  G  S  D
ACCGGCGTGTTCGTCGGCGCCTTCTCCTACGGTTACGGCACCGGTGCGGA     700
 T  G  V  F  V  G  A  F  S  Y  G  Y  G  T  G  A  D
CACCGACGGCTTCGGCGCGACCGGCTCGCAGACCAGTGTGCTCTCCGGCC     750
  T  D  G  F  G  A  T  G  S  Q  T  S  V  L  S  G
GGCTGTCGTACTTCTACGGTCTGGAGGGTCCGGCGGTCACGGTCGACACG     800
R  L  S  Y  F  Y  G  L  E  G  P  A  V  T  V  D  T
GCGTGTTCGTCGTCGCTGGTGGCGCTGCACCAGGCCGGGCAGTCGCTGCG     850
 A  C  S  S  S  L  V  A  L  H  Q  A  G  Q  S  L  R
CTCCGGCGAATGCTCGCTCGCCCTGGTCGGCGGCGTCACGGTGATGGCGT     900
  S  G  E  C  S  L  A  L  V  G  G  V  T  V  M  A
CTCCCGGCGGCTTCGTGGAGTTCTCCCGGCAGCGCGGCCTCGCGCCGGAC     950
S  P  G  G  F  V  E  F  S  R  Q  R  G  L  A  P  D
GGCCGGGCGAAGGCGTTCGGCGCGGGTGCGGACGGCACGAGCTTCGCCGA    1000
 G  R  A  K  A  F  G  A  G  A  D  G  T  S  F  A  E
GGGTGCCGGTGTGCTGATCGTCGAGAGGCTCTCCGACGCCGAACGCAACG    1050
  G  A  G  V  L  I  V  E  R  L  S  D  A  E  R  N
GTCACACCGTCCTGGCGGTCGTCCGTGGTTCGGCGGTCAACCAGGATGGT    1100
G  H  T  V  L  A  V  V  R  G  S  A  V  N  Q  D  G
GCCTCCAACGGGCTGTCGGCGCCGAACGGGCCGTCGCAGGAGCGGGTGAT    1150
 A  S  N  G  L  S  A  P  N  G  P  S  Q  E  R  V  I
CCGGCAGGCCCTGGCCAACGCCGGGCTCACCCCGGCGGACGTGGACGCCG    1200
  R  Q  A  L  A  N  A  G  L  T  P  A  D  V  D  A
TCGAGGCCCACGGCACCGGCACCAGGCTGGGCGACCCCATCGAGGCACAG    1250
V  E  A  H  G  T  G  T  R  L  G  D  P  I  E  A  Q
GCGGTACTGGCCACCTACGGACAGGAGCGCGCCACCCCCCTGCTGCTGGG    1300
 A  V  L  A  T  Y  G  Q  E  R  A  T  P  L  L  L  G
CTCGCTGAAGTCCAACATCGGCCACGCCCAGGCCGCGTCCGGCGTCGCCG    1350
  S  L  K  S  N  I  G  H  A  Q  A  A  S  G  V  A
GCATCATCAAGATGGTGCAGGCCCTCCGGCACGGGGAGCTGCCGCCGACG    1400
G  I  I  K  M  V  Q  A  L  R  R  G  E  L  P  P  T
CTGCACGCCGACGAGCCGTCGCCGCACGTCGACTGGACGGCCGGCGCCGT    1450
 L  H  A  D  E  P  S  P  H  V  D  W  T  A  G  A  V
CGAACTGCTGACGTCGGCCCGGCCGTGGCCCGAGACCGACCGGCCTAGGC    1500
 E  L  L  T  S  A  R  P  W  P  E  T  D  R  P  R
GGGCGGGCGTGTCGTCCTTCGGAGTCAGCGGCACCAACGCCCACGTCATC    1550
R  A  G  V  S  S  F  G  V  S  G  T  N  A  H  V  I
CTGGAGAGCGCACCCCCCGCTCAGCCCGCGGAGGAGGCGCAGCCTGTTGA    1600
 L  E  S  A  P  P  A  Q  P  A  E  E  A  Q  P  V  E
GACGCCGGTGGTGGCCTCGGATGTGCTGCCGCTGGTGATATCGGCCAAGA    1650
  T  P  V  V  A  S  D  V  L  P  L  V  I  S  A  K
CCCAGCCCGCCCTGACCGAACACGAAGACCGGCTGCGCGCCTACCTGGCG    1700
T  Q  P  A  L  T  E  H  E  D  R  L  R  A  Y  L  A
GCGTCGCCCGGGGCGGATATACGGGCTGTGGCATCGACGCTGGCGGTGAC    1750
 A  S  P  G  A  D  I  R  A  V  A  S  T  L  A  V  T
ACGGTCGGTGTTCGAGCACCGCGCCGTACTCCTTGGAGATGACACCGTCA    1800
  R  S  V  F  E  H  R  A  V  L  L  G  D  D  T  V
CCGGCACCGQGGTGACCGACCCCAGGATCGTGTTTGTCTTTCCCGGGCAG    1850
T  G  T  A  V  T  D  P  R  I  V  F  V  F  P  G  Q
GGGTGGCAGTGGCTGGGGATGGGCAGTGCACTGCGCGATTCGTCGGTGGT    1900
 G  W  Q  W  L  G  M  G  S  A  L  R  D  S  S  V  V
GTTCGCCGAGCGGATGGCCGAGTGTGCGGCGGCGTTGCGCGAGTTCGTGG    1950
  F  A  E  R  M  A  E  C  A  A  A  L  R  E  F  V
ACTGGGATCTGTTCACGGTTCTGGATGATCCGGCGGTGGTGGACCGGGTT    2000
D  W  D  L  F  T  V  L  D  D  P  A  V  V  D  R  V
GATGTGGTCCAGCCCGCTTCCTGGGCGATGATGGTTTCCCTGGCCGCGGT    2050
 D  V  V  Q  P  A  S  W  A  M  M  V  S  L  A  A  V
GTGGCAGGCGGCCGGTGTGCGGCCGGATGCGGTGATCGGCCATTCGCAGG    2100
  W  Q  A  A  G  V  R  P  D  A  V  I  G  H  S  Q
GTGAGATCGCCGCAGCTTGTGTGGCGGGTGCGGTGTCACTACGCGATGCC    2150
G  E  I  A  A  A  C  V  A  G  A  V  S  L  R  D  A
GCCCGGATCGTGACCTTGCGCAGCCAGGCGATCGCCCGGGGCCTGGCGGG    2200
 A  R  I  V  T  L  R  S  Q  A  I  A  R  G  L  A  G
CCGGGGCGCGATGGCATCCGTCGCCCTGCCCGCGCAGGATGTCGAGCTGG    2250
  R  G  A  M  A  S  V  A  L  P  A  Q  D  V  E  L
TCGACGGGGCCTGGATCGCCGCCCACAACGGGCCCGCCTCCACCGTGATC    2300
V  D  G  A  W  I  A  A  H  N  G  P  A  S  T  V  I
GCGGGCACCCCGGAAGCGGTCGACCATGTCCTCACCGCTCATGAGGCACA    2350
 A  G  T  P  E  A  V  D  H  V  L  T  A  H  E  A  Q
AGGGGTGCGGGTGCGGCGGATCACCGTCGACTATGCCTCGCACACCCCGC    2400
  G  V  R  V  R  R  I  T  V  D  Y  A  S  H  T  P
ACGTCGAGCTGATCCGCGACGAACTACTCGACATCACTAGCGACAGCAGC    2450
H  V  E  L  I  R  D  E  L  L  D  I  T  S  D  S  S
TCGCAGACCCCGCTCGTGCCGTGGCTGTCGACCGTGGACGGCACCTGGGT    2500
 S  Q  T  P  L  V  P  W  L  S  T  V  D  G  T  W  V
CGACAGCCCGCTGGACGGGGAGTACTGGTACCGGAACCTGCGTGAACCGG    2550
  D  S  P  L  D  G  E  Y  W  Y  R  N  L  R  E  P
TCGGTTTCCACCCCGCCGTCAGCCAGTTGCAGGCCCAGGGCGACACCGTG    2600
V  G  F  H  P  A  V  S  Q  L  Q  A  Q  G  D  T  V
TTCGTCGAGGTCAGCGCCAGCCCGGTGTTGTTGCAGGCGATGGACGACGA    2650
```

-continued

```
 F  V  E  V  S  A  S  P  V  L  L  Q  A  M  D  D  D
TGTCGTCACGGTTGCCACGCTGCGTCGTGACGACGGCGACGCCACCCGGA    2700
 V  V  T  V  A  T  L  R  R  D  D  G  D  A  T  R
TGCTCACCGCCCTGGCACAGGCCTATGTCCACGGCGTCACCGTCGACTGG    2750
M  L  T  A  L  A  Q  A  Y  V  H  G  V  T  V  D  W
CCCGCCATCCTCGGCACCACCACAACCCGGGTACTGGACCTTCCGACCTA    2800
 P  A  I  L  G  T  T  T  T  R  V  L  D  L  P  T  Y
CGCCTTCCAACACCAGCGGTACTGGCTCGAGTCGGCACGCCCGGCCGCAT    2850
  A  F  Q  H  Q  R  Y  W  L  E  S  A  R  P  A  A
CCGACGCGGGCCACCCCGTGCTGGGCTCCGGTATCGCCCTCGCCGGGTCG    2900
S  D  A  G  H  P  V  L  G  S  G  I  A  L  A  G  S
CCGGGCCGGGTGTTCACGGGTTCCGTGCCGACCGGTGCGGACCGCGCGGT    2950
 P  G  R  V  F  T  G  S  V  P  T  G  A  D  R  A  V
GTTCGTCGCCGAGCTGGCGCTGGCCGCCGCGGACGCGGTCGACTGCGCCA    3000
  F  V  A  E  L  A  L  A  A  A  D  A  V  D  C  A
CGGTCGAGCGGCTCGACATCGCCTCCGTGCCCGGCCGGCCGGGCCATGGC    3050
T  V  E  R  L  D  I  A  S  V  P  G  R  P  G  H  G
CGGACGACCGTACAGACCTGGGTCGACGAGCCGGCGGACGACGGCCGGCG    3100
 R  T  T  V  Q  T  W  V  D  E  P  A  D  D  G  R  R
CCGGTTCACCGTGCACACCCGCACCGGCGACGCCCCGTGGACGCTGCACG    3150
  R  F  T  V  H  T  R  T  G  D  A  P  W  T  L  H
CCGAGGGGGTGCTGCGCCCCCATGGCACGGCCCTGCCCGATGCGGCCGAC    3200
A  E  G  V  L  R  P  H  G  T  A  L  P  D  A  A  D
GCCGAGTGGCCCCCACCGGGgGCGGTGCCCGCGGACGGGCTGCCGGGTGT    3250
A  E  W  P  P  P  G  A  V  P  A  D  G  L  P  G  V
GTGGCGCCGGGGGGACCAGGTCTTCGCCGAGGCCGAGGTGGACGGACCGG    3300
  W  R  R  G  D  Q  V  F  A  E  A  E  V  D  G  P
ACGGTTTCGTGGTGCACCCCGACCTGCTCGACGCGGTCTTCTCCGCGGTC    3350
D  G  F  V  V  H  P  D  L  L  D  A  V  F  S  A  V
GGCGACGGAAGCCGCCAGCCGGCCGGATGGCGCGACCTGACGGTGCACGC    3400
 G  D  G  S  R  Q  P  A  G  W  R  D  L  T  V  H  A
GTCGGACGCCACCGTACTGCGCGCCTGCCTCACCCGGCGCACCGACGGAG    3450
  S  D  A  T  V  L  R  A  C  L  T  R  R  T  D  G
CCATGGGATTCGCCGCCTTCGACGGCGCCGGCCtGCCGGTACTCACCGCG    3500
A  M  G  F  A  A  F  D  G  A  G  L  P  V  L  T  A
GAGGCGGTGACGCTGCGGGAGGTGGCGTCACCGTCCGGCTCCGAGGAGTC    3550
 E  A  V  T  L  R  E  V  A  S  P  S  G  S  E  E  S
GGACGGCCTGCACCGGTTGGAGTGGCTCGCGGTCGCCGAGGCGGTCTACG    3600
  D  G  L  H  R  L  E  W  L  A  V  A  E  A  V  Y
ACGGTGACCTGCCCGAGGGACATGTCCTGATCACCGCCGCCCACCCCGAC    3650
D  G  D  L  P  E  G  H  V  I  T  T  A  A  H  P  D
GACCCCGAGGACATACCCACCCGCGCCCACACCCGCGCCACCCGCGTCCT    3700
 D  P  E  D  I  P  T  R  A  H  T  R  A  T  R  V  L
GACCGCCCTGCAACACCACCTCACCACCACCGACCACACCCTCATCGTCC    3750
  T  A  L  Q  H  H  L  T  T  T  D  H  T  L  I  V
ACACCACCACCGACCCCGCCGGCGCCACCGTCACCGGCCTCACCCGCACC    3800
H  T  T  T  D  P  A  G  A  T  V  T  G  L  T  R  T
GCCCAGAACGAACACCCCCACCGCATCCGCCTCATCGAAACCGACCACCC    3850
 A  Q  N  E  H  P  H  R  I  R  L  I  E  T  D  H  P
CCACACCCCCCTCCCCCTGGCCCAACTCGCCACCCTCGACCACCCCCACC    3900
  H  T  P  L  P  L  A  Q  L  A  T  L  D  H  P  H
TCCGCCTCACCCACCACACCCTCCACCACCCCCACCTCACCCCCCTCCAC    3950
L  R  L  T  H  H  T  L  H  H  P  H  L  T  P  L  H
ACCACCACCCCACCCACCACCACCCCCCTCAACCCCGAACACGCCATCAT    4000
 T  T  T  P  P  T  T  T  P  L  N  P  E  H  A  I  I
CATCACCGGCGGCTCCGGCACCCTCGCCGGCATCCTCGCCCGCCACCTGA    4050
  I  T  G  G  S  G  T  L  A  G  I  L  A  R  H  L
ACCACCCCCACACCTACCTCCTCTCCCGCACCCCACCCCCCGACGCCACC    4100
N  H  P  H  T  Y  L  L  S  R  T  P  P  P  D  A  T
CCCGGCACCCACCTCCCCTGCGACGTCGGCGACCCCCACCAACTCGCCAC    4150
 P  G  T  H  L  P  C  D  V  G  D  P  H  Q  L  A  T
CACCCTCACCCACATCCCCCAACCCCTCACCGCCATCTTCCACACCGCCG    4200
  T  L  T  H  I  P  Q  P  L  T  A  I  F  H  T  A
CCACCCTCGACGACGGCATCCTCCACGCCCTCACCCCCGACCGCCTCACC    4250
A  T  L  D  D  G  I  L  H  A  L  T  P  D  R  L  T
ACCGTCCTCCACCCCAAAGCCAACGCCGCCTGGCACCTGCACCACCTCAC    4300
 T  V  L  H  P  K  A  N  A  A  W  H  L  H  H  L  T
CCAAAACCAACCCCTCACCCACTTCGTCCTCTACTCCAGCGCCGCCGCCG    4350
  Q  N  Q  P  L  T  H  F  V  L  Y  S  S  A  A  A
TCCTCGGCAGCCCCGGACAAGGAAACTACGCCGCCGCCAACGCCTTCCTC    4400
V  L  G  S  P  G  Q  G  N  Y  A  A  A  N  A  F  L
GACGCCCTCGCCACCCACCGCCACACCCTCGGCCAACCCGCCACCTCCAT    4450
 D  A  L  A  T  H  R  H  T  L  G  Q  P  A  T  S  I
CGCCTGGGGCATGTGGCACACCACCAGCACCCTCACCGGACAACTCGACG    4500
  A  W  G  M  W  H  T  T  S  T  L  T  G  Q  L  D
ACGCCGACCGGGACCGCATCCGCCGCGGCGGTTTCCTCCCGATCACGGAC    4550
D  A  D  R  D  R  I  R  R  G  G  F  L  P  I  T  D
CACGAGGGCATGGGGATGCAT
 D  E  G
```

The NheII-XhoI restriction fragment that encodes module 8 of the FK-520 PKS with the endogenous AT domain replaced by the AT domain of module 12 (specific for malonyl CoA) of the rapamycin PKS has the DNA sequence and encodes the amino acid sequence shown below. (SEQ ID NOS 20–21)

```
AGATCTGGCAGCTCGCCGAAGCGCTGCTGACGCTCGTCCGGGAGAGCACC     50
 Q  L  A  E  A  L  L  T  L  V  R  E  S  T
GCCGCCGTGCTCGGCCACGTGGGTGGCGAGGACATCCCCGCGACGGCGGC    100
 A  A  V  L  G  H  V  G  G  E  D  I  P  A  T  A  A
GTTCAAGGACCTCGGCATCGACTCGCTCACCGCGGTCCAGCTGCGCAACG    150
  F  K  D  L  G  I  D  S  L  T  A  V  Q  L  R  N
CCCTCACCGAGGCGACCGGTGTGCGGCTGAACGCCACGGCGGTCTTCGAC    200
A  L  T  E  A  T  G  V  R  L  N  A  T  A  V  F  D
TTCCCGACCCCGCACGTGCTCGCCGGGAAGCTCGGCGACGAACTGACCGG    250
 F  P  T  P  H  V  L  A  G  K  L  G  D  E  L  T  G
CACCCGCGCGCCCGTCGTGCCCCGGACCGCGGCCACGGCCGGTGCGCACG    300
  T  R  A  P  V  V  P  R  T  A  A  T  A  G  A  H
ACGAGCCGCTGGCGATCGTGGGAATGGCCTGCCGGCTGCCCGGCGGGGTC    350
D  E  P  L  A  I  V  G  M  A  C  R  L  P  G  G  V
GCGTCACCCGAGGAGCTCTGGCACCTCGTGGCATCCGGCACCGACGCCAT    400
 A  S  P  E  E  L  W  H  L  V  A  S  G  T  D  A  I
CACGGAGTTCCCGACGGACCGCGGCTGGGACGTCGACGCGATCTACGACC    450
  T  E  F  P  T  D  R  G  W  D  V  D  A  I  Y  D
CGGACCCCGACGCGATCGGCAAGACCTTCGTCCGGCACGGTGGCTTCCTC    500
P  D  P  D  A  I  G  K  T  F  V  R  H  G  G  F  L
ACCGGCGCGACAGGCTTCGACGCGGCGTTCTTCGGCATCAGCCCGCGCGA    550
 T  G  A  T  G  F  D  A  A  F  F  G  I  S  P  R  E
GGCCCTCGCGATGGACCCGCAGCAGCGGGTGCTCCTGGAGACGTCGTGGG    600
  A  L  A  M  D  P  Q  Q  R  V  L  L  E  T  S  W
AGGCGTTCGAAAGCGCCGGCATCACCCCGGACTCGACCCGCGGCAGCGAC    650
E  A  F  E  S  A  G  I  T  P  D  S  T  R  G  S  D
ACCGGCGTGTTCGTCGGCGCCTTCTCCTACGGTTACGGCACCGGTGCGGA    700
 T  G  V  F  V  G  A  F  S  Y  G  Y  G  T  G  A  D
CACCGACGGCTTCGGCGCGACCGGCTCGCAGACCAGTGTGCTCTCCGGCC    750
  T  D  G  F  G  A  T  G  S  Q  T  S  V  L  S  G
GGCTGTCGTACTTCTACGGTCTGGAGGGTCCGGCGGTCACGGTCGACACG    800
R  L  S  Y  F  Y  G  L  E  G  P  A  V  T  V  D  T
GCGTGTTCGTCGTCGCTGGTGGCGCTGCACCAGGCCGGGCAGTCGCTGCG    850
 A  C  S  S  S  L  V  A  L  H  Q  A  G  Q  S  L  R
CTCCGGCGAATGCTCGCTCGCCCTGGTCGGCGGCGTCACGGTGATGGCGT    900
  S  G  E  C  S  L  A  L  V  G  G  V  T  V  M  A
CTCCCGGCGGCTTCGTGGAGTTCTCCCGGCAGCGCGGCCTCGCGCCGGAC    950
S  P  G  G  F  V  E  F  S  R  Q  R  G  L  A  P  D
GGCCGGGCGAAGGCGTTCGGCGCGGGTGCGGACGGCACGAGCTTCGCCGA   1000
 G  R  A  K  A  F  G  A  G  A  D  G  T  S  F  A  E
GGGTGCCGGTGTGCTGATCGTCGAGAGGCTCTCCGACGCCGAACGCAACG   1050
  G  A  G  V  L  I  V  E  R  L  S  D  A  E  R  N
GTCACACCGTCCTGGCGGTCGTCCGTGGTTCGGCGGTCAACCAGGATGGT   1100
G  H  T  V  L  A  V  V  R  G  S  A  V  N  Q  D  G
GCCTCCAACGGGCTGTCGGCGCCGAACGGGCCGTCGCAGGAGCGGGTGAT   1150
 A  S  N  G  L  S  A  P  N  G  P  S  Q  E  R  V  I
CCGGCAGGCCCTGGCCAACGCCGGGCTCACCCCGGCGGACGTGGACGCCG   1200
  R  Q  A  L  A  N  A  G  L  T  P  A  D  V  D  A
TCGAGGCCCACGGCACCGGCACCAGGCTGGGCGACCCCATCGAGGCACAG   1250
V  E  A  H  G  T  G  T  R  L  G  D  P  I  E  A  Q
GCGGTACTGGCCACCTACGGACAGGAGCGCGCCACCCCCCTGCTGCTGGG   1300
 A  V  L  A  T  Y  G  Q  E  R  A  T  P  L  L  L  G
CTCGCTGAAGTCCAACATCGGCCACGCCCAGGCCGCGTCCGGCGTCGCCG   1350
  S  L  K  S  N  I  G  H  A  Q  A  A  S  G  V  A
GCATCATCAAGATGGTGCAGGCCCTCCGGCACGGGGAGCTGCCGCCGACG   1400
G  I  I  K  M  V  Q  A  L  R  H  G  E  L  P  P  T
CTGCACGCCGACGAGCCGTCGCCGCACGTCGACTGGACGGCCGGCGCCGT   1450
 L  H  A  D  E  P  S  P  H  V  D  W  T  A  G  A  V
CGAACTGCTGACGTCGGCCCGGCCGTGGCCCGAGACCGACCGGCCACGGC   1500
  E  L  L  T  S  A  R  P  W  P  E  T  D  R  P  R
GTGCCGCCGTCTCCTCGTTCGGGGTGAGCGGCACCAACGCCCACGTCATC   1550
R  A  A  V  S  S  F  G  V  S  G  T  N  A  H  V  I
CTGGAGGCCGGACCGGTAACGGAGACGCCCGCGGCATCGCCTTCCGGTGA   1600
 L  E  A  G  F  V  T  E  T  P  A  A  S  P  S  G  D
CCTTCCCCTGCTGGTGTCGGCACGCTCACCGGAAGCGCTCGACGAGCAGA   1650
  L  P  L  L  V  S  A  R  S  P  E  A  L  D  E  Q
TCCGCCGACTGCGCGCCTACCTGGACACCACCCCGGACGTCGACCGGGTG   1700
I  R  R  L  R  A  Y  L  D  T  T  P  D  V  D  R  V
GCCGTGGCACAGACGCTGGCCCGGCGCACACACTTCGCCCACCGCGCCGT   1750
 A  V  A  Q  T  L  A  R  R  T  H  F  A  H  R  A  V
GCTGCTCGGTGACACCGTCATCACCACACCCCCCGCGGACCGGCCCGACG   1800
  L  L  G  D  T  V  I  T  T  P  P  A  D  R  P  D
AACTCGTCTTCGTCTACTCCGGCCAGGGCACCCAGCATCCCGCGATGGGC   1850
E  L  V  E  V  Y  S  G  Q  G  T  Q  H  P  A  M  G
GAGCAGCTAGCCGCCGCGTTCCCCGTCTTCGCGCGGATCCATCAGCAGGT   1900
```

-continued

```
E  Q  L  A  A  A  F  P  V  F  A  R  I  H  Q  Q  V
GTGGGACCTGCTCGATGTGCCCGATCTGGAGGTGAACGAGACCGGTTACG     1950
 W  D  L  L  D  V  P  D  L  E  V  N  E  T  G  Y
CCCAGCCGGCCCTGTTCGCAATGCAGGTGGCTCTGTTCGGGCTGCTGGAA     2000
A  Q  P  A  L  F  A  M  Q  V  A  L  F  G  L  L  E
TCGTGGGGTGTACGACCGGACGCGGTGATCGGCCATTCGGTGGGTGAGCT     2050
 S  W  G  V  R  P  D  A  V  I  G  H  S  V  G  E  L
TGCGGCTGCGTATGTGTCCGGGGTGTGGTCGTTGGAGGATGCCTGCACTT     2100
  A  A  A  Y  V  S  G  V  W  S  L  E  D  A  C  T
TGGTGTCGGCGCGGGCTCGTCTGATGCAGGCTCTGCCCGCGGGTGGGGTG     2150
L  V  S  A  R  A  R  L  M  Q  A  L  P  A  G  G  V
ATGGTCGCTGTCCCGGTCTCGGAGGATGAGGCCCGGGCCGTGCTGGGTGA     2200
 M  V  A  V  P  V  S  E  D  E  A  R  A  V  L  G  E
GGGTGTGGAGATCGCCGCGGTCAACGGCCCGTCGTCGGTGGTTCTCTCCG     2250
  G  V  E  I  A  A  V  N  G  P  S  S  V  V  L  S
GTGATGAGGCCGCCGTGCTGCAGGCCGCGGAGGGGCTGGGGAAGTGGACG     2300
G  D  E  A  A  V  L  Q  A  A  E  G  L  G  K  W  T
CGGCTGGCGACCAGCCACGCGTTCCATTCCGCCCGTATGGAACCCATGCT     2350
 R  L  A  T  S  H  A  F  H  S  A  R  M  E  P  M  L
GGAGGAGTTCCGGGCGGTCGCCGAAGGCCTGACCTACCGGACGCCGCAGG     2400
  E  E  F  R  A  V  A  E  G  L  T  Y  R  T  P  Q
TCTCCATGGCCGTTGGTGATCAGGTGACCACCGCTGAGTACTGGGTGCGG     2450
V  S  M  A  V  G  D  Q  V  T  T  A  E  Y  W  V  R
CAGGTCCGGGACACGGTCCGGTTCGGCGAGCAGGTGGCCTCGTACGAGGA     2500
 Q  V  R  D  T  V  R  E  G  E  Q  V  A  S  Y  E  D
CGCCGTGTTCGTCGAGCTGGGTGCCGACCGGTCACTGGCCCGCCTGGTCG     2550
  A  V  E  V  E  L  G  A  D  R  S  L  A  R  L  V
ACGGTGTCGCGATGCTGCACGGCGACCACGAAATCCAGGCCGCGATCGGC     2600
D  G  V  A  M  L  H  G  D  H  E  I  Q  A  A  I  G
GCCCTGGCCCACCTGTATGTCAACGGCGTCACGGTCGACTGGCCCGCGCT     2650
 A  L  A  H  L  Y  V  N  G  V  T  V  D  W  P  A  L
CCTGGGCGATGCTCCGGCAACACGGGTGCTGGACCTTCCGACATACGCCT     2700
  L  G  D  A  P  A  T  R  V  L  D  L  P  T  Y  A
TCCAGCACCAGCGCTACTGGCTCGAGTCGGCACGCCCGGCCGCATCCGAC     2750
F  Q  H  Q  R  Y  W  L  E  S  A  R  P  A  A  S  D
GCGGGCCACCCCGTGCTGGGCTCCGGTATCGCCCTCGCCGGGTCGCCGGG     2800
 A  G  H  P  V  L  G  S  G  I  A  L  A  G  S  P  G
CCGGGTGTTCACGGGTTCCGTGCCGACCGGTGCGGACCGCGCGGTGTTCG     2850
  R  V  F  T  G  S  V  P  T  G  A  D  R  A  V  F
TCGCCGAGCTGGCGCTGGCCGCCGCGGACGCGGTCGACTGCGCCACGGTC     2900
V  A  E  L  A  L  A  A  A  D  A  V  D  C  A  T  V
GAGCGGCTCGACATCGCCTCCGTGCCCGGCCGGCCGGGCCATGGCCGGAC     2950
 E  R  L  D  I  A  S  V  P  G  R  P  G  H  G  R  T
GACCGTACAGACCTGGGTCGACGAGCCGGCGGACGACGGCCGGCGCCGGT     3000
  T  V  Q  T  W  V  D  E  P  A  D  D  G  R  R  R
TCACCGTGCACACCCGCACCGGCGACGCCCCGTGGACGCTGCACGCCGAG     3050
F  T  V  H  T  R  T  G  D  A  P  W  T  L  H  A  E
GGGGTGCTGCGCCCCCATGGCACGGCCCTGCCCGATGCGGCCGACGCCGA     3100
 G  V  L  R  P  H  G  T  A  L  P  D  A  A  D  A  E
GTGGCCCCCACCGGGCGCGGTGCCCGCGGACGGGCTGCCGGGTGTGTGGC     3150
  W  P  P  P  G  A  V  P  A  D  G  L  P  G  V  W
GCCGGGGGGACCAGGTCTTCGCCGAGGCCGAGGTGGACGGACCGGACGGT     3200
R  R  G  D  Q  V  F  A  E  A  E  V  D  G  P  D  G
TTCGTGGTGCACCCCGACCTGCTCGACGCGGTCTTCTCCGCGGTCGGCGA     3250
 F  V  V  H  P  D  L  L  D  A  V  F  S  A  V  G  D
CGGAAGCCGCCAGCCGGCCGGATGGCCCGACCTGACGGTGCACGCGTCGG     3300
  G  S  R  Q  P  A  G  W  R  D  L  T  V  H  A  S
ACGCCACCGTACTGCGCGCCTGCCTCACCCGGCGCACCGACGGAGCCATG     3350
D  A  T  V  L  R  A  C  L  T  R  R  T  D  G  A  M
GGATTCGCCGCCTTCGACGGCGCCGGCCTGCCGGTACTCACCGCGGAGGC     3400
 G  F  A  A  F  D  G  A  G  L  P  V  L  T  A  E  A
GGTGACGCTGCGGGAGGTGGCGTCACCGTCCGGCTCCGAGGAGTCGGACG     3450
  V  T  L  R  E  V  A  S  P  S  G  S  E  E  S  D
GCCTGCACCGGTTGGAGTGGCTCGCGGTCGCCGAGGCGGTCTACGACGGT     3500
G  L  H  R  L  E  W  L  A  V  A  E  A  V  Y  D  G
GACCTGCCCGAGGGACATGTCCTGATCACCGCCGCCCACCCCGACGACCC     3550
 D  L  P  E  G  H  V  L  I  T  A  A  H  P  D  D  P
CGAGGACATACCCACCCGCGCCCACACCCGCGCCACCCGCGTCCTGACCG     3600
  E  D  I  P  T  R  A  H  T  R  A  T  R  V  L  T
CCCTGCAACACCACCTCACCACCACCGACCACACCCTCATCGTCCACACC     3650
A  L  Q  H  H  L  T  T  T  D  H  T  L  I  V  H  T
ACCACCGACCCCGCCGGCGCCACCGTCACCGGCCTCACCCGCACCGCCCA     3700
 T  T  D  P  A  G  A  T  V  T  G  L  T  R  T  A  Q
GAACGAACACCCCCACCGCATCCGCCTCATCGAAACCGACCACCCCCACA     3750
  N  E  H  P  H  R  I  R  L  I  E  T  D  H  P  H
CCCCCCTCCCCCTGGCCCAACTCGCCACCCTCGACCACCCCCACCTCCGC     3800
T  F  L  P  L  A  Q  L  A  T  L  D  H  P  H  L  R
CTCACCCACCACACCCTCCACCACCCCCACCTCACCCCCCTCCACACCAC     3850
 L  T  H  H  T  L  H  H  P  H  L  T  P  L  H  T  T
CACCCCACCCACCACCACCCCCCTCAACCCCGAACACGCCATCATCATCA     3900
```

-continued

```
 T  P  P  T  T  T  P  L  N  P  E  H  A  I  I  I
CCGGCGGCTCCGGCACCCTCGCCGGCATCCTCGCCCGCCACCTGAACCAC    3950
T  G  G  S  G  T  L  A  G  I  L  A  R  H  L  N  H
CCCCACACCTACCTCCTCTCCCGCACCCCACCCCCCGACGCCACCCCCGG    4000
 P  H  T  Y  L  L  S  R  T  P  P  P  D  A  T  P  G
CACCCACCTCCCCTGCGACGTCGGCGACCCCCACCAACTCGCCACCACCC    4050
 T  H  L  P  C  D  V  G  D  P  H  Q  L  A  T  T
TCACCCACATCCCCCAACCCCTCACCGCCATCTTCCACACCGCCGCCACC    4100
L  T  H  I  P  Q  P  L  T  A  I  F  H  T  A  A  T
CTCGACGACGGCATCCTCCACGCCCTCACCCCCGACCGCCTCACCACCGT    4150
 L  D  D  G  I  L  H  A  L  T  P  D  R  L  T  T  V
CCTCCACCCCAAAGCCAACGCCGCCTGGCACCTGCACCACCTCACCCAAA    4200
 L  H  P  K  A  N  A  A  W  H  L  H  H  L  T  Q
ACCAACCCCTCACCCACTTCGTCCTCTACTCCAGCGCCGCCGCCGTCCTC    4250
N  Q  P  L  T  H  F  V  L  Y  S  S  A  A  A  V  L
GGCAGCCCCGGACAAGGAAACTACGCCGCCGCCAACGCCTTCCTCGACGC    4300
 G  S  P  G  Q  G  N  Y  A  A  A  N  A  F  L  D  A
CCTCGCCACCCACCGCCACACCCTCGGCCAACCCGCCACCTCCATCGCCT    4350
 L  A  T  H  R  H  T  L  G  Q  P  A  T  S  I  A
GGGGCATGTGGCACACCACCAGCACCCTCACCGGACAACTCGACGACGCC    4400
W  G  M  W  H  T  T  S  T  L  T  G  Q  L  D  D  A
GACCGGGACCGCATCCGCCGCGGCGGTTTCCTCCCGATCACGGACGACGA    4450
 D  R  D  R  I  R  R  G  G  F  L  F  I  T  D  D  E
GGGCATGGGGATGCAT
 G
```

The NheII-XhoI restriction fragment that encodes module 8 of the FK-520 PKS with the endogenous AT domain replaced by the AT domain of module 13 (specific for methylmalonyl CoA) of the rapamycin PKS has the DNA sequence and encodes the amino acid sequence shown below. (SEQ ID NOS 22–23)

```
AGATCTGGCAGCTCGCCGAAGCGCTGCTGACGCTCGTCCGGGAGAGCACC      50
 Q  L  A  E  A  L  L  T  L  V  R  E  S  T
GCCGCCGTGCTCGGCCACGTGGGTGGCGAGGACATCCCCGCGACGGCGGC     100
 A  A  V  L  G  H  V  G  G  E  D  I  P  A  T  A  A
GTTCAAGGACCTCGGCATCGACTCGCTCACCGCGGTCCAGCTGCGCAACG     150
  F  K  D  L  G  I  D  S  L  T  A  V  Q  L  R  N
CCCTCACCGAGGCGACCGGTGTGCGGCTGAACGCCACGGCGGTCTTCGAC     200
A  L  T  E  A  T  G  V  R  L  N  A  T  A  V  F  D
TTCCCGACCCCGCACGTGCTCGCCGGGAAGCTCGGCGACGAACTGACCGG     250
 F  P  T  P  H  V  L  A  G  K  L  G  D  E  L  T  G
CACCCGCGCGCCCGTCGTGCCCCGGACCGCGGCCACGGCCGGTGCGCACG     300
  T  R  A  P  V  V  P  R  T  A  A  T  A  G  A  H
ACGAGCCGCTGGCGATCGTGGGAATGGCCTGCCGGCTGCCCGGCGGGGTC     350
D  E  P  L  A  I  V  G  M  A  C  R  L  P  G  G  V
GCGTCACCCGAGGAGCTGTGGCACCTCGTGGCATCCGGCACCGACGCCAT     400
 A  S  P  E  E  L  W  H  L  V  A  S  G  T  D  A  I
CACGGAGTTCCCGACGGACCGCGGCTGGGACGTCGACGCGATCTACGACC     450
  T  E  F  P  T  D  R  G  W  D  V  D  A  I  Y  D
CGGACCCCGACGCGATCGGCAAGACCTTCGTCCGGCACGGTGGCTTCCTC     500
P  D  P  D  A  I  G  K  T  F  V  R  H  G  G  F  L
ACCGGCGCGACAGGCTTCGACGCGGCGTTCTTCGGCATCAGCCCGCGCGA     550
 T  G  A  T  G  F  D  A  A  F  F  G  I  S  P  R  E
GGCCCTCGCGATGGACCCGCAGCAGCGGGTGCTCCTGGAGACGTCGTGGG     600
  A  L  A  M  D  P  Q  Q  R  V  L  L  E  T  S  W
AGGCGTTCGAAAGCGCCGGCATCACCCCGGACTCGACCCGCGGCAGCGAC     650
E  A  F  E  S  A  G  I  T  P  D  S  T  R  G  S  D
ACCGGCGTGTTCGTCGGCGCCTTCTCCTACGGTTACGGCACCGGTGCGGA     700
 T  G  V  F  V  G  A  F  S  Y  G  Y  G  T  G  A  D
CACCGACGGCTTCGGCGCGACCGGCTCGCAGACCAGTGTGCTCTCCGGCC     750
  T  D  G  F  G  A  T  G  S  Q  T  S  V  L  S  G
GGCTGTCGTACTTCTACGGTCTGGAGGGTCCGGCGGTCACGGTCGACACG     800
R  L  S  Y  F  Y  G  L  E  G  P  A  V  T  V  D  T
GCGTGTTCGTCGTCGCTGGTGGCGCTGCACCAGGCCGGGCAGTCGCTGCG     850
 A  C  S  S  S  L  V  A  L  H  Q  A  G  Q  S  L  R
CTCCGGCGAATGCTCGCTCGCCCTGGTCGGCGGCGTCACGGTGATGGCGT     900
  S  G  E  C  S  L  A  L  V  G  G  V  T  V  M  A
CTCCCGGCGGCTTCGTGGAGTTCTCCCGGCAGCGCGGCCTCGCGCCGGAC     950
S  P  G  G  F  V  E  F  S  R  Q  R  G  L  A  P  D
GGCCGGGCGAAGGCGTTCGGCGCGGGTGCGGACGGCACGAGCTTCGCCGA    1000
 G  R  A  K  A  F  G  A  G  A  D  G  T  S  F  A  E
GGGTGCCGGTGTGCTGATCGTCGAGAGGCTCTCCGACGCCGAACGCAACG    1050
  G  A  G  V  L  I  V  E  R  L  S  D  A  E  R  N
GTCACACCGTCCTGGCGGTCGTCCGTGGTTCGGCGGTCAACCAGGATGGT    1100
G  H  T  V  L  A  V  V  R  G  S  A  V  N  Q  D  G
GCCTCCAACGGGCTGTCGGCGCCGAACGGGCCGTCGCAGGAGCGGGTGAT    1150
 A  S  N  G  L  S  A  P  N  G  P  S  Q  E  R  V  I
```

-continued

```
CCGGCAGGCCCTGGCCAACGCCGGGCTCACCCCGGCGGACGTGGACGCCG  1200
  R  Q  A  L  A  N  A  G  L  T  P  A  D  V  D  A
TCGAGGCCCACGGCACCGGCACCAGGCTGGGCGACCCCATCGAGGCACAG  1250
V  E  A  H  G  T  G  T  R  L  G  D  P  I  E  A  Q
GCGGTACTGGCCACCTACGGACAGGAGCGCGCCACCCCCCTGCTGCTGGG  1300
 A  V  L  A  T  Y  G  Q  E  R  A  T  P  L  L  L  G
CTCGCTGAAGTCCAACATCGGCCACGCCCAGGCCGCGTCCGGCGTCGCCG  1350
  S  L  K  S  N  I  G  H  A  Q  A  A  S  G  V  A
GCATCATCAAGATGGTGCAGGCCCTCCGGCACGGGGAGCTGCCGCCGACG  1400
G  I  I  K  M  V  Q  A  L  R  H  G  E  L  P  P  T
CTGCACGCCGACGAGCCGTCGCCGCACGTCGACTGGACGGCCGGCGCCGT  1450
 L  H  A  D  E  P  S  P  H  V  D  W  T  A  G  A  V
CGAACTGCTGACGTCGGCCCGGCCGTGGCCCGAGACCGACCGGCCACGGC  1500
  E  L  L  T  S  A  R  P  W  P  E  T  D  R  P  R
GTGCCGCCGTCTCCTCGTTCGGGGTGAGCGGCACCAACGCCCACGTCATC  1550
R  A  A  V  S  S  F  G  V  S  G  T  N  A  H  V  I
CTGGAGGCCGGACCGGTAACGGAGACGCCCGCGGCATCGCCTTCCGGTGA  1600
 L  E  A  G  P  V  T  E  T  P  A  A  S  P  S  G  D
CCTTCCCCTGCTGGTGTCGGCACGCTCACCGGAAGCGCTCGACGAGCAGA  1650
  L  P  L  L  V  S  A  R  S  P  E  A  L  D  E  Q
TCCGCCGACTGCGCGCCTACCTGGACACCACCCCGGACGTCGACCGGGTG  1700
I  R  R  L  R  A  Y  L  D  T  T  P  D  V  D  R  V
GCCGTGGCACAGACGCTGGCCCGGCGCACACACTTCGCCCACCGCGCCGT  1750
 A  V  A  Q  T  L  A  R  R  T  H  F  A  H  R  A  V
GCTGCTCGGTGACACCGTCATCACCACACCCCCCGCGGACCGGCCCGACG  1800
  L  L  G  D  T  V  I  T  T  P  P  A  D  R  P  D
AACTCGTCTTCGTCTACTCCGGCCAGGGCACCCAGCATCCCGCGATGGGC  1850
E  L  V  F  V  Y  S  G  Q  G  T  Q  H  P  A  M  G
GAGCAGCTAGCCGATTCGTCGGTGGTGTTCGCCGAGCGGATGGCCGAGTG  1900
 E  Q  L  A  D  S  S  V  V  F  A  E  R  M  A  E  C
TGCGGCGGCGTTGCGCGAGTTCGTGGACTGGGATCTGTTCACGGTTCTGG  1950
  A  A  A  L  R  E  F  V  D  W  D  L  F  T  V  L
ATGATCCGGCGGTGGTGGACCGGGTTGATGTGGTCCAGCCCGCTTCCTGG  2000
D  D  P  A  V  V  D  R  V  D  V  V  Q  P  A  S  W
GCGATGATGGTTTCCCTGGCCGCGGTGTGGCAGGCGGCCGGTGTGCGGCC  2050
 A  M  M  V  S  L  A  A  V  W  Q  A  A  G  V  R  P
GGATGCGGTGATCGGCCATTCGCAGGGTGAGATCGCCGCAGCTTGTGTGG  2100
  D  A  V  I  G  H  S  Q  G  E  I  A  A  A  C  V
CGGGTGCGGTGTCACTACGCGATGCCGCCCGGATCGTGACCTTGCGCAGC  2150
A  G  A  V  S  L  R  D  A  A  R  I  V  T  L  R  S
CAGGCGATCGCCCGGGGCCTGGCGGGCCGGGGCGCGATGGCATCCGTCGC  2200
 Q  A  I  A  R  G  L  A  G  R  G  A  M  A  S  V  A
CCTGCCCGCGCAGGATGTCGAGCTGGTCGACGGGGCCTGGATCGCCGCCC  2250
  L  P  A  Q  D  V  E  L  V  D  G  A  W  I  A  A
ACAACGGGCCCGCCTCCACCGTGATCGCGGGCACCCCGGAAGCGGTCGAC  2300
H  N  G  P  A  S  T  V  I  A  G  T  P  E  A  V  D
CATGTCCTCACCGCTCATGAGGCACAACGGGTGCGGGTGCGGCGGATCAC  2350
 H  V  L  T  A  H  E  A  Q  G  V  R  V  R  R  I  T
CGTCGACTATGCCTCGCACACCCCGCACGTCGAGCTGATCCGCGACGAAC  2400
  V  D  Y  A  S  H  T  P  H  V  E  L  I  R  D  E
TACTCGACATCACTAGCGACAGCAGCTCGCAGACCCCGCTCGTGCCGTGG  2450
L  L  D  I  T  S  D  S  S  S  Q  T  P  L  V  P  W
CTGTCGACCGTGGACGGCACCTGGGTCGACAGCCCGCTGGACGGGGAGTA  2500
 L  S  T  V  D  G  T  W  V  D  S  P  L  D  G  E  Y
CTGGTACCGGAACCTGCGTGAACCGGTCGGTTTCCACCCCGCCGTCAGCC  2550
  W  Y  R  N  L  R  E  P  V  G  F  H  P  A  V  S
AGTTGCAGGCCCACCGCCACACCGTGTTCGTCGAGGTCACCCCCAGCCCG  2600
Q  L  Q  A  Q  G  D  T  V  F  V  E  V  S  A  S  P
GTGTTGTTGCAGGCGATCGACGACGATGTCGTCACGGTTGCCACGCTGCG  2650
 V  L  L  Q  A  M  D  D  D  V  V  T  V  A  T  L  R
TCGTGACGACGGCGACCCCACCCGGATGCTCACCCCCCTCGCACAGGCCT  2700
  R  D  D  G  D  A  T  R  M  L  T  A  L  A  Q  A
ATGTCCACGCCGTCACCCTCCACTGCCCCGCCATCCTCGCCACCACCACA  2750
Y  V  H  G  V  T  V  D  W  P  A  I  L  G  T  T  T
ACCCGGCTACTGCACCTTCCCACCTACGCCTTCCAACACCAGCGGTACTG  2800
 T  R  V  L  D  L  P  T  Y  A  F  Q  H  Q  R  Y  W
GCTCGAGTCGGCACGCCCGGCCCCATCCGACCCGCGCCACCCCGTCCTGG  2850
  L  E  S  A  R  P  A  A  S  D  A  G  H  P  V  L
GCTCCGGTATCGCCCTCGCCCGCTCGCCGGGCCGGGTCTTCACGGGTTCC  2900
G  S  G  I  A  L  A  G  S  P  G  R  V  F  T  G  S
GTGCCCACCGGTGCGGACCGCGCCCTCTTCGTCGCCGAGCTGGCCCTGGC  2950
 V  P  T  G  A  D  R  A  V  F  V  A  E  L  A  L  A
CGCCGCGGACGCGGTCCACTCCGCCACGGTCGAGCGGCTCCACATCGCCT  3000
  A  A  D  A  V  D  C  A  T  V  E  R  L  D  I  A
CCGTCCCCGGCCGGCCGGCCCATCGCCGGACGACCCTACACACCTGGGTC  3050
S  V  P  G  R  P  G  H  G  R  T  T  V  Q  T  W  V
GACGACCCGCCCGACCACCCCCGGCGCCCCTTCACCGTGCACACCCGCAC  3100
 D  E  P  A  D  D  G  R  R  R  F  T  V  H  T  R  T
CGGCGACGCCCCGTGGACGCTGCACGCCGAGGGGGTGCTGCGCCCCCATG  3150
  G  D  A  P  W  T  L  H  A  E  G  V  L  R  P  H
```

-continued

```
GCACGGCCCTCCCCCATGCGGCCGACGCCCAGTGCCCCCCACCCGCCGCG  3200
G  T  A  L  P  D  A  A  D  A  E  W  P  P  P  G  A
GTGCCCGCCGACGCGCTGCCGCGTGTGTGGCGCCGCGGCGACCAGGTCTT  3250
 V  P  A  D  G  L  P  G  V  W  R  R  G  D  Q  V  F
CGCCCAGGCCGAGCTGGACGGACCCGACCGTTTCGTGGTGCACCCCGACC  3300
  A  E  A  E  V  D  G  P  D  G  F  V  V  H  P  D
TGCTCGACGCGGTCTTCTCCGCGGTCGGCGACGCAAGCCGCCAGCCGGCC  3350
L  L  D  A  V  F  S  A  V  G  D  G  S  R  Q  P  A
GGATGCCCCCACCTGACCGTGCACCCCTCGCACCCCACCGTACTCCGCGC  3400
 G  W  R  D  L  T  V  H  A  S  D  A  T  V  L  R  A
CTGCCTCACCCCGCGCACCCACGGAGCCATCGGATTCGCCGCCTTCGACG  3450
  C  L  T  R  R  T  D  G  A  M  G  F  A  A  F  D
GCGCCGGCCTGCCGGTACTCACCGCCGAGGCGGTGACGCTGCGGCAGGTG  3500
G  A  G  L  P  V  L  T  A  E  A  V  T  L  R  E  V
GCGTCACCGTCCGGCTCCGAGGACTCGCACGGCCTGCACCGGTTGGAGTG  3550
 A  S  P  S  G  S  E  E  S  D  G  L  H  R  L  E  W
GCTCGCGGTCGCCGAGGCGCTCTACCACGGTGACCTCCCCGAGGGACATG  3600
  L  A  V  A  E  A  V  Y  D  G  D  L  P  E  G  H
TCCTCATCACCCCCGCCCACCCCGACCACCCCGAGGACATACCCACCCGC  3650
V  L  I  T  A  A  H  P  D  D  P  E  D  I  P  T  R
GCCCACACCCCCGCCACCCGCGTCCTGACCGCCCTGCAACACCACCTCAC  3700
 A  H  T  R  A  T  R  V  L  T  A  L  Q  H  H  L  T
CACCACCCACCACACCCTCATCCTCCACACCACCACCCACCCCGCCGGCG  3750
  T  T  D  H  T  L  I  V  H  T  T  T  D  P  A  G
CCACCGTCACCCGCCTCACCCGCACCGCCCACAACGAACACCCCCACCGC  3800
A  T  V  T  G  L  T  R  T  A  Q  N  E  H  P  H  R
ATCCGCCTCATCCAAACCCACCACCCCCACACCCCCCTCCCCCTGGCCCA  3850
 I  R  L  I  E  T  D  H  P  H  T  P  L  P  L  A  Q
ACTCGCCACCCTCGACCACCCCCACCTCCGCCTCACCCACCACACCCTCC  3900
  L  A  T  L  D  H  P  H  L  R  L  T  H  H  T  L
ACCACCCCCACCTCACCCCCCTCCACACCACCACCCCACCCACCACCACC  3950
H  H  P  H  L  T  P  L  H  T  T  T  P  P  T  T  T
CCCCTCAACCCCGAACACGCCATCATCATCACCGGCGGCTCCGGCACCCT  4000
 P  L  N  P  E  H  A  I  I  I  T  G  G  S  G  T  L
CGCCGGCATCCTCGCCCGCCACCTGAACCACCCCCACACCTACCTCCTCT  4050
  A  G  I  L  A  R  H  L  N  H  P  H  T  Y  L  L
CCCGCACCCCACCCCCCGACGCCACCCCCGGCACCCACCTCCCCTGCGAC  4100
S  R  T  P  P  P  D  A  T  P  G  T  H  L  P  C  D
GTCGGCGACCCCCACCAACTCGCCACCACCCTCACCCACATCCCCCAACC  4150
 V  G  D  P  H  Q  L  A  T  T  L  T  H  I  P  Q  P
CCTCACCGCCATCTTCCACACCGCCGCCACCCTCGACGACGGCATCCTCC  4200
  L  T  A  I  F  H  T  A  A  T  L  D  D  G  I  L
ACGCCCTCACCCCCGACCGCCTCACCACCGTCCTCCACCCCAAAGCCAAC  4250
H  A  L  T  P  D  R  L  T  T  V  L  H  P  K  A  N
GCCGCCTGGCACCTGCACCACCTCACCCAAAACCAACCCCTCACCCACTT  4300
 A  A  W  H  L  H  H  L  T  Q  N  Q  P  L  T  H  F
CGTCCTCTACTCCAGCGCCGCCGCCGTCCTCGGCAGCCCCGGACAAGGAA  4350
  V  L  Y  S  S  A  A  A  V  L  G  S  P  G  Q  G
ACTACGCCGCCGCCAACGCCTTCtTCGACGCCCTCGCCACCCACCGCCAC  4400
N  Y  A  A  A  N  A  F  L  D  A  L  A  T  H  R  H
ACCCTCGGCCAACCCGCCACCTCCATCGCCTGGGGCATGTGGCACACCAC  4450
 T  L  G  Q  P  A  T  S  I  A  W  G  M  W  H  T  T
CAGCACCCTCACCGGACAACTCGACGACGCCGACCGGGACCGCATCCGCC  4500
  S  T  L  T  G  Q  L  D  D  A  D  R  D  R  I  R
GCGGCGGTTTCCTCCCGATCACGGACGACGAGGGCATGGGGATGCAT
R  G  G  F  L  P  I  T  D  D  E  G
```

Phage KC515 DNA was prepared using the procedure described in Genetic Manipulation of Streptomyces, A Laboratory Manual, edited by D. Hopwood et al. A phage suspension prepared from 10 plates (100 mm) of confluent plaques of KC515 on S. lividans TK24 generally gave about 3 μg of phage DNA. The DNA was ligated to circularize at the cos site, subsequently digested with restriction enzymes BamHI and PstI, and dephosphorylated with SAP.

Each module 8 cassette described above was excised with restriction enzymes BglII and NsiI and ligated into the compatible BamHI and PstI sites of KC515 phage DNA prepared as described above. The ligation mixture containing KC515 and various cassettes was transfected into protoplasts of *Streptomyces lividans* TK24 using the procedure described in Genetic Manipulation of Streptomyces, A Laboratory Manual edited by D. Hopwood et al. and overlaid with TK24 spores. After 16–24 hr, the plaques were restreaked on plates overlaid with TK24 spores. Single plaques were picked and resuspended in 200 μL of nutrient broth. Phage DNA was prepared by the boiling method Hopwood et al., supra). The PCR with primers spanning the left and right boundaries of he recombinant phage was used to verify the correct phage had been isolated. In most cases, at least 80% of the plaques contained the expected insert. To confirm the presence of the resistance marker (thiostrepton), a spot test is used, as described in Lomovskaya et al. (1997), in which a plate with spots of phage is overlaid with mixture of spores of TK24 and phiC31 TK24 lysogen. After overnight incubation, the plate is overlaid with antibiotic in soft agar. A working stock is made of all phage containing desired constructs.

*Streptomyces hygroscopicus* ATCC 14891 (see U.S. Pat. No. 3,244,592, issued Apr 5, 1966, incorporated herein by reference) mycelia were infected with the recombinant phage by mixing the spores and phage ($1\times10^8$ of each); and incubating on R2YE agar (Genetic Manipulation of Streptomyces, A Laboratory Manual, edited by D. Hopwood et al.) at 30° C. for 10 days. Recombinant clones were selected and plated on minimal medium containing thiostrepton (50 μg/ml) to select for the thiostrepton resistance-conferring gene. Primary thiostrepton resistant clones were isolated and purified through a second round of single colony isolation, as necessary. To obtain thiostrepton-sensitive revertants that underwent a second recombination event to evict the phage genome, primary recombinants were propagated in liquid media for two to three days in the absence of thiostrepton and then spread on agar medium without thiostrepton to obtain spores. Spores were plated to obtain about 50 colonies per plate, and thiostrepton sensitive colonies were identified by replica plating onto thiostrepton containing agar medium. The PCR was used to determine which of the thiostrepton sensitive colonies reverted to the wild type (reversal of the initial integration event), and which contain the desired AT swap at module 8 in the ATCC 14891-derived cells. The PCR primers used amplified either the KS/AT junction or the AT/DH junction of the wild-type and the desired recombinant strains. Fermentation of the recombinant strains, followed by isolation of the metabolites and analysis by LCMS, and NMR is used to characterize the novel polyketide compounds.

EXAMPLE 2

Replacement of Methoxyl with Hydrogen or Methyl at C-13 of FK-506

The present invention also provides the 13-desmethoxy derivatives of FK-506 and the novel PKS enzymes that produce them. A variety of Streptomyces strains that produce FK-506 are known in the art, including S. isukubaensis No. 9993 (FERM BP-927), described in U.S. Pat. No. 5,624,852, incorporated herein by reference; S. *hygroscopicus* subsp. *yakushimaensis* No. 7238, described in U.S. Pat. No. 4,894,366, incorporated herein by reference; S. sp. MA6858 (ATCC 55098), described in U.S. Pat. Nos. 5,116,756, incorporated herein by reference; and S. sp. MA 6548, described in Motamedi et al., 1998, "The biosynthetic gene cluster for the macrolactone ring of the immunosuppressant FK-506, " *Eur. J. Biochem.* 256: 528–534, and Motamedi et al., 1997, "Structural organization of a multifunctional polyketide synthase involved in the biosynthesis of the macrolide immunosuppressant FK-506, " *Eur. J. Biochem.* 244: 74–80, each of which is incorporated herein by reference.

The complete sequence of the FK-506 gene cluster from Streptomyces sp. MA6548 is known, and the sequences of the corresponding gene clusters from other FK-506-producing organisms is highly homologous thereto. The novel FK-506 recombinant gene clusters of the present invention differ from the naturally occurring gene clusters in that the AT domain of module 8 of the naturally occurring PKSs is replaced by an AT domain specific for malonyl CoA or methylmalonyl CoA. These AT domain replacements are made at the DNA level, following the methodology described in Example 1.

The naturally occurring module 8 sequence for the MA6548 strain is shown below, followed by the illustrative hybrid module 8 sequences for the MA6548 strains. (SEQ ID NOS 24–25)

```
GCATGCGGCTGTACGAGGCGGCACGGCGCACCGGAAGTCCCGTGGTGGTG     50
    M  R  L  Y  E  A  A  R  R  T  G  S  P  V  V  V
GCGGCCGCGCTCGACGACGCGCCGGACGTGCCGCTGCTGCGCGGGCTGCG    100
 A  A  A  L  D  D  A  P  D  V  P  L  L  R  G  L  R
GCGTACGACCGTCCGGCGTGCCGCCGTCCGGGAACGCTCTCTCGCCGACC    150
  R  T  T  V  R  R  A  A  V  R  E  R  S  L  A  D
GCTCGCCGTGCTGCCCGACGACGAGCGCGCCGACGCCTCCCTCGCGTTCG    200
R  S  P  C  C  P  T  T  S  A  P  T  P  P  S  R  S
TCCTGGAACAGCACCGCCACCGTGCTCGGCCACCTGGGCGCCGAAGACAT    250
 S  W  N  S  T  A  T  V  L  G  H  L  G  A  E  D  I
CCCGGCGACGACGACGTTCAAGGAACTCGGCATCGACTCGCTCACCGCGG    300
  P  A  T  T  T  F  K  E  L  G  I  D  S  L  T  A
TCCACCTGCGCAACGCCCTGACCACGGCGACCGGCGTACCCCTCAACGCC    350
V  Q  L  R  N  A  L  T  T  A  T  G  V  R  L  N  A
ACAGCGGTCTTCGACTTTCCGACGCCCCGCGCGCTCGCCGCGACACTCGG    400
 T  A  V  F  D  F  P  T  P  R  A  L  A  A  R  L  G
CGACGAGCTGGCCGGTACCCGCCCGCCCGTCGCGGCCCCGACCGCGGCCA    450
  D  E  L  A  G  T  R  A  P  V  A  A  R  T  A  A
CCGCGGCCGCGCACGACCAACCCCTGGCGATCGTCGGCATCCCCTGCCGT    500
T  A  A  A  H  D  E  P  L  A  I  V  G  M  A  C  R
CTGCCGGGCGCGGTCGCGTCGCCACAGGAGCTGTCGCGTCTCGTCGCGTC    550
 L  P  G  G  V  A  S  P  Q  E  L  W  R  L  V  A  S
CGGCACCGACGCCATCACGCAGTTCCCCCCGGACCCCCGCTGCGACGTGG    600
  G  T  D  A  I  T  E  F  P  A  D  R  G  W  D  V
ACGCGCTCTACGACCCGGACCCCGACGCGATCGGCAAGACCTTCGTCCGG    650
D  A  L  Y  D  P  D  P  D  A  I  G  K  T  F  V  R
CACGGCCGCTTCCTCGACGGTGCGAQCGCCTTCGACGCGGCGTTCTTCGG    700
 H  G  G  F  L  D  G  A  T  G  F  D  A  A  F  F  G
GATCACCCCGCGCGAGGCCCTGCCCATGGACCCGCAGCAACGCGTCCTCC    750
  I  S  P  R  E  A  L  A  M  D  P  Q  Q  R  V  L
TGGACACGTCCTGGGAGGCGTTCCAAAGCGCGGGCATCACCCCCGACGCG    800
L  E  T  S  W  E  A  F  E  S  A  G  I  T  P  D  A
GCGCCGCGCAGCGACACCCCCCTCTTCATCGCCGCGTTCTCCTACGGGTA    850
 A  R  G  S  D  T  G  V  F  I  G  A  F  S  Y  G  Y
CGGCACGGGTGCCGATACCAACGGCTTCGGCCCCACAGCGTCGCAGACCA    900
  G  T  G  A  D  T  N  G  F  G  A  T  G  S  Q  T
GCGTGCTCTCCGGCCGCCTCTCCTACTTCTACGGTCTGCACGCCCCTTCG    950
S  V  L  S  G  R  L  S  Y  F  Y  G  L  E  G  P  S
GTCACGGTCGACACCGCCTGCTCGTCGTCACTGGTCGCCCTGCACCAGGC   1000
 V  T  V  D  T  A  C  S  S  S  L  V  A  L  H  Q  A
AGGGCACTCCCTCCGCTCCCCCCAATCCTCGCTCGCCCTCCTCCGCGGTG   1050
```

-continued

```
 G  Q  S  L  R  S  G  E  C  S  L  A  L  V  G  G
TCACGGTGATGGCGTCGCCCGGCCGATTCGTCGAGTTCTCCCGGCAGCGC  1100
V  T  V  M  A  S  P  G  G  F  V  E  F  S  R  Q  R
GGGCTCGCGCCGGACGGGCGGGCGAAGGCGTTCGGCGCGGGCCCGGACGG  1150
 G  L  A  P  D  G  R  A  K  A  F  G  A  G  A  D  G
TACGAGCTTCCCCCAGGGCGCCGGTCCCCTCGTGGTCGAGCGGCTCTCCG  1200
 T  S  F  A  E  G  A  G  A  L  V  V  E  R  L  S
ACGCGGAGCGCCACGCCCACACCGTCCTCGCCCTCGTACCCGGCTCCGCG  1250
D  A  E  R  H  G  H  T  V  L  A  L  V  R  G  S  A
GCTAACTCCCACCCCGCCTCGAACCCTCTGTCGGCCCCCAACCGCCCCTC  1300
 A  N  S  D  G  A  S  N  G  L  S  A  P  N  G  P  S
CCAGCAACGCGTCATCCACCAGGCCCTCGCGAACGCGAAACTCACCCCCG  1350
 Q  E  R  V  I  H  Q  A  L  A  N  A  K  L  T  P
CCGATGTCGACGCGGTCCAGGCGCACGGCACCGGCACCCCCCTCGGCGAC  1400
A  D  V  D  A  V  E  A  H  G  T  G  T  R  L  G  D
CCCATCGAGGCGCAGGCGCTGCTCCCCACGTACGGACAGGACCCGGCGAC  1450
 P  I  E  A  Q  A  L  L  A  T  Y  G  Q  D  R  A  T
GCCCCTGCTGCTCGGCTCCCTGAAGTCGAACATCGGGCACGCCCAGGCCG  1500
 P  L  L  L  G  S  L  K  S  N  I  G  H  A  Q  A
CGTCAGGGGTCGCCGGCATCATCAACATGCTCCACCCCATCCGCCACGGG  1550
A  S  G  V  A  G  I  I  K  M  V  Q  A  I  R  H  G
GAACTGCCGCCGACACTGCACGCGGACGAGCCGTCGCCGCACGTCGACTG  1600
 E  L  P  P  T  L  H  A  D  E  P  S  P  H  V  D  W
GACGGCCGGTGCCGTCGAGCTCCTGACGTCGGCCCGGCCGTGGCCGGGGA  1650
 T  A  G  A  V  E  L  L  T  S  A  R  P  W  P  G
CCGGTCGCCCGCGCCGCGCTGCCGTCTCGTCGTTCGGCGTGAGCGGCACG  1700
T  G  R  P  R  R  A  A  V  S  S  F  G  V  S  G  T
AACGCCCACATCATCCTTGAGGCAGGACCGGTCAAAACGGGACCGGTCGA  1750
 N  A  H  I  I  L  E  A  G  P  V  K  T  G  P  V  E
GGCAGGAGCGATCGAGGCAGGACCGGTCGAAGTAGGACCGGTCGAGGCTG  1800
 A  G  A  I  E  A  G  P  V  E  V  G  P  V  E  A
GACCGCTCCCCGCGGCGCCGCCGTCAGCACCGGGCGAAGACCTTCCGCTG  1850
G  P  L  P  A  A  P  P  S  A  P  G  E  D  L  P  L
CTCGTGTCGGCGCGTTCCCCGGAGGCACTCGACGAGCAGATCGGGCGCCT  1900
 L  V  S  A  R  S  P  E  A  L  D  E  Q  I  G  R  L
GCGCGCCTATCTCGACACCGGCCCGGGCGTCGACCGGGCGGCCGTGGCGC  1950
 R  A  Y  L  D  T  G  P  G  V  D  R  A  A  V  A
AGACACTGGCCCGGCGTACGCACTTCACCCACCGGGCCGTACTGCTCGGG  2000
Q  T  L  A  R  R  T  H  F  T  H  R  A  V  L  L  G
GACACCGTCATCGGCGCTCCCCCCGCGGACCAGGCCGACGAACTCGTCTT  2050
 D  T  V  I  G  A  P  P  A  D  Q  A  D  E  L  V  F
CGTCTACTCCGGTCAGGGCACCCAGCATCCCGCGATGGGCGAGCAACTCG  2100
 V  Y  S  G  Q  G  T  Q  H  P  A  M  G  E  Q  L
CGGCCGCGTTCCCCGTGTTCGCCGATGCCTGGCACGACGCGCTCCGACGG  2150
A  A  A  F  P  V  F  A  D  A  W  H  D  A  L  R  R
CTCGACGACCCCGACCCGCACGACCCCACACGGAGCCAGCACACGCTCTT  2200
 L  D  D  P  D  P  H  D  P  T  R  S  Q  H  T  L  F
CGCCCACCAGGCGGCGTTCACCGCCCTCCTGAGGTCCTGGGACATCACGC  2250
 A  H  Q  A  A  F  T  A  L  L  R  S  W  D  I  T
CGCACGCCGTCATCGGCCACTCGCTCGGCGAGATCACCGCCGCGTACGCC  2300
P  H  A  V  I  G  H  S  L  G  E  I  T  A  A  Y  A
GCCGGGATCCTGTCGCTCGACGACGCCTGCACCCTGATCACCACGCGTGC  2350
 A  G  I  L  S  L  D  D  A  C  T  L  I  T  T  R  A
CCGCCTCATGCACACGCTTCCGCCGCCCGGCGCCATGGTCACCGTGCTGA  2400
 R  L  M  H  T  L  P  P  P  G  A  M  V  T  V  L
CCAGCGAGGAGGAGGCCCGTCAGGCGCTGCGGCCGGGCGTGGAGATCGCC  2450
T  S  E  E  E  A  R  Q  A  L  R  P  G  V  E  I  A
GCGGTCTTCGGCCCGCACTCCGTCGTGCTCTCGGGCGACGAGGACGCCGT  2500
 A  V  F  G  P  H  S  V  V  L  S  G  D  E  D  A  V
GCTCGACGTCGCACAGCGGCTCGGCATCCACCACCGTCTGCCCGCGCCGC  2550
 L  D  V  A  Q  R  L  G  I  H  H  R  L  P  A  P
ACGCGGGCCACTCCGCGCACATGGAACCCGTGGCCGCCGAGCTGCTCGCC  2600
H  A  G  H  S  A  H  M  E  P  V  A  A  E  L  L  A
ACCACTCGCGAGCTCCGTTACGACCGGCCCCACACCGCCATCCCGAACGA  2650
 T  T  R  E  L  R  Y  D  R  P  H  T  A  I  P  N  D
CCCCACCACCGCCGAGTACTGGGCCGAGCAGGTCCGCAACCCCGTGCTGT  2700
 P  T  T  A  E  Y  W  A  E  Q  V  R  N  P  V  L
TCCACGCCCACACCCAGCGGTACCCCGACGCCGTGTTCGTCGAGATCGGC  2750
F  H  A  H  T  Q  R  Y  P  D  A  V  F  V  E  I  G
CCCGGCCAGGACCTCTCACCGCTGGTCGACGGCATCGCCCTGCAGAACGG  2800
 P  G  Q  D  L  S  P  L  V  D  G  I  A  L  Q  N  G
CACGGCGGACGAGGTGCACGCGCTGCACACCGCGCTCGCCCGCCTCTTCA  2850
 T  A  D  E  V  H  A  L  H  T  A  L  A  R  L  F
CACGCGGCGCCACGCTCGACTGGTCCCGCATCCTCGGCGGTGCTTCGCGG  2900
T  R  G  A  T  L  D  W  S  R  I  L  G  G  A  S  R
CACGACCCTGACGTCCCCTCGTACGCGTTCCAGCGGCGTCCCTACTGGAT  2950
 H  D  P  D  V  P  S  Y  A  F  Q  R  R  P  Y  W  I
CGAGTCGGCTCCCCCGGCCACGGCCGACTCGGGCCACCCCGTCCTCGGCA  3000
 E  S  A  P  P  A  T  A  D  S  G  H  P  V  L  G
CCGGAGTCGCCGTCGCCGGGTCGCCGGGCCGGGTGTTCACGGGTCCCGTG  3050
```

-continued

```
T  G  V  A  V  A  G  S  P  G  R  V  F  T  G  P  V
CCCGCCGGTGCGGACCGCGCGGTGTTCATCGCCGAACTGGCGCTCGCCGC  3100
 P  A  G  A  D  R  A  V  F  I  A  E  L  A  L  A  A
CGCCGACGCCACCGACTGCGCCACGGTCGAACAGCTCGACGTCACCTCCG  3150
  A  D  A  T  D  C  A  T  V  E  Q  L  D  V  T  S
TGCCCGGCGGATCCGCCCGCGGCAGGGCCACCGCGCAGACCTGGGTCGAT  3200
V  P  G  G  S  A  R  G  R  A  T  A  Q  T  W  V  D
GAACCCGCCGCCGACGGGCGGCGCCGCTTCACCGTCCACACCCGCGTCGG  3250
 E  P  A  A  D  G  R  R  R  F  T  V  H  T  R  V  G
CGACGCCCCGTGGACGCTGCACGCCGAGGGGGTTCTCCGCCCCGGCCGCG  3300
  D  A  P  W  T  L  H  A  E  G  V  L  R  P  G  R
TGCCCCAGCCCGAAGCCGTCGACACCGCCTGGCCCCCGCCGGGCGCGGTG  3350
V  P  Q  P  E  A  V  D  T  A  W  P  P  P  G  A  V
CCCGCGGACGGGCTGCCCGGGGCGTGGCGACGCGCGGACCAGGTCTTCGT  3400
 P  A  D  G  L  P  G  A  W  R  R  A  D  Q  V  F  V
CGAAGCCGAAGTCGACAGCCCTGACGGCTTCGTGGCACACCCCGACCTGC  3450
  E  A  E  V  D  S  P  D  G  F  V  A  H  P  D  L
TCGACGCGGTCTTCTCCGCGGTCGGCGACGGGAGCCGCCAGCCGACCGGA  3500
L  D  A  V  F  S  A  V  G  D  G  S  R  Q  P  T  G
TGGCGCGACCTCGCGGTGCACGCGTCGGACGCCACCGTGCTGCGCGCCTG  3550
 W  R  D  L  A  V  H  A  S  D  A  T  V  L  R  A  C
CCTCACCCGCCGCGACAGTGGTGTCGTGGAGCTCGCCGCCTTCGACGGTG  3600
  L  T  R  R  D  S  G  V  V  E  L  A  A  F  D  G
CCGGAATGCCGGTGCTCACCGCGGAGTCGGTGACGCTGGGCGAGGTCGCG  3650
A  G  M  P  V  L  T  A  E  S  V  T  L  G  E  V  A
TCGGCAGGCGGATCCGACGAGTCGGACGGTCTGCTTCGGCTTGAGTGGTT  3700
 S  A  G  G  S  D  E  S  D  G  L  L  R  L  E  W  L
GCCGGTGGCGGAGGCCCACTACGACGGTGCCGACGAGCTGCCCGAGGGCT  3750
  P  V  A  E  A  H  Y  D  G  A  D  E  L  P  E  G
ACACCCTCATCACCGCCACACACCCCGACGACCCCGACGACCCCACCAAC  3800
Y  T  L  I  T  A  T  H  P  D  D  P  D  D  P  T  N
CCCCACAACACACCCACACGCACCCACACACAAACCACACGCGTCCTCAC  3850
 P  H  N  T  P  T  R  T  H  T  Q  T  T  R  V  L  T
CGCCCTCCAACACCACCTCATCACCACCAACCACACCCTCATCGTCCACA  3900
  A  L  Q  H  H  L  I  T  T  N  H  T  L  I  V  H
CCACCACCGACCCCCCAGGCGCCGCCGTCACCGGCCTCACCCGCACCGCA  3950
T  T  T  D  P  P  G  A  A  V  T  G  L  T  R  T  A
CAAAACGAACACCCCGGCCGCATCCACCTCATCGAAACCCACCACCCCCA  4000
 Q  N  E  H  P  G  R  I  H  L  I  E  T  H  H  P  H
CACCCCACTCCCCCTCACCCAACTCACCACCCTCCACCAACCCCACCTAC  4050
  T  P  L  P  L  T  Q  L  T  T  L  H  Q  P  H  L
GCCTCACCAACAACACCCTCCACACCCCCCACCTCACCCCCATCACCACC  4100
R  L  T  N  N  T  L  H  T  P  H  L  T  P  I  T  T
CACCACAACACCACCACAACCACCCCCAACACCCCACCCCTCAACCCCAA  4150
 H  H  N  T  T  T  T  T  P  N  T  P  P  L  N  P  N
CCACGCCATCCTCATCACCGGCGGCTCCGGCACCCTCGCCGGCATCCTCG  4200
  H  A  I  L  I  T  G  G  S  G  T  L  A  G  I  L
CCCGCCACCTCAACCACCCCCACACCTACCTCCTCTCCCGCACACCACCA  4250
A  R  H  L  N  H  P  H  T  Y  L  L  S  R  T  P  P
CCCCCCACCACACCCGGCACCCACATCCCCTGCGACCTCACCGACCCCAC  4300
 P  P  T  T  P  G  T  H  I  P  C  D  L  T  D  P  T
CCAAATCACCCAAGCCCTCACCCACATACCACAACCCCTCACCGGCATCT  4350
  Q  I  T  Q  A  L  T  H  I  P  Q  P  L  T  G  I
TCCACACCGCCGCCACCCTCGACGACGCCACCCTCACCAACCTCACCCCC  4400
F  H  T  A  A  T  L  D  D  A  T  L  T  N  L  T  P
CAACACCTCACCACCACCCTCCAACCCAAAGCCGACGCCGCCTGGCACCT  4450
 Q  H  L  T  T  T  L  Q  P  K  A  D  A  A  W  H  L
CCACCACCACACCCAAAACCAACCCCTCACCCACTTCGTCCTCTACTCCA  4500
  H  H  H  T  Q  N  Q  P  L  T  H  F  V  L  Y  S
GCGCCGCCGCCACCCTCGGCAGCCCCGGCCAAGCCAACTACGCCGCCGCC  4550
S  A  A  A  T  L  G  S  P  G  Q  A  N  Y  A  A  A
AACGCCTTCCTCGACGCCCTCGCCACCCACCGCCACACCCAAGGACAACC  4600
 N  A  F  L  D  A  L  A  T  H  R  H  T  Q  G  Q  P
CGCCACCACCATCGCCTGGGGCATGTGGCACACCACCACCACACTCACCA  4650
  A  T  T  I  A  W  G  M  W  H  T  T  T  T  L  T
GCCAACTCACCGACAGCGACCGCGACCGCATCCGCCGCGGCGGCTTCCTG  4700
S  Q  L  T  D  S  D  R  D  R  I  R  R  G  G  F  L
CCGATCTCGGACGACGAGGGCATGC
 P  I  S  D  D  E  G  M
```

The AvrII-XhoI hybrid FK-506 PKS module 8 containing the AT domain of module 12 of rapamycin is shown below. (SEQ ID NOS 26–27)

```
GCATGCGGCTGTACGAGGCGGCACGGCGCACCGGAAGTCCCGTGGTGGTG    50
  M  R  L  Y  E  A  A  R  R  T  G  S  P  V  V  V
GCGGCCGCGCTCGACGACGCGCCGGACGTGCCGCTGCTGCGCGGGCTGCG   100
 A  A  A  L  D  D  A  P  D  V  P  L  L  R  G  L  R
GCGTACGACCGTCCGGCGTGCCGCCGTCCGGGAACGCTCTCTCGCCGACC   150
  R  T  T  V  R  R  A  A  V  R  E  R  S  L  A  D
GCTCGCCGTGCTGCCCGACGACGAGCGCGCCGACGCCTCCCTCGCGTTCG   200
R  S  P  C  C  P  T  T  S  A  P  T  P  P  S  R  S
TCCTGGAACAGCACCGCCACCGTGCTCGGCCACCTGGGCGCCGAAGACAT   250
 S  W  N  S  T  A  T  V  L  G  H  L  G  A  E  D  I
CCCGGCGACGACGACGTTCAAGGAACTCGGCATCGACTCGCTCACCGCGG   300
  P  A  T  T  T  F  K  E  L  G  I  D  S  L  T  A
TCCAGCTGCGCAACGCGCTGACCACGGCGACCGGCGTACGCCTCAACGCC   350
V  Q  L  R  N  A  L  T  T  A  T  G  V  R  L  N  A
ACAGCGGTCTTCGACTTTCCGACGCCGCGCGCGCTCGCCGCGAGACTCGG   400
 T  A  V  F  D  F  P  T  P  R  A  L  A  A  R  L  G
CGACGAGCTGGCCGGTACCCGCGCGCCCGTCGCGGCCCGGACCGCGGCCA   450
  D  E  L  A  G  T  R  A  P  V  A  A  R  T  A  A
CCGCGGCCGCGCACGACGAACCGCTGGCGATCGTGGGCATGGCCTGCCGT   500
T  A  A  A  H  D  E  P  L  A  I  V  G  M  A  C  R
CTGCCGGGCGGGGTCGCGTCGCCACAGGAGCTGTGGCGTCTCGTCGCGTC   550
 L  P  G  G  V  A  S  P  Q  E  L  W  R  L  V  A  S
CGGCACCGACGCCATCACGGAGTTCCCCGCGGACCGCGGCTGGGACGTGG   600
  G  T  D  A  I  T  E  F  P  A  D  R  G  W  D  V
ACGCGCTCTACGACCCGGACCCCGACGCGATCGGCAAGACCTTCGTCCGG   650
D  A  L  Y  D  P  D  P  D  A  I  G  K  T  F  V  R
CACGGCGGCTTCCTCGACGGTGCGACCGGCTTCGACGCGGCGTTCTTCGG   700
 H  G  G  F  L  D  G  A  T  G  F  D  A  A  F  F  G
GATCAGCCCGCGCGAGGCCCTGGCCATGGACCCGCAGCAACGGGTGCTCC   750
  I  S  P  R  E  A  L  A  M  D  P  Q  Q  R  V  L
TGGAGACGTCCTGGGAGGCGTTCGAAAGCGCGGGCATCACCCCGGACGCG   800
L  E  T  S  W  E  A  F  E  S  A  G  I  T  P  D  A
GCGCGGGGCAGCGACACCGGCGTGTTCATCGGCGCGTTCTCCTACGGGTA   850
 A  R  G  S  D  T  G  V  F  I  G  A  F  S  Y  G  Y
CGGCACGGGTGCGGATACCAACGGCTTCGGCGCGACAGGGTCGCAGACCA   900
  G  T  G  A  D  T  N  G  F  G  A  T  G  S  Q  T
GCGTGCTCTCCGGCCGCCTCTCGTACTTCTACGGTCTGGAGGGCCCTTCG   950
S  V  L  S  G  R  L  S  Y  F  Y  G  L  E  G  P  S
GTCACGGTCGACACCGCCTGCTCGTCGTCACTGGTCGCCCTGCACCAGGC  1000
 V  T  V  D  T  A  C  S  S  S  L  V  A  L  H  Q  A
AGGGCAGTCCCTGCGCTCGGGCGAATGCTCGCTCGCCCTGGTCGGCGGTG  1050
  G  Q  S  L  R  S  G  E  C  S  L  A  L  V  G  G
TCACGGTGATGGCGTCGCCCGGCGGATTCGTCGAGTTCTCCCGGCAGCGC  1100
V  T  V  M  A  S  P  G  G  F  V  E  F  S  R  Q  R
GGGCTCGCGCCGGACGGGCGGGCGAAGGCGTTCGGCGCGGGCGCGGACGG  1150
 G  L  A  P  D  G  R  A  K  A  F  G  A  G  A  D  G
TACGAGCTTCGCCGAGGGCGCCGGTGCCCTGGTGCTCGAGCGGCTCTCCG  1200
  T  S  F  A  E  G  A  G  A  L  V  V  E  R  L  S
ACGCGGAGCGCCACGGCCACACCGTCCTCGCCCTCGTACGCGGCTCCGCG  1250
D  A  E  R  H  G  H  T  V  L  A  L  V  R  G  S  A
GCTAACTCCGACGGCGCGTCGAACGGTCTGTCGGCGCCGAACGGCCCCTC  1300
 A  N  S  D  G  A  S  N  G  L  S  A  P  N  G  P  S
CCAGGAACGCGTCATCCACCAGGCCCTCGCGAACGCGAAACTCACCCCCG  1350
  Q  E  R  V  I  H  Q  A  L  A  N  A  K  L  T  P
CCGATGTCGACGCGGTCGAGGCGCACGGCACCGGCACCCGCCTCGGCGAC  1400
A  D  V  D  A  V  E  A  H  G  T  G  T  R  L  G  D
CCCATCGAGGCGCAGGCGCTGCTCGCGACGTACGGACAGGACCGGGCGAC  1450
 P  I  E  A  Q  A  L  L  A  T  Y  G  Q  D  R  A  T
GCCCCTGCTCCTCGGCTCGCTGAAGTCGAACATCGGGCACGCCCAGGCCG  1500
  P  L  L  L  G  S  L  K  S  N  I  G  H  A  Q  A
CGTCAGGGGTCGCCGGGATCATCAAGATGGTGCAGGCCATCCGGCACGGG  1550
A  S  G  V  A  G  I  I  K  M  V  Q  A  I  R  H  G
GAACTGCCGCCGACACTGCACGCGGACGAGCCGTCGCCGCACGTCGACTG  1600
 E  L  P  P  T  L  H  A  D  E  P  S  P  H  V  D  W
GACGGCCGGTGCCGTCGAGCTCCTGACGTCGGCCCGGCCGTGGCCGGGGA  1600
  T  A  G  A  V  E  L  L  T  S  A  R  P  W  P  G
CCGGTCGCCCTAGGCGGGCAGGCGTGTCGTCCTTCGGGATCAGTGGCACC  1700
T  G  R  P  R  R  A  G  V  S  S  F  G  I  S  G  T
AACGCCCACGTCATCCTGGAAAGCGCACCCCCCACTCAGCCTGCGGACAA  1750
 N  A  H  V  I  L  E  S  A  P  P  T  Q  P  A  D  N
CGCGGTGATCGAGCGGGCACCGGAGTGGGTGCCGTTGGTGATTTCGGCCA  1800
  A  V  I  E  R  A  P  E  W  V  P  L  V  I  S  A
GGACCCAGTCGGCTTTGACTGAGCACGAGGGCCGGTTGCGTGCGTATCTG  1850
R  T  Q  S  A  L  T  E  H  E  G  R  L  R  A  Y  L
GCGGCGTCGCCCGGGGTGGATATGCGGGCTGTGGCATCGACGCTGGCGAT  1900
 A  A  S  P  G  V  D  M  R  A  V  A  S  T  L  A  M
```

-continued

```
GACACGGTCGGTGTTCGAGCACCGTGCCGTGCTGCTGGGAGATGACACCG  1950
 T  R  S  V  E  F  H  R  A  V  L  L  G  D  D  T
TCACCGGCACCGCTGTGTCTGACCCTCGGGCGGTGTTCGTCTTCCCGGGA  2000
V  T  G  T  A  V  S  D  P  R  A  V  F  V  F  P  G
CAGGGGTCGCAGCGTGCTGGCATGGGTGAGGAACTGGCCGCCGCGTTCCC  2050
 Q  G  S  Q  R  A  G  M  G  E  E  L  A  A  A  F  P
CGTCTTCGCGCGGATCCATCAGCAGGTGTGGGACCTGCTCGATGTGCCCG  2100
  V  F  A  R  I  H  Q  Q  V  W  D  L  L  D  V  P
ATCTGGAGGTGAACGAGACCGGTTACGCCCAGCCGGCCCTGTTCGCAATG  2150
D  L  E  V  N  E  T  G  Y  A  Q  P  A  L  F  A  M
CAGGTGGCTCTGTTCGGGCTGCTGGAATCGTGGGGTGTACGACCGGACGC  2200
 Q  V  A  L  F  G  L  L  E  S  W  G  V  R  P  D  A
GGTGATCGGCCATTCGGTGGGTGAGCTTGCGGCTGCGTATGTGTCCGGGG  2250
  V  I  G  H  S  V  G  E  L  A  A  A  Y  V  S  G
TGTGGTCGTTGGAGGATGCCTGCACTTTGGTGTCGGCGCGGGCTCGTCTG  2300
V  W  S  L  E  D  A  C  T  L  V  S  A  R  A  R  L
ATGCAGGCTCTGCCCGCGGGTGGGGTGATGGTCGCTGTCCCGGTCTCGGA  2350
 M  Q  A  L  P  A  G  G  V  M  V  A  V  P  V  S  E
GGATGAGGCCCGGGCCGTGCTGGGTGAGGGTGTGGAGATCGCCGCGGTCA  2400
  D  E  A  R  A  V  L  G  E  G  V  E  I  A  A  V
ACGGCCCGTCGTCGGTGGTTCTCTCCGGTGATGAGGCCGCCGTGCTGCAG  2450
N  G  P  S  S  V  V  L  S  G  D  E  A  A  V  L  Q
GCCGCGGAGGGGCTGGGGAAGTGGACGCGGCTGGCGACCAGCCACGCGTT  2500
 A  A  E  G  L  G  K  W  T  R  L  A  T  S  H  A  F
CCATTCCGCCCGTATGGAACCCATGCTGGAGGAGTTCCGGGCGGTCGCCG  2550
  H  S  A  R  M  E  P  M  L  E  E  F  R  A  V  A
AAGGCCTGACCTACCGGACGCCGCAGGTCTCCATGGCCGTTGGTGATCAG  2600
E  G  L  T  Y  R  T  P  Q  V  S  M  A  V  G  D  Q
GTGACCACCGCTGAGTACTGGGTGCGGCAGGTCCGGGACACGGTCCGGTT  2650
 V  T  T  A  E  Y  W  V  R  Q  V  R  D  T  V  R  F
CGGCGAGCAGGTGGCCTCGTACGAGGACGCCGTGTTCGTCGAGCTGGGTG  2700
  G  E  Q  V  A  S  Y  E  D  A  V  F  V  E  L  G
CCGACCGGTCACTGGCCCGCCTGGTCGACGGTGTCGCGATGCTGCACGGC  2750
A  D  R  S  L  A  R  L  V  D  G  V  A  M  L  H  G
GACCACGAAATCCAGGCCGCGATCGGCGCCCTGGCCCACCTGTATGTCAA  2800
 D  H  E  I  Q  A  A  I  G  A  L  A  H  L  Y  V  N
CGGCGTCACGGTCGACTGGCCCGCGCTCCTGGGCGATGCTCCGGCAACAC  2850
  G  V  T  V  D  W  P  A  L  L  G  D  A  P  A  T
GGGTGCTGGACCTTCCGACATACGCCTTCCAGCACCAGCGCTACTGGCTC  2900
R  V  L  D  L  P  T  Y  A  F  Q  H  Q  R  Y  W  L
GAGTCGGCTCCCCCGGCCACGGCCGACTCGGGCCACCCCGTCCTCGGCAC  2950
 E  S  A  P  P  A  T  A  D  S  G  H  P  V  L  G  T
CGGAGTCGCCGTCGCCGGGTCGCCGGGCCGGGTGTTCACGGGTCCCGTGC  3000
  G  V  A  V  A  G  S  P  G  R  V  F  T  G  P  V
CCGCCGGTGCGGACCGCGCGGTGTTCATCGCCGAACTGGCGCTCGCCGCC  3050
P  A  G  A  D  R  A  V  F  I  A  E  L  A  L  A  A
GCCGACGCCACCGACTGCGCCACGGTCGAACAGCTCGACGTCACCTCCGT  3100
 A  D  A  T  D  C  A  T  V  E  Q  L  D  V  T  S  V
GCCCGGCGGATCCGCCCGCGGCAGGGCCACCGCGCAGACCTGGGTCGATG  3150
  P  G  G  S  A  R  G  R  A  T  A  Q  T  W  V  D
AACCCGCCGCCGACGGGCGGCGCCGCTTCACCGTCCACACCCGCGTCGGC  3200
E  P  A  A  D  G  R  R  R  F  T  V  H  T  R  V  G
GACGCCCCGTGGACGCTGCACGCCGAGGGGGTTCTCCGCCCCGGCCGCGT  3250
 D  A  P  W  T  L  H  A  E  G  V  L  R  P  G  R  V
GCCCCAGCCCGAAGCCGTCGACACCGCCTGGCCCCCGCCGGGCGCGGTGC  3300
  P  Q  P  E  A  V  D  T  A  W  P  P  P  G  A  V
CCGCGGACGGGCTGCCCGGGGCGTGGCGACGCGCGGACCAGGTCTTCGTC  3350
P  A  D  G  L  P  G  A  W  R  R  A  D  Q  V  F  V
GAAGCCGAAGTCGACAGCCCTGACGGCTTCGTGGCACACCCCGACCTGCT  3400
 E  A  E  V  D  S  P  D  G  F  V  A  H  P  D  L  L
CGACGCGGTCTTCTCCGCGGTCGGCGACGGGAGCCGCCAGCCGACCGGAT  3450
  D  A  V  F  S  A  V  G  D  G  S  R  Q  P  T  G
GGCGCGACCTCGCGGTGCACGCGTCGGACGCCACCGTGCTGCGCGCCTGC  3500
W  R  D  L  A  V  H  A  S  D  A  T  V  L  R  A  C
CTCACCCGCCGCGACAGTGGTGTCGTGGAGCTCGCCGCCTTCGACGGTGC  3550
 L  T  R  R  D  S  G  V  V  E  L  A  A  F  D  G  A
CGGAATGCCGGTGCTCACCGCGGAGTCGGTGACGCTGGGCGAGGTCGCGT  3600
  G  M  P  V  L  T  A  E  S  V  T  L  G  E  V  A
CGGCAGGCGGATCCGACGAGTCGGACGGTCTGCTTCGGCTTGAGTGGTTG  3650
S  A  G  G  S  D  E  S  D  G  L  L  R  L  E  W  L
CCGGTGGCGGAGGCCCACTACGACGGTGCCGACGAGCTGCCCGAGGGCTA  3700
 P  V  A  E  A  H  Y  D  G  A  D  E  L  P  E  G  Y
CACCCTCATCACCGCCACACACCCCGACGACCCCGACGACCCCACCAACC  3750
  T  L  I  T  A  T  H  P  D  D  P  D  D  P  T  N
CCCACAACACACCCACACGCACCCACACACAAACCACACGCGTCCTCACC  3800
P  H  N  T  P  T  R  T  H  T  Q  T  T  R  V  L  T
GCCCTCCAACACCACCTCATCACCACCAACCACACCCTCATCGTCCACAC  3850
 A  L  Q  H  H  L  I  T  T  N  H  T  L  I  V  H  T
CACCACCGACCCCCCAGGCGCCGCCGTCACCGGCCTCACCCGCACCGCAC  3900
  T  T  D  P  P  G  A  A  V  T  G  L  T  R  T  A
```

-continued

```
AAAACGAACACCCCGGCCGCATCCACCTCATCGAAACCCACCACCCCCAC  3950
Q  N  E  H  P  G  R  I  H  L  I  E  T  H  H  P  H
ACCCCACTCCCCCTCACCCAACTCACCACCCTCCACCAACCCCACCTACG  4000
 T  P  L  P  L  T  Q  L  T  T  L  H  Q  P  H  L  R
CCTCACCAACAACACCCTCCACACCCCCCACCTCACCCCCATCACCACCC  4050
  L  T  N  N  T  L  H  T  P  H  L  T  P  I  T  T
ACCACAACACCACCACAACCACCCCCAACACCCCACCCCTCAACCCCAAC  4100
H  H  N  T  T  T  T  T  P  N  T  P  P  L  N  P  N
CACGCCATCCTCATCACCGGCGGCTCCGGCACCCTCGCCGGCATCCTCGC  4150
 H  A  I  L  I  T  G  G  S  G  T  L  A  G  I  L  A
CCGCCACCTCAACCACCCCCACACCTACCTCCTCTCCCGCACACCACCAC  4200
  R  H  L  N  H  P  H  T  Y  L  L  S  R  T  P  P
CCCCCACCACACCCGGCACCCACATCCCCTGCGACCTCACCGACCCCACC  4250
P  P  T  T  P  G  T  H  I  P  C  D  L  T  D  P  T
CAAATCACCCAAGCCCTCACCCACATACCACAACCCCTCACCGGCATCTT  4300
 Q  I  T  Q  A  L  T  H  I  P  Q  P  L  T  G  I  F
CCACACCGCCGCCACCCTCGACGACGCCACCCTCACCAACCTCACCCCCC  4350
  H  T  A  A  T  L  D  D  A  T  L  T  N  L  T  P
AACACCTCACCACCACCCTCCAACCCAAAGCCGACGCCGCCTGGCACCTC  4400
Q  H  L  T  T  T  L  Q  P  K  A  D  A  A  W  H  L
CACCACCACACCCAAAACCAACCCCTCACCCACTTCGTCCTCTACTCCAG  4450
 H  H  H  T  Q  N  Q  P  L  T  H  F  V  L  Y  S  S
CGCCGCCGCCACCCTCGGCAGCCCCGGCCAAGCCAACTACGCCGCCGCCA  4500
  A  A  A  T  L  G  S  P  G  Q  A  N  Y  A  A  A
ACGCCTTCCTCGACGCCCTCGCCACCCACCGCCACACCCAAGGACAACCC  4550
N  A  F  L  D  A  L  A  T  H  R  H  T  Q  G  Q  P
GCCACCACCATCGCCTGGGGCATGTGGCACACCACCACCACACTCACCAG  4600
 A  T  T  I  A  W  G  M  W  H  T  T  T  T  L  T  S
CCAACTCACCGACAGCGACCGCGACCGCATCCGCCGCGGCGGCTTCCTGC  4650
  Q  L  T  D  S  D  R  D  R  I  R  R  G  G  F  L
CGATCTCGGACGACGAGGGCATGC
P  I  S  D  D  E  G  M
```

The AvrII-XhoI hybrid FK-506 PKS module 8 containing the AT domain of module 13 of rapamycin is shown below. (SEQ ID NOS 28–29)

```
GCATGCGGCTGTACGAGGCGGCACGGCGCACCGGAAGTCCCGTGGTGGTG    50
   M  R  L  Y  E  A  A  R  R  T  G  S  P  V  V  V
GCGGCCGCGCTCGACGACGCGCCGGACGTGCCGCTGCTGCGCGGGCTGCG   100
 A  A  A  L  D  D  A  P  D  V  P  L  L  R  G  L  R
GCGTACGACCGTCCGGCGTGCCGCCGTCCGGGAACGCTCTCTCGCCGACC   150
  R  T  T  V  R  R  A  A  V  R  E  R  S  L  A  D
GCTCGCCGTGCTGCCCGACGACGAGCGCGCCGACGCCTCCCTCGCGTTCG   200
R  S  P  C  C  P  T  T  S  A  P  T  P  P  S  R  S
TCCTGGAACAGCACCGCCACCGTGCTCGGCCACCTGGGCGCCGAAGACAT   250
 S  W  N  S  T  A  T  V  L  G  H  L  G  A  E  D  I
CCCGGCGACGACGACGTTCAAGGAACTCGGCATCGACTCGCTCACCGCGG   300
  P  A  T  T  T  F  K  E  L  G  I  D  S  L  T  A
TCCAGCTGCGCAACGCGCTGACCACGGCGACCGGCGTACGCCTCAACGCC   350
V  Q  L  R  N  A  L  T  T  A  T  G  V  R  L  N  A
ACAGCGGTCTTCGACTTTCCGACGCCGCGCGCGCTCGCCGCGAGACTCGG   400
 T  A  V  F  D  F  P  T  P  R  A  L  A  A  R  L  G
CGACGAGCTGGCCGGTACCCGCGCGCCCGTCGCGGCCCGGACCGCGGCCA   450
  D  E  L  A  G  T  R  A  P  V  A  A  R  T  A  A
CCGCGGCCGCGCACGACGAACCGCTGGCGATCGTGGGCATGGCCTGCCGT   500
T  A  A  A  H  D  E  P  L  A  I  V  G  M  A  C  R
CTGCCGGGCGGGGTCGCGTCGCCACAGGAGCTGTGGCGTCTCGTCGCGTC   550
 L  P  G  G  V  A  S  P  Q  E  L  W  R  L  V  A  S
CGGCACCGACGCCATCACGGAGTTCCCCGCGGACCGCGGCTGGGACGTGG   600
  G  T  D  A  I  T  E  F  P  A  D  R  G  W  D  V
ACGCGCTCTACGACCCGGACCCCGACGCGATCGGCAAGACCTTCGTCCGG   650
D  A  L  Y  D  P  D  P  D  A  I  G  K  T  F  V  R
CACGGCGGCTTCCTCGACGGTGCGACCGGCTTCGACGCGGCGTTCTTCGG   700
 H  G  G  F  L  D  G  A  T  G  F  D  A  A  F  F  G
GATCAGCCCGCGCGAGGCCCTGGCCATGGACCCGCAGCAACGGGTGCTCC   750
  I  S  P  R  E  A  L  A  M  D  P  Q  Q  R  V  L
TGGAGACGTCCTGGGAGGCGTTCGAAAGCGCGGGCATCACCCCGGACGCG   800
L  E  T  S  W  E  A  F  E  S  A  G  I  T  P  D  A
GCGCGGGGCAGCGACACCGGCGTGTTCATCGGCGCGTTCTCCTACGGGTA   850
 A  R  G  S  D  T  G  V  F  I  G  A  F  S  Y  G  Y
CGGCACGGGTGCGGATACCAACGGCTTCGGCGCGACAGGGTCGCAGACCA   900
  G  T  G  A  D  T  N  G  F  G  A  T  G  S  Q  T
GCGTGCTCTCCGGCCGCCTCTCGTACTTCTACGGTCTGGAGGGCCCTTCG   950
S  V  L  S  G  R  L  S  Y  F  Y  G  L  E  G  P  S
GTCACGGTCGACACCGCCTGCTCGTCGTCACTGGTCGCCCTGCACCAGGC  1000
```

-continued

```
 V  T  V  D  T  A  C  S  S  S  L  V  A  L  H  Q  A
AGGGCAGTCCCTGCGCTCGGGCGAATGCTCGCTCGCCCTGGTCGGCGGTG  1050
  G  Q  S  L  R  S  G  E  C  S  L  A  L  V  G  G
TCACGGTGATGGCGTCGCCCGGCGGATTCGTCGAGTTCTCCCGGCAGCGC  1100
V  T  V  M  A  S  P  G  G  F  V  E  F  S  R  Q  R
GGGCTCGCGCCGGACGGGCGGGCGAAGGCGTTCGGCGCGGGCGCGGACGG  1150
 G  L  A  P  D  G  R  A  K  A  F  G  A  G  A  D  G
TACGAGCTTCGCCGAGGGCGCCGGTGCCCTGGTGGTCGAGCGGCTCTCCG  1200
  T  S  F  A  E  G  A  G  A  L  V  V  E  R  L  S
ACGCGGAGCGCCACGGCCACACCGTCCTCGCCCTCGTACGCGGCTCCGCG  1250
D  A  E  R  H  G  H  T  V  L  A  L  V  R  G  S  A
GCTAACTCCGACGGCGCGTCGAACGGTCTGTCGGCGCCGAACGGCCCCTC  1300
 A  N  S  D  G  A  S  N  G  L  S  A  P  N  G  P  S
CCAGGAACGCGTCATCCACCAGGCCCTCGCGAACGCGAAACTCACCCCCG  1350
  Q  E  R  V  I  H  Q  A  L  A  N  A  K  L  T  P
CCGATGTCGACGCGGTCGAGGCGCACGGCACCGGCACCCGCCTCGGCGAC  1400
A  D  V  D  A  V  E  A  H  G  T  G  T  R  L  G  D
CCCATCGAGGCGCAGGCGCTGCTCGCGACGTACGGACAGGACCGGGCGAC  1450
 P  I  E  A  Q  A  L  L  A  T  Y  G  Q  D  R  A  T
GCCCCTGCTGCTCGGCTCGCTGAAGTCGAACATCGGGCACGCCCAGGCCG  1500
  P  L  L  L  G  S  L  K  S  N  I  G  H  A  Q  A
CGTCAGGGGTCGCCGGGATCATCAAGATGGTGCAGGCCATCCGGCACGGG  1550
A  S  G  V  A  G  I  I  K  M  V  Q  A  I  R  H  G
GAACTGCCGCCGACACTGCACGCGGACGAGCCGTCGCCGCACGTCGACTG  1600
 E  L  P  P  T  L  H  A  D  E  P  S  P  H  V  D  W
GACGGCCGGTGCCGTCGAGCTCCTGACGTCGGCCCGGCCGTGGCCGGGGA  1650
  T  A  G  A  V  E  L  L  T  S  A  R  P  W  P  G
CCGGTCGCCCTAGGCGGGCGGGCGTGTCGTCCTTCGGAGTCAGCGGCACC  1700
T  G  R  P  R  R  A  G  V  S  S  F  G  V  S  G  T
AACGCCCACGTCATCCTGGAGAGCGCACCCCCCGCTCAGCCCGCGGAGGA  1750
 N  A  H  V  I  L  E  S  A  P  P  A  Q  P  A  E  E
GGCGCAGCCTGTTGAGACGCCGGTGGTGGCCTCGGATGTGCTGCCGCTGG  1800
  A  Q  P  V  E  T  P  V  V  A  S  D  V  L  P  L
TGATATCGGCCAAGACCCAGCCCGCCCTGACCGAACACGAAGACCGGCTG  1850
V  I  S  A  K  T  Q  P  A  L  T  E  H  E  D  R  L
CGCGCCTACCTGGCGGCGTCGCCCGGGGCGGATATACGGGCTGTGGCATC  1900
 R  A  Y  L  A  A  S  P  G  A  D  I  R  A  V  A  S
GACGCTGGCGGTGACACGGTCGGTGTTCGAGCACCGCGCCGTACTCCTTG  1950
  T  L  A  V  T  R  S  V  F  E  H  R  A  V  L  L
GAGATGACACCGTCACCGGCACCGCGGTGACCGACCCCAGGATCGTGTTT  2000
G  D  D  T  V  T  G  T  A  V  T  D  P  R  I  V  F
GTCTTTCCCGGGCAGGGGTGGCAGTGGCTGGGGATGGGCAGTGCACTGCG  2050
 V  F  P  G  Q  G  W  Q  W  L  G  M  G  S  A  L  R
CGATTCGTCGGTGGTGTTCGCCGAGCGGATGGCCGAGTGTGCGGCGGCGT  2100
  D  S  S  V  V  F  A  E  R  M  A  E  C  A  A  A
TGCGCGAGTTCGTGGACTGGGATCTGTTCACGGTTCTGGATGATCCGGCG  2150
L  R  E  F  V  D  W  D  L  F  T  V  L  D  D  P  A
GTGGTGGACCGGGTTGATGTGGTCCAGCCCGCTTCCTGGGCGATGATGGT  2200
 V  V  D  R  V  D  V  V  Q  P  A  S  W  A  M  M  V
TTCCCTGGCCGCGGTGTGGCAGGCGGCCGGTGTGCGGCCGGATGCGGTGA  2250
  S  L  A  A  V  W  Q  A  A  G  V  R  P  D  A  V
TCGGCCATTCGCAGGGTGAGATCGCCGCAGCTTGTGTGGCGGGTGCGGTG  2300
I  G  H  S  Q  G  E  I  A  A  A  C  V  A  G  A  V
TCACTACGCGATGCCGCCCGGATCGTGACCTTGCGCAGCCAGGCGATCGC  2350
 S  L  R  D  A  A  R  I  V  T  L  R  S  Q  A  I  A
CCGGGGCCTGGCGGGCCGGGGCGCGATGGCATCCGTCGCCCTGCCCGCGC  2400
  R  G  L  A  G  R  G  A  M  A  S  V  A  L  P  A
AGGATGTCGAGCTGGTCGACGGGGCCTGGATCGCCGCCCACAACGGGCCC  2450
Q  D  V  E  L  V  D  G  A  W  I  A  A  H  N  G  P
GCCTCCACCGTGATCGCGGGCACCCCGGAAGCGGTCGACCATGTCCTCAC  2500
 A  S  T  V  I  A  G  T  P  E  A  V  D  H  V  L  T
CGCTCATGAGGCACAAGGGGTGCGGGTGCGGCGGATCACCGTCGACTATG  2550
  A  H  E  A  Q  G  V  R  V  R  R  I  T  V  D  Y
CCTCGCACACCCCGCACGTCGAGCTGATCCGCGACGAACTACTCGACATC  2600
A  S  H  T  P  H  V  E  L  I  R  D  E  L  L  D  I
ACTAGCGACAGCAGCTCGCAGACCCCGCTCGTGCCGTGGCTGTCGACCGT  2650
 T  S  D  S  S  S  Q  T  P  L  V  P  W  L  S  T  V
GGACGGCACCTGGGTCGACAGCCCGCTGGACGGGGAGTACTGGTACCGGA  2700
  D  G  T  W  V  D  S  P  L  D  G  E  Y  W  Y  R
ACCTGCGTGAACCGGTCGGTTTCCACCCCGCCGTCAGCCAGTTGCAGGCC  2750
N  L  R  E  P  V  G  F  H  P  A  V  S  Q  L  Q  A
CAGGGCGACACCGTGTTCGTCGAGGTCAGCGCCAGCCCGGTGTTGTTGCA  2800
 Q  G  D  T  V  F  V  E  V  S  A  S  P  V  L  L  Q
GGCGATGGACGACGATGTCGTCACGGTTGCCACGCTGCGTCGTGACGACG  2850
  A  M  D  D  D  V  V  T  V  A  T  L  R  R  D  D
GCGACGCCACCCGGATGCTCACCGCCCTGGCACAGGCCTATGTCCACGGC  2900
G  D  A  T  R  M  L  T  A  L  A  Q  A  Y  V  H  G
GTCACCGTCGACTGGCCCGCCATCCTCGGCACCACCACAACCCGGGTACT  2950
 V  T  V  D  W  P  A  I  L  G  T  T  T  T  R  V  L
GGACCTTCCGACCTACGCCTTCCAACACCAGCGGTACTGGCTCGAGTCGG  3000
```

-continued

```
 D  L  P  T  Y  A  F  Q  H  Q  R  Y  W  L  E  S
CTCCCCCGGCCACGGCCGACTCGGGCCACCQCGTCCTCGGCACCGGAGTC  3050
A  P  P  A  T  A  D  S  G  H  P  V  L  G  T  G  V
GCCGTCGCCGGGTCGCCGGGCCGGGTGTTCACGGGTCCCGTGCCCGCCGG  3100
 A  V  A  G  S  P  G  R  V  F  T  G  P  V  P  A  G
TGCGGACCGCGCGGTGTTCATCGCCGAACTGGCGCTCGCCGCCGCCGACG  3150
  A  D  R  A  V  F  I  A  E  L  A  L  A  A  A  D
CCACCGACTGCGCCACGGTCGAACAGCTCGACGTCACCTCCGTGCCCGGC  3200
A  T  D  C  A  T  V  E  Q  L  D  V  T  S  V  P  G
GGATCCGCCCGCGGCAGGGCCACCGCGCAGACCTGGGTCGATGAACCCGC  3250
 G  S  A  R  G  R  A  T  A  Q  T  W  V  D  E  P  A
CGCCGACGGGCGGCGCCGCTTCACCGTCCACACCCGCGTCGGCGACGCCC  3300
  A  D  G  R  R  R  F  T  V  H  T  R  V  G  D  A
CGTGGACGCTGCACGCCGAGGGGGTTCTCCGCCCCGGCCGCGTGCCCCAG  3350
P  W  T  L  H  A  E  G  V  L  R  P  G  R  V  P  Q
CCCGAAGCCGTCGACACCGCCTGGCCCCCGCCGGGCGCGGTGCCCGCGGA  3400
 P  E  A  V  D  T  A  W  P  P  P  G  A  V  P  A  D
CGGGCTGCCCGGGGCGTGGCGACGCGCGGACCAGGTCTTCGTCGAAGCCG  3450
  G  L  P  G  A  W  R  R  A  D  Q  V  F  V  E  A
AAGTCGACAGCCCTGACGGCTTCGTGGCACACCCCGACCTGCTCGACGCG  3500
E  V  D  S  P  D  G  F  V  A  H  P  D  L  L  D  A
GTCTTCTCCGCGGTCGGCGACGGGAGCCGCCAGCCGACCGGATGGCGCGA  3550
 V  F  S  A  V  G  D  G  S  R  Q  P  T  G  W  R  D
CCTCGCGGTGCACGCGTCGGACGCCACCGTGCTGCGCGCCTGCCTCACCC  3600
  L  A  V  H  A  S  D  A  T  V  L  R  A  C  L  T
GCCGCGACAGTGGTGTCGTGGAGCTCGCCGCCTTCGACGGTGCCGGAATG  3650
R  R  D  S  G  V  V  E  L  A  A  F  D  G  A  G  M
CCGGTGCTCACCGCGGAGTCGGTGACGCTGGGCGAGGTCGCGTCGGCAGG  3700
 P  V  L  T  A  E  S  V  T  L  G  E  V  A  S  A  G
CGGATCCGACGAGTCGGACGGTCTGCTTCGGCTTGAGTGGTTGCCGGTGG  3750
  G  S  D  E  S  D  G  L  L  R  L  E  W  L  P  V
CGGAGGCCCACTACGACGGTGCCGACGAGCTGCCCGAGGGCTACACCCTC  3800
A  E  A  H  Y  D  G  A  D  E  L  P  E  G  Y  T  L
ATCACCGCCACACACCCCGACGACCCCGACGACCCCACCAACCCCCACAA  3850
 I  T  A  T  H  P  D  D  P  D  D  P  T  N  P  H  N
CACACCCACACGCACCCACACACAAACCACACGCGTCCTCACCGCCCTCC  3900
  T  P  T  R  T  H  T  Q  T  T  R  V  L  T  A  L
AACACCACCTCATCACCACCAACCACACCCTCATCGTCCACACCACCACC  3950
Q  H  H  L  I  T  T  N  H  T  L  I  V  H  T  T  T
GACCCCCCAGGCGCCGCCGTCACCGGCCTCACCCGCACCGCACAAAACGA  4000
 D  P  P  G  A  A  V  T  G  L  T  R  T  A  Q  N  E
ACACCCCGGCCGCATCCACCTCATCGAAACCCACCACCCCCACACCCCAC  4050
  H  P  G  R  I  H  L  I  E  T  H  H  P  H  T  P
TCCCCCTCACCCAACTCACCACCCTCCACCAACCCCACCTACGCCTCACC  4100
L  P  L  T  Q  L  T  T  L  H  Q  P  H  L  R  L  T
AACAACACCCTCCACACCCCCCACCTCACCCCCATCACCACCCACCACAA  4150
 N  N  T  L  H  T  P  H  L  T  P  I  T  T  H  H  N
CACCACCACAACCACCCCCAACACCCCACCCCTCAACCCCAACCACGCCA  4200
  T  T  T  T  T  P  N  T  P  P  L  N  P  N  H  A
TCCTCATCACCGGCGGCTCCGGCACCCTCGCCGGCATCCTCGCCCGCCAC  4250
I  L  I  T  G  G  S  G  T  L  A  G  I  L  A  R  H
CTCAACCACCCCCACACCTACCTCCTCTCCCGCACACCACCACCCCCCAC  4300
 L  N  H  P  H  T  Y  L  L  S  R  T  P  P  P  P  T
CACACCCGGCACCCACATCCCCTGCGACCTCACCGACCCCACCCAAATCA  4350
  T  P  G  T  H  I  P  C  D  L  T  D  P  T  Q  I
CCCAAGCCCTCACCCACATACCACAACCCCTCACCGGCATCTTCCACACC  4400
T  Q  A  L  T  H  I  P  Q  P  L  T  G  I  F  H  T
GCCGCCACCCTCGACGACGCCACCCTCACCAACCTCACCCCCCAACACCT  4450
 A  A  T  L  D  D  A  T  L  T  N  L  T  P  Q  H  L
CACCACCACCCTCCAACCCAAAGCCGACGCCGCCTGGCACCTCCACCACC  4500
  T  T  T  L  Q  P  K  A  D  A  A  W  H  L  H  H
ACACCCAAAACCAACCCCTCACCCACTTCGTCCTCTACTCCAGCGCCGCC  4550
H  T  Q  N  Q  P  L  T  H  E  V  L  Y  S  S  A  A
GCCACCCTCGGCAGCCCCGGCCAAGCCAACTACGCCGCCGCCAACGCCTT  4600
 A  T  L  G  S  P  G  Q  A  N  Y  A  A  A  N  A  F
CCTCGACGCCCTCGCCACCCACCGCCACACCCAAGGACAACCCGCCACCA  4600
  L  D  A  L  A  T  H  R  H  T  Q  G  Q  P  A  T
CCATCGCCTGGGGCATGTGGCACACCACCACCACACTCACCAGCCAACTC  4700
T  I  A  W  G  M  W  H  T  T  T  T  L  T  S  Q  L
ACCGACAGCGACCGCGACCGCATCCGCCGCGGCGGCTTCCTGCCGATCTC  4750
 T  D  S  D  R  D  R  I  R  R  G  G  F  L  P  I  S
GGACGACGAGGGCATGC
  D  D  E  G  M
```

The NheI-XhoI hybrid FK-506 PKS module 8 containing the AT domain of module 12 of rapamycin is shown below. (SEQ ID NOS 30–31)

```
GCATGCGGCTGTACGAGGCGGCACGGCGCACCGGAAGTCCCGTGGTGGTG    50
  M  R  L  Y  E  A  A  R  R  T  G  S  P  V  V  V
GCGGCCGCGCTCGACGACGCGCCGGACGTGCCGCTGCTGCGCGGGCTGCG   100
 A  A  A  L  D  D  A  P  D  V  P  L  L  R  G  L  R
GCGTACGACCGTCCGGCGTGCCGCCGTCCGGGAACGCTCTCTCGCCGACC   150
  R  T  T  V  R  R  A  A  V  R  E  R  S  L  A  D
GCTCGCCGTGCTGCCCGACGACGAGCGCGCCGACGCCTCCCTCGCGTTCG   200
R  S  P  C  C  P  T  T  S  A  P  T  P  P  S  R  S
TCCTGGAACAGCACCGCCACCGTGCTCGGCCACCTGGGCGCCGAAGACAT   250
 S  W  N  S  T  A  T  V  L  G  H  L  G  A  E  D  I
CCCGGCGACGACGACGTTCAAGGAACTCGGCATCGACTCGCTCACCGCGG   300
  P  A  T  T  T  F  K  E  L  G  I  D  S  L  T  A
TCCAGCTGCGCAACGCGCTGACCACGGCGACCGGCGTACGCCTCAACGCC   350
V  Q  L  R  N  A  L  T  T  A  T  G  V  R  L  N  A
ACAGCGGTCTTCGACTTTCCGACGCCGCGCGCGCTCGCCGCGAGACTCGG   400
 T  A  V  F  D  F  P  T  P  R  A  L  A  A  R  L  G
CGACGAGCTGGCCGGTACCCGCGCGCCCGTCGCGGCCCGGACCGCGGCCA   450
  D  E  L  A  G  T  R  A  P  V  A  A  R  T  A  A
CCGCGGCCGCGCACGACGAACCGCTGGCGATCGTGGGCATGGCCTGCCGT   500
T  A  A  A  H  D  E  P  L  A  I  V  G  M  A  C  R
CTGCCGGGCGGGGTCGCGTCGCCACAGGAGCTGTGGCGTCTCGTCGCGTC   550
 L  P  G  G  V  A  S  P  Q  E  L  W  R  L  V  A  S
CGGCACCGACGCCATCACGGAGTTCCCCGCGGACCGCGGCTGGGACGTGG   600
  G  T  D  A  I  T  E  F  P  A  D  R  G  W  D  V
ACGCGCTCTACGAQCCGGACCCCGACGCGATCGGCAAGACCTTCGTCCGG   650
D  A  L  Y  D  P  D  P  D  A  I  G  K  T  F  V  R
CACGGCGGCTTCCTCGACGGTGCGACCGGCTTCGACGCGGCGTTCTTCGG   700
 H  G  G  F  L  D  G  A  T  G  F  D  A  A  F  F  G
GATCAGCCCGCGCGAGGCCCTGGCCATGGACCCGCAGCAACGGGTGCTCC   750
  I  S  P  R  E  A  L  A  M  D  P  Q  Q  R  V  L
TGGAGACGTCCTGGGAGGCGTTCGAAAGCGCGGGCATCACCCCGGACGCG   800
L  E  T  S  W  E  A  F  E  S  A  G  I  T  P  D  A
GCGCGGGGCAGCGACACCGGCGTGTTCATCGGCGCGTTCTCCTACGGGTA   850
 A  R  G  S  D  T  G  V  F  I  G  A  F  S  Y  G  Y
CGGCACGGGTGCGGATACCAACGGCTTCGGCGCGACAGGGTCGCAGACCA   900
  G  T  G  A  D  T  N  G  F  G  A  T  G  S  Q  T
GCGTGCTCTCCGGCCGCCTCTCGTACTTCTACGGTCTGGAGGGCCCTTCG   950
S  V  L  S  G  R  L  S  Y  F  Y  G  L  E  G  F  S
GTCACGGTCGACACCGCCTGCTCGTCGTCACTGGTCGCCCTGCACCAGGC  1000
 V  T  V  D  T  A  C  S  S  S  L  V  A  L  H  Q  A
AGGGCAGTCCCTGCGCTCGGGCGAATGCTCGCTCGCCCTGGTCGGCGGTG  1050
  G  Q  S  L  R  S  G  E  C  S  L  A  L  V  G  G
TCACGGTGATGGCGTCGCCCGGCGGATTCGTCGAGTTCTCCCGGCAGCGC  1100
V  T  V  M  A  S  P  G  G  F  V  E  F  S  R  Q  R
GGGCTCGCGCCGGACGGGCGGGCGAAGGCGTTCGGCGCGGGCGCGGACGG  1150
 G  L  A  F  D  G  R  A  K  A  F  G  A  G  A  D  G
TACGAGCTTCGCCGAGGGCGCCGGTGCCCTGGTGGTCGAGCGGCTCTCCG  1200
  T  S  F  A  E  G  A  G  A  L  V  V  E  R  L  S
ACGCGGAGCGCCACGGCCACACCGTCCTCGCCCTCGTACGCGGCTCCGCG  1250
D  A  E  R  H  G  H  T  V  L  A  L  V  R  G  S  A
GCTAACTCCGACGGCGCGTCGAACGGTCTGTCGGCGCCGAACGGCCCCTC  1300
 A  N  S  D  G  A  S  N  G  L  S  A  P  N  G  P  S
CCAGGAACGCGTCATCCACCAGGCCCTCGCGAACGCGAAACTCACCCCCG  1350
  Q  E  R  V  I  H  Q  A  L  A  N  A  K  L  T  P
CCGATGTCGACGCGGTCGAGGCGCACGGCACCGGCACCCGCCTCGGCGAC  1400
A  D  V  D  A  V  E  A  H  G  T  G  T  R  L  G  D
CCCATCGAGGCGCAGGCGCTGCTCGCGACGTACGGACAGGACCGGGCGAC  1450
 P  I  E  A  Q  A  L  L  A  T  Y  G  Q  D  R  A  T
GCCCCTGCTGCTCGGCTCGCTGAAGTCGAACATCGGGCACGCCCAGGCCG  1500
  P  L  L  L  G  S  L  K  S  N  I  G  H  A  Q  A
CGTCAGGGGTCGCCGGGATCATCAAGATGGTGCAGGCCATCCGGCACGGG  1550
A  S  G  V  A  G  I  I  K  M  V  Q  A  I  R  H  G
GAACTGCCGCCGACACTGCACGCGGACGAGCCGTCGCCGCACGTCGACTG  1600
 E  L  P  P  T  L  H  A  D  E  P  S  P  H  V  D  W
GACGGCCGGTGCCGTCGAGCTCCTGACGTCGGCCCGGCCGTGGCCGGGGA  1650
  T  A  G  A  V  E  L  L  T  S  A  R  P  W  P  G
CCGGTCGCCCGCGCCGCGCTGCCGTCTCGTCGTTCGGCGTGAGCGGCACG  1700
T  G  R  P  R  R  A  A  V  S  S  F  G  V  S  G  T
AACGCCCACATCATCCTTGAGGCAGGACCGGTCAAAACGGGACCGGTCGA  1750
 N  A  H  I  I  L  E  A  G  P  V  K  T  G  P  V  E
GGCAGGAGCGATCGAGGCAGGACCGGTCGAAGTAGGACCGGTCGAGGCTG  1800
  A  G  A  I  E  A  G  P  V  E  V  G  P  V  E  A
GACCGCTCCCCGCGGCGCCGCCGTCAGCACCGGGCGAAGACCTTCCGCTG  1850
G  P  L  P  A  A  P  P  S  A  P  G  E  D  L  P  L
CTCGTGTCGGCGCGTTCCCCGGAGGCACTCGACGAGCAGATCGGGCGCCT  1900
```

-continued

L V S A R S P E A L D E Q I G R L
GCGCGCCTATCTCGACACCGGCCCGGGCGTCGACCGGGCGGCCGTGGCGC 1950
R A Y L D T G P G V D R A A V A
AGACACTGGCCCGGCGTACGCACTTCACCCACCGGGCCGTACTGCTCGGG 2000
Q T L A R R T H F T H R A V L L G
GACACCGTCATCGGCGCTCCCCCCGCGGACCAGGCCGACGAACTCGTCTT 2050
D T V I G A P P A D Q A D E L V F
CGTCTACTCCGGTCAGGGCACCCAGCATCCCGCGATGGGCGAGCAGCTAG 2100
V Y S G Q G T Q H P A M G E Q L
CCGCCGCGTTCCCCGTCTTCGCGCGGATCCATCAGCAGGTGTGGGACCTG 2150
A A A F P V F A R I H Q Q V W D L
CTCGATGTGCCCGATCTGGAGGTGAACGAGACCGGTTACGCCCAGCCGGC 2200
L D V P D L E V N E T G Y A Q P A
CCTGTTCGCAATGCAGGTGGCTCTGTTCGGGCTGCTGGAATCGTGGGGTG 2250
L F A M Q V A L F G L L E S W G
TACGACCGGACGCGGTGATCGGCCATTCGGTGGGTGAGCTTGCGGCTGCG 2300
V R P D A V I G H S V G E L A A A
TATGTGTCCGGGGTGTGGTCGTTGGAGGATGCCTGCACTTTGGTGTCGGC 2350
Y V S G V W S L E D A C T L V S A
GCGGGCTCGTCTGATGCAGGCTCTGCCCGCGGGTGGGGTGATGGTCGCTG 2400
R A R L M Q A L P A G G V M V A
TCCCGGTCTCGGAGGATGAGGCCCGGGCCGTGCTGGGTGAGGGTGTGGAG 2450
V P V S E D E A R A V L G E G V E
ATCGCCGCGGTCAACGGCCCGTCGTCGGTGGTTCTCTCCGGTGATGAGGC 2500
I A A V N G P S S V V L S G D E A
CGCCGTGCTGCAGGCCGCGGAGGGGCTGGGGAAGTGGACGCGGCTGGCGA 2550
A V L Q A A E G L G K W T R L A
CCAGCCACGCGTTCCATTCCGCCCGTATGGAACCCATGCTGGAGGAGTTC 2600
T S H A F H S A R M E P M L E E F
CGGGCGGTCGCCGAAGGCCTGACCTACCGGACGCCGCAGGTCTCCATGGC 2650
R A V A E G L T Y R T P Q V S M A
CGTTGGTGATCAGGTGACCACCGCTGAGTACTGGGTGCGGCAGGTCCGGG 2700
V G D Q V T T A E Y W V R Q V R
ACACGGTCCGGTTCGGCGAGCAGGTGGCCTCGTACGAGGACGCCGTGTTC 2750
D T V R F G E Q V A S Y E D A V F
GTCGAGCTGGGTGCCGACCGGTCACTGGCCCGCCTGGTCGACGGTGTCGC 2800
V E L G A D R S L A R L V D G V A
GATGCTGCACGGCGACCACGAAATCCAGGCCGCGATCGGCGCCCTGGCCC 2850
M L H G D H E I Q A A I G A L A
ACCTGTATGTCAACGGCGTCACGGTCGACTGGCCCGCGCTCCTGGGCGAT 2900
H L Y V N G V T V D W F A L L G D
GCTCCGGCAACACGGGTGCTGGACCTTCCGACATACGCCTTCCAGCACCA 2950
A P A T R V L D L P T Y A F Q H Q
GCGCTACTGGCTCGAGTCGGCTCCCCCGGCCACGGCCGACTCGGGCCACC 3000
R Y W L E S A P P A T A D S G H
CCGTCCTCGGCACCGGAGTCGCCGTCGCCGGGTCGCCGGGCCGGGTGTTC 3050
P V L G T G V A V A G S P G R V F
ACGGGTCCCGTGCCCGCCGGTGCGGACCGCGCGGTGTTCATCGCCGAACT 3100
T G P V P A G A D R A V F I A E L
GGCGCTCGCCGCCGCCGACGCCACCGACTGCGCCACGGTCGAACAGCTCG 3150
A L A A A D A T D C A T V E Q L
ACGTCACCTCCGTGCCCGGCGGATCCGCCCGCGGCAGGGCCACCGCGCAG 3200
D V T S V P G G S A R G R A T A Q
ACCTGGGTCGATGAACCCGCCGCCGACGGGCGGCGCCGCTTCACCGTCCA 3250
T W V D E P A A D G R R R F T V H
CACCCGCGTCGGCGACGCCCCGTGGACGCTGCACGCCGAGGGGGTTCTCC 3300
T R V G D A P W T L H A E G V L
GCCCCGGCCGCGTGCCCCAGCCCGAAGCCGTCGACACCGCCTGGCCCCCG 3350
R P G R V P Q P E A V D T A W P P
CCGGGCGCGGTGCCCGCGGACGGGCTGCCCGGGGCGTGGCGACGCGCGGA 3400
P G A V P A D G L P G A W R R A D
CCAGGTCTTCGTCGAAGCCGAAGTCGACAGCCCTGACGGCTTCGTGGCAC 3450
Q V F V E A E V D S P D G F V A
ACCCCGACCTGCTCGACGCGGTCTTCTCCGCGGTCGGCGACGGGAGCCGC 3500
H P D L L D A V F S A V G D G S R
CAGCCGACCGGATGGCGCGACCTCGCGGTGCACGCGTCGGACGCCACCGT 3550
Q P T G W R D L A V H A S D A T V
GCTGCGCGCCTGCCTCACCCGCCGCGACAGTGGTGTCGTGGAGCTCGCCG 3600
L R A C L T R R D S G V V E L A
CCTTCGACGGTGCCGGAATGCCGQTGCTCACCGCGGAGTCGGTGACGCTG 3650
A F D G A G M P V L T A E S V T L
GGCGAGGTCGCGTCGGCAGGCGGATCCGACGAGTCGGACGGTCTGCTTCG 3700
G E V A S A G G S D E S D G L L R
GCTTGAGTGGTTGCCGGTGGCGGAGGCCCACTACGACGGTGCCGACGAGC 3750
L E W L P V A E A H Y D G A D E
TGCCCGAGGGCTACACCCTCATCACCGCCACACACCCCGACGACCCCGAC 3800
L P E G Y T L I T A T H P D D P D
GACCCCACCAACCCCCACAACACACCCACACGCACCCACACACAAACCAC 3850
D P T N P H N T P T R T H T Q T T
ACGCGTCCTCACCGCCCTCCAACACCACCTCATCACCACCAACCACACCC 3900

-continued

```
 R  V  L  T  A  L  Q  H  H  L  I  T  T  N  H  T
TCATCGTCCACACCACCACCGACCCCCCAGGCGCCGCCGTCACCGGCCTC  3950
L  I  V  H  T  T  T  D  P  P  G  A  A  V  T  G  L
ACCCGCACCGCACAAAACGAACACCCCGGCCGCATCCACCTCATCGAAAC  4000
 T  R  T  A  Q  N  E  H  P  G  R  I  H  L  I  E  T
CCACCACCCCCACACCCCACTCCCCCTCACCCAACTCACCACCCTCCACC  4050
  H  H  P  H  T  P  L  P  L  T  Q  L  T  T  L  H
AACCCCACCTACGCCTCACCAACAACACCCTCCACACCCCCCACCTCACC  4100
Q  P  H  L  R  L  T  N  N  T  L  H  T  P  H  L  T
CCCATCACCACCCACCACAACACCACCACAACCACCCCCAACACCCCACC  4150
 P  I  T  T  H  H  N  T  T  T  T  T  P  N  T  P  P
CCTCAACCCCAACCACGCCATCCTCATCACCGGCGGCTCCGGCACCCTCG  4200
  L  N  P  N  H  A  I  L  I  T  G  G  S  G  T  L
CCGGCATCCTCGCCCGCCACCTCAACCACCCCCACACCTACCTCCTCTCC  4250
A  G  I  L  A  R  H  L  N  H  P  H  T  Y  L  L  S
CGCACACCACCACCCCCCACCACACCCGGCACCCACATCCCCTGCGACCT  4300
 R  T  P  P  P  P  T  T  P  G  T  H  I  P  C  D  L
CACCGACCCCACCCAAATCACCCAAGCCCTCACCCACATACCACAACCCC  4350
  T  D  P  T  Q  I  T  Q  A  L  T  H  I  P  Q  P
TCACCGGCATCTTCCACACCGCCGCCACCCTCGACGACGCCACCCTCACC  4400
L  T  G  I  F  H  T  A  A  T  L  D  D  A  T  L  T
AACCTCACCCCCCAACACCTCACCACCACCCTCCAACCCAAAGCCGACGC  4450
 N  L  T  P  Q  H  L  T  T  T  L  Q  P  K  A  D  A
CGCCTGGCACCTCCACCACCACACCCAAAACCAACCCCTCACCCACTTCG  4500
  A  W  H  L  H  H  H  T  Q  N  Q  P  L  T  H  F
TCCTCTACTCCAGCGCCGCCGCCACCCTCGGCAGCCCCGGCCAAGCCAAC  4550
V  L  Y  S  S  A  A  A  T  L  G  S  P  G  Q  A  N
TACGCCGCCGCCAACGCCTTCCTCGACGCCCTCGCCACCCACCGCCACAC  4600
 Y  A  A  A  N  A  F  L  D  A  L  A  T  H  R  H  T
CCAAGCACAACCCGCCACCACCATCGCCTGGGGCATGTGGCACACCACCA  4650
  Q  G  Q  P  A  T  T  I  A  W  G  M  W  H  T  T
CCACACTCACCAGCCAACTCACCGACAGCGACCGCGACCGCATCCGCCGC  4700
T  T  L  T  S  Q  L  T  D  S  D  R  D  R  I  R  R
GGCGGCTTCCTGCCGATCTCGGACGACGAGGGCATGC
 G  G  F  L  P  I  S  D  D  E  G  M
```

The NheI-XhoI hybrid FK-506 PKS module 8 containing the AT domain of module 13 of rapamycin is shown below. (SEQ ID NOS 32–33)

```
GCATGCGGCTGTACGAGGCGGCAGGGCGCACCGGAAGTCCCGTGGTGGTG    50
  M  R  L  Y  E  A  A  R  R  T  G  S  P  V  V  V
GCGGCCGCGCTCGACGACGCGCCGGACGTGCCGCTGCTGCGCGGGCTGCG   100
 A  A  A  L  D  D  A  P  D  V  P  L  L  R  G  L  R
GCGTACGACCGTCCGGCGTGCCGCCGTCCGGGAACGCTCTCTCGCCGACC   150
  R  T  T  V  R  R  A  A  V  R  E  R  S  L  A  D
GCTCGCCGTGCTGCCCGACGACGAGCGCGCCGACGCCTCCCTCGCGTTCG   200
R  S  P  C  C  P  T  T  S  A  P  T  P  P  S  R  S
TCCTGGAACAGCACCGCCACCGTGCTCGGCCACCTGGGCGCCGAAGACAT   250
 S  W  N  S  T  A  T  V  L  G  H  L  G  A  E  D  I
CCCGGCGACGACGACGTTCAAGGAACTCGGCATCGACTCGCTCACCGCGG   300
  P  A  T  T  T  F  K  E  L  G  I  D  S  L  T  A
TCCAGCTGCGCAACGCGCTGACCACGGCGACCGGCGTACGCCTCAACGCC   350
V  Q  L  R  N  A  L  T  T  A  T  G  V  R  L  N  A
ACAGCGGTCTTCGACTTTCCGACGCCGCGCGCGCTCGCCGCGAGACTCGG   400
 T  A  V  F  D  F  P  T  P  R  A  L  A  A  R  L  G
CGACGAGCTGGCCGGTACCCGCGCGCCCGTCGCGGCCCGGACCGCGGCCA   450
  D  E  L  A  G  T  R  A  P  V  A  A  R  T  A  A
CCGCGGCCGCGCACGACGAACCGCTGGCGATCGTGGGCATGGCCTGCCGT   500
T  A  A  A  H  D  E  P  L  A  I  V  G  M  A  C  R
CTGCCGGGCGGGGTCGCGTCGCCACAGGAGCTGTGGCGTCTCGTCGCGTC   550
 L  P  G  G  V  A  S  P  Q  E  L  W  R  L  V  A  S
CGGCACCGACGCCATCACGGAGTTCCCCGCGGACCGCGGCTGGGACGTGG   600
  G  T  D  A  I  T  E  F  P  A  D  R  G  W  D  V
ACGCGCTCTACGACCCGGACCCCGACGCGATCGGCAAGACCTTCGTCCGG   650
D  A  L  Y  D  P  D  P  D  A  I  G  K  T  F  V  R
CACGGCGGCTTCCTCGACGGTGCGACCGGCTTCGACGCGGCGTTCTTCGG   700
 H  G  G  F  L  D  G  A  T  G  F  D  A  A  F  F  G
GATCAGCCCGCGCGAGGCCCTGGCCATGGACCCGCAGCAACGGGTGCTCC   750
  I  S  P  R  E  A  L  A  M  D  P  Q  Q  R  V  L
TGGAGACGTCCTGGGAGGCGTTCGAAAGCGCGGGCATCACCCCGGACGCG   800
L  E  T  S  W  E  A  F  E  S  A  G  I  T  P  D  A
GCGCGGGGCAGCGACACCGGCGTGTTCATCGGCGCGTTCTCCTACGGGTA   850
 A  R  G  S  D  T  G  V  F  I  G  A  F  S  Y  G  Y
CGGCACGGGTGGGGATACCAACGGCTTCGGCGCGACAGGGTCGCAGACCA   900
  G  T  G  A  D  T  N  G  F  G  A  T  G  S  Q  T
```

-continued

```
GCGTGCTCTCCGGCCGCCTCTCGTACTTCTACGGTCTGGAGGGCCCTTCG   950
S  V  L  S  G  R  L  S  Y  F  Y  G  L  E  G  P  S
GTCACGGTCGACACCGCCTGCTCGTCGTCACTGGTCGCCCTGCACCAGGC  1000
 V  T  V  D  T  A  C  S  S  S  L  V  A  L  H  Q  A
AGGGCAGTCCCTGCGCTCGGGCGAATGCTCGCTCGCCCTGGTCGGCGGTG  1050
  G  Q  S  L  R  S  G  E  C  S  L  A  L  V  G  G
TCACGGTGATGGCGTCGCCCGGCGGATTCGTCGAGTTCTCCCGGCAGCGC  1100
V  T  V  M  A  S  P  G  G  F  V  E  F  S  R  Q  R
GGGCTCGCGCCGGACGGGCGGGCGAAGGCGTTCGGCGCGGGCGCGGACGG  1150
 G  L  A  P  D  G  R  A  K  A  F  G  A  G  A  D  G
TACGAGCTTCGCCGAGGGCGCCGGTGCCCTGGTGGTCGAGCGGCTCTCCG  1200
  T  S  F  A  E  G  A  G  A  L  V  V  E  R  L  S
ACGCGGAGCGCCACGGCCACACCGTCCTCGCCCTCGTACGCGGCTCCGCG  1250
D  A  E  R  H  G  H  T  V  L  A  L  V  R  G  S  A
GCTAACTCCGACGGCGCGTCGAACGGTCTGTCGGCGCCGAACGGCCCCTC  1300
 A  N  S  D  G  A  S  N  G  L  S  A  P  N  G  P  S
CCAGGAACGCGTCATCCACCAGGCCCTCGCGAACGCGAAACTCACCCCCG  1350
  Q  E  R  V  I  H  Q  A  L  A  N  A  K  L  T  P
CCGATGTCGACGCGGTCGAGGCGCACGGCACCGGCACCCGCCTCGGCGAC  1400
A  D  V  D  A  V  E  A  H  G  T  G  T  R  L  G  D
CCCATCGAGGCGCAGGCGCTGCTCGCGACGTACGGACAGGACCGGGCGAC  1450
 P  I  E  A  Q  A  L  L  A  T  Y  G  Q  D  R  A  T
GCCCCTGCTGCTCGG&TCGCTGAAGTCGAACATCGGGCACGCCCAGGCCG  1500
  P  L  L  L  G  S  L  K  S  N  I  G  H  A  Q  A
CGTCAGGGGTCGCCGGGATCATCAAGATGGTGCAGGCCATCCGGCACGGG  1550
A  S  G  V  A  G  I  I  K  M  V  Q  A  I  R  H  G
GAACTGCCGCCGACACTGCACGCGGACGAGCCGTCGCCGCACGTCGACTG  1600
 E  L  P  P  T  L  H  A  D  E  P  S  P  H  V  D  W
GACGGCCGGTGCCGTCGAGCTCCTGACGTCGGCCCGGCCGTGGCCGGGGA  1650
  T  A  G  A  V  E  L  L  T  S  A  R  P  W  P  G
CCGGTCGCCCGCGCCGCGCTGCCGTCTCGTCGTTCGGCGTGAGCGGCACG  1700
T  G  R  P  R  R  A  A  V  S  S  F  G  V  S  G  T
AACGCCCACATCATCCTTGAGGCAGGACCGGTCAAAACGGGACCGGTCGA  1750
 N  A  H  I  I  L  E  A  G  P  V  K  T  G  P  V  E
GGCAGGAGCGATCGAGGCAGGACCGGTCGAAGTAGGACCGGTCGAGGCTG  1800
  A  G  A  I  E  A  G  P  V  E  V  G  P  V  E  A
GACCGCTCCCCGCGGCGCCGCCGTCAGCACCGGGCGAAGACCTTCCGCTG  1850
G  P  L  P  A  A  P  P  S  A  P  G  E  D  L  P  L
CTCGTGTCGGCGCGTTCCCCGGAGGCACTCGACGAGCAGATCGGGCGCCT  1900
 L  V  S  A  R  S  P  E  A  L  D  E  Q  I  G  R  L
GCGCGCCTATCTCGACACCGGCCCGGGCGTCGACCGGGCGGCCGTGGCGC  1950
  R  A  Y  L  D  T  G  P  G  V  D  R  A  A  V  A
AGACACTGGCCCGGCGTACGCACTTCACCCACCGGGCCGTACTGCTCGGG  2000
Q  T  L  A  R  R  T  H  F  T  H  R  A  V  L  L  G
GACACCGTCATCGGCGCTCCCCCCGCGGACCAGGCCGACGAACTCGTCTT  2050
 D  T  V  I  G  A  P  P  A  D  Q  A  D  E  L  V  F
CGTCTACTCCGGTCAGGGCACCCAGCATCCCGCGATGGGCGAGCAGCTAG  2100
  V  Y  S  G  Q  G  T  Q  H  P  A  M  G  E  Q  L
CCGATTCGTCGGTGGTGTTCGCCGAGCGGATGGCCGAGTGTGCGGCGGCG  2150
A  D  S  S  V  V  F  A  E  R  M  A  E  C  A  A  A
TTGCGCGAGTTCGTGGACTGGGATCTGTTCACGGTTCTGGATGATCCGGC  2200
 L  R  E  F  V  D  W  D  L  F  T  V  L  D  D  P  A
GGTGGTGGACCGGGTTGATGTGGTCCAGCCCGCTTCCTGGGCGATGATGG  2250
  V  V  D  R  V  D  V  V  Q  P  A  S  W  A  M  M
TTTCCCTGGCCGCGGTGTGGCAGGCGGCCGGTGTGCGGCCGGATGCGGTG  2300
V  S  L  A  A  V  W  Q  A  A  G  V  R  P  D  A  V
ATCGGCCATTCGCAGGGTGAGATCGCCGCAGCTTGTGTGGCGGGTGCGGT  2350
 I  G  H  S  Q  G  E  I  A  A  A  C  V  A  G  A  V
GTCACTACGCGATGCCGCCCGGATCGTGACCTTGCGCAGCCAGGCGATCG  2400
  S  L  R  D  A  A  R  I  V  T  L  R  S  Q  A  I
CCCGGGGCCTGGCGGGCCGGGGCGCGATGGCATCCGTCGCCCTGCCCGCG  2450
A  R  G  L  A  G  R  G  A  M  A  S  V  A  L  P  A
CAGGATGTCGAGCTGGTCGACGGGGCCTGGATCGCCGCCCACAACGGGCC  2500
 Q  D  V  E  L  V  D  G  A  W  I  A  A  H  N  G  P
CGCCTCCACCGTGATCGCGGGCACCCCGGAAGCGGTCGACCATGTCCTCA  2550
  A  S  T  V  I  A  G  T  P  E  A  V  D  H  V  L
CCGCTCATGAGGCACAAGGGGTGCGGGTGCGGCGGATCACCGTCGACTAT  2600
T  A  H  E  A  Q  G  V  R  V  R  R  I  T  V  D  Y
GCCTCGCACACCCCGCACGTCGAGCTGATCCGCGACGAACTACTCGACAT  2650
 A  S  H  T  P  H  V  E  L  I  R  D  E  L  L  D  I
CACTAGCGACAGCAGCTCGCAGACCCCGCTCGTGCCGTGGCTGTCGACCG  2700
  T  S  D  S  S  S  Q  T  P  L  V  F  W  L  S  T
TGGACGGCACCTGGGTCGACAGCCCGCTGGACGGGGAGTACTGGTACCGG  2750
V  D  G  T  W  V  D  S  P  L  D  G  E  Y  W  Y  R
AACCTGCGTGAACCGGTCGGTTTCCACCCCGCCGTCAGCCAGTTGCAGGC  2800
 N  L  R  E  P  V  G  F  H  P  A  V  S  Q  L  Q  A
CCAGGGCGACACCGTGTTCGTCGAGGTCAGCGCCAGCCCGGTGTTGTTGC  2850
  Q  G  D  T  V  F  V  E  V  S  A  S  P  V  L  L
AGGCGATGGACGACGATGTCGTCACGGTTGCCACGCTGCGTCGTGACGAC  2900
Q  A  M  D  D  D  V  V  T  V  A  T  L  R  R  D  D
```

-continued

```
GGCGACGCCACCCGGATGCTCACCGCCCTGGCACAGGCCTATGTCCACGG  2950
 G  D  A  T  R  M  L  T  A  L  A  Q  A  Y  V  H  G
CGTCACCGTCGACTGGCCCGCCATCCTCGGCACCACCACAACCCGGGTAC  3000
  V  T  V  D  W  P  A  I  L  G  T  T  T  T  R  V
TGGACCTTCCGACCTACGQCTTCCAACACCAGCGGTACTGGCTCGAGTCG  3050
L  D  L  P  T  Y  A  F  Q  H  Q  R  Y  W  L  E  S
GCTCCCCCGGCCACGGCCGACTCGGGCCACCCCGTCCTCGGCACCGGAGT  3100
 A  P  P  A  T  A  D  S  G  H  P  V  L  G  T  G  V
CGCCGTCGCCGGGTCGCCGGGCCGGGTGTTCACGGGTCCCGTGCCCGCCG  3150
  A  V  A  G  S  P  G  R  V  F  T  G  P  V  P  A
GTGCGGACCGCGCGGTGTTCATCGCCGAACTGGCGCTCGCCGCCGCCGAC  3200
G  A  D  R  A  V  F  I  A  E  L  A  L  A  A  A  D
GCCACCGACTGCGCCACGGTCGAACAGCTCGACGTCACCTCCGTGCCCGG  3250
 A  T  D  C  A  T  V  E  Q  L  D  V  T  S  V  P  G
CGGATCCGCCCGCGGCAGGGCCACCGCGCAGACCTGGGTCGATGAACCCG  3300
  G  S  A  R  G  R  A  T  A  Q  T  W  V  D  E  P
CCGCCGACGGGCGGCGCCGCTTCACCGTCCACACCCGCGTCGGCGACGCC  3350
A  A  D  G  R  R  R  F  T  V  H  T  R  V  G  D  A
CCGTGGACGCTGCACGCCGAGGGGGTTCTCCGCCCCGGCCGCGTGCCCCA  3400
 P  W  T  L  H  A  E  G  V  L  R  P  G  R  V  P  Q
GCCCGAAGCCGTCGACACCGCCTGGCCCCCGCCGGGCGCGGTGCCCGCGG  3450
  P  E  A  V  D  T  A  W  P  P  P  G  A  V  P  A
ACGGGCTGCCCGGGGCGTGGCGACGCGCGGACCAGGTCTTCGTCGAAGCC  3500
D  G  L  P  G  A  W  R  R  A  D  Q  V  F  V  E  A
GAAGTCGACAGCCCTGACGGCTTCGTGGCACACCCCGACCTGCTCGACGC  3550
 E  V  D  S  P  D  G  F  V  A  H  P  D  L  L  D  A
GGTCTTCTCCGCGGTCGGCGACGGGAGCCGCCAGCCGACCGGATGGCGCG  3600
  V  F  S  A  V  G  D  G  S  R  Q  P  T  G  W  R
ACCTCGCGGTGCACGCGTCGGACGCCACCGTGCTGCGCGCCTGCCTCACC  3650
D  L  A  V  H  A  S  D  A  T  V  L  R  A  C  L  T
CGCCGCGACAGTGGTGTCGTGGAGCTCGCCGCCTTCGACGGTGCCGGAAT  3700
 R  R  D  S  G  V  V  E  L  A  A  F  D  G  A  G  M
GCCGGTGCTCACCGCGGAGTCGGTGACGCTGGGCGAGGTCGCGTCGGCAG  3750
  P  V  L  T  A  E  S  V  T  L  G  E  V  A  S  A
GCGGATCCGACGAGTCGGACGGTCTGCTTCGGCTTGAGTGGTTGCCGGTG  3800
G  G  S  D  E  S  D  G  L  L  R  L  E  W  L  P  V
GCGGAGGCCCACTACGACGGTGCCGACGAGCTCCCCGAGGGCTACACCCT  3850
 A  E  A  H  Y  D  G  A  D  E  L  P  E  G  Y  T  L
CATCACCGCCACACACCCCGACGACCCCGACGACCCCACCAACCCCCACA  3900
  I  T  A  T  H  P  D  D  P  D  D  P  T  N  P  H
ACACACCCACACGCACCCACACACAAACCACACGCGTCCTCACCGCCCTC  3950
N  T  P  T  R  T  H  T  Q  T  T  R  V  L  T  A  L
CAACACCACCTCATCACCACCAACCACACCCTCATCGTCCACACCACCAC  4000
 Q  H  H  L  I  T  T  N  H  T  L  I  V  H  T  T  T
CGACCCCCCAGGCGCCGCCGTCACCGGCCTCACCCGCACCGCACAAAACG  4050
  D  P  P  G  A  A  V  T  G  L  T  R  T  A  Q  N
AACACCCCGGCCGCATCCACCTCATCGAAACCCACCACCCCCACACCCCA  4100
E  H  P  G  R  I  H  L  I  E  T  H  H  P  H  T  P
CTCCCCCTCACCCAACTCACCACCCTCCACCAACCCCACCTACGCCTCAC  4150
 L  P  L  T  Q  L  T  T  L  H  Q  P  H  L  R  L  T
CAACAACACCCTCCACACCCCCCACCTCACCCCCATCACCACCCACCACA  4200
  N  N  T  L  H  T  P  H  L  T  P  I  T  T  H  H
ACACCACCACAACCACCCCCAACACCCCACCCCTCAACCCCAACCACGCC  4250
N  T  T  T  T  T  P  N  T  P  P  L  N  P  N  H  A
ATCCTCATCACCGGCGGCTCCGGCACCCTCGCCGGCATCCTCGCCCGCCA  4300
 I  L  I  T  G  G  S  G  T  L  A  G  I  L  A  R  H
CCTCAACCACCCCCACACCTACCTCCTCTCCCGCACACCACCACCCCCCA  4350
  L  N  H  P  H  T  Y  L  L  S  R  T  P  P  P  P
CCACACCCGGCACCCACATCCCCTGCGACCTCACCGACCCCACCCAAATC  4400
T  T  P  G  T  H  I  P  C  D  L  T  D  P  T  Q  I
ACCCAAGCCCTCACCCACATACCACAACCCCTCACCGGCATCTTCCACAC  4450
 T  Q  A  L  T  H  I  P  Q  P  L  T  G  I  F  H  T
CGCCGCCACCCTCGACGACGCCACCCTCACCAACCTCACCCCCCAACACC  4500
  A  A  T  L  D  D  A  T  L  T  N  L  T  P  Q  H
TCACCACCACCCTCCAACCCAAAGCCGACGCCGCCTGGCACCTCCACCAC  4550
L  T  T  T  L  Q  P  K  A  D  A  A  W  H  L  H  H
CACACCCAAAACCAACCCCTCACCCACTTCGTCCTCTACTCCAGCGCCGC  4600
 H  T  Q  N  Q  P  L  T  H  F  V  L  Y  S  S  A  A
CGCCACCCTCGGCAGCCCCGGCCAAGCCAACTACGCCGCCGCCAACGCCT  4650
  A  T  L  G  S  P  G  Q  A  N  Y  A  A  A  N  A
TCCTCGACGCCCTCGCCACCCACCGCCACACCCAAGGACAACCCGCCACC  4700
F  L  D  A  L  A  T  H  R  H  T  Q  G  Q  P  A  T
ACCATCGCCTGGGGCATGTGGCACACCACCACCACACTCACCAGCCAACT  4750
 T  I  A  W  G  M  W  H  T  T  T  T  L  T  S  Q  L
CACCGACAGCGACCGCGACCGCATCCGCCGCGGCGGCTTCCTGCCGATCT  4800
  T  D  S  D  R  D  R  I  R  R  G  G  F  L  P  I
CGGACGACGAGGGCATGC
S  D  D  E  G  M
```

EXAMPLE 3

Recombinant PKS Genes for 13-desmethoxy FK-506 and FK-520

The present invention provides a variety of recombinant PKS genes in addition to those described in Examples 1 and 2 for producing 13-desmethoxy FK-506 and FK-520 compounds. This Example provides the construction protocols for recombinant FK-520 and FK-506 (from Streptomyces sp. MA6858 (ATCC 55098), described in U.S. Pat. Nos. 5,116,756, incorporated herein by reference) PKS genes in which the module 8 AT coding sequences have been replaced by either the rapAT3 (the AT domain from module 3 of the rapamycin PKS), rapAT12, eryAT1 (the AT domain from module 1 of the erythromycin (DEBS) PKS), or eryAT2 coding sequences. Each of these constructs provides a PKS that produces the 13-desmethoxy-13-methyl derivative, except for the rapAT12 replacement, which provides the 13-desmethoxy derivative, i.e., it has a hydrogen where the other derivatives have methyl.

FIG. 7 shows the process used to generate the AT replacement constructs. First, a fragment of ~4.5 kb containing module 8 coding sequences from the FK-520 cluster of ATCC 14891 was cloned using the convenient restriction sites SacI and SphI (Step A in FIG. 7). The choice of restriction sites used to clone a 4.0–4.5 kb fragment comprising module 8 coding sequences from other FK-520 or FK-506 clusters can be different depending on the DNA sequence, but the overall scheme is identical. The unique SacI and SphI restriction sites at the ends of the FK-520 module 8 fragment were then changed to unique BglII and NsiI sites by ligation to synthetic linkers (described in the preceding Examples, see Step B of FIG. 7). Fragments containing sequences 5' and 3' of the AT8 sequences were then amplified using primers, described above, that introduced either an AvrII site or an NheI site at two different KS/AT boundaries and an XhoI site at the AT/DH boundary (Step C of FIG. 7). Heterologous AT domains from the rapamycin and erythromycin gene clusters were amplified using primers, as described above, that introduced the same sites as just described (Step D of FIG. 7). The fragments were ligated to give hybrid modules with in-frame fusions at the KS/AT and AT/DH boundaries (Step E of FIG. 7). Finally, these hybrid modules were ligated into the BamHI and PstI sites of the KC515 vector. The resulting recombinant phage were used to transform the FK-506 and FK-520 producer strains to yield the desired recombinant cells, as described in the preceding Examples.

The following table shows the location and sequences surrounding the engineered site of each of the heterologous AT domains employed. The FK-506 hybrid construct was used as a control for the FK-520 recombinant cells produced, and a similar FK-520 hybrid construct was used as a control for the FK-506 recombinant cells.

| Heterologous AT | Enzyme | Location of Engineered Site |
|---|---|---|
| FK-506 AT8 | AvrII | GGCCGTccgcgcCGTGCGGCGGTCTCGTCGTTC |
| (hydroxymalonyl) | (SEQ ID NOS 31–35) | G R P R R A A V S S F |
| | NheI | ACCCAGCATCCCGCGATGGGTGAGCGgctcgcC |
| | (SEQ ID NOS 36–37) | T Q H P A M G E R L A |
| | XhoI | TACGCCTTCCAGCGGCGGCCCTACTGGatcgag |
| | (SEQ ID NOS 38–39) | Y A F Q R R P Y W I E |
| rapamycin AT3 | AvrII | GACCGGccccgtCGGGCGGGCGTGTCGTCCTTC |
| (methylmalonyl) | (SEQ ID NOS 40–41) | D R P R R A G V S S F |
| | NheI | TGGCAGTGGCTGGGGATGGGCAGTGCcctgcgG |
| | (SEQ ID NOS 42–43) | W Q W L G M G S A L R |
| | XhoI | TACGCCTTCCAACACCAGCGGTACTGGgtcgag |
| | (SEQ ID NOS 44–45) | Y A F Q H Q R Y W V E |
| rapamycin AT12 | AvrII | GGCCGAgcgcgcCGGGCAGGCGTGTCGTCCTTC |
| (malonyl) | (SEQ ID NOS 46–47) | G R A R R A G V S S F |
| | NheI | TCGCAGCGTGCTGGCATGGGTGAGGAactggcC |
| | (SEQ ID NOS 48–49) | S Q R A G M G E E L A |
| | XhoI | TACGCCTTCCAGCACCAGCGCTACTGGctcgag |
| | (SEQ ID NOS 50–51) | Y A F Q H Q R Y W L E |
| DEBS AT1 | AvrII | GCGCGAccgcgcCGGGCGGGGGTCTCGTCGTTC |
| (methylmalonyl) | (SEQ ID NOS 52–53) | A R P R R A G V S S F |
| | NheI | TGGCAGTGGGCGGGCATGGCCGTCGAcctgctC |
| | (SEQ ID NOS 54–55) | W Q W A G M A V D L L |
| | XhoI | TACCCGTTCCAGCGCGAGCGCGTCTGGctcgaa |
| | (SEQ ID NOS 56–57) | Y P F Q R E R V W L E |
| DEBS AT2 | AvrII | GACGGGgtgcgcCGGGCAGGTGTGTCGGCGTTC |
| (methytmalonyl) | (SEQ ID NOS 58–59) | D G V R R A G V S A F |
| | NheI | GCCCAGTGGGAAGGCATGGCGCGGGAgttgttG |
| | (SEQ ID NOS 60–61) | A Q W E G M A R E L L |
| | XhoI | TATCCTTTCCAGGGCAAGCGGTTCTGGctgctg |
| | (SEQ ID NOS 62–63) | Y P F Q G K R F W L L |

The sequences shown below provide the location of the KS/AT boundaries chosen in the FK-520 module 8 coding sequences. Regions where AvrII and NheI sites were engineered are indicated by lower case and underlining. (SEQ ID NOS 64–65)

```
CCGGCGCCGTCGAACTGCTGACGTCGGCCCGGCCGTGGCCCGAGACCGACCGGccacggc
A  G  A  V  E  L  L  T  S  A  R  P  W  P  E  T  D  R  P  R

GTGCCGCCGTCTCCTCGTTCGGGGTGAGCGGCACCAACGCCCACGTCATCCTGGAGGCCG
R  A  A  V  S  S  F  G  V  S  G  T  N  A  H  V  I  L  E  A

GACCGGTAACGGAGACGCCCGCGGCATCGCCTTCCGGTGACCTTCCCCTGCTGGTGTCGG
G  P  V  T  E  T  P  A  A  S  P  S  G  D  L  P  L  L  V  S

CACGCTCACCGGAAGCGCTCGACGAGCAGATCCGCCGACTGCGCGCCTACCTGGACACCA
A  R  S  P  E  A  L  D  E  Q  I  R  R  L  R  A  Y  L  D  T

CCCCGGACGTCGACCGGGTGGCCGTGGCACAGACGCTGGCCCGGCGCACACACTTCGCCC
T  P  D  V  D  R  V  A  V  A  Q  T  L  A  R  R  T  H  F  A

ACCGCGCCGTGCTGCTCGGTGACACCGTCATCACCACACCCCCCGCGGACCGGCCCGACG
H  R  A  V  L  L  G  D  T  V  I  T  T  P  P  A  D  R  P  D

AACTCGTCTTCGTCTACTCCGGCCAGGGCACCCAGCATCCCGCGATGGGCGAGCAgctcg
E  L  V  F  V  Y  S  G  Q  G  T  Q  H  P  A  M  G  E  Q  L

cCGCCGCCCATCCCGTGTTCGCCGACGCCTGGCATGAAGCGCTCCGCCGCCTTGACAACC
A  A  A  H  P  V  F  A  D  A  W  H  E  A  L  R  R  L  D  N
```

The sequences shown below provide the location of the AT/DH boundary chosen in the FK-520 module 8 coding sequences. The region where an XhoI site was engineered is indicated by lower case and underlining. (SEQ ID NOS 66–67)

```
TCCTCGGGGCTGGGTCACGGCACGACGCGGATGTGCCCGCGTACGCGTTCCAACGGCGGC
I  L  G  A  G  S  R  H  D  A  D  V  P  A  Y  A  F  Q  R  R

ACTACTGGatcgagTCGGCACGCCCGGCCGCATCCGACGCGGGCCACCCCGTGCTGGGCT
H  Y  W  I  E  S  A  R  P  A  A  S  D  A  G  H  P  V  L  G
```

The sequences shown below provide the location of the KS/AT boundaries chosen in the FK-506 module 8 coding sequences. Regions where AvrII and NheI sites were engineered are indicated by lower case and underlining. (SEQ ID NOS 68–69)

```
TCGGCCAGGCCGTGGCCGCGGACCGGCCGTccgcgcCGTGCGGCGGTCTCGTCGTTCGGG
 S  A  R  P  W  P  R  T  G  R  P  R  R  A  A  V  S  S  F  G

GTGAGCGGCACCAACGCCCACATCATCCTGGAGGCCGGACCCGACCAGGAGGAGCCGTCG
 V  S  G  T  N  A  H  I  I  L  E  A  G  P  D  Q  E  E  P  S

GCAGAACCGGCCGGTGACCTCCCGCTGCTCGTGTCGGCACGGTCCCCGGAGGCACTGGAC
 A  E  P  A  G  D  L  P  L  L  V  S  A  R  S  P  E  A  L  D

GAGCAGATCGGGCGCCTGCGCGACTATCTCGACGCCGCCCCCGGCGTGGACCTGGCGGCC
 E  Q  I  G  R  L  R  D  Y  L  D  A  A  P  G  V  D  L  A  A

GTGGCGCGGACACTGGCCACGCGTACGCACTTCTCCCACCGCGCCGTACTGCTCGGTGAC
 V  A  R  T  L  A  T  R  T  H  F  S  H  R  A  V  L  L  G  D

ACCGTCATCACCGCTCCCCCCGTGGAACAGCCGGGCGAGCTCGTCTTCGTCTACTCGGGA
 T  V  I  T  A  P  P  V  E  Q  P  G  E  L  V  F  V  Y  S  G

CAGGGCACCCAGCATCCCGCGATGGGTGAGCGgctcgcCGCAGCCTTCCCCGTGTTCGCC
 Q  G  T  Q  H  P  A  M  G  E  R  L  A  A  A  F  P  V  F  A

GACCCGGACGTACCCGCCTACGCCTTCCAGCGGCGGCCCTACTGGATCGAGTCCGCGCCG
 D  P  D  V  P  A  Y  A  F  Q  R  R  P  Y  W  I  E  S  A  P
```

The sequences shown below provide the location of the AT/DH boundry chosen in the FK-506 module 8 coding sequences. The region where an XhoI site was engineered is indicated by lower case and underlining. (SEQ ID NOS 70–71)

```
GACCCGGACGTACCCGCCTACGCCTTCCAGCGGCGGCCCTACTGGatcgagTCCGCGCCG
 D  P  D  V  P  A  Y  A  F  Q  R  R  P  Y  W  I  E  S  A  P
```

EXAMPLE 4

Replacement of Methoxyl with Hydrogen or Methyl at C-15 of FK-506 and FK-520

The methods and reagents of the present invention also provide novel FK-506 and FK-520 derivatives in which the methoxy group at C-15 is replaced by hydrogen or methyl. These derivatives are produced in recombinant host cells of the invention that express recombinant PKS enzymes the produce the derivatives. These recombinant PKS enzymes are prepared in accordance with the methodology of Examples 1 and 2, with the exception that AT domain of module 7, instead of module 8, is replaced. Moreover, the present invention provides recombinant PKS enzymes in which the AT domains of both modules 7 and 8 have been changed. The table below summarizes the various compounds provided by the present invention.

| Compound | C-13 | C-15 | Derivative Provided |
|---|---|---|---|
| FK-506 | hydrogen | hydrogen | 13,15-didesmethoxy-FK-506 |
| FK-506 | hydrogen | methoxy | 13-desmethoxy-FK-506 |
| FK-506 | hydrogen | methyl | 13,15-didesmethoxy-15-methyl-FK-506 |
| FK-506 | methoxy | hydrogen | 15-desmethoxy-FK-506 |
| FK-506 | methoxy | methoxy | Original Compound - FK-506 |
| FK-506 | methoxy | methyl | 15-desmethoxy-15-methyl-FK-506 |
| FK-506 | methyl | hydrogen | 13,15-didesmethoxy-13-methyl-FK-506 |
| FK-506 | methyl | methoxy | 13-desmethoxy-13-methyl-FK-506 |
| FK-506 | methyl | methyl | 13,15-didesmethoxy-13,15-dimethyl-FK-506 |
| FK-520 | hydrogen | hydrogen | 13,15-didesmethoxy FK-520 |
| FK-520 | hydrogen | methoxy | 13-desmethoxy FK-520 |
| FK-520 | hydrogen | methyl | 13,15-didesmethoxy-15-methyl-FK-520 |
| FK-520 | methoxy | hydrogen | 15-desmethoxy-FK-520 |
| FK-520 | methoxy | methoxy | Original Compound - FK-520 |
| FK-520 | methoxy | methyl | 15-desmethoxy-15-methyl-FK-520 |
| FK-520 | methyl | hydrogen | 13,15-didesmethoxy-13-methyl-FK-520 |
| FK-520 | methyl | methoxy | 13,15-desmethoxy-13-methyl-FK-520 |
| FK-520 | methyl | methyl | 13,15-didesmethoxy-13,15-dimethyl-FK-520 |

Example 5

Replacement of Methoxyl with Ethyl at C-13 and/or C-15 of FK-506 and FK-520

The present invention also provides novel FK-506 and FK-520 derivative compounds in which the methoxy groups at either or both the C-13 and C-15 positions are instead ethyl groups. These compounds are produced by novel PKS enzymes of the invention in which the AT domains of modules 8 and/or 7 are converted to ethylmalonyl specific AT domains by modification of the PKS gene that encodes the module. Ethylmalonyl specific AT domain coding sequences can be obtained from, for example, the FK-520 PKS genes, the niddamycin PKS genes, and the tylosin PKS genes. The novel PKS genes of the invention include not only those in which either or both of the AT domains of modules 7 and 8 have been converted to ethylmalonyl specific AT domains but also those in which one of the modules is converted to an ethylmalonyl specific AT domain and the other is converted to a malonyl specific or a methylmalonyl specific AT domain.

EXAMPLE 6

Neurotrophic Compounds

The compounds described in Examples 1–4, inclusive have immunosuppressant activity and can be employed as immunosuppressants in a manner and in formulations similar to those employed for FK-506. The compounds of the invention are generally effective for the prevention of organ rejection in patients receiving organ transplants and in particular can be used for immunosuppresion following orthotopic liver transplantation. These compounds also have pharmacokinetic properties and metabolism that are more advantageous for certain applications relative to those of FK-506 or FK-520. These compounds are also neurotrophic; however, for use as neurotrophins, it is desirable to modify the compounds to diminish or abolish their immunosuppressant activity. This can be readily accomplished by hydroxylating the compounds at the C-18 position using established chemical methodology or novel FK-520 PKS genes provided by the present invention.

Thus, in one aspect, the present invention provides a method for stimulating nerve growth that comprises administering a therapeutically effective dose of 18-hydroxy-FK-520. In another embodiment, the compound administered is a C-18,20-dihydroxy-FK-520 derivative. In another embodiment, the compound administered is a C-13-desmethoxy and/or C-15-desmethoxy 18-hydroxy-FK-520 derivative. In another embodiment, the compound administered is a C-13-desmethoxy and/or C-15-desmethoxy 18,20-dihydroxy-FK-520 derivative. In other embodiments, the compounds are the corresponding analogs of FK-506. The 18-hydroxy compounds of the invention can be prepared chemically, as described in U.S. Pat. No. 5,189,042, incorporated herein by reference, or by fermentation of a recombinant host cell provided by the present invention that expresses a recombinant PKS in which the module 5 DH domain has been deleted or rendered non-functional.

The chemical methodology. is as follows. A compound of the invention (~200 mg) is dissolved in 3 mL of dry methylene chloride and added to 45 μL of 2,6-lutidine, and the mixture stirred at room temperature. After 10 minutes, tert-butyldimethylsilyl trifluoromethanesulfonate (64 μL) is added by syringe. After 15 minutes, the reaction mixture is diluted with ethyl acetate, washed with saturated bicarbonate, washed with brine, and the organic phase dried over magnesium sulfate. Removal of solvent in vacuo and flash chromatography on silica gel (ethyl acetate: hexane (1:2) plus 1% methanol) gives the protected compound, which is dissolved in 95% ethanol (2.2 mL) and to which is added 53 μL of pyridine, followed by selenium dioxide (58 mg). The flask is fitted with a water condenser and heated to 70° C. on a mantle. After 20 hours, the mixture is cooled to room temperature, filtered through diatomaceous earth, and the filtrate poured into a saturated sodium bicarbonate solution. This is extracted with ethyl acetate, and the organic phase is washed with brine and dried over magnesium sulfate. The solution is concentrated and purified by flash chromatography on silica gel (ethyl acetate: hexane (1:2) plus 1% methanol) to give the protected 18-hydroxy compound. This compound is dissolved in acetonitrile and treated with aqueous HF to remove the protecting groups. After dilution with ethyl acetate, the mixture is washed with saturated bicarbonate and brine, dried over magnesium sulfate, filtered, and evaporated to yield theI 8-hydroxy compound. Thus, the present invention provides the C-18-hydroxyl derivatives of the compounds described in Examples 1–4.

Those of skill in the art will recognize that other suitable chemical procedures can be used to prepare the novel 18-hydroxy compounds of the invention. See, e.g., Kawai et al., Jan. 1993, Structure-activity profiles of macrolactam immunosuppressant FK-506 analogues, *FEBS Letters* 316 (2): 107–113, incorporated herein by reference. These methods can be used to prepare both the C18-[S]-OH and C18-[R]-OH enantiomers, with the R enantiomer showing a somewhat lower $IC_{50}$, which may be preferred in some applications. See Kawai et al., supra. Another preferred protocol is described in Umbreit and Sharpless, 1977, JACS 99(16): 1526–28, although it may be preferable to use 30 equivalents each of $SeO_2$ and t-BuOOH rather than the 0.02 and 3–4 equivalents, respectively, described in that reference.

All scientific and patent publications referenced herein are hereby incorporated by reference. The invention having now been described by way of written description and example, those of skill in the art will recognize that the invention can be practiced in a variety of embodiments, that the foregoing description and example is for purposes of illustration and not limitation of the following claims.

What is claimed is:

1. An isolated nucleic acid that comprises nucleotides in a nucleotide sequence encoding at least a domain of an extender module of fkbA, wherein the amino acid sequence of fkbA is set forth as SEQ ID NO: 72.

2. The isolated nucleic acid of claim 1, wherein said nucleic acid comprises a coding sequence identical or complementary to a sequence selected from the group consisting of:

nucleotides 52362–53576 of SEQ ID NO:1; nucleotides 53577–54716 of SEQ ID NO:1;

nucleotides 54717–55871 of SEQ ID NO:1; nucleotides 56019–56819 of SEQ ID NO:1;

nucleotides 56943–57575 of SEQ ID NO:1; nucleotides 57711–57920 of SEQ ID NO:1;

nucleotides 57990–59243 of SEQ ID NO:1; nucleotides 59244–60398 of SEQ ID NO:1;

nucleotides 60399–61412 of SEQ ID NO:1; nucleotides 61548–62180 of SEQ ID NO:1;

nucleotides 62328–62537 of SEQ ID NO:1; nucleotides 62598–63854 of SEQ ID NO:1;

nucleotides 63855–65084 of SEQ ID NO:1; nucleotides 65085–66254 of SEQ ID NO:1;

nucleotides 66399–67175 of SEQ ID NO:1; nucleotides 67299–67931 of SEQ ID NO:1;

nucleotides 68094–68303 of SEQ ID NO:1; nucleotides 68397–69653 of SEQ ID NO:1;

nucleotides 69654–70985 of SEQ ID NO:1; nucleotides 71064–71273 of SEQ ID NO:1; and a sequence that encodes an amino acid sequence identical to that encoded by any of the foregoing sequences.

3. The isolated nucleic acid of claim 1, wherein said nucleic acid comprises a coding sequence identical or complementary to nucleotides 52275–71465 of SEQ ID NO:1 or a sequence that encodes an amino acid sequence of SEQ ID NO:72.

4. The isolated nucleic acid of claim 1, wherein said nucleic acid is identical or complementary to SEQ ID NO:1.

5. The isolated nucleic acid of claim 1 wherein the nucleotide sequence encodes an extender module, said module comprising a ketosynthase domain, an acyl transferase domain, and an acyl carrier protein domain.

6. The isolated nucleic acid of claim 1 wherein the nucleotide sequence encodes an open reading frame, said open reading frame comprising coding sequences for two or more extender modules, each extender module comprising a ketosynthase domain, an acyl transferase domain, and an acyl carrier protein domain.

7. The isolated nucleic acid of claim 1 wherein the nucleotide sequence encodes a gene cluster, said gene cluster comprising two or more open reading frames, each of said open reading frames comprising coding sequences for two or more extender modules, each of said extender modules comprising a ketosynthase domain, an acyl transferase domain, and an acyl carrier protein domain.

8. The isolated nucleic acid of claim 1, wherein said nucleic acid is a recombinant vector capable of replication in or integration into the chromosome of a host cell.

9. The isolated nucleic acid of claim 8 that is selected from the group consisting of cosmid pKOS065-M27 and cosmid pKOS065-M21.

10. The isolated nucleic acid of claim 8 wherein the nucleic acid encodes the ketosynthase (KS) domain of extender module 8.

11. The isolated nucleic acid of claim 8 wherein the nucleic acid encodes the inactive dehydratase (DH) domain of extender module 8.

12. The isolated nucleic acid of claim 8 wherein the nucleic acid encodes the ketosynthase (KS) domain of extender module 7.

13. The isolated nucleic acid of claim 8 wherein the nucleic acid encodes the dehydratase (DH) domain of extender module 7.

14. A recombinant DNA vector capable of homologous recombination with the FK-520 polyketide synthase gene in a Streptomyces host cell that produces FK-520, wherein said vector comprises a nucleic acid sequence encoding at least a domain of an extender module of the fkbA enzyme, wherein the amino acid sequence of fkbA is set forth as SEQ ID NO: 72.

15. The vector as in claim 14 wherein the nucleic acid sequence encodes at least the ketosynthase (KS) domain or inactive dehydratase (DH) domain of extender module 8 of the fkbA enzyme.

16. The vector as in claim 14 wherein the nucleic acid sequence encodes at least the ketosynthase (KS) domain or dehydratase (DH) domain of extender module 7 of the fkbA enzyme.

17. A method of preparing a polyketide, said method comprising transforming a host cell with a recombinant DNA vector of claim 12, and culturing said host cell under conditions such that a polyketide synthase is produced and catalyzes the synthesis of said polyketide.

18. The method of claim 17, wherein said host cell is a Streptomyces host cell.

19. The method of claim 17, wherein said polyketide is selected from the group consisting of FK-520, 13-desmethoxy-FK-520 and 13-desmethoxy-13-methyl-FK-520.

20. The method of claim 17 wherein the polyketide is selected from the group consisting of 15-desmethoxy-FK-520; 13,15-didesmethoxy-FK-520; 15-desmethoxy-15-methyl-FK-520; 13,15-didesmethoxy-13-methyl-FK-520; and 13,15-didesmethoxy-15-methyl-FK-520.

21. The method of claim 17 wherein the polyketide is selected from the group consisting of 13-desmethoxy-18-hydroxy-FK-520; 15-desmethoxy-18-hydroxy-FK-520; and 13, 15-didesmethoxy-18-hydroxy-FK-520.

22. The isolated nucleic acid of claim 5 wherein at least one of the ketosynthase domain, the acyl transferase domain or the acyl carrier protein domain is a domain of a module of a non-FK-520 polyketide synthase.

23. The isolated nucleic acid of claim 22, wherein said non-FK-520 polyketide synthase is rapamycin polyketide synthase, FK-506 polyketide synthase, or erythromcyin polyketide synthase.

24. The vector as in claim 14 wherein the nucleic acid sequence encodes at least one domain of an extender module of the fkbA enzyme and at least one domain of a non-FK-520 polyketide synthase.

25. The vector as in claim 24 wherein the non-FK-520 polyketide synthase is rapamycin polyketide synthase, FK-506 polyketide synthase, or erythromycin polyketide synthase.

26. The vector as in claim 24 wherein the non-FK-520 synthase domain is the AT domain of extender module 3, 12, or 13 of the rapamycin polyketide synthase.

27. The vector as in claim 24 wherein the non-FK-520 synthase domain is the AT domain of extender module 1 or 2 of the erythromycin polyketide synthase.

28. A recombinant host cell that expresses a modular recombinant polyketide synthase selected from the group consisting of: (i) FK-520 polyketide synthase in which at least one acyl transferase (AT) domain of fkbA is replaced by an AT domain of a non-FK-520 modular polyketide synthase; and (ii) FK-520 polyketide synthase in which at least one dehydratase (DH) domain of fkbA has been deleted, wherein the amino acid sequence of fkbA is set forth as SEQ ID NO: 72.

29. The recombinant host cell of claim 28 that expresses the FK-520 polyketide synthase in which the AT domain of module 8 has been replaced by an AT domain that binds malonyl CoA, methylmalonyl CoA, or ethylmalonyl CoA.

30. The recombinant host cell of claim 28 that expresses an FK-520 polyketide synthase in which the AT domain of module 7 has been replaced by an AT domain that binds malonyl CoA, methylmalonyl CoA or ethylmalonyl CoA.

31. The recombinant host cell of claim 29 wherein the AT domain of module 8 of fkbA is replaced with the AT domain of module 3, 12, or 13 of rapamycin polyketide synthase.

32. The recombinant host cell of claim 29 wherein the AT domain of module 8 of fkbA is replaced with the AT domain of module 1 or 2 of the erythromycin polyketide synthase.

33. The recombinant host cell of claim 30 wherein the AT domain of module 7 of fkbA is replaced with the AT domain of module 3, 12, or 13 of rapamycin polyketide synthase.

34. The recombinant host cell of claim 30 wherein the AT domain of module 7 fkbA is replaced with the AT domain of module 1 or 2 of the erythromycin polyketide.

* * * * *

SEQUENCE LISTING

```
<160> NUMBER OF SEQ ID NOS: 72

<210> SEQ ID NO 1
<211> LENGTH: 77536
<212> TYPE: DNA
<213> ORGANISM: Streptomyces hygroscopicus
<220> FEATURE:
<221> NAME/KEY: CDS
<222> LOCATION: (52275)...(71465)

<400> SEQUENCE: 1

gatctcaggc atgaagtcct ccaggcgagg cgccgaggtg gtgaacacct cgccgctgct     60
tgtacggacc acttcagtca gcggcgattg cggaaccaag tcatccggaa taaagggcgg    120
ttacaagatc ctcacattgc gcgaccgcca gcatacgctg agttgcctca gaggcaaacc    180
gaaagggcgc gggcggtccg caccagggcg gagtacgcga cgagagtggc gcacccgcgc    240
accgtcacct ctctccccg ccggcgggat gcccggcgtg acacggttgg gctctcctcg    300
acgctgaaca cccgcgcggt gtggcgtcgg ggacaccgcc tggcatcggc cgggtgacgg    360
tacggggagg gcgtacggcg gccgtggctc gtgctcacgg ccgccgggcg gtcatccgtc    420
gagacggcac tcggcgagca gggacgcctg gtcggcacct gcgggccgga cgaccgtgtg    480
gttcgcgggc gggcggtggc cggtggtgag ccagctctcc agggcggtga aggctgagcg    540
gtgacacggc agcaaaggcc ggagtcggtc ggggaaggtg tcgacgaggg cgtcggtgtg    600
cgtgccgtcc tcgatgcggt agtagcggta ccggccgcca ggccgctgcc ggacatacgc    660
gcgtacacgt cggagcccgg gcggcaggca gcagcacgtc gagagtgcct ggatggtgat    720
cagcggcttg ccgatacgac cggtcaacgc gatgcgttcc acggccgcgt ggacgccgga    780
ggagcgggtg gcgtagtcgt agtcggcatc gcagcccggg accgtccccg gggcgcaata    840
cggtgtgccg gcttccttct ccccatcgaa gccggggtcg aactcctcgc ggtagacgcg    900
ctgcgtcaga tcccagtaga cctcgtggtg gtacggccac aagaactcgg agtcggccgg    960
gaacccggcg cggagcagcg cctcgcgcgc ctggccggct gcggggccgc ctgccgcgta   1020
ggtggggtag tcgcgcaggg cggccggcag gaaggtgaag aggttgggac cctccgcgcg   1080
ccacagggtg ccttcccagt cgactcctcc gtcgtacagc tcgggatggt tctccagctg   1140
ccagcgcacg aggtagccgc cgttggacat cccggtgacc agggtgcgct cgagcggccg   1200
```

-continued

```
gtggtagcgc tgggcgaccg acgcgcgggc ggcccgggtc agctgggtga ggcgggtgtt   1260
ccactcggcg acggcgtcgc ccggccggga gccatcacgg tagaacgcgg ggccggtgtt   1320
gcccttgtcg gtggcggcgt aggcgtaacc gcgggcgagc acccagtcgg cgatggcccg   1380
gtcgttggcg tactgctcgc ggttaccggg ggtgccggcc acgaccaggc caccgttcca   1440
gcggtcgggc agccggatga cgaactgggc gtcgtggttc cacccgtggt tggtgttggt   1500
ggtggaggtg tcggggaagt agccgtcgat ctggatcccg ggcactccgg tgggagtggc   1560
caggttcttg ggcgtcagcc ctgcccagtc cgccgggtcg gtgtggccgg tggccgccgt   1620
tcccgccgtg gtcagctcgt ccaggcagtc ggcctgctga cgtgccgccg ccgggacacg   1680
cagctgggac agacgggcgc agtgaccgtc cggggcatcg ggagcaggcc gggccgtggc   1740
cggtgagggg agcaggacgg cgactgcggc cagggtgaga gcgccgaggc cggtgcgtct   1800
tctcggggcc cgtccgacac cgaggggcag aaccatggag agcctccaga cgtgcggatg   1860
gatgacggac tggaggctag gtcgcgcacg gtggagacga acatgggtgc gcccgccatg   1920
actgaggccc ctcagaggtg ggccgccgcc atgacgggcg cgggaccgcg ggcgctccgg   1980
ggcggtgccc gcggccgcca ccggttccgg gtccccgggt cagggacagg tgtcgttcgc   2040
gacggtgaag tagccggtcg gcgactcttt caaggtggtc gtgacgaagg tgttgtacag   2100
gcccatgttc tggccggagc ccttggcgta ggtgtaaccg gcgctcgtcg tggcgcggcc   2160
cgcctggacg tgagcgtagt tgccggcggt ccagcagacg gccgtggcac cggtcgtctg   2220
cgcggtgacc gcgcccgaga gcggtccggc cttgccgtcc gcgtcccggg cggcgaccgc   2280
gtaggtgtgc gatgtgcccg ccctcaggcc ggtgtccgtg tacgacgtcg tggcggacgt   2340
ggtgatctgg gcaccgtcgc ggtggacggc gtagtcggtg gcgccgtcga cgggtttcca   2400
ggtcaggctg atggtggtgt cggtggcgcc ggtggcggcc aggccggacg gagcgggcag   2460
cgaaccgggg tcggaggcgg atccgctcag gccgaagaac tgcgtgatcc agtagctgga   2520
acagatcgag tccaggaagt aggcggcgcc ggtgctgccg cactgctgtg ctccggtgcc   2580
gggatcgacc ggggtgccgt gcccgatgcc cggcacccgg ttcacctcca cggccaccga   2640
tccgtccgcg gccaggtact cctcgtgccg ggtggagttc gggccgatca ccgaggtacg   2700
gtccggcgtc tgggacacgc cgtgcacagc ggtccactgg tcgcgcaact cgtcggcgtt   2760
gcgcggcgcg acggtggtgt ccttgtcgcc gtgccagatg gccacgcgcg gccacgggcc   2820
cgaccacgag gggtagccgt cacggacccg ccgcgcccac tggtccgcgg tcaggtcggt   2880
cccggggttc atgcacaggt acgcgctgct gacgtcggtg gcacagccga agggcaggcc   2940
ggcgacgacc gcgccggcct ggaagacgtc cggataggtg gcgagcatca ccgacgtcat   3000
ggcaccgccg gcggacagcc cggtgatgta ggtgcgctgg gggtccgcgc cgtaggcgga   3060
gacggtgtga gcggccatct gccggatcga cgcggcttcg ccctggcccc tgcggttgtc   3120
gctgctctgg aaccagttga agcacctgtt cgcgttgttc gacgacgtgg tctcggcgaa   3180
cacgagcagg aagccatagc ggtccgcgaa tgagagcagg ccggagttgt cggcgtagcc   3240
ctgggcgtcc tgggtgcaac cgtgcagggc gaacaccacc gccggctccg cgggcaggga   3300
cgcgggccgg tagacgtaca tgttcagccg gcccgggttc gtgccgaagt ccgcgacctc   3360
ggtcaggtcc gccttggtca gaccgggctt ggccaggccc gccgcggcgt gggccgtcgg   3420
cgccgggccg agcagggccg ctccgagtac gagggccacg acggccacga gacgggtgag   3480
caccccccgc cgtcccggac gcgacaacga cccgaccggc ggcgaggagg agagggggaa   3540
```

-continued

```
cagcggggtg aggattcccc ggaacggcgg cggctgcatg gcggctccct cgatgtcgtg   3600
ggggggacac ggagggctcc ctgacgtcga tcagtgggag cgccccggtg cccggcaccg   3660
taggggtggt tcaacccgca acggtatggc ccggagcacc acaccccgca ccgcgcgatg   3720
tgcgcccgga cggattgtgt cgccttgcgg aatctgatac ccggacgcga cgaacgcccc   3780
acccgacacg ggtagggcgt catggtgtcc gactcggccg gtcggccttg cctgccctgg   3840
acggaccggg cgtcggcgga ccgggcgtcg gcgggctggg cggtatggcg gccgaggacg   3900
ccagccgcgt ggggcggccg cgcccaagtg cagtacgccg accgtggccg gcgggagggc   3960
cggaccggtc agtgcagtcc cgcggccctg cgggaccgct cgtcccagac gggttccacc   4020
gcggcgaacc ggggtccgtg tccgcggcgg tagaccatca gtgtccgctc gaaggtgatg   4080
acgatgacac cgtcctggtt gtagccgatg gtgcgcacgc tgatgatgcc tacgtcaggt   4140
cggctggcgg actcccgggt gttcaggacc tcggactgcg agtagatggt gtcgccctcg   4200
aagaccgggt tcggcagcct gacccggtcc cagccgaggt tggccatcac atgctgggag   4260
atgtcggtga cgctctgccc ggtgaccagg gcgagggtga aggtggagtc caccagcggc   4320
ttgccccagg tggtgcccgc cgagtagtgg cggtcgaagt gcagcggcgc ggtgttctgc   4380
gtcaggagcg tgagccagga gttgtcggtc tccaggaccg tgcggcccag ggggtggcgg   4440
tacacgtcgc cggtggtgaa gtcctcgaag tagcggccct gccagccctc gaccacagcg   4500
gtgcgggtgg cgtcctggtc cgggttctca gtcgtcatgg cgctcattct gggaagtccc   4560
cggtccgctg tgaaatgccg aaccttcacc gggctcatac gtgcggcgca tgagccctgg   4620
accgtacgta gtcgtagaac ctcgccacca ctggcgcgcg tggtcctccg gcgagtgtga   4680
ccacgccgac cgtgcgccgc gcctgcgggt cgtcgagcgg cacggcgacg gcgtggtcac   4740
cgggcccgga cggctgccg gtgagggggg cgacggccac accgaggccg gcggcgacca    4800
gggcccgcag cgtgctcagc tcggtgctct ccaggacgac ccgcggcacg aatccggccg   4860
cggcgcacag ccggtcggtg atctggcgca gtccgaagac cggctccagt gccacgaacg   4920
cctcatcggc cagctccgcg gtccgcaccc ggcggcgtct ggccagccgg tgtccgggtg   4980
ggacgagcag gcacagtgcc tcgtcccgca gtggtgtcca ctccacatcg tccccggcgg   5040
gtcgtgggct ggtcagcccc aggtccagcc tgctgttgcg gacgtcgtcg accacggcgt   5100
cggcggcgtc gccgcgcagt tcgaaggtgg tgccgggagc cagccggcgg tacccggcga   5160
ggaggtcggg caccagccag gtgccgtagg agtgcaggaa acccagtgcc acggtgccgg   5220
tgtcggggtc gatcagggcg gtgatgcgct gctcggcgcc ggagacctca ctgatcgcgc   5280
gcagggcgtg ggcgcggaag acctcgccgt acttgttgag ccggagccgg ttctggtgcc   5340
ggtcgaacag cggcacgccc actcgtcgct ccagccgccg gatggccctg gacagggtcg   5400
gctgggagat gttgagccgt tccgcggtga tcgtcacgtg ctcgtgctcg gccaaggccg   5460
tgaaccactg caactcccgt atctccatgc agggactata cgtaccgggc atggtcctgg   5520
cgaggtttcg tcatttcaca gcggccgggc ggcggcccac agtgagtcct caccaaccag   5580
gaccccatgg gagggacccc atgtccgagc cgcatcctcg ccctgaacag gaacgccccg   5640
ccgggcccct gtccggtctg ctcgtggttt ctttggagca ggccgtcgcc gctccgttcg   5700
ccacccgcca cctggcggac ctgggcgccc gtgtcatcaa gatcgaacgc cccggcagcg   5760
gcgacctcgc ccgcggctac gaccgcacgg tgcgtggcat gtccagccac ttcgtctggc   5820
tgaaccgggg gaaggagagc gtccagctcg atgtgcgctc gccggagggc aaccggcacc   5880
tgcacgcctt ggtggaccgg gccgatgtcc tggtgcagaa tctggcaccc ggcgccgcgg   5940
```

-continued gccgcctggc atcggccacc aggtcctcgc gcggagccac cgaggctgat cacctgcgga 6000
catatccggc tacggcagta ccggctgcta ccgcggaccg caaggcgtac gacctcctgg 6060
tccagtgcga agcggggctg gtctccatca ccggcacccc cgagaccccg tccaaggtgg 6120
gcctgtccat cgcggacatc tgtgcgggga tgtacgcgta ctccggcatc ctcacggccc 6180
tgctgaagcg ggcccgcacc ggccggggct cgcagttgga ggtctcgatg ctcgaagccc 6240
tcggtgaatg gatgggatac gccgagtact acacgcgcta cggcggcacc gctccggccc 6300
gcgccggcgc cagccacgcg acgatcgccc cctacggccc gttcaccacg cgcgacgggc 6360
agacgatcaa tctcgggctc cagaacgagc gggagtgggc ttccttctgc ggtgtcgtgc 6420
tacaacgccc cggtctctgc gacgacccgc gcttttccgg caacgccgac cgggtggcgc 6480
accgcaccga gctcgacgcc ctggtgagcg aggtgacggg cacgctcacc ggcgaggaac 6540
tggtggcgcg gctggaggag gcgtcgatcg cctacgcacg ccagcgcacc gtgcgggagt 6600
tcagcgaaca cccccaactg cgtgaccgtg gacgctgggc tccgttcgac agcccggtcg 6660
gtgcgctgga gggcctgatc cccccggtca ccttccacgg cgagcacccg cggcggctgg 6720
gccgggtccc ggagctgggc gagcataccg agtccgtcct ggcgtggctg gccgcgcccc 6780
acagcgccga ccgcgaagag gccggccatg ccgaatgaac tcaccggagt cctgatcctg 6840
gccgccgtgt tcctgctcgc cggcgtacgg gggctgaaca tgggcctgct cgcgctggtc 6900
gccacctttc tgctcggggt ggtcgcactc gaccgaacgc cggacgaggt gctggcgggt 6960
ttccccgcga gcatgttcct ggtgctggtc gccgtcacgt tcctcttcgg gatcgcccgc 7020
gtcaacggca cggtggactg gctggtacgt gtcgcggtgc gggcggtggg ggcccgggtg 7080
ggagccgtcc cctgggtgct cttcggcctg gcggcactgc tctgcgcgac aggcgcggcc 7140
tcgcccgcgg cggtggcgat cgtggcgccg atcagcgtcg cgttcgccgt caggcaccgc 7200
atcgatccgc tgtacgccgg actgatggcg gtgaacgggg ccgcagccgg cagtttcgcc 7260
ccctccggga tcctgggcgg catcgtccac tcggcgctgg agaagaacca tctgcccgtc 7320
agcggcgggc tgctcttcgc aggcaccttc gccttcaacc tggcggtcgc cgcggtgtca 7380
tggctcgtcc tcgggcgcag gcgcctcgaa ccacatgacc tggacgagga caccgatccc 7440
acggaagggg acccggcttc ccgccccggc gcggaacacg tgatgacgct gaccgcgatg 7500
gccgcgctgg tgctgggaac cacggtcctc tccctggaca ccggcttcct ggccctcacc 7560
ttggcggcgt tgctggcgct gctcttcccg cgcacctccc agcaggccac caaggagatc 7620
gcctggcccg tggtgctgct ggtatgcggg atcgtgacct acgtcgccct gctccaggag 7680
ctgggcatcg tggactccct ggggaagatg atcgcggcga tcggcacccc gctgctggcc 7740
gccctggtga tctgctacgt gggcggtgtc gtctcggcct tcgcctcgac caccgggatc 7800
ctcggtgccc tgatgccgct gtccgagccg ttcctgaagt ccggtgccat cgggacgacc 7860
ggcatggtga tggccctggc ggccgcggcg accgtggtgg acgcgagtcc cttctccacc 7920
aatggtgctc tggtggtggc caacgctccc gagcggctgc ggcccggcgt gtaccagggg 7980
ttgctgtggt ggggcgccgg ggtgtgcgca ctggctcccg cggccgcctg ggcggccttc 8040
gtggtggcgt gagcgcagcg gagcgggaat cccctggagc ccgtttcccg tgctgtgtcg 8100
ctgacgtagc gtcaagtcca cgtgccgggc gggcagtacg cctagcatgt cgggcatggc 8160
taatcagata accctgtccg acacgctgct cgcttacgta cggaaggtgt ccctgcgcga 8220
tgacgaggtg ctgagccggc tgcgcgcgca gacggccgag ctgccgggcg gtggcgtact 8280

-continued

```
gccggtgcag gccgaggagg gacagttcct cgagttcctg gtgcggttga ccggcgcgcg   8340
tcaggtgctg gagatcggga cgtacaccgg ctacagcacg ctctgcctgg cccgcggatt   8400
ggcgcccggg ggccgtgtgg tgacgtgcga tgtcatgccg aagtggcccg aggtgggcga   8460
gcggtactgg gaggaggccg gggttgccga ccggatcgac gtccggatcg gcgacgcccg   8520
gaccgtcctc accgggctgc tcgacgaggc gggcgcgggg ccggagtcgt tcgacatggt   8580
gttcatcgac gccgacaagg ccggctaccc cgcctactac gaggcggcgc tgccgctggt   8640
acgccgcggc gggctgatcg tcgtcgacaa cacgctgttc ttcggccggg tggccgacga   8700
agcggtgcag gacccggaca cggtcgcggt acgcgaactc aacgcggcac tgcgcgacga   8760
cgaccgggtg gacctggcga tgctgacgac ggccgacggc gtcaccctgc tgcggaaacg   8820
gtgaccgggg cgatgtcggc ggcggtcagc gtcagcgtcg tcggcgcggg cctcgcggag   8880
ggctccagat gcaggcgttc gacgccggcg gcggaagcgc ccgccacctc ggacacgcag   8940
gggcagtcgg agtccgcgaa gcccgcgaac cggtaggcga tctccatcat gcggttgcgg   9000
tccgtacgcc ggaagtccgc caccaggtgc gcccccgcgc gggcgccctg gtccgtgagc   9060
cagttcagga tcgtcgcacc ggcaccgaac gacacgaccc ggcaggacgt ggcgagcagt   9120
ttcaggtgcc acgtcgacgg cttcttctcc agcaggatga tgccgacggc gccgtgcggg   9180
ccgaagcggt cgcccatggt gacgacgagg acctcatggg cgggatcggt gagcacgcgc   9240
gcaggtcggc gtcggagtag tgcacgccgg tcgcgttcat ctggctggtc cgcagcgtca   9300
gttcctcgac gcggctgagt tcctcctccc ccgcgggtgc gatcgtcatg gagaggtcga   9360
gcgagcgcag gaagtcctcg tcgggaccgg agtacgcctc ccgggcctgg tcgcgcgcga   9420
aacccgcctg gtacatcagg cggcgccgac gcgagtcgac cgtggacacc ggcgggctga   9480
actccggcag cgacaggagc gtggccgcct gctcggccgg gtagcaccgc acctcgggca   9540
ggtggaacgc cacctcggca cgctcggcgg gctggtcgtc gatgaacgcg atcgtggtcg   9600
gtgcgaagtt cagctccgtg gcgatctcgc ggacggactg cgacttcggc cccatccga    9660
tgcgggccag cacgaagtac tccgccacac cgaggcgttc cagacgctcc cacgcgaggt   9720
cgtggtcgtt cttgctcgcc accgcctgga ggatgccgcg gtcgtcgagc gtggtgatca   9780
cctcgcggat ctcgtcggtg aggaccacct cgtcgtcctc cagcacggtg ccccgccaca   9840
aggtgttgtc caggtcccag accagacact tgacaatggt catggctgtc ctctcaagcc   9900
gggagcgcca gcgcgtgctg ggccagcatc acccggcaca tctcgctgct gccctcgatg   9960
atctccatga gcttggcgtc gcggtacgcc cgttcgacga cgtgtccctc tctcgcgcct  10020
gccgacgcga gcacctgtgc ggcggtcgcg gccccggcgg cggctcgttc ggcggcgacg  10080
tgcttggcca ggatcgtcgc gggcaccatc tcgggcgagc cctcgtccca gtggtcgctg  10140
gcgtactcgc acacgcgggc cgcgatctgc tccgcggtcc acaggtcggc gatgtgcccg  10200
gcgacgagtt ggtggtcgcc gagcggccgg ccgaactgct cccgggtccg ggcgtgggcc  10260
accgcggcgg tgcggcaggc ccgcaggatc ccgacgcagc cccaggcgac cgacttgcgc  10320
ccgtaggcga gtgacgccgc gaccagcatc ggcagtgacg cgccggagcc ggccaggacc  10380
gcgccggccg gcacacgcac ctggtccagg tgcagatcgg cgtggccggc ggcgcggcag  10440
ccggacggct tcgggacgcg ctcgacgcgt acgccggggg tgtcggcggg cacgaccacc  10500
accgcaccgg aaccatcctc ctggagaccg aagacgacca ggtggtccgc gtaggcggcg  10560
gcagtcgtcc agaccttgtg gccgtcgacg acagcggtgt ccccgtcgag ccgaacccgc  10620
gtccgcatcg ccgacagatc gctgcccgcc tgccgctcac tgaagccgac ggccgcgagt  10680
```

```
ttcccgctgg tcagctcctt caggaaggtc gcccgctgac cggcgtcgcc gagccgctgc  10740
acggtccacg cggccatgcc ctgcgacgtc atgacactgc gcagcgaact gcagaggctg  10800
ccgacgtgtg cggtgaactc gccgttctcc cggctgccga gtcccagacc gccgtgctcg  10860
gccgccactt ccgcgcagag caggccgtcg gcgccgagcc ggacgagcag gtcgcgcggc  10920
agttcgccgg acgtgtccca ctcggcggcc cggtcaccga caaggtcggt cagcagcgcg  10980
tcacgctcag gcatcgacgg cccgcagccg gtggacgagt gcgaccatgg actcgacggt  11040
acggaagttc gcgagctgga ggtccgggcc ggcgatcgtg acgtcgaacg tcttctccag  11100
gtacacgacc agttccatcg cgaacagcga cgtgaggccg ccctccgcga acaggtcgcg  11160
gtccacgggc cagtccgacc tggtcttcgt cttgaggaac gcgaccaacg cgtgcgcgac  11220
ggggtcgtcc ttgacgggtg cggtcatgag aacaccttct cgtattcgta gaagccccgg  11280
ccggtcttcc ggccgtggtg tccctcgcgg accttgccca gcagcaggtc acaggggcgg  11340
ctgcgctcgt cgccggtgcg tttgtgcagc acccacagcg cgtcgacgag gttgtcgatg  11400
ccgatcaggt ccgcggtgcg cagcggcccg gtcggatggc cgaggcaccc cgtcatgagc  11460
gcgtcgacgt cctcgacgga cgcggtgccc tcctgcacga tccgcgccgc gtcgttgatc  11520
atcgggtgga gcagccggct cgtgacgaag ccgggcgcgt cccggacgac gatcggcttg  11580
cgccgcagcg ccgcgagcag gtccccggcg gcggccatgg ccttctcacc ggtccggggt  11640
ccgcggatca cctcgaccgt cgggatcagg tacgacgggt tcatgaagtg cgtgccgagc  11700
aggtcctcgg gccgggccac ggagtcggcc agttcgtcaa ccgggatcga cgacgtgttc  11760
gtgatgaccg ggataccggg cgccgctgcc gagaccgtgg cgagtacctc cgccttgacc  11820
tcggcgtcct cgacgacggc ctcgatcacc gcggtggccg taccgatcgc gggcagcgcg  11880
gacgtggccg tccgcagcac accggggtcg gcctcggcgg gcccggccac gagttgtgcc  11940
gtccgcagtt cggtggcgat ccgcgcccgc gccgccgtaa ggatctcctc ggacgtgtcg  12000
acgagtgtca ccgggacgcc gtggcgcagc gcgagcgtgg tgatgccggt gcccatcact  12060
cccgcgccga gcacgatcag ctggtggtcc acgctgtttc ctccctccgg ggtcaccatg  12120
gcagcgagta cgggtcgagg acgtcttccg gggtcgaccc gatcgcgtcc ttgcggccga  12180
ggccgagttc gtcggcgaag ccgagcagca cgtcgaacgc gatgtggtcg gcgaacgcgc  12240
tgcccgtcga gtcgaggacg ctcaggctgt cccggtggtc cgccgcggtg tccggtgccg  12300
cgcacagggc cgccagcgac gggccgagct cgcggtccgg cagttgctgg tactcgccct  12360
cggcgcgggc ctgccccgga tggtcgacgc agatgaacgc gtcgtcgagc agggtcttcg  12420
gcagttcggt cttgcccggc tcgtcggcgc cgatggcgtt cacatgcagg tgcggcagcc  12480
gcggctcggc gggcagcacc ggccctttgc ccgagggcac cgaggtgacg gtggacagga  12540
catccgcggc ggcggcggcc tccgccggat cggtcacctt gaccggcagt ccgaggaacg  12600
cgatgcggtc cgcgaacgac gccgcgtggc cggggtcggt gtcgctgacc aggatccgct  12660
cgatgggcag gaccctgctg agcgcgtgcg cctgggtcac cgcctgtgcg cccgcgccga  12720
tcagcgtgag cgtggcgctg tcggaccggg ccagcagccg gctcgcgacg gcggcgaccg  12780
cgccggtccg catcgcggtg atcacgcctg cgtcggcgag ggcggtcaga ctgccgctgt  12840
cgtcgtcgag gcgcgacatc gtgccgacga tcgtcggcag ccggaagcgc ggatagttgt  12900
gcggactgta cgaaaccgtc ttcatggtca cgccgacacc ggggacccgg tacggcatga  12960
actcgatgac gccgggaatg tcgccgccgc ggacgaatcc ggtacgcggc ggcgcctcgg  13020
```

-continued

```
cgaactcgcc gcggccgagc gcggcgaacc cgtcgtgcag ctcgctgatc agccggtcca  13080
tcatcacgtc gcggccgatc acggagagaa tccgcttgat gtcacgttgg cgcaggaccc  13140
tggtctgcat gtgtcacctc cctttcgtgg ccggagctgt cttggtggtg ccgctcgggg  13200
cggcttccgt tctcatcgca gctccctgtc gatgaggtcg aaaatctcgt ccgcggtcgc  13260
gtccgcggac agcacgccgg ccggcgtggt cgggcgggtc tcccgccgcc agcggttgag  13320
cagggcgtcc agccgggttc cgatcgcgtc cgcctggcgg gcgcccgggt cgacaccggc  13380
aacgagtgct tccagccggt cgagctgcgc gagcaccacg gtcaccgggt cgtccgggga  13440
cagcagttca ccgatgcggt cggcgagtgc gcgcggcgac gggtagtcga agacgagcgt  13500
ggcggacagt cgcagaccgg tcgcctcgtt gaggccgttg cgcagctgca ccgcgatgag  13560
cgagtccaca ccgagttccc ggaacgccgc gtcctccggg atgtcctccg ggtcggcgtg  13620
gcccaggacg gccgctgcct tctgccggac gagggcgagc aggtcggtgg ggcgttcctg  13680
ctcgttgcgg gcgctccggc gggccgacgg cttgggccgg ccacgcagca gcgggaggtc  13740
cggcggcagg tcgcccgcca cggcgacgac actgcccgtt ccggtgtgga cggcggcgtc  13800
gtacatgcgc atgccctgtt cggcggtgag cgcgctcgcc ccacccttgc gcatacggcg  13860
ccggtcggcg tcggtcaggt ccgcggtcag gccactcgcc tggtcccaca gcccccacgc  13920
gatcgacagc cctggcagcc cttgtgcacg ccggtgttcg gcgagcgcgt cgaggaacgc  13980
gttcgccgcc gcgtagttgc cctgaccggg ggtgcccagc acaccggccg ccgacgagta  14040
gacgacgaat gcggcgaggt cggtgtcgcg ggtgagccgg tgcaggtgcc aggcggcgtc  14100
ggccttgggt ttgaggacgg tgtcgatgcg gtcgggggtg aggttgtcga gcagggcgtc  14160
gtcgagggtt ccggcggtgt ggaagacggc ggtgaggggt tgagggatgt gggcgagggt  14220
ggtggcgagt tggtgggggt cgccgacgtc gcaggggagg tgggtgccgg gggtggtgtc  14280
ggggggtggg gtgcgggaga ggaggtaggt gtgggggtgg ttcaggtggc gggcgaggat  14340
gccggcgagg gtgccggagc cgccggtgat gacgacggcc ccctcggggt ccagcggccg  14400
cgggaccgtg aggacgatct tgccggtgtg ctcgccgcgg ctcatggtcg ccagcgcctc  14460
gcggacctgc cgcatgtcgt gcaccgtcac cggcagcggg tgcagcacac cgcgcgcgaa  14520
caggccgagc agctccgcga tgatctcctt gagccggtcg ggccccgcgt ccatcaggtc  14580
gaacggtcgc tggacggcgt gccggatgtc cgtcttcccc atctcgatga accggccacc  14640
cggcgcgagc aggccgacgg acgcgtcgag gagttcaccg gtgagcgagt tgagcacgac  14700
gtcgaccggc gggaacgcgt cggcgaacgc ggtgctgcgg gaatcggcca gatgcgctcc  14760
gtccaggtcc accagatggc gcttcgcggc gctggtggtc gcgtacacct ccgcgcccag  14820
gtgccgcgcg atctgccggg cggcggaacc gacaccgccg gtggccgcgt ggatcaggac  14880
cttctcgccg gggcgcagcc cggcgaggtc gaccaggccg taccacgcgg tcgcgaacgc  14940
ggtcatcacg gacgccgcct gcgggaacgt ccagccgtcc ggcatccggc cgagcatccg  15000
gtggtcggcg atgaccgtgg ggccgaagcc ggtgccgacg aggccgaaga cgcggtcgcc  15060
cggtgccaga ccggagacgt cggcgccggt ctccaggacg atgcccgcgg cctcgccgcc  15120
gagcacgccc tgaccggggt aggtgccgag cgcgatcagc acatcgcgga agttgaggcc  15180
cgccgcacgc acaccgatcc ggacctcggc cggggcgagg gggcgccggg gctccgccga  15240
gtcggccgcg gtgaggccgt cgagggtgcc cgtccgcgcc ggccggatca gccacgtgtc  15300
gctgtccggc acggtgagcg gctccggcac ccgggtgagg cgggccgcct cgaaccggcc  15360
gccgcgcagc cgcagacgcg gctcgccgag tgcgacggcg atgcgctgct gctcgggggc  15420
```

```
gagcgtgacg ccggactcgg tctcgacgtg gacgaaccgg ccgggctgct cggcctgggc  15480
ggcgcgcagc agtccggccg ccgcgccggt ggcgaggccc gcggtggtgt gcacgagcag  15540
atccccgccg gagccggtca gggcggtcag cagccgggtg gtgagcgcac gcgtctcggc  15600
caccgggtcg tcgccatcag cggcaggcaa cgtgatgacg tccacgtcgg tcgcggggac  15660
atccgtgggt gcggcgacct cgatccaggt gagacgcatc aggccggtgc cgacgggtgg  15720
ggacagcggg cgggtgcgga ccgtccggat ctcggcgacg agttggccgg cggagtcggc  15780
gacgcgcaga ctcagctcgt cgccgtcacg agtgatcacg gctcggagca tggccgagcc  15840
cgtggcgacg aaccgggccc ccttccaggc gaacggcaga cccgcagcgc tgtcgtccgg  15900
cgtggtgagg gcgacggcgt gcagggccgc gtcgagcagc gccggatgca caccgaaacc  15960
gtccgcctcg gcggcctgct cgtcgggcag cgccacctcg gcatacacgg tgtcaccatc  16020
acgccaggca gcccgcaacc cctggaacgc cgacccgtac tcataaccgg catcccgcag  16080
ttcgtcatag aaccccgaga cgtcgacggc cacggccgtg accggcggcc actgcgagaa  16140
cggctccaca ccgacaacac cgggggtgtc gggggtgtcg ggggtcaggg tgccgctggc  16200
gtgccgggtc cagctgcccg tgccctcggt acgcgcgtgg acggtcaccg gccgccgtcc  16260
ggcctcatca gccccttcca cggtcaccga cacatccacc gctgcggtca ccggcaccac  16320
aagggggggat tcgatgacca gctcgtccac tatcccgcaa ccggtctcgt caccggcccg  16380
gatgaccagc tccacaaacg ccgtacccgg cagcaggacc gtgccccgca ccgcgtgatc  16440
agccagccag gggtgagtgc gcaatgagat ccggccagtg agaacaacac caccatcgtc  16500
ggcgggcagc gctgtgacag cggccagcat cggatgcgcc gcacccgtca accccgccgc  16560
cgacagatcg gtggcaccgg ccgcctccag ccagtaccgc ctgtgctcga acgcgtacgt  16620
gggcagatcc agcagccgtc ccggcaccgg ttcgaccacc gtgtcccagt ccactgccgt  16680
gcccagggtc cacgcctgcg ccaacgccgt cagccaccgc tcccagccgc cgtcaccggt  16740
ccgcaacgac gccaccgtgt gagcctgctc catcgccggc agcagcaccg gatgggcact  16800
gcactccacg aacaccgacc catccagctc cgccaccgcc gcgtccaacg ccaccggacg  16860
acgcagattc cggtaccagt acccctcatc caccggctcc gtcacccagg cgctgtccac  16920
ggtcgaccac cacgccaccg acgcggcctt ccctgccacc ccctccagta ccttggccag  16980
ttcatcctcg atggcttcca cgtggggcgt gtgggaggcg tagtcgaccg cgatacgacg  17040
cacccgcacg ccttcggcct cataccgcgc caccacctcc tccaccgccg acgggtcccc  17100
cgccaccacc gtcgaagccg ggccgttacg cgccgcgatc cacacaccct cgaccagacc  17160
gacctcaccg gccggcaacg ccaccgaagc catcgctccc cgcccggcca gtcgcgccgc  17220
gatgacctga ctgcgcaatg ccaccacgcg ggcggcgtcc tcgaggctga gggctccggc  17280
cacgcacgcc gccgcgatct cgccctggga gtgtccgatc accgcgtccg gcacgacccc  17340
atgcgcctgc cacagcgcgg ccaggctcac cgcgaccgcc cagctggccg gctggaccac  17400
ctccacccgc tccgccacat ccggccgcgc caacatctcc cgcacatccc agcccgtgtg  17460
cggcagcaac gcctgagcgc actcctccat acgcgcggcg aacaccgcgg agtgggccat  17520
gagttccacg cccatgccga cccactgggc gccctggccg gggaagacga acaccgtacg  17580
cggctggtcc accgccacac ccgtcacccg ggcatcgccc agcagcaccg cacggtgacc  17640
gaagacagca cgctcccgca ccaacccctg cgcgaccgcg gccacatcca caccaccccc  17700
gcgcagatac ccctccagcc gctccacctg cccccgcaga ctcacctcac cacgagccga  17760
```

-continued

```
caccggcaac ggcaccaacc cgtcaacaac cgactcccca cgcgacggcc caggaacacc  17820
ctcaaggatc acgtgcgcgt tcgtaccgct caccccgaac gacgacacac ccgcatgcgg  17880
tgcccgatcc gactcgggcc acggcctcgc ctcggtgagc agctccaccg caccggccga  17940
ccagtccaca tgcgacgacg gctcgtccac atgcagcgtc ttcggcgcga tcccgtaccg  18000
catcgccatg accatcttga tcacaccggc gacacccgcc gccgcctgcg catgaccgat  18060
gttcgacttc aacgaaccca gcagcagcgg aacctcacgc tcctgcccgt acgtcgccag  18120
aatggcctgc gcctcgatgg gatcgcccag cgtcgtcccc gtcccgtgcg cctccaccac  18180
gtccacatcg gcggcgcgca gtccggcgtt caccaacgcc tgctggatga cacgctgctg  18240
ggacgggccg ttgggggcgg acagcccgtt ggaggcaccg tcctggttca ccgccgaccc  18300
gcggacgacc gcgagaacgg tgtgtccgtt gcgctcggcg tcggagagcc gctccagcac  18360
aagaacgccg gcgccctccg cccagccggt gccgttggcg gcgtccgcga acgcgcggca  18420
gcggccgtcg ggggagagtc cgccctgctg ctggaattcc acgaacccgg tcggggtcgc  18480
catgacggtg acaccgccga ccagcgccag cgagcactcc ccgtggcgca gtgcgtgccc  18540
ggcctggtgc agcgcgacca gcgacgacga gcacgccgtg tccaccgtga acgccggtcc  18600
ctggagccca tagaagtacg agatccggcc ggtgagcacg ctgggctgca tgccgatcga  18660
gccgaacccg tccaggtccg cgccgacgcc gtacccgtac gagaaggcgc ccatgaacac  18720
gccggtgtcg ctgccgcgca gtgtgcccgg cacgatgccc gcgctctcga acgcctccca  18780
tgtcgtttcc agcaggatcc gctgctgggg gtccatggcc cgtgcctcac gggggctgat  18840
gccgaagaac gcggcatcga agccggcggc gtcggagagg aagccgccgc ggtccgtgtc  18900
cgatccgccg gtgaggccgg acgggtccca gccacggtcg gccgggaagc cggtgaccgc  18960
gtcgccgcca ctgtccacca tgcgccacag gtcgtcgggc gaggtgacgc cgcccggcag  19020
tcggcaggcc atgcccacga tggccagcgg ttcgtcacgg gtcgcggcgg ctgtgggaac  19080
agcgaccggt gcggcaccac cgaccagagc ctcgtccaac cgcgacgcga tggcccgcgg  19140
cgtcgggtag tcgaagacaa gcgtggcggg cagtcggaca ccggtcgccg cggcgagtcg  19200
gttccgcagt tcgacggcgg tcagcgagtc gatacccagt tccttgaagg ccgcgtccgc  19260
ggacacgtcc gcggcgtccg cgtggccgag caccgccgcc gcgttgtcgc ggaccagtgc  19320
cagcagcgcg gtgtcccgct cagcgccgga catggtgccg agccggtcgg cgagcggaac  19380
ggcggtggcc gccgccgggc gcgatacggc gcggcgcaga tcggcgaaaa gcggcgatgt  19440
gtgcgcggtg aggtccatcg tggccgccac ggcgaacgcg gtgccggttc cggccgcggc  19500
ttccagcagg cgcatgccca caccggccga catggggcgg aaaccgccgc ggcggacacg  19560
ggtgcggttg gtgccgctca tgctgccggt gagtccgctg tcatcggccc agaggcccca  19620
ggccagcgac agcgcgggca gtccttcggc atggcgcagc gtcgcgagtc cgtcgaggaa  19680
cccgttcgcc gccgagtagt tgccctggcc gcggccgccc atgatgcccg cgacggacga  19740
gtagaggacg aacgagcgca ggtccgcgtc ccgggtcagc tcgtgcaggt gccaggcgcc  19800
gtcggctttg ggcgcagtg tggtggcgag ccgctccggg gtgagtgccg tggtcacgcc  19860
gtcgtcgagc acggctgccg tgtggaagac cgccgtgagc ggcctgccgg cggcggcgag  19920
cgcggcggcg agctggtccc ggtcggcgac gtcacagcgg atgtggacac cgggagtgtc  19980
cgccggcggt tcgctgcgcg acagcaacag gaggtggcgg gcgccatgct cggcgacgag  20040
atgccgggcg aggagacctg ccagcacacc cgagccgccg gtgatgacca ccgtgccgtc  20100
cgggtcgagc agcggttcgg gcgtttccgc ggcggccgtg cgggtgaacc gcggcgcttc  20160
```

```
gtaccggccg tcggtgacgc ggacgtacgg ctcggccagt gtcgtggcgg cggccagcgc 20220
ctcgatgggg gtgtcggtgc cggtctccac cagcacgaac cggcccgggt gctcggcctg 20280
ggcggaccgg acgaggccgg cgaccgctcc tccgaccggt cccgcgtcga tccggacgac 20340
gagggtggtc tccgcagggc cgtcctcggc gatcacccgg tgcagctcgc cgagcacgaa 20400
ctcggtgagc cggtacgtct cgtcgaggac atccgcgccc ggttccggga gcgcggagac 20460
gatgtggacc gcgtccgcag gaccgggccc gggagtgggc agctcggtcc aggagaggcc 20520
gtacaaggag ttccgtacga cggcggcgtc gccgtcgacg ttcaccggtc gcgcggtcag 20580
cgcggcgacg gtcaccaccg gttggccgac cgggtccgtc gcatgcacgg cagcgccgtc 20640
cgggccctga gtgatcgtga cgcgcagcgt ggtggccccg gtcgtgtgga accgcacgcc 20700
gctccacgag aacggcagcc gcacctccgc ttcctgttcc gcgagcagcg gcaggcaggt 20760
gacgtgcaag gccgcgtcga acagcgccgg gtggacgcca tagtgcggcg tgtcgtccgc 20820
ctgttccccg gcgatctcca cctcggcgta cagggtttcg ccgtcgcgcc aggcggtgcg 20880
cagtccctgg aacgctgggc cgtagctgta gccggtctcg gccagccgct cgtagaacgc 20940
gctcacgtcg acgcgtcgcg cgcccggcgg cggccacgcg ggcggcggga ccgccgcgac 21000
gcttccggcc cggccgaggg tgccgctggc gtgccgggtc cagctgtccg tgccctcggt 21060
acgcgcgtgg acggtcactc gccgccgtcc ggcctcatcg gcccccttcga cggtcaccga 21120
cacatccacc gcgccggtca ccggcaccac gagcggggtc tcgatgacca gttcatccac 21180
caccccgcaa ccggtctcgt caccggcccg gatgaccagc tccacaaacg ccgtacccgg 21240
cagcagaacc gtgccccgca ccgcgtgatc agccagccag ggatgcgtac gcaacgagat 21300
ccggccagtg agaacaacac caccaccgtc gtcggcgggc agtgctgtga cggcggccag 21360
catcggatgc gccgccccgg tcagcccggc cgcggacaga tcggtggcac cggccgcctc 21420
cagccagtac cgcctgtgct cgaacgcgta ggtgggcaga tcgagcagcc gtcccggcac 21480
cggttcgacc accgtgtccc agtccactgc cgtgcccagg gtccacgcct gcgccaacgc 21540
cgtcagccac cgctcccagc cgccgtcacc ggtccgcaac gacgccaccg tgtgagcctg 21600
ttccatcgcc ggcagcagca ccggatgggc gctgcactcc acgaacacgg acccgtccag 21660
ctccgccacc gccgcgtcca gcgcgacggg gcgacgcagg ttccggtacc agtagccctc 21720
atccaccggc tcggtcaccc aggcgctgtc caccgtggac caccaggcca ccgacccggt 21780
cccgccggaa atcccctcca gtacctcggc caactcgtcc tcgatggctt ccacgtgggg 21840
cgtgtgggag gcgtagtcga ccgcgatacg gcgcactcgc acgccttcgg cctcgtaccg 21900
cgtcaccact tcttccaccg cggacgggtc ccccgccacc acagtcgaag acgggccgtt 21960
acgcgccgcg atccacacgc cctcgaccag gtccacctca ccggccggca acgccaccga 22020
agccatcgcc ccccgcccgg ccagccgccc ggcgatcacc tggctgcgca aggccaccac 22080
gcgggcggcg tcctcaaggc tgagggctcc ggccacacac gccgccgcga tctcgccctg 22140
ggagtgtccg accaccgcgt ccggcacgac cccatgcgcc tgccacagcg cggccaggct 22200
caccgcgacc gcccagctgg ccggctggac cacctccacc cgctccgcca catccggccg 22260
cgccaacatc tcccgcacat cccagcccgt gtgcggcaac aacgcccgcg cacactcctc 22320
catacgagcc gcgaacaccg cagaacacgc catcaactcc acacccatgc ccacccactg 22380
agcaccctgc ccgggaaaga cgaacaccgt acgcggctga tccaccgcca cacccatcac 22440
ccgggcatcg cccaacaaca ccgcacggtg accgaagaca gcacgctcac gcaccaaccc 22500
```

-continued

```
ctgcgcgacc gcggccacat ccacaccacc cccgcgcaga taccccctcca gccgctccac  22560
ctgcccccgc agactcacct cactccgagc cgacaccggc aacggcacca acccatcgac  22620
agccgactcc ccacgcgacg gcccgggaac accctcaagg atcacgtgcg cgttcgtacc  22680
gctcaccccg aaagcggaga caccggcccg gcgcggacgt cccgcgtcgg gccacgcccg  22740
cgcctcggtg agcagttcca ccgcgccctc ggtccagtcc acatgcgacg acggctcgtc  22800
cacatgcagc gtcttcggcg cgatgccata ccgcatcgcc atgaccatct tgatgacacc  22860
ggcgacaccc gcagccgcct gcgcatgacc gatgttcgac ttcaacgaac ccagcagcag  22920
cggaacctca cgctcctgcc cgtacgtcgc cagaatcgcg tgcgcctcga tgggatcgcc  22980
cagcgtcgtc cccgtcccgt gcgcctccac cacgtccacg tcggcggggg cgagccccgc  23040
cttgtggagg gcctggcgga tgacgcgctg ctgggagggg ccgttgggtg cggagatgcc  23100
gttggaggcg ccgtcctggt tgacggcgga ggagcggacg accgcgagga cggtgtgtcc  23160
gttgcgctcg gcgtcggaga gcttttcgac gacgaggacg ccggccccct cggcgaaacc  23220
ggtgccgtcc gccgcgtcag cgaacgcctt gcaccgtccg tccggcgcga cgccgccctg  23280
ccgggagaac tccacgaagg tctgtggtga tgccatcact gtgacaccac cgaccagcgc  23340
cagcgagcac tccccggtcc gcagcgcctg cccggcctgg tgcagcgcga ccagcgacga  23400
cgaacacgcc gtgtcgaccg tgaccgccgg accctccatg ccgaagaagt acgacagccg  23460
tccggcgagc accgcgggct gtgtgctgta ggcgccgaat ccgcccaggt ccgcgcccgt  23520
gccgtagccg tagtagaagc cgccgacgaa gacgccggtg tcgctgccgc gcagggtgtc  23580
cggcacgatg ccggcgtgtt cgagcgcctc ccaggcgatt tcgaggagga tccgctgctg  23640
cgggtcgagt gcggtggcct cgcgcggact gatgccgaag aacgcggcat cgaagtcggc  23700
ggcgcccgcg agtgcgccgg cccgcccggt ggcggactcg gcggcggcgt gcagcgcggc  23760
cacgtcccag ccgcggtcgg tggggaagtc gccgatcgcg tcgcggccgt ccgcgacgag  23820
ctgccacagc tcttccggtg aggtgacgcc gcccggcagt cggcaggcca tgccgacgac  23880
ggcgagcggc tcgttcgccg cggcgcgcag cgcggtgttc tcccggcgga gctgcgcgtt  23940
gtccttgacc gacgtccgca gcgcctcgat caggtcgttc tcggccatcg cctcatccct  24000
tcagcacgtg cgcgatgagc gcgtctgcgt ccatgtcgtc gaacagttcg tcgtccggct  24060
ccgcggtcgt ggtgctcgcg ggtgcctgtg ccggtggttc accgccgtcc ggggtcccgt  24120
tgtcgtccgg ggtcccgttg acgtccgggg ccaggagggt cagcagatga cgggtgagcg  24180
cgccggcggc gggatagtcg aagacgagcg tggccggcag cggaatgccg agggcctcgg  24240
agagccggtt gcgcaggccg agcgcggtga gcgagtcgac cccgaggtcc ttgaacgccg  24300
tggtggccgt gaccgccgcc gcgtcggtgt ggcccagcag ggtggcggcg gtgtcgcgga  24360
cgacgccgag cagcacctgt tcccgttcct tgtggggcag gtccggcagg cgttccagca  24420
gggagccgcc gtcggtcgcg gagcgccggg tggggcgctg gatcggtcgc cacagcggtg  24480
acgggtcgcc gggcccgggt ggggcggtcg ccacgaccac ggcttccccg gtggcgcacg  24540
cggcgtcgag gaggtcggtc agccggtccg ccgcggcggt gaacgccacg gccggcaggc  24600
cttgtgcccg gcgcaggtcg gccagggcct ggagcggtcc ggccgcctcg ccggacggaa  24660
cggcgagaac gaacgcggtc aggtcgaggt cgcgggtcag gcggtgcagt tcccaggccg  24720
actcggcggt gccgtccgcg tggacgaccg cggtcaccgg ggtttccggc actgtgcccg  24780
gctcgtaccg gatcacttcg gcgccgtgtc cgcccgaggtg tccggcgagt tcctccgaac  24840
cgcccgcgag gaggacggtg tcgccgtacg aggccgcggc cgtggtgggc gcggcgggga  24900
```

```
cgaggcgggg cgcttcgagg cgcccgtcgg ccaggcgcag gtgcggttcg tcgaggcggg  24960
agagggcggc ggcgcggcgg ggggtgaccg tgtcggtggt ctccacgagc acgagccggc  25020
ccggttccgc ggtgtcgagc agtgcggcga cggcaccggc gacgggcccg gcctcggcgg  25080
acaccaccag cgtggcgccg gcggtcctcg ggtcgtccag tgcggtacgg acctcgtcgg  25140
gaccggatac cgggacgacg atgacgtcgg gcgtggcgtc gtcgccgagg tcggtgtacc  25200
ggcgggccgt ggtgccgggt gccgccgggg cccggacgcc ggtccaggtg cgccggaaca  25260
gccgcacgtc cccgtccggg cccgtcgtgg cggggggccg ggtgatgagc gagccgatct  25320
gagccaccgg ccgtcccagt tcgtcggcga ggtgcacgcg ggcgccgccc tcgccctcgc  25380
cgtggacgaa ggtgacgcgc agtttcgtgg cgccgctggt gtggacacgg acgccggtga  25440
acgcgaacgg caaccgtacc cccgcgttct cggcggccgc gccgatgctg cccgcttgca  25500
gcgcggtgac gagcagcgcc gggtgcagtg tgtagcgggc ggcgtccctg gcgagggcgc  25560
cgtcgagggc gacttcggcg cagacggtgt ctccgtggct ccacgcggcg gacatgccgc  25620
ggaactcggg gccgaactcg tatcccgcgt cgtcgagtcg ctggtagaag gccgcgacgt  25680
cgaccggttc cgcgtgctcg ggcggccagg gccccggcgt ggtggccggt tcggtggtgg  25740
cgatgccggc gaagccggag gcgtggcggg tccatgtccg gtcgccgtcc gtccgggcgt  25800
ggacgcgcac ggcacggcgt ccggtgtcgt cgggcgcggc gacggtcacg cgcacctgga  25860
cggcgccggt ggcgggcagg accagcggtg tctcgacgac cagttcgtcg agcaggtcgc  25920
agcctgcctc gtcggcgccg cgtccggcca attccaggaa ggcgggtccg ggcagcagta  25980
cggcgccgtc gacggagtga ccggccagcc atgggtgggt ggccagcgag aaccggccgg  26040
tgagcagcac ctcgtcggag tcggggagcg ccaccgacgc ggcgagcagc gggtggtcga  26100
cggcgtcgag tccgaggccg gaagcgtccg tgccggccgc ggtctcgatc cagtagcgct  26160
catggtggaa ggcgtatgtg ggcaggtcgt gtgccgtcgc cgtcgcgggg acgaccgccg  26220
cccagtcgac gggcacgccg gttgtgtgcg cctcggccag cgcggtgagc agccggtgga  26280
ctcccccgcc gcggcggagc gtggcgacgg tcgcgccgtc gatcgcgggc agcagcacgg  26340
ggtgcgcgct gacctcgacg aacacggtgt cacccggctc gcgggcagcg gtcacggccg  26400
tggcgaagcc tacggggtgg cgcatgttgc ggaaccagta ctcgtcgtcg agcggcgcgt  26460
cgatccagcg ttcgtcggcg gtggagaacc acgggatctc gggcgtgcgc gaggtggtgt  26520
ccgcgacgat ccgctggagt tcgtcgtaca gcgggtcgac gaacggggtg tgggtcgggc  26580
agtcgacggc gatgcggcgc acccagacgc cgcgggcctc gtagtcggcg atcagcgttt  26640
cgacggcgtc cgggcgcccg gcgacggtcg tggtggtggc gccgttgcgg cccgcgaccc  26700
agacgccgtc gatccgggcg gcatccgcct cgacgtcggc ggccgggagc gcgaccgagc  26760
ccatcgcgcc gcgtccggcg agttcgcgca ggagcaggag aacgctgcgc agcgcgacga  26820
ggcgggcacc gtcctccagg gtgagcgctc cggcgacaca ggccgcggcg atctcgccct  26880
gggagtgtcc gatgacggcg tccgggcgta cgcccgcggc ctcccacacg gcggccagcg  26940
acaccatgac ggcccagcag acggggtgca cgacgtcgac gcggcgggtc acctccgggt  27000
cgtcgagcat ggcgatgggg tcccagcccg tgtgcgggat cagcgcgtcg gcgcattggc  27060
gcatcctggc ggcgaacacc ggggaggccg ccatcagttc gacgcccatg ccgcgccact  27120
gcggtccttg tccggggaag acgaagacgg tgcgcggctc ggtgagcgcc gtgccggtga  27180
cgacgtcgtc gtcgagcagc acggcgcggt gcgggaacgt cgtacgcctg gcgagcaggc  27240
```

-continued

```
ccgcggcgat ggcgcgcggg tcgtggccgg gacgggcggc gaggtgctcg cggagtcggc  27300
ggacctggcc gtcgagggcc gtggcggtcc gcgccgagac gggcagtggt gtgagcggcg  27360
tggcgatcag cggctcaccg ggcttcgagg ccgacggctc ctcggccggc ggctccccgg  27420
ccgggtgggc ttccagcagg acgtgggcgt tggtgccgct gacgccgaag gaggacacac  27480
cggcgcgccg cgggcggtcg gtctcgggcc agggccgggc atcggtgagg agttcgacgg  27540
cgccggccgt ccagtcgacg tgcgaggacg gcgtgtccac gtgcagggtg cgcggcaggg  27600
tgccgtgccg catggcgagg accatcttga tgacaccggc gacacccgcg gcggcctgag  27660
tgtggccgat gttggacttc agcgagccca gcagcaccgg ggtgtcgcgc ccctgcccgt  27720
aggtggccag caccgcctgt gcctcgatgg gatcgcccag cctggtgccg gtgccgtgcg  27780
cctccacggc gtccacgtcc gccggggtga gcccggcgtt ggccagggcc tgccggatca  27840
cccgctcctg cgagggcccg ttcggcgccg acaacccgtt ggaagcaccg tcctggttga  27900
ccgccgaacc ccggacaacc gccagcacac ggtggccgtt gcgctcggca tcggagagcc  27960
tctcgacgat cagcacaccg gacccctcgg cgaaaccggt gccgtcagcc gcatccgcga  28020
acgccttgca gcgcgcgtcg ggcgcgagac cccgctgctg ggagaactcg acgaagccgg  28080
acggcgaggc catcaccgtg acgccgccga ccagggcgag cgagcattcg ccggagcgca  28140
gtgactgccc ggcctggtgc agcgccacca gcgacgacga acacgccgtg tcgaccgtga  28200
ccgccggacc ctccagaccg tagaagtacg acagccgacc ggacagcaca ctggtctggg  28260
tgccggtcgc gccgaaaccg cccaggtcgg tgccgagtcc gtacccgtcg gagaaggcgc  28320
ccatgaacac gccggtgtcg cttccgcgca gcgactccgg gaggatcccg gcgtgttcca  28380
gcgcctccca cgaggtctcc aggaccagac gctgctgcgg gtccatcgcc agcgcctcac  28440
gcggactgat cccgaagaac gccgcgtcga agtccgccac cccggcgagg aagccaccat  28500
gacgcacggt cgacgtgccc ggatgatccg gatcgggatc gtacagcccg tccacgtccc  28560
aaccacggtc cgtcggaaac gccgtgatcc cgtcaccacc cgactccagc agccgccaca  28620
agtcctccgg cgacgcgacc ccacccggca gccggcaggc catccccacg atcgccaacg  28680
gctcgtcctg ccggacggcc gcggtcgtgg tgcgggtcgg cgatgccgtc cggccggaca  28740
gcgccgcggt gagcttcgcc gcgacggcgc gcggcgtcgg gaagtcgaag accgcggtgg  28800
cgggcagccg tacgcccgtc gcctcggtga aggcgttgcg cagccggatc gccatgagcg  28860
agtcgacgcc gagttccttg aacgtggcgg tcgcctcgac ccgtgcggca ccgtcgtggc  28920
cgagtacggc cgcggtgcac tgccggacga cggcgagcac gtccttttcg gcgtccgcgg  28980
cggagagccg cgcgatccgg tcggcgaggg tggtggcgcc ggccgcccgg cgccgcggct  29040
cccggcgcgg tgcgcgcagc aggggcgagc tgccgaggcc ggccgggtcg gcggcgacca  29100
gcgccgggtc cgaggaccgc aacgccgcgt cgaacagcgt cagtccgcct tcggcggtca  29160
gcgccgtcac gccgtcgcgg cgcatgcggg cgccggtgcc gaccgtcagc ccgctctccg  29220
gttcccacag gccccaggcc acggacaacg cgggcagtcc ggctgcccgg cgctgttcgg  29280
ccagcgcgtc gaggaacgcg ttcgcggccg cgtagttgcc ctgtccgggg ctgccgagca  29340
caccggcggc cgacgagtag aggacgaacg cggccagttc cgtgtcctgg gtgagttcgt  29400
gcaggtgcca cgcggcgtcc accttcgggc gcagcaccgt ctcgagccgg tcgggggtga  29460
gcgcggtgag gacgccgtcg tcgaggacgg ccgcggtgtg cacgacggcc gtgagcgggt  29520
gcgccgggtc gatccccgcc agtacggagg cgagttcgtc ccggtcggcg acgtcgcagg  29580
cgatcgccgt gacctcggcg ccgggcacgt cgctcgccgt gccgctgcgc gacagcatca  29640
```

-continued

```
gcagccggcg cacgccgtgg cgttcgacga ggtggcggct gatgatgccg gccagcgtcc  29700
cggagccacc ggtgacgagc acggtgccgt ccgggtcgag cgccggagcg tcacccgccg  29760
ggaccgccgg ggccagacgg cgggcgtaca cctggccgtc acgcagcacc acctggggct  29820
catcgagcgc ggtggccgct gcgagcagcg gctcggcggt gtccggggcg gcgtcgacga  29880
ggacgatccg gccggggtgt tcggcctgcg cggtccgcac cagtccggcg gccgcggccg  29940
acgcgagacc gggcccggtg tggacggcca ggaccgcgtc ggcgtaccgg tcgtcggtga  30000
ggaagcgctg cacggcggtc aggacgccgg cgcccagttc gcgggtgtcg tcgagcgggg  30060
caccgccgcc gccgtgcgcg gggaggatca ccacgtccgg gaccgtcggg tcgtcgaggc  30120
ggccggtcgt cgcggtcgtg ggcggcagct ccgggagctc ggccagcacc gggcgcagca  30180
ggcccggaac ggctcccgtg atcgtcaggg ggcgcctgcg cacggcgccg atggtggcga  30240
cgggcccgcc ggtctcgtcc gcgaggtgta cgccgtcagc ggtgacggcg acgcgtaccg  30300
ccgtggcgcc ggtggcgtgg acgcggacgt cgtcgaacgc gtacggaagg tggtcccctt  30360
ccgcggcgag gcggagtgcg gcgccgagca gcgccgggtg caggccgtac cgtccggcgt  30420
cggcgagctg tccgtcggcg agggccactt ccgcccagac ggcgtcgtcg tcggcccaga  30480
cggcgcgcgg gcggggcagc gcgggcccgt ccgtgtaccc ggctcgggcc agacggtcgg  30540
cgatgtcgtc ggggtccacc ggccgggccg tggcgggcgg ccacgtcgac ggcatctccc  30600
gcacggccgg ggccgtccgc gggtcggggg cgaggattcc gtgcgcgtgc tcggtccact  30660
cccccgccgc gtgccgcgtg tgcacggtga ccgcgcggcg gccgtccgcc ccgggcgcgc  30720
tcaccgtgac ggagagcgcg agcgcaccgg accgcggcag cgtgaggggg gtgtccacgg  30780
tgaacgtgtc gagggcgccg cagccggctt cgtcgcccgc ccggatcgcc agatccagga  30840
gggccgcggc gggcagcacc gcgaggccgt gcagggagtg cgccagcgga tcggcggcgt  30900
cgacccggcc ggtgagcacc aggtcgccgg tgccgggcag ggtgaccgcc gcggtcagcg  30960
ccgggtgcgc gaccggcgtc tgtccggccg gggccgcgtc gcccgcggtc tgggtgccga  31020
gccagtagcg gacccgctcg aacgggtacg tcggcgggtg cgaggcgcgt gccggcgcgg  31080
ggtcgatgac cttcggccag tcgaccgtga cgccgtcggt gtgcagccgg gcgagcgcgg  31140
tcagggcgga tcgcggttcg tcgtcggcgt gcagcatcgg gatgccgtcg acgagtcggg  31200
tcaggctccg gtccgggccg atctccagga gcaccgcccc gtcgtgcgcg gcgacctgtt  31260
ccccgaaccg gacggtgtcg cggacctgtc gtacccagta ctccggcgtg gtgcaggcgg  31320
cgcccgcggc catcgggatc ctcggctcgt ggtacgtcag gctctccgcg accttgcgga  31380
actcctcgag catcggctcc atccgcgccg agtggaacgc gtggctggtc cgcaggcggg  31440
tgaagcggcc gagccgggcc gcgacgtcga gcaccgcctc ctcgtcaccg gagagcacga  31500
tcgacgcggg cccgttgacc gcggcgatct ccacgccgtc ccgcagcagc ggcagcgcgt  31560
cccgttccga cgcgatcacg gcggccatcg ccccgccgga cggcagcgcc tgcatcaggc  31620
gggcccgtgc ggacaccagc ctgcacgcgt cctccaggga ccagacgccg gcgacgtacg  31680
cggcggccag ctcgccgatc gaatggccca cgaaggcgtc cgggcgtacg ccccacgcct  31740
cgagctgtgc gccgagtgcg acctggagcg cgaacaccgc gggctgggcg tacccggtgt  31800
cgtggaggtc gagcccggcg ggcacgtcga gggcgtccag cacctcgcgg cgagtgcggg  31860
cgaagacgtc gtaggcggcg gccagtccgt cgcccatgcc gggacgttgt gagccctgtc  31920
cggagaagag ccacacgagg cggcggtccg gttctgcggc gccggtgacc gtgtcggtgc  31980
```

-continued

```
cgatcagcgc ggcccggtgc gggaaggccg tgcgggcgag cagggccgcg gccaccgcgc  32040
gctcgtcctc ctcgccggtg gcgaggtggg cgcgcaggcg gtgtacctgt gcgtcgagtg  32100
cctgcggggt gcgtgccgag agcagcaggg gcagcggtcc ggtgtcgggt gccggggcgg  32160
gttcgggggc cggtcggggg tggctttcga ggatgatgtg agcgttggtg ccgctaacgc  32220
cgaaggagga caccccggcg cgccgtgggc ggtcggtttc gggccagggg cgggcgtcgg  32280
tgaggagttc gacggcgccg gccgtccagt cgacgtgcga ggacggcgtg tccacgtgca  32340
gggtgcgcgg cagggtgccg tgccgcatgg cgaggaccat cttgatgaca ccggcgacgc  32400
ccgcggcggc ctgagtgtgg ccgatgttgg acttcagcga gcccagcagc accggggtgt  32460
cgcgatgctg cccgtaggtg gccagtaccg cctgcgcctc gatggggtcg cccagcctgg  32520
tcccggtgcc atgcgcctcg acagcgtcca catccgccgg ggtgagcccg gcgttggcca  32580
gcgcctgccg gatcacccgc tcctgcgacg gcccgttcgg cgccgacaac ccgttggaag  32640
caccgtcctg gttgaccgcc gaaccacgca cgaccgccag gacattgtgg ccgtgccgct  32700
cggcgtcgga gagcctctcg acgatcagca caccggatcc ctcggcgaaa ccggtgccat  32760
cagccgcatc cgcgaacgcc ttgcagcggc cgtccgggga gaggccccgc tgctgggaga  32820
agtccacgaa gccggacggc gaggccatca ccgtgacgcc gccgaccacg gcgagcgagc  32880
actcccccga gcgcagcgac tgcccggcct ggtgcagcgc caccagcgac gacgaacacg  32940
ccgtgtccac cgtgaccgcc ggaccctcca aaccgtagaa gtacgacagc cgaccggaca  33000
gcacactggt ctgggtgctg gtggcaccga aaccgccgcg gtcggctcca gtgccgtacc  33060
cgtagaagta gccgcccatg aacacgccgg tgtcgcttcc gcgcagcgac tccgggagga  33120
tcccggcgtg ttccagcgcc tcccacgagg tctccaggac cagacgctgc tgcgggtcca  33180
tcgccagcgc ctcacgcgga ctgatcccga agaacgccgc gtcgaagtcc gccaccccgg  33240
cgaggaagcc accatgacgc acggtcgacg tgcccggatg atccggatcg ggatcgtaca  33300
gcccgtccac gtcccaacca cggtccgtcg gaaacgccgt gatcccgtca ccacccgact  33360
ccagcagccg ccacaagtcc tccggcgacg cgaccccacc cggcagccgg caggccatcc  33420
ccacgatcgc caacggctcg tcctgccgga cggccgcggt cggggtacgc cgccgggtgg  33480
tggcccgcgc gccggccagt tcgtccaggt gggcggcgag cgcctgcgcc gtggggtggt  33540
cgaagacgag cgtagcgggc agcgtcaggc ccgtcgcgtc ggccagccgg ttgcgcagtt  33600
cgacgccggt cagcgagtcg aagcccactt ccctgaacgc gcgcgcgggt gcgatggcgt  33660
gggcgtcgcg gtggccgagc accgcggcag cgctggtacg gacgaggtcg agcatgtcgc  33720
gcgcggccgg aggtgcggac gtgcgccgga cggccggcac gagggtgcgt aggaccggcg  33780
ggacccggtc ggacgcggcg acggcggcga ggtcgagccg gatcggcacg agcgcgggcc  33840
ggtcggtgtg cagggccgcg tcgaacaggg cgagcccctg tgcggccgtc atcggggtca  33900
tgccgttgcg ggcgatgcgg gccaggtcgg tggcggtcag ccgcccgccc atcccgtccg  33960
ccgcgtccca cagtccccag gcgagcgaga cggcgggcag cccctggtgg tgccggtggc  34020
gggcgagcgc gtcgaggaac gcgttgccgg tcgcgtagtt ggcctgaccc gcgccgccga  34080
acgtggcgga tatggacgag tacaggacga acgcggccag gtcgagatcg cgcgtcagct  34140
cgtgcaggtg ccaggcgacg tccgccttga cccgcagcac ggcgtcccac tgctccggcc  34200
gcatggtcgt cacggccgcg tcgtcgacga tcccggccat gtgcacgacg gcgcgcagcc  34260
gctgggcgac gtcggcgacg actgcggcca gctcgtcgcg gtcgacgacg tcggcggcca  34320
cgtaccgcac gcggtcgtcc tccggcgtgt cgccgggccg gccgttgcgg gacaccacga  34380
```

-continued

```
cgacctcggc ggcctcgtgc acggtgagca ggtggtccac gaggaggcgg ccgagcccgc  34440
cggtgccgcc ggtgacgagg acggtcccgc cggtcagcgg ggaggttccg gtggccgcgg  34500
cgacacggcg cagacgggcc gcacgcgctg tgccgtcggc gacccggacg tgcggctcgt  34560
cgccggcggc gagcccggcc gctatggcgg cgggcgtgat ctcgtccgct tcgatcaggg  34620
cgacgcggcc gggatgctcc gtctccgccg tccggaccag gccgccgagc gcttcctgcg  34680
cgggatcgcc ggtacgggtg gccacgatga gccgggatcg cgcccagcgc ggctcggcga  34740
gccaggtctg cacggtggtg agcaggtcgc ggcccagctc ccgggtccgg gcgccgggcg  34800
aggtgcccgg gtcgccgggt tccacggcca ggaccacgac cggggggtgc tcgccgtcgg  34860
gcacgtcggc gaggtacgtc cagtcgggga cgggtgacgc gggcacgggc acccaggcga  34920
tctcgaacag cgcctcggca tcggggtcgg cggcccgcac ggtcaggctg tcgacgtcaa  34980
ggaccggtga gccgtgctcg tccgtggcga cgatgcggac catgtcgggg ccgacgcgtt  35040
ccagcagcac gcgcagcgcg gtcgcggcgc gcgcgtggat cctcacgccg gaccaggaga  35100
acgccagccg gcgccgctcc gggtccgtga agaccgtccc gagggcgtgc agggccgcgt  35160
cgagcagcac ggggtgcagc ccgtaccggg cgtcggtgag ctgttcggcg aggcggaccg  35220
acgcgtaggc gcggccctcc cccgtccaca tcgcggtcat ggcccggaac gcgggcccgt  35280
acgagagcgg cagcgcgtcg tagaagccgg tcaggtcggc cgggtcggcg tcggcgggcg  35340
gccagtccac gggctccgcc ggaccgccag tgtccacgct cagcgctccg gtcgcactga  35400
gcgcccaggg gcccgtgccg gtacggctgt gcagactcac cgaccgccgt ccggacacct  35460
cggttccgac ggtggcctgg atctccgtgt cgccgtcgcc gtcgaccacc accggcgcga  35520
cgatggtcag ctccgcgatc tccggcgtgc cgagccgggc tcccgcttcg gcgagcagtt  35580
ccacgagcgc cgagccgggc acgatgaccc ggccgtccac ctcgtggtcg gcgagccagg  35640
gctgacggcg taccgagaca ccgcggtggc cagcgcgccc tcgccgtcgg gcgaggtcga  35700
cccacgagcc gagcagcggg tggccggacg ttcccgccgg ttccgcgtcg atccagtagc  35760
ggtcacggcg gaacgggtac gtgggcagcg gcaccacccg acgcgtcgcg aacgaccagg  35820
tgacgggcac gccccggacc cagagcgcgg cgagcgaccg agtgaagcgg tccaggccgc  35880
cctcgcctcg ccgcagtgtg ccggtgacga ccgtatgcgc atgcccggcg agcgtgtcct  35940
ccagtgcggt ggtgagcacg ggatgcgcgc tgacctcgac gaacgcgcgg tatccgcggt  36000
ccgccaggtg gccggtcgcg gcggcgaacc gaacggtgcg gcgcaggttg tcgtaccagt  36060
aggcggcgtc cgcgggccgg tccagccacg cctcgtccac ggtggagaag aacgggacgt  36120
ccggcgtgcg cggagtgatg ccggcgagag cgtcgagcag cgcgccgcgg atcgtttcga  36180
catgcgcggt gtgcgacgcg tagtcgacgg cgatccggcg ggcgcggggg gtggcggcca  36240
gcagctcctc cacggcgtcg gccgcaccgg cgacaacgat cgacgcgggt ccgttgaccg  36300
cggcgacctc caggcgcccg gcccacacgg cggcgtcgaa gtcggcgggc ggcaccgaga  36360
ccatgccgcc ctgcccggcc agttcggtgg cgacgagtcg gctgcgcacc gcgacgacct  36420
tcgcggcgtc gtccagggtg agcaccccgg cgacgcaggc cgcggcgact tcgccctggg  36480
agtggccgac gaccgcggcc ggggcgaccc cgtgcgcacg ccacagctcc gccagcgcca  36540
ccatcaccgc gaacgacgcg ggctgcacga catcgacccg gtcgaacgcg ggcgctccgg  36600
gccgctgggc gatgacgtcc agcaggtccc atccggtgtg cggggcgagc gccgtggcgc  36660
actcgcggag ccgccgggcg aacacgggct cggtggcgag cagttcggca cccatgccgg  36720
```

-continued

```
cccactggga gccctgcccg gggaacgcga acacgacacg tgtgtcggtg acgtcggcgg  36780
ttcccgtcac ggcccccggc acttcggcac cacgggcgaa cgcctccgcc tctcgggccg  36840
gcacgaccgc ccggtggcgc atggccgtcc gggtggtggc gagcgagtgg ccgaccgcgg  36900
ccgcggcgcc agtgagcggg gccagctgtc ccgcgacgtc ccgcagtccc tccggggtcc  36960
gggccgacat cggccagacc acgtcctcgg gcaccggctc ggcttcgggt gcggacacgg  37020
gtgcgggcgc ggcgggggc ccggcctcca ggacgacatg ggcgttggtg ccgctgatgc  37080
cgaacgacga gacacccgca cgccgggcgc gcccggtgac cggccacggc tcactgcggt  37140
gcagcagccg gatgtcgccg tcccagtcga cgtgccggga cggctcgtcg acgtgcagcg  37200
tgcgcggcag gacgccgtgc cgcatcgcca tgaccatctt gatgacgccg gcgacgccgg  37260
ccgcggcctg ggtgtggccg atgttcgact tgagcgagcc gatcagcagc ggatgcacgc  37320
gttcgcgccc gtaggccact tgcagggcct gggcctcgac ggggtcgccg agacgggtgc  37380
cggtgccgtg tgcctccacg gcgtcgacgt cacccggcgc caggccggcg tcggcgagcg  37440
cacgctggat gacgcgctgc tgcgcaggcc cgttcggggc ggacagcccg ttcgacgcgc  37500
cgtcggagtt gaccgcggag ccgcgcacca gcgccagcac ggggtggccg tggcgggtgg  37560
cgtcggagag ccgctccagc accaggacac cggcgccctc ggcgaagctc gtgccgtccg  37620
cggtgtccgc gaaggccttg gcacggccgt cgggggcgag cccgcgctgc cgggagaact  37680
cgacgaaccc ggtcgtcgtc gccatcaccg tgacaccgcc gaccagggcg agcgagcact  37740
cccccgagcg cagcgaccgc gcggcctggt gcagcgccac cagcgacgac gaacacgccg  37800
tgtcgacggt gaccgacggg ccctccagac cgaagtagta cgagagccgc ccggagagaa  37860
cgctggtcgg cgtgccggtc gccccgaaac cgcccaggtc cacgcccgcg ccgtagccct  37920
gggtgaacgc gcccatgaat acgccggtgt cgctgccgcg gacgctttcg ggcaggatgc  37980
ccgctcgttc gaacgcctcc cacgacgctt cgaggaccag acgctgctgc gggtccatcg  38040
ccagcgcctc acgcgggctg atcccgaaga acgcggcgtc gaagtcggcg gcgccggtga  38100
ggaagccgcc gtgacgcacg gaaaccttgc cgaccgcgtc ggggttcggg tcgtagagcg  38160
cggcgaggtc ccagccgcgg tcggcgggga actcggtgat cgcgtccccg ccggagtcga  38220
ccagccgcca caggtcctcc ggtgaccgca cgccaccggg catccggcac gccatggcca  38280
cgatcgccag cggctcgttc cccgccaccg tcggtgcggg cactgtcgcc gccggagcgg  38340
caggggccgg ctcaccccgc cgttcctcat ccaggcgggc ggcgagcgcg gccggtgtcg  38400
ggtggtcgaa gacggccgtc gcggagagcc gtacccccgt cgtctcggcg aggctgttgc  38460
gcaaccggac accgctgagc gagtcgatgc cgaggtcctt gaacgccgtc gtgggcgtga  38520
tctcggaggc gtcggcgtgg ccgagcacgg cggccgtggc cgcacacacg atggccagca  38580
ggtcacgatc gcggtcgcgg tcgcggtcgc ggttgtcctc cgcacgggcg gcgatgcggc  38640
gctcggtccg ctgccggacg ggctcggtgg gaatcgccgc gaccatgaac ggcacgtccg  38700
cggcgaggct cgcgtcgatg aagtgggtgc cctcggcctc ggtgagcggc cggaacccgt  38760
cgcgcacccg ctgccggtcg gcgtcgtcaa gttgtccggt gagggtgctg gtggtgtgcc  38820
acatgcccca ggcgatggag gtggcgggtt ggccgagggt gtggcggtgg gtggcgaggg  38880
cgtcgaggaa ggcgttggcg gcggcgtagt ttccttgtcc ggggctgccg aggacggcgg  38940
cggcgctgga gtagaggacg aagtgggtga ggggttggtt ttgggtgagg tggtgcaggt  39000
gccaggcggc gttggctttg gggtggagga cggtggtgag gcggtcgggg gtgagggcgt  39060
cgaggatgcc gtcgtcgagg gtggcggcgg tgtggaagac ggcggtgagg ggttgggggga  39120
```

-continued tgtgggcgag ggtggtggcg agttggtggg ggtcgccgac gtcgcagggg aggtgggtgc 39180
cgggggtggt gtcggggggt ggggtgcggg agaggaggta ggtgtggggg tggttcaggt 39240
ggcgggcgag gatgccggcg agggtgccgg agccgccggt gatgatgatg gcgtgttcgg 39300
ggttgagggg ggtggtggtg ggtggggtgg tggtgtggag gggggtgagg tggggtcggt 39360
ggagggtgtg gtgggtgagg cggaggtggg ggtggtcgag ggtggcgagt tgggccaggg 39420
ggaggggagt gtgggggtgg tcggtttcga tgaggcggat gcggtggggg tgttcgttct 39480
gggcggtgcg ggtgaggccg gtgacggtgg cgccggcggg gtcggtggtg gtgtggacga 39540
tgagggtgtg gtcggtggtg gtgaggtggt gttgcagggc ggtcaggacg cgggtggcgc 39600
gggtgtgggc gcgggtgggt atgtcctcgg ggtcgtcggg gtgggcggcg gtgatcagga 39660
cgtgtccctc gggcaggtca ccgtcgtaga ccgcctcggc gaccgcgagc cactccaacc 39720
ggagcgggtt cggccccgac ggggtgtcgg cccgctccct cagcaccagc gagtccaccg 39780
acacgacagg acggccatcc gggtcggcca cgcgcacggc gacgccggcc tccccccggg 39840
tgagggcgac gcgcaccgcg gcggccccgg tggcgttcag gcgcacgccc gtccaggaga 39900
acggcagctc gatcccgccg cccgcgtcga ggcgcccggc gtgcagggcc gcgtcgagca 39960
gtgccggatg cacaccgaaa ccgtccgcct cggcggcctg ctcgtcgggc agcgccacct 40020
cggcatacac ggtgtcacca tcacgccagg cagcccgcaa cccctggaac gccgacccgt 40080
actcataacc ggcatcccgc agttcgtcat agaaccccga gacgtcgacg gccgcggccg 40140
tggccggcgg ccactgcgag aacggctcac cggaagcgtt ggaggtatcc ggggtgtcgg 40200
gggtcagggt gccgctggcg tgccgggtcc agctgcccgt gccctcggta cgcgcgtgga 40260
cggtcaccgg ccgccgtccg gcctcatcgg ccccttccac ggtcaccgac acatccaccg 40320
ctgcggtcac cggcaccacg agcggggatt cgatgaccag ttcatccacc accccgcaac 40380
cggtctcgtc accggcccgg atgaccagct ccacaaacgc cgtacccggc agcagaaccg 40440
tgccccgcac cgcgtgatca gccagccagg gatgcgtacg caatgagatc cggccggtga 40500
gaacaacacc accaccgtcg tcggcgggca gtgctgtgac ggcggccagc atcggatgcg 40560
ccgccccggt cagcccggcc gcggacaggt cggtggcacc ggccgcctcc agccagtacc 40620
gcctgtgctc gaacgcgtag gtgggcagat ccagcagccg ccccggcacc ggttcgacca 40680
ccgtgcccca gtccaccccc gcacccagag tccacgcctg cgccaacgcc cccagccacc 40740
gctcccagcc accgtcacca gtccgcaacg acgccaccgt gcgggcctgt tccatcgccg 40800
gcagcagcac cggatgggca ctgcactcca cgaacaccga cccgtccagc tccgccaccg 40860
ccgcatccag cgcgacaggg cgacgcaggt tccggtacca gtacccctca tccaccggct 40920
cggtcaccca ggcgctgtcc acggtcgacc accacgccac cgacccggtc ccgccggaaa 40980
ttcccttcag tacctcagcg agttcgtcct cgatggcctc cacgtgaggc gtgtgggagg 41040
cgtagtcgac cgcgatacga cgcacccgca ccccatcagc ctcataccgc gccaccacct 41100
cctccaccgc cgacgggtcc cccgccacca ccgtcgaagc cggaccatta cgcgccgcga 41160
tccacacacc ctcgaccaga cccacctcac cggccggcaa cgccaccgaa gccatcgccc 41220
cccggccggc cagccgcgcc gcgatcaccc gactgcgcaa cgccaccacg cgggcggcgt 41280
cctccaggct gagggctccg gccacacacg ccgccgcgat ctccccctgc gagtgtccga 41340
ccacagcgtc cggcacgacc ccatgcgcct gccacagcgc ggccaggctc accgcgaccg 41400
cccagctggc cggctggacc acctccaccc gctccgccac atccgaccgc gacaacatct 41460

-continued

```
cccgcacatc ccagcccgtg tgcggcaaca acgcccgcgc acactcctcc atacgagccg  41520
cgaacaccgc ggaacggtcc atgagttcca cgcccatgcc cacccactgg gcaccctgcc  41580
cggggaagac gaacaccgta cgcggctgat ccaccgccac acccatcacc cgggcatcac  41640
ccagcagcac cgcacggtga ccgaagacag cacgctcacg caccaacccc tgcgcgaccg  41700
cggccacatc caccccaccc ccgcgcagat accccctccag ccgctccacc tgcccccgca  41760
gactcacctc accacgagcc gacaccggca acggcaccaa cccatcacca cccgactcca  41820
cacgcgacgg cccaggaaca ccctccagga tcacgtgcgc gttcgtaccg ctcaccccga  41880
acgacgacac acccgcatgc ggtgcccgat ccgactcggg ccacggcctc gcctcggtga  41940
gcagctccac cgcaccggcc gaccagtcca catgcgacga cggctcgtcc acgtgcagcg  42000
tcttcggcgc gatcccatgc cgcatcgcca tgaccatctt gatgacaccg gcgacacccg  42060
cagccgcctg cgcatgaccg atgttcgact tgaccgaacc gaggtagagc ggcgtgtcgc  42120
ggtcctgccc gtaggccgcg aggacggcct gcgcctcgat cgggtcgccc agccgcgtgc  42180
cggtgccgtg cgcctccacc acgtccacat cggcggcgcg cagtccggcg ttgaccaacg  42240
cctgccggat cacgcgctgc tgggcgacgc cgttgggggc ggacagtccg ttggaggcac  42300
cgtcctggtt caccgccgag ccgcggacga ccgcgagaac ggtgtgcccg ttgcgctcgg  42360
cgtcggagag ccgctccagc acgagaacgc cgacgccctc ggcgaagccg gtcccgtccg  42420
ccgcgtcggc gaacgccttg caccgtccgt ccggggagag tccgcgctgc cgggagaact  42480
ccacgagctc tgcggtgttc gccatgacgg tgacaccgcc gaccagcgcc agggagcact  42540
ccccggcccg cagtgcctgt gccgcctggt gcagggcgac cagcgacgac gagcacgccg  42600
tgtcgaccgt gaccgccggg ccctgaagtc cgtacacgta cgagaggcgc ccggacagga  42660
cgctcgtctg cgtcgccgtg acaccgagcc cgcccaggtc ccggccgacg ccgtagccct  42720
ggttgaacgc gcccatgaac acgccggtgt cgctctcccg gagcctgtcc ggcacgatgc  42780
cggcgttctc gaacgcctcc caggaggtct ccaggatcag gcgctgctgg gggtccatcg  42840
ccagcgcctc gttcggactg atgccgaaga acgcggcgtc gaacccggcg ccggccagga  42900
atccgccgtg gcgtgtcgtg gagcggccgg ccgcgtccgg gtccgggtcg tacagcgcgt  42960
cgacgtccca gccccggtcg gtggggaact cggtgatcgc ctcggtaccg gcggcgacga  43020
gccgccacag gtcctccggc gaggcgaccc cgccgggcag tcggcacgcc atgccgacga  43080
tcgcgacggg gtcgccggag ccgagggtct gggcggtcgc gggtgccgct gtcgcggagc  43140
cggcgaggtg ggcggcgaac gcacgcggag tggggtggtc gaacgcggtt gacgcgggca  43200
cccgcagacc cgtccgcgcg gcgacggtgt tggtgaactc gacggtggtg agcgagtcga  43260
ggccgttctc gcggaacgtg cggtccgggg agcagtgtcc ggcgcccggc aggcccagga  43320
cggtggcgac gctgtcgcgg accaggtcga gcagtacgtc ctcccggccc gcacgggccg  43380
cggcgaggcg gttcgcccac tcctgttccg tggcgtcggg ctcggccggt ccggtcagtg  43440
cggtgaggat cggcggcgtg gcgcccgcca tcgtcgcggc ccgcgccccg gcggaaccgg  43500
tccgggccac gatgtacgag ccgccgcccg cgatggcctt ctcgatcagg tcgccggtga  43560
gcgccggccg ttcgatgccg ggcagcgcgc ggacggtgac ggtggggagt ccctccgcgg  43620
cccgtggccg ggtgtgggcg tcggcgccgg ccgggccgtc gagcaggacg tgcacgagcg  43680
cgccggggtt cgcggcttcc tcggctgcgg tggtcacgtg ggtgaggccg gtctcgtcgc  43740
ggagcaggcc ggcgacggtg tcggcgtcct ccccggtgac caggaccggc gcgtccgggc  43800
cgatcggagg cggcacggtg aggaccatct tgccggtgtg ccgggcgtgg ctcatccacg  43860
```

-continued

```
cgaacgcgtc ccgcgcacgg cggatgtccc acggctgcac cggcagcggg cacagctcac  43920
cgcggtcgaa caggtcgagg agcagttcga ggatctcccg caggcgcgcg ggatccacgt  43980
cggccaggtc gaacggctgc tgggcggcgt ggcggatgtc ggtcttgccc atctcgacga  44040
accggccgcc cggtgcgagc aggccgatgg acgcgtcgag gagttcaccg gtgagcgagt  44100
tgagcacgac gtcgaccggc gggaaggtgt cggcgaacgc ggcgctgcgg gagttcgcca  44160
catggtcggt gtcgaagccg tcggcgtgca gcaggtgttg tttggcggga ctggcggtgg  44220
cgtacacctc ggcgccgagg tggcgggcga tccgggtcgc cgccatgccg acaccgcccg  44280
tcgcggcgtg gaccaggacc ttctggccgg gtcgcagctc gcccgcgtcg acgaggccgt  44340
accaggcggt ggcgaacacg atgggcacgg acgcggcgat ggggaacgac catccccgtg  44400
ggatccgtgc gaccagccgc cggtccgcga ccacgctgcg ccggaacgcg tcctgcacga  44460
gaccgaacac gcggtcgccg ggggccaggt cgtcgacgcc gggtccgact tcggtcacga  44520
tgcccgcggc ctccccgccc atctcgccct cgcccgggta ggtgccgagc gcgatcagca  44580
cgtcgcggaa gttcagcccc gcggcgcgga cgtcgatgcg gacctcgccg gcggccaggg  44640
gcgcggcggg acgtcgagcg gggcgacgac gaggtcgcgg agcgttccgg aggcgggcgg  44700
gcgcagcgcc cactggcgcg gtcggcaggg gggtggtgtc cgcgcgtacc agccggggca  44760
cgtaggccac gccggcccgc agcgcgatct ggggttcgcc gagcgaggcc gcggcgggga  44820
cgaggtcgtc atcgccgtcc gtgtccacca gcacgaacga tccgggttcg gcggcctggc  44880
ggcgcagcgc ctcgtcccag agccgggcct ggtccgcgtc cgggatctcg gccgggccga  44940
cgcccaccgc gcggcgggtg acgaccgtcc ggcggggtga cggggtgccg ggcaggtcgc  45000
gccgctccca gaccagttcg cacagcgtgg cctcgccact gccggtggcg accagatggg  45060
ccggcagccc cgcgagccgc gcgcgctgga ccttgcccga cgcggtgcgg gggatcgtgg  45120
tgacgtgcca gatctcgtcg ggcaccttga agtaggcgag ccggcggcgg cactcggcga  45180
ggatcgcctc ggcggggacg cgggggccgt cggaaacgac gtagagcacg ggtatgtcgc  45240
cgaggacggg gtgcgggcgg cccgccgcgg cggcgtcccg gacaccggcc acctcctggg  45300
cgacggtctc gatctcccgg gggtggatgt tctccccgcc gcggatgatc agctccttga  45360
cccggccggt gatcgtcacg tgtccggtct cggcctgacg tgcgaggtcc ccggtgcggt  45420
accagccgtc cacgagcacc tgggcggtcg cctccggctg ggcgtggtag ccgagcatga  45480
ggctcggccc gctcgcccac agctcgccct cctcgccggg tgccacgtcg gcgccggaca  45540
ccgggtcgac gaaccgcagc gacaggcccg gcacgggcag cccgcacgag ccgggaaccc  45600
gcgcatcctc cagggtgttg gcggtgagcg agccggtcgt ctcggtgcag ccgtacgtgt  45660
cgagcagggg cacgccgaac gtcgcctcga aatccctggt gagcgacgcc ggcgaggtgg  45720
atccggcgac cagcgccacg cgcagcgcgc gagcccgcgg ctcgccggac acggcgccga  45780
ggaggtagcg gtacatcgtc ggcacgccga cgagcacggt gctggagtgt tcggccaggg  45840
cgtcgaggac gtcacgcgcg acgaagccgc ccaggatacg ggcggacgcg ccgaccgtga  45900
ggacggcgag caggcagagg tggtggccga ggctgtggaa cagcggggcg ggccagagca  45960
gttcgtcgtc ctcggtcagc cgccaggacg gcacgtcgca gtgcatcgcg gaccacaggc  46020
cgctgcgctg tgcggaaacc acgcccttgg gacggccggt ggtgccggag gtgtagagca  46080
tccaggcggg ttcgtccagg ccgaggtcgt cgcggggcgg gcacggcggc tcggtcccgg  46140
cgaggtcctc gtaggagacg cagtccggtg cccggcgccc gacgagcacg acggtggcgt  46200
```

-continued

```
cggtgccggt gcggcgcacc tggtcgaggt gggtttcgtc ggtgaccagc acggtcgcgc 46260
cggagtccgt caggaagtgg gcgagttcgg cgtcggcggc gtccgggttg agcgggacgg 46320
cgacggcggc ggcgcgggcg gcggcgaggt agacctcgat ggtctcgatc cggttgccga 46380
gcagcatcgc gacccggtcg ccgcggtcga cgccggacgc ggcgaggtgt ccggcgagcc 46440
ggccggcccg gagccggagt tgcgtgtacg tcacggcgcg ttgggaatcc gtgtaggcga 46500
tccggtcgcc gcgtcgctcg gcatggatgc ggagcaattc gtgcaacggc cggattggtt 46560
ccacacgcgc catggaaaca cctttctctc gaccaaccgc acaacagcac ggaaccggcc 46620
acgagtagac gccggcgacg ctagcagcgt tttccggacc gccacccct gaagatcccc 46680
ctaccgtggc cggcctcccc ggacgctcat ctaggggtt gcacgcatac cgccgtgcgt 46740
aattgccttc ctgatgaccg atgccggacg ccagggaagg gtggaggcgt tgtccatatc 46800
tgtcacggcg ccgtattgcc gcttcgagaa gaccggatca ccggacctcg agggtgacga 46860
gacggtgctc ggcctgatcg agcacggcac cggccacacc gacgtgtcgc tggtggacgg 46920
tgctccccgg accgccgtgc acaccacgac ccgtgacgac gaggcgttca ccgaggtctg 46980
gcacgcacag cgccctgtcg agtccggcat ggacaacggc atcgcctggg cccgcaccga 47040
cgcgtacctg ttcggtgtcg tgcgcaccgg cgagagcggc aggtacgccg atgccaccgc 47100
ggccctctac acgaacgtct tccagctcac ccggtcgctg ggtatcccc tgctcgcccg 47160
gacctggaac tacgtcagcg gtatcaacac gacgaacgcg gacgggctgg aggtgtaccg 47220
ggacttctgc gtgggccgcg cccaggcgct cgacgagggc gggatcgacc cggccaccat 47280
gcccgcggcc accggtatcg gcgcccacgg gggcggcatc acctgcgtgt tcctcgccgc 47340
ccggggcgga gtgcggatca acatcgagaa ccccgccgtc ctcacggccc accactaccc 47400
gacgacgtac ggtccgcggc ccccggtctt cgcacgggcc acctggctgg gcccgccgga 47460
gggggccgg ctgttcatct ccgcgacggc cggcatcctc ggacaccgaa cggtgcacca 47520
cggtgatgtg accggccagt gcgaggtcgc cctcgacaac atggcccggg tcatcggcgc 47580
ggagaacctg cggcgccacg gcgtccagcg ggggcacgtc ctcgccgacg tggaccacct 47640
caaggtctac gtccgccgcc gcgaggatct cgatacggtc cgccgggtct gcgccgcacg 47700
cctgtcgagc accgcggccg tcgccctttt gcacaccgac atagcccgcg aggatctgct 47760
cgtcgaaatc gaaggcatgg tggcgtgaca atacccggta aaaggcccgc gacgctgcgc 47820
ctcggcggat ccgcgaagag aaagaagagc gtcaccgcac agcgcggcag cccggtcctt 47880
tcgtccttcg cacagcggcg gatctggttt ctccagcaat tggacccgga gagcaacgcc 47940
tataatctcc cgctcgtgca acgcctgcgc ggtctattgg acgcgccggc cctggagcgt 48000
gcgctggcgc tcgtcgtcgc gcgccacgag gcgttgcgga cggtgttcga caccgccgac 48060
ggcgagcccc tccagcgggt gcttcccgcc ccggaacacc tcctgcgcca cgcgcgggcg 48120
ggcagcgagg aggacgccgc ccggctcgtc cgcgacgaga tcgccgcgcc gttcgacctc 48180
gccaccgggc cgttgatcag ggccctgctg atccgcctcg gtgacgacga ccacgttctc 48240
gcggtgaccg tgcaccatgt cgccggcgac ggctggtcgt tcgggctcct ccaacatgaa 48300
ctcgcagccc actacacggc gctgcgcgac actgcccgcc ctgccgaact gccgccgttg 48360
ccggtgcagt acgccgactt cgccgcctgg gagcggcgcg aactcaccgg cgccggactg 48420
gacaggcgtc tggcctactg gcgcgagcaa ctccggggcg ccccggcgcg gctcgccctc 48480
cccaccgacc gtccccgccc gccggtcgcc gacgcggacg cgggcatggc cgagtggcgg 48540
ccgccggccg cgctggccac cgcggtcctc acgctcgcgc gcgactccgg tgcgtccgtg 48600
```

```
ttcatgaccc tgctggcggc cttccaagcg gtcctcgccc ggcaggcggg cacgcgggac  48660
gtgctggtcg gcacgcccgt ggcgaaccgt acgcgggcgg cgtacgaggg cctgatcggc  48720
atgttcgtca acacgctcgc gctgcgcggc gacctctcgg gcgatccgtc gttccgggaa  48780
ctcctcgacc gctgccgggc cacgaccacg gacgcgttcg cccacgccga cctgccgttc  48840
gagaacgtca tcgaactcgt cgcaccggaa cgcgacctgt cggtcaaccc ggtcgtccag  48900
gtgctgttgc aggtgctgcg gcgcgacgcg gcgacggccg cgctgcccgg catcgcggcc  48960
gaaccgttcc gcaccggacg ctggttcacc cgcttcgacc tcgaattcca tgtgtacgag  49020
gagccgggtg gcgcgctgac cggcgaactg ctctacagcc gtgcgctgtt cgacgagcca  49080
cggatcacgg ggttgctgga ggagttcacg gcggtgcttc aggcggtcac cgccgacccg  49140
gacgtacggc tgtcgcggct gccggccggc gacgcgacgg cggcagcgcc cgtggtgccc  49200
tcgaacgaca cggcgcggga cctgcccgtc gacacgctgc cgggcctgct ggcccggtac  49260
gccgcacgca cccccggcgc cgtggccgtc accgacccgc acatctccct cacctacgcg  49320
cagctggacc ggcgggcgaa ccgcctcgcg cacctgctcc gcgcgcgcgg caccgccacc  49380
ggcgacctgg tcgggatctg cgccgatcgc ggcgccgacc tgatcgtcgg catcgtgggg  49440
atcctcaagg cgggcgccgc ttatgtgccg ctggaccccg aacatcctcc ggagcgcacg  49500
gcgttcgtgc tggccgacgc gcagctgacc acggtggtgg cgcacgaggt ctaccgttcc  49560
cggttccccg atgtgccgca cgtggtggcg ttggacgacc cggagctgga ccggcagccg  49620
gacgacacgg cgccggacgt cgagctggac cgggacagcc tcgcctacgc gatctacacg  49680
tccgggtcga ccggcaggcc gaaggccgtg ctcatgccgg gtgtcagcgc cgtcaacctg  49740
ctgctctggc aggagcgcac gatgggccgc gagccggcca gccgcaccgt ccagttcgtg  49800
acgcccacgt tcgactactc ggtgcaggag atcttttccg cgctgctggg cggcacgctc  49860
gtcatcccgc cggacgaggt gcggttcgac ccgccgggac tcgcccggtg gatggacgaa  49920
caggcgatta cccggatcta cgcgccgacg gccgtactgc gcgcgctgat cgagcacgtc  49980
gatccgcaca gcgaccagct cgccgccctg cggcacctgt gccagggcgg cgaggcgctg  50040
atcctcgacg cgcggttgcg cgagctgtgc cggcaccggc cccacctgcg cgtgcacaat  50100
cactacggtc cggccgaaag ccagctcatc accgggtaca cgctgcccgc cgaccccgac  50160
gcgtggcccg ccaccgcacc gatcggcccg ccgatcgaca acacccgcat ccatctgctc  50220
gacgaggcga tgcggccggt tccggacggt atgccggggc agctctgcgt cgccggcgtc  50280
ggcctcgccc gtgggtacct ggcccgtccc gagctgaccg ccgagcgctg ggtgccggga  50340
gatgcggtcg gcgaggagcg catgtacctc accggcgacc tggcccgccg cgcgcccgac  50400
ggcgacctgg aattcctcgg ccggatcgac gaccaggtca agatccgcgg catccgcgtc  50460
gaaccgggtg agatcgagag cctgctcgcc gaggacgccc gcgtcacgca ggcggcggtg  50520
tccgtgcgcg aggaccggcg gggcgagaag ttcctggccg cgtacgtcgt accggtggcc  50580
ggccggcacg gcgacgactt cgccgcgtcg ctgcgcgcgg gactggccgc ccggctgccc  50640
gccgcgctcg tgccctccgc cgtcgtcctg gtggagcgac tgccgaggac cacgagcggc  50700
aaggtggacc ggcgcgcgct gcccgacccg gagccgggcc cggcgtcgac cggggcggtt  50760
acgccccgca ccgatgccga gcggacggtg tgccggatct tccaggaggt gctcgacgtc  50820
ccgcgggtcg gtgccgacga cgacttcttc acgctcggcg ggcactccct gctcgccacc  50880
cgggtcgtct cccgcatccg cgccgagctg ggtgccgatg tcccgctgcg tacgctcttc  50940
```

-continued

```
gacgggcgga cgcccgccgc gctcgcccgt gcggcggacg aggccggccc ggccgccctg  51000

cccccgatcg cgccctccgc ggagaacggg ccggcccccc tcaccgcggc acaggaacag  51060

atgctgcact cgcacggctc gctgctcgcc gcgccctcct acacggtcgc cccgtacggg  51120

ttccggctgc gcgggccact cgaccgcgaa gcgctcgacg cggcactgac ccggatcgcc  51180

gcgcgccacg agccgctgcg gaccgggttc cgcgatcggg aacaggtcgt ccggccgccc  51240

gctccggtgc gcgccgaggt ggttccggtg ccggtcggcg acgtcgacgc cgcggtccgg  51300

gtcgcccacc gggagctgac ccggccgttc gacctcgtga acgggtcgtt gctgcgtgcc  51360

gtgctgctgc cgctgggcgc cgaggatcac gtgctgctgc tgatgctgca ccacctcgcc  51420

ggtgacggat ggtccttcga cctcctggtc cgggagttgt cggggacgca accggacctt  51480

ccggtgtcct acacggacgt ggcccggtgg gaacggagtc cggccgtgat cgcggccagg  51540

gagaacgacc gggcctactg gcgccggcgg ctgggggggcg ccaccgcgcc ggagctgccc  51600

gcggtccggc ccggcggggc accgaccggg cgggcgttcc tgtggacgct caaggacacc  51660

gccgtcctgg cggcacgccg ggtcgcggac gcccacgacg cgacgttgca cgaaaccgtg  51720

ctcggcgcct tcgccctggt cgtggcggag accgccgaca ccgacgacgt gctcgtcgcg  51780

acgccgttcg cggaccgggg gtacgccggg accgaccacc tcatcggctt cttcgcgaag  51840

gtcctcgcgc tgcgcctcga cctcggcggc acgccgtcgt tccccgaggt gctgcgccgg  51900

gtgcacaccg cgatggtggg cgcgcacgcc caccaggcgg tgccctactc cgcgctgcgc  51960

gccgaggacc ccgcgctgcc gccggccccc gtgtcgttcc agctcatcag cgcgctcagc  52020

gcggaactgc ggctgcccgg catgcacacc gagccgttcc ccgtcgtcgc cgagaccgtc  52080

gacgagatga ccggcgaact gtcgatcaac ctcttcgacg acggtcgcac cgtctccggc  52140

gcggtggtcc acgatgccgc gctgctcgac cgtgccaccg tcgacgattt gctcacccgg  52200

gtggaggcga cgctgcgtgc cgccgcgggc gacctcaccg tacgcgtcac cggttacgtg  52260

gaaagcgagt agcc atg ccc gag cag gac aag aca gtc gag tac ctt cgc    52310
                Met Pro Glu Gln Asp Lys Thr Val Glu Tyr Leu Arg
                 1               5                  10

tgg gcg acc gcg gaa ctc cag aag acc cgt gcg gaa ctc gcc gcg cac    52358
Trp Ala Thr Ala Glu Leu Gln Lys Thr Arg Ala Glu Leu Ala Ala His
         15                  20                  25

agc gag ccg ttg gcg atc gtg ggg atg gcc tgc cgg ctg ccc ggc ggg    52406
Ser Glu Pro Leu Ala Ile Val Gly Met Ala Cys Arg Leu Pro Gly Gly
     30                  35                  40

gtc gcg tcg ccg gag gac ctg tgg cag ttg ctg gag tcc ggt ggc gac    52454
Val Ala Ser Pro Glu Asp Leu Trp Gln Leu Leu Glu Ser Gly Gly Asp
 45                  50                  55                  60

ggc atc acc gcg ttc ccc acg gac cgg ggc tgg gag acc acc gcc gac    52502
Gly Ile Thr Ala Phe Pro Thr Asp Arg Gly Trp Glu Thr Thr Ala Asp
                 65                  70                  75

ggt cgc ggc ggc ttc ctc acc ggg gcg gcc ggc ttc gac gcg gcg ttc    52550
Gly Arg Gly Gly Phe Leu Thr Gly Ala Ala Gly Phe Asp Ala Ala Phe
             80                  85                  90

ttc ggc atc agc ccg cgc gag gcg ctg gcg atg gac ccg cag cag cgc    52598
Phe Gly Ile Ser Pro Arg Glu Ala Leu Ala Met Asp Pro Gln Gln Arg
         95                 100                 105

ctg gcc ctg gag acc tcg tgg gag gcg ttc gag cac gcg ggc atc gat    52646
Leu Ala Leu Glu Thr Ser Trp Glu Ala Phe Glu His Ala Gly Ile Asp
    110                 115                 120

ccg cag acg ctg cgg ggc agt gac acg ggg gtg ttc ctc ggc gcg ttc    52694
Pro Gln Thr Leu Arg Gly Ser Asp Thr Gly Val Phe Leu Gly Ala Phe
125                 130                 135                 140
```

-continued

```
ttc cag ggg tac ggc atc ggc gcc gac ttc gac ggt tac ggc acc acg     52742
Phe Gln Gly Tyr Gly Ile Gly Ala Asp Phe Asp Gly Tyr Gly Thr Thr
                145                 150                 155

agc att cac acg agc gtg ctc tcc ggc cgc ctc gcg tac ttc tac ggt     52790
Ser Ile His Thr Ser Val Leu Ser Gly Arg Leu Ala Tyr Phe Tyr Gly
            160                 165                 170

ctg gag ggt ccg gcg gtc acg gtc gac acg gcg tgt tcg tcg tcg ctg     52838
Leu Glu Gly Pro Ala Val Thr Val Asp Thr Ala Cys Ser Ser Ser Leu
        175                 180                 185

gtg gcg ctg cac cag gcc ggg cag tcg ctg cgc tcc ggc gaa tgc tcg     52886
Val Ala Leu His Gln Ala Gly Gln Ser Leu Arg Ser Gly Glu Cys Ser
    190                 195                 200

ctc gcc ctg gtc ggc ggc gtc acg gtg atg gcc tcg ccg gcg ggg ttc     52934
Leu Ala Leu Val Gly Gly Val Thr Val Met Ala Ser Pro Ala Gly Phe
205                 210                 215                 220

gcg gac ttc tcc gag cag ggc ggc ctg gcc ccc gac gcg cgc tgc aag     52982
Ala Asp Phe Ser Glu Gln Gly Gly Leu Ala Pro Asp Ala Arg Cys Lys
                225                 230                 235

gcc ttc gcg gaa gcg gct gac ggc acc ggt ttc gcc gag ggg tcc ggc     53030
Ala Phe Ala Glu Ala Ala Asp Gly Thr Gly Phe Ala Glu Gly Ser Gly
            240                 245                 250

gtc ctg atc gtc gag aag ctc tcc gac gcc gag cgc aac ggc cac cgc     53078
Val Leu Ile Val Glu Lys Leu Ser Asp Ala Glu Arg Asn Gly His Arg
        255                 260                 265

gtg ctg gcg gtc gtc cgg ggt tcc gcc gtc aac cag gac ggt gcc tcc     53126
Val Leu Ala Val Val Arg Gly Ser Ala Val Asn Gln Asp Gly Ala Ser
    270                 275                 280

aac ggg ctg tcc gcg ccg aac ggg ccg tcg cag gag cgg gtg atc cgg     53174
Asn Gly Leu Ser Ala Pro Asn Gly Pro Ser Gln Glu Arg Val Ile Arg
285                 290                 295                 300

cag gcc ctg gcc aac gcc gga ctc acc ccg gcg gac gtg gac gcc gtc     53222
Gln Ala Leu Ala Asn Ala Gly Leu Thr Pro Ala Asp Val Asp Ala Val
                305                 310                 315

gag gcc cac ggc acc ggc acc agg ctg ggc gac ccc atc gag gca cag     53270
Glu Ala His Gly Thr Gly Thr Arg Leu Gly Asp Pro Ile Glu Ala Gln
            320                 325                 330

gcc gtg ctg gcc acc tac ggg cag ggg cgc gac acc cct gtg ctg ctg     53318
Ala Val Leu Ala Thr Tyr Gly Gln Gly Arg Asp Thr Pro Val Leu Leu
        335                 340                 345

ggc tcg ctg aag tcc aac atc ggc cac acc cag gcc gcc gcg ggc gtc     53366
Gly Ser Leu Lys Ser Asn Ile Gly His Thr Gln Ala Ala Ala Gly Val
    350                 355                 360

gcc ggt gtc atc aag atg gtc ctc gcc atg cgg cac ggc acc ctg ccc     53414
Ala Gly Val Ile Lys Met Val Leu Ala Met Arg His Gly Thr Leu Pro
365                 370                 375                 380

cgc acc ctg cac gtg gac acg ccg tcc tcg cac gtc gac tgg acg gcc     53462
Arg Thr Leu His Val Asp Thr Pro Ser Ser His Val Asp Trp Thr Ala
                385                 390                 395

ggc gcc gtc gaa ctc ctc acc gac gcc cgg ccc tgg ccc gaa acc gac     53510
Gly Ala Val Glu Leu Leu Thr Asp Ala Arg Pro Trp Pro Glu Thr Asp
            400                 405                 410

cgc cca cgg cgc gcc ggt gtc tcc tcc ttc ggc gtc agc ggc acc aac     53558
Arg Pro Arg Arg Ala Gly Val Ser Ser Phe Gly Val Ser Gly Thr Asn
        415                 420                 425

gcc cac atc atc ctc gaa agc cac ccc cga ccg gcc ccc gaa ccc gcc     53606
Ala His Ile Ile Leu Glu Ser His Pro Arg Pro Ala Pro Glu Pro Ala
    430                 435                 440

ccg gca ccc gac acc gga ccg ctg ccg ctg ctg ctc tcg gcc cgc acc     53654
Pro Ala Pro Asp Thr Gly Pro Leu Pro Leu Leu Leu Ser Ala Arg Thr
```

-continued

```
445                 450                 455                 460

ccg cag gca ctc gac gca cag gta cac cgc ctg cgc gcg ttc ctc gac     53702
Pro Gln Ala Leu Asp Ala Gln Val His Arg Leu Arg Ala Phe Leu Asp
                465                 470                 475

gac aac ccc ggc gcg gac cgg gtc gcc gtc gcg cag aca ctc gcc cgg     53750
Asp Asn Pro Gly Ala Asp Arg Val Ala Val Ala Gln Thr Leu Ala Arg
            480                 485                 490

cgc acc cag ttc gag cac cgc gcc gtg ctg ctc ggc gac acg ctc atc     53798
Arg Thr Gln Phe Glu His Arg Ala Val Leu Leu Gly Asp Thr Leu Ile
        495                 500                 505

acc gtg agc ccg aac gcc ggc cgc gga ccg gtg gtc ttc gtc tac tcg     53846
Thr Val Ser Pro Asn Ala Gly Arg Gly Pro Val Val Phe Val Tyr Ser
    510                 515                 520

ggg caa agc acg ctg cac ccg cac acc ggg cgg caa ctc gcg tcc acc     53894
Gly Gln Ser Thr Leu His Pro His Thr Gly Arg Gln Leu Ala Ser Thr
525                 530                 535                 540

tac ccc gtg ttc gcc gaa gcg tgg cgc gag gcc ctc gac cac ctc gac     53942
Tyr Pro Val Phe Ala Glu Ala Trp Arg Glu Ala Leu Asp His Leu Asp
                545                 550                 555

ccc acc cag ggc ccg gcc acg cac ttc gcc cac cag acc gcg ctc acc     53990
Pro Thr Gln Gly Pro Ala Thr His Phe Ala His Gln Thr Ala Leu Thr
            560                 565                 570

gcg ctc ctg cgg tcc tgg ggc atc acc ccg cac gcg gtc atc ggc cac     54038
Ala Leu Leu Arg Ser Trp Gly Ile Thr Pro His Ala Val Ile Gly His
        575                 580                 585

tcc ctc ggt gag atc acc gcc gcg cac gcc gcc ggt gtc ctg tcc ctg     54086
Ser Leu Gly Glu Ile Thr Ala Ala His Ala Ala Gly Val Leu Ser Leu
    590                 595                 600

agg gac gcg ggc gcg ctc ctc acc acc cgc acc cgc ctg atg gac caa     54134
Arg Asp Ala Gly Ala Leu Leu Thr Thr Arg Thr Arg Leu Met Asp Gln
605                 610                 615                 620

ctg ccg tcg ggc ggc gcg atg gtc acc gtc ctg acc agc gag gaa aag     54182
Leu Pro Ser Gly Gly Ala Met Val Thr Val Leu Thr Ser Glu Glu Lys
                625                 630                 635

gca cgc cag gtg ctg cgg ccg ggc gtg gag atc gcc gcc gtc aac ggc     54230
Ala Arg Gln Val Leu Arg Pro Gly Val Glu Ile Ala Ala Val Asn Gly
            640                 645                 650

ccc cac tcc ctc gtg ctg tcc ggg gac gag gaa gcc gta ctc gaa gcc     54278
Pro His Ser Leu Val Leu Ser Gly Asp Glu Glu Ala Val Leu Glu Ala
        655                 660                 665

gcc cgg cag ctc ggc atc cac cac cgc ctg ccg acc cgc cac gcc ggc     54326
Ala Arg Gln Leu Gly Ile His His Arg Leu Pro Thr Arg His Ala Gly
    670                 675                 680

cac tcc gag cgc atg cag cca ctc gtc gcc ccc ctc ctc gac gtc gcc     54374
His Ser Glu Arg Met Gln Pro Leu Val Ala Pro Leu Leu Asp Val Ala
685                 690                 695                 700

cgg acc ctg acg tac cac cag ccc cac acc gcc atc ccc ggc gac ccc     54422
Arg Thr Leu Thr Tyr His Gln Pro His Thr Ala Ile Pro Gly Asp Pro
                705                 710                 715

acc acc gcc gaa tac tgg gcg cac cag gtc cgc gac caa gta cgt ttc     54470
Thr Thr Ala Glu Tyr Trp Ala His Gln Val Arg Asp Gln Val Arg Phe
            720                 725                 730

cag gcg cac acc gag cag tac ccg ggc gcg acg ttc ctc gag atc ggc     54518
Gln Ala His Thr Glu Gln Tyr Pro Gly Ala Thr Phe Leu Glu Ile Gly
        735                 740                 745

ccc aac cag gac ctc tcg ccg ctc gtc gac ggc gtt gcc gcc cag acc     54566
Pro Asn Gln Asp Leu Ser Pro Leu Val Asp Gly Val Ala Ala Gln Thr
    750                 755                 760

ggt acg ccc gac gag gtg cgg gcg ctg cac acc gcg ctc gcg cag ctc     54614
```

-continued

```
Gly Thr Pro Asp Glu Val Arg Ala Leu His Thr Ala Leu Ala Gln Leu
765                 770                 775                 780

cac gtc cgc ggc gtc gcg atc gac tgg acg ctc gtc ctc ggc ggg gac    54662
His Val Arg Gly Val Ala Ile Asp Trp Thr Leu Val Leu Gly Gly Asp
                785                 790                 795

cgc gcg ccc gtc acg ctg ccc acg tat ccg ttc cag cac aag gac tac    54710
Arg Ala Pro Val Thr Leu Pro Thr Tyr Pro Phe Gln His Lys Asp Tyr
            800                 805                 810

tgg ctg cgg ccc acc tcc cgg gcc gat gtg acc ggc gcg ggg cag gag    54758
Trp Leu Arg Pro Thr Ser Arg Ala Asp Val Thr Gly Ala Gly Gln Glu
        815                 820                 825

cag gtg gcg cac ccg ctg ctc ggc gcc gcg gtc gcg ctg ccc ggc acg    54806
Gln Val Ala His Pro Leu Leu Gly Ala Ala Val Ala Leu Pro Gly Thr
    830                 835                 840

ggc gga gtc gtc ctg acc ggc cgc ctg tcg ctg gcc tcc cat ccg tgg    54854
Gly Gly Val Val Leu Thr Gly Arg Leu Ser Leu Ala Ser His Pro Trp
845                 850                 855                 860

ctc ggc gag cac gcg gtc gac ggc acc gtg ctc ctg ccc ggc gcg gcc    54902
Leu Gly Glu His Ala Val Asp Gly Thr Val Leu Leu Pro Gly Ala Ala
                865                 870                 875

ttc ctc gaa ctc gcg gcg cgc gcc ggc gac gag gtc ggc tgc gac ctg    54950
Phe Leu Glu Leu Ala Ala Arg Ala Gly Asp Glu Val Gly Cys Asp Leu
            880                 885                 890

ctg cac gaa ctc gtc atc gag acg ccg ctc gtg ctg ccc gcg acc ggc    54998
Leu His Glu Leu Val Ile Glu Thr Pro Leu Val Leu Pro Ala Thr Gly
        895                 900                 905

ggt gtg gcg gtc tcc gtc gag atc gcc gaa ccc gac gac acg ggg cgg    55046
Gly Val Ala Val Ser Val Glu Ile Ala Glu Pro Asp Asp Thr Gly Arg
    910                 915                 920

cgg gcg gtc acc gtc cac gcg cgg gcc gac ggc tcg ggc ctg tgg acc    55094
Arg Ala Val Thr Val His Ala Arg Ala Asp Gly Ser Gly Leu Trp Thr
925                 930                 935                 940

cga cac gcc ggc gga ttc ctc ggc acg gca ccg gca ccg gcc acg gcc    55142
Arg His Ala Gly Gly Phe Leu Gly Thr Ala Pro Ala Pro Ala Thr Ala
                945                 950                 955

acg gac ccg gca ccc tgg ccg ccc gcg gaa gcc gga ccg gtc gac gtc    55190
Thr Asp Pro Ala Pro Trp Pro Pro Ala Glu Ala Gly Pro Val Asp Val
            960                 965                 970

gcc gac gtc tac gac cgg ttc gag gac atc ggg tac tcc tac gga ccg    55238
Ala Asp Val Tyr Asp Arg Phe Glu Asp Ile Gly Tyr Ser Tyr Gly Pro
        975                 980                 985

ggc ttc cgg ggg ctg cgg gcc gcc tgg cgc gcc ggc gac acc gtg tac    55286
Gly Phe Arg Gly Leu Arg Ala Ala Trp Arg Ala Gly Asp Thr Val Tyr
    990                 995                 1000

gcc gag gtc gcg ctc ccc gac gag cag agc gcc gac gcc gcc cgt ttc    55334
Ala Glu Val Ala Leu Pro Asp Glu Gln Ser Ala Asp Ala Ala Arg Phe
1005                1010                1015                1020

acg ctg cac ccc gcg ctg ctc gac gcc gcg ttc cag gcc ggc gcg ctg    55382
Thr Leu His Pro Ala Leu Leu Asp Ala Ala Phe Gln Ala Gly Ala Leu
                1025                1030                1035

gcc gcg ctc gac gca ccc ggc ggg gcg gcc cga ctg ccg ttc tcg ttc    55430
Ala Ala Leu Asp Ala Pro Gly Gly Ala Ala Arg Leu Pro Phe Ser Phe
            1040                1045                1050

cag gac gtc cgc atc cac gcg gcc ggg gcg acg cgg ctg cgg gtc acg    55478
Gln Asp Val Arg Ile His Ala Ala Gly Ala Thr Arg Leu Arg Val Thr
        1055                1060                1065

gtc ggc cgc gac ggc gag cgc agc acc gtc cgc atg acc ggc ccg gac    55526
Val Gly Arg Asp Gly Glu Arg Ser Thr Val Arg Met Thr Gly Pro Asp
    1070                1075                1080
```

-continued

```
ggg cag ctg gtg gcc gtg gtc ggt gcc gtg ctg tcg cgc ccg tac gcg    55574
Gly Gln Leu Val Ala Val Val Gly Ala Val Leu Ser Arg Pro Tyr Ala
1085                1090                1095                1100

gaa ggc tcc ggt gac ggc ctg ctg cgc ccg gtc tgg acc gag ctg ccg    55622
Glu Gly Ser Gly Asp Gly Leu Leu Arg Pro Val Trp Thr Glu Leu Pro
                1105                1110                1115

atg ccc gtc ccg tcc gcg gac gat ccg cgc gtg gag gtc ctc ggc gcc    55670
Met Pro Val Pro Ser Ala Asp Asp Pro Arg Val Glu Val Leu Gly Ala
            1120                1125                1130

gac ccg ggc gac ggc gac gtt ccg gcg gcc acc cgg gag ctg acc gcc    55718
Asp Pro Gly Asp Gly Asp Val Pro Ala Ala Thr Arg Glu Leu Thr Ala
        1135                1140                1145

cgc gtc ctc ggc gcg ctc cag cgc cac ctg tcc gcc gcc gag gac acc    55766
Arg Val Leu Gly Ala Leu Gln Arg His Leu Ser Ala Ala Glu Asp Thr
    1150                1155                1160

acc ttg gtg gta cgg acc ggc acc ggc ccg gcc gct gcc gcc gcc gcg    55814
Thr Leu Val Val Arg Thr Gly Thr Gly Pro Ala Ala Ala Ala Ala Ala
1165                1170                1175                1180

ggt ctg gtc cgc tcg gcg cag gcg gag aac ccc ggc cgc gtc gtg ctc    55862
Gly Leu Val Arg Ser Ala Gln Ala Glu Asn Pro Gly Arg Val Val Leu
                1185                1190                1195

gtc gag gcg tcc ccg gac acc tcg gtg gag ctg ctc gcc gcg tgc gcc    55910
Val Glu Ala Ser Pro Asp Thr Ser Val Glu Leu Leu Ala Ala Cys Ala
            1200                1205                1210

gcg ctg gac gaa ccg cag ctg gcc gtc cgg gac ggc gtg ctc ttc gcg    55958
Ala Leu Asp Glu Pro Gln Leu Ala Val Arg Asp Gly Val Leu Phe Ala
        1215                1220                1225

ccg cgg ctg gtc cgg atg tcc gac ccc gcg cac ggc ccg ctg tcc ctg    56006
Pro Arg Leu Val Arg Met Ser Asp Pro Ala His Gly Pro Leu Ser Leu
    1230                1235                1240

ccg gac ggc gac tgg ctg ctc acc cgg tcc gcc tcc ggc acg ttg cac    56054
Pro Asp Gly Asp Trp Leu Leu Thr Arg Ser Ala Ser Gly Thr Leu His
1245                1250                1255                1260

gac gtc gcg ctc ata gcc gac gac acg ccc cgg cgg gcg ctc gaa gcc    56102
Asp Val Ala Leu Ile Ala Asp Asp Thr Pro Arg Arg Ala Leu Glu Ala
                1265                1270                1275

ggc gag gtc cgc atc gac gtc cgc gcg gcc gga ctg aac ttc cgc gat    56150
Gly Glu Val Arg Ile Asp Val Arg Ala Ala Gly Leu Asn Phe Arg Asp
            1280                1285                1290

gtg ctg atc gcg ctc ggg acg tac acc ggg gcc acg gcc atg ggc ggc    56198
Val Leu Ile Ala Leu Gly Thr Tyr Thr Gly Ala Thr Ala Met Gly Gly
        1295                1300                1305

gag gcc gcg ggc gtc gtg gtg gag acc ggg ccc ggc gtg gac gac ctg    56246
Glu Ala Ala Gly Val Val Val Glu Thr Gly Pro Gly Val Asp Asp Leu
    1310                1315                1320

tcc ccc ggc gac cgg gtg ttc ggc ctg acc cgg ggc ggc atc ggc ccg    56294
Ser Pro Gly Asp Arg Val Phe Gly Leu Thr Arg Gly Gly Ile Gly Pro
1325                1330                1335                1340

acg gcc gtc acc gac cgg cgc tgg ctg gcc cgg atc ccc gac ggc tgg    56342
Thr Ala Val Thr Asp Arg Arg Trp Leu Ala Arg Ile Pro Asp Gly Trp
                1345                1350                1355

agc ttc acc acg gcg gcg tcc gtc ccg atc gtg ttc gcg acc gcg tgg    56390
Ser Phe Thr Thr Ala Ala Ser Val Pro Ile Val Phe Ala Thr Ala Trp
            1360                1365                1370

tac ggc ctg gtc gac ctc ggc aca ctg cgc gcc ggc gag aag gtc ctc    56438
Tyr Gly Leu Val Asp Leu Gly Thr Leu Arg Ala Gly Glu Lys Val Leu
        1375                1380                1385

gtc cac gcg gcc acc ggc ggt gtc ggc atg gcc gcc gca cag atc gcc    56486
Val His Ala Ala Thr Gly Gly Val Gly Met Ala Ala Ala Gln Ile Ala
    1390                1395                1400
```

-continued

```
cgc cac ctg ggc gcc gag ctc tac gcc acc gcc agt acc ggc aag cag    56534
Arg His Leu Gly Ala Glu Leu Tyr Ala Thr Ala Ser Thr Gly Lys Gln
1405                1410                1415                1420

cac gtc ctg cgc gcc gcc ggg ctg ccc gac acg cac atc gcc gac tct    56582
His Val Leu Arg Ala Ala Gly Leu Pro Asp Thr His Ile Ala Asp Ser
                1425                1430                1435

cgg acg acc gcg ttc cgg acc gct ttc ccg cgc atg gac gtc gtc ctg    56630
Arg Thr Thr Ala Phe Arg Thr Ala Phe Pro Arg Met Asp Val Val Leu
            1440                1445                1450

aac gcg ctg acc ggc gag ttc atc gac gcg tcg ctc gac ctg ctg gac    56678
Asn Ala Leu Thr Gly Glu Phe Ile Asp Ala Ser Leu Asp Leu Leu Asp
        1455                1460                1465

gcc gac ggc cgg ttc gtc gag atg ggc cgc acc gag ctg cgc gac ccg    56726
Ala Asp Gly Arg Phe Val Glu Met Gly Arg Thr Glu Leu Arg Asp Pro
    1470                1475                1480

gcc gcg atc gtc ccc gcc tac ctg ccg ttc gac ctg ctg gac gcg ggc    56774
Ala Ala Ile Val Pro Ala Tyr Leu Pro Phe Asp Leu Leu Asp Ala Gly
1485                1490                1495                1500

gcc gac cgc atc ggc gag atc ctg ggc gaa ctg ctc cgg ctg ttc gac    56822
Ala Asp Arg Ile Gly Glu Ile Leu Gly Glu Leu Leu Arg Leu Phe Asp
                1505                1510                1515

gcg ggc gcg ctg gag ccg ctg ccg gtc cgt gcc tgg gac gtc cgg cag    56870
Ala Gly Ala Leu Glu Pro Leu Pro Val Arg Ala Trp Asp Val Arg Gln
            1520                1525                1530

gca cgc gac gcg ctc ggc tgg atg agc cgc gcc cgc cac atc ggc aag    56918
Ala Arg Asp Ala Leu Gly Trp Met Ser Arg Ala Arg His Ile Gly Lys
        1535                1540                1545

aac gtc ctg acg ctg ccc cgg ccg ctc gac ccg gag ggc gcc gtc gtc    56966
Asn Val Leu Thr Leu Pro Arg Pro Leu Asp Pro Glu Gly Ala Val Val
    1550                1555                1560

ctc acc ggc ggc tcc ggc acg ctc gcc ggc atc ctc gcc cgc cac ctg    57014
Leu Thr Gly Gly Ser Gly Thr Leu Ala Gly Ile Leu Ala Arg His Leu
1565                1570                1575                1580

cgc gaa cgg cat gtc tac ctg ctg tcc cgg acg gca ccg ccc gag ggg    57062
Arg Glu Arg His Val Tyr Leu Leu Ser Arg Thr Ala Pro Pro Glu Gly
                1585                1590                1595

acg ccc ggc gtc cac ctg ccc tgc gac gtc ggt gac cgg gac cag ctg    57110
Thr Pro Gly Val His Leu Pro Cys Asp Val Gly Asp Arg Asp Gln Leu
            1600                1605                1610

gcg gcg gcc ctg gag cgg gtg gac cgg ccg atc acc gcc gtg gtg cac    57158
Ala Ala Ala Leu Glu Arg Val Asp Arg Pro Ile Thr Ala Val Val His
        1615                1620                1625

ctc gcc ggt gcg ctg gac gac ggc acc gtc gcg tcg ctc acc ccc gag    57206
Leu Ala Gly Ala Leu Asp Asp Gly Thr Val Ala Ser Leu Thr Pro Glu
    1630                1635                1640

cgt ttc gac acg gtg ctg cgc ccg aag gcc gac ggc gcc tgg tac ctg    57254
Arg Phe Asp Thr Val Leu Arg Pro Lys Ala Asp Gly Ala Trp Tyr Leu
1645                1650                1655                1660

cac gag ctg acg aag gag cag gac ctc gcc gcg ttc gtg ctc tac tcg    57302
His Glu Leu Thr Lys Glu Gln Asp Leu Ala Ala Phe Val Leu Tyr Ser
                1665                1670                1675

tcg gcc gcc ggc gtg ctc ggc aac gcc ggc cag ggc aac tac gtc gcc    57350
Ser Ala Ala Gly Val Leu Gly Asn Ala Gly Gln Gly Asn Tyr Val Ala
            1680                1685                1690

gcg aac gcg ttc ctc gac gcg ctc gcc gag ctg cgc cac ggt tcc ggg    57398
Ala Asn Ala Phe Leu Asp Ala Leu Ala Glu Leu Arg His Gly Ser Gly
        1695                1700                1705

ctg ccg gcc ctc tcc atc gcc tgg ggg ctc tgg gag gac gtg agc ggg    57446
Leu Pro Ala Leu Ser Ile Ala Trp Gly Leu Trp Glu Asp Val Ser Gly
```

-continued

```
    1710                1715                1720

ctc acc gcg gcg ctc ggc gaa gcc gac cgg gac cgg atg cgg cgc agc    57494
Leu Thr Ala Ala Leu Gly Glu Ala Asp Arg Asp Arg Met Arg Arg Ser
1725                1730                1735                1740

ggt ttc cgg gcc atc acc gcg caa cag ggc atg cac ctg tac gag gcg    57542
Gly Phe Arg Ala Ile Thr Ala Gln Gln Gly Met His Leu Tyr Glu Ala
                1745                1750                1755

gcc ggc cgc acc gga agt ccc gtg gtg gtc gcg gcg gcg ctc gac gac    57590
Ala Gly Arg Thr Gly Ser Pro Val Val Val Ala Ala Ala Leu Asp Asp
            1760                1765                1770

gcg ccg gac gtg ccg ctg ctg cgc ggc ctg cgg cgg acg acc gtc cgg    57638
Ala Pro Asp Val Pro Leu Leu Arg Gly Leu Arg Arg Thr Thr Val Arg
        1775                1780                1785

cgg gcc gcc gtc cgg gag tgt tcg tcc gcc gac cgg ctc gcc gcg ctg    57686
Arg Ala Ala Val Arg Glu Cys Ser Ser Ala Asp Arg Leu Ala Ala Leu
    1790                1795                1800

acc ggc gac gag ctc gcc gaa gcg ctg ctg acg ctc gtc cgg gag agc    57734
Thr Gly Asp Glu Leu Ala Glu Ala Leu Leu Thr Leu Val Arg Glu Ser
1805                1810                1815                1820

acc gcc gcc gtg ctc ggc cac gtg ggt ggc gag gac atc ccc gcg acg    57782
Thr Ala Ala Val Leu Gly His Val Gly Gly Glu Asp Ile Pro Ala Thr
                1825                1830                1835

gcg gcg ttc aag gac ctc ggc atc gac tcg ctc acc gcg gtc cag ctg    57830
Ala Ala Phe Lys Asp Leu Gly Ile Asp Ser Leu Thr Ala Val Gln Leu
            1840                1845                1850

cgc aac gcc ctc acc gag gcg acc ggt gtg cgg ctg aac gcc acg gcg    57878
Arg Asn Ala Leu Thr Glu Ala Thr Gly Val Arg Leu Asn Ala Thr Ala
        1855                1860                1865

gtc ttc gac ttc ccg acc ccg cac gtg ctc gcc ggg aag ctc ggc gac    57926
Val Phe Asp Phe Pro Thr Pro His Val Leu Ala Gly Lys Leu Gly Asp
    1870                1875                1880

gaa ctg acc ggc acc cgc gcg ccc gtc gtg ccc cgg acc gcg gcc acg    57974
Glu Leu Thr Gly Thr Arg Ala Pro Val Val Pro Arg Thr Ala Ala Thr
1885                1890                1895                1900

gcc ggt gcg cac gac gag ccg ctg gcg atc gtg gga atg gcc tgc cgg    58022
Ala Gly Ala His Asp Glu Pro Leu Ala Ile Val Gly Met Ala Cys Arg
                1905                1910                1915

ctg ccc ggc ggg gtc gcg tca ccc gag gag ctg tgg cac ctc gtg gca    58070
Leu Pro Gly Gly Val Ala Ser Pro Glu Glu Leu Trp His Leu Val Ala
            1920                1925                1930

tcc ggc acc gac gcc atc acg gag ttc ccg acg gac cgc ggc tgg gac    58118
Ser Gly Thr Asp Ala Ile Thr Glu Phe Pro Thr Asp Arg Gly Trp Asp
        1935                1940                1945

gtc gac gcg atc tac gac ccg gac ccc gac gcg atc ggc aag acc ttc    58166
Val Asp Ala Ile Tyr Asp Pro Asp Pro Asp Ala Ile Gly Lys Thr Phe
    1950                1955                1960

gtc cgg cac ggt ggc ttc ctc acc ggc gcg aca ggc ttc gac gcg gcg    58214
Val Arg His Gly Gly Phe Leu Thr Gly Ala Thr Gly Phe Asp Ala Ala
1965                1970                1975                1980

ttc ttc ggc atc agc ccg cgc gag gcc ctc gcg atg gac ccg cag cag    58262
Phe Phe Gly Ile Ser Pro Arg Glu Ala Leu Ala Met Asp Pro Gln Gln
                1985                1990                1995

cgg gtg ctc ctg gag acg tcg tgg gag gcg ttc gaa agc gcc ggc atc    58310
Arg Val Leu Leu Glu Thr Ser Trp Glu Ala Phe Glu Ser Ala Gly Ile
            2000                2005                2010

acc ccg gac tcg acc cgc ggc agc gac acc ggc gtg ttc gtc ggc gcc    58358
Thr Pro Asp Ser Thr Arg Gly Ser Asp Thr Gly Val Phe Val Gly Ala
        2015                2020                2025

ttc tcc tac ggt tac ggc acc ggt gcg gac acc gac ggc ttc ggc gcg    58406
```

-continued

```
Phe Ser Tyr Gly Tyr Gly Thr Gly Ala Asp Thr Asp Gly Phe Gly Ala
    2030                2035                2040

acc ggc tcg cag acc agt gtg ctc tcc ggc cgg ctg tcg tac ttc tac    58454
Thr Gly Ser Gln Thr Ser Val Leu Ser Gly Arg Leu Ser Tyr Phe Tyr
2045                2050                2055                2060

ggt ctg gag ggt ccg gcg gtc acg gtc gac acg gcg tgt tcg tcg tcg    58502
Gly Leu Glu Gly Pro Ala Val Thr Val Asp Thr Ala Cys Ser Ser Ser
                2065                2070                2075

ctg gtg gcg ctg cac cag gcc ggg cag tcg ctg cgc tcc ggc gaa tgc    58550
Leu Val Ala Leu His Gln Ala Gly Gln Ser Leu Arg Ser Gly Glu Cys
            2080                2085                2090

tcg ctc gcc ctg gtc ggc ggc gtc acg gtg atg gcg tct ccc ggc ggc    58598
Ser Leu Ala Leu Val Gly Gly Val Thr Val Met Ala Ser Pro Gly Gly
        2095                2100                2105

ttc gtg gag ttc tcc cgg cag cgc ggc ctc gcg ccg gac ggc cgg gcg    58646
Phe Val Glu Phe Ser Arg Gln Arg Gly Leu Ala Pro Asp Gly Arg Ala
    2110                2115                2120

aag gcg ttc ggc gcg ggt gcg gac ggc acg agc ttc gcc gag ggt gcc    58694
Lys Ala Phe Gly Ala Gly Ala Asp Gly Thr Ser Phe Ala Glu Gly Ala
2125                2130                2135                2140

ggt gtg ctg atc gtc gag agg ctc tcc gac gcc gaa cgc aac ggt cac    58742
Gly Val Leu Ile Val Glu Arg Leu Ser Asp Ala Glu Arg Asn Gly His
                2145                2150                2155

acc gtc ctg gcg gtc gtc cgt ggt tcg gcg gtc aac cag gat ggt gcc    58790
Thr Val Leu Ala Val Val Arg Gly Ser Ala Val Asn Gln Asp Gly Ala
            2160                2165                2170

tcc aac ggg ctg tcg gcg ccg aac ggg ccg tcg cag gag cgg gtg atc    58838
Ser Asn Gly Leu Ser Ala Pro Asn Gly Pro Ser Gln Glu Arg Val Ile
        2175                2180                2185

cgg cag gcc ctg gcc aac gcc ggg ctc acc ccg gcg gac gtg gac gcc    58886
Arg Gln Ala Leu Ala Asn Ala Gly Leu Thr Pro Ala Asp Val Asp Ala
    2190                2195                2200

gtc gag gcc cac ggc acc ggc acc agg ctg ggc gac ccc atc gag gca    58934
Val Glu Ala His Gly Thr Gly Thr Arg Leu Gly Asp Pro Ile Glu Ala
2205                2210                2215                2220

cag gcg gta ctg gcc acc tac gga cag gag cgc gcc acc ccc ctg ctg    58982
Gln Ala Val Leu Ala Thr Tyr Gly Gln Glu Arg Ala Thr Pro Leu Leu
                2225                2230                2235

ctg ggc tcg ctg aag tcc aac atc ggc cac gcc cag gcc gcg tcc ggc    59030
Leu Gly Ser Leu Lys Ser Asn Ile Gly His Ala Gln Ala Ala Ser Gly
            2240                2245                2250

gtc gcc ggc atc atc aag atg gtg cag gcc ctc cgg cac ggg gag ctg    59078
Val Ala Gly Ile Ile Lys Met Val Gln Ala Leu Arg His Gly Glu Leu
        2255                2260                2265

ccg ccg acg ctg cac gcc gac gag ccg tcg ccg cac gtc gac tgg acg    59126
Pro Pro Thr Leu His Ala Asp Glu Pro Ser Pro His Val Asp Trp Thr
    2270                2275                2280

gcc ggc gcc gtc gaa ctg ctg acg tcg gcc cgg ccg tgg ccc gag acc    59174
Ala Gly Ala Val Glu Leu Leu Thr Ser Ala Arg Pro Trp Pro Glu Thr
2285                2290                2295                2300

gac cgg cca cgg cgt gcc gcc gtc tcc tcg ttc ggg gtg agc ggc acc    59222
Asp Arg Pro Arg Arg Ala Ala Val Ser Ser Phe Gly Val Ser Gly Thr
                2305                2310                2315

aac gcc cac gtc atc ctg gag gcc gga ccg gta acg gag acg ccc gcg    59270
Asn Ala His Val Ile Leu Glu Ala Gly Pro Val Thr Glu Thr Pro Ala
            2320                2325                2330

gca tcg cct tcc ggt gac ctt ccc ctg ctg gtg tcg gca cgc tca ccg    59318
Ala Ser Pro Ser Gly Asp Leu Pro Leu Leu Val Ser Ala Arg Ser Pro
        2335                2340                2345
```

-continued

```
gaa gcg ctc gac gag cag atc cgc cga ctg cgc gcc tac ctg gac acc     59366
Glu Ala Leu Asp Glu Gln Ile Arg Arg Leu Arg Ala Tyr Leu Asp Thr
    2350                2355                2360

acc ccg gac gtc gac cgg gtg gcc gtg gca cag acg ctg gcc cgg cgc     59414
Thr Pro Asp Val Asp Arg Val Ala Val Ala Gln Thr Leu Ala Arg Arg
2365                2370                2375                2380

aca cac ttc gcc cac cgc gcc gtg ctg ctc ggt gac acc gtc atc acc     59462
Thr His Phe Ala His Arg Ala Val Leu Leu Gly Asp Thr Val Ile Thr
                2385                2390                2395

aca ccc ccc gcg gac cgg ccc gac gaa ctc gtc ttc gtc tac tcc ggc     59510
Thr Pro Pro Ala Asp Arg Pro Asp Glu Leu Val Phe Val Tyr Ser Gly
            2400                2405                2410

cag ggc acc cag cat ccc gcg atg ggc gag cag ctc gcc gcc gcc cat     59558
Gln Gly Thr Gln His Pro Ala Met Gly Glu Gln Leu Ala Ala Ala His
        2415                2420                2425

ccc gtg ttc gcc gac gcc tgg cat gaa gcg ctc cgc cgc ctt gac aac     59606
Pro Val Phe Ala Asp Ala Trp His Glu Ala Leu Arg Arg Leu Asp Asn
    2430                2435                2440

ccc gac ccc cac gac ccc acg cac agc cag cat gtg ctc ttc gcc cac     59654
Pro Asp Pro His Asp Pro Thr His Ser Gln His Val Leu Phe Ala His
2445                2450                2455                2460

cag gcg gcg ttc acc gcc ctc ctg cgg tcc tgg ggc atc acc ccg cac     59702
Gln Ala Ala Phe Thr Ala Leu Leu Arg Ser Trp Gly Ile Thr Pro His
                2465                2470                2475

gcg gtc atc ggc cac tcg ctg ggc gag atc acc gcg gcg cac gcc gcc     59750
Ala Val Ile Gly His Ser Leu Gly Glu Ile Thr Ala Ala His Ala Ala
            2480                2485                2490

ggc atc ctg tcg ctg gac gac gcg tgc acc ctg atc acc acg cgc gcc     59798
Gly Ile Leu Ser Leu Asp Asp Ala Cys Thr Leu Ile Thr Thr Arg Ala
        2495                2500                2505

cgc ctc atg cac acg ctc ccg cca ccc ggt gcc atg gtc acc gta ctg     59846
Arg Leu Met His Thr Leu Pro Pro Pro Gly Ala Met Val Thr Val Leu
    2510                2515                2520

acc agc gaa gag aag gca cgc cag gcg ttg cgg ccg ggc gtg gag atc     59894
Thr Ser Glu Glu Lys Ala Arg Gln Ala Leu Arg Pro Gly Val Glu Ile
2525                2530                2535                2540

gcc gcc gtc aac ggg ccc cac tcc atc gtg ctg tcc ggg gac gag gac     59942
Ala Ala Val Asn Gly Pro His Ser Ile Val Leu Ser Gly Asp Glu Asp
                2545                2550                2555

gcc gtg ctc acc gtc gcc ggg cag ctc ggc atc cac cac cgc ctg ccc     59990
Ala Val Leu Thr Val Ala Gly Gln Leu Gly Ile His His Arg Leu Pro
            2560                2565                2570

gcc ccg cac gcc ggg cac tcc gcg cac atg gag ccc gtg gcc gcc gag     60038
Ala Pro His Ala Gly His Ser Ala His Met Glu Pro Val Ala Ala Glu
        2575                2580                2585

ctg ctc gcc acc acc cgc ggg ctc cgc tac cac cct ccc cac acc tcc     60086
Leu Leu Ala Thr Thr Arg Gly Leu Arg Tyr His Pro Pro His Thr Ser
    2590                2595                2600

att ccg aac gac ccc acc acc gct gag tac tgg gcc gag cag gtc cgc     60134
Ile Pro Asn Asp Pro Thr Thr Ala Glu Tyr Trp Ala Glu Gln Val Arg
2605                2610                2615                2620

aag ccc gtg ctg ttc cac gcc cac gcg cag cag tac ccg gac gcc gtg     60182
Lys Pro Val Leu Phe His Ala His Ala Gln Gln Tyr Pro Asp Ala Val
                2625                2630                2635

ttc gtg gag atc ggc ccc gcc cag gac ctc tcc ccg ctc gtc gac ggg     60230
Phe Val Glu Ile Gly Pro Ala Gln Asp Leu Ser Pro Leu Val Asp Gly
            2640                2645                2650

atc ccg ctg cag aac ggc acc gcg gac gag gtg cac gcg ctg cac acc     60278
Ile Pro Leu Gln Asn Gly Thr Ala Asp Glu Val His Ala Leu His Thr
        2655                2660                2665
```

-continued

```
gcg ctc gcg cac ctc tac gcg cgc ggt gcc acg ctc gac tgg ccc cgc    60326
Ala Leu Ala His Leu Tyr Ala Arg Gly Ala Thr Leu Asp Trp Pro Arg
    2670                2675                2680

atc ctc ggg gct ggg tca cgg cac gac gcg gat gtg ccc gcg tac gcg    60374
Ile Leu Gly Ala Gly Ser Arg His Asp Ala Asp Val Pro Ala Tyr Ala
2685                2690                2695                2700

ttc caa cgg cgg cac tac tgg atc gag tcg gca cgc ccg gcc gca tcc    60422
Phe Gln Arg Arg His Tyr Trp Ile Glu Ser Ala Arg Pro Ala Ala Ser
                2705                2710                2715

gac gcg ggc cac ccc gtg ctg ggc tcc ggt atc gcc ctc gcc ggg tcg    60470
Asp Ala Gly His Pro Val Leu Gly Ser Gly Ile Ala Leu Ala Gly Ser
            2720                2725                2730

ccg ggc cgg gtg ttc acg ggt tcc gtg ccg acc ggt gcg gac cgc gcg    60518
Pro Gly Arg Val Phe Thr Gly Ser Val Pro Thr Gly Ala Asp Arg Ala
        2735                2740                2745

gtg ttc gtc gcc gag ctg gcg ctg gcc gcc gcg gac gcg gtc gac tgc    60566
Val Phe Val Ala Glu Leu Ala Leu Ala Ala Ala Asp Ala Val Asp Cys
    2750                2755                2760

gcc acg gtc gag cgg ctc gac atc gcc tcc gtg ccc ggc cgg ccg ggc    60614
Ala Thr Val Glu Arg Leu Asp Ile Ala Ser Val Pro Gly Arg Pro Gly
2765                2770                2775                2780

cat ggc cgg acg acc gta cag acc tgg gtc gac gag ccg gcg gac gac    60662
His Gly Arg Thr Thr Val Gln Thr Trp Val Asp Glu Pro Ala Asp Asp
                2785                2790                2795

ggc cgg cgc cgg ttc acc gtg cac acc cgc acc ggc gac gcc ccg tgg    60710
Gly Arg Arg Arg Phe Thr Val His Thr Arg Thr Gly Asp Ala Pro Trp
            2800                2805                2810

acg ctg cac gcc gag ggg gtg ctg cgc ccc cat ggc acg gcc ctg ccc    60758
Thr Leu His Ala Glu Gly Val Leu Arg Pro His Gly Thr Ala Leu Pro
        2815                2820                2825

gat gcg gcc gac gcc gag tgg ccc cca ccg ggc gcg gtg ccc gcg gac    60806
Asp Ala Ala Asp Ala Glu Trp Pro Pro Pro Gly Ala Val Pro Ala Asp
    2830                2835                2840

ggg ctg ccg ggt gtg tgg cgc cgg ggg gac cag gtc ttc gcc gag gcc    60854
Gly Leu Pro Gly Val Trp Arg Arg Gly Asp Gln Val Phe Ala Glu Ala
2845                2850                2855                2860

gag gtg gac gga ccg gac ggt ttc gtg gtg cac ccc gac ctg ctc gac    60902
Glu Val Asp Gly Pro Asp Gly Phe Val Val His Pro Asp Leu Leu Asp
                2865                2870                2875

gcg gtc ttc tcc gcg gtc ggc gac gga agc cgc cag ccg gcc gga tgg    60950
Ala Val Phe Ser Ala Val Gly Asp Gly Ser Arg Gln Pro Ala Gly Trp
            2880                2885                2890

cgc gac ctg acg gtg cac gcg tcg gac gcc acc gta ctg cgc gcc tgc    60998
Arg Asp Leu Thr Val His Ala Ser Asp Ala Thr Val Leu Arg Ala Cys
        2895                2900                2905

ctc acc cgg cgc acc gac gga gcc atg gga ttc gcc gcc ttc gac ggc    61046
Leu Thr Arg Arg Thr Asp Gly Ala Met Gly Phe Ala Ala Phe Asp Gly
    2910                2915                2920

gcc ggc ctg ccg gta ctc acc gcg gag gcg gtg acg ctg cgg gag gtg    61094
Ala Gly Leu Pro Val Leu Thr Ala Glu Ala Val Thr Leu Arg Glu Val
2925                2930                2935                2940

gcg tca ccg tcc ggc tcc gag gag tcg gac ggc ctg cac cgg ttg gag    61142
Ala Ser Pro Ser Gly Ser Glu Glu Ser Asp Gly Leu His Arg Leu Glu
                2945                2950                2955

tgg ctc gcg gtc gcc gag gcg gtc tac gac ggt gac ctg ccc gag gga    61190
Trp Leu Ala Val Ala Glu Ala Val Tyr Asp Gly Asp Leu Pro Glu Gly
            2960                2965                2970

cat gtc ctg atc acc gcc gcc cac ccc gac gac ccc gag gac ata ccc    61238
His Val Leu Ile Thr Ala Ala His Pro Asp Asp Pro Glu Asp Ile Pro
```

-continued

```
        2975                2980                2985

acc cgc gcc cac acc cgc gcc acc cgc gtc ctg acc gcc ctg caa cac    61286
Thr Arg Ala His Thr Arg Ala Thr Arg Val Leu Thr Ala Leu Gln His
    2990                2995                3000

cac ctc acc acc acc gac cac acc ctc atc gtc cac acc acc acc gac    61334
His Leu Thr Thr Thr Asp His Thr Leu Ile Val His Thr Thr Thr Asp
3005                3010                3015                3020

ccc gcc ggc gcc acc gtc acc ggc ctc acc cgc acc gcc cag aac gaa    61382
Pro Ala Gly Ala Thr Val Thr Gly Leu Thr Arg Thr Ala Gln Asn Glu
                3025                3030                3035

cac ccc cac cgc atc cgc ctc atc gaa acc gac cac ccc cac acc ccc    61430
His Pro His Arg Ile Arg Leu Ile Glu Thr Asp His Pro His Thr Pro
            3040                3045                3050

ctc ccc ctg gcc caa ctc gcc acc ctc gac cac ccc cac ctc cgc ctc    61478
Leu Pro Leu Ala Gln Leu Ala Thr Leu Asp His Pro His Leu Arg Leu
        3055                3060                3065

acc cac cac acc ctc cac cac ccc cac ctc acc ccc ctc cac acc acc    61526
Thr His His Thr Leu His His Pro His Leu Thr Pro Leu His Thr Thr
    3070                3075                3080

acc cca ccc acc acc acc ccc ctc aac ccc gaa cac gcc atc atc atc    61574
Thr Pro Pro Thr Thr Thr Pro Leu Asn Pro Glu His Ala Ile Ile Ile
3085                3090                3095                3100

acc ggc ggc tcc ggc acc ctc gcc ggc atc ctc gcc cgc cac ctg aac    61622
Thr Gly Gly Ser Gly Thr Leu Ala Gly Ile Leu Ala Arg His Leu Asn
                3105                3110                3115

cac ccc cac acc tac ctc ctc tcc cgc acc cca ccc ccc gac gcc acc    61670
His Pro His Thr Tyr Leu Leu Ser Arg Thr Pro Pro Pro Asp Ala Thr
            3120                3125                3130

ccc ggc acc cac ctc ccc tgc gac gtc ggc gac ccc cac caa ctc gcc    61718
Pro Gly Thr His Leu Pro Cys Asp Val Gly Asp Pro His Gln Leu Ala
        3135                3140                3145

acc acc ctc acc cac atc ccc caa ccc ctc acc gcc atc ttc cac acc    61766
Thr Thr Leu Thr His Ile Pro Gln Pro Leu Thr Ala Ile Phe His Thr
    3150                3155                3160

gcc gcc acc ctc gac gac ggc atc ctc cac gcc ctc acc ccc gac cgc    61814
Ala Ala Thr Leu Asp Asp Gly Ile Leu His Ala Leu Thr Pro Asp Arg
3165                3170                3175                3180

ctc acc acc gtc ctc cac ccc aaa gcc aac gcc gcc tgg cac ctg cac    61862
Leu Thr Thr Val Leu His Pro Lys Ala Asn Ala Ala Trp His Leu His
                3185                3190                3195

cac ctc acc caa aac caa ccc ctc acc cac ttc gtc ctc tac tcc agc    61910
His Leu Thr Gln Asn Gln Pro Leu Thr His Phe Val Leu Tyr Ser Ser
            3200                3205                3210

gcc gcc gcc gtc ctc ggc agc ccc gga caa gga aac tac gcc gcc gcc    61958
Ala Ala Ala Val Leu Gly Ser Pro Gly Gln Gly Asn Tyr Ala Ala Ala
        3215                3220                3225

aac gcc ttc ctc gac gcc ctc gcc acc cac cgc cac acc ctc ggc caa    62006
Asn Ala Phe Leu Asp Ala Leu Ala Thr His Arg His Thr Leu Gly Gln
    3230                3235                3240

ccc gcc acc tcc atc gcc tgg ggc atg tgg cac acc acc agc acc ctc    62054
Pro Ala Thr Ser Ile Ala Trp Gly Met Trp His Thr Thr Ser Thr Leu
3245                3250                3255                3260

acc gga caa ctc gac gac gcc gac cgg gac cgc atc cgc cgc ggc ggt    62102
Thr Gly Gln Leu Asp Asp Ala Asp Arg Asp Arg Ile Arg Arg Gly Gly
                3265                3270                3275

ttc ctc ccg atc acg gac gac gag ggc atg cgc ctc tac gag gcg gcc    62150
Phe Leu Pro Ile Thr Asp Asp Glu Gly Met Arg Leu Tyr Glu Ala Ala
            3280                3285                3290

gtc ggc tcc ggc gag gac ttc gtc atg gcc gcc gcg atg gac ccg gca    62198
```

-continued

```
Val Gly Ser Gly Glu Asp Phe Val Met Ala Ala Ala Met Asp Pro Ala
        3295                3300                3305

cag ccg atg acc ggc tcc gta ccg ccc atc ctg agc ggc ctg cgc agg    62246
Gln Pro Met Thr Gly Ser Val Pro Pro Ile Leu Ser Gly Leu Arg Arg
    3310                3315                3320

agc gcg cgg cgc gtc gcc cgt gcc ggg cag acg ttc gcc cag cgg ctc    62294
Ser Ala Arg Arg Val Ala Arg Ala Gly Gln Thr Phe Ala Gln Arg Leu
3325                3330                3335                3340

gcc gag ctg ccc gac gcc gac cgc ggc gcg gcg ctg acc acc ctc gtc    62342
Ala Glu Leu Pro Asp Ala Asp Arg Gly Ala Ala Leu Thr Thr Leu Val
                3345                3350                3355

tcg gac gcc acg gcc gcc gtg ctc ggc cac gcc gac gcc tcc gag atc    62390
Ser Asp Ala Thr Ala Ala Val Leu Gly His Ala Asp Ala Ser Glu Ile
            3360                3365                3370

gcg ccg acc acg acg ttc aag gac ctc ggc atc gac tcg ctc acc gcg    62438
Ala Pro Thr Thr Thr Phe Lys Asp Leu Gly Ile Asp Ser Leu Thr Ala
        3375                3380                3385

atc gag ctg cgc aac cgg ctc gcg gag gcg acc ggg ctg cgg ctg agt    62486
Ile Glu Leu Arg Asn Arg Leu Ala Glu Ala Thr Gly Leu Arg Leu Ser
    3390                3395                3400

gcc acg ctg gtg ttc gac cac ccg aca cct cgg gtc ctc gcc gcc aag    62534
Ala Thr Leu Val Phe Asp His Pro Thr Pro Arg Val Leu Ala Ala Lys
3405                3410                3415                3420

ctc cgc acc gat ctg ttc ggc acg gcc gtg ccc acg ccc gcg cgg acg    62582
Leu Arg Thr Asp Leu Phe Gly Thr Ala Val Pro Thr Pro Ala Arg Thr
                3425                3430                3435

gca cgg acc cac cac gac gag cca ctc gcg atc gtc ggc atg gcg tgc    62630
Ala Arg Thr His His Asp Glu Pro Leu Ala Ile Val Gly Met Ala Cys
            3440                3445                3450

cga ctg ccc ggc ggg gtc gcc tcg ccg gag gac ctg tgg cag ctc gtg    62678
Arg Leu Pro Gly Gly Val Ala Ser Pro Glu Asp Leu Trp Gln Leu Val
        3455                3460                3465

gcg tcc ggc acc gac gcg atc acc gag ttc ccc acc gac cgc ggc tgg    62726
Ala Ser Gly Thr Asp Ala Ile Thr Glu Phe Pro Thr Asp Arg Gly Trp
    3470                3475                3480

gac atc gac cgg ctg ttc gac ccg gac ccg gac gcc ccc ggc aag acc    62774
Asp Ile Asp Arg Leu Phe Asp Pro Asp Pro Asp Ala Pro Gly Lys Thr
3485                3490                3495                3500

tac gtc cgg cac ggc ggc ttc ctc gcc gag gcc gcc ggc ttc gat gcc    62822
Tyr Val Arg His Gly Gly Phe Leu Ala Glu Ala Ala Gly Phe Asp Ala
                3505                3510                3515

gcg ttc ttc ggc atc agc ccg cgc gag gca cgg gcc atg gac ccg cag    62870
Ala Phe Phe Gly Ile Ser Pro Arg Glu Ala Arg Ala Met Asp Pro Gln
            3520                3525                3530

cag cgc gtc atc ctc gaa acc tcc tgg gag gcg ttc gag aac gcg ggc    62918
Gln Arg Val Ile Leu Glu Thr Ser Trp Glu Ala Phe Glu Asn Ala Gly
        3535                3540                3545

atc gtg ccg gac acg ctg cgc ggc agc gac acc ggc gtg ttc atg ggc    62966
Ile Val Pro Asp Thr Leu Arg Gly Ser Asp Thr Gly Val Phe Met Gly
    3550                3555                3560

gcg ttc tcc cat ggg tac ggc gcc ggc gtc gac ctg ggc ggg ttc ggc    63014
Ala Phe Ser His Gly Tyr Gly Ala Gly Val Asp Leu Gly Gly Phe Gly
3565                3570                3575                3580

gcc acc gcc acg cag aac agc gtg ctc tcc ggc cgg ttg tcg tac ttc    63062
Ala Thr Ala Thr Gln Asn Ser Val Leu Ser Gly Arg Leu Ser Tyr Phe
                3585                3590                3595

ttc ggc atg gag ggc ccg gcc gtc acc gtc gac acc gcc tgc tcg tcg    63110
Phe Gly Met Glu Gly Pro Ala Val Thr Val Asp Thr Ala Cys Ser Ser
            3600                3605                3610
```

-continued

```
tcg ctg gtc gcc ctg cac cag gcg gca cag gcg ctg cgg act gga gaa    63158
Ser Leu Val Ala Leu His Gln Ala Ala Gln Ala Leu Arg Thr Gly Glu
        3615                3620                3625

tgc tcg ctg gcg ctc gcc ggc ggt gtc acg gtg atg ccc acc ccg ctg    63206
Cys Ser Leu Ala Leu Ala Gly Gly Val Thr Val Met Pro Thr Pro Leu
    3630                3635                3640

ggc tac gtc gag ttc tgc cgc cag cgg gga ctc gcc ccc gac ggc cgt    63254
Gly Tyr Val Glu Phe Cys Arg Gln Arg Gly Leu Ala Pro Asp Gly Arg
3645                3650                3655                3660

tgc cag gcc ttc gcg gaa ggc gcc gac ggc acg agc ttc tcg gag ggc    63302
Cys Gln Ala Phe Ala Glu Gly Ala Asp Gly Thr Ser Phe Ser Glu Gly
                3665                3670                3675

gcc ggc gtt ctt gtg ctg gag cgg ctc tcc gac gcc gag cgc aac gga    63350
Ala Gly Val Leu Val Leu Glu Arg Leu Ser Asp Ala Glu Arg Asn Gly
            3680                3685                3690

cac acc gtc ctc gcg gtc gtc cgc tcc tcc gcc gtc aac cag gac ggc    63398
His Thr Val Leu Ala Val Val Arg Ser Ser Ala Val Asn Gln Asp Gly
        3695                3700                3705

gcc tcc aac ggc atc tcc gca ccc aac ggc ccc tcc cag cag cgc gtc    63446
Ala Ser Asn Gly Ile Ser Ala Pro Asn Gly Pro Ser Gln Gln Arg Val
    3710                3715                3720

atc cgc cag gcc ctc gac aag gcc ggg ctc gcc ccc gcc gac gtg gac    63494
Ile Arg Gln Ala Leu Asp Lys Ala Gly Leu Ala Pro Ala Asp Val Asp
3725                3730                3735                3740

gtg gtg gag gcc cac ggc acc gga acc ccg ctg ggc gac ccg atc gag    63542
Val Val Glu Ala His Gly Thr Gly Thr Pro Leu Gly Asp Pro Ile Glu
                3745                3750                3755

gca cag gcc atc atc gcg acc tac ggc cag gac cgc gac aca ccg ctc    63590
Ala Gln Ala Ile Ile Ala Thr Tyr Gly Gln Asp Arg Asp Thr Pro Leu
            3760                3765                3770

tac ctc ggt tcg gtc aag tcg aac atc gga cac acc cag acc acc gcc    63638
Tyr Leu Gly Ser Val Lys Ser Asn Ile Gly His Thr Gln Thr Thr Ala
        3775                3780                3785

ggt gtc gcc ggc gtc atc aag atg gtc atg gcg atg cgc cac ggc atc    63686
Gly Val Ala Gly Val Ile Lys Met Val Met Ala Met Arg His Gly Ile
    3790                3795                3800

gcg ccg aag aca ctg cac gtg gac gag ccg tcg tcg cat gtg gac tgg    63734
Ala Pro Lys Thr Leu His Val Asp Glu Pro Ser Ser His Val Asp Trp
3805                3810                3815                3820

acc gag ggt gcg gtg gaa ctg ctc acc gag gcg agg ccg tgg ccc gac    63782
Thr Glu Gly Ala Val Glu Leu Leu Thr Glu Ala Arg Pro Trp Pro Asp
                3825                3830                3835

gcg gga cgc ccg cgc cgc gcg ggc gtg tcg tcg ctc ggt atc agc ggt    63830
Ala Gly Arg Pro Arg Arg Ala Gly Val Ser Ser Leu Gly Ile Ser Gly
            3840                3845                3850

acg aac gcc cac gtg atc ctt gag ggt gtt ccc ggg ccg tcg cgt gtg    63878
Thr Asn Ala His Val Ile Leu Glu Gly Val Pro Gly Pro Ser Arg Val
        3855                3860                3865

gag ccg tct gtt gac ggg ttg gtg ccg ttg ccg gtg tcg gct cgg agt    63926
Glu Pro Ser Val Asp Gly Leu Val Pro Leu Pro Val Ser Ala Arg Ser
    3870                3875                3880

gag gcg agt ctg cgg ggg cag gtg gag cgg ctg gag ggg tat ctg cgc    63974
Glu Ala Ser Leu Arg Gly Gln Val Glu Arg Leu Glu Gly Tyr Leu Arg
3885                3890                3895                3900

ggg agt gtg gat gtg gcc gcg gtc gcg cag ggg ttg gtg cgt gag cgt    64022
Gly Ser Val Asp Val Ala Ala Val Ala Gln Gly Leu Val Arg Glu Arg
                3905                3910                3915

gct gtc ttc ggt cac cgt gcg gta ctg ctg ggt gat gcc cgg gtg atg    64070
Ala Val Phe Gly His Arg Ala Val Leu Leu Gly Asp Ala Arg Val Met
            3920                3925                3930
```

-continued

```
ggt gtg gcg gtg gat cag ccg cgt acg gtg ttc gtc ttt ccc ggg cag    64118
Gly Val Ala Val Asp Gln Pro Arg Thr Val Phe Val Phe Pro Gly Gln
        3935                3940                3945

ggt gct cag tgg gtg ggc atg ggt gtg gag ttg atg gac cgt tct gcg    64166
Gly Ala Gln Trp Val Gly Met Gly Val Glu Leu Met Asp Arg Ser Ala
    3950                3955                3960

gtg ttc gcg gct cgt atg gag gag tgt gcg cgg gcg ttg ttg ccg cac    64214
Val Phe Ala Ala Arg Met Glu Glu Cys Ala Arg Ala Leu Leu Pro His
3965                3970                3975                3980

acg ggc tgg gat gtg cgg gag atg ttg gcg cgg ccg gat gtg gcg gag    64262
Thr Gly Trp Asp Val Arg Glu Met Leu Ala Arg Pro Asp Val Ala Glu
                3985                3990                3995

cgg gtg gag gtg gtc cag ccg gcc agc tgg gcg gtc gcg gtc agc ctg    64310
Arg Val Glu Val Val Gln Pro Ala Ser Trp Ala Val Ala Val Ser Leu
            4000                4005                4010

gcc gca ctg tgg cag gcc cac ggg gtc gta ccc gac gcg gtg atc gga    64358
Ala Ala Leu Trp Gln Ala His Gly Val Val Pro Asp Ala Val Ile Gly
        4015                4020                4025

cac tcc cag ggc gag atc gcg gcg gcg tgc gtg gcc ggg gcc ctc agc    64406
His Ser Gln Gly Glu Ile Ala Ala Ala Cys Val Ala Gly Ala Leu Ser
    4030                4035                4040

ctt gag gac gcc gcc cgc gtg gtg gcc ttg cgc agc cag gtc atc gcg    64454
Leu Glu Asp Ala Ala Arg Val Val Ala Leu Arg Ser Gln Val Ile Ala
4045                4050                4055                4060

gcg cga ctg gcc ggg cgg gga gcg atg gct tcg gtg gca ttg ccg gcc    64502
Ala Arg Leu Ala Gly Arg Gly Ala Met Ala Ser Val Ala Leu Pro Ala
                4065                4070                4075

ggt gag gtc ggt ctg gtc gag ggc gtg tgg atc gcg gcg cgt aac ggc    64550
Gly Glu Val Gly Leu Val Glu Gly Val Trp Ile Ala Ala Arg Asn Gly
            4080                4085                4090

ccc gcc tcg aca gtc gtg gcc ggc gag ccg tcg gcg gtg gag gac gtg    64598
Pro Ala Ser Thr Val Val Ala Gly Glu Pro Ser Ala Val Glu Asp Val
        4095                4100                4105

gtg acg cgg tat gag acc gaa ggc gtg cga gtg cgt cgt atc gcc gtc    64646
Val Thr Arg Tyr Glu Thr Glu Gly Val Arg Val Arg Arg Ile Ala Val
    4110                4115                4120

gac tac gcc tcc cac acg ccc cac gtg gaa gcc atc gag gac gaa ctc    64694
Asp Tyr Ala Ser His Thr Pro His Val Glu Ala Ile Glu Asp Glu Leu
4125                4130                4135                4140

gct gag gta ctg aag gga gtt gca ggg aag gcc gcg tcg gtg gcg tgg    64742
Ala Glu Val Leu Lys Gly Val Ala Gly Lys Ala Ala Ser Val Ala Trp
                4145                4150                4155

tgg tcg acc gtg gac agc gcc tgg gtg acc gag ccg gtg gat gag agt    64790
Trp Ser Thr Val Asp Ser Ala Trp Val Thr Glu Pro Val Asp Glu Ser
            4160                4165                4170

tac tgg tac cgg aac ctg cgt cgc ccc gtc gcg ctg gac gcg gcg gtg    64838
Tyr Trp Tyr Arg Asn Leu Arg Arg Pro Val Ala Leu Asp Ala Ala Val
        4175                4180                4185

gcg gag ctg gac ggg tcc gtg ttc gtg gag tgc agc gcc cat ccg gtg    64886
Ala Glu Leu Asp Gly Ser Val Phe Val Glu Cys Ser Ala His Pro Val
    4190                4195                4200

ctg ctg ccg gcg atg gaa cag gcc cac acg gtg gcg tcg ttg cgc acc    64934
Leu Leu Pro Ala Met Glu Gln Ala His Thr Val Ala Ser Leu Arg Thr
4205                4210                4215                4220

ggt gac ggc ggc tgg gag cga tgg ctg acg gcg ttg gcg cag gcg tgg    64982
Gly Asp Gly Gly Trp Glu Arg Trp Leu Thr Ala Leu Ala Gln Ala Trp
                4225                4230                4235

acc ctg ggc gcg gca gtg gac tgg gac acg gtg gtc gaa ccg gtg cca    65030
Thr Leu Gly Ala Ala Val Asp Trp Asp Thr Val Val Glu Pro Val Pro
```

-continued

```
            4240                4245                4250

ggg cgg ctg ctc gat ctg ccc acc tac gcg ttc gag cgc cgg cgc tac    65078
Gly Arg Leu Leu Asp Leu Pro Thr Tyr Ala Phe Glu Arg Arg Arg Tyr
        4255                4260                4265

tgg ctg gaa gcg gcc ggt gcc acc gac ctg tcc gcg gcc ggg ctg aca    65126
Trp Leu Glu Ala Ala Gly Ala Thr Asp Leu Ser Ala Ala Gly Leu Thr
    4270                4275                4280

ggg gca gca cat ccc atg ctg gcc gcc atc acg gca cta ccc gcc gac    65174
Gly Ala Ala His Pro Met Leu Ala Ala Ile Thr Ala Leu Pro Ala Asp
4285                4290                4295                4300

gac ggt ggt gtt gtt ctc acc ggc cgg atc tcg ttg cgc acg cat ccc    65222
Asp Gly Gly Val Val Leu Thr Gly Arg Ile Ser Leu Arg Thr His Pro
                4305                4310                4315

tgg ctg gct gat cac gcg gtg cgg ggc acg gtc ctg ctg ccg ggc acg    65270
Trp Leu Ala Asp His Ala Val Arg Gly Thr Val Leu Leu Pro Gly Thr
            4320                4325                4330

gcc ttt gtg gag ctg gtc atc cgg gcc ggt gac gag acc ggt tgc ggg    65318
Ala Phe Val Glu Leu Val Ile Arg Ala Gly Asp Glu Thr Gly Cys Gly
        4335                4340                4345

ata gtg gat gaa ctg gtc atc gaa tcc ccc ctc gtg gtg ccg gcg acc    65366
Ile Val Asp Glu Leu Val Ile Glu Ser Pro Leu Val Val Pro Ala Thr
    4350                4355                4360

gca gcc gtg gat ctg tcg gtg acc gtg gaa gga gct gac gag gcc gga    65414
Ala Ala Val Asp Leu Ser Val Thr Val Glu Gly Ala Asp Glu Ala Gly
4365                4370                4375                4380

cgg cgg cga gtg acc gtc cac gcc cgc acc gaa ggc acc ggc agc tgg    65462
Arg Arg Arg Val Thr Val His Ala Arg Thr Glu Gly Thr Gly Ser Trp
                4385                4390                4395

acc cgg cac gcc agc ggc acc ctg acc ccc gac acc ccc gac acc ccc    65510
Thr Arg His Ala Ser Gly Thr Leu Thr Pro Asp Thr Pro Asp Thr Pro
            4400                4405                4410

aac gct tcc ggt gtt gtc ggt gcg gag ccg ttc tcg cag tgg cca cct    65558
Asn Ala Ser Gly Val Val Gly Ala Glu Pro Phe Ser Gln Trp Pro Pro
        4415                4420                4425

gcc act gcc gcg gcc gtc gac acc tcg gag ttc tac ttg cgc ctg gac    65606
Ala Thr Ala Ala Ala Val Asp Thr Ser Glu Phe Tyr Leu Arg Leu Asp
    4430                4435                4440

gcg ctg ggc tac cgg ttc gga ccc atg ttc cgc gga atg cgg gct gcc    65654
Ala Leu Gly Tyr Arg Phe Gly Pro Met Phe Arg Gly Met Arg Ala Ala
4445                4450                4455                4460

tgg cgt gat ggt gac acc gtg tac gcc gag gtc gcg ctc ccc gag gac    65702
Trp Arg Asp Gly Asp Thr Val Tyr Ala Glu Val Ala Leu Pro Glu Asp
                4465                4470                4475

cgt gcc gcc gac gcg gac ggt ttc ggc atg cac ccg gcg ctg ctc gac    65750
Arg Ala Ala Asp Ala Asp Gly Phe Gly Met His Pro Ala Leu Leu Asp
            4480                4485                4490

gcg gcc ttg cag agc ggc agc ctg ctc atg ctg gaa tcg gac ggc gag    65798
Ala Ala Leu Gln Ser Gly Ser Leu Leu Met Leu Glu Ser Asp Gly Glu
        4495                4500                4505

cag agc gtg caa ctg ccg ttc tcc tgg cac ggc gtc cgg ttc cac gcg    65846
Gln Ser Val Gln Leu Pro Phe Ser Trp His Gly Val Arg Phe His Ala
    4510                4515                4520

acg ggc gcg acc atg ctg cgg gtg gcg gtc gta ccg ggc ccg gac ggc    65894
Thr Gly Ala Thr Met Leu Arg Val Ala Val Val Pro Gly Pro Asp Gly
4525                4530                4535                4540

ctc cgg ctg cat gcc gcg gac agc ggg aac cgt ccc gtc gcg acg atc    65942
Leu Arg Leu His Ala Ala Asp Ser Gly Asn Arg Pro Val Ala Thr Ile
                4545                4550                4555

gac gcg ctc gtg acc cgg tcc ccg gaa gcg gac ctc gcg ccc gcc gat    65990
```

-continued

```
Asp Ala Leu Val Thr Arg Ser Pro Glu Ala Asp Leu Ala Pro Ala Asp
            4560                4565                4570

ccg atg ctg cgg gtc ggg tgg gcc ccg gtg ccc gta cct gcc ggg gcc    66038
Pro Met Leu Arg Val Gly Trp Ala Pro Val Pro Val Pro Ala Gly Ala
        4575                4580                4585

ggt ccg tcc gac gcg gac gtg ctg acg ctg cgc ggc gac gac gcc gac    66086
Gly Pro Ser Asp Ala Asp Val Leu Thr Leu Arg Gly Asp Asp Ala Asp
    4590                4595                4600

ccg ctc ggg gag acc cgg gac ctg acc acc cgt gtt ctc gac gcg ctg    66134
Pro Leu Gly Glu Thr Arg Asp Leu Thr Thr Arg Val Leu Asp Ala Leu
4605                4610                4615                4620

ctc cgg gcc gac cgg ccg gtg atc ttc cag gtg acc ggt ggc ctc gcc    66182
Leu Arg Ala Asp Arg Pro Val Ile Phe Gln Val Thr Gly Gly Leu Ala
                4625                4630                4635

gcc aag gcg gcc gca ggc ctg gtc cgc acc gct cag aac gag cag ccc    66230
Ala Lys Ala Ala Ala Gly Leu Val Arg Thr Ala Gln Asn Glu Gln Pro
            4640                4645                4650

ggc cgc ttc ttc ctc gtc gaa acg gac ccg gga gag gtc ctg gac ggc    66278
Gly Arg Phe Phe Leu Val Glu Thr Asp Pro Gly Glu Val Leu Asp Gly
        4655                4660                4665

gcg aag cgc gac gcg atc gcg gca ctc ggc gag ccc cat gtg cgg ctg    66326
Ala Lys Arg Asp Ala Ile Ala Ala Leu Gly Glu Pro His Val Arg Leu
    4670                4675                4680

cgc gac ggc ctc ttc gag gca gcc cgg ctg atg cgg gcc acg ccg tcc    66374
Arg Asp Gly Leu Phe Glu Ala Ala Arg Leu Met Arg Ala Thr Pro Ser
4685                4690                4695                4700

ctg acg ctc ccg gac acc ggg tcg tgg cag ctg cgg ccg tcc gcc acc    66422
Leu Thr Leu Pro Asp Thr Gly Ser Trp Gln Leu Arg Pro Ser Ala Thr
                4705                4710                4715

ggt tcc ctc gac gac ctt gcc gtc gtc ccc acc gac gcc ccg gac cgg    66470
Gly Ser Leu Asp Asp Leu Ala Val Val Pro Thr Asp Ala Pro Asp Arg
            4720                4725                4730

ccg ctc gcg gcc ggc gag gtg cgg atc gcg gta cgc gcg gcg ggc ctg    66518
Pro Leu Ala Ala Gly Glu Val Arg Ile Ala Val Arg Ala Ala Gly Leu
        4735                4740                4745

aac ttc cgg gat gtc acg gtc gcg ctc ggt gtg gtc gcc gat gcg cgt    66566
Asn Phe Arg Asp Val Thr Val Ala Leu Gly Val Val Ala Asp Ala Arg
    4750                4755                4760

ccg ctc ggc agc gag gcc gcg ggt gtc gtc ctg gag acc ggc ccc ggt    66614
Pro Leu Gly Ser Glu Ala Ala Gly Val Val Leu Glu Thr Gly Pro Gly
4765                4770                4775                4780

gtg cac gac ctg gcg ccc ggc gac cgg gtc ctg ggg atg ctc gcg ggc    66662
Val His Asp Leu Ala Pro Gly Asp Arg Val Leu Gly Met Leu Ala Gly
                4785                4790                4795

gcc ttc gga ccg gtc gcg atc acc gac cgg cgg ctg ctc ggc cgg atg    66710
Ala Phe Gly Pro Val Ala Ile Thr Asp Arg Arg Leu Leu Gly Arg Met
            4800                4805                4810

ccg gac ggc tgg acg ttc ccg cag gcg gcg tcc gtg atg acc gcg ttc    66758
Pro Asp Gly Trp Thr Phe Pro Gln Ala Ala Ser Val Met Thr Ala Phe
        4815                4820                4825

gcg acc gcg tgg tac ggc ctg gtc gac ctg gcc ggg ctg cgc ccc ggc    66806
Ala Thr Ala Trp Tyr Gly Leu Val Asp Leu Ala Gly Leu Arg Pro Gly
    4830                4835                4840

gag aag gtc ctg atc cac gcg gcg gcg acc ggt gtc ggc gcg gcg gcc    66854
Glu Lys Val Leu Ile His Ala Ala Ala Thr Gly Val Gly Ala Ala Ala
4845                4850                4855                4860

gtc cag atc gcg cgg cat ctg ggc gcg gag gtg tac gcg acc acc agc    66902
Val Gln Ile Ala Arg His Leu Gly Ala Glu Val Tyr Ala Thr Thr Ser
                4865                4870                4875
```

-continued

```
gcc gcg aag cgc cat ctg gtg gac ctg gac gga gcg cat ctg gcc gat    66950
Ala Ala Lys Arg His Leu Val Asp Leu Asp Gly Ala His Leu Ala Asp
            4880                4885                4890

tcc cgc agc acc gcg ttc gcc gac gcg ttc ccg ccg gtc gat gtc gtg    66998
Ser Arg Ser Thr Ala Phe Ala Asp Ala Phe Pro Pro Val Asp Val Val
        4895                4900                4905

ctc aac tcg ctc acc ggt gaa ttc ctc gac gcg tcc gtc ggc ctg ctc    67046
Leu Asn Ser Leu Thr Gly Glu Phe Leu Asp Ala Ser Val Gly Leu Leu
    4910                4915                4920

gcg gcg ggt ggc cgg ttc atc gag atg ggg aag acg gac atc cgg cac    67094
Ala Ala Gly Gly Arg Phe Ile Glu Met Gly Lys Thr Asp Ile Arg His
4925                4930                4935                4940

gcc gtc cag cag ccg ttc gac ctg atg gac gcc ggc ccc gac cgg atg    67142
Ala Val Gln Gln Pro Phe Asp Leu Met Asp Ala Gly Pro Asp Arg Met
                4945                4950                4955

cag cgg atc atc gtc gag ctg ctc ggc ctg ttc gcg cgc gac gtg ctg    67190
Gln Arg Ile Ile Val Glu Leu Leu Gly Leu Phe Ala Arg Asp Val Leu
            4960                4965                4970

cac ccg ctg ccg gtc cac gcc tgg gac gtg cgg cag gcg cgg gag gcg    67238
His Pro Leu Pro Val His Ala Trp Asp Val Arg Gln Ala Arg Glu Ala
        4975                4980                4985

ttc ggc tgg atg agc agc ggg cgt cac acc ggc aag ctg gtg ctg acg    67286
Phe Gly Trp Met Ser Ser Gly Arg His Thr Gly Lys Leu Val Leu Thr
    4990                4995                5000

gtc ccg cgg ccg ctg gat ccc gag ggg gcc gtc gtc atc acc ggc ggc    67334
Val Pro Arg Pro Leu Asp Pro Glu Gly Ala Val Val Ile Thr Gly Gly
5005                5010                5015                5020

tcc ggc acc ctc gcc ggc atc ctc gcc cgc cac ctg ggc cac ccc cac    67382
Ser Gly Thr Leu Ala Gly Ile Leu Ala Arg His Leu Gly His Pro His
                5025                5030                5035

acc tac ctg ctc tcc cgc acc cca ccc ccc gac acc acc ccc ggc acc    67430
Thr Tyr Leu Leu Ser Arg Thr Pro Pro Pro Asp Thr Thr Pro Gly Thr
            5040                5045                5050

cac ctc ccc tgc gac gtc ggc gac ccc cac caa ctc gcc acc acc ctc    67478
His Leu Pro Cys Asp Val Gly Asp Pro His Gln Leu Ala Thr Thr Leu
        5055                5060                5065

gcc cgc atc ccc caa ccc ctc acc gcc gtc ttc cac acc gcc gga acc    67526
Ala Arg Ile Pro Gln Pro Leu Thr Ala Val Phe His Thr Ala Gly Thr
    5070                5075                5080

ctc gac gac gcc ctg ctc gac aac ctc acc ccc gac cgc gtc gac acc    67574
Leu Asp Asp Ala Leu Leu Asp Asn Leu Thr Pro Asp Arg Val Asp Thr
5085                5090                5095                5100

gtc ctc aaa ccc aag gcc gac gcc gcc tgg cac ctg cac cgg ctc acc    67622
Val Leu Lys Pro Lys Ala Asp Ala Ala Trp His Leu His Arg Leu Thr
                5105                5110                5115

cgc gac acc gac ctc gcc gcg ttc gtc gtc tac tcc gcg gtc gcc ggc    67670
Arg Asp Thr Asp Leu Ala Ala Phe Val Val Tyr Ser Ala Val Ala Gly
            5120                5125                5130

ctc atg ggc agc ccg ggg cag ggc aac tac gtc gcg gcg aac gcg ttc    67718
Leu Met Gly Ser Pro Gly Gln Gly Asn Tyr Val Ala Ala Asn Ala Phe
        5135                5140                5145

ctc gac gcg ctc gcc gaa cac cgc cgt gcg caa ggg ctg ccc gcg cag    67766
Leu Asp Ala Leu Ala Glu His Arg Arg Ala Gln Gly Leu Pro Ala Gln
    5150                5155                5160

tcc ctc gca tgg ggc atg tgg gcg gac gtc agc gcg ctc acc gcg aaa    67814
Ser Leu Ala Trp Gly Met Trp Ala Asp Val Ser Ala Leu Thr Ala Lys
5165                5170                5175                5180

ctc acc gac gcg gac cgc cag cgc atc cgg cgc agc gga ttc ccg ccg    67862
Leu Thr Asp Ala Asp Arg Gln Arg Ile Arg Arg Ser Gly Phe Pro Pro
                5185                5190                5195
```

-continued

```
ttg agc gcc gcg gac ggc atg cgg ctg ttc gac gcg gcg acg cgt acc    67910
Leu Ser Ala Ala Asp Gly Met Arg Leu Phe Asp Ala Ala Thr Arg Thr
            5200                5205                5210

ccg gaa ccg gtc gtc gtc gcg acg acc gtc gac ctc acc cag ctc gac    67958
Pro Glu Pro Val Val Val Ala Thr Thr Val Asp Leu Thr Gln Leu Asp
        5215                5220                5225

ggc gcc gtc gcg ccg ttg ctc cgc ggt ctg gcc gcg cac cgg gcc ggg    68006
Gly Ala Val Ala Pro Leu Leu Arg Gly Leu Ala Ala His Arg Ala Gly
    5230                5235                5240

ccg gcg cgc acg gtc gcc cgc aac gcc ggc gaa gag ccc ctg gcc gtg    68054
Pro Ala Arg Thr Val Ala Arg Asn Ala Gly Glu Glu Pro Leu Ala Val
5245                5250                5255                5260

cgt ctt gcc ggg cgt acc gcc gcc gag cag cgg cgc atc atg cag gag    68102
Arg Leu Ala Gly Arg Thr Ala Ala Glu Gln Arg Arg Ile Met Gln Glu
                5265                5270                5275

gtc gtg ctc cgc cac gcg gcc gcg gtc ctc gcg tac ggg ctg ggc gac    68150
Val Val Leu Arg His Ala Ala Ala Val Leu Ala Tyr Gly Leu Gly Asp
            5280                5285                5290

cgc gtg gcg gcg gac cgt ccg ttc cgc gag ctc ggt ttc gat tcg ctg    68198
Arg Val Ala Ala Asp Arg Pro Phe Arg Glu Leu Gly Phe Asp Ser Leu
        5295                5300                5305

acc gcg gtc gac ctg cgc aat cgg ctc gcg gcc gag acg ggg ctg cgg    68246
Thr Ala Val Asp Leu Arg Asn Arg Leu Ala Ala Glu Thr Gly Leu Arg
    5310                5315                5320

ctg ccg acg acg ctg gtg ttc agc cac ccg acg gcg gag gcg ctc acc    68294
Leu Pro Thr Thr Leu Val Phe Ser His Pro Thr Ala Glu Ala Leu Thr
5325                5330                5335                5340

gcc cac ctg ctc gac ctg atc gac gct ccc acc gcc cgg atc gcc ggg    68342
Ala His Leu Leu Asp Leu Ile Asp Ala Pro Thr Ala Arg Ile Ala Gly
                5345                5350                5355

gag tcc ctg ccc gcg gtg acg gcc gct ccc gtg gcg gcc gcg cgg gac    68390
Glu Ser Leu Pro Ala Val Thr Ala Ala Pro Val Ala Ala Ala Arg Asp
            5360                5365                5370

cag gac gag ccg atc gcc atc gtg gcg atg gcg tgc cgg ctg ccc ggt    68438
Gln Asp Glu Pro Ile Ala Ile Val Ala Met Ala Cys Arg Leu Pro Gly
        5375                5380                5385

ggt gtg acg tcg ccc gag gac ctg tgg cgg ctc gtc gag tcc ggc acc    68486
Gly Val Thr Ser Pro Glu Asp Leu Trp Arg Leu Val Glu Ser Gly Thr
    5390                5395                5400

gac gcg atc acc acg cct cct gac gac cgc ggc tgg gac gtc gac gcg    68534
Asp Ala Ile Thr Thr Pro Pro Asp Asp Arg Gly Trp Asp Val Asp Ala
5405                5410                5415                5420

ctg tac gac gcg gac ccg gac gcg gcc ggc aag gcg tac aac ctg cgg    68582
Leu Tyr Asp Ala Asp Pro Asp Ala Ala Gly Lys Ala Tyr Asn Leu Arg
                5425                5430                5435

ggc ggt tac ctg gcc ggg gcg gcg gag ttc gac gcg gcg ttc ttc gac    68630
Gly Gly Tyr Leu Ala Gly Ala Ala Glu Phe Asp Ala Ala Phe Phe Asp
            5440                5445                5450

atc agt ccg cgc gaa gcg ctc ggc atg gac ccg cag caa cgc ctg ctg    68678
Ile Ser Pro Arg Glu Ala Leu Gly Met Asp Pro Gln Gln Arg Leu Leu
        5455                5460                5465

ctc gaa acg gcg tgg gag gcg atc gag cgc ggc cgg atc agt ccg gcg    68726
Leu Glu Thr Ala Trp Glu Ala Ile Glu Arg Gly Arg Ile Ser Pro Ala
    5470                5475                5480

tcg ctc cgc ggc cgg gag gtc ggc gtc tat gtc ggt gcg gcc gcg cag    68774
Ser Leu Arg Gly Arg Glu Val Gly Val Tyr Val Gly Ala Ala Ala Gln
5485                5490                5495                5500

ggc tac ggg ctg ggc gcc gag gac acc gag ggc cac gcg atc acc ggt    68822
Gly Tyr Gly Leu Gly Ala Glu Asp Thr Glu Gly His Ala Ile Thr Gly
```

-continued

```
                5505                5510                5515

ggt tcc acg agc ctg ctg tcc gga cgg ctg gcg tac gtg ctc ggg ctg    68870
Gly Ser Thr Ser Leu Leu Ser Gly Arg Leu Ala Tyr Val Leu Gly Leu
            5520                5525                5530

gag ggc ccg gcg gtc acc gtg gac acg gcg tgc tcg tcg tct ctg gtc    68918
Glu Gly Pro Ala Val Thr Val Asp Thr Ala Cys Ser Ser Ser Leu Val
        5535                5540                5545

gcg ctg cat ctg gcg tgc cag ggg ctg cgc ctg ggc gag tgc gaa ctc    68966
Ala Leu His Leu Ala Cys Gln Gly Leu Arg Leu Gly Glu Cys Glu Leu
    5550                5555                5560

gct ctg gcc gga ggg gtc tcc gta ctg agt tcg ccg gcc gcg ttc gtg    69014
Ala Leu Ala Gly Gly Val Ser Val Leu Ser Ser Pro Ala Ala Phe Val
5565                5570                5575                5580

gag ttc tcc cgc cag cgc ggg ctc gcg gcc gac ggg cgc tgc aag tcg    69062
Glu Phe Ser Arg Gln Arg Gly Leu Ala Ala Asp Gly Arg Cys Lys Ser
                5585                5590                5595

ttc ggc gcg ggc gcg gac ggc acg acg tgg tcc gag ggc gtg ggc gtg    69110
Phe Gly Ala Gly Ala Asp Gly Thr Thr Trp Ser Glu Gly Val Gly Val
            5600                5605                5610

ctc gta ctg gaa cgg ctc tcc gac gcc gag cgg ctc ggg cac acc gtg    69158
Leu Val Leu Glu Arg Leu Ser Asp Ala Glu Arg Leu Gly His Thr Val
        5615                5620                5625

ctc gcc gtc gtc cgc ggc agc gcc gtc acg tcc gac ggc gcc tcc aac    69206
Leu Ala Val Val Arg Gly Ser Ala Val Thr Ser Asp Gly Ala Ser Asn
    5630                5635                5640

ggc ctc acc gcg ccg aac ggg ctc tcg cag cag cgg gtc atc cgg aag    69254
Gly Leu Thr Ala Pro Asn Gly Leu Ser Gln Gln Arg Val Ile Arg Lys
5645                5650                5655                5660

gcg ctc gcc gcg gcc ggg ctg acc ggc gcc gac gtg gac gtc gtc gag    69302
Ala Leu Ala Ala Ala Gly Leu Thr Gly Ala Asp Val Asp Val Val Glu
                5665                5670                5675

ggg cac ggc acc ggc acc cgg ctc ggc gac ccg gtc gag gcg gac gcg    69350
Gly His Gly Thr Gly Thr Arg Leu Gly Asp Pro Val Glu Ala Asp Ala
            5680                5685                5690

ctg ctc gcg acg tac ggg cag gac cgt ccg gca ccg gtc tgg ctg ggc    69398
Leu Leu Ala Thr Tyr Gly Gln Asp Arg Pro Ala Pro Val Trp Leu Gly
        5695                5700                5705

tcg ctg aag tcg aac atc gga cat gcc acg gcc gcg gcc ggt gtc gcg    69446
Ser Leu Lys Ser Asn Ile Gly His Ala Thr Ala Ala Ala Gly Val Ala
    5710                5715                5720

ggc gtc atc aag atg gtg cag gcg atc ggc gcg ggc acg atg ccg cgg    69494
Gly Val Ile Lys Met Val Gln Ala Ile Gly Ala Gly Thr Met Pro Arg
5725                5730                5735                5740

acg ctg cat gtg gag gag ccc tcg ccc gcc gtc gac tgg agc acc gga    69542
Thr Leu His Val Glu Glu Pro Ser Pro Ala Val Asp Trp Ser Thr Gly
                5745                5750                5755

cag gtg tcc ctg ctc ggc tcc aac cgg ccc tgg ccg gac gac gag cgt    69590
Gln Val Ser Leu Leu Gly Ser Asn Arg Pro Trp Pro Asp Asp Glu Arg
            5760                5765                5770

ccg cgc cgg gcg gcc gtc tcc gcg ttc ggg ctc agc ggg acg aac gcg    69638
Pro Arg Arg Ala Ala Val Ser Ala Phe Gly Leu Ser Gly Thr Asn Ala
        5775                5780                5785

cac gtc atc ctg gaa cag cac cgt ccg gcg ccc gtg gcg tcc cag ccg    69686
His Val Ile Leu Glu Gln His Arg Pro Ala Pro Val Ala Ser Gln Pro
    5790                5795                5800

ccc cgg ccg ccc cgt gag gag tcc cag ccg ctg ccg tgg gtg ctc tcc    69734
Pro Arg Pro Pro Arg Glu Glu Ser Gln Pro Leu Pro Trp Val Leu Ser
5805                5810                5815                5820

gcg cgg act ccg gcc gcg ctg cgg gcc cag gcg gcc cgg ctg cgc gac    69782
```

-continued

```
Ala Arg Thr Pro Ala Ala Leu Arg Ala Gln Ala Ala Arg Leu Arg Asp
                5825                5830                5835

cac ctc gcg gcg gca ccg gac gcg gat ccg ttg gac atc ggg tac gcg    69830
His Leu Ala Ala Ala Pro Asp Ala Asp Pro Leu Asp Ile Gly Tyr Ala
            5840                5845                5850

ctg gcc acc agc cgc gcc cag ttc gcc cac cgt gcc gcg gtc gtc gcc    69878
Leu Ala Thr Ser Arg Ala Gln Phe Ala His Arg Ala Ala Val Val Ala
        5855                5860                5865

acc acc ccg gac gga ttc cgt gcc gcg ctc gac ggc ctc gcg gac ggc    69926
Thr Thr Pro Asp Gly Phe Arg Ala Ala Leu Asp Gly Leu Ala Asp Gly
    5870                5875                5880

gcg gag gcg ccc gga gtc gtc acc ggg acc gct cag gag cgg cgc gtc    69974
Ala Glu Ala Pro Gly Val Val Thr Gly Thr Ala Gln Glu Arg Arg Val
5885                5890                5895                5900

gcc ttc ctc ttc gac ggc cag ggc gcc cag cgc gcc gga atg ggg cgc    70022
Ala Phe Leu Phe Asp Gly Gln Gly Ala Gln Arg Ala Gly Met Gly Arg
                5905                5910                5915

gag ctc cac cgc cgg ttc ccc gtc ttc gcc gcc gcg tgg gac gag gtc    70070
Glu Leu His Arg Arg Phe Pro Val Phe Ala Ala Ala Trp Asp Glu Val
            5920                5925                5930

tcc gac gcg ttc ggc aag cac ctc aag cac tcc ccc acg gac gtc tac    70118
Ser Asp Ala Phe Gly Lys His Leu Lys His Ser Pro Thr Asp Val Tyr
        5935                5940                5945

cac ggc gaa cac ggc gct ctc gcc cat gac acc ctg tac gcc cag gcc    70166
His Gly Glu His Gly Ala Leu Ala His Asp Thr Leu Tyr Ala Gln Ala
    5950                5955                5960

ggc ctg ttc acg ctc gaa gtg gcg ctg ctg cgg ctg ctg gag cac tgg    70214
Gly Leu Phe Thr Leu Glu Val Ala Leu Leu Arg Leu Leu Glu His Trp
5965                5970                5975                5980

ggg gtg cgg ccg gac gtg ctc gtc ggg cac tcc gtc ggc gag gtg acc    70262
Gly Val Arg Pro Asp Val Leu Val Gly His Ser Val Gly Glu Val Thr
                5985                5990                5995

gcg gcg tac gcg gcg ggg gtg ctc acc ctg gcg gac gcg acg gag ttg    70310
Ala Ala Tyr Ala Ala Gly Val Leu Thr Leu Ala Asp Ala Thr Glu Leu
            6000                6005                6010

atc gtg gcc cgg ggg cgg gcg ctg cgg gcg ctg ccg ccc ggg gcg atg    70358
Ile Val Ala Arg Gly Arg Ala Leu Arg Ala Leu Pro Pro Gly Ala Met
        6015                6020                6025

ctc gcc gtc gac gga agc ccg gcg gag gtc ggc gcc cgc acg gat ctg    70406
Leu Ala Val Asp Gly Ser Pro Ala Glu Val Gly Ala Arg Thr Asp Leu
    6030                6035                6040

gac atc gcc gcg gtc aac ggc ccg tcc gcc gtg gtg ctc gcc ggt tcg    70454
Asp Ile Ala Ala Val Asn Gly Pro Ser Ala Val Val Leu Ala Gly Ser
6045                6050                6055                6060

ccg gac gat gtg gcg gcg ttc gaa cgg gag tgg tcg gcg gcc ggg cgg    70502
Pro Asp Asp Val Ala Ala Phe Glu Arg Glu Trp Ser Ala Ala Gly Arg
                6065                6070                6075

cgc acg aaa cgg ctc gac gtc ggg cac gcg ttc cac tcc cgg cac gtc    70550
Arg Thr Lys Arg Leu Asp Val Gly His Ala Phe His Ser Arg His Val
            6080                6085                6090

gac ggt gcg ctc gac ggc ttc cgt acg gtg ctg gag tcg ctc gcg ttc    70598
Asp Gly Ala Leu Asp Gly Phe Arg Thr Val Leu Glu Ser Leu Ala Phe
        6095                6100                6105

ggc gcg gcg cgg ctg ccg gtg gtg tcc acg acg acg ggc cgg gac gcc    70646
Gly Ala Ala Arg Leu Pro Val Val Ser Thr Thr Thr Gly Arg Asp Ala
    6110                6115                6120

gcg gac gac ctc ata acg ccc gcg cac tgg ctg cgc cat gcg cgt cgg    70694
Ala Asp Asp Leu Ile Thr Pro Ala His Trp Leu Arg His Ala Arg Arg
6125                6130                6135                6140
```

-continued

```
ccg gtg ctg ttc tcg gat gcc gtc cgg gag ctg gcc gac cgc ggc gtc    70742
Pro Val Leu Phe Ser Asp Ala Val Arg Glu Leu Ala Asp Arg Gly Val
                6145                6150                6155

acc acg ttc gtg gcc gtc ggc ccc tcc ggc tcc ctg gcg tcg gcc gcg    70790
Thr Thr Phe Val Ala Val Gly Pro Ser Gly Ser Leu Ala Ser Ala Ala
            6160                6165                6170

gcg gag agc gcc ggg gag gac gcc ggg acc tac cac gcg gtg ctg cgc    70838
Ala Glu Ser Ala Gly Glu Asp Ala Gly Thr Tyr His Ala Val Leu Arg
        6175                6180                6185

gcc cgg acc ggt gag gag acc gcg gcg ctg acc gcc ctc gcc gag ctg    70886
Ala Arg Thr Gly Glu Glu Thr Ala Ala Leu Thr Ala Leu Ala Glu Leu
    6190                6195                6200

cac gcc cac ggc gtc ccg gtc gac ctg gcc gcg gta ctg gcc ggt ggc    70934
His Ala His Gly Val Pro Val Asp Leu Ala Ala Val Leu Ala Gly Gly
6205                6210                6215                6220

cgg cca gtg gac ctt ccc gtg tac gcg ttc cag cac cgt tcc tac tgg    70982
Arg Pro Val Asp Leu Pro Val Tyr Ala Phe Gln His Arg Ser Tyr Trp
                6225                6230                6235

ctg gcc ccg gcc gtg gcg ggg gcg ccg gcc acc gtg gcg gac acc ggg    71030
Leu Ala Pro Ala Val Ala Gly Ala Pro Ala Thr Val Ala Asp Thr Gly
            6240                6245                6250

ggt ccg gcg gag tcc gag ccg gag gac ctc acc gtc gcc gag atc gtc    71078
Gly Pro Ala Glu Ser Glu Pro Glu Asp Leu Thr Val Ala Glu Ile Val
        6255                6260                6265

cgt cgg cgc acc gcg gcg ctg ctc ggc gtc acg gac ccc gcc gac gtc    71126
Arg Arg Arg Thr Ala Ala Leu Leu Gly Val Thr Asp Pro Ala Asp Val
    6270                6275                6280

gat gcg gaa gcg acg ttc ttc gcg ctc ggt ttc gac tca ctg gcg gtg    71174
Asp Ala Glu Ala Thr Phe Phe Ala Leu Gly Phe Asp Ser Leu Ala Val
6285                6290                6295                6300

cag cgg ctg cgc aac cag ctc gcc tcg gca acc ggg ctg gac ctg ccg    71222
Gln Arg Leu Arg Asn Gln Leu Ala Ser Ala Thr Gly Leu Asp Leu Pro
                6305                6310                6315

gcg gcc gtc ctg ttc gac cac gac acc ccg gcc gcg ctc acc gcg ttc    71270
Ala Ala Val Leu Phe Asp His Asp Thr Pro Ala Ala Leu Thr Ala Phe
            6320                6325                6330

ctc cag gac cgg atc gag gcc ggc cag gac cgg atc gag gcc ggc gag    71318
Leu Gln Asp Arg Ile Glu Ala Gly Gln Asp Arg Ile Glu Ala Gly Glu
        6335                6340                6345

gac gac gac gcg ccc acc gtg ctc tcg ctc ctg gag gag atg gag tcg    71366
Asp Asp Asp Ala Pro Thr Val Leu Ser Leu Leu Glu Glu Met Glu Ser
    6350                6355                6360

ctc gac gcc gcg gac atc gcg gcg acg ccg gcc ccg gag cgt gcg gcc    71414
Leu Asp Ala Ala Asp Ile Ala Ala Thr Pro Ala Pro Glu Arg Ala Ala
6365                6370                6375                6380

atc gcc gat ctg ctc gac aag ctc gcc cat acc tgg aag gac tac cga    71462
Ile Ala Asp Leu Leu Asp Lys Leu Ala His Thr Trp Lys Asp Tyr Arg
                6385                6390                6395

tga gcaccgatac gcacgaggga acgccgcccg ccggccgctg cccattcgcg        71515
 *

atccaggacg gtcaccgcgc catcctggag agcggcacgg tgggttcgtt cgacctgttc  71575

ggcgtcaagc actggctggt cgccgccgcc gaggacgtca agctggtcac caacgatccg  71635

cggttcagct cggccgcgcc gtccgagatg ctgcccgacc ggcggcccgg ctggttctcc  71695

gggatggact caccggagca caaccgctac cggcagaaga tcgcggggga cttcacactg  71755

cgcgcggcgc gcaagcggga ggacttcgtc gccgaggccg ccgacgcctg cctggacgac  71815

atcgaggccg cgggacccgg caccgacctc atccccgggt acgccaagcg gctgccctcc  71875
```

-continued

```
ctcgtcatca acgcgctgta cgggctcacc cctgaggagg gggccgtgct ggaggcacgg  71935
atgcgcgaca tcaccggctc ggccgatctg gacagcgtca agacgctgac cgacgacttc  71995
ttcgggcacg cgctgcggct ggtccgcgcg aagcgtgacg agcggggcga ggacctgctg  72055
caccggctgg cctcggccga cgacggcgag atctcgctca gcgacgacga ggcgacgggc  72115
gtgttcgcga cgctgctgtt cgccggccac gactcggtgc agcagatggt cggctactgc  72175
ctctacgcac tgctcagcca ccccgagcag caggcggcgc tgcgcgcgcg cccggagctg  72235
gtcgacaacg cggtcgagga gatgctccgt ttcctgcccg tcaaccagat gggcgtaccg  72295
cgcgtctgtg tcgaggacgt cgatgtgcgg ggcgtgcgca tccgtgcggg cgacaacgtg  72355
atcccgctct actcgacggc caaccgcgac cccgaggtgt tcccgcagcc cgacaccttc  72415
gatgtgacgc gcccgctgga gggcaacttc gcgttcggcc acggcattca caagtgtccc  72475
ggccagcaca tcgcccgggt gctcatcaag gtcgcctgcc tgcggttgtt cgagcgtttc  72535
ccggacgtcc ggctggccgg cgacgtgccg atgaacgagg ggctcgggct gttcagcccg  72595
gccgagctgc gggtcacctg gggggcggca tgagtcaccc ggtggagacg ttgcggttgc  72655
cgaacgggac gacggtcgcg cacatcaacg cgggcgaggc gcagttcctc taccgggaga  72715
tcttcaccca gcgctgctac ctgcgccacg gtgtcgacct gcgcccgggg gacgtggtgt  72775
tcgacgtcgg cgcgaacatc ggcatgttca cgcttttcgc gcatctggag tgtcctggtg  72835
tgaccgtgca cgccttcgag cccgcgcccg tgccgttcgc ggcgctgcgg gcgaacgtga  72895
cgcggcacgg catcccgggc caggcggacc agtgcgcggt ctccgacagc tccggcaccc  72955
ggaagatgac cttctatccc gacgccacgc tgatgtccgg tttccacgcg gatgccgcgg  73015
cccggacgga gctgttgcgc acgctcggcc tcaacggcgg ctacaccgcc gaggacgtcg  73075
acaccatgct cgcgcaactg cccgacgtca gcgaggagat cgaaacccct gtggtccggc  73135
tctccgacgt catcgcggag cgcggtatcg aggccatcgg cctgctgaag gtcgacgtgg  73195
agaagagcga acggcaggtc ttcgccggcc tcgaggacac cgactggccc cgtatccgcc  73255
aggtcgtcgc ggaggtccac gacatcgacg gcgcgctcga ggaggtcgtc acgctgctcc  73315
gcggccatgg cttcaccgtg gtcgccgagc aggaaccgct gttcgccggc acgggcatcc  73375
accaggtcgc cgcgcggcgg gtggccggct gagcgccgtc ggggccgcgg ccgtccgcac  73435
cggcggccgc ggtgcggacg gcggctcagc cggcgtcgga cagttccttg ggcagttgct  73495
gacggccctt cacccccagc ttgcggaaca cgttggtgag gtgctgttcc accgtgctgg  73555
aggtgacgaa cagctggctg gcgatctcct tgttggtgcg cccgaccgcg gcgtgcgacg  73615
ccacccgccg ctccgcctcg gtcagcgatg tgatccgctg cgccggcgtc acgtcctggg  73675
tgccgtccgc gtccgaggac tccccaccga gccgccggag gagcggcacg gctccgcact  73735
gggtcgcgag gtgccgtgcg cggcggaaca gtccccgcgc acggctgtgc cgccggagca  73795
tgccgcacgc ttcgcccatg tcggcgagga cgcgggccag ctcgtactgg tcgcggcaca  73855
tgatgagcag atcggcggcc tcgtcgagca gttcgatccg cttggccggc ggactgtagg  73915
ccgcctgcac ccgcagcgtc atcacccgcg cccgggaccc catcggccgg gacagctgct  73975
cggagatgag cctcagcccc tcgtcacggc cgcggccgag cagcagaagc gcttcggcgg  74035
cgtcgacccg ccacagggcc aggcccggca cgtcgacgga ccagcgtcgc atccgctccc  74095
cgcagtcccg gaacgcgttg tacgccgccc ggtaccgccc ggccgcgaga tggtgttgcc  74155
cacgggccca gaccatgtgc agtccgaaga ggctgtcgga ggtctcctcc ggcaacggct  74215
cggcgagcca ccgctccgcc cggtccaggt cgcccagtcg gatcgcggcg gccacggtgc  74275
```

```
tgctcagcgg caatgcggcg gccatccccc aggagggcac gacccggggg gcgagcgcgg  74335
cctcgccgca ttcgacggcg gcggtcaggt cgccgcggcg cagcgcggcc tcggcgcgga  74395
accccgcgtg gaccgcctcg tcggccgggg tccgcatgtt gtcgtcaccg gccagcttgt  74455
cgacccagga ctggacggca tcggtgtcct cggcgtagag cagggccagc aacgccatca  74515
tggtcgtggt ccggtccgtc gtgacccggg agtgctggag cacgtactcg gctttggcct  74575
cggcctgttc ggaccagccg cgcagcgcgt tgctcagggc cttgtcggcg acggcgcggt  74635
gccggacggc tccggaaaac gaggcgacct cgtcctcggc cggcggatcg gccggacgcg  74695
gcggatcggc cgcgccggga tagatcagcg cgagggacag gtccgcgacg cgcaggtgcg  74755
cccggccctg ctcgctcggg gcggcggagc gctgggccgc caggacctcg gcggcctcgc  74815
ccggccgccc gtccatcgcc agccagcagg cgagcgacac ggcgtgctcg ctggagagga  74875
gccgttcccg cgacgcggtg agcagctcgg gcacatgccg gccggatctg gcgggatcgc  74935
agagccgctc gatggcggcg gtgtcgacgc gcagtgcggc gtggacggcg gggtcgtcgg  74995
aggcccggta ggcgaactcc aggtaggtga cggcctcgtc gagctcgccg cgcaggtggt  75055
gctcgcgcgc ggcgtcggtg aacagcccgg cgacctcggc gccgtgcacc cggccggtac  75115
ccatctggtg gcgggcgagc accttgctgg ccacgccgcg gtcccgcagc agttccagcg  75175
ccagctcgtg caggccacgc cgctcggcgg cggagaggtc gtcgagtacg acggagcggg  75235
ccgcggggtg cgggaaccgc ccttcccgca gcagccgccc ctcgaccagc tgttcgtggg  75295
cctgctcgac cgcctcggtg tcgaggccgg tcatccgctg gacgagggtg agttcgacac  75355
tctcgccgag cacggcggaa gctcgggcga cgctcagcgc ggccgggccg caacgataga  75415
gcgacccgag gtaggcgagc cggtacgccc gccccgcgac cacttccagg caccctgagg  75475
tccgtgtccg tgcctcccgg atgtcgtcga tcaggccgtg gccgaggagc aggttgccgc  75535
cggtcgcccg gaacgcctgg gccaccacgt cgtcgtgcgc gtcctggccg aggtgccggc  75595
gcacgagttc ggtggtctgc gcctcggtga gcgggcgcag cgcgatctcc tggtagtggc  75655
gcagactcag cagtgccgcc cggaattggg agtgggcggg cgtcggccgg agcagctcgg  75715
tcagcacgat ggcgacacgg gcccggctga tgcggcgcgc gaggtggagc aggcagcgca  75775
gcgacggcgc gtcggcgtgg tgcacgtcgt cgatgccgat cagtacgggc cgctccgcgg  75835
cgagcgtcag caccgtgcgg gtgagttcgg tccccaggcg gttgtcgacg tcggccggca  75895
ggttttcgca cgatgccgtc agccggacca gctccggtgt ccgggcggcc agctcgggct  75955
ggtcgaggag ctggccgagc atgccgtacg gcagggcccg ctcctccatg gagcacaccg  76015
cgcgaagggt gacgaagccg gccttggccg cggcggcgtc gaggagttcg gtcttgccgc  76075
aggcgatcgg cccggtgacg gcggcgacga cgccccgccc gccccccgct cgggtgagcg  76135
cccggtggag ggaaccgaac tcgtcatcgc gggcgatcag gtctggggga gataagcgcg  76195
ctatcacgaa tggaactacc tcgcgaccgt cgtggaaacc cataggcatc acatggcttg  76255
ttgatctgta cggctgtgat tcagcctggc gggatgctgt gctacagatg ggaagatgtg  76315
atctagggcc gtgccgttcc ctcaggagcc gaccgccccc ggcgccaccc gccgtacccc  76375
ctgggccacc agctcggcga cccgctcctg gtggtcgacg aggtagaagt gcccgccggg  76435
gaagacctcc accgtggtcg gcgcggtcgt gtgcccggcc caggcgtggg cctgctccac  76495
cgtcgtcttc ggatcgtcgt caccgatgca caccgtgatc ggcgtctcca gcggcggcgc  76555
gggctcccac cggtacgtct ccgccgcgta gtagtccgcc cgcaacggcg ccaggatcag  76615
```

-continued

```
cgcgcgcatt tcgtcgtccg ccatcacatc ggcgctcgtc ccgccgaggc cgatgaccgc  76675

cgccagcagc tcgtcgtcgg acgcgaggtg gtcctggtcg gcgcgcggct gcgacggcgc  76735

ccgccggccc gagacgatca ggtgcgccac cgggagccgc tgggccagct cgaacgcgag  76795

tgtcgcgccc atgctgtggc cgaacagcac cagcggacgg tccagccccg gcttcaacgc  76855

ctcggccacg aggccggcga gaacacgcag gtcgcgcacc gcctcctcgt cgcggcggtc  76915

ctggcggccg gggtactgca cggcgtacac gtccgccacc ggggcgagcg cacgggccag  76975

cggaaggtag aacgtcgccg atccgccggc gtggggcagc agcaccaccc gtaccggggc  77035

ctcgggcgtg gggaagaact gccgcagcca gagttccgag ctcaccgcac cccctcggcc  77095

gcgacctggg gagcccggaa ccgggtgatc tcggccaagt gcttctcccg catctccggg  77155

tcggtcacgc cccatccctc ctccggcgcc agacagagga cgccgacttt gccgttgtgc  77215

acattgcgat gcacatcgcg caccgccgac ccgacgtcgt cgagcgggta ggtcaccgac  77275

agcgtcgggt gcaccatccc cttgcagatc aggcggttcg cctcccacgc ctcacgatag  77335

ttcgcgaagt gggtaccgat gatccgcttc acggacatcc acaggtaccg attgtcaaag  77395

gcgtgctcgt atcccgaggt tgacgcgcag gtgacgatcg tgccaccccg acgtgtcacg  77455

tagacactcg cgccgaacgt cgcgcgcccc gggtgctcga acacgatgtc gggatcgtca  77515

ccgccggtca gctcccggat c                                            77536
```

<210> SEQ ID NO 2
<211> LENGTH: 360
<212> TYPE: PRT
<213> ORGANISM: Streptomyces sp.

<400> SEQUENCE: 2

```
Met Thr Ile Val Lys Cys Leu Val Trp Asp Leu Asp Asn Thr Leu Trp
  1               5                  10                  15

Arg Gly Thr Val Leu Glu Asp Asp Glu Val Val Leu Thr Asp Glu Ile
             20                  25                  30

Arg Glu Val Ile Thr Thr Leu Asp Asp Arg Gly Ile Leu Gln Ala Val
         35                  40                  45

Ala Ser Lys Asn Asp His Asp Leu Ala Trp Glu Arg Leu Glu Arg Leu
     50                  55                  60

Gly Val Ala Glu Tyr Phe Val Leu Ala Arg Ile Gly Trp Gly Pro Lys
 65                  70                  75                  80

Ser Gln Ser Val Arg Glu Ile Ala Thr Glu Leu Asn Phe Ala Pro Thr
                 85                  90                  95

Thr Ile Ala Phe Ile Asp Asp Gln Pro Ala Glu Arg Ala Glu Val Ala
            100                 105                 110

Phe His Leu Pro Glu Val Arg Cys Tyr Pro Ala Glu Gln Ala Ala Thr
        115                 120                 125

Leu Leu Ser Leu Pro Glu Phe Ser Pro Pro Val Ser Thr Val Asp Ser
    130                 135                 140

Arg Arg Arg Arg Leu Met Tyr Gln Ala Gly Phe Ala Arg Asp Gln Ala
145                 150                 155                 160

Arg Glu Ala Tyr Ser Gly Pro Asp Glu Asp Phe Leu Arg Ser Leu Asp
                165                 170                 175

Leu Ser Met Thr Ile Ala Pro Ala Gly Glu Glu Glu Leu Ser Arg Val
            180                 185                 190

Glu Glu Leu Thr Leu Arg Thr Ser Gln Met Asn Ala Thr Gly Val His
        195                 200                 205
```

-continued

```
Tyr Ser Asp Ala Asp Leu Arg Ala Leu Leu Thr Asp Pro Ala His Glu
    210                 215                 220

Val Leu Val Val Thr Met Gly Asp Arg Phe Gly Pro His Gly Ala Val
225                 230                 235                 240

Gly Ile Ile Leu Leu Glu Lys Lys Pro Ser Thr Trp His Leu Lys Leu
                245                 250                 255

Leu Ala Thr Ser Cys Arg Val Val Ser Phe Gly Ala Gly Ala Thr Ile
            260                 265                 270

Leu Asn Trp Leu Thr Asp Gln Gly Ala Arg Ala Gly Ala His Leu Val
        275                 280                 285

Ala Asp Phe Arg Arg Thr Asp Arg Asn Arg Met Met Glu Ile Ala Tyr
    290                 295                 300

Arg Phe Ala Gly Phe Ala Asp Ser Asp Cys Pro Cys Val Ser Glu Val
305                 310                 315                 320

Ala Gly Ala Ser Ala Ala Gly Val Glu Arg Leu His Leu Glu Pro Ser
                325                 330                 335

Ala Arg Pro Ala Pro Thr Thr Leu Thr Leu Thr Ala Ala Asp Ile Ala
            340                 345                 350

Pro Val Thr Val Ser Ala Ala Gly
        355                 360


<210> SEQ ID NO 3
<211> LENGTH: 22
<212> TYPE: DNA
<213> ORGANISM: Artificial Sequence
<220> FEATURE:
<223> OTHER INFORMATION: Description of Artificial Sequence: Linker

<400> SEQUENCE: 3

ctagtgggca gatctggcag ct                                              22


<210> SEQ ID NO 4
<211> LENGTH: 14
<212> TYPE: DNA
<213> ORGANISM: Artificial Sequence
<220> FEATURE:
<223> OTHER INFORMATION: Description of Artificial Sequence: Linker

<400> SEQUENCE: 4

gccagatctg ccca                                                       14


<210> SEQ ID NO 5
<211> LENGTH: 12
<212> TYPE: DNA
<213> ORGANISM: Artificial Sequence
<220> FEATURE:
<223> OTHER INFORMATION: Description of Artificial Sequence: Linker

<400> SEQUENCE: 5

gggatgcatg gc                                                         12


<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Linker

<400> SEQUENCE: 6

ttaagccatg catccccatg                                                 20
```

-continued

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 7
cgactcacta gtgggcagat ctgg 24

<210> SEQ ID NO 8
<211> LENGTH: 29
<212> TYPE: DNA
<213> ORGANISM: Artificial Sequence
<220> FEATURE:
<223> OTHER INFORMATION: Description of Artificial Sequence: primer

<400> SEQUENCE: 8
cacgcctagg ccggtcggtc tcgggccac 29

<210> SEQ ID NO 9
<211> LENGTH: 30
<212> TYPE: DNA
<213> ORGANISM: Artificial Sequence
<220> FEATURE:
<223> OTHER INFORMATION: Description of Artificial Sequence: primer

<400> SEQUENCE: 9
gcggctagct gctcgcccat cgcgggatgc 30

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: primer

<400> SEQUENCE: 10
gatgtacagc tcgagtcggc acgcccggcc gcatc 35

<210> SEQ ID NO 11
<211> LENGTH: 23
<212> TYPE: DNA
<213> ORGANISM: Artificial Sequence
<220> FEATURE:
<223> OTHER INFORMATION: Description of Artificial Sequence: primer

<400> SEQUENCE: 11
cgactcactt aagccatgca tcc 23

<210> SEQ ID NO 12
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 12
atcctaggcg ggcrggygtg tcgtccttcg g 31

<210> SEQ ID NO 13
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 13

```
atgctagccg ccgcgttccc cgtcttcgcg cg                                32
```

<210> SEQ ID NO 14
<211> LENGTH: 32
<212> TYPE: DNA
<213> ORGANISM: Artificial Sequence
<220> FEATURE:
<223> OTHER INFORMATION: Description of Artificial Sequence: primer

<400> SEQUENCE: 14

```
atgctagcgg attcgtcggt ggtgttcgcc ga                                32
```

<210> SEQ ID NO 15
<211> LENGTH: 31
<212> TYPE: DNA
<213> ORGANISM: Artificial Sequence
<220> FEATURE:
<223> OTHER INFORMATION: Description of Artificial Sequence: primer

<400> SEQUENCE: 15

```
atctcgagcc agtascgctg gtgytggaag g                                 31
```

<210> SEQ ID NO 16
<211> LENGTH: 4478
<212> TYPE: DNA
<213> ORGANISM: Artificial Sequence
<220> FEATURE:
<223> OTHER INFORMATION: Description of Artificial Sequence: DNA encoding synthetic PKS synthase fragment
<220> FEATURE:
<221> NAME/KEY: CDS
<222> LOCATION: (3)..(4466)

<400> SEQUENCE: 16

```
ag atc tgg cag ctc gcc gaa gcg ctg ctg acg ctc gtc cgg gag agc       47
   Ile Trp Gln Leu Ala Glu Ala Leu Leu Thr Leu Val Arg Glu Ser
     1               5                  10                  15

acc gcc gcc gtg ctc ggc cac gtg ggt ggc gag gac atc ccc gcg acg       95
Thr Ala Ala Val Leu Gly His Val Gly Gly Glu Asp Ile Pro Ala Thr
                20                  25                  30

gcg gcg ttc aag gac ctc ggc atc gac tcg ctc acc gcg gtc cag ctg      143
Ala Ala Phe Lys Asp Leu Gly Ile Asp Ser Leu Thr Ala Val Gln Leu
            35                  40                  45

cgc aac gcc ctc acc gag gcg acc ggt gtg cgg ctg aac gcc acg gcg      191
Arg Asn Ala Leu Thr Glu Ala Thr Gly Val Arg Leu Asn Ala Thr Ala
        50                  55                  60

gtc ttc gac ttc ccg acc ccg cac gtg ctc gcc ggg aag ctc ggc gac      239
Val Phe Asp Phe Pro Thr Pro His Val Leu Ala Gly Lys Leu Gly Asp
     65                  70                  75

gaa ctg acc ggc acc cgc gcg ccc gtc gtg ccc cgg acc gcg gcc acg      287
Glu Leu Thr Gly Thr Arg Ala Pro Val Val Pro Arg Thr Ala Ala Thr
 80                  85                  90                  95

gcc ggt gcg cac gac gag ccg ctg gcg atc gtg gga atg gcc tgc cgg      335
Ala Gly Ala His Asp Glu Pro Leu Ala Ile Val Gly Met Ala Cys Arg
                100                 105                 110

ctg ccc ggc ggg gtc gcg tca ccc gag gag ctg tgg cac ctc gtg gca      383
Leu Pro Gly Gly Val Ala Ser Pro Glu Glu Leu Trp His Leu Val Ala
            115                 120                 125

tcc ggc acc gac gcc atc acg gag ttc ccg acg gac cgc ggc tgg gac      431
Ser Gly Thr Asp Ala Ile Thr Glu Phe Pro Thr Asp Arg Gly Trp Asp
        130                 135                 140

gtc gac gcg atc tac gac ccg gac ccc gac gcg atc ggc aag acc ttc      479
```

-continued

```
Val Asp Ala Ile Tyr Asp Pro Asp Pro Asp Ala Ile Gly Lys Thr Phe
    145                 150                 155

gtc cgg cac ggt ggc ttc ctc acc ggc gcg aca ggc ttc gac gcg gcg      527
Val Arg His Gly Gly Phe Leu Thr Gly Ala Thr Gly Phe Asp Ala Ala
160                 165                 170                 175

ttc ttc ggc atc agc ccg cgc gag gcc ctc gcg atg gac ccg cag cag      575
Phe Phe Gly Ile Ser Pro Arg Glu Ala Leu Ala Met Asp Pro Gln Gln
                180                 185                 190

cgg gtg ctc ctg gag acg tcg tgg gag gcg ttc gaa agc gcc ggc atc      623
Arg Val Leu Leu Glu Thr Ser Trp Glu Ala Phe Glu Ser Ala Gly Ile
            195                 200                 205

acc ccg gac tcg acc cgc ggc agc gac acc ggc gtg ttc gtc ggc gcc      671
Thr Pro Asp Ser Thr Arg Gly Ser Asp Thr Gly Val Phe Val Gly Ala
        210                 215                 220

ttc tcc tac ggt tac ggc acc ggt gcg gac acc gac ggc ttc ggc gcg      719
Phe Ser Tyr Gly Tyr Gly Thr Gly Ala Asp Thr Asp Gly Phe Gly Ala
    225                 230                 235

acc ggc tcg cag acc agt gtg ctc tcc ggc cgg ctg tcg tac ttc tac      767
Thr Gly Ser Gln Thr Ser Val Leu Ser Gly Arg Leu Ser Tyr Phe Tyr
240                 245                 250                 255

ggt ctg gag ggt ccg gcg gtc acg gtc gac acg gcg tgt tcg tcg tcg      815
Gly Leu Glu Gly Pro Ala Val Thr Val Asp Thr Ala Cys Ser Ser Ser
                260                 265                 270

ctg gtg gcg ctg cac cag gcc ggg cag tcg ctg cgc tcc ggc gaa tgc      863
Leu Val Ala Leu His Gln Ala Gly Gln Ser Leu Arg Ser Gly Glu Cys
            275                 280                 285

tcg ctc gcc ctg gtc ggc ggc gtc acg gtg atg gcg tct ccc ggc ggc      911
Ser Leu Ala Leu Val Gly Gly Val Thr Val Met Ala Ser Pro Gly Gly
        290                 295                 300

ttc gtg gag ttc tcc cgg cag cgc ggc ctc gcg ccg gac ggc cgg gcg      959
Phe Val Glu Phe Ser Arg Gln Arg Gly Leu Ala Pro Asp Gly Arg Ala
    305                 310                 315

aag gcg ttc ggc gcg ggt gcg gac ggc acg agc ttc gcc gag ggt gcc     1007
Lys Ala Phe Gly Ala Gly Ala Asp Gly Thr Ser Phe Ala Glu Gly Ala
320                 325                 330                 335

ggt gtg ctg atc gtc gag agg ctc tcc gac gcc gaa cgc aac ggt cac     1055
Gly Val Leu Ile Val Glu Arg Leu Ser Asp Ala Glu Arg Asn Gly His
                340                 345                 350

acc gtc ctg gcg gtc gtc cgt ggt tcg gcg gtc aac cag gat ggt gcc     1103
Thr Val Leu Ala Val Val Arg Gly Ser Ala Val Asn Gln Asp Gly Ala
            355                 360                 365

tcc aac ggg ctg tcg gcg ccg aac ggg ccg tcg cag gag cgg gtg atc     1151
Ser Asn Gly Leu Ser Ala Pro Asn Gly Pro Ser Gln Glu Arg Val Ile
        370                 375                 380

cgg cag gcc ctg gcc aac gcc ggg ctc acc ccg gcg gac gtg gac gcc     1199
Arg Gln Ala Leu Ala Asn Ala Gly Leu Thr Pro Ala Asp Val Asp Ala
    385                 390                 395

gtc gag gcc cac ggc acc ggc acc agg ctg ggc gac ccc atc gag gca     1247
Val Glu Ala His Gly Thr Gly Thr Arg Leu Gly Asp Pro Ile Glu Ala
400                 405                 410                 415

cag gcg gta ctg gcc acc tac gga cag gag cgc gcc acc ccc ctg ctg     1295
Gln Ala Val Leu Ala Thr Tyr Gly Gln Glu Arg Ala Thr Pro Leu Leu
                420                 425                 430

ctg ggc tcg ctg aag tcc aac atc ggc cac gcc cag gcc gcg tcc ggc     1343
Leu Gly Ser Leu Lys Ser Asn Ile Gly His Ala Gln Ala Ala Ser Gly
            435                 440                 445

gtc gcc ggc atc atc aag atg gtg cag gcc ctc cgg cac ggg gag ctg     1391
Val Ala Gly Ile Ile Lys Met Val Gln Ala Leu Arg His Gly Glu Leu
        450                 455                 460
```

-continued

```
ccg ccg acg ctg cac gcc gac gag ccg tcg ccg cac gtc gac tgg acg      1439
Pro Pro Thr Leu His Ala Asp Glu Pro Ser Pro His Val Asp Trp Thr
    465                 470                 475

gcc ggc gcc gtc gaa ctg ctg acg tcg gcc cgg ccg tgg ccc gag acc      1487
Ala Gly Ala Val Glu Leu Leu Thr Ser Ala Arg Pro Trp Pro Glu Thr
480                 485                 490                 495

gac cgg cct agg cgg gca ggc gtg tcg tcc ttc ggg atc agt ggc acc      1535
Asp Arg Pro Arg Arg Ala Gly Val Ser Ser Phe Gly Ile Ser Gly Thr
                500                 505                 510

aac gcc cac gtc atc ctg gaa agc gca ccc ccc act cag cct gcg gac      1583
Asn Ala His Val Ile Leu Glu Ser Ala Pro Pro Thr Gln Pro Ala Asp
            515                 520                 525

aac gcg gtg atc gag cgg gca ccg gag tgg gtg ccg ttg gtg att tcg      1631
Asn Ala Val Ile Glu Arg Ala Pro Glu Trp Val Pro Leu Val Ile Ser
        530                 535                 540

gcc agg acc cag tcg gct ttg act gag cac gag ggc cgg ttg cgt gcg      1679
Ala Arg Thr Gln Ser Ala Leu Thr Glu His Glu Gly Arg Leu Arg Ala
    545                 550                 555

tat ctg gcg gcg tcg ccc ggg gtg gat atg cgg gct gtg gca tcg acg      1727
Tyr Leu Ala Ala Ser Pro Gly Val Asp Met Arg Ala Val Ala Ser Thr
560                 565                 570                 575

ctg gcg atg aca cgg tcg gtg ttc gag cac cgt gcc gtg ctg ctg gga      1775
Leu Ala Met Thr Arg Ser Val Phe Glu His Arg Ala Val Leu Leu Gly
                580                 585                 590

gat gac acc gtc acc ggc acc gct gtg tct gac cct cgg gcg gtg ttc      1823
Asp Asp Thr Val Thr Gly Thr Ala Val Ser Asp Pro Arg Ala Val Phe
            595                 600                 605

gtc ttc ccg gga cag ggg tcg cag cgt gct ggc atg ggt gag gaa ctg      1871
Val Phe Pro Gly Gln Gly Ser Gln Arg Ala Gly Met Gly Glu Glu Leu
        610                 615                 620

gcc gcc gcg ttc ccc gtc ttc gcg cgg atc cat cag cag gtg tgg gac      1919
Ala Ala Ala Phe Pro Val Phe Ala Arg Ile His Gln Gln Val Trp Asp
    625                 630                 635

ctg ctc gat gtg ccc gat ctg gag gtg aac gag acc ggt tac gcc cag      1967
Leu Leu Asp Val Pro Asp Leu Glu Val Asn Glu Thr Gly Tyr Ala Gln
640                 645                 650                 655

ccg gcc ctg ttc gca atg cag gtg gct ctg ttc ggg ctg ctg gaa tcg      2015
Pro Ala Leu Phe Ala Met Gln Val Ala Leu Phe Gly Leu Leu Glu Ser
                660                 665                 670

tgg ggt gta cga ccg gac gcg gtg atc ggc cat tcg gtg ggt gag ctt      2063
Trp Gly Val Arg Pro Asp Ala Val Ile Gly His Ser Val Gly Glu Leu
            675                 680                 685

gcg gct gcg tat gtg tcc ggg gtg tgg tcg ttg gag gat gcc tgc act      2111
Ala Ala Ala Tyr Val Ser Gly Val Trp Ser Leu Glu Asp Ala Cys Thr
        690                 695                 700

ttg gtg tcg gcg cgg gct cgt ctg atg cag gct ctg ccc gcg ggt ggg      2159
Leu Val Ser Ala Arg Ala Arg Leu Met Gln Ala Leu Pro Ala Gly Gly
    705                 710                 715

gtg atg gtc gct gtc ccg gtc tcg gag gat gag gcc cgg gcc gtg ctg      2207
Val Met Val Ala Val Pro Val Ser Glu Asp Glu Ala Arg Ala Val Leu
720                 725                 730                 735

ggt gag ggt gtg gag atc gcc gcg gtc aac ggc ccg tcg tcg gtg gtt      2255
Gly Glu Gly Val Glu Ile Ala Ala Val Asn Gly Pro Ser Ser Val Val
                740                 745                 750

ctc tcc ggt gat gag gcc gcc gtg ctg cag gcc gcg gag ggg ctg ggg      2303
Leu Ser Gly Asp Glu Ala Ala Val Leu Gln Ala Ala Glu Gly Leu Gly
            755                 760                 765

aag tgg acg cgg ctg gcg acc agc cac gcg ttc cat tcc gcc cgt atg      2351
Lys Trp Thr Arg Leu Ala Thr Ser His Ala Phe His Ser Ala Arg Met
        770                 775                 780
```

-continued

```
gaa ccc atg ctg gag gag ttc cgg gcg gtc gcc gaa ggc ctg acc tac      2399
Glu Pro Met Leu Glu Glu Phe Arg Ala Val Ala Glu Gly Leu Thr Tyr
    785                 790                 795

cgg acg ccg cag gtc tcc atg gcc gtt ggt gat cag gtg acc acc gct      2447
Arg Thr Pro Gln Val Ser Met Ala Val Gly Asp Gln Val Thr Thr Ala
800                 805                 810                 815

gag tac tgg gtg cgg cag gtc cgg gac acg gtc cgg ttc ggc gag cag      2495
Glu Tyr Trp Val Arg Gln Val Arg Asp Thr Val Arg Phe Gly Glu Gln
                820                 825                 830

gtg gcc tcg tac gag gac gcc gtg ttc gtc gag ctg ggt gcc gac cgg      2543
Val Ala Ser Tyr Glu Asp Ala Val Phe Val Glu Leu Gly Ala Asp Arg
            835                 840                 845

tca ctg gcc cgc ctg gtc gac ggt gtc gcg atg ctg cac ggc gac cac      2591
Ser Leu Ala Arg Leu Val Asp Gly Val Ala Met Leu His Gly Asp His
        850                 855                 860

gaa atc cag gcc gcg atc ggc gcc ctg gcc cac ctg tat gtc aac ggc      2639
Glu Ile Gln Ala Ala Ile Gly Ala Leu Ala His Leu Tyr Val Asn Gly
    865                 870                 875

gtc acg gtc gac tgg ccc gcg ctc ctg ggc gat gct ccg gca aca cgg      2687
Val Thr Val Asp Trp Pro Ala Leu Leu Gly Asp Ala Pro Ala Thr Arg
880                 885                 890                 895

gtg ctg gac ctt ccg aca tac gcc ttc cag cac cag cgc tac tgg ctc      2735
Val Leu Asp Leu Pro Thr Tyr Ala Phe Gln His Gln Arg Tyr Trp Leu
                900                 905                 910

gag tcg gca cgc ccg gcc gca tcc gac gcg ggc cac ccc gtg ctg ggc      2783
Glu Ser Ala Arg Pro Ala Ala Ser Asp Ala Gly His Pro Val Leu Gly
            915                 920                 925

tcc ggt atc gcc ctc gcc ggg tcg ccg ggc cgg gtg ttc acg ggt tcc      2831
Ser Gly Ile Ala Leu Ala Gly Ser Pro Gly Arg Val Phe Thr Gly Ser
        930                 935                 940

gtg ccg acc ggt gcg gac cgc gcg gtg ttc gtc gcc gag ctg gcg ctg      2879
Val Pro Thr Gly Ala Asp Arg Ala Val Phe Val Ala Glu Leu Ala Leu
    945                 950                 955

gcc gcc gcg gac gcg gtc gac tgc gcc acg gtc gag cgg ctc gac atc      2927
Ala Ala Ala Asp Ala Val Asp Cys Ala Thr Val Glu Arg Leu Asp Ile
960                 965                 970                 975

gcc tcc gtg ccc ggc cgg ccg ggc cat ggc cgg acg acc gta cag acc      2975
Ala Ser Val Pro Gly Arg Pro Gly His Gly Arg Thr Thr Val Gln Thr
                980                 985                 990

tgg gtc gac gag ccg gcg gac gac ggc cgg cgc cgg ttc acc gtg cac      3023
Trp Val Asp Glu Pro Ala Asp Asp Gly Arg Arg Arg Phe Thr Val His
            995                1000                1005

acc cgc acc ggc gac gcc ccg tgg acg ctg cac gcc gag ggg gtg ctg      3071
Thr Arg Thr Gly Asp Ala Pro Trp Thr Leu His Ala Glu Gly Val Leu
       1010                1015                1020

cgc ccc cat ggc acg gcc ctg ccc gat gcg gcc gac gcc gag tgg ccc      3119
Arg Pro His Gly Thr Ala Leu Pro Asp Ala Ala Asp Ala Glu Trp Pro
   1025                1030                1035

cca ccg ggc gcg gtg ccc gcg gac ggg ctg ccg ggt gtg tgg cgc cgg      3167
Pro Pro Gly Ala Val Pro Ala Asp Gly Leu Pro Gly Val Trp Arg Arg
1040               1045                1050                1055

ggg gac cag gtc ttc gcc gag gcc gag gtg gac gga ccg gac ggt ttc      3215
Gly Asp Gln Val Phe Ala Glu Ala Glu Val Asp Gly Pro Asp Gly Phe
               1060                1065                1070

gtg gtg cac ccc gac ctg ctc gac gcg gtc ttc tcc gcg gtc ggc gac      3263
Val Val His Pro Asp Leu Leu Asp Ala Val Phe Ser Ala Val Gly Asp
           1075                1080                1085

gga agc cgc cag ccg gcc gga tgg cgc gac ctg acg gtg cac gcg tcg      3311
Gly Ser Arg Gln Pro Ala Gly Trp Arg Asp Leu Thr Val His Ala Ser
```

-continued

```
      1090                1095                1100

gac gcc acc gta ctg cgc gcc tgc ctc acc cgg cgc acc gac gga gcc     3359
Asp Ala Thr Val Leu Arg Ala Cys Leu Thr Arg Arg Thr Asp Gly Ala
   1105                1110                1115

atg gga ttc gcc gcc ttc gac ggc gcc ggc ctg ccg gta ctc acc gcg     3407
Met Gly Phe Ala Ala Phe Asp Gly Ala Gly Leu Pro Val Leu Thr Ala
1120                1125                1130                1135

gag gcg gtg acg ctg cgg gag gtg gcg tca ccg tcc ggc tcc gag gag     3455
Glu Ala Val Thr Leu Arg Glu Val Ala Ser Pro Ser Gly Ser Glu Glu
                1140                1145                1150

tcg gac ggc ctg cac cgg ttg gag tgg ctc gcg gtc gcc gag gcg gtc     3503
Ser Asp Gly Leu His Arg Leu Glu Trp Leu Ala Val Ala Glu Ala Val
            1155                1160                1165

tac gac ggt gac ctg ccc gag gga cat gtc ctg atc acc gcc gcc cac     3551
Tyr Asp Gly Asp Leu Pro Glu Gly His Val Leu Ile Thr Ala Ala His
        1170                1175                1180

ccc gac gac ccc gag gac ata ccc acc cgc gcc cac acc cgc gcc acc     3599
Pro Asp Asp Pro Glu Asp Ile Pro Thr Arg Ala His Thr Arg Ala Thr
   1185                1190                1195

cgc gtc ctg acc gcc ctg caa cac cac ctc acc acc acc gac cac acc     3647
Arg Val Leu Thr Ala Leu Gln His His Leu Thr Thr Thr Asp His Thr
1200                1205                1210                1215

ctc atc gtc cac acc acc acc gac ccc gcc ggc gcc acc gtc acc ggc     3695
Leu Ile Val His Thr Thr Thr Asp Pro Ala Gly Ala Thr Val Thr Gly
                1220                1225                1230

ctc acc cgc acc gcc cag aac gaa cac ccc cac cgc atc cgc ctc atc     3743
Leu Thr Arg Thr Ala Gln Asn Glu His Pro His Arg Ile Arg Leu Ile
            1235                1240                1245

gaa acc gac cac ccc cac acc ccc ctc ccc ctg gcc caa ctc gcc acc     3791
Glu Thr Asp His Pro His Thr Pro Leu Pro Leu Ala Gln Leu Ala Thr
        1250                1255                1260

ctc gac cac ccc cac ctc cgc ctc acc cac cac acc ctc cac cac ccc     3839
Leu Asp His Pro His Leu Arg Leu Thr His His Thr Leu His His Pro
   1265                1270                1275

cac ctc acc ccc ctc cac acc acc acc cca ccc acc acc acc ccc ctc     3887
His Leu Thr Pro Leu His Thr Thr Thr Pro Pro Thr Thr Thr Pro Leu
1280                1285                1290                1295

aac ccc gaa cac gcc atc atc atc acc ggc ggc tcc ggc acc ctc gcc     3935
Asn Pro Glu His Ala Ile Ile Ile Thr Gly Gly Ser Gly Thr Leu Ala
                1300                1305                1310

ggc atc ctc gcc cgc cac ctg aac cac ccc cac acc tac ctc ctc tcc     3983
Gly Ile Leu Ala Arg His Leu Asn His Pro His Thr Tyr Leu Leu Ser
            1315                1320                1325

cgc acc cca ccc ccc gac gcc acc ccc ggc acc cac ctc ccc tgc gac     4031
Arg Thr Pro Pro Pro Asp Ala Thr Pro Gly Thr His Leu Pro Cys Asp
        1330                1335                1340

gtc ggc gac ccc cac caa ctc gcc acc acc ctc acc cac atc ccc caa     4079
Val Gly Asp Pro His Gln Leu Ala Thr Thr Leu Thr His Ile Pro Gln
   1345                1350                1355

ccc ctc acc gcc atc ttc cac acc gcc gcc acc ctc gac gac ggc atc     4127
Pro Leu Thr Ala Ile Phe His Thr Ala Ala Thr Leu Asp Asp Gly Ile
1360                1365                1370                1375

ctc cac gcc ctc acc ccc gac cgc ctc acc acc gtc ctc cac ccc aaa     4175
Leu His Ala Leu Thr Pro Asp Arg Leu Thr Thr Val Leu His Pro Lys
                1380                1385                1390

gcc aac gcc gcc tgg cac ctg cac cac ctc acc caa aac caa ccc ctc     4223
Ala Asn Ala Ala Trp His Leu His His Leu Thr Gln Asn Gln Pro Leu
            1395                1400                1405

acc cac ttc gtc ctc tac tcc agc gcc gcc gcc gtc ctc ggc agc ccc     4271
```

-continued

```
Thr His Phe Val Leu Tyr Ser Ser Ala Ala Ala Val Leu Gly Ser Pro
       1410                1415                1420

gga caa gga aac tac gcc gcc gcc aac gcc ttc ctc gac gcc ctc gcc     4319
Gly Gln Gly Asn Tyr Ala Ala Ala Asn Ala Phe Leu Asp Ala Leu Ala
   1425                1430                1435

acc cac cgc cac acc ctc ggc caa ccc gcc acc tcc atc gcc tgg ggc     4367
Thr His Arg His Thr Leu Gly Gln Pro Ala Thr Ser Ile Ala Trp Gly
1440                1445                1450                1455

atg tgg cac acc acc agc acc ctc acc gga caa ctc gac gac gcc gac     4415
Met Trp His Thr Thr Ser Thr Leu Thr Gly Gln Leu Asp Asp Ala Asp
               1460                1465                1470

cgg gac cgc atc cgc cgc ggc ggt ttc ctc ccg atc acg gac gac gag     4463
Arg Asp Arg Ile Arg Arg Gly Gly Phe Leu Pro Ile Thr Asp Asp Glu
           1475                1480                1485

ggc atggggatgc at                                                   4478
Gly


<210> SEQ ID NO 17
<211> LENGTH: 1488
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 17

Ile Trp Gln Leu Ala Glu Ala Leu Leu Thr Leu Val Arg Glu Ser Thr
  1               5                  10                  15

Ala Ala Val Leu Gly His Val Gly Gly Glu Asp Ile Pro Ala Thr Ala
             20                  25                  30

Ala Phe Lys Asp Leu Gly Ile Asp Ser Leu Thr Ala Val Gln Leu Arg
         35                  40                  45

Asn Ala Leu Thr Glu Ala Thr Gly Val Arg Leu Asn Ala Thr Ala Val
     50                  55                  60

Phe Asp Phe Pro Thr Pro His Val Leu Ala Gly Lys Leu Gly Asp Glu
 65                  70                  75                  80

Leu Thr Gly Thr Arg Ala Pro Val Val Pro Arg Thr Ala Ala Thr Ala
                 85                  90                  95

Gly Ala His Asp Glu Pro Leu Ala Ile Val Gly Met Ala Cys Arg Leu
            100                 105                 110

Pro Gly Gly Val Ala Ser Pro Glu Glu Leu Trp His Leu Val Ala Ser
        115                 120                 125

Gly Thr Asp Ala Ile Thr Glu Phe Pro Thr Asp Arg Gly Trp Asp Val
    130                 135                 140

Asp Ala Ile Tyr Asp Pro Asp Pro Asp Ala Ile Gly Lys Thr Phe Val
145                 150                 155                 160

Arg His Gly Gly Phe Leu Thr Gly Ala Thr Gly Phe Asp Ala Ala Phe
                165                 170                 175

Phe Gly Ile Ser Pro Arg Glu Ala Leu Ala Met Asp Pro Gln Gln Arg
            180                 185                 190

Val Leu Leu Glu Thr Ser Trp Glu Ala Phe Glu Ser Ala Gly Ile Thr
        195                 200                 205

Pro Asp Ser Thr Arg Gly Ser Asp Thr Gly Val Phe Val Gly Ala Phe
    210                 215                 220

Ser Tyr Gly Tyr Gly Thr Gly Ala Asp Thr Asp Gly Phe Gly Ala Thr
225                 230                 235                 240

Gly Ser Gln Thr Ser Val Leu Ser Gly Arg Leu Ser Tyr Phe Tyr Gly
```

-continued

```
                245                 250                 255

Leu Glu Gly Pro Ala Val Thr Val Asp Thr Ala Cys Ser Ser Ser Leu
            260                 265                 270

Val Ala Leu His Gln Ala Gly Gln Ser Leu Arg Ser Gly Glu Cys Ser
        275                 280                 285

Leu Ala Leu Val Gly Gly Val Thr Val Met Ala Ser Pro Gly Gly Phe
    290                 295                 300

Val Glu Phe Ser Arg Gln Arg Gly Leu Ala Pro Asp Gly Arg Ala Lys
305                 310                 315                 320

Ala Phe Gly Ala Gly Ala Asp Gly Thr Ser Phe Ala Glu Gly Ala Gly
                325                 330                 335

Val Leu Ile Val Glu Arg Leu Ser Asp Ala Glu Arg Asn Gly His Thr
            340                 345                 350

Val Leu Ala Val Val Arg Gly Ser Ala Val Asn Gln Asp Gly Ala Ser
        355                 360                 365

Asn Gly Leu Ser Ala Pro Asn Gly Pro Ser Gln Glu Arg Val Ile Arg
    370                 375                 380

Gln Ala Leu Ala Asn Ala Gly Leu Thr Pro Ala Asp Val Asp Ala Val
385                 390                 395                 400

Glu Ala His Gly Thr Gly Thr Arg Leu Gly Asp Pro Ile Glu Ala Gln
                405                 410                 415

Ala Val Leu Ala Thr Tyr Gly Gln Glu Arg Ala Thr Pro Leu Leu Leu
            420                 425                 430

Gly Ser Leu Lys Ser Asn Ile Gly His Ala Gln Ala Ala Ser Gly Val
        435                 440                 445

Ala Gly Ile Ile Lys Met Val Gln Ala Leu Arg His Gly Glu Leu Pro
    450                 455                 460

Pro Thr Leu His Ala Asp Glu Pro Ser Pro His Val Asp Trp Thr Ala
465                 470                 475                 480

Gly Ala Val Glu Leu Leu Thr Ser Ala Arg Pro Trp Pro Glu Thr Asp
                485                 490                 495

Arg Pro Arg Arg Ala Gly Val Ser Ser Phe Gly Ile Ser Gly Thr Asn
            500                 505                 510

Ala His Val Ile Leu Glu Ser Ala Pro Pro Thr Gln Pro Ala Asp Asn
        515                 520                 525

Ala Val Ile Glu Arg Ala Pro Glu Trp Val Pro Leu Val Ile Ser Ala
    530                 535                 540

Arg Thr Gln Ser Ala Leu Thr Glu His Glu Gly Arg Leu Arg Ala Tyr
545                 550                 555                 560

Leu Ala Ala Ser Pro Gly Val Asp Met Arg Ala Val Ala Ser Thr Leu
                565                 570                 575

Ala Met Thr Arg Ser Val Phe Glu His Arg Ala Val Leu Leu Gly Asp
            580                 585                 590

Asp Thr Val Thr Gly Thr Ala Val Ser Asp Pro Arg Ala Val Phe Val
        595                 600                 605

Phe Pro Gly Gln Gly Ser Gln Arg Ala Gly Met Gly Glu Glu Leu Ala
    610                 615                 620

Ala Ala Phe Pro Val Phe Ala Arg Ile His Gln Gln Val Trp Asp Leu
625                 630                 635                 640

Leu Asp Val Pro Asp Leu Glu Val Asn Glu Thr Gly Tyr Ala Gln Pro
                645                 650                 655

Ala Leu Phe Ala Met Gln Val Ala Leu Phe Gly Leu Leu Glu Ser Trp
            660                 665                 670
```

```
Gly Val Arg Pro Asp Ala Val Ile Gly His Ser Val Gly Glu Leu Ala
        675                 680                 685

Ala Ala Tyr Val Ser Gly Val Trp Ser Leu Glu Asp Ala Cys Thr Leu
    690                 695                 700

Val Ser Ala Arg Ala Arg Leu Met Gln Ala Leu Pro Ala Gly Gly Val
705                 710                 715                 720

Met Val Ala Val Pro Val Ser Glu Asp Glu Ala Arg Ala Val Leu Gly
                725                 730                 735

Glu Gly Val Glu Ile Ala Ala Val Asn Gly Pro Ser Ser Val Val Leu
            740                 745                 750

Ser Gly Asp Glu Ala Ala Val Leu Gln Ala Ala Glu Gly Leu Gly Lys
        755                 760                 765

Trp Thr Arg Leu Ala Thr Ser His Ala Phe His Ser Ala Arg Met Glu
    770                 775                 780

Pro Met Leu Glu Glu Phe Arg Ala Val Ala Glu Gly Leu Thr Tyr Arg
785                 790                 795                 800

Thr Pro Gln Val Ser Met Ala Val Gly Asp Gln Val Thr Thr Ala Glu
                805                 810                 815

Tyr Trp Val Arg Gln Val Arg Asp Thr Val Arg Phe Gly Glu Gln Val
            820                 825                 830

Ala Ser Tyr Glu Asp Ala Val Phe Val Glu Leu Gly Ala Asp Arg Ser
        835                 840                 845

Leu Ala Arg Leu Val Asp Gly Val Ala Met Leu His Gly Asp His Glu
    850                 855                 860

Ile Gln Ala Ala Ile Gly Ala Leu Ala His Leu Tyr Val Asn Gly Val
865                 870                 875                 880

Thr Val Asp Trp Pro Ala Leu Leu Gly Asp Ala Pro Ala Thr Arg Val
                885                 890                 895

Leu Asp Leu Pro Thr Tyr Ala Phe Gln His Gln Arg Tyr Trp Leu Glu
            900                 905                 910

Ser Ala Arg Pro Ala Ala Ser Asp Ala Gly His Pro Val Leu Gly Ser
        915                 920                 925

Gly Ile Ala Leu Ala Gly Ser Pro Gly Arg Val Phe Thr Gly Ser Val
    930                 935                 940

Pro Thr Gly Ala Asp Arg Ala Val Phe Val Ala Glu Leu Ala Leu Ala
945                 950                 955                 960

Ala Ala Asp Ala Val Asp Cys Ala Thr Val Glu Arg Leu Asp Ile Ala
                965                 970                 975

Ser Val Pro Gly Arg Pro Gly His Gly Arg Thr Thr Val Gln Thr Trp
            980                 985                 990

Val Asp Glu Pro Ala Asp Asp Gly Arg Arg Arg Phe Thr Val His Thr
        995                 1000                1005

Arg Thr Gly Asp Ala Pro Trp Thr Leu His Ala Glu Gly Val Leu Arg
    1010                1015                1020

Pro His Gly Thr Ala Leu Pro Asp Ala Ala Asp Ala Glu Trp Pro Pro
1025                1030                1035                1040

Pro Gly Ala Val Pro Ala Asp Gly Leu Pro Gly Val Trp Arg Arg Gly
                1045                1050                1055

Asp Gln Val Phe Ala Glu Ala Glu Val Asp Gly Pro Asp Gly Phe Val
            1060                1065                1070

Val His Pro Asp Leu Leu Asp Ala Val Phe Ser Ala Val Gly Asp Gly
        1075                1080                1085
```

-continued

```
Ser Arg Gln Pro Ala Gly Trp Arg Asp Leu Thr Val His Ala Ser Asp
    1090                1095                1100

Ala Thr Val Leu Arg Ala Cys Leu Thr Arg Arg Thr Asp Gly Ala Met
1105                1110                1115                1120

Gly Phe Ala Ala Phe Asp Gly Ala Gly Leu Pro Val Leu Thr Ala Glu
                1125                1130                1135

Ala Val Thr Leu Arg Glu Val Ala Ser Pro Ser Gly Ser Glu Glu Ser
            1140                1145                1150

Asp Gly Leu His Arg Leu Glu Trp Leu Ala Val Ala Glu Ala Val Tyr
        1155                1160                1165

Asp Gly Asp Leu Pro Glu Gly His Val Leu Ile Thr Ala Ala His Pro
    1170                1175                1180

Asp Asp Pro Glu Asp Ile Pro Thr Arg Ala His Thr Arg Ala Thr Arg
1185                1190                1195                1200

Val Leu Thr Ala Leu Gln His His Leu Thr Thr Thr Asp His Thr Leu
                1205                1210                1215

Ile Val His Thr Thr Thr Asp Pro Ala Gly Ala Thr Val Thr Gly Leu
            1220                1225                1230

Thr Arg Thr Ala Gln Asn Glu His Pro His Arg Ile Arg Leu Ile Glu
        1235                1240                1245

Thr Asp His Pro His Thr Pro Leu Pro Leu Ala Gln Leu Ala Thr Leu
    1250                1255                1260

Asp His Pro His Leu Arg Leu Thr His His Thr Leu His His Pro His
1265                1270                1275                1280

Leu Thr Pro Leu His Thr Thr Thr Pro Pro Thr Thr Thr Pro Leu Asn
                1285                1290                1295

Pro Glu His Ala Ile Ile Ile Thr Gly Gly Ser Gly Thr Leu Ala Gly
            1300                1305                1310

Ile Leu Ala Arg His Leu Asn His Pro His Thr Tyr Leu Leu Ser Arg
        1315                1320                1325

Thr Pro Pro Pro Asp Ala Thr Pro Gly Thr His Leu Pro Cys Asp Val
    1330                1335                1340

Gly Asp Pro His Gln Leu Ala Thr Thr Leu Thr His Ile Pro Gln Pro
1345                1350                1355                1360

Leu Thr Ala Ile Phe His Thr Ala Ala Thr Leu Asp Asp Gly Ile Leu
                1365                1370                1375

His Ala Leu Thr Pro Asp Arg Leu Thr Thr Val Leu His Pro Lys Ala
            1380                1385                1390

Asn Ala Ala Trp His Leu His His Leu Thr Gln Asn Gln Pro Leu Thr
        1395                1400                1405

His Phe Val Leu Tyr Ser Ser Ala Ala Ala Val Leu Gly Ser Pro Gly
    1410                1415                1420

Gln Gly Asn Tyr Ala Ala Ala Asn Ala Phe Leu Asp Ala Leu Ala Thr
1425                1430                1435                1440

His Arg His Thr Leu Gly Gln Pro Ala Thr Ser Ile Ala Trp Gly Met
                1445                1450                1455

Trp His Thr Thr Ser Thr Leu Thr Gly Gln Leu Asp Asp Ala Asp Arg
            1460                1465                1470

Asp Arg Ile Arg Arg Gly Gly Phe Leu Pro Ile Thr Asp Asp Glu Gly
        1475                1480                1485
```

<210> SEQ ID NO 18
<211> LENGTH: 4571
<212> TYPE: DNA

```
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (9)..(4559)

<400> SEQUENCE: 18

agatctgg cag ctc gcc gaa gcg ctg ctg acg ctc gtc cgg gag agc acc      50
         Gln Leu Ala Glu Ala Leu Leu Thr Leu Val Arg Glu Ser Thr
           1               5                  10

gcc gcc gtg ctc ggc cac gtg ggt ggc gag gac atc ccc gcg acg gcg       98
Ala Ala Val Leu Gly His Val Gly Gly Glu Asp Ile Pro Ala Thr Ala
 15                  20                  25                  30

gcg ttc aag gac ctc ggc atc gac tcg ctc acc gcg gtc cag ctg cgc      146
Ala Phe Lys Asp Leu Gly Ile Asp Ser Leu Thr Ala Val Gln Leu Arg
                 35                  40                  45

aac gcc ctc acc gag gcg acc ggt gtg cgg ctg aac gcc acg gcg gtc      194
Asn Ala Leu Thr Glu Ala Thr Gly Val Arg Leu Asn Ala Thr Ala Val
             50                  55                  60

ttc gac ttc ccg acc ccg cac gtg ctc gcc ggg aag ctc ggc gac gaa      242
Phe Asp Phe Pro Thr Pro His Val Leu Ala Gly Lys Leu Gly Asp Glu
         65                  70                  75

ctg acc ggc acc cgc gcg ccc gtc gtg ccc cgg acc gcg gcc acg gcc      290
Leu Thr Gly Thr Arg Ala Pro Val Val Pro Arg Thr Ala Ala Thr Ala
     80                  85                  90

ggt gcg cac gac gag ccg ctg gcg atc gtg gga atg gcc tgc cgg ctg      338
Gly Ala His Asp Glu Pro Leu Ala Ile Val Gly Met Ala Cys Arg Leu
 95                 100                 105                 110

ccc ggc ggg gtc gcg tca ccc gag gag ctg tgg cac ctc gtg gca tcc      386
Pro Gly Gly Val Ala Ser Pro Glu Glu Leu Trp His Leu Val Ala Ser
                115                 120                 125

ggc acc gac gcc atc acg gag ttc ccg acg gac cgc ggc tgg gac gtc      434
Gly Thr Asp Ala Ile Thr Glu Phe Pro Thr Asp Arg Gly Trp Asp Val
            130                 135                 140

gac gcg atc tac gac ccg gac ccc gac gcg atc ggc aag acc ttc gtc      482
Asp Ala Ile Tyr Asp Pro Asp Pro Asp Ala Ile Gly Lys Thr Phe Val
        145                 150                 155

cgg cac ggt ggc ttc ctc acc ggc gcg aca ggc ttc gac gcg gcg ttc      530
Arg His Gly Gly Phe Leu Thr Gly Ala Thr Gly Phe Asp Ala Ala Phe
    160                 165                 170

ttc ggc atc agc ccg cgc gag gcc ctc gcg atg gac ccg cag cag cgg      578
Phe Gly Ile Ser Pro Arg Glu Ala Leu Ala Met Asp Pro Gln Gln Arg
175                 180                 185                 190

gtg ctc ctg gag acg tcg tgg gag gcg ttc gaa agc gcc ggc atc acc      626
Val Leu Leu Glu Thr Ser Trp Glu Ala Phe Glu Ser Ala Gly Ile Thr
                195                 200                 205

ccg gac tcg acc cgc ggc agc gac acc ggc gtg ttc gtc ggc gcc ttc      674
Pro Asp Ser Thr Arg Gly Ser Asp Thr Gly Val Phe Val Gly Ala Phe
            210                 215                 220

tcc tac ggt tac ggc acc ggt gcg gac acc gac ggc ttc ggc gcg acc      722
Ser Tyr Gly Tyr Gly Thr Gly Ala Asp Thr Asp Gly Phe Gly Ala Thr
        225                 230                 235

ggc tcg cag acc agt gtg ctc tcc ggc cgg ctg tcg tac ttc tac ggt      770
Gly Ser Gln Thr Ser Val Leu Ser Gly Arg Leu Ser Tyr Phe Tyr Gly
    240                 245                 250

ctg gag ggt ccg gcg gtc acg gtc gac acg gcg tgt tcg tcg tcg ctg      818
Leu Glu Gly Pro Ala Val Thr Val Asp Thr Ala Cys Ser Ser Ser Leu
255                 260                 265                 270

gtg gcg ctg cac cag gcc ggg cag tcg ctg cgc tcc ggc gaa tgc tcg      866
```

-continued

```
Val Ala Leu His Gln Ala Gly Gln Ser Leu Arg Ser Gly Glu Cys Ser
                275                 280                 285

ctc gcc ctg gtc ggc ggc gtc acg gtg atg gcg tct ccc ggc ggc ttc      914
Leu Ala Leu Val Gly Gly Val Thr Val Met Ala Ser Pro Gly Gly Phe
            290                 295                 300

gtg gag ttc tcc cgg cag cgc ggc ctc gcg ccg gac ggc cgg gcg aag      962
Val Glu Phe Ser Arg Gln Arg Gly Leu Ala Pro Asp Gly Arg Ala Lys
        305                 310                 315

gcg ttc ggc gcg ggt gcg gac ggc acg agc ttc gcc gag ggt gcc ggt     1010
Ala Phe Gly Ala Gly Ala Asp Gly Thr Ser Phe Ala Glu Gly Ala Gly
    320                 325                 330

gtg ctg atc gtc gag agg ctc tcc gac gcc gaa cgc aac ggt cac acc     1058
Val Leu Ile Val Glu Arg Leu Ser Asp Ala Glu Arg Asn Gly His Thr
335                 340                 345                 350

gtc ctg gcg gtc gtc cgt ggt tcg gcg gtc aac cag gat ggt gcc tcc     1106
Val Leu Ala Val Val Arg Gly Ser Ala Val Asn Gln Asp Gly Ala Ser
                355                 360                 365

aac ggg ctg tcg gcg ccg aac ggg ccg tcg cag gag cgg gtg atc cgg     1154
Asn Gly Leu Ser Ala Pro Asn Gly Pro Ser Gln Glu Arg Val Ile Arg
            370                 375                 380

cag gcc ctg gcc aac gcc ggg ctc acc ccg gcg gac gtg gac gcc gtc     1202
Gln Ala Leu Ala Asn Ala Gly Leu Thr Pro Ala Asp Val Asp Ala Val
        385                 390                 395

gag gcc cac ggc acc ggc acc agg ctg ggc gac ccc atc gag gca cag     1250
Glu Ala His Gly Thr Gly Thr Arg Leu Gly Asp Pro Ile Glu Ala Gln
    400                 405                 410

gcg gta ctg gcc acc tac gga cag gag cgc gcc acc ccc ctg ctg ctg     1298
Ala Val Leu Ala Thr Tyr Gly Gln Glu Arg Ala Thr Pro Leu Leu Leu
415                 420                 425                 430

ggc tcg ctg aag tcc aac atc ggc cac gcc cag gcc gcg tcc ggc gtc     1346
Gly Ser Leu Lys Ser Asn Ile Gly His Ala Gln Ala Ala Ser Gly Val
                435                 440                 445

gcc ggc atc atc aag atg gtg cag gcc ctc cgg cac ggg gag ctg ccg     1394
Ala Gly Ile Ile Lys Met Val Gln Ala Leu Arg His Gly Glu Leu Pro
            450                 455                 460

ccg acg ctg cac gcc gac gag ccg tcg ccg cac gtc gac tgg acg gcc     1442
Pro Thr Leu His Ala Asp Glu Pro Ser Pro His Val Asp Trp Thr Ala
        465                 470                 475

ggc gcc gtc gaa ctg ctg acg tcg gcc cgg ccg tgg ccc gag acc gac     1490
Gly Ala Val Glu Leu Leu Thr Ser Ala Arg Pro Trp Pro Glu Thr Asp
    480                 485                 490

cgg cct agg cgg gcg ggc gtg tcg tcc ttc gga gtc agc ggc acc aac     1538
Arg Pro Arg Arg Ala Gly Val Ser Ser Phe Gly Val Ser Gly Thr Asn
495                 500                 505                 510

gcc cac gtc atc ctg gag agc gca ccc ccc gct cag ccc gcg gag gag     1586
Ala His Val Ile Leu Glu Ser Ala Pro Pro Ala Gln Pro Ala Glu Glu
                515                 520                 525

gcg cag cct gtt gag acg ccg gtg gtg gcc tcg gat gtg ctg ccg ctg     1634
Ala Gln Pro Val Glu Thr Pro Val Val Ala Ser Asp Val Leu Pro Leu
            530                 535                 540

gtg ata tcg gcc aag acc cag ccc gcc ctg acc gaa cac gaa gac cgg     1682
Val Ile Ser Ala Lys Thr Gln Pro Ala Leu Thr Glu His Glu Asp Arg
        545                 550                 555

ctg cgc gcc tac ctg gcg gcg tcg ccc ggg gcg gat ata cgg gct gtg     1730
Leu Arg Ala Tyr Leu Ala Ala Ser Pro Gly Ala Asp Ile Arg Ala Val
    560                 565                 570

gca tcg acg ctg gcg gtg aca cgg tcg gtg ttc gag cac cgc gcc gta     1778
Ala Ser Thr Leu Ala Val Thr Arg Ser Val Phe Glu His Arg Ala Val
575                 580                 585                 590
```

-continued

```
ctc ctt gga gat gac acc gtc acc ggc acc gcg gtg acc gac ccc agg      1826
Leu Leu Gly Asp Asp Thr Val Thr Gly Thr Ala Val Thr Asp Pro Arg
                595                 600                 605

atc gtg ttt gtc ttt ccc ggg cag ggg tgg cag tgg ctg ggg atg ggc      1874
Ile Val Phe Val Phe Pro Gly Gln Gly Trp Gln Trp Leu Gly Met Gly
            610                 615                 620

agt gca ctg cgc gat tcg tcg gtg gtg ttc gcc gag cgg atg gcc gag      1922
Ser Ala Leu Arg Asp Ser Ser Val Val Phe Ala Glu Arg Met Ala Glu
        625                 630                 635

tgt gcg gcg gcg ttg cgc gag ttc gtg gac tgg gat ctg ttc acg gtt      1970
Cys Ala Ala Ala Leu Arg Glu Phe Val Asp Trp Asp Leu Phe Thr Val
    640                 645                 650

ctg gat gat ccg gcg gtg gtg gac cgg gtt gat gtg gtc cag ccc gct      2018
Leu Asp Asp Pro Ala Val Val Asp Arg Val Asp Val Val Gln Pro Ala
655                 660                 665                 670

tcc tgg gcg atg atg gtt tcc ctg gcc gcg gtg tgg cag gcg gcc ggt      2066
Ser Trp Ala Met Met Val Ser Leu Ala Ala Val Trp Gln Ala Ala Gly
                675                 680                 685

gtg cgg ccg gat gcg gtg atc ggc cat tcg cag ggt gag atc gcc gca      2114
Val Arg Pro Asp Ala Val Ile Gly His Ser Gln Gly Glu Ile Ala Ala
            690                 695                 700

gct tgt gtg gcg ggt gcg gtg tca cta cgc gat gcc gcc cgg atc gtg      2162
Ala Cys Val Ala Gly Ala Val Ser Leu Arg Asp Ala Ala Arg Ile Val
        705                 710                 715

acc ttg cgc agc cag gcg atc gcc cgg ggc ctg gcg ggc cgg ggc gcg      2210
Thr Leu Arg Ser Gln Ala Ile Ala Arg Gly Leu Ala Gly Arg Gly Ala
    720                 725                 730

atg gca tcc gtc gcc ctg ccc gcg cag gat gtc gag ctg gtc gac ggg      2258
Met Ala Ser Val Ala Leu Pro Ala Gln Asp Val Glu Leu Val Asp Gly
735                 740                 745                 750

gcc tgg atc gcc gcc cac aac ggg ccc gcc tcc acc gtg atc gcg ggc      2306
Ala Trp Ile Ala Ala His Asn Gly Pro Ala Ser Thr Val Ile Ala Gly
                755                 760                 765

acc ccg gaa gcg gtc gac cat gtc ctc acc gct cat gag gca caa ggg      2354
Thr Pro Glu Ala Val Asp His Val Leu Thr Ala His Glu Ala Gln Gly
            770                 775                 780

gtg cgg gtg cgg cgg atc acc gtc gac tat gcc tcg cac acc ccg cac      2402
Val Arg Val Arg Arg Ile Thr Val Asp Tyr Ala Ser His Thr Pro His
        785                 790                 795

gtc gag ctg atc cgc gac gaa cta ctc gac atc act agc gac agc agc      2450
Val Glu Leu Ile Arg Asp Glu Leu Leu Asp Ile Thr Ser Asp Ser Ser
    800                 805                 810

tcg cag acc ccg ctc gtg ccg tgg ctg tcg acc gtg gac ggc acc tgg      2498
Ser Gln Thr Pro Leu Val Pro Trp Leu Ser Thr Val Asp Gly Thr Trp
815                 820                 825                 830

gtc gac agc ccg ctg gac ggg gag tac tgg tac cgg aac ctg cgt gaa      2546
Val Asp Ser Pro Leu Asp Gly Glu Tyr Trp Tyr Arg Asn Leu Arg Glu
                835                 840                 845

ccg gtc ggt ttc cac ccc gcc gtc agc cag ttg cag gcc cag ggc gac      2594
Pro Val Gly Phe His Pro Ala Val Ser Gln Leu Gln Ala Gln Gly Asp
            850                 855                 860

acc gtg ttc gtc gag gtc agc gcc agc ccg gtg ttg ttg cag gcg atg      2642
Thr Val Phe Val Glu Val Ser Ala Ser Pro Val Leu Leu Gln Ala Met
        865                 870                 875

gac gac gat gtc gtc acg gtt gcc acg ctg cgt cgt gac gac ggc gac      2690
Asp Asp Asp Val Val Thr Val Ala Thr Leu Arg Arg Asp Asp Gly Asp
    880                 885                 890

gcc acc cgg atg ctc acc gcc ctg gca cag gcc tat gtc cac ggc gtc      2738
Ala Thr Arg Met Leu Thr Ala Leu Ala Gln Ala Tyr Val His Gly Val
895                 900                 905                 910
```

-continued

```
acc gtc gac tgg ccc gcc atc ctc ggc acc acc aca acc cgg gta ctg     2786
Thr Val Asp Trp Pro Ala Ile Leu Gly Thr Thr Thr Thr Arg Val Leu
                915                 920                 925

gac ctt ccg acc tac gcc ttc caa cac cag cgg tac tgg ctc gag tcg     2834
Asp Leu Pro Thr Tyr Ala Phe Gln His Gln Arg Tyr Trp Leu Glu Ser
            930                 935                 940

gca cgc ccg gcc gca tcc gac gcg ggc cac ccc gtg ctg ggc tcc ggt     2882
Ala Arg Pro Ala Ala Ser Asp Ala Gly His Pro Val Leu Gly Ser Gly
        945                 950                 955

atc gcc ctc gcc ggg tcg ccg ggc cgg gtg ttc acg ggt tcc gtg ccg     2930
Ile Ala Leu Ala Gly Ser Pro Gly Arg Val Phe Thr Gly Ser Val Pro
    960                 965                 970

acc ggt gcg gac cgc gcg gtg ttc gtc gcc gag ctg gcg ctg gcc gcc     2978
Thr Gly Ala Asp Arg Ala Val Phe Val Ala Glu Leu Ala Leu Ala Ala
975                 980                 985                 990

gcg gac gcg gtc gac tgc gcc acg gtc gag cgg ctc gac atc gcc tcc     3026
Ala Asp Ala Val Asp Cys Ala Thr Val Glu Arg Leu Asp Ile Ala Ser
                995                1000                1005

gtg ccc ggc cgg ccg ggc cat ggc cgg acg acc gta cag acc tgg gtc     3074
Val Pro Gly Arg Pro Gly His Gly Arg Thr Thr Val Gln Thr Trp Val
           1010                1015                1020

gac gag ccg gcg gac gac ggc cgg cgc cgg ttc acc gtg cac acc cgc     3122
Asp Glu Pro Ala Asp Asp Gly Arg Arg Arg Phe Thr Val His Thr Arg
       1025                1030                1035

acc ggc gac gcc ccg tgg acg ctg cac gcc gag ggg gtg ctg cgc ccc     3170
Thr Gly Asp Ala Pro Trp Thr Leu His Ala Glu Gly Val Leu Arg Pro
   1040                1045                1050

cat ggc acg gcc ctg ccc gat gcg gcc gac gcc gag tgg ccc cca ccg     3218
His Gly Thr Ala Leu Pro Asp Ala Ala Asp Ala Glu Trp Pro Pro Pro
1055                1060                1065                1070

ggc gcg gtg ccc gcg gac ggg ctg ccg ggt gtg tgg cgc cgg ggg gac     3266
Gly Ala Val Pro Ala Asp Gly Leu Pro Gly Val Trp Arg Arg Gly Asp
               1075                1080                1085

cag gtc ttc gcc gag gcc gag gtg gac gga ccg gac ggt ttc gtg gtg     3314
Gln Val Phe Ala Glu Ala Glu Val Asp Gly Pro Asp Gly Phe Val Val
           1090                1095                1100

cac ccc gac ctg ctc gac gcg gtc ttc tcc gcg gtc ggc gac gga agc     3362
His Pro Asp Leu Leu Asp Ala Val Phe Ser Ala Val Gly Asp Gly Ser
       1105                1110                1115

cgc cag ccg gcc gga tgg cgc gac ctg acg gtg cac gcg tcg gac gcc     3410
Arg Gln Pro Ala Gly Trp Arg Asp Leu Thr Val His Ala Ser Asp Ala
   1120                1125                1130

acc gta ctg cgc gcc tgc ctc acc cgg cgc acc gac gga gcc atg gga     3458
Thr Val Leu Arg Ala Cys Leu Thr Arg Arg Thr Asp Gly Ala Met Gly
1135                1140                1145                1150

ttc gcc gcc ttc gac ggc gcc ggc ctg ccg gta ctc acc gcg gag gcg     3506
Phe Ala Ala Phe Asp Gly Ala Gly Leu Pro Val Leu Thr Ala Glu Ala
               1155                1160                1165

gtg acg ctg cgg gag gtg gcg tca ccg tcc ggc tcc gag gag tcg gac     3554
Val Thr Leu Arg Glu Val Ala Ser Pro Ser Gly Ser Glu Glu Ser Asp
           1170                1175                1180

ggc ctg cac cgg ttg gag tgg ctc gcg gtc gcc gag gcg gtc tac gac     3602
Gly Leu His Arg Leu Glu Trp Leu Ala Val Ala Glu Ala Val Tyr Asp
       1185                1190                1195

ggt gac ctg ccc gag gga cat gtc ctg atc acc gcc gcc cac ccc gac     3650
Gly Asp Leu Pro Glu Gly His Val Leu Ile Thr Ala Ala His Pro Asp
   1200                1205                1210

gac ccc gag gac ata ccc acc cgc gcc cac acc cgc gcc acc cgc gtc     3698
Asp Pro Glu Asp Ile Pro Thr Arg Ala His Thr Arg Ala Thr Arg Val
```

-continued

```
1215                1220                1225                1230

ctg acc gcc ctg caa cac cac ctc acc acc acc gac cac acc ctc atc      3746
Leu Thr Ala Leu Gln His His Leu Thr Thr Thr Asp His Thr Leu Ile
               1235                1240                1245

gtc cac acc acc acc gac ccc gcc ggc gcc acc gtc acc ggc ctc acc      3794
Val His Thr Thr Thr Asp Pro Ala Gly Ala Thr Val Thr Gly Leu Thr
           1250                1255                1260

cgc acc gcc cag aac gaa cac ccc cac cgc atc cgc ctc atc gaa acc      3842
Arg Thr Ala Gln Asn Glu His Pro His Arg Ile Arg Leu Ile Glu Thr
       1265                1270                1275

gac cac ccc cac acc ccc ctc ccc ctg gcc caa ctc gcc acc ctc gac      3890
Asp His Pro His Thr Pro Leu Pro Leu Ala Gln Leu Ala Thr Leu Asp
   1280                1285                1290

cac ccc cac ctc cgc ctc acc cac cac acc ctc cac cac ccc cac ctc      3938
His Pro His Leu Arg Leu Thr His His Thr Leu His His Pro His Leu
1295                1300                1305                1310

acc ccc ctc cac acc acc acc cca ccc acc acc acc ccc ctc aac ccc      3986
Thr Pro Leu His Thr Thr Thr Pro Pro Thr Thr Thr Pro Leu Asn Pro
               1315                1320                1325

gaa cac gcc atc atc atc acc ggc ggc tcc ggc acc ctc gcc ggc atc      4034
Glu His Ala Ile Ile Ile Thr Gly Gly Ser Gly Thr Leu Ala Gly Ile
           1330                1335                1340

ctc gcc cgc cac ctg aac cac ccc cac acc tac ctc ctc tcc cgc acc      4082
Leu Ala Arg His Leu Asn His Pro His Thr Tyr Leu Leu Ser Arg Thr
       1345                1350                1355

cca ccc ccc gac gcc acc ccc ggc acc cac ctc ccc tgc gac gtc ggc      4130
Pro Pro Pro Asp Ala Thr Pro Gly Thr His Leu Pro Cys Asp Val Gly
   1360                1365                1370

gac ccc cac caa ctc gcc acc acc ctc acc cac atc ccc caa ccc ctc      4178
Asp Pro His Gln Leu Ala Thr Thr Leu Thr His Ile Pro Gln Pro Leu
1375                1380                1385                1390

acc gcc atc ttc cac acc gcc gcc acc ctc gac gac ggc atc ctc cac      4226
Thr Ala Ile Phe His Thr Ala Ala Thr Leu Asp Asp Gly Ile Leu His
               1395                1400                1405

gcc ctc acc ccc gac cgc ctc acc acc gtc ctc cac ccc aaa gcc aac      4274
Ala Leu Thr Pro Asp Arg Leu Thr Thr Val Leu His Pro Lys Ala Asn
           1410                1415                1420

gcc gcc tgg cac ctg cac cac ctc acc caa aac caa ccc ctc acc cac      4322
Ala Ala Trp His Leu His His Leu Thr Gln Asn Gln Pro Leu Thr His
       1425                1430                1435

ttc gtc ctc tac tcc agc gcc gcc gcc gtc ctc ggc agc ccc gga caa      4370
Phe Val Leu Tyr Ser Ser Ala Ala Ala Val Leu Gly Ser Pro Gly Gln
   1440                1445                1450

gga aac tac gcc gcc gcc aac gcc ttc ctc gac gcc ctc gcc acc cac      4418
Gly Asn Tyr Ala Ala Ala Asn Ala Phe Leu Asp Ala Leu Ala Thr His
1455                1460                1465                1470

cgc cac acc ctc ggc caa ccc gcc acc tcc atc gcc tgg ggc atg tgg      4466
Arg His Thr Leu Gly Gln Pro Ala Thr Ser Ile Ala Trp Gly Met Trp
               1475                1480                1485

cac acc acc agc acc ctc acc gga caa ctc gac gac gcc gac cgg gac      4514
His Thr Thr Ser Thr Leu Thr Gly Gln Leu Asp Asp Ala Asp Arg Asp
           1490                1495                1500

cgc atc cgc cgc ggc ggt ttc ctc ccg atc acg gac gac gag ggc          4559
Arg Ile Arg Arg Gly Gly Phe Leu Pro Ile Thr Asp Asp Glu Gly
       1505                1510                1515

atggggatgc at                                                        4571


<210> SEQ ID NO 19
<211> LENGTH: 1517
```

-continued

```
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 19

Gln Leu Ala Glu Ala Leu Leu Thr Leu Val Arg Glu Ser Thr Ala Ala
  1               5                  10                  15

Val Leu Gly His Val Gly Gly Glu Asp Ile Pro Ala Thr Ala Ala Phe
             20                  25                  30

Lys Asp Leu Gly Ile Asp Ser Leu Thr Ala Val Gln Leu Arg Asn Ala
         35                  40                  45

Leu Thr Glu Ala Thr Gly Val Arg Leu Asn Ala Thr Ala Val Phe Asp
     50                  55                  60

Phe Pro Thr Pro His Val Leu Ala Gly Lys Leu Gly Asp Glu Leu Thr
 65                  70                  75                  80

Gly Thr Arg Ala Pro Val Val Pro Arg Thr Ala Ala Thr Ala Gly Ala
                 85                  90                  95

His Asp Glu Pro Leu Ala Ile Val Gly Met Ala Cys Arg Leu Pro Gly
            100                 105                 110

Gly Val Ala Ser Pro Glu Glu Leu Trp His Leu Val Ala Ser Gly Thr
        115                 120                 125

Asp Ala Ile Thr Glu Phe Pro Thr Asp Arg Gly Trp Asp Val Asp Ala
    130                 135                 140

Ile Tyr Asp Pro Asp Pro Asp Ala Ile Gly Lys Thr Phe Val Arg His
145                 150                 155                 160

Gly Gly Phe Leu Thr Gly Ala Thr Gly Phe Asp Ala Ala Phe Phe Gly
                165                 170                 175

Ile Ser Pro Arg Glu Ala Leu Ala Met Asp Pro Gln Gln Arg Val Leu
            180                 185                 190

Leu Glu Thr Ser Trp Glu Ala Phe Glu Ser Ala Gly Ile Thr Pro Asp
        195                 200                 205

Ser Thr Arg Gly Ser Asp Thr Gly Val Phe Val Gly Ala Phe Ser Tyr
    210                 215                 220

Gly Tyr Gly Thr Gly Ala Asp Thr Asp Gly Phe Gly Ala Thr Gly Ser
225                 230                 235                 240

Gln Thr Ser Val Leu Ser Gly Arg Leu Ser Tyr Phe Tyr Gly Leu Glu
                245                 250                 255

Gly Pro Ala Val Thr Val Asp Thr Ala Cys Ser Ser Ser Leu Val Ala
            260                 265                 270

Leu His Gln Ala Gly Gln Ser Leu Arg Ser Gly Glu Cys Ser Leu Ala
        275                 280                 285

Leu Val Gly Gly Val Thr Val Met Ala Ser Pro Gly Gly Phe Val Glu
    290                 295                 300

Phe Ser Arg Gln Arg Gly Leu Ala Pro Asp Gly Arg Ala Lys Ala Phe
305                 310                 315                 320

Gly Ala Gly Ala Asp Gly Thr Ser Phe Ala Glu Gly Ala Gly Val Leu
                325                 330                 335

Ile Val Glu Arg Leu Ser Asp Ala Glu Arg Asn Gly His Thr Val Leu
            340                 345                 350

Ala Val Val Arg Gly Ser Ala Val Asn Gln Asp Gly Ala Ser Asn Gly
        355                 360                 365

Leu Ser Ala Pro Asn Gly Pro Ser Gln Glu Arg Val Ile Arg Gln Ala
    370                 375                 380
```

-continued

```
Leu Ala Asn Ala Gly Leu Thr Pro Ala Asp Val Asp Ala Val Glu Ala
385                 390                 395                 400

His Gly Thr Gly Thr Arg Leu Gly Asp Pro Ile Glu Ala Gln Ala Val
                405                 410                 415

Leu Ala Thr Tyr Gly Gln Glu Arg Ala Thr Pro Leu Leu Leu Gly Ser
            420                 425                 430

Leu Lys Ser Asn Ile Gly His Ala Gln Ala Ala Ser Gly Val Ala Gly
        435                 440                 445

Ile Ile Lys Met Val Gln Ala Leu Arg His Gly Glu Leu Pro Pro Thr
    450                 455                 460

Leu His Ala Asp Glu Pro Ser Pro His Val Asp Trp Thr Ala Gly Ala
465                 470                 475                 480

Val Glu Leu Leu Thr Ser Ala Arg Pro Trp Pro Glu Thr Asp Arg Pro
                485                 490                 495

Arg Arg Ala Gly Val Ser Ser Phe Gly Val Ser Gly Thr Asn Ala His
            500                 505                 510

Val Ile Leu Glu Ser Ala Pro Pro Ala Gln Pro Ala Glu Glu Ala Gln
        515                 520                 525

Pro Val Glu Thr Pro Val Val Ala Ser Asp Val Leu Pro Leu Val Ile
    530                 535                 540

Ser Ala Lys Thr Gln Pro Ala Leu Thr Glu His Glu Asp Arg Leu Arg
545                 550                 555                 560

Ala Tyr Leu Ala Ala Ser Pro Gly Ala Asp Ile Arg Ala Val Ala Ser
                565                 570                 575

Thr Leu Ala Val Thr Arg Ser Val Phe Glu His Arg Ala Val Leu Leu
            580                 585                 590

Gly Asp Asp Thr Val Thr Gly Thr Ala Val Thr Asp Pro Arg Ile Val
        595                 600                 605

Phe Val Phe Pro Gly Gln Gly Trp Gln Trp Leu Gly Met Gly Ser Ala
    610                 615                 620

Leu Arg Asp Ser Ser Val Val Phe Ala Glu Arg Met Ala Glu Cys Ala
625                 630                 635                 640

Ala Ala Leu Arg Glu Phe Val Asp Trp Asp Leu Phe Thr Val Leu Asp
                645                 650                 655

Asp Pro Ala Val Val Asp Arg Val Asp Val Val Gln Pro Ala Ser Trp
            660                 665                 670

Ala Met Met Val Ser Leu Ala Ala Val Trp Gln Ala Ala Gly Val Arg
        675                 680                 685

Pro Asp Ala Val Ile Gly His Ser Gln Gly Glu Ile Ala Ala Ala Cys
    690                 695                 700

Val Ala Gly Ala Val Ser Leu Arg Asp Ala Ala Arg Ile Val Thr Leu
705                 710                 715                 720

Arg Ser Gln Ala Ile Ala Arg Gly Leu Ala Gly Arg Gly Ala Met Ala
                725                 730                 735

Ser Val Ala Leu Pro Ala Gln Asp Val Glu Leu Val Asp Gly Ala Trp
            740                 745                 750

Ile Ala Ala His Asn Gly Pro Ala Ser Thr Val Ile Ala Gly Thr Pro
        755                 760                 765

Glu Ala Val Asp His Val Leu Thr Ala His Glu Ala Gln Gly Val Arg
    770                 775                 780

Val Arg Arg Ile Thr Val Asp Tyr Ala Ser His Thr Pro His Val Glu
785                 790                 795                 800
```

-continued

```
Leu Ile Arg Asp Glu Leu Leu Asp Ile Thr Ser Asp Ser Ser Ser Gln
                805                 810                 815

Thr Pro Leu Val Pro Trp Leu Ser Thr Val Asp Gly Thr Trp Val Asp
            820                 825                 830

Ser Pro Leu Asp Gly Glu Tyr Trp Tyr Arg Asn Leu Arg Glu Pro Val
        835                 840                 845

Gly Phe His Pro Ala Val Ser Gln Leu Gln Ala Gln Gly Asp Thr Val
    850                 855                 860

Phe Val Glu Val Ser Ala Ser Pro Val Leu Leu Gln Ala Met Asp Asp
865                 870                 875                 880

Asp Val Val Thr Val Ala Thr Leu Arg Arg Asp Asp Gly Asp Ala Thr
                885                 890                 895

Arg Met Leu Thr Ala Leu Ala Gln Ala Tyr Val His Gly Val Thr Val
            900                 905                 910

Asp Trp Pro Ala Ile Leu Gly Thr Thr Thr Thr Arg Val Leu Asp Leu
        915                 920                 925

Pro Thr Tyr Ala Phe Gln His Gln Arg Tyr Trp Leu Glu Ser Ala Arg
    930                 935                 940

Pro Ala Ala Ser Asp Ala Gly His Pro Val Leu Gly Ser Gly Ile Ala
945                 950                 955                 960

Leu Ala Gly Ser Pro Gly Arg Val Phe Thr Gly Ser Val Pro Thr Gly
                965                 970                 975

Ala Asp Arg Ala Val Phe Val Ala Glu Leu Ala Leu Ala Ala Ala Asp
            980                 985                 990

Ala Val Asp Cys Ala Thr Val Glu Arg Leu Asp Ile Ala Ser Val Pro
        995                 1000                1005

Gly Arg Pro Gly His Gly Arg Thr Thr Val Gln Thr Trp Val Asp Glu
    1010                1015                1020

Pro Ala Asp Asp Gly Arg Arg Arg Phe Thr Val His Thr Arg Thr Gly
1025                1030                1035                1040

Asp Ala Pro Trp Thr Leu His Ala Glu Gly Val Leu Arg Pro His Gly
                1045                1050                1055

Thr Ala Leu Pro Asp Ala Ala Asp Ala Glu Trp Pro Pro Pro Gly Ala
            1060                1065                1070

Val Pro Ala Asp Gly Leu Pro Gly Val Trp Arg Arg Gly Asp Gln Val
        1075                1080                1085

Phe Ala Glu Ala Glu Val Asp Gly Pro Asp Gly Phe Val Val His Pro
    1090                1095                1100

Asp Leu Leu Asp Ala Val Phe Ser Ala Val Gly Asp Gly Ser Arg Gln
1105                1110                1115                1120

Pro Ala Gly Trp Arg Asp Leu Thr Val His Ala Ser Asp Ala Thr Val
                1125                1130                1135

Leu Arg Ala Cys Leu Thr Arg Arg Thr Asp Gly Ala Met Gly Phe Ala
            1140                1145                1150

Ala Phe Asp Gly Ala Gly Leu Pro Val Leu Thr Ala Glu Ala Val Thr
        1155                1160                1165

Leu Arg Glu Val Ala Ser Pro Ser Gly Ser Glu Glu Ser Asp Gly Leu
    1170                1175                1180

His Arg Leu Glu Trp Leu Ala Val Ala Glu Ala Val Tyr Asp Gly Asp
1185                1190                1195                1200

Leu Pro Glu Gly His Val Leu Ile Thr Ala Ala His Pro Asp Asp Pro
                1205                1210                1215

Glu Asp Ile Pro Thr Arg Ala His Thr Arg Ala Thr Arg Val Leu Thr
```

-continued

```
            1220                1225                1230

Ala Leu Gln His His Leu Thr Thr Thr Asp His Thr Leu Ile Val His
        1235                1240                1245

Thr Thr Thr Asp Pro Ala Gly Ala Thr Val Thr Gly Leu Thr Arg Thr
    1250                1255                1260

Ala Gln Asn Glu His Pro His Arg Ile Arg Leu Ile Glu Thr Asp His
1265                1270                1275                1280

Pro His Thr Pro Leu Pro Leu Ala Gln Leu Ala Thr Leu Asp His Pro
                1285                1290                1295

His Leu Arg Leu Thr His His Thr Leu His His Pro His Leu Thr Pro
            1300                1305                1310

Leu His Thr Thr Thr Pro Pro Thr Thr Thr Pro Leu Asn Pro Glu His
        1315                1320                1325

Ala Ile Ile Ile Thr Gly Gly Ser Gly Thr Leu Ala Gly Ile Leu Ala
    1330                1335                1340

Arg His Leu Asn His Pro His Thr Tyr Leu Leu Ser Arg Thr Pro Pro
1345                1350                1355                1360

Pro Asp Ala Thr Pro Gly Thr His Leu Pro Cys Asp Val Gly Asp Pro
                1365                1370                1375

His Gln Leu Ala Thr Thr Leu Thr His Ile Pro Gln Pro Leu Thr Ala
            1380                1385                1390

Ile Phe His Thr Ala Ala Thr Leu Asp Asp Gly Ile Leu His Ala Leu
        1395                1400                1405

Thr Pro Asp Arg Leu Thr Thr Val Leu His Pro Lys Ala Asn Ala Ala
    1410                1415                1420

Trp His Leu His His Leu Thr Gln Asn Gln Pro Leu Thr His Phe Val
1425                1430                1435                1440

Leu Tyr Ser Ser Ala Ala Ala Val Leu Gly Ser Pro Gly Gln Gly Asn
                1445                1450                1455

Tyr Ala Ala Ala Asn Ala Phe Leu Asp Ala Leu Ala Thr His Arg His
            1460                1465                1470

Thr Leu Gly Gln Pro Ala Thr Ser Ile Ala Trp Gly Met Trp His Thr
        1475                1480                1485

Thr Ser Thr Leu Thr Gly Gln Leu Asp Asp Ala Asp Arg Asp Arg Ile
    1490                1495                1500

Arg Arg Gly Gly Phe Leu Pro Ile Thr Asp Asp Glu Gly
1505                1510                1515


<210> SEQ ID NO 20
<211> LENGTH: 4466
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (9)..(4454)

<400> SEQUENCE: 20

agatctgg cag ctc gcc gaa gcg ctg ctg acg ctc gtc cgg gag agc acc      50
         Gln Leu Ala Glu Ala Leu Leu Thr Leu Val Arg Glu Ser Thr
           1               5                  10

gcc gcc gtg ctc ggc cac gtg ggt ggc gag gac atc ccc gcg acg gcg       98
Ala Ala Val Leu Gly His Val Gly Gly Glu Asp Ile Pro Ala Thr Ala
 15                  20                  25                  30

gcg ttc aag gac ctc ggc atc gac tcg ctc acc gcg gtc cag ctg cgc      146
```

-continued

```
Ala Phe Lys Asp Leu Gly Ile Asp Ser Leu Thr Ala Val Gln Leu Arg
                35                  40                  45

aac gcc ctc acc gag gcg acc ggt gtg cgg ctg aac gcc acg gcg gtc      194
Asn Ala Leu Thr Glu Ala Thr Gly Val Arg Leu Asn Ala Thr Ala Val
            50                  55                  60

ttc gac ttc ccg acc ccg cac gtg ctc gcc ggg aag ctc ggc gac gaa      242
Phe Asp Phe Pro Thr Pro His Val Leu Ala Gly Lys Leu Gly Asp Glu
        65                  70                  75

ctg acc ggc acc cgc gcg ccc gtc gtg ccc cgg acc gcg gcc acg gcc      290
Leu Thr Gly Thr Arg Ala Pro Val Val Pro Arg Thr Ala Ala Thr Ala
    80                  85                  90

ggt gcg cac gac gag ccg ctg gcg atc gtg gga atg gcc tgc cgg ctg      338
Gly Ala His Asp Glu Pro Leu Ala Ile Val Gly Met Ala Cys Arg Leu
 95                 100                 105                 110

ccc ggc ggg gtc gcg tca ccc gag gag ctg tgg cac ctc gtg gca tcc      386
Pro Gly Gly Val Ala Ser Pro Glu Glu Leu Trp His Leu Val Ala Ser
                115                 120                 125

ggc acc gac gcc atc acg gag ttc ccg acg gac cgc ggc tgg gac gtc      434
Gly Thr Asp Ala Ile Thr Glu Phe Pro Thr Asp Arg Gly Trp Asp Val
            130                 135                 140

gac gcg atc tac gac ccg gac ccc gac gcg atc ggc aag acc ttc gtc      482
Asp Ala Ile Tyr Asp Pro Asp Pro Asp Ala Ile Gly Lys Thr Phe Val
        145                 150                 155

cgg cac ggt ggc ttc ctc acc ggc gcg aca ggc ttc gac gcg gcg ttc      530
Arg His Gly Gly Phe Leu Thr Gly Ala Thr Gly Phe Asp Ala Ala Phe
    160                 165                 170

ttc ggc atc agc ccg cgc gag gcc ctc gcg atg gac ccg cag cag cgg      578
Phe Gly Ile Ser Pro Arg Glu Ala Leu Ala Met Asp Pro Gln Gln Arg
175                 180                 185                 190

gtg ctc ctg gag acg tcg tgg gag gcg ttc gaa agc gcc ggc atc acc      626
Val Leu Leu Glu Thr Ser Trp Glu Ala Phe Glu Ser Ala Gly Ile Thr
                195                 200                 205

ccg gac tcg acc cgc ggc agc gac acc ggc gtg ttc gtc ggc gcc ttc      674
Pro Asp Ser Thr Arg Gly Ser Asp Thr Gly Val Phe Val Gly Ala Phe
            210                 215                 220

tcc tac ggt tac ggc acc ggt gcg gac acc gac ggc ttc ggc gcg acc      722
Ser Tyr Gly Tyr Gly Thr Gly Ala Asp Thr Asp Gly Phe Gly Ala Thr
        225                 230                 235

ggc tcg cag acc agt gtg ctc tcc ggc cgg ctg tcg tac ttc tac ggt      770
Gly Ser Gln Thr Ser Val Leu Ser Gly Arg Leu Ser Tyr Phe Tyr Gly
    240                 245                 250

ctg gag ggt ccg gcg gtc acg gtc gac acg gcg tgt tcg tcg tcg ctg      818
Leu Glu Gly Pro Ala Val Thr Val Asp Thr Ala Cys Ser Ser Ser Leu
255                 260                 265                 270

gtg gcg ctg cac cag gcc ggg cag tcg ctg cgc tcc ggc gaa tgc tcg      866
Val Ala Leu His Gln Ala Gly Gln Ser Leu Arg Ser Gly Glu Cys Ser
                275                 280                 285

ctc gcc ctg gtc ggc ggc gtc acg gtg atg gcg tct ccc ggc ggc ttc      914
Leu Ala Leu Val Gly Gly Val Thr Val Met Ala Ser Pro Gly Gly Phe
            290                 295                 300

gtg gag ttc tcc cgg cag cgc ggc ctc gcg ccg gac ggc cgg gcg aag      962
Val Glu Phe Ser Arg Gln Arg Gly Leu Ala Pro Asp Gly Arg Ala Lys
        305                 310                 315

gcg ttc ggc gcg ggt gcg gac ggc acg agc ttc gcc gag ggt gcc ggt     1010
Ala Phe Gly Ala Gly Ala Asp Gly Thr Ser Phe Ala Glu Gly Ala Gly
    320                 325                 330

gtg ctg atc gtc gag agg ctc tcc gac gcc gaa cgc aac ggt cac acc     1058
Val Leu Ile Val Glu Arg Leu Ser Asp Ala Glu Arg Asn Gly His Thr
335                 340                 345                 350
```

-continued

```
gtc ctg gcg gtc gtc cgt ggt tcg gcg gtc aac cag gat ggt gcc tcc      1106
Val Leu Ala Val Val Arg Gly Ser Ala Val Asn Gln Asp Gly Ala Ser
                355                 360                 365

aac ggg ctg tcg gcg ccg aac ggg ccg tcg cag gag cgg gtg atc cgg      1154
Asn Gly Leu Ser Ala Pro Asn Gly Pro Ser Gln Glu Arg Val Ile Arg
            370                 375                 380

cag gcc ctg gcc aac gcc ggg ctc acc ccg gcg gac gtg gac gcc gtc      1202
Gln Ala Leu Ala Asn Ala Gly Leu Thr Pro Ala Asp Val Asp Ala Val
        385                 390                 395

gag gcc cac ggc acc ggc acc agg ctg ggc gac ccc atc gag gca cag      1250
Glu Ala His Gly Thr Gly Thr Arg Leu Gly Asp Pro Ile Glu Ala Gln
    400                 405                 410

gcg gta ctg gcc acc tac gga cag gag cgc gcc acc ccc ctg ctg ctg      1298
Ala Val Leu Ala Thr Tyr Gly Gln Glu Arg Ala Thr Pro Leu Leu Leu
415                 420                 425                 430

ggc tcg ctg aag tcc aac atc ggc cac gcc cag gcc gcg tcc ggc gtc      1346
Gly Ser Leu Lys Ser Asn Ile Gly His Ala Gln Ala Ala Ser Gly Val
                435                 440                 445

gcc ggc atc atc aag atg gtg cag gcc ctc cgg cac ggg gag ctg ccg      1394
Ala Gly Ile Ile Lys Met Val Gln Ala Leu Arg His Gly Glu Leu Pro
            450                 455                 460

ccg acg ctg cac gcc gac gag ccg tcg ccg cac gtc gac tgg acg gcc      1442
Pro Thr Leu His Ala Asp Glu Pro Ser Pro His Val Asp Trp Thr Ala
        465                 470                 475

ggc gcc gtc gaa ctg ctg acg tcg gcc cgg ccg tgg ccc gag acc gac      1490
Gly Ala Val Glu Leu Leu Thr Ser Ala Arg Pro Trp Pro Glu Thr Asp
    480                 485                 490

cgg cca cgg cgt gcc gcc gtc tcc tcg ttc ggg gtg agc ggc acc aac      1538
Arg Pro Arg Arg Ala Ala Val Ser Ser Phe Gly Val Ser Gly Thr Asn
495                 500                 505                 510

gcc cac gtc atc ctg gag gcc gga ccg gta acg gag acg ccc gcg gca      1586
Ala His Val Ile Leu Glu Ala Gly Pro Val Thr Glu Thr Pro Ala Ala
                515                 520                 525

tcg cct tcc ggt gac ctt ccc ctg ctg gtg tcg gca cgc tca ccg gaa      1634
Ser Pro Ser Gly Asp Leu Pro Leu Leu Val Ser Ala Arg Ser Pro Glu
            530                 535                 540

gcg ctc gac gag cag atc cgc cga ctg cgc gcc tac ctg gac acc acc      1682
Ala Leu Asp Glu Gln Ile Arg Arg Leu Arg Ala Tyr Leu Asp Thr Thr
        545                 550                 555

ccg gac gtc gac cgg gtg gcc gtg gca cag acg ctg gcc cgg cgc aca      1730
Pro Asp Val Asp Arg Val Ala Val Ala Gln Thr Leu Ala Arg Arg Thr
    560                 565                 570

cac ttc gcc cac cgc gcc gtg ctg ctc ggt gac acc gtc atc acc aca      1778
His Phe Ala His Arg Ala Val Leu Leu Gly Asp Thr Val Ile Thr Thr
575                 580                 585                 590

ccc ccc gcg gac cgg ccc gac gaa ctc gtc ttc gtc tac tcc ggc cag      1826
Pro Pro Ala Asp Arg Pro Asp Glu Leu Val Phe Val Tyr Ser Gly Gln
                595                 600                 605

ggc acc cag cat ccc gcg atg ggc gag cag cta gcc gcc gcg ttc ccc      1874
Gly Thr Gln His Pro Ala Met Gly Glu Gln Leu Ala Ala Ala Phe Pro
            610                 615                 620

gtc ttc gcg cgg atc cat cag cag gtg tgg gac ctg ctc gat gtg ccc      1922
Val Phe Ala Arg Ile His Gln Gln Val Trp Asp Leu Leu Asp Val Pro
        625                 630                 635

gat ctg gag gtg aac gag acc ggt tac gcc cag ccg gcc ctg ttc gca      1970
Asp Leu Glu Val Asn Glu Thr Gly Tyr Ala Gln Pro Ala Leu Phe Ala
    640                 645                 650

atg cag gtg gct ctg ttc ggg ctg ctg gaa tcg tgg ggt gta cga ccg      2018
Met Gln Val Ala Leu Phe Gly Leu Leu Glu Ser Trp Gly Val Arg Pro
655                 660                 665                 670
```

-continued

```
gac gcg gtg atc ggc cat tcg gtg ggt gag ctt gcg gct gcg tat gtg     2066
Asp Ala Val Ile Gly His Ser Val Gly Glu Leu Ala Ala Ala Tyr Val
                675                 680                 685

tcc ggg gtg tgg tcg ttg gag gat gcc tgc act ttg gtg tcg gcg cgg     2114
Ser Gly Val Trp Ser Leu Glu Asp Ala Cys Thr Leu Val Ser Ala Arg
            690                 695                 700

gct cgt ctg atg cag gct ctg ccc gcg ggt ggg gtg atg gtc gct gtc     2162
Ala Arg Leu Met Gln Ala Leu Pro Ala Gly Gly Val Met Val Ala Val
        705                 710                 715

ccg gtc tcg gag gat gag gcc cgg gcc gtg ctg ggt gag ggt gtg gag     2210
Pro Val Ser Glu Asp Glu Ala Arg Ala Val Leu Gly Glu Gly Val Glu
    720                 725                 730

atc gcc gcg gtc aac ggc ccg tcg tcg gtg gtt ctc tcc ggt gat gag     2258
Ile Ala Ala Val Asn Gly Pro Ser Ser Val Val Leu Ser Gly Asp Glu
735                 740                 745                 750

gcc gcc gtg ctg cag gcc gcg gag ggg ctg ggg aag tgg acg cgg ctg     2306
Ala Ala Val Leu Gln Ala Ala Glu Gly Leu Gly Lys Trp Thr Arg Leu
                755                 760                 765

gcg acc agc cac gcg ttc cat tcc gcc cgt atg gaa ccc atg ctg gag     2354
Ala Thr Ser His Ala Phe His Ser Ala Arg Met Glu Pro Met Leu Glu
            770                 775                 780

gag ttc cgg gcg gtc gcc gaa ggc ctg acc tac cgg acg ccg cag gtc     2402
Glu Phe Arg Ala Val Ala Glu Gly Leu Thr Tyr Arg Thr Pro Gln Val
        785                 790                 795

tcc atg gcc gtt ggt gat cag gtg acc acc gct gag tac tgg gtg cgg     2450
Ser Met Ala Val Gly Asp Gln Val Thr Thr Ala Glu Tyr Trp Val Arg
    800                 805                 810

cag gtc cgg gac acg gtc cgg ttc ggc gag cag gtg gcc tcg tac gag     2498
Gln Val Arg Asp Thr Val Arg Phe Gly Glu Gln Val Ala Ser Tyr Glu
815                 820                 825                 830

gac gcc gtg ttc gtc gag ctg ggt gcc gac cgg tca ctg gcc cgc ctg     2546
Asp Ala Val Phe Val Glu Leu Gly Ala Asp Arg Ser Leu Ala Arg Leu
                835                 840                 845

gtc gac ggt gtc gcg atg ctg cac ggc gac cac gaa atc cag gcc gcg     2594
Val Asp Gly Val Ala Met Leu His Gly Asp His Glu Ile Gln Ala Ala
            850                 855                 860

atc ggc gcc ctg gcc cac ctg tat gtc aac ggc gtc acg gtc gac tgg     2642
Ile Gly Ala Leu Ala His Leu Tyr Val Asn Gly Val Thr Val Asp Trp
        865                 870                 875

ccc gcg ctc ctg ggc gat gct ccg gca aca cgg gtg ctg gac ctt ccg     2690
Pro Ala Leu Leu Gly Asp Ala Pro Ala Thr Arg Val Leu Asp Leu Pro
    880                 885                 890

aca tac gcc ttc cag cac cag cgc tac tgg ctc gag tcg gca cgc ccg     2738
Thr Tyr Ala Phe Gln His Gln Arg Tyr Trp Leu Glu Ser Ala Arg Pro
895                 900                 905                 910

gcc gca tcc gac gcg ggc cac ccc gtg ctg ggc tcc ggt atc gcc ctc     2786
Ala Ala Ser Asp Ala Gly His Pro Val Leu Gly Ser Gly Ile Ala Leu
                915                 920                 925

gcc ggg tcg ccg ggc cgg gtg ttc acg ggt tcc gtg ccg acc ggt gcg     2834
Ala Gly Ser Pro Gly Arg Val Phe Thr Gly Ser Val Pro Thr Gly Ala
            930                 935                 940

gac cgc gcg gtg ttc gtc gcc gag ctg gcg ctg gcc gcc gcg gac gcg     2882
Asp Arg Ala Val Phe Val Ala Glu Leu Ala Leu Ala Ala Ala Asp Ala
        945                 950                 955

gtc gac tgc gcc acg gtc gag cgg ctc gac atc gcc tcc gtg ccc ggc     2930
Val Asp Cys Ala Thr Val Glu Arg Leu Asp Ile Ala Ser Val Pro Gly
    960                 965                 970

cgg ccg ggc cat ggc cgg acg acc gta cag acc tgg gtc gac gag ccg     2978
Arg Pro Gly His Gly Arg Thr Thr Val Gln Thr Trp Val Asp Glu Pro
```

-continued

```
975                 980                 985                 990

gcg gac gac ggc cgg cgc cgg ttc acc gtg cac acc cgc acc ggc gac     3026
Ala Asp Asp Gly Arg Arg Arg Phe Thr Val His Thr Arg Thr Gly Asp
                995                1000                1005

gcc ccg tgg acg ctg cac gcc gag ggg gtg ctg cgc ccc cat ggc acg     3074
Ala Pro Trp Thr Leu His Ala Glu Gly Val Leu Arg Pro His Gly Thr
           1010                1015                1020

gcc ctg ccc gat gcg gcc gac gcc gag tgg ccc cca ccg ggc gcg gtg     3122
Ala Leu Pro Asp Ala Ala Asp Ala Glu Trp Pro Pro Pro Gly Ala Val
       1025                1030                1035

ccc gcg gac ggg ctg ccg ggt gtg tgg cgc cgg ggg gac cag gtc ttc     3170
Pro Ala Asp Gly Leu Pro Gly Val Trp Arg Arg Gly Asp Gln Val Phe
   1040                1045                1050

gcc gag gcc gag gtg gac gga ccg gac ggt ttc gtg gtg cac ccc gac     3218
Ala Glu Ala Glu Val Asp Gly Pro Asp Gly Phe Val Val His Pro Asp
1055               1060                1065                1070

ctg ctc gac gcg gtc ttc tcc gcg gtc ggc gac gga agc cgc cag ccg     3266
Leu Leu Asp Ala Val Phe Ser Ala Val Gly Asp Gly Ser Arg Gln Pro
               1075                1080                1085

gcc gga tgg cgc gac ctg acg gtg cac gcg tcg gac gcc acc gta ctg     3314
Ala Gly Trp Arg Asp Leu Thr Val His Ala Ser Asp Ala Thr Val Leu
           1090                1095                1100

cgc gcc tgc ctc acc cgg cgc acc gac gga gcc atg gga ttc gcc gcc     3362
Arg Ala Cys Leu Thr Arg Arg Thr Asp Gly Ala Met Gly Phe Ala Ala
       1105                1110                1115

ttc gac ggc gcc ggc ctg ccg gta ctc acc gcg gag gcg gtg acg ctg     3410
Phe Asp Gly Ala Gly Leu Pro Val Leu Thr Ala Glu Ala Val Thr Leu
   1120                1125                1130

cgg gag gtg gcg tca ccg tcc ggc tcc gag gag tcg gac ggc ctg cac     3458
Arg Glu Val Ala Ser Pro Ser Gly Ser Glu Glu Ser Asp Gly Leu His
1135               1140                1145                1150

cgg ttg gag tgg ctc gcg gtc gcc gag gcg gtc tac gac ggt gac ctg     3506
Arg Leu Glu Trp Leu Ala Val Ala Glu Ala Val Tyr Asp Gly Asp Leu
               1155                1160                1165

ccc gag gga cat gtc ctg atc acc gcc gcc cac ccc gac gac ccc gag     3554
Pro Glu Gly His Val Leu Ile Thr Ala Ala His Pro Asp Asp Pro Glu
           1170                1175                1180

gac ata ccc acc cgc gcc cac acc cgc gcc acc cgc gtc ctg acc gcc     3602
Asp Ile Pro Thr Arg Ala His Thr Arg Ala Thr Arg Val Leu Thr Ala
       1185                1190                1195

ctg caa cac cac ctc acc acc acc gac cac acc ctc atc gtc cac acc     3650
Leu Gln His His Leu Thr Thr Thr Asp His Thr Leu Ile Val His Thr
   1200                1205                1210

acc acc gac ccc gcc ggc gcc acc gtc acc ggc ctc acc cgc acc gcc     3698
Thr Thr Asp Pro Ala Gly Ala Thr Val Thr Gly Leu Thr Arg Thr Ala
1215               1220                1225                1230

cag aac gaa cac ccc cac cgc atc cgc ctc atc gaa acc gac cac ccc     3746
Gln Asn Glu His Pro His Arg Ile Arg Leu Ile Glu Thr Asp His Pro
               1235                1240                1245

cac acc ccc ctc ccc ctg gcc caa ctc gcc acc ctc gac cac ccc cac     3794
His Thr Pro Leu Pro Leu Ala Gln Leu Ala Thr Leu Asp His Pro His
           1250                1255                1260

ctc cgc ctc acc cac cac acc ctc cac cac ccc cac ctc acc ccc ctc     3842
Leu Arg Leu Thr His His Thr Leu His His Pro His Leu Thr Pro Leu
       1265                1270                1275

cac acc acc acc cca ccc acc acc acc ccc ctc aac ccc gaa cac gcc     3890
His Thr Thr Thr Pro Pro Thr Thr Thr Pro Leu Asn Pro Glu His Ala
   1280                1285                1290

atc atc atc acc ggc ggc tcc ggc acc ctc gcc ggc atc ctc gcc cgc     3938
```

-continued

```
Ile Ile Ile Thr Gly Gly Ser Gly Thr Leu Ala Gly Ile Leu Ala Arg
1295                1300                1305                1310

cac ctg aac cac ccc cac acc tac ctc ctc tcc cgc acc cca ccc ccc     3986
His Leu Asn His Pro His Thr Tyr Leu Leu Ser Arg Thr Pro Pro Pro
                1315                1320                1325

gac gcc acc ccc ggc acc cac ctc ccc tgc gac gtc ggc gac ccc cac     4034
Asp Ala Thr Pro Gly Thr His Leu Pro Cys Asp Val Gly Asp Pro His
            1330                1335                1340

caa ctc gcc acc acc ctc acc cac atc ccc caa ccc ctc acc gcc atc     4082
Gln Leu Ala Thr Thr Leu Thr His Ile Pro Gln Pro Leu Thr Ala Ile
        1345                1350                1355

ttc cac acc gcc gcc acc ctc gac gac ggc atc ctc cac gcc ctc acc     4130
Phe His Thr Ala Ala Thr Leu Asp Asp Gly Ile Leu His Ala Leu Thr
    1360                1365                1370

ccc gac cgc ctc acc acc gtc ctc cac ccc aaa gcc aac gcc gcc tgg     4178
Pro Asp Arg Leu Thr Thr Val Leu His Pro Lys Ala Asn Ala Ala Trp
1375                1380                1385                1390

cac ctg cac cac ctc acc caa aac caa ccc ctc acc cac ttc gtc ctc     4226
His Leu His His Leu Thr Gln Asn Gln Pro Leu Thr His Phe Val Leu
                1395                1400                1405

tac tcc agc gcc gcc gcc gtc ctc ggc agc ccc gga caa gga aac tac     4274
Tyr Ser Ser Ala Ala Ala Val Leu Gly Ser Pro Gly Gln Gly Asn Tyr
            1410                1415                1420

gcc gcc gcc aac gcc ttc ctc gac gcc ctc gcc acc cac cgc cac acc     4322
Ala Ala Ala Asn Ala Phe Leu Asp Ala Leu Ala Thr His Arg His Thr
        1425                1430                1435

ctc ggc caa ccc gcc acc tcc atc gcc tgg ggc atg tgg cac acc acc     4370
Leu Gly Gln Pro Ala Thr Ser Ile Ala Trp Gly Met Trp His Thr Thr
    1440                1445                1450

agc acc ctc acc gga caa ctc gac gac gcc gac cgg gac cgc atc cgc     4418
Ser Thr Leu Thr Gly Gln Leu Asp Asp Ala Asp Arg Asp Arg Ile Arg
1455                1460                1465                1470

cgc ggc ggt ttc ctc ccg atc acg gac gac gag ggc atggggatgc at       4466
Arg Gly Gly Phe Leu Pro Ile Thr Asp Asp Glu Gly
                1475                1480


<210> SEQ ID NO 21
<211> LENGTH: 1482
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 21

Gln Leu Ala Glu Ala Leu Leu Thr Leu Val Arg Glu Ser Thr Ala Ala
  1               5                  10                  15

Val Leu Gly His Val Gly Gly Glu Asp Ile Pro Ala Thr Ala Ala Phe
            20                  25                  30

Lys Asp Leu Gly Ile Asp Ser Leu Thr Ala Val Gln Leu Arg Asn Ala
        35                  40                  45

Leu Thr Glu Ala Thr Gly Val Arg Leu Asn Ala Thr Ala Val Phe Asp
    50                  55                  60

Phe Pro Thr Pro His Val Leu Ala Gly Lys Leu Gly Asp Glu Leu Thr
65                  70                  75                  80

Gly Thr Arg Ala Pro Val Val Pro Arg Thr Ala Ala Thr Ala Gly Ala
                85                  90                  95

His Asp Glu Pro Leu Ala Ile Val Gly Met Ala Cys Arg Leu Pro Gly
            100                 105                 110
```

-continued

```
Gly Val Ala Ser Pro Glu Glu Leu Trp His Leu Val Ala Ser Gly Thr
        115                 120                 125

Asp Ala Ile Thr Glu Phe Pro Thr Asp Arg Gly Trp Asp Val Asp Ala
    130                 135                 140

Ile Tyr Asp Pro Asp Pro Asp Ala Ile Gly Lys Thr Phe Val Arg His
145                 150                 155                 160

Gly Gly Phe Leu Thr Gly Ala Thr Gly Phe Asp Ala Ala Phe Phe Gly
                165                 170                 175

Ile Ser Pro Arg Glu Ala Leu Ala Met Asp Pro Gln Gln Arg Val Leu
            180                 185                 190

Leu Glu Thr Ser Trp Glu Ala Phe Glu Ser Ala Gly Ile Thr Pro Asp
        195                 200                 205

Ser Thr Arg Gly Ser Asp Thr Gly Val Phe Val Gly Ala Phe Ser Tyr
    210                 215                 220

Gly Tyr Gly Thr Gly Ala Asp Thr Asp Gly Phe Gly Ala Thr Gly Ser
225                 230                 235                 240

Gln Thr Ser Val Leu Ser Gly Arg Leu Ser Tyr Phe Tyr Gly Leu Glu
                245                 250                 255

Gly Pro Ala Val Thr Val Asp Thr Ala Cys Ser Ser Ser Leu Val Ala
            260                 265                 270

Leu His Gln Ala Gly Gln Ser Leu Arg Ser Gly Glu Cys Ser Leu Ala
        275                 280                 285

Leu Val Gly Gly Val Thr Val Met Ala Ser Pro Gly Gly Phe Val Glu
    290                 295                 300

Phe Ser Arg Gln Arg Gly Leu Ala Pro Asp Gly Arg Ala Lys Ala Phe
305                 310                 315                 320

Gly Ala Gly Ala Asp Gly Thr Ser Phe Ala Glu Gly Ala Gly Val Leu
                325                 330                 335

Ile Val Glu Arg Leu Ser Asp Ala Glu Arg Asn Gly His Thr Val Leu
            340                 345                 350

Ala Val Val Arg Gly Ser Ala Val Asn Gln Asp Gly Ala Ser Asn Gly
        355                 360                 365

Leu Ser Ala Pro Asn Gly Pro Ser Gln Glu Arg Val Ile Arg Gln Ala
    370                 375                 380

Leu Ala Asn Ala Gly Leu Thr Pro Ala Asp Val Asp Ala Val Glu Ala
385                 390                 395                 400

His Gly Thr Gly Thr Arg Leu Gly Asp Pro Ile Glu Ala Gln Ala Val
                405                 410                 415

Leu Ala Thr Tyr Gly Gln Glu Arg Ala Thr Pro Leu Leu Leu Gly Ser
            420                 425                 430

Leu Lys Ser Asn Ile Gly His Ala Gln Ala Ala Ser Gly Val Ala Gly
        435                 440                 445

Ile Ile Lys Met Val Gln Ala Leu Arg His Gly Glu Leu Pro Pro Thr
    450                 455                 460

Leu His Ala Asp Glu Pro Ser Pro His Val Asp Trp Thr Ala Gly Ala
465                 470                 475                 480

Val Glu Leu Leu Thr Ser Ala Arg Pro Trp Pro Glu Thr Asp Arg Pro
                485                 490                 495

Arg Arg Ala Ala Val Ser Ser Phe Gly Val Ser Gly Thr Asn Ala His
            500                 505                 510

Val Ile Leu Glu Ala Gly Pro Val Thr Glu Thr Pro Ala Ala Ser Pro
        515                 520                 525

Ser Gly Asp Leu Pro Leu Leu Val Ser Ala Arg Ser Pro Glu Ala Leu
```

-continued

```
    530                 535                 540

Asp Glu Gln Ile Arg Arg Leu Arg Ala Tyr Leu Asp Thr Thr Pro Asp
545                 550                 555                 560

Val Asp Arg Val Ala Val Ala Gln Thr Leu Ala Arg Arg Thr His Phe
                565                 570                 575

Ala His Arg Ala Val Leu Leu Gly Asp Thr Val Ile Thr Thr Pro Pro
            580                 585                 590

Ala Asp Arg Pro Asp Glu Leu Val Phe Val Tyr Ser Gly Gln Gly Thr
        595                 600                 605

Gln His Pro Ala Met Gly Glu Gln Leu Ala Ala Ala Phe Pro Val Phe
    610                 615                 620

Ala Arg Ile His Gln Gln Val Trp Asp Leu Leu Asp Val Pro Asp Leu
625                 630                 635                 640

Glu Val Asn Glu Thr Gly Tyr Ala Gln Pro Ala Leu Phe Ala Met Gln
                645                 650                 655

Val Ala Leu Phe Gly Leu Leu Glu Ser Trp Gly Val Arg Pro Asp Ala
            660                 665                 670

Val Ile Gly His Ser Val Gly Glu Leu Ala Ala Ala Tyr Val Ser Gly
        675                 680                 685

Val Trp Ser Leu Glu Asp Ala Cys Thr Leu Val Ser Ala Arg Ala Arg
    690                 695                 700

Leu Met Gln Ala Leu Pro Ala Gly Gly Val Met Val Ala Val Pro Val
705                 710                 715                 720

Ser Glu Asp Glu Ala Arg Ala Val Leu Gly Glu Gly Val Glu Ile Ala
                725                 730                 735

Ala Val Asn Gly Pro Ser Ser Val Val Leu Ser Gly Asp Glu Ala Ala
            740                 745                 750

Val Leu Gln Ala Ala Glu Gly Leu Gly Lys Trp Thr Arg Leu Ala Thr
        755                 760                 765

Ser His Ala Phe His Ser Ala Arg Met Glu Pro Met Leu Glu Glu Phe
    770                 775                 780

Arg Ala Val Ala Glu Gly Leu Thr Tyr Arg Thr Pro Gln Val Ser Met
785                 790                 795                 800

Ala Val Gly Asp Gln Val Thr Thr Ala Glu Tyr Trp Val Arg Gln Val
                805                 810                 815

Arg Asp Thr Val Arg Phe Gly Glu Gln Val Ala Ser Tyr Glu Asp Ala
            820                 825                 830

Val Phe Val Glu Leu Gly Ala Asp Arg Ser Leu Ala Arg Leu Val Asp
        835                 840                 845

Gly Val Ala Met Leu His Gly Asp His Glu Ile Gln Ala Ala Ile Gly
    850                 855                 860

Ala Leu Ala His Leu Tyr Val Asn Gly Val Thr Val Asp Trp Pro Ala
865                 870                 875                 880

Leu Leu Gly Asp Ala Pro Ala Thr Arg Val Leu Asp Leu Pro Thr Tyr
                885                 890                 895

Ala Phe Gln His Gln Arg Tyr Trp Leu Glu Ser Ala Arg Pro Ala Ala
            900                 905                 910

Ser Asp Ala Gly His Pro Val Leu Gly Ser Gly Ile Ala Leu Ala Gly
        915                 920                 925

Ser Pro Gly Arg Val Phe Thr Gly Ser Val Pro Thr Gly Ala Asp Arg
    930                 935                 940

Ala Val Phe Val Ala Glu Leu Ala Leu Ala Ala Ala Asp Ala Val Asp
945                 950                 955                 960
```

```
Cys Ala Thr Val Glu Arg Leu Asp Ile Ala Ser Val Pro Gly Arg Pro
                965                 970                 975

Gly His Gly Arg Thr Thr Val Gln Thr Trp Val Asp Glu Pro Ala Asp
            980                 985                 990

Asp Gly Arg Arg Arg Phe Thr Val His Thr Arg Thr Gly Asp Ala Pro
        995                 1000                1005

Trp Thr Leu His Ala Glu Gly Val Leu Arg Pro His Gly Thr Ala Leu
    1010                1015                1020

Pro Asp Ala Ala Asp Ala Glu Trp Pro Pro Pro Gly Ala Val Pro Ala
1025                1030                1035                1040

Asp Gly Leu Pro Gly Val Trp Arg Arg Gly Asp Gln Val Phe Ala Glu
                1045                1050                1055

Ala Glu Val Asp Gly Pro Asp Gly Phe Val Val His Pro Asp Leu Leu
            1060                1065                1070

Asp Ala Val Phe Ser Ala Val Gly Asp Gly Ser Arg Gln Pro Ala Gly
        1075                1080                1085

Trp Arg Asp Leu Thr Val His Ala Ser Asp Ala Thr Val Leu Arg Ala
    1090                1095                1100

Cys Leu Thr Arg Arg Thr Asp Gly Ala Met Gly Phe Ala Ala Phe Asp
1105                1110                1115                1120

Gly Ala Gly Leu Pro Val Leu Thr Ala Glu Ala Val Thr Leu Arg Glu
                1125                1130                1135

Val Ala Ser Pro Ser Gly Ser Glu Glu Ser Asp Gly Leu His Arg Leu
            1140                1145                1150

Glu Trp Leu Ala Val Ala Glu Ala Val Tyr Asp Gly Asp Leu Pro Glu
        1155                1160                1165

Gly His Val Leu Ile Thr Ala Ala His Pro Asp Asp Pro Glu Asp Ile
    1170                1175                1180

Pro Thr Arg Ala His Thr Arg Ala Thr Arg Val Leu Thr Ala Leu Gln
1185                1190                1195                1200

His His Leu Thr Thr Thr Asp His Thr Leu Ile Val His Thr Thr Thr
                1205                1210                1215

Asp Pro Ala Gly Ala Thr Val Thr Gly Leu Thr Arg Thr Ala Gln Asn
            1220                1225                1230

Glu His Pro His Arg Ile Arg Leu Ile Glu Thr Asp His Pro His Thr
        1235                1240                1245

Pro Leu Pro Leu Ala Gln Leu Ala Thr Leu Asp His Pro His Leu Arg
    1250                1255                1260

Leu Thr His His Thr Leu His His Pro His Leu Thr Pro Leu His Thr
1265                1270                1275                1280

Thr Thr Pro Pro Thr Thr Thr Pro Leu Asn Pro Glu His Ala Ile Ile
                1285                1290                1295

Ile Thr Gly Gly Ser Gly Thr Leu Ala Gly Ile Leu Ala Arg His Leu
            1300                1305                1310

Asn His Pro His Thr Tyr Leu Leu Ser Arg Thr Pro Pro Pro Asp Ala
        1315                1320                1325

Thr Pro Gly Thr His Leu Pro Cys Asp Val Gly Asp Pro His Gln Leu
    1330                1335                1340

Ala Thr Thr Leu Thr His Ile Pro Gln Pro Leu Thr Ala Ile Phe His
1345                1350                1355                1360

Thr Ala Ala Thr Leu Asp Asp Gly Ile Leu His Ala Leu Thr Pro Asp
                1365                1370                1375
```

-continued

```
Arg Leu Thr Thr Val Leu His Pro Lys Ala Asn Ala Ala Trp His Leu
            1380                1385                1390

His His Leu Thr Gln Asn Gln Pro Leu Thr His Phe Val Leu Tyr Ser
        1395                1400                1405

Ser Ala Ala Ala Val Leu Gly Ser Pro Gly Gln Gly Asn Tyr Ala Ala
    1410                1415                1420

Ala Asn Ala Phe Leu Asp Ala Leu Ala Thr His Arg His Thr Leu Gly
1425                1430                1435                1440

Gln Pro Ala Thr Ser Ile Ala Trp Gly Met Trp His Thr Thr Ser Thr
                1445                1450                1455

Leu Thr Gly Gln Leu Asp Asp Ala Asp Arg Asp Arg Ile Arg Arg Gly
            1460                1465                1470

Gly Phe Leu Pro Ile Thr Asp Asp Glu Gly
        1475                1480


<210> SEQ ID NO 22
<211> LENGTH: 4547
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (9)..(4535)

<400> SEQUENCE: 22

agatctgg cag ctc gcc gaa gcg ctg ctg acg ctc gtc cgg gag agc acc      50
         Gln Leu Ala Glu Ala Leu Leu Thr Leu Val Arg Glu Ser Thr
           1               5                  10

gcc gcc gtg ctc ggc cac gtg ggt ggc gag gac atc ccc gcg acg gcg       98
Ala Ala Val Leu Gly His Val Gly Gly Glu Asp Ile Pro Ala Thr Ala
 15                  20                  25                  30

gcg ttc aag gac ctc ggc atc gac tcg ctc acc gcg gtc cag ctg cgc      146
Ala Phe Lys Asp Leu Gly Ile Asp Ser Leu Thr Ala Val Gln Leu Arg
                 35                  40                  45

aac gcc ctc acc gag gcg acc ggt gtg cgg ctg aac gcc acg gcg gtc      194
Asn Ala Leu Thr Glu Ala Thr Gly Val Arg Leu Asn Ala Thr Ala Val
             50                  55                  60

ttc gac ttc ccg acc ccg cac gtg ctc gcc ggg aag ctc ggc gac gaa      242
Phe Asp Phe Pro Thr Pro His Val Leu Ala Gly Lys Leu Gly Asp Glu
         65                  70                  75

ctg acc ggc acc cgc gcg ccc gtc gtg ccc cgg acc gcg gcc acg gcc      290
Leu Thr Gly Thr Arg Ala Pro Val Val Pro Arg Thr Ala Ala Thr Ala
     80                  85                  90

ggt gcg cac gac gag ccg ctg gcg atc gtg gga atg gcc tgc cgg ctg      338
Gly Ala His Asp Glu Pro Leu Ala Ile Val Gly Met Ala Cys Arg Leu
 95                 100                 105                 110

ccc ggc ggg gtc gcg tca ccc gag gag ctg tgg cac ctc gtg gca tcc      386
Pro Gly Gly Val Ala Ser Pro Glu Glu Leu Trp His Leu Val Ala Ser
                115                 120                 125

ggc acc gac gcc atc acg gag ttc ccg acg gac cgc ggc tgg gac gtc      434
Gly Thr Asp Ala Ile Thr Glu Phe Pro Thr Asp Arg Gly Trp Asp Val
            130                 135                 140

gac gcg atc tac gac ccg gac ccc gac gcg atc ggc aag acc ttc gtc      482
Asp Ala Ile Tyr Asp Pro Asp Pro Asp Ala Ile Gly Lys Thr Phe Val
        145                 150                 155

cgg cac ggt ggc ttc ctc acc ggc gcg aca ggc ttc gac gcg gcg ttc      530
Arg His Gly Gly Phe Leu Thr Gly Ala Thr Gly Phe Asp Ala Ala Phe
    160                 165                 170
```

-continued

```
ttc ggc atc agc ccg cgc gag gcc ctc gcg atg gac ccg cag cag cgg      578
Phe Gly Ile Ser Pro Arg Glu Ala Leu Ala Met Asp Pro Gln Gln Arg
175                 180                 185                 190

gtg ctc ctg gag acg tcg tgg gag gcg ttc gaa agc gcc ggc atc acc      626
Val Leu Leu Glu Thr Ser Trp Glu Ala Phe Glu Ser Ala Gly Ile Thr
                195                 200                 205

ccg gac tcg acc cgc ggc agc gac acc ggc gtg ttc gtc ggc gcc ttc      674
Pro Asp Ser Thr Arg Gly Ser Asp Thr Gly Val Phe Val Gly Ala Phe
            210                 215                 220

tcc tac ggt tac ggc acc ggt gcg gac acc gac ggc ttc ggc gcg acc      722
Ser Tyr Gly Tyr Gly Thr Gly Ala Asp Thr Asp Gly Phe Gly Ala Thr
        225                 230                 235

ggc tcg cag acc agt gtg ctc tcc ggc cgg ctg tcg tac ttc tac ggt      770
Gly Ser Gln Thr Ser Val Leu Ser Gly Arg Leu Ser Tyr Phe Tyr Gly
    240                 245                 250

ctg gag ggt ccg gcg gtc acg gtc gac acg gcg tgt tcg tcg tcg ctg      818
Leu Glu Gly Pro Ala Val Thr Val Asp Thr Ala Cys Ser Ser Ser Leu
255                 260                 265                 270

gtg gcg ctg cac cag gcc ggg cag tcg ctg cgc tcc ggc gaa tgc tcg      866
Val Ala Leu His Gln Ala Gly Gln Ser Leu Arg Ser Gly Glu Cys Ser
                275                 280                 285

ctc gcc ctg gtc ggc ggc gtc acg gtg atg gcg tct ccc ggc ggc ttc      914
Leu Ala Leu Val Gly Gly Val Thr Val Met Ala Ser Pro Gly Gly Phe
            290                 295                 300

gtg gag ttc tcc cgg cag cgc ggc ctc gcg ccg gac ggc cgg gcg aag      962
Val Glu Phe Ser Arg Gln Arg Gly Leu Ala Pro Asp Gly Arg Ala Lys
        305                 310                 315

gcg ttc ggc gcg ggt gcg gac ggc acg agc ttc gcc gag ggt gcc ggt     1010
Ala Phe Gly Ala Gly Ala Asp Gly Thr Ser Phe Ala Glu Gly Ala Gly
    320                 325                 330

gtg ctg atc gtc gag agg ctc tcc gac gcc gaa cgc aac ggt cac acc     1058
Val Leu Ile Val Glu Arg Leu Ser Asp Ala Glu Arg Asn Gly His Thr
335                 340                 345                 350

gtc ctg gcg gtc gtc cgt ggt tcg gcg gtc aac cag gat ggt gcc tcc     1106
Val Leu Ala Val Val Arg Gly Ser Ala Val Asn Gln Asp Gly Ala Ser
                355                 360                 365

aac ggg ctg tcg gcg ccg aac ggg ccg tcg cag gag cgg gtg atc cgg     1154
Asn Gly Leu Ser Ala Pro Asn Gly Pro Ser Gln Glu Arg Val Ile Arg
            370                 375                 380

cag gcc ctg gcc aac gcc ggg ctc acc ccg gcg gac gtg gac gcc gtc     1202
Gln Ala Leu Ala Asn Ala Gly Leu Thr Pro Ala Asp Val Asp Ala Val
        385                 390                 395

gag gcc cac ggc acc ggc acc agg ctg ggc gac ccc atc gag gca cag     1250
Glu Ala His Gly Thr Gly Thr Arg Leu Gly Asp Pro Ile Glu Ala Gln
    400                 405                 410

gcg gta ctg gcc acc tac gga cag gag cgc gcc acc ccc ctg ctg ctg     1298
Ala Val Leu Ala Thr Tyr Gly Gln Glu Arg Ala Thr Pro Leu Leu Leu
415                 420                 425                 430

ggc tcg ctg aag tcc aac atc ggc cac gcc cag gcc gcg tcc ggc gtc     1346
Gly Ser Leu Lys Ser Asn Ile Gly His Ala Gln Ala Ala Ser Gly Val
                435                 440                 445

gcc ggc atc atc aag atg gtg cag gcc ctc cgg cac ggg gag ctg ccg     1394
Ala Gly Ile Ile Lys Met Val Gln Ala Leu Arg His Gly Glu Leu Pro
            450                 455                 460

ccg acg ctg cac gcc gac gag ccg tcg ccg cac gtc gac tgg acg gcc     1442
Pro Thr Leu His Ala Asp Glu Pro Ser Pro His Val Asp Trp Thr Ala
        465                 470                 475

ggc gcc gtc gaa ctg ctg acg tcg gcc cgg ccg tgg ccc gag acc gac     1490
Gly Ala Val Glu Leu Leu Thr Ser Ala Arg Pro Trp Pro Glu Thr Asp
    480                 485                 490
```

-continued

```
cgg cca cgg cgt gcc gcc gtc tcc tcg ttc ggg gtg agc ggc acc aac     1538
Arg Pro Arg Arg Ala Ala Val Ser Ser Phe Gly Val Ser Gly Thr Asn
495                 500                 505                 510

gcc cac gtc atc ctg gag gcc gga ccg gta acg gag acg ccc gcg gca     1586
Ala His Val Ile Leu Glu Ala Gly Pro Val Thr Glu Thr Pro Ala Ala
                515                 520                 525

tcg cct tcc ggt gac ctt ccc ctg ctg gtg tcg gca cgc tca ccg gaa     1634
Ser Pro Ser Gly Asp Leu Pro Leu Leu Val Ser Ala Arg Ser Pro Glu
            530                 535                 540

gcg ctc gac gag cag atc cgc cga ctg cgc gcc tac ctg gac acc acc     1682
Ala Leu Asp Glu Gln Ile Arg Arg Leu Arg Ala Tyr Leu Asp Thr Thr
        545                 550                 555

ccg gac gtc gac cgg gtg gcc gtg gca cag acg ctg gcc cgg cgc aca     1730
Pro Asp Val Asp Arg Val Ala Val Ala Gln Thr Leu Ala Arg Arg Thr
    560                 565                 570

cac ttc gcc cac cgc gcc gtg ctg ctc ggt gac acc gtc atc acc aca     1778
His Phe Ala His Arg Ala Val Leu Leu Gly Asp Thr Val Ile Thr Thr
575                 580                 585                 590

ccc ccc gcg gac cgg ccc gac gaa ctc gtc ttc gtc tac tcc ggc cag     1826
Pro Pro Ala Asp Arg Pro Asp Glu Leu Val Phe Val Tyr Ser Gly Gln
                595                 600                 605

ggc acc cag cat ccc gcg atg ggc gag cag cta gcc gat tcg tcg gtg     1874
Gly Thr Gln His Pro Ala Met Gly Glu Gln Leu Ala Asp Ser Ser Val
            610                 615                 620

gtg ttc gcc gag cgg atg gcc gag tgt gcg gcg gcg ttg cgc gag ttc     1922
Val Phe Ala Glu Arg Met Ala Glu Cys Ala Ala Ala Leu Arg Glu Phe
        625                 630                 635

gtg gac tgg gat ctg ttc acg gtt ctg gat gat ccg gcg gtg gtg gac     1970
Val Asp Trp Asp Leu Phe Thr Val Leu Asp Asp Pro Ala Val Val Asp
    640                 645                 650

cgg gtt gat gtg gtc cag ccc gct tcc tgg gcg atg atg gtt tcc ctg     2018
Arg Val Asp Val Val Gln Pro Ala Ser Trp Ala Met Met Val Ser Leu
655                 660                 665                 670

gcc gcg gtg tgg cag gcg gcc ggt gtg cgg ccg gat gcg gtg atc ggc     2066
Ala Ala Val Trp Gln Ala Ala Gly Val Arg Pro Asp Ala Val Ile Gly
                675                 680                 685

cat tcg cag ggt gag atc gcc gca gct tgt gtg gcg ggt gcg gtg tca     2114
His Ser Gln Gly Glu Ile Ala Ala Ala Cys Val Ala Gly Ala Val Ser
            690                 695                 700

cta cgc gat gcc gcc cgg atc gtg acc ttg cgc agc cag gcg atc gcc     2162
Leu Arg Asp Ala Ala Arg Ile Val Thr Leu Arg Ser Gln Ala Ile Ala
        705                 710                 715

cgg ggc ctg gcg ggc cgg ggc gcg atg gca tcc gtc gcc ctg ccc gcg     2210
Arg Gly Leu Ala Gly Arg Gly Ala Met Ala Ser Val Ala Leu Pro Ala
    720                 725                 730

cag gat gtc gag ctg gtc gac ggg gcc tgg atc gcc gcc cac aac ggg     2258
Gln Asp Val Glu Leu Val Asp Gly Ala Trp Ile Ala Ala His Asn Gly
735                 740                 745                 750

ccc gcc tcc acc gtg atc gcg ggc acc ccg gaa gcg gtc gac cat gtc     2306
Pro Ala Ser Thr Val Ile Ala Gly Thr Pro Glu Ala Val Asp His Val
                755                 760                 765

ctc acc gct cat gag gca caa ggg gtg cgg gtg cgg cgg atc acc gtc     2354
Leu Thr Ala His Glu Ala Gln Gly Val Arg Val Arg Arg Ile Thr Val
            770                 775                 780

gac tat gcc tcg cac acc ccg cac gtc gag ctg atc cgc gac gaa cta     2402
Asp Tyr Ala Ser His Thr Pro His Val Glu Leu Ile Arg Asp Glu Leu
        785                 790                 795

ctc gac atc act agc gac agc agc tcg cag acc ccg ctc gtg ccg tgg     2450
Leu Asp Ile Thr Ser Asp Ser Ser Ser Gln Thr Pro Leu Val Pro Trp
```

-continued

```
    800                 805                 810

ctg tcg acc gtg gac ggc acc tgg gtc gac agc ccg ctg gac ggg gag     2498
Leu Ser Thr Val Asp Gly Thr Trp Val Asp Ser Pro Leu Asp Gly Glu
815                 820                 825                 830

tac tgg tac cgg aac ctg cgt gaa ccg gtc ggt ttc cac ccc gcc gtc     2546
Tyr Trp Tyr Arg Asn Leu Arg Glu Pro Val Gly Phe His Pro Ala Val
                835                 840                 845

agc cag ttg cag gcc cag ggc gac acc gtg ttc gtc gag gtc agc gcc     2594
Ser Gln Leu Gln Ala Gln Gly Asp Thr Val Phe Val Glu Val Ser Ala
            850                 855                 860

agc ccg gtg ttg ttg cag gcg atg gac gac gat gtc gtc acg gtt gcc     2642
Ser Pro Val Leu Leu Gln Ala Met Asp Asp Asp Val Val Thr Val Ala
        865                 870                 875

acg ctg cgt cgt gac gac ggc gac gcc acc cgg atg ctc acc gcc ctg     2690
Thr Leu Arg Arg Asp Asp Gly Asp Ala Thr Arg Met Leu Thr Ala Leu
    880                 885                 890

gca cag gcc tat gtc cac ggc gtc acc gtc gac tgg ccc gcc atc ctc     2738
Ala Gln Ala Tyr Val His Gly Val Thr Val Asp Trp Pro Ala Ile Leu
895                 900                 905                 910

ggc acc acc aca acc cgg gta ctg gac ctt ccg acc tac gcc ttc caa     2786
Gly Thr Thr Thr Thr Arg Val Leu Asp Leu Pro Thr Tyr Ala Phe Gln
                915                 920                 925

cac cag cgg tac tgg ctc gag tcg gca cgc ccg gcc gca tcc gac gcg     2834
His Gln Arg Tyr Trp Leu Glu Ser Ala Arg Pro Ala Ala Ser Asp Ala
            930                 935                 940

ggc cac ccc gtg ctg ggc tcc ggt atc gcc ctc gcc ggg tcg ccg ggc     2882
Gly His Pro Val Leu Gly Ser Gly Ile Ala Leu Ala Gly Ser Pro Gly
        945                 950                 955

cgg gtg ttc acg ggt tcc gtg ccg acc ggt gcg gac cgc gcg gtg ttc     2930
Arg Val Phe Thr Gly Ser Val Pro Thr Gly Ala Asp Arg Ala Val Phe
    960                 965                 970

gtc gcc gag ctg gcg ctg gcc gcc gcg gac gcg gtc gac tgc gcc acg     2978
Val Ala Glu Leu Ala Leu Ala Ala Ala Asp Ala Val Asp Cys Ala Thr
975                 980                 985                 990

gtc gag cgg ctc gac atc gcc tcc gtg ccc ggc cgg ccg ggc cat ggc     3026
Val Glu Arg Leu Asp Ile Ala Ser Val Pro Gly Arg Pro Gly His Gly
                995                1000                1005

cgg acg acc gta cag acc tgg gtc gac gag ccg gcg gac gac ggc cgg     3074
Arg Thr Thr Val Gln Thr Trp Val Asp Glu Pro Ala Asp Asp Gly Arg
           1010                1015                1020

cgc cgg ttc acc gtg cac acc cgc acc ggc gac gcc ccg tgg acg ctg     3122
Arg Arg Phe Thr Val His Thr Arg Thr Gly Asp Ala Pro Trp Thr Leu
       1025                1030                1035

cac gcc gag ggg gtg ctg cgc ccc cat ggc acg gcc ctg ccc gat gcg     3170
His Ala Glu Gly Val Leu Arg Pro His Gly Thr Ala Leu Pro Asp Ala
   1040                1045                1050

gcc gac gcc gag tgg ccc cca ccg ggc gcg gtg ccc gcg gac ggg ctg     3218
Ala Asp Ala Glu Trp Pro Pro Pro Gly Ala Val Pro Ala Asp Gly Leu
1055                1060                1065                1070

ccg ggt gtg tgg cgc cgg ggg gac cag gtc ttc gcc gag gcc gag gtg     3266
Pro Gly Val Trp Arg Arg Gly Asp Gln Val Phe Ala Glu Ala Glu Val
               1075                1080                1085

gac gga ccg gac ggt ttc gtg gtg cac ccc gac ctg ctc gac gcg gtc     3314
Asp Gly Pro Asp Gly Phe Val Val His Pro Asp Leu Leu Asp Ala Val
           1090                1095                1100

ttc tcc gcg gtc ggc gac gga agc cgc cag ccg gcc gga tgg cgc gac     3362
Phe Ser Ala Val Gly Asp Gly Ser Arg Gln Pro Ala Gly Trp Arg Asp
       1105                1110                1115

ctg acg gtg cac gcg tcg gac gcc acc gta ctg cgc gcc tgc ctc acc     3410
```

-continued

```
Leu Thr Val His Ala Ser Asp Ala Thr Val Leu Arg Ala Cys Leu Thr
   1120                1125                1130

cgg cgc acc gac gga gcc atg gga ttc gcc gcc ttc gac ggc gcc ggc     3458
Arg Arg Thr Asp Gly Ala Met Gly Phe Ala Ala Phe Asp Gly Ala Gly
1135                1140                1145                1150

ctg ccg gta ctc acc gcg gag gcg gtg acg ctg cgg gag gtg gcg tca     3506
Leu Pro Val Leu Thr Ala Glu Ala Val Thr Leu Arg Glu Val Ala Ser
               1155                1160                1165

ccg tcc ggc tcc gag gag tcg gac ggc ctg cac cgg ttg gag tgg ctc     3554
Pro Ser Gly Ser Glu Glu Ser Asp Gly Leu His Arg Leu Glu Trp Leu
           1170                1175                1180

gcg gtc gcc gag gcg gtc tac gac ggt gac ctg ccc gag gga cat gtc     3602
Ala Val Ala Glu Ala Val Tyr Asp Gly Asp Leu Pro Glu Gly His Val
       1185                1190                1195

ctg atc acc gcc gcc cac ccc gac gac ccc gag gac ata ccc acc cgc     3650
Leu Ile Thr Ala Ala His Pro Asp Asp Pro Glu Asp Ile Pro Thr Arg
   1200                1205                1210

gcc cac acc cgc gcc acc cgc gtc ctg acc gcc ctg caa cac cac ctc     3698
Ala His Thr Arg Ala Thr Arg Val Leu Thr Ala Leu Gln His His Leu
1215                1220                1225                1230

acc acc acc gac cac acc ctc atc gtc cac acc acc acc gac ccc gcc     3746
Thr Thr Thr Asp His Thr Leu Ile Val His Thr Thr Thr Asp Pro Ala
               1235                1240                1245

ggc gcc acc gtc acc ggc ctc acc cgc acc gcc cag aac gaa cac ccc     3794
Gly Ala Thr Val Thr Gly Leu Thr Arg Thr Ala Gln Asn Glu His Pro
           1250                1255                1260

cac cgc atc cgc ctc atc gaa acc gac cac ccc cac acc ccc ctc ccc     3842
His Arg Ile Arg Leu Ile Glu Thr Asp His Pro His Thr Pro Leu Pro
       1265                1270                1275

ctg gcc caa ctc gcc acc ctc gac cac ccc cac ctc cgc ctc acc cac     3890
Leu Ala Gln Leu Ala Thr Leu Asp His Pro His Leu Arg Leu Thr His
   1280                1285                1290

cac acc ctc cac cac ccc cac ctc acc ccc ctc cac acc acc acc cca     3938
His Thr Leu His His Pro His Leu Thr Pro Leu His Thr Thr Thr Pro
1295                1300                1305                1310

ccc acc acc acc ccc ctc aac ccc gaa cac gcc atc atc atc acc ggc     3986
Pro Thr Thr Thr Pro Leu Asn Pro Glu His Ala Ile Ile Ile Thr Gly
               1315                1320                1325

ggc tcc ggc acc ctc gcc ggc atc ctc gcc cgc cac ctg aac cac ccc     4034
Gly Ser Gly Thr Leu Ala Gly Ile Leu Ala Arg His Leu Asn His Pro
           1330                1335                1340

cac acc tac ctc ctc tcc cgc acc cca ccc ccc gac gcc acc ccc ggc     4082
His Thr Tyr Leu Leu Ser Arg Thr Pro Pro Pro Asp Ala Thr Pro Gly
       1345                1350                1355

acc cac ctc ccc tgc gac gtc ggc gac ccc cac caa ctc gcc acc acc     4130
Thr His Leu Pro Cys Asp Val Gly Asp Pro His Gln Leu Ala Thr Thr
   1360                1365                1370

ctc acc cac atc ccc caa ccc ctc acc gcc atc ttc cac acc gcc gcc     4178
Leu Thr His Ile Pro Gln Pro Leu Thr Ala Ile Phe His Thr Ala Ala
1375                1380                1385                1390

acc ctc gac gac ggc atc ctc cac gcc ctc acc ccc gac cgc ctc acc     4226
Thr Leu Asp Asp Gly Ile Leu His Ala Leu Thr Pro Asp Arg Leu Thr
               1395                1400                1405

acc gtc ctc cac ccc aaa gcc aac gcc gcc tgg cac ctg cac cac ctc     4274
Thr Val Leu His Pro Lys Ala Asn Ala Ala Trp His Leu His His Leu
           1410                1415                1420

acc caa aac caa ccc ctc acc cac ttc gtc ctc tac tcc agc gcc gcc     4322
Thr Gln Asn Gln Pro Leu Thr His Phe Val Leu Tyr Ser Ser Ala Ala
       1425                1430                1435
```

-continued

```
gcc gtc ctc ggc agc ccc gga caa gga aac tac gcc gcc gcc aac gcc     4370
Ala Val Leu Gly Ser Pro Gly Gln Gly Asn Tyr Ala Ala Ala Asn Ala
   1440                1445                1450

ttc ctc gac gcc ctc gcc acc cac cgc cac acc ctc ggc caa ccc gcc     4418
Phe Leu Asp Ala Leu Ala Thr His Arg His Thr Leu Gly Gln Pro Ala
1455                1460                1465                1470

acc tcc atc gcc tgg ggc atg tgg cac acc acc agc acc ctc acc gga     4466
Thr Ser Ile Ala Trp Gly Met Trp His Thr Thr Ser Thr Leu Thr Gly
               1475                1480                1485

caa ctc gac gac gcc gac cgg gac cgc atc cgc cgc ggc ggt ttc ctc     4514
Gln Leu Asp Asp Ala Asp Arg Asp Arg Ile Arg Arg Gly Gly Phe Leu
           1490                1495                1500

ccg atc acg gac gac gag ggc atggggatgc at                           4547
Pro Ile Thr Asp Asp Glu Gly
       1505
```

<210> SEQ ID NO 23
<211> LENGTH: 1509
<212> TYPE: PRT
<213> ORGANISM: Artificial Sequence
<220> FEATURE:
<223> OTHER INFORMATION: Description of Artificial Sequence: Synthetic PKS synthase fragment

<400> SEQUENCE: 23

```
Gln Leu Ala Glu Ala Leu Leu Thr Leu Val Arg Glu Ser Thr Ala Ala
  1               5                  10                  15

Val Leu Gly His Val Gly Gly Glu Asp Ile Pro Ala Thr Ala Ala Phe
            20                  25                  30

Lys Asp Leu Gly Ile Asp Ser Leu Thr Ala Val Gln Leu Arg Asn Ala
        35                  40                  45

Leu Thr Glu Ala Thr Gly Val Arg Leu Asn Ala Thr Ala Val Phe Asp
     50                  55                  60

Phe Pro Thr Pro His Val Leu Ala Gly Lys Leu Gly Asp Glu Leu Thr
 65                  70                  75                  80

Gly Thr Arg Ala Pro Val Val Pro Arg Thr Ala Ala Thr Ala Gly Ala
                 85                  90                  95

His Asp Glu Pro Leu Ala Ile Val Gly Met Ala Cys Arg Leu Pro Gly
            100                 105                 110

Gly Val Ala Ser Pro Glu Glu Leu Trp His Leu Val Ala Ser Gly Thr
        115                 120                 125

Asp Ala Ile Thr Glu Phe Pro Thr Asp Arg Gly Trp Asp Val Asp Ala
    130                 135                 140

Ile Tyr Asp Pro Asp Pro Asp Ala Ile Gly Lys Thr Phe Val Arg His
145                 150                 155                 160

Gly Gly Phe Leu Thr Gly Ala Thr Gly Phe Asp Ala Ala Phe Phe Gly
                165                 170                 175

Ile Ser Pro Arg Glu Ala Leu Ala Met Asp Pro Gln Gln Arg Val Leu
            180                 185                 190

Leu Glu Thr Ser Trp Glu Ala Phe Glu Ser Ala Gly Ile Thr Pro Asp
        195                 200                 205

Ser Thr Arg Gly Ser Asp Thr Gly Val Phe Val Gly Ala Phe Ser Tyr
    210                 215                 220

Gly Tyr Gly Thr Gly Ala Asp Thr Asp Gly Phe Gly Ala Thr Gly Ser
225                 230                 235                 240

Gln Thr Ser Val Leu Ser Gly Arg Leu Ser Tyr Phe Tyr Gly Leu Glu
                245                 250                 255
```

-continued

```
Gly Pro Ala Val Thr Val Asp Thr Ala Cys Ser Ser Ser Leu Val Ala
            260                 265                 270

Leu His Gln Ala Gly Gln Ser Leu Arg Ser Gly Glu Cys Ser Leu Ala
        275                 280                 285

Leu Val Gly Gly Val Thr Val Met Ala Ser Pro Gly Gly Phe Val Glu
    290                 295                 300

Phe Ser Arg Gln Arg Gly Leu Ala Pro Asp Gly Arg Ala Lys Ala Phe
305                 310                 315                 320

Gly Ala Gly Ala Asp Gly Thr Ser Phe Ala Glu Gly Ala Gly Val Leu
                325                 330                 335

Ile Val Glu Arg Leu Ser Asp Ala Glu Arg Asn Gly His Thr Val Leu
            340                 345                 350

Ala Val Val Arg Gly Ser Ala Val Asn Gln Asp Gly Ala Ser Asn Gly
        355                 360                 365

Leu Ser Ala Pro Asn Gly Pro Ser Gln Glu Arg Val Ile Arg Gln Ala
    370                 375                 380

Leu Ala Asn Ala Gly Leu Thr Pro Ala Asp Val Asp Ala Val Glu Ala
385                 390                 395                 400

His Gly Thr Gly Thr Arg Leu Gly Asp Pro Ile Glu Ala Gln Ala Val
                405                 410                 415

Leu Ala Thr Tyr Gly Gln Glu Arg Ala Thr Pro Leu Leu Leu Gly Ser
            420                 425                 430

Leu Lys Ser Asn Ile Gly His Ala Gln Ala Ala Ser Gly Val Ala Gly
        435                 440                 445

Ile Ile Lys Met Val Gln Ala Leu Arg His Gly Glu Leu Pro Pro Thr
    450                 455                 460

Leu His Ala Asp Glu Pro Ser Pro His Val Asp Trp Thr Ala Gly Ala
465                 470                 475                 480

Val Glu Leu Leu Thr Ser Ala Arg Pro Trp Pro Glu Thr Asp Arg Pro
                485                 490                 495

Arg Arg Ala Ala Val Ser Ser Phe Gly Val Ser Gly Thr Asn Ala His
            500                 505                 510

Val Ile Leu Glu Ala Gly Pro Val Thr Glu Thr Pro Ala Ala Ser Pro
        515                 520                 525

Ser Gly Asp Leu Pro Leu Leu Val Ser Ala Arg Ser Pro Glu Ala Leu
    530                 535                 540

Asp Glu Gln Ile Arg Arg Leu Arg Ala Tyr Leu Asp Thr Thr Pro Asp
545                 550                 555                 560

Val Asp Arg Val Ala Val Ala Gln Thr Leu Ala Arg Arg Thr His Phe
                565                 570                 575

Ala His Arg Ala Val Leu Leu Gly Asp Thr Val Ile Thr Thr Pro Pro
            580                 585                 590

Ala Asp Arg Pro Asp Glu Leu Val Phe Val Tyr Ser Gly Gln Gly Thr
        595                 600                 605

Gln His Pro Ala Met Gly Glu Gln Leu Ala Asp Ser Ser Val Val Phe
    610                 615                 620

Ala Glu Arg Met Ala Glu Cys Ala Ala Ala Leu Arg Glu Phe Val Asp
625                 630                 635                 640

Trp Asp Leu Phe Thr Val Leu Asp Asp Pro Ala Val Val Asp Arg Val
                645                 650                 655

Asp Val Val Gln Pro Ala Ser Trp Ala Met Met Val Ser Leu Ala Ala
            660                 665                 670

Val Trp Gln Ala Ala Gly Val Arg Pro Asp Ala Val Ile Gly His Ser
```

-continued

```
        675                 680                 685

Gln Gly Glu Ile Ala Ala Ala Cys Val Ala Gly Ala Val Ser Leu Arg
    690                 695                 700

Asp Ala Ala Arg Ile Val Thr Leu Arg Ser Gln Ala Ile Ala Arg Gly
705                 710                 715                 720

Leu Ala Gly Arg Gly Ala Met Ala Ser Val Ala Leu Pro Ala Gln Asp
                725                 730                 735

Val Glu Leu Val Asp Gly Ala Trp Ile Ala Ala His Asn Gly Pro Ala
            740                 745                 750

Ser Thr Val Ile Ala Gly Thr Pro Glu Ala Val Asp His Val Leu Thr
        755                 760                 765

Ala His Glu Ala Gln Gly Val Arg Val Arg Arg Ile Thr Val Asp Tyr
    770                 775                 780

Ala Ser His Thr Pro His Val Glu Leu Ile Arg Asp Glu Leu Leu Asp
785                 790                 795                 800

Ile Thr Ser Asp Ser Ser Ser Gln Thr Pro Leu Val Pro Trp Leu Ser
                805                 810                 815

Thr Val Asp Gly Thr Trp Val Asp Ser Pro Leu Asp Gly Glu Tyr Trp
            820                 825                 830

Tyr Arg Asn Leu Arg Glu Pro Val Gly Phe His Pro Ala Val Ser Gln
        835                 840                 845

Leu Gln Ala Gln Gly Asp Thr Val Phe Val Glu Val Ser Ala Ser Pro
    850                 855                 860

Val Leu Leu Gln Ala Met Asp Asp Asp Val Val Thr Val Ala Thr Leu
865                 870                 875                 880

Arg Arg Asp Asp Gly Asp Ala Thr Arg Met Leu Thr Ala Leu Ala Gln
                885                 890                 895

Ala Tyr Val His Gly Val Thr Val Asp Trp Pro Ala Ile Leu Gly Thr
            900                 905                 910

Thr Thr Thr Arg Val Leu Asp Leu Pro Thr Tyr Ala Phe Gln His Gln
        915                 920                 925

Arg Tyr Trp Leu Glu Ser Ala Arg Pro Ala Ala Ser Asp Ala Gly His
    930                 935                 940

Pro Val Leu Gly Ser Gly Ile Ala Leu Ala Gly Ser Pro Gly Arg Val
945                 950                 955                 960

Phe Thr Gly Ser Val Pro Thr Gly Ala Asp Arg Ala Val Phe Val Ala
                965                 970                 975

Glu Leu Ala Leu Ala Ala Ala Asp Ala Val Asp Cys Ala Thr Val Glu
            980                 985                 990

Arg Leu Asp Ile Ala Ser Val Pro Gly Arg Pro Gly His Gly Arg Thr
        995                 1000                1005

Thr Val Gln Thr Trp Val Asp Glu Pro Ala Asp Asp Gly Arg Arg Arg
    1010                1015                1020

Phe Thr Val His Thr Arg Thr Gly Asp Ala Pro Trp Thr Leu His Ala
1025                1030                1035                1040

Glu Gly Val Leu Arg Pro His Gly Thr Ala Leu Pro Asp Ala Ala Asp
                1045                1050                1055

Ala Glu Trp Pro Pro Pro Gly Ala Val Pro Ala Asp Gly Leu Pro Gly
            1060                1065                1070

Val Trp Arg Arg Gly Asp Gln Val Phe Ala Glu Ala Glu Val Asp Gly
        1075                1080                1085

Pro Asp Gly Phe Val Val His Pro Asp Leu Leu Asp Ala Val Phe Ser
    1090                1095                1100
```

-continued

```
Ala Val Gly Asp Gly Ser Arg Gln Pro Ala Gly Trp Arg Asp Leu Thr
1105                1110                1115                1120

Val His Ala Ser Asp Ala Thr Val Leu Arg Ala Cys Leu Thr Arg Arg
                1125                1130                1135

Thr Asp Gly Ala Met Gly Phe Ala Ala Phe Asp Gly Ala Gly Leu Pro
            1140                1145                1150

Val Leu Thr Ala Glu Ala Val Thr Leu Arg Glu Val Ala Ser Pro Ser
        1155                1160                1165

Gly Ser Glu Glu Ser Asp Gly Leu His Arg Leu Glu Trp Leu Ala Val
    1170                1175                1180

Ala Glu Ala Val Tyr Asp Gly Asp Leu Pro Glu Gly His Val Leu Ile
1185                1190                1195                1200

Thr Ala Ala His Pro Asp Asp Pro Glu Asp Ile Pro Thr Arg Ala His
                1205                1210                1215

Thr Arg Ala Thr Arg Val Leu Thr Ala Leu Gln His His Leu Thr Thr
            1220                1225                1230

Thr Asp His Thr Leu Ile Val His Thr Thr Thr Asp Pro Ala Gly Ala
        1235                1240                1245

Thr Val Thr Gly Leu Thr Arg Thr Ala Gln Asn Glu His Pro His Arg
    1250                1255                1260

Ile Arg Leu Ile Glu Thr Asp His Pro His Thr Pro Leu Pro Leu Ala
1265                1270                1275                1280

Gln Leu Ala Thr Leu Asp His Pro His Leu Arg Leu Thr His His Thr
                1285                1290                1295

Leu His His Pro His Leu Thr Pro Leu His Thr Thr Thr Pro Pro Thr
            1300                1305                1310

Thr Thr Pro Leu Asn Pro Glu His Ala Ile Ile Ile Thr Gly Gly Ser
        1315                1320                1325

Gly Thr Leu Ala Gly Ile Leu Ala Arg His Leu Asn His Pro His Thr
    1330                1335                1340

Tyr Leu Leu Ser Arg Thr Pro Pro Pro Asp Ala Thr Pro Gly Thr His
1345                1350                1355                1360

Leu Pro Cys Asp Val Gly Asp Pro His Gln Leu Ala Thr Thr Leu Thr
                1365                1370                1375

His Ile Pro Gln Pro Leu Thr Ala Ile Phe His Thr Ala Ala Thr Leu
            1380                1385                1390

Asp Asp Gly Ile Leu His Ala Leu Thr Pro Asp Arg Leu Thr Thr Val
        1395                1400                1405

Leu His Pro Lys Ala Asn Ala Ala Trp His Leu His His Leu Thr Gln
    1410                1415                1420

Asn Gln Pro Leu Thr His Phe Val Leu Tyr Ser Ser Ala Ala Ala Val
1425                1430                1435                1440

Leu Gly Ser Pro Gly Gln Gly Asn Tyr Ala Ala Ala Asn Ala Phe Leu
                1445                1450                1455

Asp Ala Leu Ala Thr His Arg His Thr Leu Gly Gln Pro Ala Thr Ser
            1460                1465                1470

Ile Ala Trp Gly Met Trp His Thr Thr Ser Thr Leu Thr Gly Gln Leu
        1475                1480                1485

Asp Asp Ala Asp Arg Asp Arg Ile Arg Arg Gly Gly Phe Leu Pro Ile
    1490                1495                1500

Thr Asp Asp Glu Gly
1505
```

-continued

<210> SEQ ID NO 24
<211> LENGTH: 4725
<212> TYPE: DNA
<213> ORGANISM: Artificial Sequence
<220> FEATURE:
<223> OTHER INFORMATION: Description of Artificial Sequence: DNA encoding synthetic PKS synthase fragment
<220> FEATURE:
<221> NAME/KEY: CDS
<222> LOCATION: (3)..(4724)

<400> SEQUENCE: 24

```
gc atg cgg ctg tac gag gcg gca cgg cgc acc gga agt ccc gtg gtg        47
   Met Arg Leu Tyr Glu Ala Ala Arg Arg Thr Gly Ser Pro Val Val
     1               5                  10                  15

gtg gcg gcc gcg ctc gac gac gcg ccg gac gtg ccg ctg ctg cgc ggg       95
Val Ala Ala Ala Leu Asp Asp Ala Pro Asp Val Pro Leu Leu Arg Gly
                20                  25                  30

ctg cgg cgt acg acc gtc cgg cgt gcc gcc gtc cgg gaa cgc tct ctc      143
Leu Arg Arg Thr Thr Val Arg Arg Ala Ala Val Arg Glu Arg Ser Leu
            35                  40                  45

gcc gac cgc tcg ccg tgc tgc ccg acg acg agc gcg ccg acg cct ccc      191
Ala Asp Arg Ser Pro Cys Cys Pro Thr Thr Ser Ala Pro Thr Pro Pro
        50                  55                  60

tcg cgt tcg tcc tgg aac agc acc gcc acc gtg ctc ggc cac ctg ggc      239
Ser Arg Ser Ser Trp Asn Ser Thr Ala Thr Val Leu Gly His Leu Gly
     65                  70                  75

gcc gaa gac atc ccg gcg acg acg acg ttc aag gaa ctc ggc atc gac      287
Ala Glu Asp Ile Pro Ala Thr Thr Thr Phe Lys Glu Leu Gly Ile Asp
 80                  85                  90                  95

tcg ctc acc gcg gtc cag ctg cgc aac gcg ctg acc acg gcg acc ggc      335
Ser Leu Thr Ala Val Gln Leu Arg Asn Ala Leu Thr Thr Ala Thr Gly
                100                 105                 110

gta cgc ctc aac gcc aca gcg gtc ttc gac ttt ccg acg ccg cgc gcg      383
Val Arg Leu Asn Ala Thr Ala Val Phe Asp Phe Pro Thr Pro Arg Ala
            115                 120                 125

ctc gcc gcg aga ctc ggc gac gag ctg gcc ggt acc cgc gcg ccc gtc      431
Leu Ala Ala Arg Leu Gly Asp Glu Leu Ala Gly Thr Arg Ala Pro Val
        130                 135                 140

gcg gcc cgg acc gcg gcc acc gcg gcc gcg cac gac gaa ccg ctg gcg      479
Ala Ala Arg Thr Ala Ala Thr Ala Ala Ala His Asp Glu Pro Leu Ala
    145                 150                 155

atc gtg ggc atg gcc tgc cgt ctg ccg ggc ggg gtc gcg tcg cca cag      527
Ile Val Gly Met Ala Cys Arg Leu Pro Gly Gly Val Ala Ser Pro Gln
160                 165                 170                 175

gag ctg tgg cgt ctc gtc gcg tcc ggc acc gac gcc atc acg gag ttc      575
Glu Leu Trp Arg Leu Val Ala Ser Gly Thr Asp Ala Ile Thr Glu Phe
                180                 185                 190

ccc gcg gac cgc ggc tgg gac gtg gac gcg ctc tac gac ccg gac ccc      623
Pro Ala Asp Arg Gly Trp Asp Val Asp Ala Leu Tyr Asp Pro Asp Pro
            195                 200                 205

gac gcg atc ggc aag acc ttc gtc cgg cac ggc ggc ttc ctc gac ggt      671
Asp Ala Ile Gly Lys Thr Phe Val Arg His Gly Gly Phe Leu Asp Gly
        210                 215                 220

gcg acc ggc ttc gac gcg gcg ttc ttc ggg atc agc ccg cgc gag gcc      719
Ala Thr Gly Phe Asp Ala Ala Phe Phe Gly Ile Ser Pro Arg Glu Ala
    225                 230                 235

ctg gcc atg gac ccg cag caa cgg gtg ctc ctg gag acg tcc tgg gag      767
Leu Ala Met Asp Pro Gln Gln Arg Val Leu Leu Glu Thr Ser Trp Glu
240                 245                 250                 255

gcg ttc gaa agc gcg ggc atc acc ccg gac gcg gcg cgg ggc agc gac      815
```

-continued

```
Ala Phe Glu Ser Ala Gly Ile Thr Pro Asp Ala Ala Arg Gly Ser Asp
            260                 265                 270

acc ggc gtg ttc atc ggc gcg ttc tcc tac ggg tac ggc acg ggt gcg      863
Thr Gly Val Phe Ile Gly Ala Phe Ser Tyr Gly Tyr Gly Thr Gly Ala
        275                 280                 285

gat acc aac ggc ttc ggc gcg aca ggg tcg cag acc agc gtg ctc tcc      911
Asp Thr Asn Gly Phe Gly Ala Thr Gly Ser Gln Thr Ser Val Leu Ser
    290                 295                 300

ggc cgc ctc tcg tac ttc tac ggt ctg gag ggc cct tcg gtc acg gtc      959
Gly Arg Leu Ser Tyr Phe Tyr Gly Leu Glu Gly Pro Ser Val Thr Val
305                 310                 315

gac acc gcc tgc tcg tcg tca ctg gtc gcc ctg cac cag gca ggg cag     1007
Asp Thr Ala Cys Ser Ser Ser Leu Val Ala Leu His Gln Ala Gly Gln
320                 325                 330                 335

tcc ctg cgc tcg ggc gaa tgc tcg ctc gcc ctg gtc ggc ggt gtc acg     1055
Ser Leu Arg Ser Gly Glu Cys Ser Leu Ala Leu Val Gly Gly Val Thr
            340                 345                 350

gtg atg gcg tcg ccc ggc gga ttc gtc gag ttc tcc cgg cag cgc ggg     1103
Val Met Ala Ser Pro Gly Gly Phe Val Glu Phe Ser Arg Gln Arg Gly
        355                 360                 365

ctc gcg ccg gac ggg cgg gcg aag gcg ttc ggc gcg ggc gcg gac ggt     1151
Leu Ala Pro Asp Gly Arg Ala Lys Ala Phe Gly Ala Gly Ala Asp Gly
    370                 375                 380

acg agc ttc gcc gag ggc gcc ggt gcc ctg gtg gtc gag cgg ctc tcc     1199
Thr Ser Phe Ala Glu Gly Ala Gly Ala Leu Val Val Glu Arg Leu Ser
385                 390                 395

gac gcg gag cgc cac ggc cac acc gtc ctc gcc ctc gta cgc ggc tcc     1247
Asp Ala Glu Arg His Gly His Thr Val Leu Ala Leu Val Arg Gly Ser
400                 405                 410                 415

gcg gct aac tcc gac ggc gcg tcg aac ggt ctg tcg gcg ccg aac ggc     1295
Ala Ala Asn Ser Asp Gly Ala Ser Asn Gly Leu Ser Ala Pro Asn Gly
            420                 425                 430

ccc tcc cag gaa cgc gtc atc cac cag gcc ctc gcg aac gcg aaa ctc     1343
Pro Ser Gln Glu Arg Val Ile His Gln Ala Leu Ala Asn Ala Lys Leu
        435                 440                 445

acc ccc gcc gat gtc gac gcg gtc gag gcg cac ggc acc ggc acc cgc     1391
Thr Pro Ala Asp Val Asp Ala Val Glu Ala His Gly Thr Gly Thr Arg
    450                 455                 460

ctc ggc gac ccc atc gag gcg cag gcg ctg ctc gcg acg tac gga cag     1439
Leu Gly Asp Pro Ile Glu Ala Gln Ala Leu Leu Ala Thr Tyr Gly Gln
465                 470                 475

gac cgg gcg acg ccc ctg ctg ctc ggc tcg ctg aag tcg aac atc ggg     1487
Asp Arg Ala Thr Pro Leu Leu Leu Gly Ser Leu Lys Ser Asn Ile Gly
480                 485                 490                 495

cac gcc cag gcc gcg tca ggg gtc gcc ggg atc atc aag atg gtg cag     1535
His Ala Gln Ala Ala Ser Gly Val Ala Gly Ile Ile Lys Met Val Gln
            500                 505                 510

gcc atc cgg cac ggg gaa ctg ccg ccg aca ctg cac gcg gac gag ccg     1583
Ala Ile Arg His Gly Glu Leu Pro Pro Thr Leu His Ala Asp Glu Pro
        515                 520                 525

tcg ccg cac gtc gac tgg acg gcc ggt gcc gtc gag ctc ctg acg tcg     1631
Ser Pro His Val Asp Trp Thr Ala Gly Ala Val Glu Leu Leu Thr Ser
    530                 535                 540

gcc cgg ccg tgg ccg ggg acc ggt cgc ccg cgc cgc gct gcc gtc tcg     1679
Ala Arg Pro Trp Pro Gly Thr Gly Arg Pro Arg Arg Ala Ala Val Ser
545                 550                 555

tcg ttc ggc gtg agc ggc acg aac gcc cac atc atc ctt gag gca gga     1727
Ser Phe Gly Val Ser Gly Thr Asn Ala His Ile Ile Leu Glu Ala Gly
560                 565                 570                 575
```

-continued

```
ccg gtc aaa acg gga ccg gtc gag gca gga gcg atc gag gca gga ccg     1775
Pro Val Lys Thr Gly Pro Val Glu Ala Gly Ala Ile Glu Ala Gly Pro
                580                 585                 590

gtc gaa gta gga ccg gtc gag gct gga ccg ctc ccc gcg gcg ccg ccg     1823
Val Glu Val Gly Pro Val Glu Ala Gly Pro Leu Pro Ala Ala Pro Pro
            595                 600                 605

tca gca ccg ggc gaa gac ctt ccg ctg ctc gtg tcg gcg cgt tcc ccg     1871
Ser Ala Pro Gly Glu Asp Leu Pro Leu Leu Val Ser Ala Arg Ser Pro
        610                 615                 620

gag gca ctc gac gag cag atc ggg cgc ctg cgc gcc tat ctc gac acc     1919
Glu Ala Leu Asp Glu Gln Ile Gly Arg Leu Arg Ala Tyr Leu Asp Thr
    625                 630                 635

ggc ccg ggc gtc gac cgg gcg gcc gtg gcg cag aca ctg gcc cgg cgt     1967
Gly Pro Gly Val Asp Arg Ala Ala Val Ala Gln Thr Leu Ala Arg Arg
640                 645                 650                 655

acg cac ttc acc cac cgg gcc gta ctg ctc ggg gac acc gtc atc ggc     2015
Thr His Phe Thr His Arg Ala Val Leu Leu Gly Asp Thr Val Ile Gly
                660                 665                 670

gct ccc ccc gcg gac cag gcc gac gaa ctc gtc ttc gtc tac tcc ggt     2063
Ala Pro Pro Ala Asp Gln Ala Asp Glu Leu Val Phe Val Tyr Ser Gly
            675                 680                 685

cag ggc acc cag cat ccc gcg atg ggc gag caa ctc gcg gcc gcg ttc     2111
Gln Gly Thr Gln His Pro Ala Met Gly Glu Gln Leu Ala Ala Ala Phe
        690                 695                 700

ccc gtg ttc gcc gat gcc tgg cac gac gcg ctc cga cgg ctc gac gac     2159
Pro Val Phe Ala Asp Ala Trp His Asp Ala Leu Arg Arg Leu Asp Asp
    705                 710                 715

ccc gac ccg cac gac ccc aca cgg agc cag cac acg ctc ttc gcc cac     2207
Pro Asp Pro His Asp Pro Thr Arg Ser Gln His Thr Leu Phe Ala His
720                 725                 730                 735

cag gcg gcg ttc acc gcc ctc ctg agg tcc tgg gac atc acg ccg cac     2255
Gln Ala Ala Phe Thr Ala Leu Leu Arg Ser Trp Asp Ile Thr Pro His
                740                 745                 750

gcc gtc atc ggc cac tcg ctc ggc gag atc acc gcc gcg tac gcc gcc     2303
Ala Val Ile Gly His Ser Leu Gly Glu Ile Thr Ala Ala Tyr Ala Ala
            755                 760                 765

ggg atc ctg tcg ctc gac gac gcc tgc acc ctg atc acc acg cgt gcc     2351
Gly Ile Leu Ser Leu Asp Asp Ala Cys Thr Leu Ile Thr Thr Arg Ala
        770                 775                 780

cgc ctc atg cac acg ctt ccg ccg ccc ggc gcc atg gtc acc gtg ctg     2399
Arg Leu Met His Thr Leu Pro Pro Pro Gly Ala Met Val Thr Val Leu
    785                 790                 795

acc agc gag gag gag gcc cgt cag gcg ctg cgg ccg ggc gtg gag atc     2447
Thr Ser Glu Glu Glu Ala Arg Gln Ala Leu Arg Pro Gly Val Glu Ile
800                 805                 810                 815

gcc gcg gtc ttc ggc ccg cac tcc gtc gtg ctc tcg ggc gac gag gac     2495
Ala Ala Val Phe Gly Pro His Ser Val Val Leu Ser Gly Asp Glu Asp
                820                 825                 830

gcc gtg ctc gac gtc gca cag cgg ctc ggc atc cac cac cgt ctg ccc     2543
Ala Val Leu Asp Val Ala Gln Arg Leu Gly Ile His His Arg Leu Pro
            835                 840                 845

gcg ccg cac gcg ggc cac tcc gcg cac atg gaa ccc gtg gcc gcc gag     2591
Ala Pro His Ala Gly His Ser Ala His Met Glu Pro Val Ala Ala Glu
        850                 855                 860

ctg ctc gcc acc act cgc gag ctc cgt tac gac cgg ccc cac acc gcc     2639
Leu Leu Ala Thr Thr Arg Glu Leu Arg Tyr Asp Arg Pro His Thr Ala
    865                 870                 875

atc ccg aac gac ccc acc acc gcc gag tac tgg gcc gag cag gtc cgc     2687
Ile Pro Asn Asp Pro Thr Thr Ala Glu Tyr Trp Ala Glu Gln Val Arg
880                 885                 890                 895
```

-continued

```
aac ccc gtg ctg ttc cac gcc cac acc cag cgg tac ccc gac gcc gtg     2735
Asn Pro Val Leu Phe His Ala His Thr Gln Arg Tyr Pro Asp Ala Val
                900                 905                 910

ttc gtc gag atc ggc ccc ggc cag gac ctc tca ccg ctg gtc gac ggc     2783
Phe Val Glu Ile Gly Pro Gly Gln Asp Leu Ser Pro Leu Val Asp Gly
            915                 920                 925

atc gcc ctg cag aac ggc acg gcg gac gag gtg cac gcg ctg cac acc     2831
Ile Ala Leu Gln Asn Gly Thr Ala Asp Glu Val His Ala Leu His Thr
        930                 935                 940

gcg ctc gcc cgc ctc ttc aca cgc ggc gcc acg ctc gac tgg tcc cgc     2879
Ala Leu Ala Arg Leu Phe Thr Arg Gly Ala Thr Leu Asp Trp Ser Arg
    945                 950                 955

atc ctc ggc ggt gct tcg cgg cac gac cct gac gtc ccc tcg tac gcg     2927
Ile Leu Gly Gly Ala Ser Arg His Asp Pro Asp Val Pro Ser Tyr Ala
960                 965                 970                 975

ttc cag cgg cgt ccc tac tgg atc gag tcg gct ccc ccg gcc acg gcc     2975
Phe Gln Arg Arg Pro Tyr Trp Ile Glu Ser Ala Pro Pro Ala Thr Ala
                980                 985                 990

gac tcg ggc cac ccc gtc ctc ggc acc gga gtc gcc gtc gcc ggg tcg     3023
Asp Ser Gly His Pro Val Leu Gly Thr Gly Val Ala Val Ala Gly Ser
            995                 1000                1005

ccg ggc cgg gtg ttc acg ggt ccc gtg ccc gcc ggt gcg gac cgc gcg     3071
Pro Gly Arg Val Phe Thr Gly Pro Val Pro Ala Gly Ala Asp Arg Ala
        1010                1015                1020

gtg ttc atc gcc gaa ctg gcg ctc gcc gcc gcc gac gcc acc gac tgc     3119
Val Phe Ile Ala Glu Leu Ala Leu Ala Ala Ala Asp Ala Thr Asp Cys
    1025                1030                1035

gcc acg gtc gaa cag ctc gac gtc acc tcc gtg ccc ggc gga tcc gcc     3167
Ala Thr Val Glu Gln Leu Asp Val Thr Ser Val Pro Gly Gly Ser Ala
1040                1045                1050                1055

cgc ggc agg gcc acc gcg cag acc tgg gtc gat gaa ccc gcc gcc gac     3215
Arg Gly Arg Ala Thr Ala Gln Thr Trp Val Asp Glu Pro Ala Ala Asp
                1060                1065                1070

ggg cgg cgc cgc ttc acc gtc cac acc cgc gtc ggc gac gcc ccg tgg     3263
Gly Arg Arg Arg Phe Thr Val His Thr Arg Val Gly Asp Ala Pro Trp
            1075                1080                1085

acg ctg cac gcc gag ggg gtt ctc cgc ccc ggc cgc gtg ccc cag ccc     3311
Thr Leu His Ala Glu Gly Val Leu Arg Pro Gly Arg Val Pro Gln Pro
        1090                1095                1100

gaa gcc gtc gac acc gcc tgg ccc ccg ccg ggc gcg gtg ccc gcg gac     3359
Glu Ala Val Asp Thr Ala Trp Pro Pro Pro Gly Ala Val Pro Ala Asp
    1105                1110                1115

ggg ctg ccc ggg gcg tgg cga cgc gcg gac cag gtc ttc gtc gaa gcc     3407
Gly Leu Pro Gly Ala Trp Arg Arg Ala Asp Gln Val Phe Val Glu Ala
1120                1125                1130                1135

gaa gtc gac agc cct gac ggc ttc gtg gca cac ccc gac ctg ctc gac     3455
Glu Val Asp Ser Pro Asp Gly Phe Val Ala His Pro Asp Leu Leu Asp
                1140                1145                1150

gcg gtc ttc tcc gcg gtc ggc gac ggg agc cgc cag ccg acc gga tgg     3503
Ala Val Phe Ser Ala Val Gly Asp Gly Ser Arg Gln Pro Thr Gly Trp
            1155                1160                1165

cgc gac ctc gcg gtg cac gcg tcg gac gcc acc gtg ctg cgc gcc tgc     3551
Arg Asp Leu Ala Val His Ala Ser Asp Ala Thr Val Leu Arg Ala Cys
        1170                1175                1180

ctc acc cgc cgc gac agt ggt gtc gtg gag ctc gcc gcc ttc gac ggt     3599
Leu Thr Arg Arg Asp Ser Gly Val Val Glu Leu Ala Ala Phe Asp Gly
    1185                1190                1195

gcc gga atg ccg gtg ctc acc gcg gag tcg gtg acg ctg ggc gag gtc     3647
Ala Gly Met Pro Val Leu Thr Ala Glu Ser Val Thr Leu Gly Glu Val
```

-continued

```
1200                1205                1210                1215

gcg tcg gca ggc gga tcc gac gag tcg gac ggt ctg ctt cgg ctt gag      3695
Ala Ser Ala Gly Gly Ser Asp Glu Ser Asp Gly Leu Leu Arg Leu Glu
               1220                1225                1230

tgg ttg ccg gtg gcg gag gcc cac tac gac ggt gcc gac gag ctg ccc      3743
Trp Leu Pro Val Ala Glu Ala His Tyr Asp Gly Ala Asp Glu Leu Pro
           1235                1240                1245

gag ggc tac acc ctc atc acc gcc aca cac ccc gac gac ccc gac gac      3791
Glu Gly Tyr Thr Leu Ile Thr Ala Thr His Pro Asp Asp Pro Asp Asp
       1250                1255                1260

ccc acc aac ccc cac aac aca ccc aca cgc acc cac aca caa acc aca      3839
Pro Thr Asn Pro His Asn Thr Pro Thr Arg Thr His Thr Gln Thr Thr
   1265                1270                1275

cgc gtc ctc acc gcc ctc caa cac cac ctc atc acc acc aac cac acc      3887
Arg Val Leu Thr Ala Leu Gln His His Leu Ile Thr Thr Asn His Thr
1280                1285                1290                1295

ctc atc gtc cac acc acc acc gac ccc cca ggc gcc gcc gtc acc ggc      3935
Leu Ile Val His Thr Thr Thr Asp Pro Pro Gly Ala Ala Val Thr Gly
               1300                1305                1310

ctc acc cgc acc gca caa aac gaa cac ccc ggc cgc atc cac ctc atc      3983
Leu Thr Arg Thr Ala Gln Asn Glu His Pro Gly Arg Ile His Leu Ile
           1315                1320                1325

gaa acc cac cac ccc cac acc cca ctc ccc ctc acc caa ctc acc acc      4031
Glu Thr His His Pro His Thr Pro Leu Pro Leu Thr Gln Leu Thr Thr
       1330                1335                1340

ctc cac caa ccc cac cta cgc ctc acc aac aac acc ctc cac acc ccc      4079
Leu His Gln Pro His Leu Arg Leu Thr Asn Asn Thr Leu His Thr Pro
   1345                1350                1355

cac ctc acc ccc atc acc acc cac cac aac acc acc aca acc acc ccc      4127
His Leu Thr Pro Ile Thr Thr His His Asn Thr Thr Thr Thr Thr Pro
1360                1365                1370                1375

aac acc cca ccc ctc aac ccc aac cac gcc atc ctc atc acc ggc ggc      4175
Asn Thr Pro Pro Leu Asn Pro Asn His Ala Ile Leu Ile Thr Gly Gly
               1380                1385                1390

tcc ggc acc ctc gcc ggc atc ctc gcc cgc cac ctc aac cac ccc cac      4223
Ser Gly Thr Leu Ala Gly Ile Leu Ala Arg His Leu Asn His Pro His
           1395                1400                1405

acc tac ctc ctc tcc cgc aca cca cca ccc ccc acc aca ccc ggc acc      4271
Thr Tyr Leu Leu Ser Arg Thr Pro Pro Pro Pro Thr Thr Pro Gly Thr
       1410                1415                1420

cac atc ccc tgc gac ctc acc gac ccc acc caa atc acc caa gcc ctc      4319
His Ile Pro Cys Asp Leu Thr Asp Pro Thr Gln Ile Thr Gln Ala Leu
   1425                1430                1435

acc cac ata cca caa ccc ctc acc ggc atc ttc cac acc gcc gcc acc      4367
Thr His Ile Pro Gln Pro Leu Thr Gly Ile Phe His Thr Ala Ala Thr
1440                1445                1450                1455

ctc gac gac gcc acc ctc acc aac ctc acc ccc caa cac ctc acc acc      4415
Leu Asp Asp Ala Thr Leu Thr Asn Leu Thr Pro Gln His Leu Thr Thr
               1460                1465                1470

acc ctc caa ccc aaa gcc gac gcc gcc tgg cac ctc cac cac cac acc      4463
Thr Leu Gln Pro Lys Ala Asp Ala Ala Trp His Leu His His His Thr
           1475                1480                1485

caa aac caa ccc ctc acc cac ttc gtc ctc tac tcc agc gcc gcc gcc      4511
Gln Asn Gln Pro Leu Thr His Phe Val Leu Tyr Ser Ser Ala Ala Ala
       1490                1495                1500

acc ctc ggc agc ccc ggc caa gcc aac tac gcc gcc gcc aac gcc ttc      4559
Thr Leu Gly Ser Pro Gly Gln Ala Asn Tyr Ala Ala Ala Asn Ala Phe
   1505                1510                1515

ctc gac gcc ctc gcc acc cac cgc cac acc caa gga caa ccc gcc acc      4607
```

-continued

```
Leu Asp Ala Leu Ala Thr His Arg His Thr Gln Gly Gln Pro Ala Thr
1520                1525                1530                1535

acc atc gcc tgg ggc atg tgg cac acc acc aca ctc acc agc caa      4655
Thr Ile Ala Trp Gly Met Trp His Thr Thr Thr Leu Thr Ser Gln
               1540                1545                1550

ctc acc gac agc gac cgc gac cgc atc cgc cgc ggc ggc ttc ctg ccg  4703
Leu Thr Asp Ser Asp Arg Asp Arg Ile Arg Arg Gly Gly Phe Leu Pro
           1555                1560                1565

atc tcg gac gac gag ggc atg c                                    4725
Ile Ser Asp Asp Glu Gly Met
       1570


<210> SEQ ID NO 25
<211> LENGTH: 1574
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 25

Met Arg Leu Tyr Glu Ala Ala Arg Arg Thr Gly Ser Pro Val Val Val
  1               5                  10                  15

Ala Ala Ala Leu Asp Asp Ala Pro Asp Val Pro Leu Leu Arg Gly Leu
             20                  25                  30

Arg Arg Thr Thr Val Arg Arg Ala Ala Val Arg Glu Arg Ser Leu Ala
         35                  40                  45

Asp Arg Ser Pro Cys Cys Pro Thr Thr Ser Ala Pro Thr Pro Pro Ser
     50                  55                  60

Arg Ser Ser Trp Asn Ser Thr Ala Thr Val Leu Gly His Leu Gly Ala
 65                  70                  75                  80

Glu Asp Ile Pro Ala Thr Thr Thr Phe Lys Glu Leu Gly Ile Asp Ser
                 85                  90                  95

Leu Thr Ala Val Gln Leu Arg Asn Ala Leu Thr Thr Ala Thr Gly Val
            100                 105                 110

Arg Leu Asn Ala Thr Ala Val Phe Asp Phe Pro Thr Pro Arg Ala Leu
        115                 120                 125

Ala Ala Arg Leu Gly Asp Glu Leu Ala Gly Thr Arg Ala Pro Val Ala
    130                 135                 140

Ala Arg Thr Ala Ala Thr Ala Ala Ala His Asp Glu Pro Leu Ala Ile
145                 150                 155                 160

Val Gly Met Ala Cys Arg Leu Pro Gly Gly Val Ala Ser Pro Gln Glu
                165                 170                 175

Leu Trp Arg Leu Val Ala Ser Gly Thr Asp Ala Ile Thr Glu Phe Pro
            180                 185                 190

Ala Asp Arg Gly Trp Asp Val Asp Ala Leu Tyr Asp Pro Asp Pro Asp
        195                 200                 205

Ala Ile Gly Lys Thr Phe Val Arg His Gly Gly Phe Leu Asp Gly Ala
    210                 215                 220

Thr Gly Phe Asp Ala Ala Phe Phe Gly Ile Ser Pro Arg Glu Ala Leu
225                 230                 235                 240

Ala Met Asp Pro Gln Gln Arg Val Leu Leu Glu Thr Ser Trp Glu Ala
                245                 250                 255

Phe Glu Ser Ala Gly Ile Thr Pro Asp Ala Ala Arg Gly Ser Asp Thr
            260                 265                 270

Gly Val Phe Ile Gly Ala Phe Ser Tyr Gly Tyr Gly Thr Gly Ala Asp
        275                 280                 285
```

-continued

```
Thr Asn Gly Phe Gly Ala Thr Gly Ser Gln Thr Ser Val Leu Ser Gly
    290                 295                 300

Arg Leu Ser Tyr Phe Tyr Gly Leu Glu Gly Pro Ser Val Thr Val Asp
305                 310                 315                 320

Thr Ala Cys Ser Ser Ser Leu Val Ala Leu His Gln Ala Gly Gln Ser
                325                 330                 335

Leu Arg Ser Gly Glu Cys Ser Leu Ala Leu Val Gly Gly Val Thr Val
            340                 345                 350

Met Ala Ser Pro Gly Gly Phe Val Glu Phe Ser Arg Gln Arg Gly Leu
        355                 360                 365

Ala Pro Asp Gly Arg Ala Lys Ala Phe Gly Ala Gly Ala Asp Gly Thr
    370                 375                 380

Ser Phe Ala Glu Gly Ala Gly Ala Leu Val Val Glu Arg Leu Ser Asp
385                 390                 395                 400

Ala Glu Arg His Gly His Thr Val Leu Ala Leu Val Arg Gly Ser Ala
                405                 410                 415

Ala Asn Ser Asp Gly Ala Ser Asn Gly Leu Ser Ala Pro Asn Gly Pro
            420                 425                 430

Ser Gln Glu Arg Val Ile His Gln Ala Leu Ala Asn Ala Lys Leu Thr
        435                 440                 445

Pro Ala Asp Val Asp Ala Val Glu Ala His Gly Thr Gly Thr Arg Leu
    450                 455                 460

Gly Asp Pro Ile Glu Ala Gln Ala Leu Leu Ala Thr Tyr Gly Gln Asp
465                 470                 475                 480

Arg Ala Thr Pro Leu Leu Leu Gly Ser Leu Lys Ser Asn Ile Gly His
                485                 490                 495

Ala Gln Ala Ala Ser Gly Val Ala Gly Ile Ile Lys Met Val Gln Ala
            500                 505                 510

Ile Arg His Gly Glu Leu Pro Pro Thr Leu His Ala Asp Glu Pro Ser
        515                 520                 525

Pro His Val Asp Trp Thr Ala Gly Ala Val Glu Leu Leu Thr Ser Ala
    530                 535                 540

Arg Pro Trp Pro Gly Thr Gly Arg Pro Arg Arg Ala Ala Val Ser Ser
545                 550                 555                 560

Phe Gly Val Ser Gly Thr Asn Ala His Ile Ile Leu Glu Ala Gly Pro
                565                 570                 575

Val Lys Thr Gly Pro Val Glu Ala Gly Ala Ile Glu Ala Gly Pro Val
            580                 585                 590

Glu Val Gly Pro Val Glu Ala Gly Pro Leu Pro Ala Ala Pro Pro Ser
        595                 600                 605

Ala Pro Gly Glu Asp Leu Pro Leu Leu Val Ser Ala Arg Ser Pro Glu
    610                 615                 620

Ala Leu Asp Glu Gln Ile Gly Arg Leu Arg Ala Tyr Leu Asp Thr Gly
625                 630                 635                 640

Pro Gly Val Asp Arg Ala Ala Val Ala Gln Thr Leu Ala Arg Arg Thr
                645                 650                 655

His Phe Thr His Arg Ala Val Leu Leu Gly Asp Thr Val Ile Gly Ala
            660                 665                 670

Pro Pro Ala Asp Gln Ala Asp Glu Leu Val Phe Val Tyr Ser Gly Gln
        675                 680                 685

Gly Thr Gln His Pro Ala Met Gly Glu Gln Leu Ala Ala Ala Phe Pro
    690                 695                 700
```

-continued

```
Val Phe Ala Asp Ala Trp His Asp Ala Leu Arg Arg Leu Asp Asp Pro
705                 710                 715                 720

Asp Pro His Asp Pro Thr Arg Ser Gln His Thr Leu Phe Ala His Gln
                725                 730                 735

Ala Ala Phe Thr Ala Leu Leu Arg Ser Trp Asp Ile Thr Pro His Ala
            740                 745                 750

Val Ile Gly His Ser Leu Gly Glu Ile Thr Ala Ala Tyr Ala Ala Gly
        755                 760                 765

Ile Leu Ser Leu Asp Asp Ala Cys Thr Leu Ile Thr Thr Arg Ala Arg
    770                 775                 780

Leu Met His Thr Leu Pro Pro Pro Gly Ala Met Val Thr Val Leu Thr
785                 790                 795                 800

Ser Glu Glu Glu Ala Arg Gln Ala Leu Arg Pro Gly Val Glu Ile Ala
                805                 810                 815

Ala Val Phe Gly Pro His Ser Val Val Leu Ser Gly Asp Glu Asp Ala
            820                 825                 830

Val Leu Asp Val Ala Gln Arg Leu Gly Ile His His Arg Leu Pro Ala
        835                 840                 845

Pro His Ala Gly His Ser Ala His Met Glu Pro Val Ala Ala Glu Leu
    850                 855                 860

Leu Ala Thr Thr Arg Glu Leu Arg Tyr Asp Arg Pro His Thr Ala Ile
865                 870                 875                 880

Pro Asn Asp Pro Thr Thr Ala Glu Tyr Trp Ala Glu Gln Val Arg Asn
                885                 890                 895

Pro Val Leu Phe His Ala His Thr Gln Arg Tyr Pro Asp Ala Val Phe
            900                 905                 910

Val Glu Ile Gly Pro Gly Gln Asp Leu Ser Pro Leu Val Asp Gly Ile
        915                 920                 925

Ala Leu Gln Asn Gly Thr Ala Asp Glu Val His Ala Leu His Thr Ala
    930                 935                 940

Leu Ala Arg Leu Phe Thr Arg Gly Ala Thr Leu Asp Trp Ser Arg Ile
945                 950                 955                 960

Leu Gly Gly Ala Ser Arg His Asp Pro Asp Val Pro Ser Tyr Ala Phe
                965                 970                 975

Gln Arg Arg Pro Tyr Trp Ile Glu Ser Ala Pro Pro Ala Thr Ala Asp
            980                 985                 990

Ser Gly His Pro Val Leu Gly Thr Gly Val Ala Val Ala Gly Ser Pro
        995                 1000                1005

Gly Arg Val Phe Thr Gly Pro Val Pro Ala Gly Ala Asp Arg Ala Val
    1010                1015                1020

Phe Ile Ala Glu Leu Ala Leu Ala Ala Ala Asp Ala Thr Asp Cys Ala
1025                1030                1035                1040

Thr Val Glu Gln Leu Asp Val Thr Ser Val Pro Gly Gly Ser Ala Arg
                1045                1050                1055

Gly Arg Ala Thr Ala Gln Thr Trp Val Asp Glu Pro Ala Ala Asp Gly
            1060                1065                1070

Arg Arg Arg Phe Thr Val His Thr Arg Val Gly Asp Ala Pro Trp Thr
        1075                1080                1085

Leu His Ala Glu Gly Val Leu Arg Pro Gly Arg Val Pro Gln Pro Glu
    1090                1095                1100

Ala Val Asp Thr Ala Trp Pro Pro Pro Gly Ala Val Pro Ala Asp Gly
1105                1110                1115                1120

Leu Pro Gly Ala Trp Arg Arg Ala Asp Gln Val Phe Val Glu Ala Glu
```

-continued

```
                1125                1130                1135

Val Asp Ser Pro Asp Gly Phe Val Ala His Pro Asp Leu Leu Asp Ala
            1140                1145                1150

Val Phe Ser Ala Val Gly Asp Gly Ser Arg Gln Pro Thr Gly Trp Arg
        1155                1160                1165

Asp Leu Ala Val His Ala Ser Asp Ala Thr Val Leu Arg Ala Cys Leu
    1170                1175                1180

Thr Arg Arg Asp Ser Gly Val Val Glu Leu Ala Ala Phe Asp Gly Ala
1185                1190                1195                1200

Gly Met Pro Val Leu Thr Ala Glu Ser Val Thr Leu Gly Glu Val Ala
                1205                1210                1215

Ser Ala Gly Gly Ser Asp Glu Ser Asp Gly Leu Leu Arg Leu Glu Trp
            1220                1225                1230

Leu Pro Val Ala Glu Ala His Tyr Asp Gly Ala Asp Glu Leu Pro Glu
        1235                1240                1245

Gly Tyr Thr Leu Ile Thr Ala Thr His Pro Asp Asp Pro Asp Asp Pro
    1250                1255                1260

Thr Asn Pro His Asn Thr Pro Thr Arg Thr His Thr Gln Thr Thr Arg
1265                1270                1275                1280

Val Leu Thr Ala Leu Gln His His Leu Ile Thr Thr Asn His Thr Leu
                1285                1290                1295

Ile Val His Thr Thr Thr Asp Pro Pro Gly Ala Ala Val Thr Gly Leu
            1300                1305                1310

Thr Arg Thr Ala Gln Asn Glu His Pro Gly Arg Ile His Leu Ile Glu
        1315                1320                1325

Thr His His Pro His Thr Pro Leu Pro Leu Thr Gln Leu Thr Thr Leu
    1330                1335                1340

His Gln Pro His Leu Arg Leu Thr Asn Asn Thr Leu His Thr Pro His
1345                1350                1355                1360

Leu Thr Pro Ile Thr Thr His His Asn Thr Thr Thr Thr Thr Pro Asn
                1365                1370                1375

Thr Pro Pro Leu Asn Pro Asn His Ala Ile Leu Ile Thr Gly Gly Ser
            1380                1385                1390

Gly Thr Leu Ala Gly Ile Leu Ala Arg His Leu Asn His Pro His Thr
        1395                1400                1405

Tyr Leu Leu Ser Arg Thr Pro Pro Pro Pro Thr Thr Pro Gly Thr His
    1410                1415                1420

Ile Pro Cys Asp Leu Thr Asp Pro Thr Gln Ile Thr Gln Ala Leu Thr
1425                1430                1435                1440

His Ile Pro Gln Pro Leu Thr Gly Ile Phe His Thr Ala Ala Thr Leu
                1445                1450                1455

Asp Asp Ala Thr Leu Thr Asn Leu Thr Pro Gln His Leu Thr Thr Thr
            1460                1465                1470

Leu Gln Pro Lys Ala Asp Ala Ala Trp His Leu His His His Thr Gln
        1475                1480                1485

Asn Gln Pro Leu Thr His Phe Val Leu Tyr Ser Ser Ala Ala Ala Thr
    1490                1495                1500

Leu Gly Ser Pro Gly Gln Ala Asn Tyr Ala Ala Ala Asn Ala Phe Leu
1505                1510                1515                1520

Asp Ala Leu Ala Thr His Arg His Thr Gln Gly Gln Pro Ala Thr Thr
                1525                1530                1535

Ile Ala Trp Gly Met Trp His Thr Thr Thr Thr Leu Thr Ser Gln Leu
            1540                1545                1550
```

```
Thr Asp Ser Asp Arg Asp Arg Ile Arg Arg Gly Gly Phe Leu Pro Ile
        1555                1560                1565

Ser Asp Asp Glu Gly Met
    1570


<210> SEQ ID NO 26
<211> LENGTH: 4674
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (3)..(4673)

<400> SEQUENCE: 26

gc atg cgg ctg tac gag gcg gca cgg cgc acc gga agt ccc gtg gtg        47
   Met Arg Leu Tyr Glu Ala Ala Arg Arg Thr Gly Ser Pro Val Val
     1               5                  10                  15

gtg gcg gcc gcg ctc gac gac gcg ccg gac gtg ccg ctg ctg cgc ggg       95
Val Ala Ala Ala Leu Asp Asp Ala Pro Asp Val Pro Leu Leu Arg Gly
                20                  25                  30

ctg cgg cgt acg acc gtc cgg cgt gcc gcc gtc cgg gaa cgc tct ctc      143
Leu Arg Arg Thr Thr Val Arg Arg Ala Ala Val Arg Glu Arg Ser Leu
            35                  40                  45

gcc gac cgc tcg ccg tgc tgc ccg acg acg agc gcg ccg acg cct ccc      191
Ala Asp Arg Ser Pro Cys Cys Pro Thr Thr Ser Ala Pro Thr Pro Pro
        50                  55                  60

tcg cgt tcg tcc tgg aac agc acc gcc acc gtg ctc ggc cac ctg ggc      239
Ser Arg Ser Ser Trp Asn Ser Thr Ala Thr Val Leu Gly His Leu Gly
    65                  70                  75

gcc gaa gac atc ccg gcg acg acg acg ttc aag gaa ctc ggc atc gac      287
Ala Glu Asp Ile Pro Ala Thr Thr Thr Phe Lys Glu Leu Gly Ile Asp
 80                  85                  90                  95

tcg ctc acc gcg gtc cag ctg cgc aac gcg ctg acc acg gcg acc ggc      335
Ser Leu Thr Ala Val Gln Leu Arg Asn Ala Leu Thr Thr Ala Thr Gly
                100                 105                 110

gta cgc ctc aac gcc aca gcg gtc ttc gac ttt ccg acg ccg cgc gcg      383
Val Arg Leu Asn Ala Thr Ala Val Phe Asp Phe Pro Thr Pro Arg Ala
            115                 120                 125

ctc gcc gcg aga ctc ggc gac gag ctg gcc ggt acc cgc gcg ccc gtc      431
Leu Ala Ala Arg Leu Gly Asp Glu Leu Ala Gly Thr Arg Ala Pro Val
        130                 135                 140

gcg gcc cgg acc gcg gcc acc gcg gcc gcg cac gac gaa ccg ctg gcg      479
Ala Ala Arg Thr Ala Ala Thr Ala Ala Ala His Asp Glu Pro Leu Ala
    145                 150                 155

atc gtg ggc atg gcc tgc cgt ctg ccg ggc ggg gtc gcg tcg cca cag      527
Ile Val Gly Met Ala Cys Arg Leu Pro Gly Gly Val Ala Ser Pro Gln
160                 165                 170                 175

gag ctg tgg cgt ctc gtc gcg tcc ggc acc gac gcc atc acg gag ttc      575
Glu Leu Trp Arg Leu Val Ala Ser Gly Thr Asp Ala Ile Thr Glu Phe
                180                 185                 190

ccc gcg gac cgc ggc tgg gac gtg gac gcg ctc tac gac ccg gac ccc      623
Pro Ala Asp Arg Gly Trp Asp Val Asp Ala Leu Tyr Asp Pro Asp Pro
            195                 200                 205

gac gcg atc ggc aag acc ttc gtc cgg cac ggc ggc ttc ctc gac ggt      671
Asp Ala Ile Gly Lys Thr Phe Val Arg His Gly Gly Phe Leu Asp Gly
        210                 215                 220

gcg acc ggc ttc gac gcg gcg ttc ttc ggg atc agc ccg cgc gag gcc      719
Ala Thr Gly Phe Asp Ala Ala Phe Phe Gly Ile Ser Pro Arg Glu Ala
```

-continued

```
    225                 230                 235

ctg gcc atg gac ccg cag caa cgg gtg ctc ctg gag acg tcc tgg gag      767
Leu Ala Met Asp Pro Gln Gln Arg Val Leu Leu Glu Thr Ser Trp Glu
240                 245                 250                 255

gcg ttc gaa agc gcg ggc atc acc ccg gac gcg gcg cgg ggc agc gac      815
Ala Phe Glu Ser Ala Gly Ile Thr Pro Asp Ala Ala Arg Gly Ser Asp
                260                 265                 270

acc ggc gtg ttc atc ggc gcg ttc tcc tac ggg tac ggc acg ggt gcg      863
Thr Gly Val Phe Ile Gly Ala Phe Ser Tyr Gly Tyr Gly Thr Gly Ala
            275                 280                 285

gat acc aac ggc ttc ggc gcg aca ggg tcg cag acc agc gtg ctc tcc      911
Asp Thr Asn Gly Phe Gly Ala Thr Gly Ser Gln Thr Ser Val Leu Ser
        290                 295                 300

ggc cgc ctc tcg tac ttc tac ggt ctg gag ggc cct tcg gtc acg gtc      959
Gly Arg Leu Ser Tyr Phe Tyr Gly Leu Glu Gly Pro Ser Val Thr Val
    305                 310                 315

gac acc gcc tgc tcg tcg tca ctg gtc gcc ctg cac cag gca ggg cag     1007
Asp Thr Ala Cys Ser Ser Ser Leu Val Ala Leu His Gln Ala Gly Gln
320                 325                 330                 335

tcc ctg cgc tcg ggc gaa tgc tcg ctc gcc ctg gtc ggc ggt gtc acg     1055
Ser Leu Arg Ser Gly Glu Cys Ser Leu Ala Leu Val Gly Gly Val Thr
                340                 345                 350

gtg atg gcg tcg ccc ggc gga ttc gtc gag ttc tcc cgg cag cgc ggg     1103
Val Met Ala Ser Pro Gly Gly Phe Val Glu Phe Ser Arg Gln Arg Gly
            355                 360                 365

ctc gcg ccg gac ggg cgg gcg aag gcg ttc ggc gcg ggc gcg gac ggt     1151
Leu Ala Pro Asp Gly Arg Ala Lys Ala Phe Gly Ala Gly Ala Asp Gly
        370                 375                 380

acg agc ttc gcc gag ggc gcc ggt gcc ctg gtg gtc gag cgg ctc tcc     1199
Thr Ser Phe Ala Glu Gly Ala Gly Ala Leu Val Val Glu Arg Leu Ser
    385                 390                 395

gac gcg gag cgc cac ggc cac acc gtc ctc gcc ctc gta cgc ggc tcc     1247
Asp Ala Glu Arg His Gly His Thr Val Leu Ala Leu Val Arg Gly Ser
400                 405                 410                 415

gcg gct aac tcc gac ggc gcg tcg aac ggt ctg tcg gcg ccg aac ggc     1295
Ala Ala Asn Ser Asp Gly Ala Ser Asn Gly Leu Ser Ala Pro Asn Gly
                420                 425                 430

ccc tcc cag gaa cgc gtc atc cac cag gcc ctc gcg aac gcg aaa ctc     1343
Pro Ser Gln Glu Arg Val Ile His Gln Ala Leu Ala Asn Ala Lys Leu
            435                 440                 445

acc ccc gcc gat gtc gac gcg gtc gag gcg cac ggc acc ggc acc cgc     1391
Thr Pro Ala Asp Val Asp Ala Val Glu Ala His Gly Thr Gly Thr Arg
        450                 455                 460

ctc ggc gac ccc atc gag gcg cag gcg ctg ctc gcg acg tac gga cag     1439
Leu Gly Asp Pro Ile Glu Ala Gln Ala Leu Leu Ala Thr Tyr Gly Gln
    465                 470                 475

gac cgg gcg acg ccc ctg ctg ctc ggc tcg ctg aag tcg aac atc ggg     1487
Asp Arg Ala Thr Pro Leu Leu Leu Gly Ser Leu Lys Ser Asn Ile Gly
480                 485                 490                 495

cac gcc cag gcc gcg tca ggg gtc gcc ggg atc atc aag atg gtg cag     1535
His Ala Gln Ala Ala Ser Gly Val Ala Gly Ile Ile Lys Met Val Gln
                500                 505                 510

gcc atc cgg cac ggg gaa ctg ccg ccg aca ctg cac gcg gac gag ccg     1583
Ala Ile Arg His Gly Glu Leu Pro Pro Thr Leu His Ala Asp Glu Pro
            515                 520                 525

tcg ccg cac gtc gac tgg acg gcc ggt gcc gtc gag ctc ctg acg tcg     1631
Ser Pro His Val Asp Trp Thr Ala Gly Ala Val Glu Leu Leu Thr Ser
        530                 535                 540

gcc cgg ccg tgg ccg ggg acc ggt cgc cct agg cgg gca ggc gtg tcg     1679
```

-continued

```
Ala Arg Pro Trp Pro Gly Thr Gly Arg Pro Arg Arg Ala Gly Val Ser
    545                 550                 555

tcc ttc ggg atc agt ggc acc aac gcc cac gtc atc ctg gaa agc gca      1727
Ser Phe Gly Ile Ser Gly Thr Asn Ala His Val Ile Leu Glu Ser Ala
560                 565                 570                 575

ccc ccc act cag cct gcg gac aac gcg gtg atc gag cgg gca ccg gag      1775
Pro Pro Thr Gln Pro Ala Asp Asn Ala Val Ile Glu Arg Ala Pro Glu
                580                 585                 590

tgg gtg ccg ttg gtg att tcg gcc agg acc cag tcg gct ttg act gag      1823
Trp Val Pro Leu Val Ile Ser Ala Arg Thr Gln Ser Ala Leu Thr Glu
            595                 600                 605

cac gag ggc cgg ttg cgt gcg tat ctg gcg gcg tcg ccc ggg gtg gat      1871
His Glu Gly Arg Leu Arg Ala Tyr Leu Ala Ala Ser Pro Gly Val Asp
        610                 615                 620

atg cgg gct gtg gca tcg acg ctg gcg atg aca cgg tcg gtg ttc gag      1919
Met Arg Ala Val Ala Ser Thr Leu Ala Met Thr Arg Ser Val Phe Glu
    625                 630                 635

cac cgt gcc gtg ctg ctg gga gat gac acc gtc acc ggc acc gct gtg      1967
His Arg Ala Val Leu Leu Gly Asp Asp Thr Val Thr Gly Thr Ala Val
640                 645                 650                 655

tct gac cct cgg gcg gtg ttc gtc ttc ccg gga cag ggg tcg cag cgt      2015
Ser Asp Pro Arg Ala Val Phe Val Phe Pro Gly Gln Gly Ser Gln Arg
                660                 665                 670

gct ggc atg ggt gag gaa ctg gcc gcc gcg ttc ccc gtc ttc gcg cgg      2063
Ala Gly Met Gly Glu Glu Leu Ala Ala Ala Phe Pro Val Phe Ala Arg
            675                 680                 685

atc cat cag cag gtg tgg gac ctg ctc gat gtg ccc gat ctg gag gtg      2111
Ile His Gln Gln Val Trp Asp Leu Leu Asp Val Pro Asp Leu Glu Val
        690                 695                 700

aac gag acc ggt tac gcc cag ccg gcc ctg ttc gca atg cag gtg gct      2159
Asn Glu Thr Gly Tyr Ala Gln Pro Ala Leu Phe Ala Met Gln Val Ala
    705                 710                 715

ctg ttc ggg ctg ctg gaa tcg tgg ggt gta cga ccg gac gcg gtg atc      2207
Leu Phe Gly Leu Leu Glu Ser Trp Gly Val Arg Pro Asp Ala Val Ile
720                 725                 730                 735

ggc cat tcg gtg ggt gag ctt gcg gct gcg tat gtg tcc ggg gtg tgg      2255
Gly His Ser Val Gly Glu Leu Ala Ala Ala Tyr Val Ser Gly Val Trp
                740                 745                 750

tcg ttg gag gat gcc tgc act ttg gtg tcg gcg cgg gct cgt ctg atg      2303
Ser Leu Glu Asp Ala Cys Thr Leu Val Ser Ala Arg Ala Arg Leu Met
            755                 760                 765

cag gct ctg ccc gcg ggt ggg gtg atg gtc gct gtc ccg gtc tcg gag      2351
Gln Ala Leu Pro Ala Gly Gly Val Met Val Ala Val Pro Val Ser Glu
        770                 775                 780

gat gag gcc cgg gcc gtg ctg ggt gag ggt gtg gag atc gcc gcg gtc      2399
Asp Glu Ala Arg Ala Val Leu Gly Glu Gly Val Glu Ile Ala Ala Val
    785                 790                 795

aac ggc ccg tcg tcg gtg gtt ctc tcc ggt gat gag gcc gcc gtg ctg      2447
Asn Gly Pro Ser Ser Val Val Leu Ser Gly Asp Glu Ala Ala Val Leu
800                 805                 810                 815

cag gcc gcg gag ggg ctg ggg aag tgg acg cgg ctg gcg acc agc cac      2495
Gln Ala Ala Glu Gly Leu Gly Lys Trp Thr Arg Leu Ala Thr Ser His
                820                 825                 830

gcg ttc cat tcc gcc cgt atg gaa ccc atg ctg gag gag ttc cgg gcg      2543
Ala Phe His Ser Ala Arg Met Glu Pro Met Leu Glu Glu Phe Arg Ala
            835                 840                 845

gtc gcc gaa ggc ctg acc tac cgg acg ccg cag gtc tcc atg gcc gtt      2591
Val Ala Glu Gly Leu Thr Tyr Arg Thr Pro Gln Val Ser Met Ala Val
        850                 855                 860
```

-continued

```
ggt gat cag gtg acc acc gct gag tac tgg gtg cgg cag gtc cgg gac      2639
Gly Asp Gln Val Thr Thr Ala Glu Tyr Trp Val Arg Gln Val Arg Asp
    865                 870                 875

acg gtc cgg ttc ggc gag cag gtg gcc tcg tac gag gac gcc gtg ttc      2687
Thr Val Arg Phe Gly Glu Gln Val Ala Ser Tyr Glu Asp Ala Val Phe
880                 885                 890                 895

gtc gag ctg ggt gcc gac cgg tca ctg gcc cgc ctg gtc gac ggt gtc      2735
Val Glu Leu Gly Ala Asp Arg Ser Leu Ala Arg Leu Val Asp Gly Val
                900                 905                 910

gcg atg ctg cac ggc gac cac gaa atc cag gcc gcg atc ggc gcc ctg      2783
Ala Met Leu His Gly Asp His Glu Ile Gln Ala Ala Ile Gly Ala Leu
            915                 920                 925

gcc cac ctg tat gtc aac ggc gtc acg gtc gac tgg ccc gcg ctc ctg      2831
Ala His Leu Tyr Val Asn Gly Val Thr Val Asp Trp Pro Ala Leu Leu
        930                 935                 940

ggc gat gct ccg gca aca cgg gtg ctg gac ctt ccg aca tac gcc ttc      2879
Gly Asp Ala Pro Ala Thr Arg Val Leu Asp Leu Pro Thr Tyr Ala Phe
    945                 950                 955

cag cac cag cgc tac tgg ctc gag tcg gct ccc ccg gcc acg gcc gac      2927
Gln His Gln Arg Tyr Trp Leu Glu Ser Ala Pro Pro Ala Thr Ala Asp
960                 965                 970                 975

tcg ggc cac ccc gtc ctc ggc acc gga gtc gcc gtc gcc ggg tcg ccg      2975
Ser Gly His Pro Val Leu Gly Thr Gly Val Ala Val Ala Gly Ser Pro
                980                 985                 990

ggc cgg gtg ttc acg ggt ccc gtg ccc gcc ggt gcg gac cgc gcg gtg      3023
Gly Arg Val Phe Thr Gly Pro Val Pro Ala Gly Ala Asp Arg Ala Val
            995                 1000                1005

ttc atc gcc gaa ctg gcg ctc gcc gcc gcc gac gcc acc gac tgc gcc      3071
Phe Ile Ala Glu Leu Ala Leu Ala Ala Ala Asp Ala Thr Asp Cys Ala
       1010                1015                1020

acg gtc gaa cag ctc gac gtc acc tcc gtg ccc ggc gga tcc gcc cgc      3119
Thr Val Glu Gln Leu Asp Val Thr Ser Val Pro Gly Gly Ser Ala Arg
   1025                1030                1035

ggc agg gcc acc gcg cag acc tgg gtc gat gaa ccc gcc gcc gac ggg      3167
Gly Arg Ala Thr Ala Gln Thr Trp Val Asp Glu Pro Ala Ala Asp Gly
1040                1045                1050                1055

cgg cgc cgc ttc acc gtc cac acc cgc gtc ggc gac gcc ccg tgg acg      3215
Arg Arg Arg Phe Thr Val His Thr Arg Val Gly Asp Ala Pro Trp Thr
               1060                1065                1070

ctg cac gcc gag ggg gtt ctc cgc ccc ggc cgc gtg ccc cag ccc gaa      3263
Leu His Ala Glu Gly Val Leu Arg Pro Gly Arg Val Pro Gln Pro Glu
           1075                1080                1085

gcc gtc gac acc gcc tgg ccc ccg ccg ggc gcg gtg ccc gcg gac ggg      3311
Ala Val Asp Thr Ala Trp Pro Pro Pro Gly Ala Val Pro Ala Asp Gly
       1090                1095                1100

ctg ccc ggg gcg tgg cga cgc gcg gac cag gtc ttc gtc gaa gcc gaa      3359
Leu Pro Gly Ala Trp Arg Arg Ala Asp Gln Val Phe Val Glu Ala Glu
   1105                1110                1115

gtc gac agc cct gac ggc ttc gtg gca cac ccc gac ctg ctc gac gcg      3407
Val Asp Ser Pro Asp Gly Phe Val Ala His Pro Asp Leu Leu Asp Ala
1120                1125                1130                1135

gtc ttc tcc gcg gtc ggc gac ggg agc cgc cag ccg acc gga tgg cgc      3455
Val Phe Ser Ala Val Gly Asp Gly Ser Arg Gln Pro Thr Gly Trp Arg
               1140                1145                1150

gac ctc gcg gtg cac gcg tcg gac gcc acc gtg ctg cgc gcc tgc ctc      3503
Asp Leu Ala Val His Ala Ser Asp Ala Thr Val Leu Arg Ala Cys Leu
           1155                1160                1165

acc cgc cgc gac agt ggt gtc gtg gag ctc gcc gcc ttc gac ggt gcc      3551
Thr Arg Arg Asp Ser Gly Val Val Glu Leu Ala Ala Phe Asp Gly Ala
       1170                1175                1180
```

-continued

```
gga atg ccg gtg ctc acc gcg gag tcg gtg acg ctg ggc gag gtc gcg     3599
Gly Met Pro Val Leu Thr Ala Glu Ser Val Thr Leu Gly Glu Val Ala
   1185                1190                1195

tcg gca ggc gga tcc gac gag tcg gac ggt ctg ctt cgg ctt gag tgg     3647
Ser Ala Gly Gly Ser Asp Glu Ser Asp Gly Leu Leu Arg Leu Glu Trp
1200                1205                1210                1215

ttg ccg gtg gcg gag gcc cac tac gac ggt gcc gac gag ctg ccc gag     3695
Leu Pro Val Ala Glu Ala His Tyr Asp Gly Ala Asp Glu Leu Pro Glu
               1220                1225                1230

ggc tac acc ctc atc acc gcc aca cac ccc gac gac ccc gac gac ccc     3743
Gly Tyr Thr Leu Ile Thr Ala Thr His Pro Asp Asp Pro Asp Asp Pro
           1235                1240                1245

acc aac ccc cac aac aca ccc aca cgc acc cac aca caa acc aca cgc     3791
Thr Asn Pro His Asn Thr Pro Thr Arg Thr His Thr Gln Thr Thr Arg
       1250                1255                1260

gtc ctc acc gcc ctc caa cac cac ctc atc acc acc aac cac acc ctc     3839
Val Leu Thr Ala Leu Gln His His Leu Ile Thr Thr Asn His Thr Leu
   1265                1270                1275

atc gtc cac acc acc acc gac ccc cca ggc gcc gcc gtc acc ggc ctc     3887
Ile Val His Thr Thr Thr Asp Pro Pro Gly Ala Ala Val Thr Gly Leu
1280                1285                1290                1295

acc cgc acc gca caa aac gaa cac ccc ggc cgc atc cac ctc atc gaa     3935
Thr Arg Thr Ala Gln Asn Glu His Pro Gly Arg Ile His Leu Ile Glu
               1300                1305                1310

acc cac cac ccc cac acc cca ctc ccc ctc acc caa ctc acc acc ctc     3983
Thr His His Pro His Thr Pro Leu Pro Leu Thr Gln Leu Thr Thr Leu
           1315                1320                1325

cac caa ccc cac cta cgc ctc acc aac aac acc ctc cac acc ccc cac     4031
His Gln Pro His Leu Arg Leu Thr Asn Asn Thr Leu His Thr Pro His
       1330                1335                1340

ctc acc ccc atc acc acc cac cac aac acc acc aca acc acc ccc aac     4079
Leu Thr Pro Ile Thr Thr His His Asn Thr Thr Thr Thr Thr Pro Asn
   1345                1350                1355

acc cca ccc ctc aac ccc aac cac gcc atc ctc atc acc ggc ggc tcc     4127
Thr Pro Pro Leu Asn Pro Asn His Ala Ile Leu Ile Thr Gly Gly Ser
1360                1365                1370                1375

ggc acc ctc gcc ggc atc ctc gcc cgc cac ctc aac cac ccc cac acc     4175
Gly Thr Leu Ala Gly Ile Leu Ala Arg His Leu Asn His Pro His Thr
               1380                1385                1390

tac ctc ctc tcc cgc aca cca cca ccc ccc acc aca ccc ggc acc cac     4223
Tyr Leu Leu Ser Arg Thr Pro Pro Pro Pro Thr Thr Pro Gly Thr His
           1395                1400                1405

atc ccc tgc gac ctc acc gac ccc acc caa atc acc caa gcc ctc acc     4271
Ile Pro Cys Asp Leu Thr Asp Pro Thr Gln Ile Thr Gln Ala Leu Thr
       1410                1415                1420

cac ata cca caa ccc ctc acc ggc atc ttc cac acc gcc gcc acc ctc     4319
His Ile Pro Gln Pro Leu Thr Gly Ile Phe His Thr Ala Ala Thr Leu
   1425                1430                1435

gac gac gcc acc ctc acc aac ctc acc ccc caa cac ctc acc acc acc     4367
Asp Asp Ala Thr Leu Thr Asn Leu Thr Pro Gln His Leu Thr Thr Thr
1440                1445                1450                1455

ctc caa ccc aaa gcc gac gcc gcc tgg cac ctc cac cac cac acc caa     4415
Leu Gln Pro Lys Ala Asp Ala Ala Trp His Leu His His His Thr Gln
               1460                1465                1470

aac caa ccc ctc acc cac ttc gtc ctc tac tcc agc gcc gcc gcc acc     4463
Asn Gln Pro Leu Thr His Phe Val Leu Tyr Ser Ser Ala Ala Ala Thr
           1475                1480                1485

ctc ggc agc ccc ggc caa gcc aac tac gcc gcc gcc aac gcc ttc ctc     4511
Leu Gly Ser Pro Gly Gln Ala Asn Tyr Ala Ala Ala Asn Ala Phe Leu
```

-continued

```
    1490                1495                1500

gac gcc ctc gcc acc cac cgc cac acc caa gga caa ccc gcc acc acc     4559
Asp Ala Leu Ala Thr His Arg His Thr Gln Gly Gln Pro Ala Thr Thr
   1505                1510                1515

atc gcc tgg ggc atg tgg cac acc acc acc aca ctc acc agc caa ctc     4607
Ile Ala Trp Gly Met Trp His Thr Thr Thr Thr Leu Thr Ser Gln Leu
1520                1525                1530                1535

acc gac agc gac cgc gac cgc atc cgc cgc ggc ggc ttc ctg ccg atc     4655
Thr Asp Ser Asp Arg Asp Arg Ile Arg Arg Gly Gly Phe Leu Pro Ile
               1540                1545                1550

tcg gac gac gag ggc atg c                                            4674
Ser Asp Asp Glu Gly Met
           1555


<210> SEQ ID NO 27
<211> LENGTH: 1557
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 27

Met Arg Leu Tyr Glu Ala Ala Arg Arg Thr Gly Ser Pro Val Val Val
  1               5                  10                  15

Ala Ala Ala Leu Asp Asp Ala Pro Asp Val Pro Leu Leu Arg Gly Leu
             20                  25                  30

Arg Arg Thr Thr Val Arg Arg Ala Ala Val Arg Glu Arg Ser Leu Ala
        35                  40                  45

Asp Arg Ser Pro Cys Cys Pro Thr Thr Ser Ala Pro Thr Pro Pro Ser
    50                  55                  60

Arg Ser Ser Trp Asn Ser Thr Ala Thr Val Leu Gly His Leu Gly Ala
 65                  70                  75                  80

Glu Asp Ile Pro Ala Thr Thr Thr Phe Lys Glu Leu Gly Ile Asp Ser
                 85                  90                  95

Leu Thr Ala Val Gln Leu Arg Asn Ala Leu Thr Thr Ala Thr Gly Val
            100                 105                 110

Arg Leu Asn Ala Thr Ala Val Phe Asp Phe Pro Thr Pro Arg Ala Leu
        115                 120                 125

Ala Ala Arg Leu Gly Asp Glu Leu Ala Gly Thr Arg Ala Pro Val Ala
    130                 135                 140

Ala Arg Thr Ala Ala Thr Ala Ala Ala His Asp Glu Pro Leu Ala Ile
145                 150                 155                 160

Val Gly Met Ala Cys Arg Leu Pro Gly Gly Val Ala Ser Pro Gln Glu
                165                 170                 175

Leu Trp Arg Leu Val Ala Ser Gly Thr Asp Ala Ile Thr Glu Phe Pro
            180                 185                 190

Ala Asp Arg Gly Trp Asp Val Asp Ala Leu Tyr Asp Pro Asp Pro Asp
        195                 200                 205

Ala Ile Gly Lys Thr Phe Val Arg His Gly Gly Phe Leu Asp Gly Ala
    210                 215                 220

Thr Gly Phe Asp Ala Ala Phe Phe Gly Ile Ser Pro Arg Glu Ala Leu
225                 230                 235                 240

Ala Met Asp Pro Gln Gln Arg Val Leu Leu Glu Thr Ser Trp Glu Ala
                245                 250                 255

Phe Glu Ser Ala Gly Ile Thr Pro Asp Ala Ala Arg Gly Ser Asp Thr
            260                 265                 270
```

-continued

```
Gly Val Phe Ile Gly Ala Phe Ser Tyr Gly Tyr Gly Thr Gly Ala Asp
        275                 280                 285

Thr Asn Gly Phe Gly Ala Thr Gly Ser Gln Thr Ser Val Leu Ser Gly
    290                 295                 300

Arg Leu Ser Tyr Phe Tyr Gly Leu Glu Gly Pro Ser Val Thr Val Asp
305                 310                 315                 320

Thr Ala Cys Ser Ser Ser Leu Val Ala Leu His Gln Ala Gly Gln Ser
                325                 330                 335

Leu Arg Ser Gly Glu Cys Ser Leu Ala Leu Val Gly Gly Val Thr Val
            340                 345                 350

Met Ala Ser Pro Gly Gly Phe Val Glu Phe Ser Arg Gln Arg Gly Leu
        355                 360                 365

Ala Pro Asp Gly Arg Ala Lys Ala Phe Gly Ala Gly Ala Asp Gly Thr
    370                 375                 380

Ser Phe Ala Glu Gly Ala Gly Ala Leu Val Val Glu Arg Leu Ser Asp
385                 390                 395                 400

Ala Glu Arg His Gly His Thr Val Leu Ala Leu Val Arg Gly Ser Ala
                405                 410                 415

Ala Asn Ser Asp Gly Ala Ser Asn Gly Leu Ser Ala Pro Asn Gly Pro
            420                 425                 430

Ser Gln Glu Arg Val Ile His Gln Ala Leu Ala Asn Ala Lys Leu Thr
        435                 440                 445

Pro Ala Asp Val Asp Ala Val Glu Ala His Gly Thr Gly Thr Arg Leu
    450                 455                 460

Gly Asp Pro Ile Glu Ala Gln Ala Leu Leu Ala Thr Tyr Gly Gln Asp
465                 470                 475                 480

Arg Ala Thr Pro Leu Leu Leu Gly Ser Leu Lys Ser Asn Ile Gly His
                485                 490                 495

Ala Gln Ala Ala Ser Gly Val Ala Gly Ile Ile Lys Met Val Gln Ala
            500                 505                 510

Ile Arg His Gly Glu Leu Pro Pro Thr Leu His Ala Asp Glu Pro Ser
        515                 520                 525

Pro His Val Asp Trp Thr Ala Gly Ala Val Glu Leu Leu Thr Ser Ala
    530                 535                 540

Arg Pro Trp Pro Gly Thr Gly Arg Pro Arg Arg Ala Gly Val Ser Ser
545                 550                 555                 560

Phe Gly Ile Ser Gly Thr Asn Ala His Val Ile Leu Glu Ser Ala Pro
                565                 570                 575

Pro Thr Gln Pro Ala Asp Asn Ala Val Ile Glu Arg Ala Pro Glu Trp
            580                 585                 590

Val Pro Leu Val Ile Ser Ala Arg Thr Gln Ser Ala Leu Thr Glu His
        595                 600                 605

Glu Gly Arg Leu Arg Ala Tyr Leu Ala Ala Ser Pro Gly Val Asp Met
    610                 615                 620

Arg Ala Val Ala Ser Thr Leu Ala Met Thr Arg Ser Val Phe Glu His
625                 630                 635                 640

Arg Ala Val Leu Leu Gly Asp Asp Thr Val Thr Gly Thr Ala Val Ser
                645                 650                 655

Asp Pro Arg Ala Val Phe Val Phe Pro Gly Gln Gly Ser Gln Arg Ala
            660                 665                 670

Gly Met Gly Glu Glu Leu Ala Ala Ala Phe Pro Val Phe Ala Arg Ile
        675                 680                 685
```

-continued

```
His Gln Gln Val Trp Asp Leu Leu Asp Val Pro Asp Leu Glu Val Asn
    690                 695                 700

Glu Thr Gly Tyr Ala Gln Pro Ala Leu Phe Ala Met Gln Val Ala Leu
705                 710                 715                 720

Phe Gly Leu Leu Glu Ser Trp Gly Val Arg Pro Asp Ala Val Ile Gly
                725                 730                 735

His Ser Val Gly Glu Leu Ala Ala Ala Tyr Val Ser Gly Val Trp Ser
            740                 745                 750

Leu Glu Asp Ala Cys Thr Leu Val Ser Ala Arg Ala Arg Leu Met Gln
        755                 760                 765

Ala Leu Pro Ala Gly Gly Val Met Val Ala Val Pro Val Ser Glu Asp
    770                 775                 780

Glu Ala Arg Ala Val Leu Gly Glu Gly Val Glu Ile Ala Ala Val Asn
785                 790                 795                 800

Gly Pro Ser Ser Val Val Leu Ser Gly Asp Glu Ala Ala Val Leu Gln
                805                 810                 815

Ala Ala Glu Gly Leu Gly Lys Trp Thr Arg Leu Ala Thr Ser His Ala
            820                 825                 830

Phe His Ser Ala Arg Met Glu Pro Met Leu Glu Glu Phe Arg Ala Val
        835                 840                 845

Ala Glu Gly Leu Thr Tyr Arg Thr Pro Gln Val Ser Met Ala Val Gly
    850                 855                 860

Asp Gln Val Thr Thr Ala Glu Tyr Trp Val Arg Gln Val Arg Asp Thr
865                 870                 875                 880

Val Arg Phe Gly Glu Gln Val Ala Ser Tyr Glu Asp Ala Val Phe Val
                885                 890                 895

Glu Leu Gly Ala Asp Arg Ser Leu Ala Arg Leu Val Asp Gly Val Ala
            900                 905                 910

Met Leu His Gly Asp His Glu Ile Gln Ala Ala Ile Gly Ala Leu Ala
        915                 920                 925

His Leu Tyr Val Asn Gly Val Thr Val Asp Trp Pro Ala Leu Leu Gly
    930                 935                 940

Asp Ala Pro Ala Thr Arg Val Leu Asp Leu Pro Thr Tyr Ala Phe Gln
945                 950                 955                 960

His Gln Arg Tyr Trp Leu Glu Ser Ala Pro Pro Ala Thr Ala Asp Ser
                965                 970                 975

Gly His Pro Val Leu Gly Thr Gly Val Ala Val Ala Gly Ser Pro Gly
            980                 985                 990

Arg Val Phe Thr Gly Pro Val Pro Ala Gly Ala Asp Arg Ala Val Phe
        995                 1000                1005

Ile Ala Glu Leu Ala Leu Ala Ala Ala Asp Ala Thr Asp Cys Ala Thr
    1010                1015                1020

Val Glu Gln Leu Asp Val Thr Ser Val Pro Gly Gly Ser Ala Arg Gly
1025                1030                1035                1040

Arg Ala Thr Ala Gln Thr Trp Val Asp Glu Pro Ala Ala Asp Gly Arg
                1045                1050                1055

Arg Arg Phe Thr Val His Thr Arg Val Gly Asp Ala Pro Trp Thr Leu
            1060                1065                1070

His Ala Glu Gly Val Leu Arg Pro Gly Arg Val Pro Gln Pro Glu Ala
        1075                1080                1085

Val Asp Thr Ala Trp Pro Pro Pro Gly Ala Val Pro Ala Asp Gly Leu
    1090                1095                1100

Pro Gly Ala Trp Arg Arg Ala Asp Gln Val Phe Val Glu Ala Glu Val
```

-continued

```
1105                1110                1115                1120

Asp Ser Pro Asp Gly Phe Val Ala His Pro Asp Leu Leu Asp Ala Val
                1125                1130                1135

Phe Ser Ala Val Gly Asp Gly Ser Arg Gln Pro Thr Gly Trp Arg Asp
            1140                1145                1150

Leu Ala Val His Ala Ser Asp Ala Thr Val Leu Arg Ala Cys Leu Thr
        1155                1160                1165

Arg Arg Asp Ser Gly Val Val Glu Leu Ala Ala Phe Asp Gly Ala Gly
    1170                1175                1180

Met Pro Val Leu Thr Ala Glu Ser Val Thr Leu Gly Glu Val Ala Ser
1185                1190                1195                1200

Ala Gly Gly Ser Asp Glu Ser Asp Gly Leu Leu Arg Leu Glu Trp Leu
                1205                1210                1215

Pro Val Ala Glu Ala His Tyr Asp Gly Ala Asp Glu Leu Pro Glu Gly
            1220                1225                1230

Tyr Thr Leu Ile Thr Ala Thr His Pro Asp Asp Pro Asp Asp Pro Thr
        1235                1240                1245

Asn Pro His Asn Thr Pro Thr Arg Thr His Thr Gln Thr Thr Arg Val
    1250                1255                1260

Leu Thr Ala Leu Gln His His Leu Ile Thr Thr Asn His Thr Leu Ile
1265                1270                1275                1280

Val His Thr Thr Thr Asp Pro Pro Gly Ala Ala Val Thr Gly Leu Thr
                1285                1290                1295

Arg Thr Ala Gln Asn Glu His Pro Gly Arg Ile His Leu Ile Glu Thr
           1300                1305                1310

His His Pro His Thr Pro Leu Pro Leu Thr Gln Leu Thr Thr Leu His
        1315                1320                1325

Gln Pro His Leu Arg Leu Thr Asn Asn Thr Leu His Thr Pro His Leu
    1330                1335                1340

Thr Pro Ile Thr Thr His His Asn Thr Thr Thr Thr Thr Pro Asn Thr
1345                1350                1355                1360

Pro Pro Leu Asn Pro Asn His Ala Ile Leu Ile Thr Gly Gly Ser Gly
                1365                1370                1375

Thr Leu Ala Gly Ile Leu Ala Arg His Leu Asn His Pro His Thr Tyr
            1380                1385                1390

Leu Leu Ser Arg Thr Pro Pro Pro Pro Thr Thr Pro Gly Thr His Ile
        1395                1400                1405

Pro Cys Asp Leu Thr Asp Pro Thr Gln Ile Thr Gln Ala Leu Thr His
    1410                1415                1420

Ile Pro Gln Pro Leu Thr Gly Ile Phe His Thr Ala Ala Thr Leu Asp
1425                1430                1435                1440

Asp Ala Thr Leu Thr Asn Leu Thr Pro Gln His Leu Thr Thr Thr Leu
                1445                1450                1455

Gln Pro Lys Ala Asp Ala Ala Trp His Leu His His His Thr Gln Asn
            1460                1465                1470

Gln Pro Leu Thr His Phe Val Leu Tyr Ser Ser Ala Ala Ala Thr Leu
        1475                1480                1485

Gly Ser Pro Gly Gln Ala Asn Tyr Ala Ala Ala Asn Ala Phe Leu Asp
    1490                1495                1500

Ala Leu Ala Thr His Arg His Thr Gln Gly Gln Pro Ala Thr Thr Ile
1505                1510                1515                1520

Ala Trp Gly Met Trp His Thr Thr Thr Thr Leu Thr Ser Gln Leu Thr
                1525                1530                1535
```

```
Asp Ser Asp Arg Asp Arg Ile Arg Arg Gly Gly Phe Leu Pro Ile Ser
            1540                1545                1550

Asp Asp Glu Gly Met
        1555


<210> SEQ ID NO 28
<211> LENGTH: 4767
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (3)..(4766)

<400> SEQUENCE: 28

gc atg cgg ctg tac gag gcg gca cgg cgc acc gga agt ccc gtg gtg        47
   Met Arg Leu Tyr Glu Ala Ala Arg Arg Thr Gly Ser Pro Val Val
     1               5                  10                  15

gtg gcg gcc gcg ctc gac gac gcg ccg gac gtg ccg ctg ctg cgc ggg        95
Val Ala Ala Ala Leu Asp Asp Ala Pro Asp Val Pro Leu Leu Arg Gly
                 20                  25                  30

ctg cgg cgt acg acc gtc cgg cgt gcc gcc gtc cgg gaa cgc tct ctc       143
Leu Arg Arg Thr Thr Val Arg Arg Ala Ala Val Arg Glu Arg Ser Leu
            35                  40                  45

gcc gac cgc tcg ccg tgc tgc ccg acg acg agc gcg ccg acg cct ccc       191
Ala Asp Arg Ser Pro Cys Cys Pro Thr Thr Ser Ala Pro Thr Pro Pro
        50                  55                  60

tcg cgt tcg tcc tgg aac agc acc gcc acc gtg ctc ggc cac ctg ggc       239
Ser Arg Ser Ser Trp Asn Ser Thr Ala Thr Val Leu Gly His Leu Gly
     65                  70                  75

gcc gaa gac atc ccg gcg acg acg acg ttc aag gaa ctc ggc atc gac       287
Ala Glu Asp Ile Pro Ala Thr Thr Thr Phe Lys Glu Leu Gly Ile Asp
 80                  85                  90                  95

tcg ctc acc gcg gtc cag ctg cgc aac gcg ctg acc acg gcg acc ggc       335
Ser Leu Thr Ala Val Gln Leu Arg Asn Ala Leu Thr Thr Ala Thr Gly
                100                 105                 110

gta cgc ctc aac gcc aca gcg gtc ttc gac ttt ccg acg ccg cgc gcg       383
Val Arg Leu Asn Ala Thr Ala Val Phe Asp Phe Pro Thr Pro Arg Ala
            115                 120                 125

ctc gcc gcg aga ctc ggc gac gag ctg gcc ggt acc cgc gcg ccc gtc       431
Leu Ala Ala Arg Leu Gly Asp Glu Leu Ala Gly Thr Arg Ala Pro Val
        130                 135                 140

gcg gcc cgg acc gcg gcc acc gcg gcc gcg cac gac gaa ccg ctg gcg       479
Ala Ala Arg Thr Ala Ala Thr Ala Ala Ala His Asp Glu Pro Leu Ala
    145                 150                 155

atc gtg ggc atg gcc tgc cgt ctg ccg ggc ggg gtc gcg tcg cca cag       527
Ile Val Gly Met Ala Cys Arg Leu Pro Gly Gly Val Ala Ser Pro Gln
160                 165                 170                 175

gag ctg tgg cgt ctc gtc gcg tcc ggc acc gac gcc atc acg gag ttc       575
Glu Leu Trp Arg Leu Val Ala Ser Gly Thr Asp Ala Ile Thr Glu Phe
                180                 185                 190

ccc gcg gac cgc ggc tgg gac gtg gac gcg ctc tac gac ccg gac ccc       623
Pro Ala Asp Arg Gly Trp Asp Val Asp Ala Leu Tyr Asp Pro Asp Pro
            195                 200                 205

gac gcg atc ggc aag acc ttc gtc cgg cac ggc ggc ttc ctc gac ggt       671
Asp Ala Ile Gly Lys Thr Phe Val Arg His Gly Gly Phe Leu Asp Gly
        210                 215                 220

gcg acc ggc ttc gac gcg gcg ttc ttc ggg atc agc ccg cgc gag gcc       719
Ala Thr Gly Phe Asp Ala Ala Phe Phe Gly Ile Ser Pro Arg Glu Ala
```

-continued

```
    225                 230                 235

ctg gcc atg gac ccg cag caa cgg gtg ctc ctg gag acg tcc tgg gag      767
Leu Ala Met Asp Pro Gln Gln Arg Val Leu Leu Glu Thr Ser Trp Glu
240                 245                 250                 255

gcg ttc gaa agc gcg ggc atc acc ccg gac gcg gcg cgg ggc agc gac      815
Ala Phe Glu Ser Ala Gly Ile Thr Pro Asp Ala Ala Arg Gly Ser Asp
                260                 265                 270

acc ggc gtg ttc atc ggc gcg ttc tcc tac ggg tac ggc acg ggt gcg      863
Thr Gly Val Phe Ile Gly Ala Phe Ser Tyr Gly Tyr Gly Thr Gly Ala
            275                 280                 285

gat acc aac ggc ttc ggc gcg aca ggg tcg cag acc agc gtg ctc tcc      911
Asp Thr Asn Gly Phe Gly Ala Thr Gly Ser Gln Thr Ser Val Leu Ser
        290                 295                 300

ggc cgc ctc tcg tac ttc tac ggt ctg gag ggc cct tcg gtc acg gtc      959
Gly Arg Leu Ser Tyr Phe Tyr Gly Leu Glu Gly Pro Ser Val Thr Val
    305                 310                 315

gac acc gcc tgc tcg tcg tca ctg gtc gcc ctg cac cag gca ggg cag     1007
Asp Thr Ala Cys Ser Ser Ser Leu Val Ala Leu His Gln Ala Gly Gln
320                 325                 330                 335

tcc ctg cgc tcg ggc gaa tgc tcg ctc gcc ctg gtc ggc ggt gtc acg     1055
Ser Leu Arg Ser Gly Glu Cys Ser Leu Ala Leu Val Gly Gly Val Thr
                340                 345                 350

gtg atg gcg tcg ccc ggc gga ttc gtc gag ttc tcc cgg cag cgc ggg     1103
Val Met Ala Ser Pro Gly Gly Phe Val Glu Phe Ser Arg Gln Arg Gly
            355                 360                 365

ctc gcg ccg gac ggg cgg gcg aag gcg ttc ggc gcg ggc gcg gac ggt     1151
Leu Ala Pro Asp Gly Arg Ala Lys Ala Phe Gly Ala Gly Ala Asp Gly
        370                 375                 380

acg agc ttc gcc gag ggc gcc ggt gcc ctg gtg gtc gag cgg ctc tcc     1199
Thr Ser Phe Ala Glu Gly Ala Gly Ala Leu Val Val Glu Arg Leu Ser
    385                 390                 395

gac gcg gag cgc cac ggc cac acc gtc ctc gcc ctc gta cgc ggc tcc     1247
Asp Ala Glu Arg His Gly His Thr Val Leu Ala Leu Val Arg Gly Ser
400                 405                 410                 415

gcg gct aac tcc gac ggc gcg tcg aac ggt ctg tcg gcg ccg aac ggc     1295
Ala Ala Asn Ser Asp Gly Ala Ser Asn Gly Leu Ser Ala Pro Asn Gly
                420                 425                 430

ccc tcc cag gaa cgc gtc atc cac cag gcc ctc gcg aac gcg aaa ctc     1343
Pro Ser Gln Glu Arg Val Ile His Gln Ala Leu Ala Asn Ala Lys Leu
            435                 440                 445

acc ccc gcc gat gtc gac gcg gtc gag gcg cac ggc acc ggc acc cgc     1391
Thr Pro Ala Asp Val Asp Ala Val Glu Ala His Gly Thr Gly Thr Arg
        450                 455                 460

ctc ggc gac ccc atc gag gcg cag gcg ctg ctc gcg acg tac gga cag     1439
Leu Gly Asp Pro Ile Glu Ala Gln Ala Leu Leu Ala Thr Tyr Gly Gln
    465                 470                 475

gac cgg gcg acg ccc ctg ctg ctc ggc tcg ctg aag tcg aac atc ggg     1487
Asp Arg Ala Thr Pro Leu Leu Leu Gly Ser Leu Lys Ser Asn Ile Gly
480                 485                 490                 495

cac gcc cag gcc gcg tca ggg gtc gcc ggg atc atc aag atg gtg cag     1535
His Ala Gln Ala Ala Ser Gly Val Ala Gly Ile Ile Lys Met Val Gln
                500                 505                 510

gcc atc cgg cac ggg gaa ctg ccg ccg aca ctg cac gcg gac gag ccg     1583
Ala Ile Arg His Gly Glu Leu Pro Pro Thr Leu His Ala Asp Glu Pro
            515                 520                 525

tcg ccg cac gtc gac tgg acg gcc ggt gcc gtc gag ctc ctg acg tcg     1631
Ser Pro His Val Asp Trp Thr Ala Gly Ala Val Glu Leu Leu Thr Ser
        530                 535                 540

gcc cgg ccg tgg ccg ggg acc ggt cgc cct agg cgg gcg ggc gtg tcg     1679
```

-continued

```
Ala Arg Pro Trp Pro Gly Thr Gly Arg Pro Arg Arg Ala Gly Val Ser
    545                 550                 555

tcc ttc gga gtc agc ggc acc aac gcc cac gtc atc ctg gag agc gca     1727
Ser Phe Gly Val Ser Gly Thr Asn Ala His Val Ile Leu Glu Ser Ala
560                 565                 570                 575

ccc ccc gct cag ccc gcg gag gag gcg cag cct gtt gag acg ccg gtg     1775
Pro Pro Ala Gln Pro Ala Glu Glu Ala Gln Pro Val Glu Thr Pro Val
                580                 585                 590

gtg gcc tcg gat gtg ctg ccg ctg gtg ata tcg gcc aag acc cag ccc     1823
Val Ala Ser Asp Val Leu Pro Leu Val Ile Ser Ala Lys Thr Gln Pro
            595                 600                 605

gcc ctg acc gaa cac gaa gac cgg ctg cgc gcc tac ctg gcg gcg tcg     1871
Ala Leu Thr Glu His Glu Asp Arg Leu Arg Ala Tyr Leu Ala Ala Ser
        610                 615                 620

ccc ggg gcg gat ata cgg gct gtg gca tcg acg ctg gcg gtg aca cgg     1919
Pro Gly Ala Asp Ile Arg Ala Val Ala Ser Thr Leu Ala Val Thr Arg
    625                 630                 635

tcg gtg ttc gag cac cgc gcc gta ctc ctt gga gat gac acc gtc acc     1967
Ser Val Phe Glu His Arg Ala Val Leu Leu Gly Asp Asp Thr Val Thr
640                 645                 650                 655

ggc acc gcg gtg acc gac ccc agg atc gtg ttt gtc ttt ccc ggg cag     2015
Gly Thr Ala Val Thr Asp Pro Arg Ile Val Phe Val Phe Pro Gly Gln
                660                 665                 670

ggg tgg cag tgg ctg ggg atg ggc agt gca ctg cgc gat tcg tcg gtg     2063
Gly Trp Gln Trp Leu Gly Met Gly Ser Ala Leu Arg Asp Ser Ser Val
            675                 680                 685

gtg ttc gcc gag cgg atg gcc gag tgt gcg gcg gcg ttg cgc gag ttc     2111
Val Phe Ala Glu Arg Met Ala Glu Cys Ala Ala Ala Leu Arg Glu Phe
        690                 695                 700

gtg gac tgg gat ctg ttc acg gtt ctg gat gat ccg gcg gtg gtg gac     2159
Val Asp Trp Asp Leu Phe Thr Val Leu Asp Asp Pro Ala Val Val Asp
    705                 710                 715

cgg gtt gat gtg gtc cag ccc gct tcc tgg gcg atg atg gtt tcc ctg     2207
Arg Val Asp Val Val Gln Pro Ala Ser Trp Ala Met Met Val Ser Leu
720                 725                 730                 735

gcc gcg gtg tgg cag gcg gcc ggt gtg cgg ccg gat gcg gtg atc ggc     2255
Ala Ala Val Trp Gln Ala Ala Gly Val Arg Pro Asp Ala Val Ile Gly
                740                 745                 750

cat tcg cag ggt gag atc gcc gca gct tgt gtg gcg ggt gcg gtg tca     2303
His Ser Gln Gly Glu Ile Ala Ala Ala Cys Val Ala Gly Ala Val Ser
            755                 760                 765

cta cgc gat gcc gcc cgg atc gtg acc ttg cgc agc cag gcg atc gcc     2351
Leu Arg Asp Ala Ala Arg Ile Val Thr Leu Arg Ser Gln Ala Ile Ala
        770                 775                 780

cgg ggc ctg gcg ggc cgg ggc gcg atg gca tcc gtc gcc ctg ccc gcg     2399
Arg Gly Leu Ala Gly Arg Gly Ala Met Ala Ser Val Ala Leu Pro Ala
    785                 790                 795

cag gat gtc gag ctg gtc gac ggg gcc tgg atc gcc gcc cac aac ggg     2447
Gln Asp Val Glu Leu Val Asp Gly Ala Trp Ile Ala Ala His Asn Gly
800                 805                 810                 815

ccc gcc tcc acc gtg atc gcg ggc acc ccg gaa gcg gtc gac cat gtc     2495
Pro Ala Ser Thr Val Ile Ala Gly Thr Pro Glu Ala Val Asp His Val
                820                 825                 830

ctc acc gct cat gag gca caa ggg gtg cgg gtg cgg cgg atc acc gtc     2543
Leu Thr Ala His Glu Ala Gln Gly Val Arg Val Arg Arg Ile Thr Val
            835                 840                 845

gac tat gcc tcg cac acc ccg cac gtc gag ctg atc cgc gac gaa cta     2591
Asp Tyr Ala Ser His Thr Pro His Val Glu Leu Ile Arg Asp Glu Leu
        850                 855                 860
```

-continued

```
ctc gac atc act agc gac agc agc tcg cag acc ccg ctc gtg ccg tgg     2639
Leu Asp Ile Thr Ser Asp Ser Ser Ser Gln Thr Pro Leu Val Pro Trp
    865                 870                 875

ctg tcg acc gtg gac ggc acc tgg gtc gac agc ccg ctg gac ggg gag     2687
Leu Ser Thr Val Asp Gly Thr Trp Val Asp Ser Pro Leu Asp Gly Glu
880                 885                 890                 895

tac tgg tac cgg aac ctg cgt gaa ccg gtc ggt ttc cac ccc gcc gtc     2735
Tyr Trp Tyr Arg Asn Leu Arg Glu Pro Val Gly Phe His Pro Ala Val
                900                 905                 910

agc cag ttg cag gcc cag ggc gac acc gtg ttc gtc gag gtc agc gcc     2783
Ser Gln Leu Gln Ala Gln Gly Asp Thr Val Phe Val Glu Val Ser Ala
            915                 920                 925

agc ccg gtg ttg ttg cag gcg atg gac gac gat gtc gtc acg gtt gcc     2831
Ser Pro Val Leu Leu Gln Ala Met Asp Asp Asp Val Val Thr Val Ala
        930                 935                 940

acg ctg cgt cgt gac gac ggc gac gcc acc cgg atg ctc acc gcc ctg     2879
Thr Leu Arg Arg Asp Asp Gly Asp Ala Thr Arg Met Leu Thr Ala Leu
    945                 950                 955

gca cag gcc tat gtc cac ggc gtc acc gtc gac tgg ccc gcc atc ctc     2927
Ala Gln Ala Tyr Val His Gly Val Thr Val Asp Trp Pro Ala Ile Leu
960                 965                 970                 975

ggc acc acc aca acc cgg gta ctg gac ctt ccg acc tac gcc ttc caa     2975
Gly Thr Thr Thr Thr Arg Val Leu Asp Leu Pro Thr Tyr Ala Phe Gln
                980                 985                 990

cac cag cgg tac tgg ctc gag tcg gct ccc ccg gcc acg gcc gac tcg     3023
His Gln Arg Tyr Trp Leu Glu Ser Ala Pro Pro Ala Thr Ala Asp Ser
            995                 1000                1005

ggc cac ccc gtc ctc ggc acc gga gtc gcc gtc gcc ggg tcg ccg ggc     3071
Gly His Pro Val Leu Gly Thr Gly Val Ala Val Ala Gly Ser Pro Gly
       1010                1015                1020

cgg gtg ttc acg ggt ccc gtg ccc gcc ggt gcg gac cgc gcg gtg ttc     3119
Arg Val Phe Thr Gly Pro Val Pro Ala Gly Ala Asp Arg Ala Val Phe
   1025                1030                1035

atc gcc gaa ctg gcg ctc gcc gcc gcc gac gcc acc gac tgc gcc acg     3167
Ile Ala Glu Leu Ala Leu Ala Ala Ala Asp Ala Thr Asp Cys Ala Thr
1040                1045                1050                1055

gtc gaa cag ctc gac gtc acc tcc gtg ccc ggc gga tcc gcc cgc ggc     3215
Val Glu Gln Leu Asp Val Thr Ser Val Pro Gly Gly Ser Ala Arg Gly
               1060                1065                1070

agg gcc acc gcg cag acc tgg gtc gat gaa ccc gcc gcc gac ggg cgg     3263
Arg Ala Thr Ala Gln Thr Trp Val Asp Glu Pro Ala Ala Asp Gly Arg
           1075                1080                1085

cgc cgc ttc acc gtc cac acc cgc gtc ggc gac gcc ccg tgg acg ctg     3311
Arg Arg Phe Thr Val His Thr Arg Val Gly Asp Ala Pro Trp Thr Leu
       1090                1095                1100

cac gcc gag ggg gtt ctc cgc ccc ggc cgc gtg ccc cag ccc gaa gcc     3359
His Ala Glu Gly Val Leu Arg Pro Gly Arg Val Pro Gln Pro Glu Ala
   1105                1110                1115

gtc gac acc gcc tgg ccc ccg ccg ggc gcg gtg ccc gcg gac ggg ctg     3407
Val Asp Thr Ala Trp Pro Pro Pro Gly Ala Val Pro Ala Asp Gly Leu
1120                1125                1130                1135

ccc ggg gcg tgg cga cgc gcg gac cag gtc ttc gtc gaa gcc gaa gtc     3455
Pro Gly Ala Trp Arg Arg Ala Asp Gln Val Phe Val Glu Ala Glu Val
               1140                1145                1150

gac agc cct gac ggc ttc gtg gca cac ccc gac ctg ctc gac gcg gtc     3503
Asp Ser Pro Asp Gly Phe Val Ala His Pro Asp Leu Leu Asp Ala Val
           1155                1160                1165

ttc tcc gcg gtc ggc gac ggg agc cgc cag ccg acc gga tgg cgc gac     3551
Phe Ser Ala Val Gly Asp Gly Ser Arg Gln Pro Thr Gly Trp Arg Asp
       1170                1175                1180
```

```
ctc gcg gtg cac gcg tcg gac gcc acc gtg ctg cgc gcc tgc ctc acc     3599
Leu Ala Val His Ala Ser Asp Ala Thr Val Leu Arg Ala Cys Leu Thr
   1185                1190                1195

cgc cgc gac agt ggt gtc gtg gag ctc gcc gcc ttc gac ggt gcc gga     3647
Arg Arg Asp Ser Gly Val Val Glu Leu Ala Ala Phe Asp Gly Ala Gly
1200                1205                1210                1215

atg ccg gtg ctc acc gcg gag tcg gtg acg ctg ggc gag gtc gcg tcg     3695
Met Pro Val Leu Thr Ala Glu Ser Val Thr Leu Gly Glu Val Ala Ser
               1220                1225                1230

gca ggc gga tcc gac gag tcg gac ggt ctg ctt cgg ctt gag tgg ttg     3743
Ala Gly Gly Ser Asp Glu Ser Asp Gly Leu Leu Arg Leu Glu Trp Leu
           1235                1240                1245

ccg gtg gcg gag gcc cac tac gac ggt gcc gac gag ctg ccc gag ggc     3791
Pro Val Ala Glu Ala His Tyr Asp Gly Ala Asp Glu Leu Pro Glu Gly
       1250                1255                1260

tac acc ctc atc acc gcc aca cac ccc gac gac ccc gac gac ccc acc     3839
Tyr Thr Leu Ile Thr Ala Thr His Pro Asp Asp Pro Asp Asp Pro Thr
   1265                1270                1275

aac ccc cac aac aca ccc aca cgc acc cac aca caa acc aca cgc gtc     3887
Asn Pro His Asn Thr Pro Thr Arg Thr His Thr Gln Thr Thr Arg Val
1280                1285                1290                1295

ctc acc gcc ctc caa cac cac ctc atc acc acc aac cac acc ctc atc     3935
Leu Thr Ala Leu Gln His His Leu Ile Thr Thr Asn His Thr Leu Ile
               1300                1305                1310

gtc cac acc acc acc gac ccc cca ggc gcc gcc gtc acc ggc ctc acc     3983
Val His Thr Thr Thr Asp Pro Pro Gly Ala Ala Val Thr Gly Leu Thr
           1315                1320                1325

cgc acc gca caa aac gaa cac ccc ggc cgc atc cac ctc atc gaa acc     4031
Arg Thr Ala Gln Asn Glu His Pro Gly Arg Ile His Leu Ile Glu Thr
       1330                1335                1340

cac cac ccc cac acc cca ctc ccc ctc acc caa ctc acc acc ctc cac     4079
His His Pro His Thr Pro Leu Pro Leu Thr Gln Leu Thr Thr Leu His
   1345                1350                1355

caa ccc cac cta cgc ctc acc aac aac acc ctc cac acc ccc cac ctc     4127
Gln Pro His Leu Arg Leu Thr Asn Asn Thr Leu His Thr Pro His Leu
1360                1365                1370                1375

acc ccc atc acc acc cac cac aac acc acc aca acc acc ccc aac acc     4175
Thr Pro Ile Thr Thr His His Asn Thr Thr Thr Thr Thr Pro Asn Thr
               1380                1385                1390

cca ccc ctc aac ccc aac cac gcc atc ctc atc acc ggc ggc tcc ggc     4223
Pro Pro Leu Asn Pro Asn His Ala Ile Leu Ile Thr Gly Gly Ser Gly
           1395                1400                1405

acc ctc gcc ggc atc ctc gcc cgc cac ctc aac cac ccc cac acc tac     4271
Thr Leu Ala Gly Ile Leu Ala Arg His Leu Asn His Pro His Thr Tyr
       1410                1415                1420

ctc ctc tcc cgc aca cca cca ccc ccc acc aca ccc ggc acc cac atc     4319
Leu Leu Ser Arg Thr Pro Pro Pro Pro Thr Thr Pro Gly Thr His Ile
   1425                1430                1435

ccc tgc gac ctc acc gac ccc acc caa atc acc caa gcc ctc acc cac     4367
Pro Cys Asp Leu Thr Asp Pro Thr Gln Ile Thr Gln Ala Leu Thr His
1440                1445                1450                1455

ata cca caa ccc ctc acc ggc atc ttc cac acc gcc gcc acc ctc gac     4415
Ile Pro Gln Pro Leu Thr Gly Ile Phe His Thr Ala Ala Thr Leu Asp
               1460                1465                1470

gac gcc acc ctc acc aac ctc acc ccc caa cac ctc acc acc acc ctc     4463
Asp Ala Thr Leu Thr Asn Leu Thr Pro Gln His Leu Thr Thr Thr Leu
           1475                1480                1485

caa ccc aaa gcc gac gcc gcc tgg cac ctc cac cac cac acc caa aac     4511
Gln Pro Lys Ala Asp Ala Ala Trp His Leu His His His Thr Gln Asn
```

```
      1490                1495                1500

caa ccc ctc acc cac ttc gtc ctc tac tcc agc gcc gcc gcc acc ctc     4559
Gln Pro Leu Thr His Phe Val Leu Tyr Ser Ser Ala Ala Ala Thr Leu
   1505                1510                1515

ggc agc ccc ggc caa gcc aac tac gcc gcc gcc aac gcc ttc ctc gac     4607
Gly Ser Pro Gly Gln Ala Asn Tyr Ala Ala Ala Asn Ala Phe Leu Asp
1520                1525                1530                1535

gcc ctc gcc acc cac cgc cac acc caa gga caa ccc gcc acc acc atc     4655
Ala Leu Ala Thr His Arg His Thr Gln Gly Gln Pro Ala Thr Thr Ile
               1540                1545                1550

gcc tgg ggc atg tgg cac acc acc acc aca ctc acc agc caa ctc acc     4703
Ala Trp Gly Met Trp His Thr Thr Thr Thr Leu Thr Ser Gln Leu Thr
           1555                1560                1565

gac agc gac cgc gac cgc atc cgc cgc ggc ggc ttc ctg ccg atc tcg     4751
Asp Ser Asp Arg Asp Arg Ile Arg Arg Gly Gly Phe Leu Pro Ile Ser
       1570                1575                1580

gac gac gag ggc atg c                                               4767
Asp Asp Glu Gly Met
   1585


<210> SEQ ID NO 29
<211> LENGTH: 1588
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 29

Met Arg Leu Tyr Glu Ala Ala Arg Arg Thr Gly Ser Pro Val Val Val
  1               5                  10                  15

Ala Ala Ala Leu Asp Asp Ala Pro Asp Val Pro Leu Leu Arg Gly Leu
             20                  25                  30

Arg Arg Thr Thr Val Arg Arg Ala Ala Val Arg Glu Arg Ser Leu Ala
         35                  40                  45

Asp Arg Ser Pro Cys Cys Pro Thr Thr Ser Ala Pro Thr Pro Pro Ser
     50                  55                  60

Arg Ser Ser Trp Asn Ser Thr Ala Thr Val Leu Gly His Leu Gly Ala
 65                  70                  75                  80

Glu Asp Ile Pro Ala Thr Thr Thr Phe Lys Glu Leu Gly Ile Asp Ser
                 85                  90                  95

Leu Thr Ala Val Gln Leu Arg Asn Ala Leu Thr Thr Ala Thr Gly Val
            100                 105                 110

Arg Leu Asn Ala Thr Ala Val Phe Asp Phe Pro Thr Pro Arg Ala Leu
        115                 120                 125

Ala Ala Arg Leu Gly Asp Glu Leu Ala Gly Thr Arg Ala Pro Val Ala
    130                 135                 140

Ala Arg Thr Ala Ala Thr Ala Ala Ala His Asp Glu Pro Leu Ala Ile
145                 150                 155                 160

Val Gly Met Ala Cys Arg Leu Pro Gly Gly Val Ala Ser Pro Gln Glu
                165                 170                 175

Leu Trp Arg Leu Val Ala Ser Gly Thr Asp Ala Ile Thr Glu Phe Pro
            180                 185                 190

Ala Asp Arg Gly Trp Asp Val Asp Ala Leu Tyr Asp Pro Asp Pro Asp
        195                 200                 205

Ala Ile Gly Lys Thr Phe Val Arg His Gly Gly Phe Leu Asp Gly Ala
    210                 215                 220
```

-continued

```
Thr Gly Phe Asp Ala Ala Phe Phe Gly Ile Ser Pro Arg Glu Ala Leu
225                 230                 235                 240

Ala Met Asp Pro Gln Gln Arg Val Leu Leu Glu Thr Ser Trp Glu Ala
                245                 250                 255

Phe Glu Ser Ala Gly Ile Thr Pro Asp Ala Ala Arg Gly Ser Asp Thr
            260                 265                 270

Gly Val Phe Ile Gly Ala Phe Ser Tyr Gly Tyr Gly Thr Gly Ala Asp
        275                 280                 285

Thr Asn Gly Phe Gly Ala Thr Gly Ser Gln Thr Ser Val Leu Ser Gly
    290                 295                 300

Arg Leu Ser Tyr Phe Tyr Gly Leu Glu Gly Pro Ser Val Thr Val Asp
305                 310                 315                 320

Thr Ala Cys Ser Ser Ser Leu Val Ala Leu His Gln Ala Gly Gln Ser
                325                 330                 335

Leu Arg Ser Gly Glu Cys Ser Leu Ala Leu Val Gly Gly Val Thr Val
            340                 345                 350

Met Ala Ser Pro Gly Gly Phe Val Glu Phe Ser Arg Gln Arg Gly Leu
        355                 360                 365

Ala Pro Asp Gly Arg Ala Lys Ala Phe Gly Ala Gly Ala Asp Gly Thr
    370                 375                 380

Ser Phe Ala Glu Gly Ala Gly Ala Leu Val Val Glu Arg Leu Ser Asp
385                 390                 395                 400

Ala Glu Arg His Gly His Thr Val Leu Ala Leu Val Arg Gly Ser Ala
                405                 410                 415

Ala Asn Ser Asp Gly Ala Ser Asn Gly Leu Ser Ala Pro Asn Gly Pro
            420                 425                 430

Ser Gln Glu Arg Val Ile His Gln Ala Leu Ala Asn Ala Lys Leu Thr
        435                 440                 445

Pro Ala Asp Val Asp Ala Val Glu Ala His Gly Thr Gly Thr Arg Leu
    450                 455                 460

Gly Asp Pro Ile Glu Ala Gln Ala Leu Leu Ala Thr Tyr Gly Gln Asp
465                 470                 475                 480

Arg Ala Thr Pro Leu Leu Leu Gly Ser Leu Lys Ser Asn Ile Gly His
                485                 490                 495

Ala Gln Ala Ala Ser Gly Val Ala Gly Ile Ile Lys Met Val Gln Ala
            500                 505                 510

Ile Arg His Gly Glu Leu Pro Pro Thr Leu His Ala Asp Glu Pro Ser
        515                 520                 525

Pro His Val Asp Trp Thr Ala Gly Ala Val Glu Leu Leu Thr Ser Ala
    530                 535                 540

Arg Pro Trp Pro Gly Thr Gly Arg Pro Arg Arg Ala Gly Val Ser Ser
545                 550                 555                 560

Phe Gly Val Ser Gly Thr Asn Ala His Val Ile Leu Glu Ser Ala Pro
                565                 570                 575

Pro Ala Gln Pro Ala Glu Glu Ala Gln Pro Val Glu Thr Pro Val Val
            580                 585                 590

Ala Ser Asp Val Leu Pro Leu Val Ile Ser Ala Lys Thr Gln Pro Ala
        595                 600                 605

Leu Thr Glu His Glu Asp Arg Leu Arg Ala Tyr Leu Ala Ala Ser Pro
    610                 615                 620

Gly Ala Asp Ile Arg Ala Val Ala Ser Thr Leu Ala Val Thr Arg Ser
625                 630                 635                 640

Val Phe Glu His Arg Ala Val Leu Leu Gly Asp Asp Thr Val Thr Gly
```

-continued

```
                645                 650                 655

Thr Ala Val Thr Asp Pro Arg Ile Val Phe Val Phe Pro Gly Gln Gly
            660                 665                 670

Trp Gln Trp Leu Gly Met Gly Ser Ala Leu Arg Asp Ser Ser Val Val
        675                 680                 685

Phe Ala Glu Arg Met Ala Glu Cys Ala Ala Ala Leu Arg Glu Phe Val
    690                 695                 700

Asp Trp Asp Leu Phe Thr Val Leu Asp Asp Pro Ala Val Val Asp Arg
705                 710                 715                 720

Val Asp Val Val Gln Pro Ala Ser Trp Ala Met Met Val Ser Leu Ala
                725                 730                 735

Ala Val Trp Gln Ala Ala Gly Val Arg Pro Asp Ala Val Ile Gly His
            740                 745                 750

Ser Gln Gly Glu Ile Ala Ala Ala Cys Val Ala Gly Ala Val Ser Leu
        755                 760                 765

Arg Asp Ala Ala Arg Ile Val Thr Leu Arg Ser Gln Ala Ile Ala Arg
    770                 775                 780

Gly Leu Ala Gly Arg Gly Ala Met Ala Ser Val Ala Leu Pro Ala Gln
785                 790                 795                 800

Asp Val Glu Leu Val Asp Gly Ala Trp Ile Ala Ala His Asn Gly Pro
                805                 810                 815

Ala Ser Thr Val Ile Ala Gly Thr Pro Glu Ala Val Asp His Val Leu
            820                 825                 830

Thr Ala His Glu Ala Gln Gly Val Arg Val Arg Arg Ile Thr Val Asp
        835                 840                 845

Tyr Ala Ser His Thr Pro His Val Glu Leu Ile Arg Asp Glu Leu Leu
    850                 855                 860

Asp Ile Thr Ser Asp Ser Ser Ser Gln Thr Pro Leu Val Pro Trp Leu
865                 870                 875                 880

Ser Thr Val Asp Gly Thr Trp Val Asp Ser Pro Leu Asp Gly Glu Tyr
                885                 890                 895

Trp Tyr Arg Asn Leu Arg Glu Pro Val Gly Phe His Pro Ala Val Ser
            900                 905                 910

Gln Leu Gln Ala Gln Gly Asp Thr Val Phe Val Glu Val Ser Ala Ser
        915                 920                 925

Pro Val Leu Leu Gln Ala Met Asp Asp Asp Val Val Thr Val Ala Thr
    930                 935                 940

Leu Arg Arg Asp Asp Gly Asp Ala Thr Arg Met Leu Thr Ala Leu Ala
945                 950                 955                 960

Gln Ala Tyr Val His Gly Val Thr Val Asp Trp Pro Ala Ile Leu Gly
                965                 970                 975

Thr Thr Thr Thr Arg Val Leu Asp Leu Pro Thr Tyr Ala Phe Gln His
            980                 985                 990

Gln Arg Tyr Trp Leu Glu Ser Ala Pro Pro Ala Thr Ala Asp Ser Gly
        995                 1000                1005

His Pro Val Leu Gly Thr Gly Val Ala Val Ala Gly Ser Pro Gly Arg
    1010                1015                1020

Val Phe Thr Gly Pro Val Pro Ala Gly Ala Asp Arg Ala Val Phe Ile
1025                1030                1035                1040

Ala Glu Leu Ala Leu Ala Ala Ala Asp Ala Thr Asp Cys Ala Thr Val
                1045                1050                1055

Glu Gln Leu Asp Val Thr Ser Val Pro Gly Gly Ser Ala Arg Gly Arg
            1060                1065                1070
```

-continued

```
Ala Thr Ala Gln Thr Trp Val Asp Glu Pro Ala Ala Asp Gly Arg Arg
        1075                1080                1085

Arg Phe Thr Val His Thr Arg Val Gly Asp Ala Pro Trp Thr Leu His
    1090                1095                1100

Ala Glu Gly Val Leu Arg Pro Gly Arg Val Pro Gln Pro Glu Ala Val
1105                1110                1115                1120

Asp Thr Ala Trp Pro Pro Pro Gly Ala Val Pro Ala Asp Gly Leu Pro
                1125                1130                1135

Gly Ala Trp Arg Arg Ala Asp Gln Val Phe Val Glu Ala Glu Val Asp
            1140                1145                1150

Ser Pro Asp Gly Phe Val Ala His Pro Asp Leu Leu Asp Ala Val Phe
        1155                1160                1165

Ser Ala Val Gly Asp Gly Ser Arg Gln Pro Thr Gly Trp Arg Asp Leu
    1170                1175                1180

Ala Val His Ala Ser Asp Ala Thr Val Leu Arg Ala Cys Leu Thr Arg
1185                1190                1195                1200

Arg Asp Ser Gly Val Val Glu Leu Ala Ala Phe Asp Gly Ala Gly Met
                1205                1210                1215

Pro Val Leu Thr Ala Glu Ser Val Thr Leu Gly Glu Val Ala Ser Ala
            1220                1225                1230

Gly Gly Ser Asp Glu Ser Asp Gly Leu Leu Arg Leu Glu Trp Leu Pro
        1235                1240                1245

Val Ala Glu Ala His Tyr Asp Gly Ala Asp Glu Leu Pro Glu Gly Tyr
    1250                1255                1260

Thr Leu Ile Thr Ala Thr His Pro Asp Asp Pro Asp Asp Pro Thr Asn
1265                1270                1275                1280

Pro His Asn Thr Pro Thr Arg Thr His Thr Gln Thr Thr Arg Val Leu
                1285                1290                1295

Thr Ala Leu Gln His His Leu Ile Thr Thr Asn His Thr Leu Ile Val
            1300                1305                1310

His Thr Thr Thr Asp Pro Pro Gly Ala Ala Val Thr Gly Leu Thr Arg
        1315                1320                1325

Thr Ala Gln Asn Glu His Pro Gly Arg Ile His Leu Ile Glu Thr His
    1330                1335                1340

His Pro His Thr Pro Leu Pro Leu Thr Gln Leu Thr Thr Leu His Gln
1345                1350                1355                1360

Pro His Leu Arg Leu Thr Asn Asn Thr Leu His Thr Pro His Leu Thr
                1365                1370                1375

Pro Ile Thr Thr His His Asn Thr Thr Thr Thr Thr Pro Asn Thr Pro
            1380                1385                1390

Pro Leu Asn Pro Asn His Ala Ile Leu Ile Thr Gly Gly Ser Gly Thr
        1395                1400                1405

Leu Ala Gly Ile Leu Ala Arg His Leu Asn His Pro His Thr Tyr Leu
    1410                1415                1420

Leu Ser Arg Thr Pro Pro Pro Pro Thr Thr Pro Gly Thr His Ile Pro
1425                1430                1435                1440

Cys Asp Leu Thr Asp Pro Thr Gln Ile Thr Gln Ala Leu Thr His Ile
                1445                1450                1455

Pro Gln Pro Leu Thr Gly Ile Phe His Thr Ala Ala Thr Leu Asp Asp
            1460                1465                1470

Ala Thr Leu Thr Asn Leu Thr Pro Gln His Leu Thr Thr Thr Leu Gln
        1475                1480                1485
```

-continued

```
Pro Lys Ala Asp Ala Ala Trp His Leu His His His Thr Gln Asn Gln
    1490                1495                1500

Pro Leu Thr His Phe Val Leu Tyr Ser Ser Ala Ala Ala Thr Leu Gly
1505                1510                1515                1520

Ser Pro Gly Gln Ala Asn Tyr Ala Ala Ala Asn Ala Phe Leu Asp Ala
                1525                1530                1535

Leu Ala Thr His Arg His Thr Gln Gly Gln Pro Ala Thr Thr Ile Ala
            1540                1545                1550

Trp Gly Met Trp His Thr Thr Thr Thr Leu Thr Ser Gln Leu Thr Asp
        1555                1560                1565

Ser Asp Arg Asp Arg Ile Arg Arg Gly Gly Phe Leu Pro Ile Ser Asp
    1570                1575                1580

Asp Glu Gly Met
1585


<210> SEQ ID NO 30
<211> LENGTH: 4737
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (3)..(4736)

<400> SEQUENCE: 30

gc atg cgg ctg tac gag gcg gca cgg cgc acc gga agt ccc gtg gtg        47
   Met Arg Leu Tyr Glu Ala Ala Arg Arg Thr Gly Ser Pro Val Val
     1               5                  10                  15

gtg gcg gcc gcg ctc gac gac gcg ccg gac gtg ccg ctg ctg cgc ggg       95
Val Ala Ala Ala Leu Asp Asp Ala Pro Asp Val Pro Leu Leu Arg Gly
                20                  25                  30

ctg cgg cgt acg acc gtc cgg cgt gcc gcc gtc cgg gaa cgc tct ctc      143
Leu Arg Arg Thr Thr Val Arg Arg Ala Ala Val Arg Glu Arg Ser Leu
            35                  40                  45

gcc gac cgc tcg ccg tgc tgc ccg acg acg agc gcg ccg acg cct ccc      191
Ala Asp Arg Ser Pro Cys Cys Pro Thr Thr Ser Ala Pro Thr Pro Pro
        50                  55                  60

tcg cgt tcg tcc tgg aac agc acc gcc acc gtg ctc ggc cac ctg ggc      239
Ser Arg Ser Ser Trp Asn Ser Thr Ala Thr Val Leu Gly His Leu Gly
     65                  70                  75

gcc gaa gac atc ccg gcg acg acg acg ttc aag gaa ctc ggc atc gac      287
Ala Glu Asp Ile Pro Ala Thr Thr Thr Phe Lys Glu Leu Gly Ile Asp
 80                  85                  90                  95

tcg ctc acc gcg gtc cag ctg cgc aac gcg ctg acc acg gcg acc ggc      335
Ser Leu Thr Ala Val Gln Leu Arg Asn Ala Leu Thr Thr Ala Thr Gly
                100                 105                 110

gta cgc ctc aac gcc aca gcg gtc ttc gac ttt ccg acg ccg cgc gcg      383
Val Arg Leu Asn Ala Thr Ala Val Phe Asp Phe Pro Thr Pro Arg Ala
            115                 120                 125

ctc gcc gcg aga ctc ggc gac gag ctg gcc ggt acc cgc gcg ccc gtc      431
Leu Ala Ala Arg Leu Gly Asp Glu Leu Ala Gly Thr Arg Ala Pro Val
        130                 135                 140

gcg gcc cgg acc gcg gcc acc gcg gcc gcg cac gac gaa ccg ctg gcg      479
Ala Ala Arg Thr Ala Ala Thr Ala Ala Ala His Asp Glu Pro Leu Ala
    145                 150                 155

atc gtg ggc atg gcc tgc cgt ctg ccg ggc ggg gtc gcg tcg cca cag      527
Ile Val Gly Met Ala Cys Arg Leu Pro Gly Gly Val Ala Ser Pro Gln
160                 165                 170                 175
```

-continued

```
gag ctg tgg cgt ctc gtc gcg tcc ggc acc gac gcc atc acg gag ttc      575
Glu Leu Trp Arg Leu Val Ala Ser Gly Thr Asp Ala Ile Thr Glu Phe
            180                 185                 190

ccc gcg gac cgc ggc tgg gac gtg gac gcg ctc tac gac ccg gac ccc      623
Pro Ala Asp Arg Gly Trp Asp Val Asp Ala Leu Tyr Asp Pro Asp Pro
            195                 200                 205

gac gcg atc ggc aag acc ttc gtc cgg cac ggc ggc ttc ctc gac ggt      671
Asp Ala Ile Gly Lys Thr Phe Val Arg His Gly Gly Phe Leu Asp Gly
        210                 215                 220

gcg acc ggc ttc gac gcg gcg ttc ttc ggg atc agc ccg cgc gag gcc      719
Ala Thr Gly Phe Asp Ala Ala Phe Phe Gly Ile Ser Pro Arg Glu Ala
    225                 230                 235

ctg gcc atg gac ccg cag caa cgg gtg ctc ctg gag acg tcc tgg gag      767
Leu Ala Met Asp Pro Gln Gln Arg Val Leu Leu Glu Thr Ser Trp Glu
240                 245                 250                 255

gcg ttc gaa agc gcg ggc atc acc ccg gac gcg gcg cgg ggc agc gac      815
Ala Phe Glu Ser Ala Gly Ile Thr Pro Asp Ala Ala Arg Gly Ser Asp
            260                 265                 270

acc ggc gtg ttc atc ggc gcg ttc tcc tac ggg tac ggc acg ggt gcg      863
Thr Gly Val Phe Ile Gly Ala Phe Ser Tyr Gly Tyr Gly Thr Gly Ala
            275                 280                 285

gat acc aac ggc ttc ggc gcg aca ggg tcg cag acc agc gtg ctc tcc      911
Asp Thr Asn Gly Phe Gly Ala Thr Gly Ser Gln Thr Ser Val Leu Ser
        290                 295                 300

ggc cgc ctc tcg tac ttc tac ggt ctg gag ggc cct tcg gtc acg gtc      959
Gly Arg Leu Ser Tyr Phe Tyr Gly Leu Glu Gly Pro Ser Val Thr Val
    305                 310                 315

gac acc gcc tgc tcg tcg tca ctg gtc gcc ctg cac cag gca ggg cag     1007
Asp Thr Ala Cys Ser Ser Ser Leu Val Ala Leu His Gln Ala Gly Gln
320                 325                 330                 335

tcc ctg cgc tcg ggc gaa tgc tcg ctc gcc ctg gtc ggc ggt gtc acg     1055
Ser Leu Arg Ser Gly Glu Cys Ser Leu Ala Leu Val Gly Gly Val Thr
            340                 345                 350

gtg atg gcg tcg ccc ggc gga ttc gtc gag ttc tcc cgg cag cgc ggg     1103
Val Met Ala Ser Pro Gly Gly Phe Val Glu Phe Ser Arg Gln Arg Gly
            355                 360                 365

ctc gcg ccg gac ggg cgg gcg aag gcg ttc ggc gcg ggc gcg gac ggt     1151
Leu Ala Pro Asp Gly Arg Ala Lys Ala Phe Gly Ala Gly Ala Asp Gly
        370                 375                 380

acg agc ttc gcc gag ggc gcc ggt gcc ctg gtg gtc gag cgg ctc tcc     1199
Thr Ser Phe Ala Glu Gly Ala Gly Ala Leu Val Val Glu Arg Leu Ser
    385                 390                 395

gac gcg gag cgc cac ggc cac acc gtc ctc gcc ctc gta cgc ggc tcc     1247
Asp Ala Glu Arg His Gly His Thr Val Leu Ala Leu Val Arg Gly Ser
400                 405                 410                 415

gcg gct aac tcc gac ggc gcg tcg aac ggt ctg tcg gcg ccg aac ggc     1295
Ala Ala Asn Ser Asp Gly Ala Ser Asn Gly Leu Ser Ala Pro Asn Gly
            420                 425                 430

ccc tcc cag gaa cgc gtc atc cac cag gcc ctc gcg aac gcg aaa ctc     1343
Pro Ser Gln Glu Arg Val Ile His Gln Ala Leu Ala Asn Ala Lys Leu
            435                 440                 445

acc ccc gcc gat gtc gac gcg gtc gag gcg cac ggc acc ggc acc cgc     1391
Thr Pro Ala Asp Val Asp Ala Val Glu Ala His Gly Thr Gly Thr Arg
        450                 455                 460

ctc ggc gac ccc atc gag gcg cag gcg ctg ctc gcg acg tac gga cag     1439
Leu Gly Asp Pro Ile Glu Ala Gln Ala Leu Leu Ala Thr Tyr Gly Gln
    465                 470                 475

gac cgg gcg acg ccc ctg ctg ctc ggc tcg ctg aag tcg aac atc ggg     1487
Asp Arg Ala Thr Pro Leu Leu Leu Gly Ser Leu Lys Ser Asn Ile Gly
480                 485                 490                 495
```

-continued

```
cac gcc cag gcc gcg tca ggg gtc gcc ggg atc atc aag atg gtg cag      1535
His Ala Gln Ala Ala Ser Gly Val Ala Gly Ile Ile Lys Met Val Gln
                500                 505                 510

gcc atc cgg cac ggg gaa ctg ccg ccg aca ctg cac gcg gac gag ccg      1583
Ala Ile Arg His Gly Glu Leu Pro Pro Thr Leu His Ala Asp Glu Pro
            515                 520                 525

tcg ccg cac gtc gac tgg acg gcc ggt gcc gtc gag ctc ctg acg tcg      1631
Ser Pro His Val Asp Trp Thr Ala Gly Ala Val Glu Leu Leu Thr Ser
        530                 535                 540

gcc cgg ccg tgg ccg ggg acc ggt cgc ccg cgc cgc gct gcc gtc tcg      1679
Ala Arg Pro Trp Pro Gly Thr Gly Arg Pro Arg Arg Ala Ala Val Ser
    545                 550                 555

tcg ttc ggc gtg agc ggc acg aac gcc cac atc atc ctt gag gca gga      1727
Ser Phe Gly Val Ser Gly Thr Asn Ala His Ile Ile Leu Glu Ala Gly
560                 565                 570                 575

ccg gtc aaa acg gga ccg gtc gag gca gga gcg atc gag gca gga ccg      1775
Pro Val Lys Thr Gly Pro Val Glu Ala Gly Ala Ile Glu Ala Gly Pro
                580                 585                 590

gtc gaa gta gga ccg gtc gag gct gga ccg ctc ccc gcg gcg ccg ccg      1823
Val Glu Val Gly Pro Val Glu Ala Gly Pro Leu Pro Ala Ala Pro Pro
            595                 600                 605

tca gca ccg ggc gaa gac ctt ccg ctg ctc gtg tcg gcg cgt tcc ccg      1871
Ser Ala Pro Gly Glu Asp Leu Pro Leu Leu Val Ser Ala Arg Ser Pro
        610                 615                 620

gag gca ctc gac gag cag atc ggg cgc ctg cgc gcc tat ctc gac acc      1919
Glu Ala Leu Asp Glu Gln Ile Gly Arg Leu Arg Ala Tyr Leu Asp Thr
    625                 630                 635

ggc ccg ggc gtc gac cgg gcg gcc gtg gcg cag aca ctg gcc cgg cgt      1967
Gly Pro Gly Val Asp Arg Ala Ala Val Ala Gln Thr Leu Ala Arg Arg
640                 645                 650                 655

acg cac ttc acc cac cgg gcc gta ctg ctc ggg gac acc gtc atc ggc      2015
Thr His Phe Thr His Arg Ala Val Leu Leu Gly Asp Thr Val Ile Gly
                660                 665                 670

gct ccc ccc gcg gac cag gcc gac gaa ctc gtc ttc gtc tac tcc ggt      2063
Ala Pro Pro Ala Asp Gln Ala Asp Glu Leu Val Phe Val Tyr Ser Gly
            675                 680                 685

cag ggc acc cag cat ccc gcg atg ggc gag cag cta gcc gcc gcg ttc      2111
Gln Gly Thr Gln His Pro Ala Met Gly Glu Gln Leu Ala Ala Ala Phe
        690                 695                 700

ccc gtc ttc gcg cgg atc cat cag cag gtg tgg gac ctg ctc gat gtg      2159
Pro Val Phe Ala Arg Ile His Gln Gln Val Trp Asp Leu Leu Asp Val
    705                 710                 715

ccc gat ctg gag gtg aac gag acc ggt tac gcc cag ccg gcc ctg ttc      2207
Pro Asp Leu Glu Val Asn Glu Thr Gly Tyr Ala Gln Pro Ala Leu Phe
720                 725                 730                 735

gca atg cag gtg gct ctg ttc ggg ctg ctg gaa tcg tgg ggt gta cga      2255
Ala Met Gln Val Ala Leu Phe Gly Leu Leu Glu Ser Trp Gly Val Arg
                740                 745                 750

ccg gac gcg gtg atc ggc cat tcg gtg ggt gag ctt gcg gct gcg tat      2303
Pro Asp Ala Val Ile Gly His Ser Val Gly Glu Leu Ala Ala Ala Tyr
            755                 760                 765

gtg tcc ggg gtg tgg tcg ttg gag gat gcc tgc act ttg gtg tcg gcg      2351
Val Ser Gly Val Trp Ser Leu Glu Asp Ala Cys Thr Leu Val Ser Ala
        770                 775                 780

cgg gct cgt ctg atg cag gct ctg ccc gcg ggt ggg gtg atg gtc gct      2399
Arg Ala Arg Leu Met Gln Ala Leu Pro Ala Gly Gly Val Met Val Ala
    785                 790                 795

gtc ccg gtc tcg gag gat gag gcc cgg gcc gtg ctg ggt gag ggt gtg      2447
Val Pro Val Ser Glu Asp Glu Ala Arg Ala Val Leu Gly Glu Gly Val
```

-continued

```
800                 805                 810                 815

gag atc gcc gcg gtc aac ggc ccg tcg tcg gtg gtt ctc tcc ggt gat      2495
Glu Ile Ala Ala Val Asn Gly Pro Ser Ser Val Val Leu Ser Gly Asp
                820                 825                 830

gag gcc gcc gtg ctg cag gcc gcg gag ggg ctg ggg aag tgg acg cgg      2543
Glu Ala Ala Val Leu Gln Ala Ala Glu Gly Leu Gly Lys Trp Thr Arg
            835                 840                 845

ctg gcg acc agc cac gcg ttc cat tcc gcc cgt atg gaa ccc atg ctg      2591
Leu Ala Thr Ser His Ala Phe His Ser Ala Arg Met Glu Pro Met Leu
        850                 855                 860

gag gag ttc cgg gcg gtc gcc gaa ggc ctg acc tac cgg acg ccg cag      2639
Glu Glu Phe Arg Ala Val Ala Glu Gly Leu Thr Tyr Arg Thr Pro Gln
    865                 870                 875

gtc tcc atg gcc gtt ggt gat cag gtg acc acc gct gag tac tgg gtg      2687
Val Ser Met Ala Val Gly Asp Gln Val Thr Thr Ala Glu Tyr Trp Val
880                 885                 890                 895

cgg cag gtc cgg gac acg gtc cgg ttc ggc gag cag gtg gcc tcg tac      2735
Arg Gln Val Arg Asp Thr Val Arg Phe Gly Glu Gln Val Ala Ser Tyr
                900                 905                 910

gag gac gcc gtg ttc gtc gag ctg ggt gcc gac cgg tca ctg gcc cgc      2783
Glu Asp Ala Val Phe Val Glu Leu Gly Ala Asp Arg Ser Leu Ala Arg
            915                 920                 925

ctg gtc gac ggt gtc gcg atg ctg cac ggc gac cac gaa atc cag gcc      2831
Leu Val Asp Gly Val Ala Met Leu His Gly Asp His Glu Ile Gln Ala
        930                 935                 940

gcg atc ggc gcc ctg gcc cac ctg tat gtc aac ggc gtc acg gtc gac      2879
Ala Ile Gly Ala Leu Ala His Leu Tyr Val Asn Gly Val Thr Val Asp
    945                 950                 955

tgg ccc gcg ctc ctg ggc gat gct ccg gca aca cgg gtg ctg gac ctt      2927
Trp Pro Ala Leu Leu Gly Asp Ala Pro Ala Thr Arg Val Leu Asp Leu
960                 965                 970                 975

ccg aca tac gcc ttc cag cac cag cgc tac tgg ctc gag tcg gct ccc      2975
Pro Thr Tyr Ala Phe Gln His Gln Arg Tyr Trp Leu Glu Ser Ala Pro
                980                 985                 990

ccg gcc acg gcc gac tcg ggc cac ccc gtc ctc ggc acc gga gtc gcc      3023
Pro Ala Thr Ala Asp Ser Gly His Pro Val Leu Gly Thr Gly Val Ala
            995                 1000                1005

gtc gcc ggg tcg ccg ggc cgg gtg ttc acg ggt ccc gtg ccc gcc ggt      3071
Val Ala Gly Ser Pro Gly Arg Val Phe Thr Gly Pro Val Pro Ala Gly
       1010                1015                1020

gcg gac cgc gcg gtg ttc atc gcc gaa ctg gcg ctc gcc gcc gcc gac      3119
Ala Asp Arg Ala Val Phe Ile Ala Glu Leu Ala Leu Ala Ala Ala Asp
   1025                1030                1035

gcc acc gac tgc gcc acg gtc gaa cag ctc gac gtc acc tcc gtg ccc      3167
Ala Thr Asp Cys Ala Thr Val Glu Gln Leu Asp Val Thr Ser Val Pro
1040               1045                1050                1055

ggc gga tcc gcc cgc ggc agg gcc acc gcg cag acc tgg gtc gat gaa      3215
Gly Gly Ser Ala Arg Gly Arg Ala Thr Ala Gln Thr Trp Val Asp Glu
               1060                1065                1070

ccc gcc gcc gac ggg cgg cgc cgc ttc acc gtc cac acc cgc gtc ggc      3263
Pro Ala Ala Asp Gly Arg Arg Arg Phe Thr Val His Thr Arg Val Gly
           1075                1080                1085

gac gcc ccg tgg acg ctg cac gcc gag ggg gtt ctc cgc ccc ggc cgc      3311
Asp Ala Pro Trp Thr Leu His Ala Glu Gly Val Leu Arg Pro Gly Arg
       1090                1095                1100

gtg ccc cag ccc gaa gcc gtc gac acc gcc tgg ccc ccg ccg ggc gcg      3359
Val Pro Gln Pro Glu Ala Val Asp Thr Ala Trp Pro Pro Pro Gly Ala
   1105                1110                1115

gtg ccc gcg gac ggg ctg ccc ggg gcg tgg cga cgc gcg gac cag gtc      3407
```

-continued

```
Val Pro Ala Asp Gly Leu Pro Gly Ala Trp Arg Arg Ala Asp Gln Val
1120                1125                1130                1135

ttc gtc gaa gcc gaa gtc gac agc cct gac ggc ttc gtg gca cac ccc     3455
Phe Val Glu Ala Glu Val Asp Ser Pro Asp Gly Phe Val Ala His Pro
                1140                1145                1150

gac ctg ctc gac gcg gtc ttc tcc gcg gtc ggc gac ggg agc cgc cag     3503
Asp Leu Leu Asp Ala Val Phe Ser Ala Val Gly Asp Gly Ser Arg Gln
            1155                1160                1165

ccg acc gga tgg cgc gac ctc gcg gtg cac gcg tcg gac gcc acc gtg     3551
Pro Thr Gly Trp Arg Asp Leu Ala Val His Ala Ser Asp Ala Thr Val
        1170                1175                1180

ctg cgc gcc tgc ctc acc cgc cgc gac agt ggt gtc gtg gag ctc gcc     3599
Leu Arg Ala Cys Leu Thr Arg Arg Asp Ser Gly Val Val Glu Leu Ala
    1185                1190                1195

gcc ttc gac ggt gcc gga atg ccg gtg ctc acc gcg gag tcg gtg acg     3647
Ala Phe Asp Gly Ala Gly Met Pro Val Leu Thr Ala Glu Ser Val Thr
1200                1205                1210                1215

ctg ggc gag gtc gcg tcg gca ggc gga tcc gac gag tcg gac ggt ctg     3695
Leu Gly Glu Val Ala Ser Ala Gly Gly Ser Asp Glu Ser Asp Gly Leu
                1220                1225                1230

ctt cgg ctt gag tgg ttg ccg gtg gcg gag gcc cac tac gac ggt gcc     3743
Leu Arg Leu Glu Trp Leu Pro Val Ala Glu Ala His Tyr Asp Gly Ala
            1235                1240                1245

gac gag ctg ccc gag ggc tac acc ctc atc acc gcc aca cac ccc gac     3791
Asp Glu Leu Pro Glu Gly Tyr Thr Leu Ile Thr Ala Thr His Pro Asp
        1250                1255                1260

gac ccc gac gac ccc acc aac ccc cac aac aca ccc aca cgc acc cac     3839
Asp Pro Asp Asp Pro Thr Asn Pro His Asn Thr Pro Thr Arg Thr His
    1265                1270                1275

aca caa acc aca cgc gtc ctc acc gcc ctc caa cac cac ctc atc acc     3887
Thr Gln Thr Thr Arg Val Leu Thr Ala Leu Gln His His Leu Ile Thr
1280                1285                1290                1295

acc aac cac acc ctc atc gtc cac acc acc acc gac ccc cca ggc gcc     3935
Thr Asn His Thr Leu Ile Val His Thr Thr Thr Asp Pro Pro Gly Ala
                1300                1305                1310

gcc gtc acc ggc ctc acc cgc acc gca caa aac gaa cac ccc ggc cgc     3983
Ala Val Thr Gly Leu Thr Arg Thr Ala Gln Asn Glu His Pro Gly Arg
            1315                1320                1325

atc cac ctc atc gaa acc cac cac ccc cac acc cca ctc ccc ctc acc     4031
Ile His Leu Ile Glu Thr His His Pro His Thr Pro Leu Pro Leu Thr
        1330                1335                1340

caa ctc acc acc ctc cac caa ccc cac cta cgc ctc acc aac aac acc     4079
Gln Leu Thr Thr Leu His Gln Pro His Leu Arg Leu Thr Asn Asn Thr
    1345                1350                1355

ctc cac acc ccc cac ctc acc ccc atc acc acc cac cac aac acc acc     4127
Leu His Thr Pro His Leu Thr Pro Ile Thr Thr His His Asn Thr Thr
1360                1365                1370                1375

aca acc acc ccc aac acc cca ccc ctc aac ccc aac cac gcc atc ctc     4175
Thr Thr Thr Pro Asn Thr Pro Pro Leu Asn Pro Asn His Ala Ile Leu
                1380                1385                1390

atc acc ggc ggc tcc ggc acc ctc gcc ggc atc ctc gcc cgc cac ctc     4223
Ile Thr Gly Gly Ser Gly Thr Leu Ala Gly Ile Leu Ala Arg His Leu
            1395                1400                1405

aac cac ccc cac acc tac ctc ctc tcc cgc aca cca cca ccc ccc acc     4271
Asn His Pro His Thr Tyr Leu Leu Ser Arg Thr Pro Pro Pro Pro Thr
        1410                1415                1420

aca ccc ggc acc cac atc ccc tgc gac ctc acc gac ccc acc caa atc     4319
Thr Pro Gly Thr His Ile Pro Cys Asp Leu Thr Asp Pro Thr Gln Ile
    1425                1430                1435
```

-continued

```
acc caa gcc ctc acc cac ata cca caa ccc ctc acc ggc atc ttc cac     4367
Thr Gln Ala Leu Thr His Ile Pro Gln Pro Leu Thr Gly Ile Phe His
1440                1445                1450                1455

acc gcc gcc acc ctc gac gac gcc acc ctc acc aac ctc acc ccc caa     4415
Thr Ala Ala Thr Leu Asp Asp Ala Thr Leu Thr Asn Leu Thr Pro Gln
               1460                1465                1470

cac ctc acc acc acc ctc caa ccc aaa gcc gac gcc gcc tgg cac ctc     4463
His Leu Thr Thr Thr Leu Gln Pro Lys Ala Asp Ala Ala Trp His Leu
           1475                1480                1485

cac cac cac acc caa aac caa ccc ctc acc cac ttc gtc ctc tac tcc     4511
His His His Thr Gln Asn Gln Pro Leu Thr His Phe Val Leu Tyr Ser
       1490                1495                1500

agc gcc gcc gcc acc ctc ggc agc ccc ggc caa gcc aac tac gcc gcc     4559
Ser Ala Ala Ala Thr Leu Gly Ser Pro Gly Gln Ala Asn Tyr Ala Ala
   1505                1510                1515

gcc aac gcc ttc ctc gac gcc ctc gcc acc cac cgc cac acc caa gga     4607
Ala Asn Ala Phe Leu Asp Ala Leu Ala Thr His Arg His Thr Gln Gly
1520                1525                1530                1535

caa ccc gcc acc acc atc gcc tgg ggc atg tgg cac acc acc acc aca     4655
Gln Pro Ala Thr Thr Ile Ala Trp Gly Met Trp His Thr Thr Thr Thr
               1540                1545                1550

ctc acc agc caa ctc acc gac agc gac cgc gac cgc atc cgc cgc ggc     4703
Leu Thr Ser Gln Leu Thr Asp Ser Asp Arg Asp Arg Ile Arg Arg Gly
           1555                1560                1565

ggc ttc ctg ccg atc tcg gac gac gag ggc atg c                       4737
Gly Phe Leu Pro Ile Ser Asp Asp Glu Gly Met
       1570                1575


<210> SEQ ID NO 31
<211> LENGTH: 1578
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 31

Met Arg Leu Tyr Glu Ala Ala Arg Arg Thr Gly Ser Pro Val Val Val
  1               5                  10                  15

Ala Ala Ala Leu Asp Asp Ala Pro Asp Val Pro Leu Leu Arg Gly Leu
             20                  25                  30

Arg Arg Thr Thr Val Arg Arg Ala Ala Val Arg Glu Arg Ser Leu Ala
         35                  40                  45

Asp Arg Ser Pro Cys Cys Pro Thr Thr Ser Ala Pro Thr Pro Pro Ser
     50                  55                  60

Arg Ser Ser Trp Asn Ser Thr Ala Thr Val Leu Gly His Leu Gly Ala
 65                  70                  75                  80

Glu Asp Ile Pro Ala Thr Thr Thr Phe Lys Glu Leu Gly Ile Asp Ser
                 85                  90                  95

Leu Thr Ala Val Gln Leu Arg Asn Ala Leu Thr Thr Ala Thr Gly Val
            100                 105                 110

Arg Leu Asn Ala Thr Ala Val Phe Asp Phe Pro Thr Pro Arg Ala Leu
        115                 120                 125

Ala Ala Arg Leu Gly Asp Glu Leu Ala Gly Thr Arg Ala Pro Val Ala
    130                 135                 140

Ala Arg Thr Ala Ala Thr Ala Ala Ala His Asp Glu Pro Leu Ala Ile
145                 150                 155                 160

Val Gly Met Ala Cys Arg Leu Pro Gly Gly Val Ala Ser Pro Gln Glu
                165                 170                 175
```

-continued

```
Leu Trp Arg Leu Val Ala Ser Gly Thr Asp Ala Ile Thr Glu Phe Pro
            180                 185                 190

Ala Asp Arg Gly Trp Asp Val Asp Ala Leu Tyr Asp Pro Asp Pro Asp
        195                 200                 205

Ala Ile Gly Lys Thr Phe Val Arg His Gly Gly Phe Leu Asp Gly Ala
    210                 215                 220

Thr Gly Phe Asp Ala Ala Phe Phe Gly Ile Ser Pro Arg Glu Ala Leu
225                 230                 235                 240

Ala Met Asp Pro Gln Gln Arg Val Leu Leu Glu Thr Ser Trp Glu Ala
                245                 250                 255

Phe Glu Ser Ala Gly Ile Thr Pro Asp Ala Ala Arg Gly Ser Asp Thr
            260                 265                 270

Gly Val Phe Ile Gly Ala Phe Ser Tyr Gly Tyr Gly Thr Gly Ala Asp
        275                 280                 285

Thr Asn Gly Phe Gly Ala Thr Gly Ser Gln Thr Ser Val Leu Ser Gly
    290                 295                 300

Arg Leu Ser Tyr Phe Tyr Gly Leu Glu Gly Pro Ser Val Thr Val Asp
305                 310                 315                 320

Thr Ala Cys Ser Ser Ser Leu Val Ala Leu His Gln Ala Gly Gln Ser
                325                 330                 335

Leu Arg Ser Gly Glu Cys Ser Leu Ala Leu Val Gly Gly Val Thr Val
            340                 345                 350

Met Ala Ser Pro Gly Gly Phe Val Glu Phe Ser Arg Gln Arg Gly Leu
        355                 360                 365

Ala Pro Asp Gly Arg Ala Lys Ala Phe Gly Ala Gly Ala Asp Gly Thr
    370                 375                 380

Ser Phe Ala Glu Gly Ala Gly Ala Leu Val Val Glu Arg Leu Ser Asp
385                 390                 395                 400

Ala Glu Arg His Gly His Thr Val Leu Ala Leu Val Arg Gly Ser Ala
                405                 410                 415

Ala Asn Ser Asp Gly Ala Ser Asn Gly Leu Ser Ala Pro Asn Gly Pro
            420                 425                 430

Ser Gln Glu Arg Val Ile His Gln Ala Leu Ala Asn Ala Lys Leu Thr
        435                 440                 445

Pro Ala Asp Val Asp Ala Val Glu Ala His Gly Thr Gly Thr Arg Leu
    450                 455                 460

Gly Asp Pro Ile Glu Ala Gln Ala Leu Leu Ala Thr Tyr Gly Gln Asp
465                 470                 475                 480

Arg Ala Thr Pro Leu Leu Leu Gly Ser Leu Lys Ser Asn Ile Gly His
                485                 490                 495

Ala Gln Ala Ala Ser Gly Val Ala Gly Ile Ile Lys Met Val Gln Ala
            500                 505                 510

Ile Arg His Gly Glu Leu Pro Pro Thr Leu His Ala Asp Glu Pro Ser
        515                 520                 525

Pro His Val Asp Trp Thr Ala Gly Ala Val Glu Leu Leu Thr Ser Ala
    530                 535                 540

Arg Pro Trp Pro Gly Thr Gly Arg Pro Arg Arg Ala Ala Val Ser Ser
545                 550                 555                 560

Phe Gly Val Ser Gly Thr Asn Ala His Ile Ile Leu Glu Ala Gly Pro
                565                 570                 575

Val Lys Thr Gly Pro Val Glu Ala Gly Ala Ile Glu Ala Gly Pro Val
            580                 585                 590
```

-continued

```
Glu Val Gly Pro Val Glu Ala Gly Pro Leu Pro Ala Ala Pro Pro Ser
        595                 600                 605

Ala Pro Gly Glu Asp Leu Pro Leu Leu Val Ser Ala Arg Ser Pro Glu
    610                 615                 620

Ala Leu Asp Glu Gln Ile Gly Arg Leu Arg Ala Tyr Leu Asp Thr Gly
625                 630                 635                 640

Pro Gly Val Asp Arg Ala Ala Val Ala Gln Thr Leu Ala Arg Arg Thr
                645                 650                 655

His Phe Thr His Arg Ala Val Leu Leu Gly Asp Thr Val Ile Gly Ala
            660                 665                 670

Pro Pro Ala Asp Gln Ala Asp Glu Leu Val Phe Val Tyr Ser Gly Gln
        675                 680                 685

Gly Thr Gln His Pro Ala Met Gly Glu Gln Leu Ala Ala Ala Phe Pro
    690                 695                 700

Val Phe Ala Arg Ile His Gln Gln Val Trp Asp Leu Leu Asp Val Pro
705                 710                 715                 720

Asp Leu Glu Val Asn Glu Thr Gly Tyr Ala Gln Pro Ala Leu Phe Ala
                725                 730                 735

Met Gln Val Ala Leu Phe Gly Leu Leu Glu Ser Trp Gly Val Arg Pro
            740                 745                 750

Asp Ala Val Ile Gly His Ser Val Gly Glu Leu Ala Ala Ala Tyr Val
        755                 760                 765

Ser Gly Val Trp Ser Leu Glu Asp Ala Cys Thr Leu Val Ser Ala Arg
    770                 775                 780

Ala Arg Leu Met Gln Ala Leu Pro Ala Gly Gly Val Met Val Ala Val
785                 790                 795                 800

Pro Val Ser Glu Asp Glu Ala Arg Ala Val Leu Gly Glu Gly Val Glu
                805                 810                 815

Ile Ala Ala Val Asn Gly Pro Ser Ser Val Val Leu Ser Gly Asp Glu
            820                 825                 830

Ala Ala Val Leu Gln Ala Ala Glu Gly Leu Gly Lys Trp Thr Arg Leu
        835                 840                 845

Ala Thr Ser His Ala Phe His Ser Ala Arg Met Glu Pro Met Leu Glu
    850                 855                 860

Glu Phe Arg Ala Val Ala Glu Gly Leu Thr Tyr Arg Thr Pro Gln Val
865                 870                 875                 880

Ser Met Ala Val Gly Asp Gln Val Thr Thr Ala Glu Tyr Trp Val Arg
                885                 890                 895

Gln Val Arg Asp Thr Val Arg Phe Gly Glu Gln Val Ala Ser Tyr Glu
            900                 905                 910

Asp Ala Val Phe Val Glu Leu Gly Ala Asp Arg Ser Leu Ala Arg Leu
        915                 920                 925

Val Asp Gly Val Ala Met Leu His Gly Asp His Glu Ile Gln Ala Ala
    930                 935                 940

Ile Gly Ala Leu Ala His Leu Tyr Val Asn Gly Val Thr Val Asp Trp
945                 950                 955                 960

Pro Ala Leu Leu Gly Asp Ala Pro Ala Thr Arg Val Leu Asp Leu Pro
                965                 970                 975

Thr Tyr Ala Phe Gln His Gln Arg Tyr Trp Leu Glu Ser Ala Pro Pro
            980                 985                 990

Ala Thr Ala Asp Ser Gly His Pro Val Leu Gly Thr Gly Val Ala Val
        995                 1000                1005

Ala Gly Ser Pro Gly Arg Val Phe Thr Gly Pro Val Pro Ala Gly Ala
```

-continued

```
    1010                1015                1020

Asp Arg Ala Val Phe Ile Ala Glu Leu Ala Leu Ala Ala Ala Asp Ala
1025                1030                1035                1040

Thr Asp Cys Ala Thr Val Glu Gln Leu Asp Val Thr Ser Val Pro Gly
                1045                1050                1055

Gly Ser Ala Arg Gly Arg Ala Thr Ala Gln Thr Trp Val Asp Glu Pro
            1060                1065                1070

Ala Ala Asp Gly Arg Arg Arg Phe Thr Val His Thr Arg Val Gly Asp
        1075                1080                1085

Ala Pro Trp Thr Leu His Ala Glu Gly Val Leu Arg Pro Gly Arg Val
    1090                1095                1100

Pro Gln Pro Glu Ala Val Asp Thr Ala Trp Pro Pro Pro Gly Ala Val
1105                1110                1115                1120

Pro Ala Asp Gly Leu Pro Gly Ala Trp Arg Arg Ala Asp Gln Val Phe
                1125                1130                1135

Val Glu Ala Glu Val Asp Ser Pro Asp Gly Phe Val Ala His Pro Asp
            1140                1145                1150

Leu Leu Asp Ala Val Phe Ser Ala Val Gly Asp Gly Ser Arg Gln Pro
        1155                1160                1165

Thr Gly Trp Arg Asp Leu Ala Val His Ala Ser Asp Ala Thr Val Leu
    1170                1175                1180

Arg Ala Cys Leu Thr Arg Arg Asp Ser Gly Val Val Glu Leu Ala Ala
1185                1190                1195                1200

Phe Asp Gly Ala Gly Met Pro Val Leu Thr Ala Glu Ser Val Thr Leu
                1205                1210                1215

Gly Glu Val Ala Ser Ala Gly Gly Ser Asp Glu Ser Asp Gly Leu Leu
            1220                1225                1230

Arg Leu Glu Trp Leu Pro Val Ala Glu Ala His Tyr Asp Gly Ala Asp
        1235                1240                1245

Glu Leu Pro Glu Gly Tyr Thr Leu Ile Thr Ala Thr His Pro Asp Asp
    1250                1255                1260

Pro Asp Asp Pro Thr Asn Pro His Asn Thr Pro Thr Arg Thr His Thr
1265                1270                1275                1280

Gln Thr Thr Arg Val Leu Thr Ala Leu Gln His His Leu Ile Thr Thr
                1285                1290                1295

Asn His Thr Leu Ile Val His Thr Thr Thr Asp Pro Pro Gly Ala Ala
            1300                1305                1310

Val Thr Gly Leu Thr Arg Thr Ala Gln Asn Glu His Pro Gly Arg Ile
        1315                1320                1325

His Leu Ile Glu Thr His His Pro His Thr Pro Leu Pro Leu Thr Gln
    1330                1335                1340

Leu Thr Thr Leu His Gln Pro His Leu Arg Leu Thr Asn Asn Thr Leu
1345                1350                1355                1360

His Thr Pro His Leu Thr Pro Ile Thr Thr His His Asn Thr Thr Thr
                1365                1370                1375

Thr Thr Pro Asn Thr Pro Pro Leu Asn Pro Asn His Ala Ile Leu Ile
            1380                1385                1390

Thr Gly Gly Ser Gly Thr Leu Ala Gly Ile Leu Ala Arg His Leu Asn
        1395                1400                1405

His Pro His Thr Tyr Leu Leu Ser Arg Thr Pro Pro Pro Pro Thr Thr
    1410                1415                1420

Pro Gly Thr His Ile Pro Cys Asp Leu Thr Asp Pro Thr Gln Ile Thr
1425                1430                1435                1440
```

-continued

```
Gln Ala Leu Thr His Ile Pro Gln Pro Leu Thr Gly Ile Phe His Thr
                1445                1450                1455

Ala Ala Thr Leu Asp Asp Ala Thr Leu Thr Asn Leu Thr Pro Gln His
            1460                1465                1470

Leu Thr Thr Thr Leu Gln Pro Lys Ala Asp Ala Ala Trp His Leu His
        1475                1480                1485

His His Thr Gln Asn Gln Pro Leu Thr His Phe Val Leu Tyr Ser Ser
    1490                1495                1500

Ala Ala Ala Thr Leu Gly Ser Pro Gly Gln Ala Asn Tyr Ala Ala Ala
1505                1510                1515                1520

Asn Ala Phe Leu Asp Ala Leu Ala Thr His Arg His Thr Gln Gly Gln
                1525                1530                1535

Pro Ala Thr Thr Ile Ala Trp Gly Met Trp His Thr Thr Thr Thr Leu
            1540                1545                1550

Thr Ser Gln Leu Thr Asp Ser Asp Arg Asp Arg Ile Arg Arg Gly Gly
        1555                1560                1565

Phe Leu Pro Ile Ser Asp Asp Glu Gly Met
    1570                1575
```

```
<210> SEQ ID NO 32
<211> LENGTH: 4818
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (3)..(4817)

<400> SEQUENCE: 32
```

```
gc atg cgg ctg tac gag gcg gca cgg cgc acc gga agt ccc gtg gtg        47
   Met Arg Leu Tyr Glu Ala Ala Arg Arg Thr Gly Ser Pro Val Val
     1               5                  10                  15

gtg gcg gcc gcg ctc gac gac gcg ccg gac gtg ccg ctg ctg cgc ggg       95
Val Ala Ala Ala Leu Asp Asp Ala Pro Asp Val Pro Leu Leu Arg Gly
                20                  25                  30

ctg cgg cgt acg acc gtc cgg cgt gcc gcc gtc cgg gaa cgc tct ctc      143
Leu Arg Arg Thr Thr Val Arg Arg Ala Ala Val Arg Glu Arg Ser Leu
            35                  40                  45

gcc gac cgc tcg ccg tgc tgc ccg acg acg agc gcg ccg acg cct ccc      191
Ala Asp Arg Ser Pro Cys Cys Pro Thr Thr Ser Ala Pro Thr Pro Pro
        50                  55                  60

tcg cgt tcg tcc tgg aac agc acc gcc acc gtg ctc ggc cac ctg ggc      239
Ser Arg Ser Ser Trp Asn Ser Thr Ala Thr Val Leu Gly His Leu Gly
     65                  70                  75

gcc gaa gac atc ccg gcg acg acg acg ttc aag gaa ctc ggc atc gac      287
Ala Glu Asp Ile Pro Ala Thr Thr Thr Phe Lys Glu Leu Gly Ile Asp
 80                  85                  90                  95

tcg ctc acc gcg gtc cag ctg cgc aac gcg ctg acc acg gcg acc ggc      335
Ser Leu Thr Ala Val Gln Leu Arg Asn Ala Leu Thr Thr Ala Thr Gly
                100                 105                 110

gta cgc ctc aac gcc aca gcg gtc ttc gac ttt ccg acg ccg cgc gcg      383
Val Arg Leu Asn Ala Thr Ala Val Phe Asp Phe Pro Thr Pro Arg Ala
            115                 120                 125

ctc gcc gcg aga ctc ggc gac gag ctg gcc ggt acc cgc gcg ccc gtc      431
Leu Ala Ala Arg Leu Gly Asp Glu Leu Ala Gly Thr Arg Ala Pro Val
        130                 135                 140

gcg gcc cgg acc gcg gcc acc gcg gcc gcg cac gac gaa ccg ctg gcg      479
```

-continued

```
Ala Ala Arg Thr Ala Ala Thr Ala Ala Ala His Asp Glu Pro Leu Ala
    145                 150                 155

atc gtg ggc atg gcc tgc cgt ctg ccg ggc ggg gtc gcg tcg cca cag      527
Ile Val Gly Met Ala Cys Arg Leu Pro Gly Gly Val Ala Ser Pro Gln
160                 165                 170                 175

gag ctg tgg cgt ctc gtc gcg tcc ggc acc gac gcc atc acg gag ttc      575
Glu Leu Trp Arg Leu Val Ala Ser Gly Thr Asp Ala Ile Thr Glu Phe
                180                 185                 190

ccc gcg gac cgc ggc tgg gac gtg gac gcg ctc tac gac ccg gac ccc      623
Pro Ala Asp Arg Gly Trp Asp Val Asp Ala Leu Tyr Asp Pro Asp Pro
            195                 200                 205

gac gcg atc ggc aag acc ttc gtc cgg cac ggc ggc ttc ctc gac ggt      671
Asp Ala Ile Gly Lys Thr Phe Val Arg His Gly Gly Phe Leu Asp Gly
        210                 215                 220

gcg acc ggc ttc gac gcg gcg ttc ttc ggg atc agc ccg cgc gag gcc      719
Ala Thr Gly Phe Asp Ala Ala Phe Phe Gly Ile Ser Pro Arg Glu Ala
    225                 230                 235

ctg gcc atg gac ccg cag caa cgg gtg ctc ctg gag acg tcc tgg gag      767
Leu Ala Met Asp Pro Gln Gln Arg Val Leu Leu Glu Thr Ser Trp Glu
240                 245                 250                 255

gcg ttc gaa agc gcg ggc atc acc ccg gac gcg gcg cgg ggc agc gac      815
Ala Phe Glu Ser Ala Gly Ile Thr Pro Asp Ala Ala Arg Gly Ser Asp
                260                 265                 270

acc ggc gtg ttc atc ggc gcg ttc tcc tac ggg tac ggc acg ggt gcg      863
Thr Gly Val Phe Ile Gly Ala Phe Ser Tyr Gly Tyr Gly Thr Gly Ala
            275                 280                 285

gat acc aac ggc ttc ggc gcg aca ggg tcg cag acc agc gtg ctc tcc      911
Asp Thr Asn Gly Phe Gly Ala Thr Gly Ser Gln Thr Ser Val Leu Ser
        290                 295                 300

ggc cgc ctc tcg tac ttc tac ggt ctg gag ggc cct tcg gtc acg gtc      959
Gly Arg Leu Ser Tyr Phe Tyr Gly Leu Glu Gly Pro Ser Val Thr Val
    305                 310                 315

gac acc gcc tgc tcg tcg tca ctg gtc gcc ctg cac cag gca ggg cag     1007
Asp Thr Ala Cys Ser Ser Ser Leu Val Ala Leu His Gln Ala Gly Gln
320                 325                 330                 335

tcc ctg cgc tcg ggc gaa tgc tcg ctc gcc ctg gtc ggc ggt gtc acg     1055
Ser Leu Arg Ser Gly Glu Cys Ser Leu Ala Leu Val Gly Gly Val Thr
                340                 345                 350

gtg atg gcg tcg ccc ggc gga ttc gtc gag ttc tcc cgg cag cgc ggg     1103
Val Met Ala Ser Pro Gly Gly Phe Val Glu Phe Ser Arg Gln Arg Gly
            355                 360                 365

ctc gcg ccg gac ggg cgg gcg aag gcg ttc ggc gcg ggc gcg gac ggt     1151
Leu Ala Pro Asp Gly Arg Ala Lys Ala Phe Gly Ala Gly Ala Asp Gly
        370                 375                 380

acg agc ttc gcc gag ggc gcc ggt gcc ctg gtg gtc gag cgg ctc tcc     1199
Thr Ser Phe Ala Glu Gly Ala Gly Ala Leu Val Val Glu Arg Leu Ser
    385                 390                 395

gac gcg gag cgc cac ggc cac acc gtc ctc gcc ctc gta cgc ggc tcc     1247
Asp Ala Glu Arg His Gly His Thr Val Leu Ala Leu Val Arg Gly Ser
400                 405                 410                 415

gcg gct aac tcc gac ggc gcg tcg aac ggt ctg tcg gcg ccg aac ggc     1295
Ala Ala Asn Ser Asp Gly Ala Ser Asn Gly Leu Ser Ala Pro Asn Gly
                420                 425                 430

ccc tcc cag gaa cgc gtc atc cac cag gcc ctc gcg aac gcg aaa ctc     1343
Pro Ser Gln Glu Arg Val Ile His Gln Ala Leu Ala Asn Ala Lys Leu
            435                 440                 445

acc ccc gcc gat gtc gac gcg gtc gag gcg cac ggc acc ggc acc cgc     1391
Thr Pro Ala Asp Val Asp Ala Val Glu Ala His Gly Thr Gly Thr Arg
        450                 455                 460
```

-continued

```
ctc ggc gac ccc atc gag gcg cag gcg ctg ctc gcg acg tac gga cag      1439
Leu Gly Asp Pro Ile Glu Ala Gln Ala Leu Leu Ala Thr Tyr Gly Gln
    465                 470                 475

gac cgg gcg acg ccc ctg ctg ctc ggc tcg ctg aag tcg aac atc ggg      1487
Asp Arg Ala Thr Pro Leu Leu Leu Gly Ser Leu Lys Ser Asn Ile Gly
480                 485                 490                 495

cac gcc cag gcc gcg tca ggg gtc gcc ggg atc atc aag atg gtg cag      1535
His Ala Gln Ala Ala Ser Gly Val Ala Gly Ile Ile Lys Met Val Gln
                500                 505                 510

gcc atc cgg cac ggg gaa ctg ccg ccg aca ctg cac gcg gac gag ccg      1583
Ala Ile Arg His Gly Glu Leu Pro Pro Thr Leu His Ala Asp Glu Pro
            515                 520                 525

tcg ccg cac gtc gac tgg acg gcc ggt gcc gtc gag ctc ctg acg tcg      1631
Ser Pro His Val Asp Trp Thr Ala Gly Ala Val Glu Leu Leu Thr Ser
        530                 535                 540

gcc cgg ccg tgg ccg ggg acc ggt cgc ccg cgc cgc gct gcc gtc tcg      1679
Ala Arg Pro Trp Pro Gly Thr Gly Arg Pro Arg Arg Ala Ala Val Ser
    545                 550                 555

tcg ttc ggc gtg agc ggc acg aac gcc cac atc atc ctt gag gca gga      1727
Ser Phe Gly Val Ser Gly Thr Asn Ala His Ile Ile Leu Glu Ala Gly
560                 565                 570                 575

ccg gtc aaa acg gga ccg gtc gag gca gga gcg atc gag gca gga ccg      1775
Pro Val Lys Thr Gly Pro Val Glu Ala Gly Ala Ile Glu Ala Gly Pro
                580                 585                 590

gtc gaa gta gga ccg gtc gag gct gga ccg ctc ccc gcg gcg ccg ccg      1823
Val Glu Val Gly Pro Val Glu Ala Gly Pro Leu Pro Ala Ala Pro Pro
            595                 600                 605

tca gca ccg ggc gaa gac ctt ccg ctg ctc gtg tcg gcg cgt tcc ccg      1871
Ser Ala Pro Gly Glu Asp Leu Pro Leu Leu Val Ser Ala Arg Ser Pro
        610                 615                 620

gag gca ctc gac gag cag atc ggg cgc ctg cgc gcc tat ctc gac acc      1919
Glu Ala Leu Asp Glu Gln Ile Gly Arg Leu Arg Ala Tyr Leu Asp Thr
    625                 630                 635

ggc ccg ggc gtc gac cgg gcg gcc gtg gcg cag aca ctg gcc cgg cgt      1967
Gly Pro Gly Val Asp Arg Ala Ala Val Ala Gln Thr Leu Ala Arg Arg
640                 645                 650                 655

acg cac ttc acc cac cgg gcc gta ctg ctc ggg gac acc gtc atc ggc      2015
Thr His Phe Thr His Arg Ala Val Leu Leu Gly Asp Thr Val Ile Gly
                660                 665                 670

gct ccc ccc gcg gac cag gcc gac gaa ctc gtc ttc gtc tac tcc ggt      2063
Ala Pro Pro Ala Asp Gln Ala Asp Glu Leu Val Phe Val Tyr Ser Gly
            675                 680                 685

cag ggc acc cag cat ccc gcg atg ggc gag cag cta gcc gat tcg tcg      2111
Gln Gly Thr Gln His Pro Ala Met Gly Glu Gln Leu Ala Asp Ser Ser
        690                 695                 700

gtg gtg ttc gcc gag cgg atg gcc gag tgt gcg gcg gcg ttg cgc gag      2159
Val Val Phe Ala Glu Arg Met Ala Glu Cys Ala Ala Ala Leu Arg Glu
    705                 710                 715

ttc gtg gac tgg gat ctg ttc acg gtt ctg gat gat ccg gcg gtg gtg      2207
Phe Val Asp Trp Asp Leu Phe Thr Val Leu Asp Asp Pro Ala Val Val
720                 725                 730                 735

gac cgg gtt gat gtg gtc cag ccc gct tcc tgg gcg atg atg gtt tcc      2255
Asp Arg Val Asp Val Val Gln Pro Ala Ser Trp Ala Met Met Val Ser
                740                 745                 750

ctg gcc gcg gtg tgg cag gcg gcc ggt gtg cgg ccg gat gcg gtg atc      2303
Leu Ala Ala Val Trp Gln Ala Ala Gly Val Arg Pro Asp Ala Val Ile
            755                 760                 765

ggc cat tcg cag ggt gag atc gcc gca gct tgt gtg gcg ggt gcg gtg      2351
Gly His Ser Gln Gly Glu Ile Ala Ala Ala Cys Val Ala Gly Ala Val
        770                 775                 780
```

-continued

```
tca cta cgc gat gcc gcc cgg atc gtg acc ttg cgc agc cag gcg atc     2399
Ser Leu Arg Asp Ala Ala Arg Ile Val Thr Leu Arg Ser Gln Ala Ile
    785                 790                 795

gcc cgg ggc ctg gcg ggc cgg ggc gcg atg gca tcc gtc gcc ctg ccc     2447
Ala Arg Gly Leu Ala Gly Arg Gly Ala Met Ala Ser Val Ala Leu Pro
800                 805                 810                 815

gcg cag gat gtc gag ctg gtc gac ggg gcc tgg atc gcc gcc cac aac     2495
Ala Gln Asp Val Glu Leu Val Asp Gly Ala Trp Ile Ala Ala His Asn
                820                 825                 830

ggg ccc gcc tcc acc gtg atc gcg ggc acc ccg gaa gcg gtc gac cat     2543
Gly Pro Ala Ser Thr Val Ile Ala Gly Thr Pro Glu Ala Val Asp His
            835                 840                 845

gtc ctc acc gct cat gag gca caa ggg gtg cgg gtg cgg cgg atc acc     2591
Val Leu Thr Ala His Glu Ala Gln Gly Val Arg Val Arg Arg Ile Thr
        850                 855                 860

gtc gac tat gcc tcg cac acc ccg cac gtc gag ctg atc cgc gac gaa     2639
Val Asp Tyr Ala Ser His Thr Pro His Val Glu Leu Ile Arg Asp Glu
    865                 870                 875

cta ctc gac atc act agc gac agc agc tcg cag acc ccg ctc gtg ccg     2687
Leu Leu Asp Ile Thr Ser Asp Ser Ser Ser Gln Thr Pro Leu Val Pro
880                 885                 890                 895

tgg ctg tcg acc gtg gac ggc acc tgg gtc gac agc ccg ctg gac ggg     2735
Trp Leu Ser Thr Val Asp Gly Thr Trp Val Asp Ser Pro Leu Asp Gly
                900                 905                 910

gag tac tgg tac cgg aac ctg cgt gaa ccg gtc ggt ttc cac ccc gcc     2783
Glu Tyr Trp Tyr Arg Asn Leu Arg Glu Pro Val Gly Phe His Pro Ala
            915                 920                 925

gtc agc cag ttg cag gcc cag ggc gac acc gtg ttc gtc gag gtc agc     2831
Val Ser Gln Leu Gln Ala Gln Gly Asp Thr Val Phe Val Glu Val Ser
        930                 935                 940

gcc agc ccg gtg ttg ttg cag gcg atg gac gac gat gtc gtc acg gtt     2879
Ala Ser Pro Val Leu Leu Gln Ala Met Asp Asp Asp Val Val Thr Val
    945                 950                 955

gcc acg ctg cgt cgt gac gac ggc gac gcc acc cgg atg ctc acc gcc     2927
Ala Thr Leu Arg Arg Asp Asp Gly Asp Ala Thr Arg Met Leu Thr Ala
960                 965                 970                 975

ctg gca cag gcc tat gtc cac ggc gtc acc gtc gac tgg ccc gcc atc     2975
Leu Ala Gln Ala Tyr Val His Gly Val Thr Val Asp Trp Pro Ala Ile
                980                 985                 990

ctc ggc acc acc aca acc cgg gta ctg gac ctt ccg acc tac gcc ttc     3023
Leu Gly Thr Thr Thr Thr Arg Val Leu Asp Leu Pro Thr Tyr Ala Phe
            995                1000                1005

caa cac cag cgg tac tgg ctc gag tcg gct ccc ccg gcc acg gcc gac     3071
Gln His Gln Arg Tyr Trp Leu Glu Ser Ala Pro Pro Ala Thr Ala Asp
       1010                1015                1020

tcg ggc cac ccc gtc ctc ggc acc gga gtc gcc gtc gcc ggg tcg ccg     3119
Ser Gly His Pro Val Leu Gly Thr Gly Val Ala Val Ala Gly Ser Pro
   1025                1030                1035

ggc cgg gtg ttc acg ggt ccc gtg ccc gcc ggt gcg gac cgc gcg gtg     3167
Gly Arg Val Phe Thr Gly Pro Val Pro Ala Gly Ala Asp Arg Ala Val
1040               1045                1050                1055

ttc atc gcc gaa ctg gcg ctc gcc gcc gcc gac gcc acc gac tgc gcc     3215
Phe Ile Ala Glu Leu Ala Leu Ala Ala Ala Asp Ala Thr Asp Cys Ala
               1060                1065                1070

acg gtc gaa cag ctc gac gtc acc tcc gtg ccc ggc gga tcc gcc cgc     3263
Thr Val Glu Gln Leu Asp Val Thr Ser Val Pro Gly Gly Ser Ala Arg
           1075                1080                1085

ggc agg gcc acc gcg cag acc tgg gtc gat gaa ccc gcc gcc gac ggg     3311
Gly Arg Ala Thr Ala Gln Thr Trp Val Asp Glu Pro Ala Ala Asp Gly
```

-continued

```
      1090                1095                1100

cgg cgc cgc ttc acc gtc cac acc cgc gtc ggc gac gcc ccg tgg acg     3359
Arg Arg Arg Phe Thr Val His Thr Arg Val Gly Asp Ala Pro Trp Thr
   1105                1110                1115

ctg cac gcc gag ggg gtt ctc cgc ccc ggc cgc gtg ccc cag ccc gaa     3407
Leu His Ala Glu Gly Val Leu Arg Pro Gly Arg Val Pro Gln Pro Glu
1120                1125                1130                1135

gcc gtc gac acc gcc tgg ccc ccg ccg ggc gcg gtg ccc gcg gac ggg     3455
Ala Val Asp Thr Ala Trp Pro Pro Pro Gly Ala Val Pro Ala Asp Gly
               1140                1145                1150

ctg ccc ggg gcg tgg cga cgc gcg gac cag gtc ttc gtc gaa gcc gaa     3503
Leu Pro Gly Ala Trp Arg Arg Ala Asp Gln Val Phe Val Glu Ala Glu
           1155                1160                1165

gtc gac agc cct gac ggc ttc gtg gca cac ccc gac ctg ctc gac gcg     3551
Val Asp Ser Pro Asp Gly Phe Val Ala His Pro Asp Leu Leu Asp Ala
       1170                1175                1180

gtc ttc tcc gcg gtc ggc gac ggg agc cgc cag ccg acc gga tgg cgc     3599
Val Phe Ser Ala Val Gly Asp Gly Ser Arg Gln Pro Thr Gly Trp Arg
   1185                1190                1195

gac ctc gcg gtg cac gcg tcg gac gcc acc gtg ctg cgc gcc tgc ctc     3647
Asp Leu Ala Val His Ala Ser Asp Ala Thr Val Leu Arg Ala Cys Leu
1200                1205                1210                1215

acc cgc cgc gac agt ggt gtc gtg gag ctc gcc gcc ttc gac ggt gcc     3695
Thr Arg Arg Asp Ser Gly Val Val Glu Leu Ala Ala Phe Asp Gly Ala
               1220                1225                1230

gga atg ccg gtg ctc acc gcg gag tcg gtg acg ctg ggc gag gtc gcg     3743
Gly Met Pro Val Leu Thr Ala Glu Ser Val Thr Leu Gly Glu Val Ala
           1235                1240                1245

tcg gca ggc gga tcc gac gag tcg gac ggt ctg ctt cgg ctt gag tgg     3791
Ser Ala Gly Gly Ser Asp Glu Ser Asp Gly Leu Leu Arg Leu Glu Trp
       1250                1255                1260

ttg ccg gtg gcg gag gcc cac tac gac ggt gcc gac gag ctg ccc gag     3839
Leu Pro Val Ala Glu Ala His Tyr Asp Gly Ala Asp Glu Leu Pro Glu
   1265                1270                1275

ggc tac acc ctc atc acc gcc aca cac ccc gac gac ccc gac gac ccc     3887
Gly Tyr Thr Leu Ile Thr Ala Thr His Pro Asp Asp Pro Asp Asp Pro
1280                1285                1290                1295

acc aac ccc cac aac aca ccc aca cgc acc cac aca caa acc aca cgc     3935
Thr Asn Pro His Asn Thr Pro Thr Arg Thr His Thr Gln Thr Thr Arg
               1300                1305                1310

gtc ctc acc gcc ctc caa cac cac ctc atc acc acc aac cac acc ctc     3983
Val Leu Thr Ala Leu Gln His His Leu Ile Thr Thr Asn His Thr Leu
           1315                1320                1325

atc gtc cac acc acc acc gac ccc cca ggc gcc gcc gtc acc ggc ctc     4031
Ile Val His Thr Thr Thr Asp Pro Pro Gly Ala Ala Val Thr Gly Leu
       1330                1335                1340

acc cgc acc gca caa aac gaa cac ccc ggc cgc atc cac ctc atc gaa     4079
Thr Arg Thr Ala Gln Asn Glu His Pro Gly Arg Ile His Leu Ile Glu
   1345                1350                1355

acc cac cac ccc cac acc cca ctc ccc ctc acc caa ctc acc acc ctc     4127
Thr His His Pro His Thr Pro Leu Pro Leu Thr Gln Leu Thr Thr Leu
1360                1365                1370                1375

cac caa ccc cac cta cgc ctc acc aac aac acc ctc cac acc ccc cac     4175
His Gln Pro His Leu Arg Leu Thr Asn Asn Thr Leu His Thr Pro His
               1380                1385                1390

ctc acc ccc atc acc acc cac cac aac acc acc aca acc acc ccc aac     4223
Leu Thr Pro Ile Thr Thr His His Asn Thr Thr Thr Thr Thr Pro Asn
           1395                1400                1405

acc cca ccc ctc aac ccc aac cac gcc atc ctc atc acc ggc ggc tcc     4271
```

-continued

```
Thr Pro Pro Leu Asn Pro Asn His Ala Ile Leu Ile Thr Gly Gly Ser
       1410                1415                1420

ggc acc ctc gcc ggc atc ctc gcc cgc cac ctc aac cac ccc cac acc     4319
Gly Thr Leu Ala Gly Ile Leu Ala Arg His Leu Asn His Pro His Thr
   1425                1430                1435

tac ctc ctc tcc cgc aca cca cca ccc ccc acc aca ccc ggc acc cac     4367
Tyr Leu Leu Ser Arg Thr Pro Pro Pro Pro Thr Thr Pro Gly Thr His
1440                1445                1450                1455

atc ccc tgc gac ctc acc gac ccc acc caa atc acc caa gcc ctc acc     4415
Ile Pro Cys Asp Leu Thr Asp Pro Thr Gln Ile Thr Gln Ala Leu Thr
               1460                1465                1470

cac ata cca caa ccc ctc acc ggc atc ttc cac acc gcc gcc acc ctc     4463
His Ile Pro Gln Pro Leu Thr Gly Ile Phe His Thr Ala Ala Thr Leu
           1475                1480                1485

gac gac gcc acc ctc acc aac ctc acc ccc caa cac ctc acc acc acc     4511
Asp Asp Ala Thr Leu Thr Asn Leu Thr Pro Gln His Leu Thr Thr Thr
       1490                1495                1500

ctc caa ccc aaa gcc gac gcc gcc tgg cac ctc cac cac cac acc caa     4559
Leu Gln Pro Lys Ala Asp Ala Ala Trp His Leu His His His Thr Gln
   1505                1510                1515

aac caa ccc ctc acc cac ttc gtc ctc tac tcc agc gcc gcc gcc acc     4607
Asn Gln Pro Leu Thr His Phe Val Leu Tyr Ser Ser Ala Ala Ala Thr
1520                1525                1530                1535

ctc ggc agc ccc ggc caa gcc aac tac gcc gcc gcc aac gcc ttc ctc     4655
Leu Gly Ser Pro Gly Gln Ala Asn Tyr Ala Ala Ala Asn Ala Phe Leu
               1540                1545                1550

gac gcc ctc gcc acc cac cgc cac acc caa gga caa ccc gcc acc acc     4703
Asp Ala Leu Ala Thr His Arg His Thr Gln Gly Gln Pro Ala Thr Thr
           1555                1560                1565

atc gcc tgg ggc atg tgg cac acc acc acc aca ctc acc agc caa ctc     4751
Ile Ala Trp Gly Met Trp His Thr Thr Thr Thr Leu Thr Ser Gln Leu
       1570                1575                1580

acc gac agc gac cgc gac cgc atc cgc cgc ggc ggc ttc ctg ccg atc     4799
Thr Asp Ser Asp Arg Asp Arg Ile Arg Arg Gly Gly Phe Leu Pro Ile
   1585                1590                1595

tcg gac gac gag ggc atg c                                           4818
Ser Asp Asp Glu Gly Met
1600                1605


<210> SEQ ID NO 33
<211> LENGTH: 1605
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 33

Met Arg Leu Tyr Glu Ala Ala Arg Arg Thr Gly Ser Pro Val Val Val
  1               5                  10                  15

Ala Ala Ala Leu Asp Asp Ala Pro Asp Val Pro Leu Leu Arg Gly Leu
             20                  25                  30

Arg Arg Thr Thr Val Arg Arg Ala Ala Val Arg Glu Arg Ser Leu Ala
         35                  40                  45

Asp Arg Ser Pro Cys Cys Pro Thr Thr Ser Ala Pro Thr Pro Pro Ser
     50                  55                  60

Arg Ser Ser Trp Asn Ser Thr Ala Thr Val Leu Gly His Leu Gly Ala
 65                  70                  75                  80

Glu Asp Ile Pro Ala Thr Thr Thr Phe Lys Glu Leu Gly Ile Asp Ser
                 85                  90                  95
```

-continued

```
Leu Thr Ala Val Gln Leu Arg Asn Ala Leu Thr Thr Ala Thr Gly Val
            100                 105                 110

Arg Leu Asn Ala Thr Ala Val Phe Asp Phe Pro Thr Pro Arg Ala Leu
        115                 120                 125

Ala Ala Arg Leu Gly Asp Glu Leu Ala Gly Thr Arg Ala Pro Val Ala
    130                 135                 140

Ala Arg Thr Ala Ala Thr Ala Ala Ala His Asp Glu Pro Leu Ala Ile
145                 150                 155                 160

Val Gly Met Ala Cys Arg Leu Pro Gly Gly Val Ala Ser Pro Gln Glu
                165                 170                 175

Leu Trp Arg Leu Val Ala Ser Gly Thr Asp Ala Ile Thr Glu Phe Pro
            180                 185                 190

Ala Asp Arg Gly Trp Asp Val Asp Ala Leu Tyr Asp Pro Asp Pro Asp
        195                 200                 205

Ala Ile Gly Lys Thr Phe Val Arg His Gly Gly Phe Leu Asp Gly Ala
    210                 215                 220

Thr Gly Phe Asp Ala Ala Phe Phe Gly Ile Ser Pro Arg Glu Ala Leu
225                 230                 235                 240

Ala Met Asp Pro Gln Gln Arg Val Leu Leu Glu Thr Ser Trp Glu Ala
                245                 250                 255

Phe Glu Ser Ala Gly Ile Thr Pro Asp Ala Ala Arg Gly Ser Asp Thr
            260                 265                 270

Gly Val Phe Ile Gly Ala Phe Ser Tyr Gly Tyr Gly Thr Gly Ala Asp
        275                 280                 285

Thr Asn Gly Phe Gly Ala Thr Gly Ser Gln Thr Ser Val Leu Ser Gly
    290                 295                 300

Arg Leu Ser Tyr Phe Tyr Gly Leu Glu Gly Pro Ser Val Thr Val Asp
305                 310                 315                 320

Thr Ala Cys Ser Ser Ser Leu Val Ala Leu His Gln Ala Gly Gln Ser
                325                 330                 335

Leu Arg Ser Gly Glu Cys Ser Leu Ala Leu Val Gly Gly Val Thr Val
            340                 345                 350

Met Ala Ser Pro Gly Gly Phe Val Glu Phe Ser Arg Gln Arg Gly Leu
        355                 360                 365

Ala Pro Asp Gly Arg Ala Lys Ala Phe Gly Ala Gly Ala Asp Gly Thr
    370                 375                 380

Ser Phe Ala Glu Gly Ala Gly Ala Leu Val Val Glu Arg Leu Ser Asp
385                 390                 395                 400

Ala Glu Arg His Gly His Thr Val Leu Ala Leu Val Arg Gly Ser Ala
                405                 410                 415

Ala Asn Ser Asp Gly Ala Ser Asn Gly Leu Ser Ala Pro Asn Gly Pro
            420                 425                 430

Ser Gln Glu Arg Val Ile His Gln Ala Leu Ala Asn Ala Lys Leu Thr
        435                 440                 445

Pro Ala Asp Val Asp Ala Val Glu Ala His Gly Thr Gly Thr Arg Leu
    450                 455                 460

Gly Asp Pro Ile Glu Ala Gln Ala Leu Leu Ala Thr Tyr Gly Gln Asp
465                 470                 475                 480

Arg Ala Thr Pro Leu Leu Leu Gly Ser Leu Lys Ser Asn Ile Gly His
                485                 490                 495

Ala Gln Ala Ala Ser Gly Val Ala Gly Ile Ile Lys Met Val Gln Ala
            500                 505                 510
```

-continued

```
Ile Arg His Gly Glu Leu Pro Pro Thr Leu His Ala Asp Glu Pro Ser
        515                 520                 525

Pro His Val Asp Trp Thr Ala Gly Ala Val Glu Leu Leu Thr Ser Ala
    530                 535                 540

Arg Pro Trp Pro Gly Thr Gly Arg Pro Arg Arg Ala Ala Val Ser Ser
545                 550                 555                 560

Phe Gly Val Ser Gly Thr Asn Ala His Ile Ile Leu Glu Ala Gly Pro
                565                 570                 575

Val Lys Thr Gly Pro Val Glu Ala Gly Ala Ile Glu Ala Gly Pro Val
            580                 585                 590

Glu Val Gly Pro Val Glu Ala Gly Pro Leu Pro Ala Ala Pro Pro Ser
        595                 600                 605

Ala Pro Gly Glu Asp Leu Pro Leu Leu Val Ser Ala Arg Ser Pro Glu
    610                 615                 620

Ala Leu Asp Glu Gln Ile Gly Arg Leu Arg Ala Tyr Leu Asp Thr Gly
625                 630                 635                 640

Pro Gly Val Asp Arg Ala Ala Val Ala Gln Thr Leu Ala Arg Arg Thr
                645                 650                 655

His Phe Thr His Arg Ala Val Leu Leu Gly Asp Thr Val Ile Gly Ala
            660                 665                 670

Pro Pro Ala Asp Gln Ala Asp Glu Leu Val Phe Val Tyr Ser Gly Gln
        675                 680                 685

Gly Thr Gln His Pro Ala Met Gly Glu Gln Leu Ala Asp Ser Ser Val
    690                 695                 700

Val Phe Ala Glu Arg Met Ala Glu Cys Ala Ala Ala Leu Arg Glu Phe
705                 710                 715                 720

Val Asp Trp Asp Leu Phe Thr Val Leu Asp Asp Pro Ala Val Val Asp
                725                 730                 735

Arg Val Asp Val Val Gln Pro Ala Ser Trp Ala Met Met Val Ser Leu
            740                 745                 750

Ala Ala Val Trp Gln Ala Ala Gly Val Arg Pro Asp Ala Val Ile Gly
        755                 760                 765

His Ser Gln Gly Glu Ile Ala Ala Ala Cys Val Ala Gly Ala Val Ser
    770                 775                 780

Leu Arg Asp Ala Ala Arg Ile Val Thr Leu Arg Ser Gln Ala Ile Ala
785                 790                 795                 800

Arg Gly Leu Ala Gly Arg Gly Ala Met Ala Ser Val Ala Leu Pro Ala
                805                 810                 815

Gln Asp Val Glu Leu Val Asp Gly Ala Trp Ile Ala Ala His Asn Gly
            820                 825                 830

Pro Ala Ser Thr Val Ile Ala Gly Thr Pro Glu Ala Val Asp His Val
        835                 840                 845

Leu Thr Ala His Glu Ala Gln Gly Val Arg Val Arg Arg Ile Thr Val
    850                 855                 860

Asp Tyr Ala Ser His Thr Pro His Val Glu Leu Ile Arg Asp Glu Leu
865                 870                 875                 880

Leu Asp Ile Thr Ser Asp Ser Ser Ser Gln Thr Pro Leu Val Pro Trp
                885                 890                 895

Leu Ser Thr Val Asp Gly Thr Trp Val Asp Ser Pro Leu Asp Gly Glu
            900                 905                 910

Tyr Trp Tyr Arg Asn Leu Arg Glu Pro Val Gly Phe His Pro Ala Val
        915                 920                 925

Ser Gln Leu Gln Ala Gln Gly Asp Thr Val Phe Val Glu Val Ser Ala
```

-continued

```
    930                 935                 940

Ser Pro Val Leu Leu Gln Ala Met Asp Asp Asp Val Val Thr Val Ala
945                 950                 955                 960

Thr Leu Arg Arg Asp Asp Gly Asp Ala Thr Arg Met Leu Thr Ala Leu
                965                 970                 975

Ala Gln Ala Tyr Val His Gly Val Thr Val Asp Trp Pro Ala Ile Leu
            980                 985                 990

Gly Thr Thr Thr Thr Arg Val Leu Asp Leu Pro Thr Tyr Ala Phe Gln
        995                 1000                1005

His Gln Arg Tyr Trp Leu Glu Ser Ala Pro Pro Ala Thr Ala Asp Ser
    1010                1015                1020

Gly His Pro Val Leu Gly Thr Gly Val Ala Val Ala Gly Ser Pro Gly
1025                1030                1035                1040

Arg Val Phe Thr Gly Pro Val Pro Ala Gly Ala Asp Arg Ala Val Phe
                1045                1050                1055

Ile Ala Glu Leu Ala Leu Ala Ala Ala Asp Ala Thr Asp Cys Ala Thr
            1060                1065                1070

Val Glu Gln Leu Asp Val Thr Ser Val Pro Gly Gly Ser Ala Arg Gly
        1075                1080                1085

Arg Ala Thr Ala Gln Thr Trp Val Asp Glu Pro Ala Ala Asp Gly Arg
    1090                1095                1100

Arg Arg Phe Thr Val His Thr Arg Val Gly Asp Ala Pro Trp Thr Leu
1105                1110                1115                1120

His Ala Glu Gly Val Leu Arg Pro Gly Arg Val Pro Gln Pro Glu Ala
                1125                1130                1135

Val Asp Thr Ala Trp Pro Pro Pro Gly Ala Val Pro Ala Asp Gly Leu
            1140                1145                1150

Pro Gly Ala Trp Arg Arg Ala Asp Gln Val Phe Val Glu Ala Glu Val
        1155                1160                1165

Asp Ser Pro Asp Gly Phe Val Ala His Pro Asp Leu Leu Asp Ala Val
    1170                1175                1180

Phe Ser Ala Val Gly Asp Gly Ser Arg Gln Pro Thr Gly Trp Arg Asp
1185                1190                1195                1200

Leu Ala Val His Ala Ser Asp Ala Thr Val Leu Arg Ala Cys Leu Thr
                1205                1210                1215

Arg Arg Asp Ser Gly Val Val Glu Leu Ala Ala Phe Asp Gly Ala Gly
            1220                1225                1230

Met Pro Val Leu Thr Ala Glu Ser Val Thr Leu Gly Glu Val Ala Ser
        1235                1240                1245

Ala Gly Gly Ser Asp Glu Ser Asp Gly Leu Leu Arg Leu Glu Trp Leu
    1250                1255                1260

Pro Val Ala Glu Ala His Tyr Asp Gly Ala Asp Glu Leu Pro Glu Gly
1265                1270                1275                1280

Tyr Thr Leu Ile Thr Ala Thr His Pro Asp Asp Pro Asp Asp Pro Thr
                1285                1290                1295

Asn Pro His Asn Thr Pro Thr Arg Thr His Thr Gln Thr Thr Arg Val
            1300                1305                1310

Leu Thr Ala Leu Gln His His Leu Ile Thr Thr Asn His Thr Leu Ile
        1315                1320                1325

Val His Thr Thr Thr Asp Pro Pro Gly Ala Ala Val Thr Gly Leu Thr
    1330                1335                1340

Arg Thr Ala Gln Asn Glu His Pro Gly Arg Ile His Leu Ile Glu Thr
1345                1350                1355                1360
```

```
His His Pro His Thr Pro Leu Pro Leu Thr Gln Leu Thr Thr Leu His
                1365                1370                1375

Gln Pro His Leu Arg Leu Thr Asn Asn Thr Leu His Thr Pro His Leu
            1380                1385                1390

Thr Pro Ile Thr Thr His His Asn Thr Thr Thr Thr Thr Pro Asn Thr
        1395                1400                1405

Pro Pro Leu Asn Pro Asn His Ala Ile Leu Ile Thr Gly Gly Ser Gly
    1410                1415                1420

Thr Leu Ala Gly Ile Leu Ala Arg His Leu Asn His Pro His Thr Tyr
1425                1430                1435                1440

Leu Leu Ser Arg Thr Pro Pro Pro Pro Thr Thr Pro Gly Thr His Ile
                1445                1450                1455

Pro Cys Asp Leu Thr Asp Pro Thr Gln Ile Thr Gln Ala Leu Thr His
            1460                1465                1470

Ile Pro Gln Pro Leu Thr Gly Ile Phe His Thr Ala Ala Thr Leu Asp
        1475                1480                1485

Asp Ala Thr Leu Thr Asn Leu Thr Pro Gln His Leu Thr Thr Thr Leu
    1490                1495                1500

Gln Pro Lys Ala Asp Ala Ala Trp His Leu His His His Thr Gln Asn
1505                1510                1515                1520

Gln Pro Leu Thr His Phe Val Leu Tyr Ser Ser Ala Ala Ala Thr Leu
                1525                1530                1535

Gly Ser Pro Gly Gln Ala Asn Tyr Ala Ala Ala Asn Ala Phe Leu Asp
            1540                1545                1550

Ala Leu Ala Thr His Arg His Thr Gln Gly Gln Pro Ala Thr Thr Ile
        1555                1560                1565

Ala Trp Gly Met Trp His Thr Thr Thr Thr Leu Thr Ser Gln Leu Thr
    1570                1575                1580

Asp Ser Asp Arg Asp Arg Ile Arg Arg Gly Gly Phe Leu Pro Ile Ser
1585                1590                1595                1600

Asp Asp Glu Gly Met
                1605
```

<210> SEQ ID NO 34
<211> LENGTH: 33
<212> TYPE: DNA
<213> ORGANISM: Artificial Sequence
<220> FEATURE:
<223> OTHER INFORMATION: Description of Artificial Sequence: DNA encoding synthetic PKS synthase fragment
<220> FEATURE:
<221> NAME/KEY: CDS
<222> LOCATION: (1)..(33)

<400> SEQUENCE: 34

```
ggc cgt ccg cgc cgt gcg gcg gtc tcg tcg ttc                           33
Gly Arg Pro Arg Arg Ala Ala Val Ser Ser Phe
  1               5                  10
```

<210> SEQ ID NO 35
<211> LENGTH: 11
<212> TYPE: PRT
<213> ORGANISM: Artificial Sequence
<220> FEATURE:
<223> OTHER INFORMATION: Description of Artificial Sequence: Synthetic PKS synthase fragment

<400> SEQUENCE: 35

```
Gly Arg Pro Arg Arg Ala Ala Val Ser Ser Phe
```

```
  1               5                   10


<210> SEQ ID NO 36
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 36

acc cag cat ccc gcg atg ggt gag cgg ctc gcc                            33
Thr Gln His Pro Ala Met Gly Glu Arg Leu Ala
  1               5                   10


<210> SEQ ID NO 37
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 37

Thr Gln His Pro Ala Met Gly Glu Arg Leu Ala
  1               5                   10


<210> SEQ ID NO 38
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 38

tac gcc ttc cag cgg cgg ccc tac tgg atc gag                            33
Tyr Ala Phe Gln Arg Arg Pro Tyr Trp Ile Glu
  1               5                   10


<210> SEQ ID NO 39
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 39

Tyr Ala Phe Gln Arg Arg Pro Tyr Trp Ile Glu
  1               5                   10


<210> SEQ ID NO 40
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 40
```

-continued

```
gac cgg ccc cgt cgg gcg ggc gtg tcg tcc ttc                            33
Asp Arg Pro Arg Arg Ala Gly Val Ser Ser Phe
  1               5                  10


<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 41

Asp Arg Pro Arg Arg Ala Gly Val Ser Ser Phe
  1               5                  10


<210> SEQ ID NO 42
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 42

tgg cag tgg ctg ggg atg ggc agt gcc ctg cgg                            33
Trp Gln Trp Leu Gly Met Gly Ser Ala Leu Arg
  1               5                  10


<210> SEQ ID NO 43
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 43

Trp Gln Trp Leu Gly Met Gly Ser Ala Leu Arg
  1               5                  10


<210> SEQ ID NO 44
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 44

tac gcc ttc caa cac cag cgg tac tgg gtc gag                            33
Tyr Ala Phe Gln His Gln Arg Tyr Trp Val Glu
  1               5                  10


<210> SEQ ID NO 45
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 45
```

```
Tyr Ala Phe Gln His Gln Arg Tyr Trp Val Glu
  1               5                  10


<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 46

ggc cga gcg cgc cgg gca ggc gtg tcg tcc ttc                          33
Gly Arg Ala Arg Arg Ala Gly Val Ser Ser Phe
  1               5                  10


<210> SEQ ID NO 47
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 47

Gly Arg Ala Arg Arg Ala Gly Val Ser Ser Phe
  1               5                  10


<210> SEQ ID NO 48
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 48

tcg cag cgt gct ggc atg ggt gag gaa ctg gcc                          33
Ser Gln Arg Ala Gly Met Gly Glu Glu Leu Ala
  1               5                  10


<210> SEQ ID NO 49
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 49

Ser Gln Arg Ala Gly Met Gly Glu Glu Leu Ala
  1               5                  10


<210> SEQ ID NO 50
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)
```

```
<400> SEQUENCE: 50

tac gcc ttc cag cac cag cgc tac tgg ctc gag                          33
Tyr Ala Phe Gln His Gln Arg Tyr Trp Leu Glu
  1               5                  10


<210> SEQ ID NO 51
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 51

Tyr Ala Phe Gln His Gln Arg Tyr Trp Leu Glu
  1               5                  10


<210> SEQ ID NO 52
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 52

gcg cga ccg cgc cgg gcg ggg gtc tcg tcg ttc                          33
Ala Arg Pro Arg Arg Ala Gly Val Ser Ser Phe
  1               5                  10


<210> SEQ ID NO 53
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 53

Ala Arg Pro Arg Arg Ala Gly Val Ser Ser Phe
  1               5                  10


<210> SEQ ID NO 54
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 54

tgg cag tgg gcg ggc atg gcc gtc gac ctg ctc                          33
Trp Gln Trp Ala Gly Met Ala Val Asp Leu Leu
  1               5                  10


<210> SEQ ID NO 55
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment
```

```
<400> SEQUENCE: 55

Trp Gln Trp Ala Gly Met Ala Val Asp Leu Leu
  1               5                  10


<210> SEQ ID NO 56
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 56

tac ccg ttc cag cgc gag cgc gtc tgg ctc gaa                         33
Tyr Pro Phe Gln Arg Glu Arg Val Trp Leu Glu
  1               5                  10


<210> SEQ ID NO 57
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 57

Tyr Pro Phe Gln Arg Glu Arg Val Trp Leu Glu
  1               5                  10


<210> SEQ ID NO 58
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 58

gac ggg gtg cgc cgg gca ggt gtg tcg gcg ttc                         33
Asp Gly Val Arg Arg Ala Gly Val Ser Ala Phe
  1               5                  10


<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 59

Asp Gly Val Arg Arg Ala Gly Val Ser Ala Phe
  1               5                  10


<210> SEQ ID NO 60
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
```

```
<221> NAME/KEY: CDS
<222> LOCATION: (1)..(33)

<400> SEQUENCE: 60

gcc cag tgg gaa ggc atg gcg cgg gag ttg ttg                        33
Ala Gln Trp Glu Gly Met Ala Arg Glu Leu Leu
  1               5                  10


<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 61

Ala Gln Trp Glu Gly Met Ala Arg Glu Leu Leu
  1               5                  10


<210> SEQ ID NO 62
<211> LENGTH: 33
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(33)

<400> SEQUENCE: 62

tat cct ttc cag ggc aag cgg ttc tgg ctg ctg                        33
Tyr Pro Phe Gln Gly Lys Arg Phe Trp Leu Leu
  1               5                  10


<210> SEQ ID NO 63
<211> LENGTH: 11
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 63

Tyr Pro Phe Gln Gly Lys Arg Phe Trp Leu Leu
  1               5                  10


<210> SEQ ID NO 64
<211> LENGTH: 480
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (3)..(479)

<400> SEQUENCE: 64

cc ggc gcc gtc gaa ctg ctg acg tcg gcc cgg ccg tgg ccc gag acc       47
   Gly Ala Val Glu Leu Leu Thr Ser Ala Arg Pro Trp Pro Glu Thr
     1               5                  10                  15

gac cgg cca cgg cgt gcc gcc gtc tcc tcg ttc ggg gtg agc ggc acc      95
Asp Arg Pro Arg Arg Ala Ala Val Ser Ser Phe Gly Val Ser Gly Thr
                 20                  25                  30

aac gcc cac gtc atc ctg gag gcc gga ccg gta acg gag acg ccc gcg     143
Asn Ala His Val Ile Leu Glu Ala Gly Pro Val Thr Glu Thr Pro Ala
```

-continued

```
            35                  40                  45

gca tcg cct tcc ggt gac ctt ccc ctg ctg gtg tcg gca cgc tca ccg      191
Ala Ser Pro Ser Gly Asp Leu Pro Leu Leu Val Ser Ala Arg Ser Pro
        50                  55                  60

gaa gcg ctc gac gag cag atc cgc cga ctg cgc gcc tac ctg gac acc      239
Glu Ala Leu Asp Glu Gln Ile Arg Arg Leu Arg Ala Tyr Leu Asp Thr
    65                  70                  75

acc ccg gac gtc gac cgg gtg gcc gtg gca cag acg ctg gcc cgg cgc      287
Thr Pro Asp Val Asp Arg Val Ala Val Ala Gln Thr Leu Ala Arg Arg
 80                  85                  90                  95

aca cac ttc gcc cac cgc gcc gtg ctg ctc ggt gac acc gtc atc acc      335
Thr His Phe Ala His Arg Ala Val Leu Leu Gly Asp Thr Val Ile Thr
                100                 105                 110

aca ccc ccc gcg gac cgg ccc gac gaa ctc gtc ttc gtc tac tcc ggc      383
Thr Pro Pro Ala Asp Arg Pro Asp Glu Leu Val Phe Val Tyr Ser Gly
            115                 120                 125

cag ggc acc cag cat ccc gcg atg ggc gag cag ctc gcc gcc gcc cat      431
Gln Gly Thr Gln His Pro Ala Met Gly Glu Gln Leu Ala Ala Ala His
        130                 135                 140

ccc gtg ttc gcc gac gcc tgg cat gaa gcg ctc cgc cgc ctt gac aac c    480
Pro Val Phe Ala Asp Ala Trp His Glu Ala Leu Arg Arg Leu Asp Asn
    145                 150                 155


<210> SEQ ID NO 65
<211> LENGTH: 159
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 65

Gly Ala Val Glu Leu Leu Thr Ser Ala Arg Pro Trp Pro Glu Thr Asp
  1               5                  10                  15

Arg Pro Arg Arg Ala Ala Val Ser Ser Phe Gly Val Ser Gly Thr Asn
            20                  25                  30

Ala His Val Ile Leu Glu Ala Gly Pro Val Thr Glu Thr Pro Ala Ala
        35                  40                  45

Ser Pro Ser Gly Asp Leu Pro Leu Leu Val Ser Ala Arg Ser Pro Glu
    50                  55                  60

Ala Leu Asp Glu Gln Ile Arg Arg Leu Arg Ala Tyr Leu Asp Thr Thr
 65                  70                  75                  80

Pro Asp Val Asp Arg Val Ala Val Ala Gln Thr Leu Ala Arg Arg Thr
                 85                  90                  95

His Phe Ala His Arg Ala Val Leu Leu Gly Asp Thr Val Ile Thr Thr
            100                 105                 110

Pro Pro Ala Asp Arg Pro Asp Glu Leu Val Phe Val Tyr Ser Gly Gln
        115                 120                 125

Gly Thr Gln His Pro Ala Met Gly Glu Gln Leu Ala Ala Ala His Pro
    130                 135                 140

Val Phe Ala Asp Ala Trp His Glu Ala Leu Arg Arg Leu Asp Asn
145                 150                 155


<210> SEQ ID NO 66
<211> LENGTH: 120
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
```

```
<220> FEATURE:
<221> NAME/KEY: CDS
<222> LOCATION: (3)..(119)

<400> SEQUENCE: 66

tc ctc ggg gct ggg tca cgg cac gac gcg gat gtg ccc gcg tac gcg        47
   Leu Gly Ala Gly Ser Arg His Asp Ala Asp Val Pro Ala Tyr Ala
     1               5                  10                  15

ttc caa cgg cgg cac tac tgg atc gag tcg gca cgc ccg gcc gca tcc       95
Phe Gln Arg Arg His Tyr Trp Ile Glu Ser Ala Arg Pro Ala Ala Ser
                20                  25                  30

gac gcg ggc cac ccc gtg ctg ggc t                                    120
Asp Ala Gly His Pro Val Leu Gly
            35


<210> SEQ ID NO 67
<211> LENGTH: 39
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 67

Leu Gly Ala Gly Ser Arg His Asp Ala Asp Val Pro Ala Tyr Ala Phe
  1               5                  10                  15

Gln Arg Arg His Tyr Trp Ile Glu Ser Ala Arg Pro Ala Ala Ser Asp
            20                  25                  30

Ala Gly His Pro Val Leu Gly
        35


<210> SEQ ID NO 68
<211> LENGTH: 480
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(480)

<400> SEQUENCE: 68

tcg gcc agg ccg tgg ccg cgg acc ggc cgt ccg cgc cgt gcg gcg gtc       48
Ser Ala Arg Pro Trp Pro Arg Thr Gly Arg Pro Arg Arg Ala Ala Val
  1               5                  10                  15

tcg tcg ttc ggg gtg agc ggc acc aac gcc cac atc atc ctg gag gcc       96
Ser Ser Phe Gly Val Ser Gly Thr Asn Ala His Ile Ile Leu Glu Ala
            20                  25                  30

gga ccc gac cag gag gag ccg tcg gca gaa ccg gcc ggt gac ctc ccg      144
Gly Pro Asp Gln Glu Glu Pro Ser Ala Glu Pro Ala Gly Asp Leu Pro
        35                  40                  45

ctg ctc gtg tcg gca cgg tcc ccg gag gca ctg gac gag cag atc ggg      192
Leu Leu Val Ser Ala Arg Ser Pro Glu Ala Leu Asp Glu Gln Ile Gly
     50                  55                  60

cgc ctg cgc gac tat ctc gac gcc gcc ccc ggc gtg gac ctg gcg gcc      240
Arg Leu Arg Asp Tyr Leu Asp Ala Ala Pro Gly Val Asp Leu Ala Ala
 65                  70                  75                  80

gtg gcg cgg aca ctg gcc acg cgt acg cac ttc tcc cac cgc gcc gta      288
Val Ala Arg Thr Leu Ala Thr Arg Thr His Phe Ser His Arg Ala Val
                85                  90                  95

ctg ctc ggt gac acc gtc atc acc gct ccc ccc gtg gaa cag ccg ggc      336
Leu Leu Gly Asp Thr Val Ile Thr Ala Pro Pro Val Glu Gln Pro Gly
            100                 105                 110
```

```
gag ctc gtc ttc gtc tac tcg gga cag ggc acc cag cat ccc gcg atg      384
Glu Leu Val Phe Val Tyr Ser Gly Gln Gly Thr Gln His Pro Ala Met
        115                 120                 125

ggt gag cgg ctc gcc gca gcc ttc ccc gtg ttc gcc gac ccg gac gta      432
Gly Glu Arg Leu Ala Ala Ala Phe Pro Val Phe Ala Asp Pro Asp Val
    130                 135                 140

ccc gcc tac gcc ttc cag cgg cgg ccc tac tgg atc gag tcc gcg ccg      480
Pro Ala Tyr Ala Phe Gln Arg Arg Pro Tyr Trp Ile Glu Ser Ala Pro
145                 150                 155                 160


<210> SEQ ID NO 69
<211> LENGTH: 160
<212> TYPE: PRT
<213> ORGANISM: Artificial Sequence
<220> FEATURE:
<223> OTHER INFORMATION: Description of Artificial Sequence: Synthetic
      PKS synthase fragment

<400> SEQUENCE: 69

Ser Ala Arg Pro Trp Pro Arg Thr Gly Arg Pro Arg Arg Ala Ala Val
  1               5                  10                  15

Ser Ser Phe Gly Val Ser Gly Thr Asn Ala His Ile Ile Leu Glu Ala
             20                  25                  30

Gly Pro Asp Gln Glu Glu Pro Ser Ala Glu Pro Ala Gly Asp Leu Pro
         35                  40                  45

Leu Leu Val Ser Ala Arg Ser Pro Glu Ala Leu Asp Glu Gln Ile Gly
     50                  55                  60

Arg Leu Arg Asp Tyr Leu Asp Ala Ala Pro Gly Val Asp Leu Ala Ala
 65                  70                  75                  80

Val Ala Arg Thr Leu Ala Thr Arg Thr His Phe Ser His Arg Ala Val
                 85                  90                  95

Leu Leu Gly Asp Thr Val Ile Thr Ala Pro Pro Val Glu Gln Pro Gly
            100                 105                 110

Glu Leu Val Phe Val Tyr Ser Gly Gln Gly Thr Gln His Pro Ala Met
        115                 120                 125

Gly Glu Arg Leu Ala Ala Ala Phe Pro Val Phe Ala Asp Pro Asp Val
    130                 135                 140

Pro Ala Tyr Ala Phe Gln Arg Arg Pro Tyr Trp Ile Glu Ser Ala Pro
145                 150                 155                 160


<210> SEQ ID NO 70
<211> LENGTH: 60
<212> TYPE: DNA
<213> ORGANISM: Artificial Sequence
<220> FEATURE:
<223> OTHER INFORMATION: Description of Artificial Sequence: DNA
      encoding synthetic PKS synthase fragment
<220> FEATURE:
<221> NAME/KEY: CDS
<222> LOCATION: (1)..(60)

<400> SEQUENCE: 70

gac ccg gac gta ccc gcc tac gcc ttc cag cgg cgg ccc tac tgg atc       48
Asp Pro Asp Val Pro Ala Tyr Ala Phe Gln Arg Arg Pro Tyr Trp Ile
  1               5                  10                  15

gag tcc gcg ccg                                                       60
Glu Ser Ala Pro
             20


<210> SEQ ID NO 71
<211> LENGTH: 20
```

-continued

<212> TYPE: PRT
<213> ORGANISM: Artificial Sequence
<220> FEATURE:
<223> OTHER INFORMATION: Description of Artificial Sequence: Synthetic
PKS synthase fragment

<400> SEQUENCE: 71

Asp Pro Asp Val Pro Ala Tyr Ala Phe Gln Arg Arg Pro Tyr Trp Ile
1 5 10 15

Glu Ser Ala Pro
20

<210> SEQ ID NO 72
<211> LENGTH: 6396
<212> TYPE: PRT
<213> ORGANISM: Streptomyces hygroscopicus

<400> SEQUENCE: 72

Met Pro Glu Gln Asp Lys Thr Val Glu Tyr Leu Arg Trp Ala Thr Ala
1 5 10 15

Glu Leu Gln Lys Thr Arg Ala Glu Leu Ala Ala His Ser Glu Pro Leu
20 25 30

Ala Ile Val Gly Met Ala Cys Arg Leu Pro Gly Gly Val Ala Ser Pro
35 40 45

Glu Asp Leu Trp Gln Leu Leu Glu Ser Gly Gly Asp Gly Ile Thr Ala
50 55 60

Phe Pro Thr Asp Arg Gly Trp Glu Thr Thr Ala Asp Gly Arg Gly Gly
65 70 75 80

Phe Leu Thr Gly Ala Ala Gly Phe Asp Ala Ala Phe Phe Gly Ile Ser
85 90 95

Pro Arg Glu Ala Leu Ala Met Asp Pro Gln Gln Arg Leu Ala Leu Glu
100 105 110

Thr Ser Trp Glu Ala Phe Glu His Ala Gly Ile Asp Pro Gln Thr Leu
115 120 125

Arg Gly Ser Asp Thr Gly Val Phe Leu Gly Ala Phe Phe Gln Gly Tyr
130 135 140

Gly Ile Gly Ala Asp Phe Asp Gly Tyr Gly Thr Thr Ser Ile His Thr
145 150 155 160

Ser Val Leu Ser Gly Arg Leu Ala Tyr Phe Tyr Gly Leu Glu Gly Pro
165 170 175

Ala Val Thr Val Asp Thr Ala Cys Ser Ser Ser Leu Val Ala Leu His
180 185 190

Gln Ala Gly Gln Ser Leu Arg Ser Gly Glu Cys Ser Leu Ala Leu Val
195 200 205

Gly Gly Val Thr Val Met Ala Ser Pro Ala Gly Phe Ala Asp Phe Ser
210 215 220

Glu Gln Gly Gly Leu Ala Pro Asp Ala Arg Cys Lys Ala Phe Ala Glu
225 230 235 240

Ala Ala Asp Gly Thr Gly Phe Ala Glu Gly Ser Gly Val Leu Ile Val
245 250 255

Glu Lys Leu Ser Asp Ala Glu Arg Asn Gly His Arg Val Leu Ala Val
260 265 270

Val Arg Gly Ser Ala Val Asn Gln Asp Gly Ala Ser Asn Gly Leu Ser
275 280 285

Ala Pro Asn Gly Pro Ser Gln Glu Arg Val Ile Arg Gln Ala Leu Ala
290 295 300

-continued

```
Asn Ala Gly Leu Thr Pro Ala Asp Val Asp Ala Val Glu Ala His Gly
305                 310                 315                 320

Thr Gly Thr Arg Leu Gly Asp Pro Ile Glu Ala Gln Ala Val Leu Ala
                325                 330                 335

Thr Tyr Gly Gln Gly Arg Asp Thr Pro Val Leu Leu Gly Ser Leu Lys
            340                 345                 350

Ser Asn Ile Gly His Thr Gln Ala Ala Ala Gly Val Ala Gly Val Ile
        355                 360                 365

Lys Met Val Leu Ala Met Arg His Gly Thr Leu Pro Arg Thr Leu His
    370                 375                 380

Val Asp Thr Pro Ser Ser His Val Asp Trp Thr Ala Gly Ala Val Glu
385                 390                 395                 400

Leu Leu Thr Asp Ala Arg Pro Trp Pro Glu Thr Asp Arg Pro Arg Arg
                405                 410                 415

Ala Gly Val Ser Ser Phe Gly Val Ser Gly Thr Asn Ala His Ile Ile
            420                 425                 430

Leu Glu Ser His Pro Arg Pro Ala Pro Glu Pro Ala Pro Ala Pro Asp
        435                 440                 445

Thr Gly Pro Leu Pro Leu Leu Leu Ser Ala Arg Thr Pro Gln Ala Leu
    450                 455                 460

Asp Ala Gln Val His Arg Leu Arg Ala Phe Leu Asp Asp Asn Pro Gly
465                 470                 475                 480

Ala Asp Arg Val Ala Val Ala Gln Thr Leu Ala Arg Arg Thr Gln Phe
                485                 490                 495

Glu His Arg Ala Val Leu Leu Gly Asp Thr Leu Ile Thr Val Ser Pro
            500                 505                 510

Asn Ala Gly Arg Gly Pro Val Val Phe Val Tyr Ser Gly Gln Ser Thr
        515                 520                 525

Leu His Pro His Thr Gly Arg Gln Leu Ala Ser Thr Tyr Pro Val Phe
    530                 535                 540

Ala Glu Ala Trp Arg Glu Ala Leu Asp His Leu Asp Pro Thr Gln Gly
545                 550                 555                 560

Pro Ala Thr His Phe Ala His Gln Thr Ala Leu Thr Ala Leu Leu Arg
                565                 570                 575

Ser Trp Gly Ile Thr Pro His Ala Val Ile Gly His Ser Leu Gly Glu
            580                 585                 590

Ile Thr Ala Ala His Ala Ala Gly Val Leu Ser Leu Arg Asp Ala Gly
        595                 600                 605

Ala Leu Leu Thr Thr Arg Thr Arg Leu Met Asp Gln Leu Pro Ser Gly
    610                 615                 620

Gly Ala Met Val Thr Val Leu Thr Ser Glu Glu Lys Ala Arg Gln Val
625                 630                 635                 640

Leu Arg Pro Gly Val Glu Ile Ala Ala Val Asn Gly Pro His Ser Leu
                645                 650                 655

Val Leu Ser Gly Asp Glu Glu Ala Val Leu Glu Ala Ala Arg Gln Leu
            660                 665                 670

Gly Ile His His Arg Leu Pro Thr Arg His Ala Gly His Ser Glu Arg
        675                 680                 685

Met Gln Pro Leu Val Ala Pro Leu Leu Asp Val Ala Arg Thr Leu Thr
    690                 695                 700

Tyr His Gln Pro His Thr Ala Ile Pro Gly Asp Pro Thr Thr Ala Glu
705                 710                 715                 720

Tyr Trp Ala His Gln Val Arg Asp Gln Val Arg Phe Gln Ala His Thr
```

-continued

```
                725                 730                 735

Glu Gln Tyr Pro Gly Ala Thr Phe Leu Glu Ile Gly Pro Asn Gln Asp
            740                 745                 750

Leu Ser Pro Leu Val Asp Gly Val Ala Ala Gln Thr Gly Thr Pro Asp
        755                 760                 765

Glu Val Arg Ala Leu His Thr Ala Leu Ala Gln Leu His Val Arg Gly
    770                 775                 780

Val Ala Ile Asp Trp Thr Leu Val Leu Gly Gly Asp Arg Ala Pro Val
785                 790                 795                 800

Thr Leu Pro Thr Tyr Pro Phe Gln His Lys Asp Tyr Trp Leu Arg Pro
                805                 810                 815

Thr Ser Arg Ala Asp Val Thr Gly Ala Gly Gln Glu Gln Val Ala His
            820                 825                 830

Pro Leu Leu Gly Ala Ala Val Ala Leu Pro Gly Thr Gly Gly Val Val
        835                 840                 845

Leu Thr Gly Arg Leu Ser Leu Ala Ser His Pro Trp Leu Gly Glu His
    850                 855                 860

Ala Val Asp Gly Thr Val Leu Leu Pro Gly Ala Ala Phe Leu Glu Leu
865                 870                 875                 880

Ala Ala Arg Ala Gly Asp Glu Val Gly Cys Asp Leu Leu His Glu Leu
                885                 890                 895

Val Ile Glu Thr Pro Leu Val Leu Pro Ala Thr Gly Gly Val Ala Val
            900                 905                 910

Ser Val Glu Ile Ala Glu Pro Asp Asp Thr Gly Arg Arg Ala Val Thr
        915                 920                 925

Val His Ala Arg Ala Asp Gly Ser Gly Leu Trp Thr Arg His Ala Gly
    930                 935                 940

Gly Phe Leu Gly Thr Ala Pro Ala Pro Ala Thr Ala Thr Asp Pro Ala
945                 950                 955                 960

Pro Trp Pro Pro Ala Glu Ala Gly Pro Val Asp Val Ala Asp Val Tyr
                965                 970                 975

Asp Arg Phe Glu Asp Ile Gly Tyr Ser Tyr Gly Pro Gly Phe Arg Gly
            980                 985                 990

Leu Arg Ala Ala Trp Arg Ala Gly Asp Thr Val Tyr Ala Glu Val Ala
        995                 1000                1005

Leu Pro Asp Glu Gln Ser Ala Asp Ala Ala Arg Phe Thr Leu His Pro
    1010                1015                1020

Ala Leu Leu Asp Ala Ala Phe Gln Ala Gly Ala Leu Ala Ala Leu Asp
1025                1030                1035                1040

Ala Pro Gly Gly Ala Ala Arg Leu Pro Phe Ser Phe Gln Asp Val Arg
                1045                1050                1055

Ile His Ala Ala Gly Ala Thr Arg Leu Arg Val Thr Val Gly Arg Asp
            1060                1065                1070

Gly Glu Arg Ser Thr Val Arg Met Thr Gly Pro Asp Gly Gln Leu Val
        1075                1080                1085

Ala Val Val Gly Ala Val Leu Ser Arg Pro Tyr Ala Glu Gly Ser Gly
    1090                1095                1100

Asp Gly Leu Leu Arg Pro Val Trp Thr Glu Leu Pro Met Pro Val Pro
1105                1110                1115                1120

Ser Ala Asp Asp Pro Arg Val Glu Val Leu Gly Ala Asp Pro Gly Asp
                1125                1130                1135

Gly Asp Val Pro Ala Ala Thr Arg Glu Leu Thr Ala Arg Val Leu Gly
            1140                1145                1150
```

```
Ala Leu Gln Arg His Leu Ser Ala Ala Glu Asp Thr Thr Leu Val Val
        1155                1160                1165

Arg Thr Gly Thr Gly Pro Ala Ala Ala Ala Ala Ala Gly Leu Val Arg
    1170                1175                1180

Ser Ala Gln Ala Glu Asn Pro Gly Arg Val Val Leu Val Glu Ala Ser
1185                1190                1195                1200

Pro Asp Thr Ser Val Glu Leu Leu Ala Ala Cys Ala Ala Leu Asp Glu
                1205                1210                1215

Pro Gln Leu Ala Val Arg Asp Gly Val Leu Phe Ala Pro Arg Leu Val
            1220                1225                1230

Arg Met Ser Asp Pro Ala His Gly Pro Leu Ser Leu Pro Asp Gly Asp
        1235                1240                1245

Trp Leu Leu Thr Arg Ser Ala Ser Gly Thr Leu His Asp Val Ala Leu
    1250                1255                1260

Ile Ala Asp Asp Thr Pro Arg Arg Ala Leu Glu Ala Gly Glu Val Arg
1265                1270                1275                1280

Ile Asp Val Arg Ala Ala Gly Leu Asn Phe Arg Asp Val Leu Ile Ala
                1285                1290                1295

Leu Gly Thr Tyr Thr Gly Ala Thr Ala Met Gly Gly Glu Ala Ala Gly
            1300                1305                1310

Val Val Val Glu Thr Gly Pro Gly Val Asp Asp Leu Ser Pro Gly Asp
        1315                1320                1325

Arg Val Phe Gly Leu Thr Arg Gly Gly Ile Gly Pro Thr Ala Val Thr
    1330                1335                1340

Asp Arg Arg Trp Leu Ala Arg Ile Pro Asp Gly Trp Ser Phe Thr Thr
1345                1350                1355                1360

Ala Ala Ser Val Pro Ile Val Phe Ala Thr Ala Trp Tyr Gly Leu Val
                1365                1370                1375

Asp Leu Gly Thr Leu Arg Ala Gly Glu Lys Val Leu Val His Ala Ala
            1380                1385                1390

Thr Gly Gly Val Gly Met Ala Ala Ala Gln Ile Ala Arg His Leu Gly
        1395                1400                1405

Ala Glu Leu Tyr Ala Thr Ala Ser Thr Gly Lys Gln His Val Leu Arg
    1410                1415                1420

Ala Ala Gly Leu Pro Asp Thr His Ile Ala Asp Ser Arg Thr Thr Ala
1425                1430                1435                1440

Phe Arg Thr Ala Phe Pro Arg Met Asp Val Val Leu Asn Ala Leu Thr
                1445                1450                1455

Gly Glu Phe Ile Asp Ala Ser Leu Asp Leu Leu Asp Ala Asp Gly Arg
            1460                1465                1470

Phe Val Glu Met Gly Arg Thr Glu Leu Arg Asp Pro Ala Ala Ile Val
        1475                1480                1485

Pro Ala Tyr Leu Pro Phe Asp Leu Leu Asp Ala Gly Ala Asp Arg Ile
    1490                1495                1500

Gly Glu Ile Leu Gly Glu Leu Leu Arg Leu Phe Asp Ala Gly Ala Leu
1505                1510                1515                1520

Glu Pro Leu Pro Val Arg Ala Trp Asp Val Arg Gln Ala Arg Asp Ala
                1525                1530                1535

Leu Gly Trp Met Ser Arg Ala Arg His Ile Gly Lys Asn Val Leu Thr
            1540                1545                1550

Leu Pro Arg Pro Leu Asp Pro Glu Gly Ala Val Val Leu Thr Gly Gly
        1555                1560                1565
```

-continued

```
Ser Gly Thr Leu Ala Gly Ile Leu Ala Arg His Leu Arg Glu Arg His
    1570                1575                1580

Val Tyr Leu Leu Ser Arg Thr Ala Pro Pro Glu Gly Thr Pro Gly Val
1585                1590                1595                1600

His Leu Pro Cys Asp Val Gly Asp Arg Asp Gln Leu Ala Ala Ala Leu
                1605                1610                1615

Glu Arg Val Asp Arg Pro Ile Thr Ala Val Val His Leu Ala Gly Ala
            1620                1625                1630

Leu Asp Asp Gly Thr Val Ala Ser Leu Thr Pro Glu Arg Phe Asp Thr
        1635                1640                1645

Val Leu Arg Pro Lys Ala Asp Gly Ala Trp Tyr Leu His Glu Leu Thr
    1650                1655                1660

Lys Glu Gln Asp Leu Ala Ala Phe Val Leu Tyr Ser Ser Ala Ala Gly
1665                1670                1675                1680

Val Leu Gly Asn Ala Gly Gln Gly Asn Tyr Val Ala Ala Asn Ala Phe
                1685                1690                1695

Leu Asp Ala Leu Ala Glu Leu Arg His Gly Ser Gly Leu Pro Ala Leu
            1700                1705                1710

Ser Ile Ala Trp Gly Leu Trp Glu Asp Val Ser Gly Leu Thr Ala Ala
        1715                1720                1725

Leu Gly Glu Ala Asp Arg Asp Arg Met Arg Arg Ser Gly Phe Arg Ala
    1730                1735                1740

Ile Thr Ala Gln Gln Gly Met His Leu Tyr Glu Ala Ala Gly Arg Thr
1745                1750                1755                1760

Gly Ser Pro Val Val Val Ala Ala Ala Leu Asp Asp Ala Pro Asp Val
                1765                1770                1775

Pro Leu Leu Arg Gly Leu Arg Arg Thr Thr Val Arg Arg Ala Ala Val
            1780                1785                1790

Arg Glu Cys Ser Ser Ala Asp Arg Leu Ala Ala Leu Thr Gly Asp Glu
        1795                1800                1805

Leu Ala Glu Ala Leu Leu Thr Leu Val Arg Glu Ser Thr Ala Ala Val
    1810                1815                1820

Leu Gly His Val Gly Gly Glu Asp Ile Pro Ala Thr Ala Ala Phe Lys
1825                1830                1835                1840

Asp Leu Gly Ile Asp Ser Leu Thr Ala Val Gln Leu Arg Asn Ala Leu
                1845                1850                1855

Thr Glu Ala Thr Gly Val Arg Leu Asn Ala Thr Ala Val Phe Asp Phe
            1860                1865                1870

Pro Thr Pro His Val Leu Ala Gly Lys Leu Gly Asp Glu Leu Thr Gly
        1875                1880                1885

Thr Arg Ala Pro Val Val Pro Arg Thr Ala Ala Thr Ala Gly Ala His
    1890                1895                1900

Asp Glu Pro Leu Ala Ile Val Gly Met Ala Cys Arg Leu Pro Gly Gly
1905                1910                1915                1920

Val Ala Ser Pro Glu Glu Leu Trp His Leu Val Ala Ser Gly Thr Asp
                1925                1930                1935

Ala Ile Thr Glu Phe Pro Thr Asp Arg Gly Trp Asp Val Asp Ala Ile
            1940                1945                1950

Tyr Asp Pro Asp Pro Asp Ala Ile Gly Lys Thr Phe Val Arg His Gly
        1955                1960                1965

Gly Phe Leu Thr Gly Ala Thr Gly Phe Asp Ala Ala Phe Phe Gly Ile
    1970                1975                1980

Ser Pro Arg Glu Ala Leu Ala Met Asp Pro Gln Gln Arg Val Leu Leu
```

-continued

```
1985                1990                1995                2000

Glu Thr Ser Trp Glu Ala Phe Glu Ser Ala Gly Ile Thr Pro Asp Ser
                2005                2010                2015

Thr Arg Gly Ser Asp Thr Gly Val Phe Val Gly Ala Phe Ser Tyr Gly
            2020                2025                2030

Tyr Gly Thr Gly Ala Asp Thr Asp Gly Phe Gly Ala Thr Gly Ser Gln
        2035                2040                2045

Thr Ser Val Leu Ser Gly Arg Leu Ser Tyr Phe Tyr Gly Leu Glu Gly
    2050                2055                2060

Pro Ala Val Thr Val Asp Thr Ala Cys Ser Ser Ser Leu Val Ala Leu
2065                2070                2075                2080

His Gln Ala Gly Gln Ser Leu Arg Ser Gly Glu Cys Ser Leu Ala Leu
                2085                2090                2095

Val Gly Gly Val Thr Val Met Ala Ser Pro Gly Gly Phe Val Glu Phe
            2100                2105                2110

Ser Arg Gln Arg Gly Leu Ala Pro Asp Gly Arg Ala Lys Ala Phe Gly
        2115                2120                2125

Ala Gly Ala Asp Gly Thr Ser Phe Ala Glu Gly Ala Gly Val Leu Ile
    2130                2135                2140

Val Glu Arg Leu Ser Asp Ala Glu Arg Asn Gly His Thr Val Leu Ala
2145                2150                2155                2160

Val Val Arg Gly Ser Ala Val Asn Gln Asp Gly Ala Ser Asn Gly Leu
                2165                2170                2175

Ser Ala Pro Asn Gly Pro Ser Gln Glu Arg Val Ile Arg Gln Ala Leu
            2180                2185                2190

Ala Asn Ala Gly Leu Thr Pro Ala Asp Val Asp Ala Val Glu Ala His
        2195                2200                2205

Gly Thr Gly Thr Arg Leu Gly Asp Pro Ile Glu Ala Gln Ala Val Leu
    2210                2215                2220

Ala Thr Tyr Gly Gln Glu Arg Ala Thr Pro Leu Leu Leu Gly Ser Leu
2225                2230                2235                2240

Lys Ser Asn Ile Gly His Ala Gln Ala Ala Ser Gly Val Ala Gly Ile
                2245                2250                2255

Ile Lys Met Val Gln Ala Leu Arg His Gly Glu Leu Pro Pro Thr Leu
            2260                2265                2270

His Ala Asp Glu Pro Ser Pro His Val Asp Trp Thr Ala Gly Ala Val
        2275                2280                2285

Glu Leu Leu Thr Ser Ala Arg Pro Trp Pro Glu Thr Asp Arg Pro Arg
    2290                2295                2300

Arg Ala Ala Val Ser Ser Phe Gly Val Ser Gly Thr Asn Ala His Val
2305                2310                2315                2320

Ile Leu Glu Ala Gly Pro Val Thr Glu Thr Pro Ala Ala Ser Pro Ser
                2325                2330                2335

Gly Asp Leu Pro Leu Leu Val Ser Ala Arg Ser Pro Glu Ala Leu Asp
            2340                2345                2350

Glu Gln Ile Arg Arg Leu Arg Ala Tyr Leu Asp Thr Thr Pro Asp Val
        2355                2360                2365

Asp Arg Val Ala Val Ala Gln Thr Leu Ala Arg Arg Thr His Phe Ala
    2370                2375                2380

His Arg Ala Val Leu Leu Gly Asp Thr Val Ile Thr Thr Pro Pro Ala
2385                2390                2395                2400

Asp Arg Pro Asp Glu Leu Val Phe Val Tyr Ser Gly Gln Gly Thr Gln
                2405                2410                2415
```

-continued

```
His Pro Ala Met Gly Glu Gln Leu Ala Ala Ala His Pro Val Phe Ala
            2420                2425                2430

Asp Ala Trp His Glu Ala Leu Arg Arg Leu Asp Asn Pro Asp Pro His
        2435                2440                2445

Asp Pro Thr His Ser Gln His Val Leu Phe Ala His Gln Ala Ala Phe
    2450                2455                2460

Thr Ala Leu Leu Arg Ser Trp Gly Ile Thr Pro His Ala Val Ile Gly
2465                2470                2475                2480

His Ser Leu Gly Glu Ile Thr Ala Ala His Ala Ala Gly Ile Leu Ser
                2485                2490                2495

Leu Asp Asp Ala Cys Thr Leu Ile Thr Thr Arg Ala Arg Leu Met His
            2500                2505                2510

Thr Leu Pro Pro Pro Gly Ala Met Val Thr Val Leu Thr Ser Glu Glu
        2515                2520                2525

Lys Ala Arg Gln Ala Leu Arg Pro Gly Val Glu Ile Ala Ala Val Asn
    2530                2535                2540

Gly Pro His Ser Ile Val Leu Ser Gly Asp Glu Asp Ala Val Leu Thr
2545                2550                2555                2560

Val Ala Gly Gln Leu Gly Ile His His Arg Leu Pro Ala Pro His Ala
                2565                2570                2575

Gly His Ser Ala His Met Glu Pro Val Ala Ala Glu Leu Leu Ala Thr
            2580                2585                2590

Thr Arg Gly Leu Arg Tyr His Pro Pro His Thr Ser Ile Pro Asn Asp
        2595                2600                2605

Pro Thr Thr Ala Glu Tyr Trp Ala Glu Gln Val Arg Lys Pro Val Leu
    2610                2615                2620

Phe His Ala His Ala Gln Gln Tyr Pro Asp Ala Val Phe Val Glu Ile
2625                2630                2635                2640

Gly Pro Ala Gln Asp Leu Ser Pro Leu Val Asp Gly Ile Pro Leu Gln
                2645                2650                2655

Asn Gly Thr Ala Asp Glu Val His Ala Leu His Thr Ala Leu Ala His
            2660                2665                2670

Leu Tyr Ala Arg Gly Ala Thr Leu Asp Trp Pro Arg Ile Leu Gly Ala
        2675                2680                2685

Gly Ser Arg His Asp Ala Asp Val Pro Ala Tyr Ala Phe Gln Arg Arg
    2690                2695                2700

His Tyr Trp Ile Glu Ser Ala Arg Pro Ala Ala Ser Asp Ala Gly His
2705                2710                2715                2720

Pro Val Leu Gly Ser Gly Ile Ala Leu Ala Gly Ser Pro Gly Arg Val
                2725                2730                2735

Phe Thr Gly Ser Val Pro Thr Gly Ala Asp Arg Ala Val Phe Val Ala
            2740                2745                2750

Glu Leu Ala Leu Ala Ala Ala Asp Ala Val Asp Cys Ala Thr Val Glu
        2755                2760                2765

Arg Leu Asp Ile Ala Ser Val Pro Gly Arg Pro Gly His Gly Arg Thr
    2770                2775                2780

Thr Val Gln Thr Trp Val Asp Glu Pro Ala Asp Asp Gly Arg Arg Arg
2785                2790                2795                2800

Phe Thr Val His Thr Arg Thr Gly Asp Ala Pro Trp Thr Leu His Ala
                2805                2810                2815

Glu Gly Val Leu Arg Pro His Gly Thr Ala Leu Pro Asp Ala Ala Asp
            2820                2825                2830
```

-continued

```
Ala Glu Trp Pro Pro Pro Gly Ala Val Pro Ala Asp Gly Leu Pro Gly
        2835                2840                2845

Val Trp Arg Arg Gly Asp Gln Val Phe Ala Glu Ala Glu Val Asp Gly
    2850                2855                2860

Pro Asp Gly Phe Val Val His Pro Asp Leu Leu Asp Ala Val Phe Ser
2865                2870                2875                2880

Ala Val Gly Asp Gly Ser Arg Gln Pro Ala Gly Trp Arg Asp Leu Thr
                2885                2890                2895

Val His Ala Ser Asp Ala Thr Val Leu Arg Ala Cys Leu Thr Arg Arg
            2900                2905                2910

Thr Asp Gly Ala Met Gly Phe Ala Ala Phe Asp Gly Ala Gly Leu Pro
        2915                2920                2925

Val Leu Thr Ala Glu Ala Val Thr Leu Arg Glu Val Ala Ser Pro Ser
    2930                2935                2940

Gly Ser Glu Glu Ser Asp Gly Leu His Arg Leu Glu Trp Leu Ala Val
2945                2950                2955                2960

Ala Glu Ala Val Tyr Asp Gly Asp Leu Pro Glu Gly His Val Leu Ile
                2965                2970                2975

Thr Ala Ala His Pro Asp Asp Pro Glu Asp Ile Pro Thr Arg Ala His
            2980                2985                2990

Thr Arg Ala Thr Arg Val Leu Thr Ala Leu Gln His His Leu Thr Thr
        2995                3000                3005

Thr Asp His Thr Leu Ile Val His Thr Thr Thr Asp Pro Ala Gly Ala
    3010                3015                3020

Thr Val Thr Gly Leu Thr Arg Thr Ala Gln Asn Glu His Pro His Arg
3025                3030                3035                3040

Ile Arg Leu Ile Glu Thr Asp His Pro His Thr Pro Leu Pro Leu Ala
                3045                3050                3055

Gln Leu Ala Thr Leu Asp His Pro His Leu Arg Leu Thr His His Thr
            3060                3065                3070

Leu His His Pro His Leu Thr Pro Leu His Thr Thr Thr Pro Pro Thr
        3075                3080                3085

Thr Thr Pro Leu Asn Pro Glu His Ala Ile Ile Ile Thr Gly Gly Ser
    3090                3095                3100

Gly Thr Leu Ala Gly Ile Leu Ala Arg His Leu Asn His Pro His Thr
3105                3110                3115                3120

Tyr Leu Leu Ser Arg Thr Pro Pro Pro Asp Ala Thr Pro Gly Thr His
                3125                3130                3135

Leu Pro Cys Asp Val Gly Asp Pro His Gln Leu Ala Thr Thr Leu Thr
            3140                3145                3150

His Ile Pro Gln Pro Leu Thr Ala Ile Phe His Thr Ala Ala Thr Leu
        3155                3160                3165

Asp Asp Gly Ile Leu His Ala Leu Thr Pro Asp Arg Leu Thr Thr Val
    3170                3175                3180

Leu His Pro Lys Ala Asn Ala Ala Trp His Leu His His Leu Thr Gln
3185                3190                3195                3200

Asn Gln Pro Leu Thr His Phe Val Leu Tyr Ser Ser Ala Ala Ala Val
                3205                3210                3215

Leu Gly Ser Pro Gly Gln Gly Asn Tyr Ala Ala Ala Asn Ala Phe Leu
            3220                3225                3230

Asp Ala Leu Ala Thr His Arg His Thr Leu Gly Gln Pro Ala Thr Ser
        3235                3240                3245

Ile Ala Trp Gly Met Trp His Thr Thr Ser Thr Leu Thr Gly Gln Leu
```

-continued

```
    3250                3255                3260

Asp Asp Ala Asp Arg Asp Arg Ile Arg Arg Gly Gly Phe Leu Pro Ile
3265                3270                3275                3280

Thr Asp Asp Glu Gly Met Arg Leu Tyr Glu Ala Ala Val Gly Ser Gly
                3285                3290                3295

Glu Asp Phe Val Met Ala Ala Ala Met Asp Pro Ala Gln Pro Met Thr
            3300                3305                3310

Gly Ser Val Pro Pro Ile Leu Ser Gly Leu Arg Arg Ser Ala Arg Arg
        3315                3320                3325

Val Ala Arg Ala Gly Gln Thr Phe Ala Gln Arg Leu Ala Glu Leu Pro
    3330                3335                3340

Asp Ala Asp Arg Gly Ala Ala Leu Thr Thr Leu Val Ser Asp Ala Thr
3345                3350                3355                3360

Ala Ala Val Leu Gly His Ala Asp Ala Ser Glu Ile Ala Pro Thr Thr
                3365                3370                3375

Thr Phe Lys Asp Leu Gly Ile Asp Ser Leu Thr Ala Ile Glu Leu Arg
            3380                3385                3390

Asn Arg Leu Ala Glu Ala Thr Gly Leu Arg Leu Ser Ala Thr Leu Val
        3395                3400                3405

Phe Asp His Pro Thr Pro Arg Val Leu Ala Ala Lys Leu Arg Thr Asp
    3410                3415                3420

Leu Phe Gly Thr Ala Val Pro Thr Pro Ala Arg Thr Ala Arg Thr His
3425                3430                3435                3440

His Asp Glu Pro Leu Ala Ile Val Gly Met Ala Cys Arg Leu Pro Gly
                3445                3450                3455

Gly Val Ala Ser Pro Glu Asp Leu Trp Gln Leu Val Ala Ser Gly Thr
            3460                3465                3470

Asp Ala Ile Thr Glu Phe Pro Thr Asp Arg Gly Trp Asp Ile Asp Arg
        3475                3480                3485

Leu Phe Asp Pro Asp Pro Asp Ala Pro Gly Lys Thr Tyr Val Arg His
    3490                3495                3500

Gly Gly Phe Leu Ala Glu Ala Ala Gly Phe Asp Ala Ala Phe Phe Gly
3505                3510                3515                3520

Ile Ser Pro Arg Glu Ala Arg Ala Met Asp Pro Gln Gln Arg Val Ile
                3525                3530                3535

Leu Glu Thr Ser Trp Glu Ala Phe Glu Asn Ala Gly Ile Val Pro Asp
            3540                3545                3550

Thr Leu Arg Gly Ser Asp Thr Gly Val Phe Met Gly Ala Phe Ser His
        3555                3560                3565

Gly Tyr Gly Ala Gly Val Asp Leu Gly Gly Phe Gly Ala Thr Ala Thr
    3570                3575                3580

Gln Asn Ser Val Leu Ser Gly Arg Leu Ser Tyr Phe Phe Gly Met Glu
3585                3590                3595                3600

Gly Pro Ala Val Thr Val Asp Thr Ala Cys Ser Ser Ser Leu Val Ala
                3605                3610                3615

Leu His Gln Ala Ala Gln Ala Leu Arg Thr Gly Glu Cys Ser Leu Ala
            3620                3625                3630

Leu Ala Gly Gly Val Thr Val Met Pro Thr Pro Leu Gly Tyr Val Glu
        3635                3640                3645

Phe Cys Arg Gln Arg Gly Leu Ala Pro Asp Gly Arg Cys Gln Ala Phe
    3650                3655                3660

Ala Glu Gly Ala Asp Gly Thr Ser Phe Ser Glu Gly Ala Gly Val Leu
3665                3670                3675                3680
```

-continued

```
Val Leu Glu Arg Leu Ser Asp Ala Glu Arg Asn Gly His Thr Val Leu
                3685                3690                3695

Ala Val Val Arg Ser Ser Ala Val Asn Gln Asp Gly Ala Ser Asn Gly
            3700                3705                3710

Ile Ser Ala Pro Asn Gly Pro Ser Gln Gln Arg Val Ile Arg Gln Ala
        3715                3720                3725

Leu Asp Lys Ala Gly Leu Ala Pro Ala Asp Val Asp Val Val Glu Ala
    3730                3735                3740

His Gly Thr Gly Thr Pro Leu Gly Asp Pro Ile Glu Ala Gln Ala Ile
3745                3750                3755                3760

Ile Ala Thr Tyr Gly Gln Asp Arg Asp Thr Pro Leu Tyr Leu Gly Ser
                3765                3770                3775

Val Lys Ser Asn Ile Gly His Thr Gln Thr Thr Ala Gly Val Ala Gly
            3780                3785                3790

Val Ile Lys Met Val Met Ala Met Arg His Gly Ile Ala Pro Lys Thr
        3795                3800                3805

Leu His Val Asp Glu Pro Ser Ser His Val Asp Trp Thr Glu Gly Ala
    3810                3815                3820

Val Glu Leu Leu Thr Glu Ala Arg Pro Trp Pro Asp Ala Gly Arg Pro
3825                3830                3835                3840

Arg Arg Ala Gly Val Ser Ser Leu Gly Ile Ser Gly Thr Asn Ala His
                3845                3850                3855

Val Ile Leu Glu Gly Val Pro Gly Pro Ser Arg Val Glu Pro Ser Val
            3860                3865                3870

Asp Gly Leu Val Pro Leu Pro Val Ser Ala Arg Ser Glu Ala Ser Leu
        3875                3880                3885

Arg Gly Gln Val Glu Arg Leu Glu Gly Tyr Leu Arg Gly Ser Val Asp
    3890                3895                3900

Val Ala Ala Val Ala Gln Gly Leu Val Arg Glu Arg Ala Val Phe Gly
3905                3910                3915                3920

His Arg Ala Val Leu Leu Gly Asp Ala Arg Val Met Gly Val Ala Val
                3925                3930                3935

Asp Gln Pro Arg Thr Val Phe Val Phe Pro Gly Gln Gly Ala Gln Trp
            3940                3945                3950

Val Gly Met Gly Val Glu Leu Met Asp Arg Ser Ala Val Phe Ala Ala
        3955                3960                3965

Arg Met Glu Glu Cys Ala Arg Ala Leu Leu Pro His Thr Gly Trp Asp
    3970                3975                3980

Val Arg Glu Met Leu Ala Arg Pro Asp Val Ala Glu Arg Val Glu Val
3985                3990                3995                4000

Val Gln Pro Ala Ser Trp Ala Val Ala Val Ser Leu Ala Ala Leu Trp
                4005                4010                4015

Gln Ala His Gly Val Val Pro Asp Ala Val Ile Gly His Ser Gln Gly
            4020                4025                4030

Glu Ile Ala Ala Ala Cys Val Ala Gly Ala Leu Ser Leu Glu Asp Ala
        4035                4040                4045

Ala Arg Val Val Ala Leu Arg Ser Gln Val Ile Ala Ala Arg Leu Ala
    4050                4055                4060

Gly Arg Gly Ala Met Ala Ser Val Ala Leu Pro Ala Gly Glu Val Gly
4065                4070                4075                4080

Leu Val Glu Gly Val Trp Ile Ala Ala Arg Asn Gly Pro Ala Ser Thr
                4085                4090                4095
```

-continued

```
Val Val Ala Gly Glu Pro Ser Ala Val Glu Asp Val Val Thr Arg Tyr
            4100                4105                4110

Glu Thr Glu Gly Val Arg Val Arg Arg Ile Ala Val Asp Tyr Ala Ser
        4115                4120                4125

His Thr Pro His Val Glu Ala Ile Glu Asp Glu Leu Ala Glu Val Leu
    4130                4135                4140

Lys Gly Val Ala Gly Lys Ala Ala Ser Val Ala Trp Trp Ser Thr Val
4145                4150                4155                4160

Asp Ser Ala Trp Val Thr Glu Pro Val Asp Glu Ser Tyr Trp Tyr Arg
                4165                4170                4175

Asn Leu Arg Arg Pro Val Ala Leu Asp Ala Ala Val Ala Glu Leu Asp
            4180                4185                4190

Gly Ser Val Phe Val Glu Cys Ser Ala His Pro Val Leu Leu Pro Ala
        4195                4200                4205

Met Glu Gln Ala His Thr Val Ala Ser Leu Arg Thr Gly Asp Gly Gly
    4210                4215                4220

Trp Glu Arg Trp Leu Thr Ala Leu Ala Gln Ala Trp Thr Leu Gly Ala
4225                4230                4235                4240

Ala Val Asp Trp Asp Thr Val Val Glu Pro Val Pro Gly Arg Leu Leu
                4245                4250                4255

Asp Leu Pro Thr Tyr Ala Phe Glu Arg Arg Arg Tyr Trp Leu Glu Ala
            4260                4265                4270

Ala Gly Ala Thr Asp Leu Ser Ala Ala Gly Leu Thr Gly Ala Ala His
        4275                4280                4285

Pro Met Leu Ala Ala Ile Thr Ala Leu Pro Ala Asp Asp Gly Gly Val
    4290                4295                4300

Val Leu Thr Gly Arg Ile Ser Leu Arg Thr His Pro Trp Leu Ala Asp
4305                4310                4315                4320

His Ala Val Arg Gly Thr Val Leu Leu Pro Gly Thr Ala Phe Val Glu
                4325                4330                4335

Leu Val Ile Arg Ala Gly Asp Glu Thr Gly Cys Gly Ile Val Asp Glu
            4340                4345                4350

Leu Val Ile Glu Ser Pro Leu Val Val Pro Ala Thr Ala Ala Val Asp
        4355                4360                4365

Leu Ser Val Thr Val Glu Gly Ala Asp Glu Ala Gly Arg Arg Arg Val
    4370                4375                4380

Thr Val His Ala Arg Thr Glu Gly Thr Gly Ser Trp Thr Arg His Ala
4385                4390                4395                4400

Ser Gly Thr Leu Thr Pro Asp Thr Pro Asp Thr Pro Asn Ala Ser Gly
                4405                4410                4415

Val Val Gly Ala Glu Pro Phe Ser Gln Trp Pro Pro Ala Thr Ala Ala
            4420                4425                4430

Ala Val Asp Thr Ser Glu Phe Tyr Leu Arg Leu Asp Ala Leu Gly Tyr
        4435                4440                4445

Arg Phe Gly Pro Met Phe Arg Gly Met Arg Ala Ala Trp Arg Asp Gly
    4450                4455                4460

Asp Thr Val Tyr Ala Glu Val Ala Leu Pro Glu Asp Arg Ala Ala Asp
4465                4470                4475                4480

Ala Asp Gly Phe Gly Met His Pro Ala Leu Leu Asp Ala Ala Leu Gln
                4485                4490                4495

Ser Gly Ser Leu Leu Met Leu Glu Ser Asp Gly Glu Gln Ser Val Gln
            4500                4505                4510

Leu Pro Phe Ser Trp His Gly Val Arg Phe His Ala Thr Gly Ala Thr
```

-continued

```
        4515                4520                4525

Met Leu Arg Val Ala Val Val Pro Gly Pro Asp Gly Leu Arg Leu His
    4530                4535                4540

Ala Ala Asp Ser Gly Asn Arg Pro Val Ala Thr Ile Asp Ala Leu Val
4545                4550                4555                4560

Thr Arg Ser Pro Glu Ala Asp Leu Ala Pro Ala Asp Pro Met Leu Arg
                4565                4570                4575

Val Gly Trp Ala Pro Val Pro Val Pro Ala Gly Ala Gly Pro Ser Asp
            4580                4585                4590

Ala Asp Val Leu Thr Leu Arg Gly Asp Asp Ala Asp Pro Leu Gly Glu
        4595                4600                4605

Thr Arg Asp Leu Thr Thr Arg Val Leu Asp Ala Leu Leu Arg Ala Asp
    4610                4615                4620

Arg Pro Val Ile Phe Gln Val Thr Gly Gly Leu Ala Ala Lys Ala Ala
4625                4630                4635                4640

Ala Gly Leu Val Arg Thr Ala Gln Asn Glu Gln Pro Gly Arg Phe Phe
                4645                4650                4655

Leu Val Glu Thr Asp Pro Gly Glu Val Leu Asp Gly Ala Lys Arg Asp
            4660                4665                4670

Ala Ile Ala Ala Leu Gly Glu Pro His Val Arg Leu Arg Asp Gly Leu
        4675                4680                4685

Phe Glu Ala Ala Arg Leu Met Arg Ala Thr Pro Ser Leu Thr Leu Pro
    4690                4695                4700

Asp Thr Gly Ser Trp Gln Leu Arg Pro Ser Ala Thr Gly Ser Leu Asp
4705                4710                4715                4720

Asp Leu Ala Val Val Pro Thr Asp Ala Pro Asp Arg Pro Leu Ala Ala
                4725                4730                4735

Gly Glu Val Arg Ile Ala Val Arg Ala Ala Gly Leu Asn Phe Arg Asp
            4740                4745                4750

Val Thr Val Ala Leu Gly Val Val Ala Asp Ala Arg Pro Leu Gly Ser
        4755                4760                4765

Glu Ala Ala Gly Val Val Leu Glu Thr Gly Pro Gly Val His Asp Leu
    4770                4775                4780

Ala Pro Gly Asp Arg Val Leu Gly Met Leu Ala Gly Ala Phe Gly Pro
4785                4790                4795                4800

Val Ala Ile Thr Asp Arg Arg Leu Leu Gly Arg Met Pro Asp Gly Trp
                4805                4810                4815

Thr Phe Pro Gln Ala Ala Ser Val Met Thr Ala Phe Ala Thr Ala Trp
            4820                4825                4830

Tyr Gly Leu Val Asp Leu Ala Gly Leu Arg Pro Gly Glu Lys Val Leu
        4835                4840                4845

Ile His Ala Ala Ala Thr Gly Val Gly Ala Ala Ala Val Gln Ile Ala
    4850                4855                4860

Arg His Leu Gly Ala Glu Val Tyr Ala Thr Thr Ser Ala Ala Lys Arg
4865                4870                4875                4880

His Leu Val Asp Leu Asp Gly Ala His Leu Ala Asp Ser Arg Ser Thr
                4885                4890                4895

Ala Phe Ala Asp Ala Phe Pro Pro Val Asp Val Val Leu Asn Ser Leu
            4900                4905                4910

Thr Gly Glu Phe Leu Asp Ala Ser Val Gly Leu Leu Ala Ala Gly Gly
        4915                4920                4925

Arg Phe Ile Glu Met Gly Lys Thr Asp Ile Arg His Ala Val Gln Gln
    4930                4935                4940
```

-continued

```
Pro Phe Asp Leu Met Asp Ala Gly Pro Asp Arg Met Gln Arg Ile Ile
4945                4950                4955                4960

Val Glu Leu Leu Gly Leu Phe Ala Arg Asp Val Leu His Pro Leu Pro
                4965                4970                4975

Val His Ala Trp Asp Val Arg Gln Ala Arg Glu Ala Phe Gly Trp Met
            4980                4985                4990

Ser Ser Gly Arg His Thr Gly Lys Leu Val Leu Thr Val Pro Arg Pro
        4995                5000                5005

Leu Asp Pro Glu Gly Ala Val Val Ile Thr Gly Gly Ser Gly Thr Leu
    5010                5015                5020

Ala Gly Ile Leu Ala Arg His Leu Gly His Pro His Thr Tyr Leu Leu
5025                5030                5035                5040

Ser Arg Thr Pro Pro Pro Asp Thr Thr Pro Gly Thr His Leu Pro Cys
                5045                5050                5055

Asp Val Gly Asp Pro His Gln Leu Ala Thr Thr Leu Ala Arg Ile Pro
            5060                5065                5070

Gln Pro Leu Thr Ala Val Phe His Thr Ala Gly Thr Leu Asp Asp Ala
        5075                5080                5085

Leu Leu Asp Asn Leu Thr Pro Asp Arg Val Asp Thr Val Leu Lys Pro
    5090                5095                5100

Lys Ala Asp Ala Ala Trp His Leu His Arg Leu Thr Arg Asp Thr Asp
5105                5110                5115                5120

Leu Ala Ala Phe Val Val Tyr Ser Ala Val Ala Gly Leu Met Gly Ser
                5125                5130                5135

Pro Gly Gln Gly Asn Tyr Val Ala Ala Asn Ala Phe Leu Asp Ala Leu
            5140                5145                5150

Ala Glu His Arg Arg Ala Gln Gly Leu Pro Ala Gln Ser Leu Ala Trp
        5155                5160                5165

Gly Met Trp Ala Asp Val Ser Ala Leu Thr Ala Lys Leu Thr Asp Ala
    5170                5175                5180

Asp Arg Gln Arg Ile Arg Arg Ser Gly Phe Pro Pro Leu Ser Ala Ala
5185                5190                5195                5200

Asp Gly Met Arg Leu Phe Asp Ala Ala Thr Arg Thr Pro Glu Pro Val
                5205                5210                5215

Val Val Ala Thr Thr Val Asp Leu Thr Gln Leu Asp Gly Ala Val Ala
            5220                5225                5230

Pro Leu Leu Arg Gly Leu Ala Ala His Arg Ala Gly Pro Ala Arg Thr
        5235                5240                5245

Val Ala Arg Asn Ala Gly Glu Glu Pro Leu Ala Val Arg Leu Ala Gly
    5250                5255                5260

Arg Thr Ala Ala Glu Gln Arg Arg Ile Met Gln Glu Val Val Leu Arg
5265                5270                5275                5280

His Ala Ala Ala Val Leu Ala Tyr Gly Leu Gly Asp Arg Val Ala Ala
                5285                5290                5295

Asp Arg Pro Phe Arg Glu Leu Gly Phe Asp Ser Leu Thr Ala Val Asp
            5300                5305                5310

Leu Arg Asn Arg Leu Ala Ala Glu Thr Gly Leu Arg Leu Pro Thr Thr
        5315                5320                5325

Leu Val Phe Ser His Pro Thr Ala Glu Ala Leu Thr Ala His Leu Leu
    5330                5335                5340

Asp Leu Ile Asp Ala Pro Thr Ala Arg Ile Ala Gly Glu Ser Leu Pro
5345                5350                5355                5360
```

-continued

```
Ala Val Thr Ala Ala Pro Val Ala Ala Ala Arg Asp Gln Asp Glu Pro
                5365                5370                5375

Ile Ala Ile Val Ala Met Ala Cys Arg Leu Pro Gly Gly Val Thr Ser
            5380                5385                5390

Pro Glu Asp Leu Trp Arg Leu Val Glu Ser Gly Thr Asp Ala Ile Thr
        5395                5400                5405

Thr Pro Pro Asp Asp Arg Gly Trp Asp Val Asp Ala Leu Tyr Asp Ala
    5410                5415                5420

Asp Pro Asp Ala Ala Gly Lys Ala Tyr Asn Leu Arg Gly Gly Tyr Leu
5425                5430                5435                5440

Ala Gly Ala Ala Glu Phe Asp Ala Ala Phe Phe Asp Ile Ser Pro Arg
                5445                5450                5455

Glu Ala Leu Gly Met Asp Pro Gln Gln Arg Leu Leu Leu Glu Thr Ala
            5460                5465                5470

Trp Glu Ala Ile Glu Arg Gly Arg Ile Ser Pro Ala Ser Leu Arg Gly
        5475                5480                5485

Arg Glu Val Gly Val Tyr Val Gly Ala Ala Ala Gln Gly Tyr Gly Leu
    5490                5495                5500

Gly Ala Glu Asp Thr Glu Gly His Ala Ile Thr Gly Gly Ser Thr Ser
5505                5510                5515                5520

Leu Leu Ser Gly Arg Leu Ala Tyr Val Leu Gly Leu Glu Gly Pro Ala
                5525                5530                5535

Val Thr Val Asp Thr Ala Cys Ser Ser Ser Leu Val Ala Leu His Leu
            5540                5545                5550

Ala Cys Gln Gly Leu Arg Leu Gly Glu Cys Glu Leu Ala Leu Ala Gly
        5555                5560                5565

Gly Val Ser Val Leu Ser Ser Pro Ala Ala Phe Val Glu Phe Ser Arg
    5570                5575                5580

Gln Arg Gly Leu Ala Ala Asp Gly Arg Cys Lys Ser Phe Gly Ala Gly
5585                5590                5595                5600

Ala Asp Gly Thr Thr Trp Ser Glu Gly Val Gly Val Leu Val Leu Glu
                5605                5610                5615

Arg Leu Ser Asp Ala Glu Arg Leu Gly His Thr Val Leu Ala Val Val
            5620                5625                5630

Arg Gly Ser Ala Val Thr Ser Asp Gly Ala Ser Asn Gly Leu Thr Ala
        5635                5640                5645

Pro Asn Gly Leu Ser Gln Gln Arg Val Ile Arg Lys Ala Leu Ala Ala
    5650                5655                5660

Ala Gly Leu Thr Gly Ala Asp Val Asp Val Val Glu Gly His Gly Thr
5665                5670                5675                5680

Gly Thr Arg Leu Gly Asp Pro Val Glu Ala Asp Ala Leu Leu Ala Thr
                5685                5690                5695

Tyr Gly Gln Asp Arg Pro Ala Pro Val Trp Leu Gly Ser Leu Lys Ser
            5700                5705                5710

Asn Ile Gly His Ala Thr Ala Ala Ala Gly Val Ala Gly Val Ile Lys
        5715                5720                5725

Met Val Gln Ala Ile Gly Ala Gly Thr Met Pro Arg Thr Leu His Val
    5730                5735                5740

Glu Glu Pro Ser Pro Ala Val Asp Trp Ser Thr Gly Gln Val Ser Leu
5745                5750                5755                5760

Leu Gly Ser Asn Arg Pro Trp Pro Asp Asp Glu Arg Pro Arg Arg Ala
                5765                5770                5775

Ala Val Ser Ala Phe Gly Leu Ser Gly Thr Asn Ala His Val Ile Leu
```

-continued

```
            5780                5785                5790

Glu Gln His Arg Pro Ala Pro Val Ala Ser Gln Pro Pro Arg Pro Pro
        5795                5800                5805

Arg Glu Glu Ser Gln Pro Leu Pro Trp Val Leu Ser Ala Arg Thr Pro
    5810                5815                5820

Ala Ala Leu Arg Ala Gln Ala Ala Arg Leu Arg Asp His Leu Ala Ala
5825                5830                5835                5840

Ala Pro Asp Ala Asp Pro Leu Asp Ile Gly Tyr Ala Leu Ala Thr Ser
                5845                5850                5855

Arg Ala Gln Phe Ala His Arg Ala Ala Val Val Ala Thr Thr Pro Asp
            5860                5865                5870

Gly Phe Arg Ala Ala Leu Asp Gly Leu Ala Asp Gly Ala Glu Ala Pro
        5875                5880                5885

Gly Val Val Thr Gly Thr Ala Gln Glu Arg Arg Val Ala Phe Leu Phe
    5890                5895                5900

Asp Gly Gln Gly Ala Gln Arg Ala Gly Met Gly Arg Glu Leu His Arg
5905                5910                5915                5920

Arg Phe Pro Val Phe Ala Ala Ala Trp Asp Glu Val Ser Asp Ala Phe
                5925                5930                5935

Gly Lys His Leu Lys His Ser Pro Thr Asp Val Tyr His Gly Glu His
            5940                5945                5950

Gly Ala Leu Ala His Asp Thr Leu Tyr Ala Gln Ala Gly Leu Phe Thr
        5955                5960                5965

Leu Glu Val Ala Leu Leu Arg Leu Leu Glu His Trp Gly Val Arg Pro
    5970                5975                5980

Asp Val Leu Val Gly His Ser Val Gly Glu Val Thr Ala Ala Tyr Ala
5985                5990                5995                6000

Ala Gly Val Leu Thr Leu Ala Asp Ala Thr Glu Leu Ile Val Ala Arg
                6005                6010                6015

Gly Arg Ala Leu Arg Ala Leu Pro Pro Gly Ala Met Leu Ala Val Asp
            6020                6025                6030

Gly Ser Pro Ala Glu Val Gly Ala Arg Thr Asp Leu Asp Ile Ala Ala
        6035                6040                6045

Val Asn Gly Pro Ser Ala Val Val Leu Ala Gly Ser Pro Asp Asp Val
    6050                6055                6060

Ala Ala Phe Glu Arg Glu Trp Ser Ala Ala Gly Arg Arg Thr Lys Arg
6065                6070                6075                6080

Leu Asp Val Gly His Ala Phe His Ser Arg His Val Asp Gly Ala Leu
                6085                6090                6095

Asp Gly Phe Arg Thr Val Leu Glu Ser Leu Ala Phe Gly Ala Ala Arg
            6100                6105                6110

Leu Pro Val Val Ser Thr Thr Thr Gly Arg Asp Ala Ala Asp Asp Leu
        6115                6120                6125

Ile Thr Pro Ala His Trp Leu Arg His Ala Arg Arg Pro Val Leu Phe
    6130                6135                6140

Ser Asp Ala Val Arg Glu Leu Ala Asp Arg Gly Val Thr Thr Phe Val
6145                6150                6155                6160

Ala Val Gly Pro Ser Gly Ser Leu Ala Ser Ala Ala Ala Glu Ser Ala
                6165                6170                6175

Gly Glu Asp Ala Gly Thr Tyr His Ala Val Leu Arg Ala Arg Thr Gly
            6180                6185                6190

Glu Glu Thr Ala Ala Leu Thr Ala Leu Ala Glu Leu His Ala His Gly
        6195                6200                6205
```

-continued

```
Val Pro Val Asp Leu Ala Ala Val Leu Ala Gly Gly Arg Pro Val Asp
    6210                6215                6220

Leu Pro Val Tyr Ala Phe Gln His Arg Ser Tyr Trp Leu Ala Pro Ala
6225                6230                6235                6240

Val Ala Gly Ala Pro Ala Thr Val Ala Asp Thr Gly Gly Pro Ala Glu
                6245                6250                6255

Ser Glu Pro Glu Asp Leu Thr Val Ala Glu Ile Val Arg Arg Arg Thr
            6260                6265                6270

Ala Ala Leu Leu Gly Val Thr Asp Pro Ala Asp Val Asp Ala Glu Ala
        6275                6280                6285

Thr Phe Phe Ala Leu Gly Phe Asp Ser Leu Ala Val Gln Arg Leu Arg
    6290                6295                6300

Asn Gln Leu Ala Ser Ala Thr Gly Leu Asp Leu Pro Ala Ala Val Leu
6305                6310                6315                6320

Phe Asp His Asp Thr Pro Ala Ala Leu Thr Ala Phe Leu Gln Asp Arg
                6325                6330                6335

Ile Glu Ala Gly Gln Asp Arg Ile Glu Ala Gly Glu Asp Asp Asp Ala
            6340                6345                6350

Pro Thr Val Leu Ser Leu Leu Glu Glu Met Glu Ser Leu Asp Ala Ala
        6355                6360                6365

Asp Ile Ala Ala Thr Pro Ala Pro Glu Arg Ala Ala Ile Ala Asp Leu
    6370                6375                6380

Leu Asp Lys Leu Ala His Thr Trp Lys Asp Tyr Arg
6385                6390                6395
```